(12) United States Patent
Yu et al.

(10) Patent No.: US 7,879,890 B2
(45) Date of Patent: Feb. 1, 2011

(54) COMPOUNDS FOR THE TREATMENT OF INFLAMMATORY DISORDERS

(75) Inventors: Wensheng Yu, Edison, NJ (US); Ling Tong, Warren, NJ (US); Lei Chen, Roselle Park, NJ (US); Joseph A. Kozlowski, Princeton, NJ (US); Brian J. Lavey, New Providence, NJ (US); Neng-Yang Shih, Warren, NJ (US); Vincent S. Madison, Mountain Lakes, NJ (US); Guowei Zhou, Livingston, NJ (US); Peter Orth, New York, NY (US); Zhuyan Guo, Scotch Plains, NJ (US); Michael K. C. Wong, North Brunswick, NJ (US); De-Yi Yang, Morris Plains, NJ (US); Seong Heon Kim, Livingston, NJ (US); Bandarpalle B. Shankar, Branchburg, NJ (US); M. Arshad Siddiqui, Newton, MA (US); Kristin E. Rosner, Watertown, MA (US); Chaoyang Dai, Acton, MA (US); Janeta Popovici-Muller, Waltham, MA (US); Vinay M. Girijavallabhan, Watertown, MA (US); Dansu Li, Watertown, MA (US); Razia Rizvi, Bloomfield, NJ (US); Aneta M. Micula, South Amboy, NJ (US); Robert Feltz, Parsippany, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/338,445

(22) Filed: Dec. 18, 2008

(65) Prior Publication Data

US 2009/0137586 A1    May 28, 2009

Related U.S. Application Data

(60) Division of application No. 11/653,676, filed on Jan. 16, 2007, now Pat. No. 7,488,745, which is a continuation-in-part of application No. 11/333,663, filed on Jan. 17, 2006, now Pat. No. 7,504,424, which is a continuation-in-part of application No. 11/180,863, filed on Jul. 13, 2005, now Pat. No. 7,482,370.

(60) Provisional application No. 60/588,502, filed on Jul. 16, 2004.

(51) Int. Cl.
*A61K 31/416* (2006.01)
*A61K 31/428* (2006.01)

(52) U.S. Cl. ............... 514/373; 514/405; 514/414

(58) Field of Classification Search ............ 514/373, 514/405, 414

See application file for complete search history.

(56) References Cited

U.S. PATENT DOCUMENTS

| 6,495,565 | B2 | 12/2002 | Duan et al. |
|---|---|---|---|
| 6,534,491 | B2 | 3/2003 | Levin et al. |
| 6,677,355 | B1 | 1/2004 | Conrad et al. |
| 7,482,370 | B2 | 1/2009 | Yu et al. |
| 7,488,745 | B2 | 2/2009 | Yu et al. |
| 7,504,424 | B2 | 3/2009 | Yu et al. |
| 7,524,842 | B2 | 4/2009 | Lavey et al. |
| 2004/0067996 | A1 | 4/2004 | Sheppeck |
| 2006/0276506 | A1 | 12/2006 | Yu et al. |
| 2007/0265299 | A1 | 11/2007 | Lavey et al. |
| 2008/0226618 | A1 | 9/2008 | Mansoor et al. |
| 2009/0111803 | A1 | 4/2009 | Yu et al. |
| 2009/0156586 | A1 | 6/2009 | Lavey et al. |
| 2009/0170875 | A1 | 7/2009 | Yu et al. |

FOREIGN PATENT DOCUMENTS

| WO | WO02/074750 | 9/2002 |
|---|---|---|
| WO | WO02/096426 | 12/2002 |
| WO | WO03/053940 | 7/2003 |
| WO | WO03/053941 | 7/2003 |
| WO | WO2004/012663 | 2/2004 |
| WO | WO2004/024698 | 3/2004 |
| WO | WO2004/024715 | 3/2004 |
| WO | WO2004/024721 | 3/2004 |
| WO | WO2004/056766 | 7/2004 |
| WO | WO2006/019768 | 2/2006 |
| WO | WO2007/084455 | 7/2007 |

OTHER PUBLICATIONS

International Search Report for International Application No. PCT/US2005/024771 dated Nov. 9, 2005.
International Search Report for International Application No. PCT/US2007/000930 dated Aug. 22, 2007.

(Continued)

*Primary Examiner*—Taofiq A Solola
(74) *Attorney, Agent, or Firm*—Eric A. Meade; Krishna G. Banerjee

(57) ABSTRACT

This invention relates to compounds of the Formula (I):

or a pharmaceutically acceptable salt, solvate, ester or isomer thereof, which can be useful for the treatment of diseases or conditions mediated by MMPs, ADAMs, TACE, aggrecanase, TNF- or combinations thereof.

11 Claims, No Drawings

OTHER PUBLICATIONS

Dinarello, C. A., et. al., "Stopping the Cuts"; Current Biology; 5(6):587-590; 1995.

Doggrell, Sheila A., TACE inhibition: a new approach to treating inflammation; Expert. Opin. Invest. Drugs, 2002, 11(7), 1003-1006.

Donnahoo, Kirstan K. et. al., Review Article: The Role of Tumor Necrosis Factor in Renal Ischemia-Reperfusion Injury; The Journal of Urology, Jul. 1999, 162, 196-203.

Feldmann, Marc et. al., Discovery of TNF-α as a therapeutic target in rheumatoid arthritis: preclinical and clinical studies; Joint Bone Spine, 2002 69: 12-18.

Knabe, J. et. al., Racemates and enantiomers of basic substituted 5-phenylhydantoins. Synthesis and antiarrhymic activity; Pharmazie, 1997, 52(12): 912-919—English abstract as it appears on p. 912.

Le, Giang T., et. al., "Inhibitors of TACE and Caspace-1 as Anti-Inflammatory Drugs"; Current Medicinal Chemistry; 12:2963-2977; 2005.

Leib, Stephen L., et. al., Inhibition of matrix metalloproteinases and tumour necrosis factor α converting enzyme as adjuvant therapy in pneumococcal meningitis; Brain, (2001) 124(9), 1734-1742.

Moriyama, Hideki, et. al., "Azasugar-Based MMP/ADAM Inhibitors as Antipsoriatic Agents"; J. Med. Chem.; 47:1930-1938; 2004.

Morimoto, Yasuo et. al., A Novel Matrix Metalloproteinase Inhibitor, Exerts Its Antidiabetic Effect by Inhibiting Tumor Necrosis Factor-α Production; Life Sciences, 1997, 61(8), 795-803.

Moss, Marcia L. et. al.., TACE and other ADAM proteases as targets for drug discovery; Drug Discovery Today, Apr. 2001, 6(8), 417-426.

Nelson, Frances C. et al. The therapeutic potential of small molecule TACE inhibitors, Exp. Opin. Invest. Drugs., 1999, 8(4), 383-392.

Newton, R. C. et. al., "Biology of TACE Inhibition"; Ann. Rheum. Dis.; 60:iii25-iii32; 2001.

Olmarker, Kjell, MD, PhD, et. al.; Selective Inhibition of Tumor Necrosis Factor-α Prevents Nucleus Pulposus-Induced Thrombus Formation, Intraneural Edema, and Reduction of Nerve Conduction Velocity; Spine, 2001, 26(8) 863-869.

Reimold, Andreas M. MD; New Indications for Treatment of Chronic Inflammation by TNF-[alpha] Blockade; American Journal of the Medical Sciences, Feb. 2003 325(2):75-92 Abstract.

Satoh, Mamoru et. al., Expression of Tumor Necrosis Factor-alpha-Converting Enzyme and Tumor Necrosis Factor-alpha in Human Myocarditis; Journal of the American College of Cardiology, 2000, 36(4), 1288-1294.

Seifert, T. et. al., TACE mRNA expression in peripheral mononuclear cells precedes new lesions on MRI in multiple sclerosis; Multiple Sclerosis 2002, 8, 447-451.

Togashi, Nobuhiko, et. al.; Effect of TNF-α-Converting Enzyme Inhibitor on Insulin Resistance in Fructose-Fed Rats; Hypertension, 2002, 39(part 2), 578-580.

Trifilieff, Alexandre et. al.,Pharmacological profile of PKF242-484 and PKF241-466, novel dual inhibitors of TNF-α converting enzyme and matrix metalloproteinases, in models of airway inflammation; British Journal of Pharmacology, 2002, vol. 135(7), 1655-1664.

Van Deventer, SJH; A place for TACE; GUT 2002 51: 5-6.

Summary of Preclinical Toxicology—Six Month Studies for Compound 9200 in mice and rats, Jun. 2009.

COMPOUNDS FOR THE TREATMENT OF INFLAMMATORY DISORDERS

CROSS-REFERENCE TO RELATED APPLICATIONS

This Application is a divisional of U.S. patent application Ser. No. 11/653,676 filed Jan. 16, 2007, now U.S. Pat. No. 7,488,745, which is a continuation-in-part (CIP) of U.S. patent application Ser. No. 11/333,663, filed Jan. 17, 2006, now U.S. Pat. No. 7,504,424, which is a CIP of U.S. patent application Ser. No. 11/180,863 filed Jul. 13, 2005, now U.S. Pat. No. 7,482,370, which claims the benefit of U.S. Provisional Application Ser. No. 60/588,502 filed Jul. 16, 2001.

FIELD OF THE INVENTION

This invention relates generally to novel hydantoin derivatives that can inhibit matrix metalloproteinases (MMPs), a disintegrin and metalloproteases (ADAMs) and/or tumor necrosis factor alpha-converting enzyme (TACE) and in so doing prevent the release of tumor necrosis factor alpha (TNF-α), pharmaceutical compositions comprising such compounds, and methods of treatment using such compounds.

BACKGROUND OF THE INVENTION

Osteo- and rheumatoid arthritis (OA and RA, respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A (1970) 424-434). There are four classes of protein degradative enzymes in mammalian cells: serine, cysteine, aspartic and metalloproteases. The available evidence supports the belief that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. Arthritis Rheum. 21, 1978, 761-766, Woessner et al. Arthritis Rheum. 26, 1983, 63-68 and Ibid. 27, 1984, 305-312). In addition, aggrecanase (a newly identified metalloprotease) has been identified that provides the specific cleavage product of proteoglycan, found in RA and OA patients (Lohmander L. S. et al. Arthritis Rheum. 36, 1993, 1214-22).

Metalloproteases (MPs) have been implicated as the key enzymes in the destruction of mammalian cartilage and bone. It can be expected that the pathogenesis of such diseases can be modified in a beneficial manner by the administration of MP inhibitors (see Wahl et al. Ann. Rep. Med. Chem. 25, 175-184, AP, San Diego, 1990).

MMPs are a family of over 20 different enzymes that are involved in a variety of biological processes important in the uncontrolled breakdown of connective tissue, including proteoglycan and collagen, leading to resorption of the extracellular matrix. This is a feature of many pathological conditions, such as RA and OA, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitor of MPs), which form inactive complexes with the MMP's.

Tumor necrosis factor alpha (TNF-α) is a cell-associated cytokine that is processed from a 26 kDa precursor form to a 17 kd active form. See Black R. A. "Tumor necrosis factor-alpha converting enzyme" Int J Biochem Cell Biol. 2002 January; 34(1):1-5 and Moss M L, White J M, Lambert M H, Andrews R C. "TACE and other ADAM proteases as targets for drug discovery" Drug Discov Today. 2001 Apr. 1; 6(8): 417-426, each of which is incorporated by reference herein.

TNF-α has been shown to play a pivotal role in immune and inflammatory responses. Inappropriate or over-expression of TNF-α is a hallmark of a number of diseases, including RA, Crohn's disease, multiple sclerosis, psoriasis and sepsis. Inhibition of TNF-α production has been shown to be beneficial in many preclinical models of inflammatory disease, making inhibition of TNF-α production or signaling an appealing target for the development of novel anti-inflammatory drugs.

TNF-α is a primary mediator in humans and animals of inflammation, fever and acute phase responses, similar to those observed during acute infection and shock. Excess TNF-α has been shown to be lethal. Blocking the effects of TNF-α with specific antibodies can be beneficial in a variety of conditions, including autoimmune diseases such as RA (Feldman et al, Lancet, (1994) 344, 1105), non-insulin dependent diabetes mellitus (Lohmander L. S. et al., Arthritis Rheum. 36 (1993) 1214-22) and Crohn's disease (Macdonald T. et al., Clin. Exp. Immunol. 81 (1990) 301).

Compounds that inhibit the production of TNF-α are therefore of therapeutic importance for the treatment of inflammatory disorders. Recently it has been shown that metalloproteases, such as TACE, are capable of converting TNF-α from its inactive to active form (Gearing et al Nature, 1994, 370, 555). Since excessive TNF-α production has been noted in several disease conditions also characterized by MMP-mediated tissue degradation, compounds which inhibit both MMPs and TNF-α production may also have a particular advantage in diseases where both mechanisms are involved.

One approach to inhibiting the harmful effects of TNF-α is to inhibit the enzyme, TACE before it can process TNF-α to its soluble form. TACE is a member of the ADAM family of type I membrane proteins and mediates the ectodomain shedding of various membrane-anchored signaling and adhesion proteins. TACE has become increasingly important in the study of several diseases, including inflammatory disease, because of its role in cleaving TNF-α from its "stalk" sequence and thus releasing the soluble form of the TNF-α protein (Black R. A. Int J Biochem Cell Biol. 2002 34, 1-5).

There are numerous patents and publications which disclose hydroxamate, sulphonamide, hydantoin, carboxylate and/or lactam based MMP inhibitors.

U.S. Pat. No. 6,677,355 and U.S. Pat. No. 6,534,491 (B2), describe compounds that are hydroxamic acid derivatives and MMP inhibitors.

U.S. Pat. No. 6,495,565 discloses lactam derivatives that are potential inhibitors of MMPs and/or TNF-α.

PCT Publications WO2002/074750, WO2002/096426, WO20040067996, WO2004012663, WO200274750 and WO2004024721 disclose hydantoin derivatives that are potential inhibitors of MMPs.

PCT Publications WO2004024698 and WO2004024715 disclose sulphonamide derivatives that are potential inhibitors of MMPs.

PCT Publications WO2004056766, WO2003053940 and WO2003053941 also describe potential inhibitors of TACE and MMPs.

There is a need in the art for inhibitors of MMPs, ADAMs, TACE, and TNF-α, which can be useful as anti-inflammatory compounds and cartilage protecting therapeutics. The inhibition of TNF-α, TACE and or other MMPs can prevent the degradation of cartilage by these enzymes, thereby alleviating the pathological conditions of OA and RA as well as many other auto-immune diseases.

SUMMARY OF THE INVENTION

In its many embodiments, the present invention provides a novel class of compounds as inhibitors of TACE, the production of TNF-α, MMPs, ADAMs or any combination thereof, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with TACE, TNF-α, MMPs, ADAMs or any combination thereof using such compounds or pharmaceutical compositions.

In one embodiment, the present application discloses a compound having the general structure shown in formula (I):

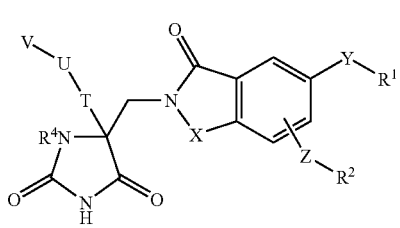

(I)

or a pharmaceutically acceptable salt, solvate, ester, or isomer thereof, wherein:

X is selected from the group consisting of —S—, —C($R^4$)$_2$— or —N($R^4$)—;

T is selected from the group consisting of H (with U and V being absent), alkyl, alkenyl, aryl, heteroaryl, heterocyclyl, cycloalkyl, alkylaryl, and arylalkyl, said aryl, heteroaryl, heterocyclyl, cycloalkyl, alkylaryl and arylalkyl being optionally fused with one or more moieties selected from the group consisting of aryl, heteroaryl, heterocyclyl, cycloalkyl, alkylaryl and arylalkyl, wherein each of any of the aforementioned alkyl, alkenyl, aryl, heteroaryl, heterocyclyl, cycloalkyl, alkylaryl and arylalkyl groups of T is unsubstituted or optionally independently substituted with one to four $R^{10}$ moieties which can be the same or different, each $R^{10}$ moiety being independently selected from the group of $R^{10}$ moieties below;

U is absent or present, and if present U is selected from the group consisting of a covalent bond, —N($R^4$)—, —N($R^4$)C($R^4$)$_2$—, —N($R^4$)C(O)—, —O—, —N($R^4$)S(O)$_2$—, —N($R^4$)C(O)N($R^4$)—, and —N($R^4$)C(S)N($R^4$)—;

V is absent or present, and if present V is selected from the group consisting of alkyl, aryl, heteroaryl, heterocyclyl and cycloalkyl, said aryl, heteroaryl, heterocyclyl, cycloalkyl, alkylaryl and arylalkyl being optionally fused with one or more moieties selected from the group consisting of aryl, heteroaryl, heterocyclyl, cycloalkyl, alkylaryl and arylalkyl, wherein each of any of the aforementioned alkyl, aryl, heteroaryl, heterocyclyl and cycloalkyl is unsubstituted or optionally independently substituted with one to four $R^{10}$ moieties which can be the same or different, each $R^{10}$ moiety being independently selected from the group of $R^{10}$ moieties below;

Y is absent or present, and if present Y is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)—S(O)$_2$, —O—, —S—, —C(O)—, —S(O)—, and —S(O)$_2$—;

Z is absent or present, and if present Z is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)—S(O)$_2$—, —O—, —S—, —C(O)—, —S(O)—, and —S(O)$_2$—;

n is 1 to 3;

$R^1$ is selected from the group consisting of H, —O$R^4$, halogen, alkyl, fluoroalkyl, aryl, heteroaryl, heterocyclyl, alkylaryl, alkylheteroaryl and arylalkyl, wherein each of the alkyl, fluoroalkyl, aryl, heteroaryl, heterocyclyl, alkylaryl, alkylheteroaryl and arylalkyl groups of $R^1$ is unsubstituted or optionally independently substituted with one to four $R^{20}$ moieties which can be the same or different, each $R^{20}$ moiety being independently selected from the group of $R^{20}$ moieties below, with the proviso that when Y is present and Y is N, S or O, then $R^1$ is not halogen;

$R^2$ is selected from the group consisting of H, —O$R^4$, halogen, alkyl, fluoroalkyl, aryl, heteroaryl, heterocyclyl, alkylaryl, alkylheteroaryl and arylalkyl, wherein each of the alkyl, fluoroalkyl, aryl, heteroaryl, heterocyclyl, alkylaryl, alkylheteroaryl and arylalkyl groups of $R^2$ is unsubstituted or optionally independently substituted with one to four $R^{20}$ moieties which can be the same or different, each $R^{20}$ moiety being independently selected from the group of $R^{20}$ moieties below, with the proviso that when Z is present and Z is N, S or O, then $R^2$ is not halogen;

each $R^4$ is the same or different and is independently selected from the group of H and alkyl, alkynyl, alkynyl, cycloalkyl, heterocyclyl, aryl, and heteroaryl wherein each of said alkynyl, alkynyl, cycloalkyl, heterocyclyl, aryl, and heteroaryl are independently optionally substituted with one or two moieties selected from the group consisting of hydroxyl, alkyl, cycloalkyl, aryl, heteroaryl, -arylheteroaryl, and -heteroarylaryl;

$R^{10}$ is selected from the group consisting of —O$R^4$, —N($R^4$)$_2$, —S(O)—$R^4$, —S(O)$_2$—$R^4$, —N($R^4$)S(O)$_2$—$R^4$, —S(O)$_2$N($R^4$)$_2$, —O(fluoroalkyl), halogen, alkyl, fluoroalkyl, aryl, heteroaryl, heterocyclyl, cycloalkyl, -alkylcycloalkyl -alkylaryl and -arylalkyl, wherein each of the alkyl, fluoroalkyl, aryl, heteroaryl, heterocyclyl, cycloalkyl, -alkylcycloalkyl, -alkylaryl and -arylalkyl groups of $R^{10}$ is unsubstituted or optionally independently substituted with one to four $R^{30}$ moieties which can be the same or different, each $R^{30}$ moiety being independently selected from the group of $R^{30}$ moieties below;

$R^{20}$ is selected from the group consisting of halogen, alkyl, fluoroalkyl; and $R^{30}$ is selected from the group consisting of halogen, alkyl, and fluoroalkyl.

The compounds of Formula I can be useful as inhibitors of TACE and may be useful in the treatment and prevention of diseases associated with TACE, TNF-α, MMPs, ADAMs or any combination thereof.

DETAILED DESCRIPTION OF THE INVENTION

In its several embodiments, the present invention provides a novel class of inhibitors of TACE, the production of TNF-α, MMPs, ADAMs or any combination thereof, pharmaceutical compositions containing one or more of the compounds, methods of preparing pharmaceutical formulations comprising one or more such compounds, and methods of treatment, prevention or amelioration of one or more of the symptoms of inflammation.

In one embodiment, the present invention provides compounds which are represented by structural Formula (I) above or a pharmaceutically acceptable salt, solvate, ester or isomer thereof, wherein the various moieties are as described above.

In another embodiment, the isomer referred to the in the preceding paragraph is a stereoisomer.

In one embodiment, T is alkyl or aryl; X is —C($R^4$)$_2$—; Y is absent; Z is absent or present; $R^2$ is selected from the group consisting of H, halogen and alkyl; and if Z is present Z is —O—.

In another embodiment, T is alkyl or aryl; X is —C($R^4$)$_2$—; Y is absent; Z is absent or present, and if present Z is —O—; and $R^2$ is selected from the group consisting of alkylaryl and alkylheteroaryl.

In another embodiment, T is alkyl or aryl; X is —N($R^4$)—; Y is absent; Z is absent or present; $R^2$ is selected from the group consisting of H, halogen and alkyl; and if Z is present Z is —O—.

In another embodiment, X is —CH$_2$— or —N($R^4$)—.

In yet another embodiment, X is —CH$_2$—.

In still another embodiment, X is —N($R^4$)—

In another embodiment, $R^4$ is H.

In another embodiment, T is alkyl.

In yet another embodiment, T is —CH$_3$.

In still another embodiment, T is aryl and said aryl is unsubstituted or optionally independently substituted with one to five $R^{10}$ moieties which can be the same or different, each $R^{10}$ moiety being independently selected from the group of $R^{10}$ moieties.

In another embodiment, $R^{10}$ is halogen.

In yet another embodiment, $R^{10}$ is heteroaryl.

In still another embodiment, $R^{10}$ is aryl.

In an embodiment U selected from the group consisting of a covalent bond, —N($R^4$)—, —N($R^4$)C(O)—, and —N($R^4$)S(O)$_2$—.

In yet another embodiment U is a covalent bond.

In still another embodiment U is —N($R^4$)—.

In yet still another embodiment, U is —N($R^4$)C(O)—.

In another embodiment, V is selected from the group consisting of aryl, heteroaryl, heterocyclyl and cycloalkyl, said aryl, heteroaryl, heterocyclyl, and cycloalkyl being optionally fused with one or more moieties selected from the group consisting of aryl, heteroaryl, heterocyclyl, or cycloalkyl, wherein each of any of said aryl, heteroaryl, heterocyclyl and cycloalkyl is unsubstituted or optionally independently substituted with one to four $R^{10}$ moieties which can be the same or different, each $R^{10}$ moiety being independently selected from the group of $R^{10}$ moieties.

In another embodiment, Y is selected from the group consisting of a covalent bond, —C($R^4$)$_2$)$_n$—, —C(O)— and —O—.

In yet another embodiment, Y is —O—.

In still another embodiment, Y is —(C($R^4$)$_2$)$_n$—.

In yet still another embodiment, Y is —C(O)—.

In another embodiment, Y is a covalent bond.

In an embodiment, $R^1$ is selected from the group consisting of —OR$^4$, H, alkyl, fluoroalkyl, alkylaryl, halogen, and heteroaryl.

In another embodiment, $R^1$ is H.

In yet another embodiment, $R^1$ is alkylaryl.

In still another embodiment, $R^1$ is alkyl.

In yet still another embodiment, $R^1$ is fluoroalkyl.

In a further embodiment, $R^1$ is halogen.

In another embodiment, $R^1$ is —OR$^4$.

In another embodiment, where $R^1$ is —OR$^4$, $R^4$ is —CH$_2$C≡CCH$_3$.

In another embodiment, where $R^1$ is —OR$^4$, $R^4$ is —CH$_2$C≡CCH$_2$OH.

In another embodiment, where $R^1$ is —OR$^4$, $R^4$ is

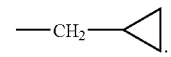

In another embodiment, the alkyl is —CH$_3$.

In still another embodiment, the alkyl is —CH$_2$CH$_3$.

In another embodiment, in formula (I), T, U, and V are taken together to form

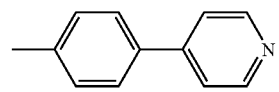

and $R^1$ is selected from the group consisting of F, Cl, OH, —OCH$_2$C≡CCH$_3$, —OCH$_2$CCCH$_2$OH, —OCH$_3$, and

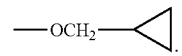

In another embodiment, in formula (I), T, U, and V are taken together to form

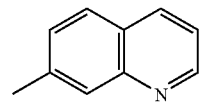

and $R^1$ is selected from the group consisting of F, Cl, OH, —OCH$_2$C≡CCH$_3$, —OCH$_2$C≡CCH$_2$OH, —OCH$_3$, and

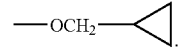

In another embodiment, in formula (I), T, U, and V are taken together to form

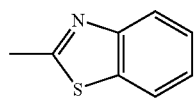

and R¹ is selected from the group consisting of F, Cl, OH, —OCH₂C≡CCH₃, —OCH₂C≡CCH₂OH, —OCH₃, and

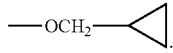

In another embodiment, in formula (I), T, U, and V are taken together to form

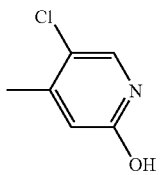

and R¹ is selected from the group consisting of F, Cl, OH, —OCH₂C≡CCH₃, —OCH₂C≡CCH₂OH, —OCH₃, and

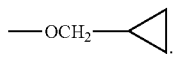

In another embodiment, in formula (I), T, U, and V are taken together to form

and R¹ is selected from the group consisting of F, Cl, OH, —OCH₂C≡CCH₃, —OCH₂C≡CCH₂OH, —OCH₃, and

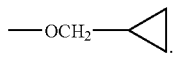

In another embodiment, in formula (I), T, U, and V are taken together to form

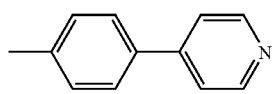

and R² is selected from the group consisting of F, Cl, OH, —OCH₂C≡CCH₃, —OCH₂C≡CCH₂OH, —OCH₃, and

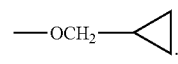

In another embodiment, in formula (I), T, U, and V are taken together to form

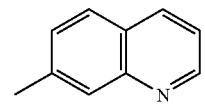

and R² is selected from the group consisting of F, Cl, OH, —OCH₂C≡CCH₃, —OCH₂C≡CCH₂OH, —OCH₃, and

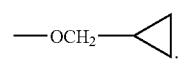

In another embodiment, in formula (I), T, U, and V are taken together to form

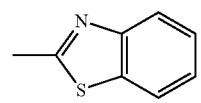

and R² is selected from the group consisting of F, Cl, OH, —OCH₂C≡CCH₃, —OCH₂C≡CCH₂OH, —OCH₃, and

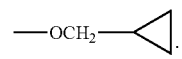

In another embodiment, in formula (I), T, U, and V are taken together to form

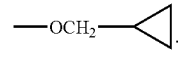

and R² is selected from the group consisting of F, Cl, OH, —OCH₂C≡CCH₃, —OCH₂C≡CCH₂OH, —OCH₃, and

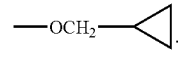

In another embodiment, in formula (I), T, U, and V are taken together to form

and R² is selected from the group consisting of F, Cl, OH, —OCH₂C≡CCH₃, —OCH₂C≡CCH₂OH, —OCH₃, and

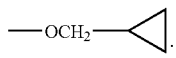

In another embodiment, the fluoroalkyl is —CH₂CF₃.

In an embodiment, halogen is selected from the group consisting of —Br, —Cl and —F.

In another embodiment, R⁴ is —CH₃.

In yet another embodiment, alkyl of R¹ is substituted with one to four R²⁰ moieties which can be the same or different, each R²⁰ moiety being independently selected from the group of R²⁰ moieties.

In another embodiment, R²⁰ is aryl.

In another embodiment, Z is selected from the group consisting of a covalent bond, —N(R⁴)—, —(C(R⁴)₂)ₙ—, —C(O)— and —O—.

In yet another embodiment, Z is —O—.

In still another embodiment, Z is a covalent bond.

In yet still another embodiment, Z is —N(R⁴)—.

In a further embodiment, Z is —C(O)—.

In another embodiment, R⁴ is alkyl.

In another embodiment, R² is selected from the group consisting of —OR⁴, H, alkyl, fluoroalkyl, alkylaryl, halogen, and heteroaryl.

In another embodiment wherein R² is —OR⁴, R⁴ is —CH₂C≡CCH₃.

In another embodiment wherein R² is —OR⁴, R⁴ is —CH₂C≡CCH₂OH.

In another embodiment wherein R² is —OR⁴, R⁴ is

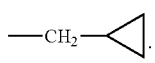

In yet another embodiment, R² is hydrogen.

In still another embodiment, R² is alkyl.

In yet still another embodiment, R² is alkylaryl.

In yet further embodiment, R² is fluoroalkyl.

In another embodiment, R² is —CH₂CF₃.

In yet another embodiment, R² is halogen.

In another embodiment, R² is heteroaryl.

In another embodiment, R⁴ is —CH₃.

Another embodiment of the invention discloses the following compounds shown in Table A below.

TABLE A

Structures

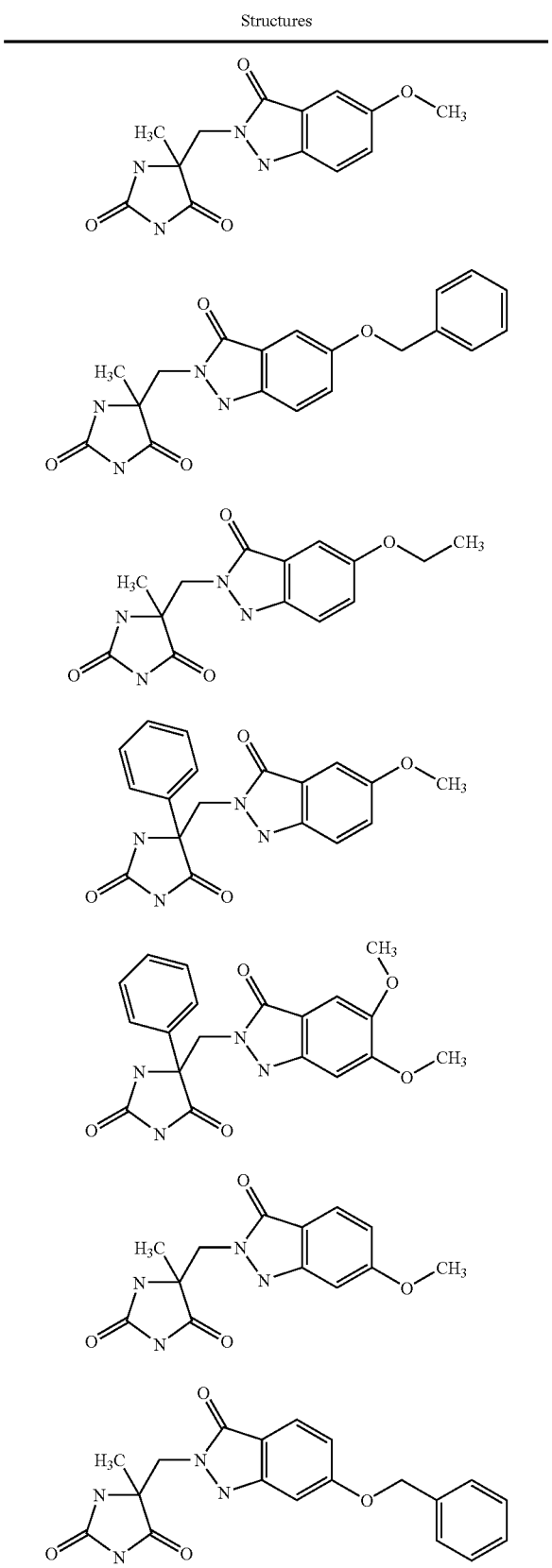

TABLE A-continued
Structures
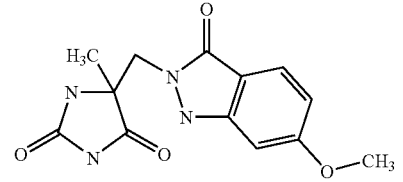
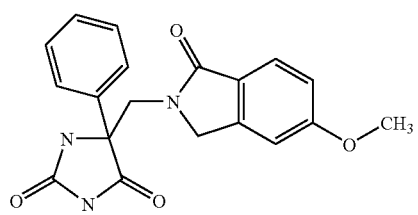
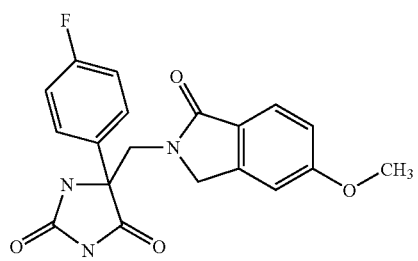
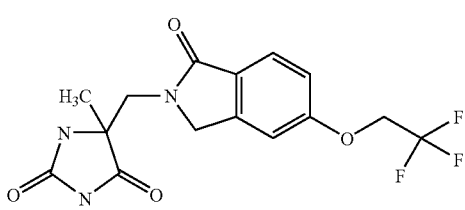
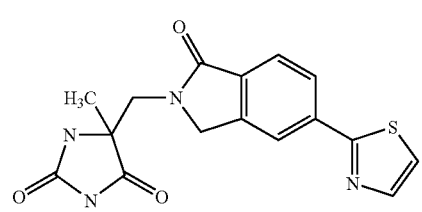
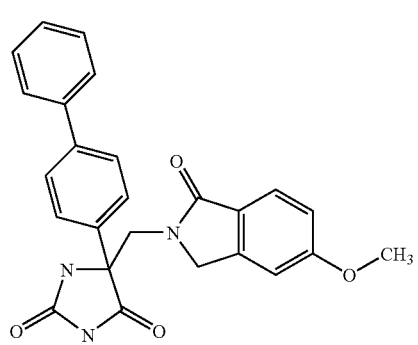
TABLE A-continued
Structures
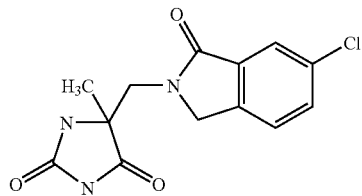
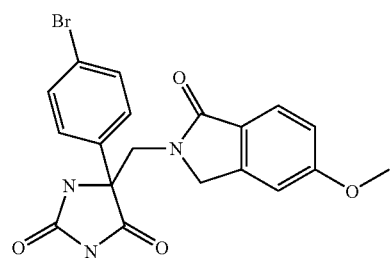
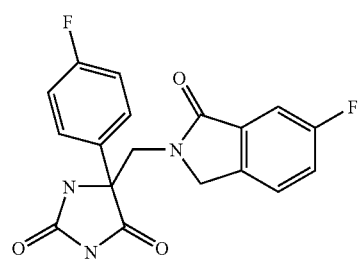
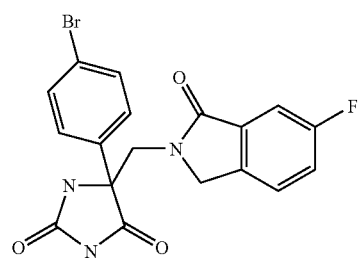
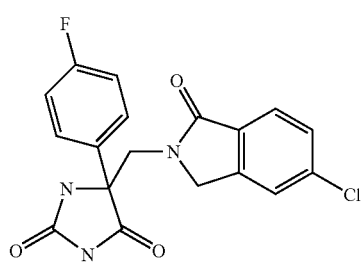
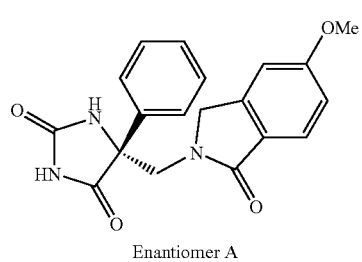
Enantiomer A TABLE A-continued
Structures
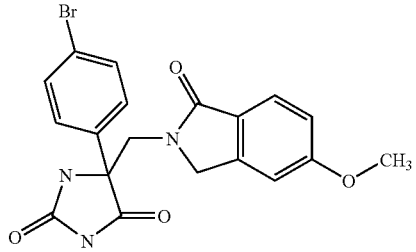

TABLE A-continued

Structures

TABLE A-continued
Structures
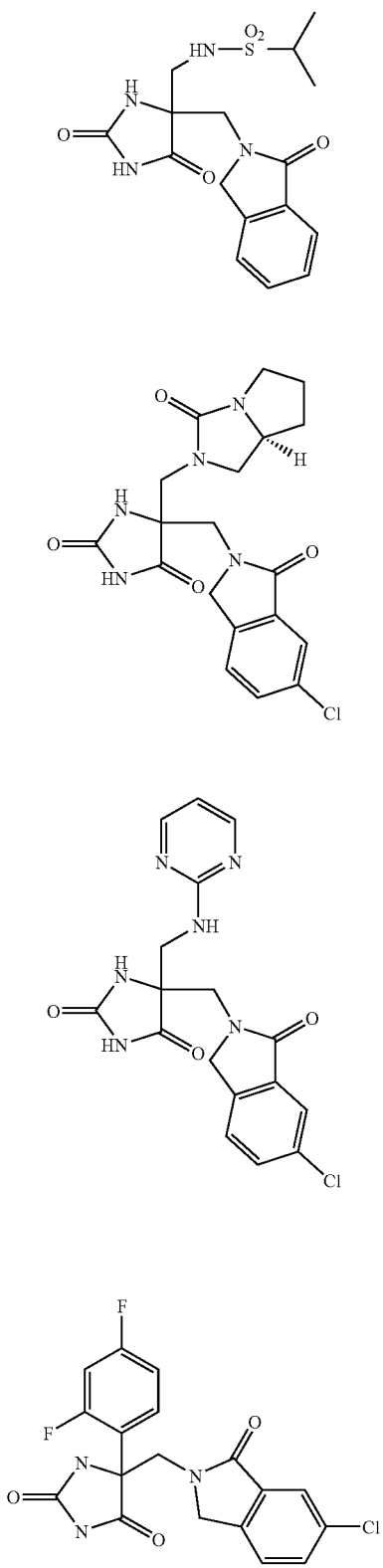
TABLE A-continued
Structures
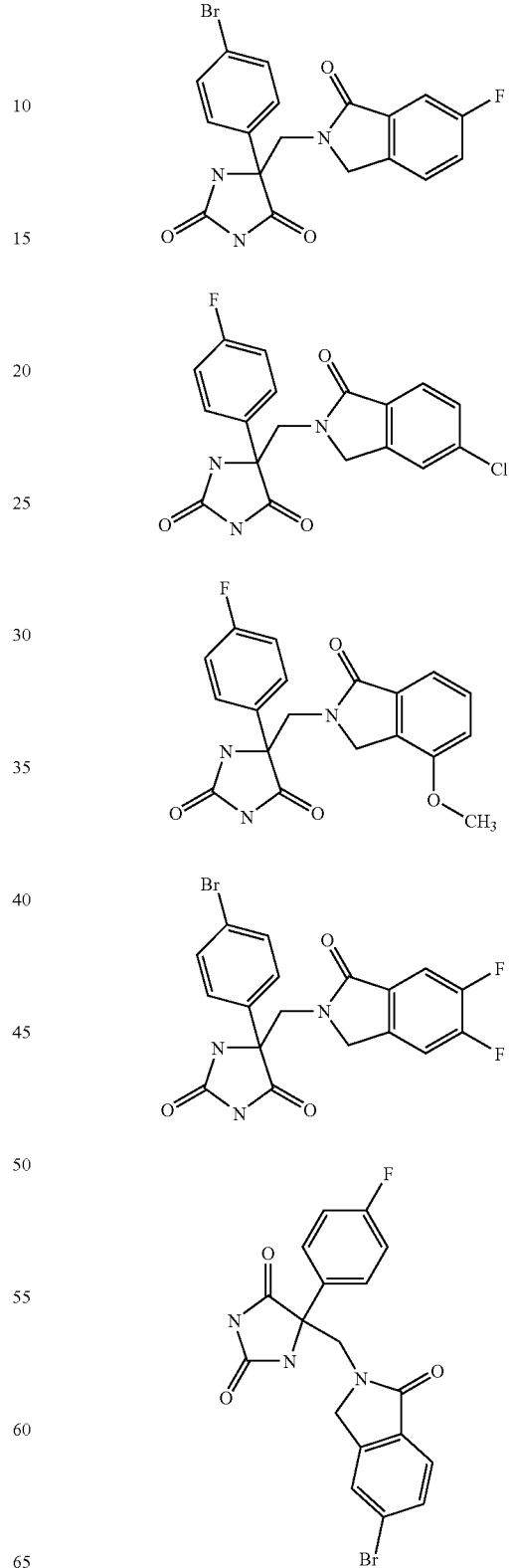

TABLE A-continued
Structures
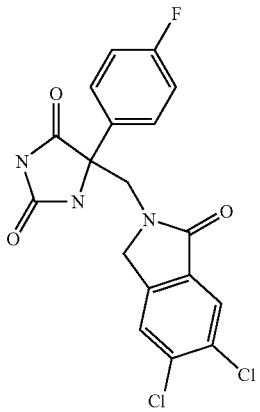
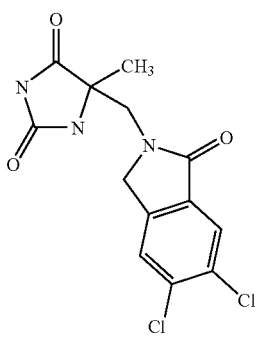
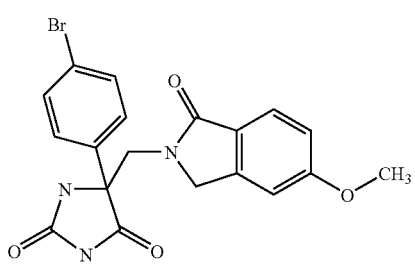
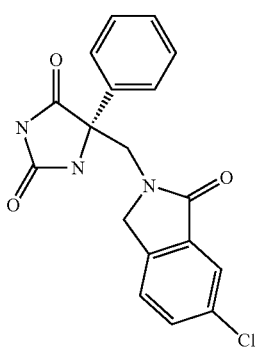
TABLE A-continued
Structures
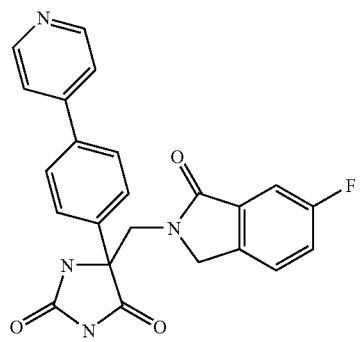
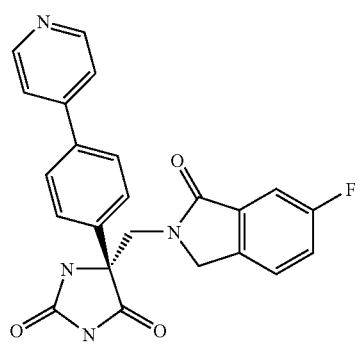
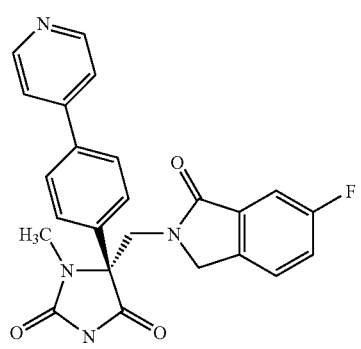
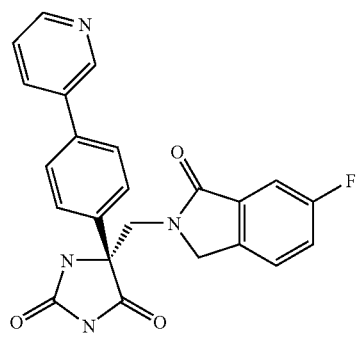

TABLE A-continued
Structures
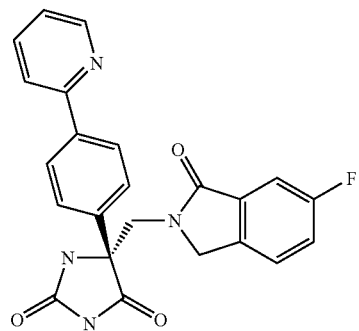
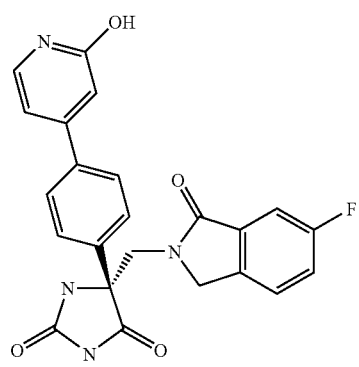
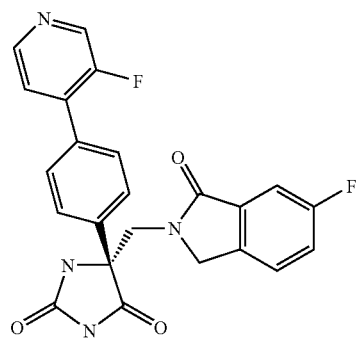
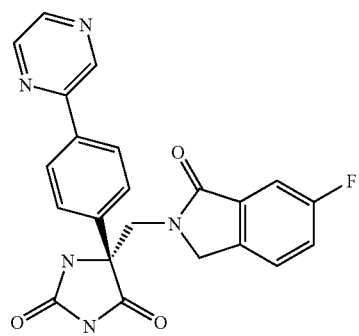
TABLE A-continued
Structures
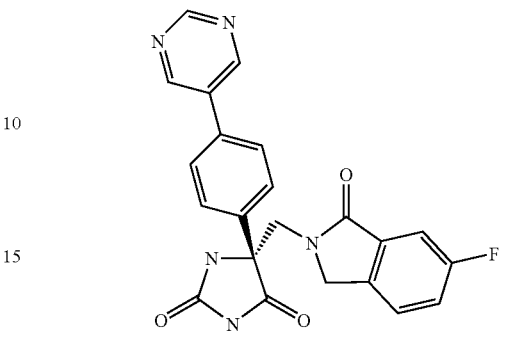
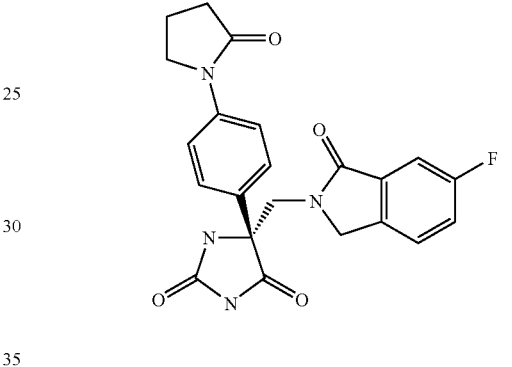
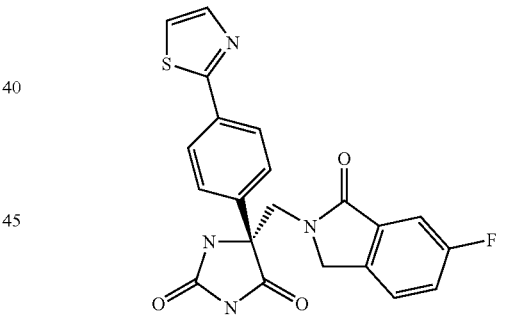
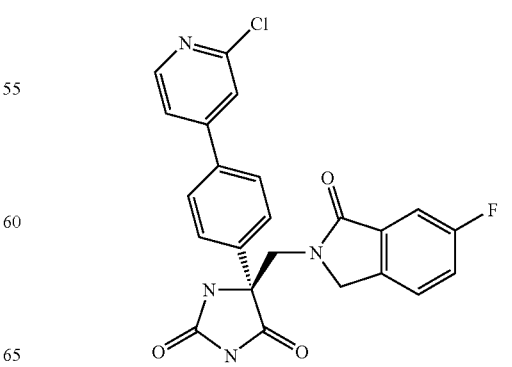

TABLE A-continued
Structures
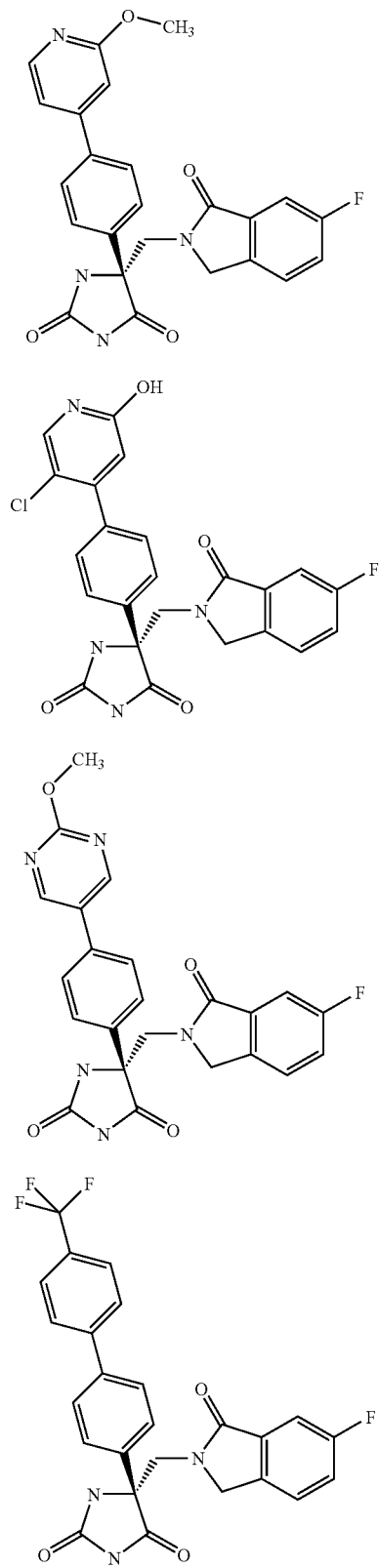
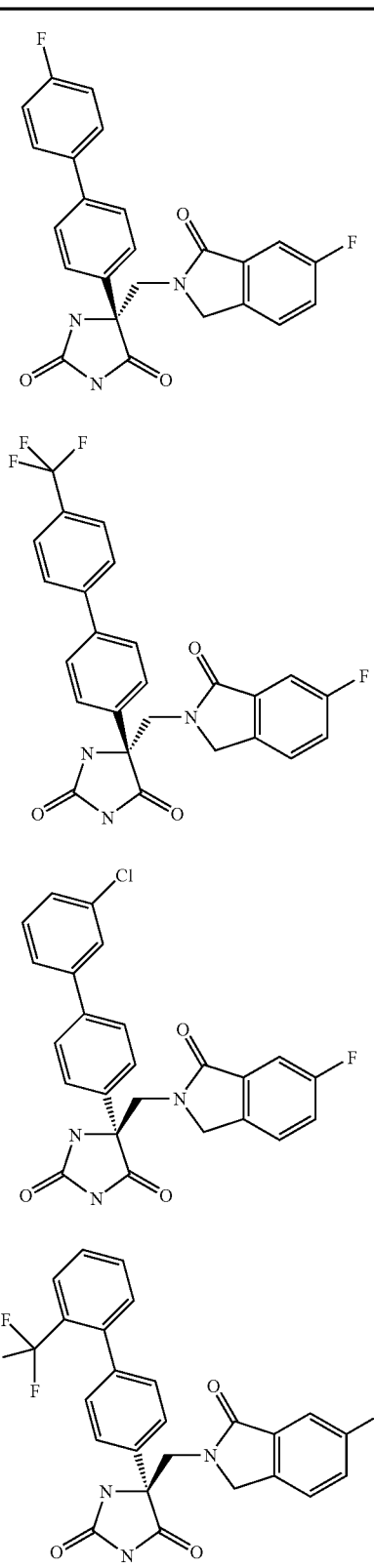

TABLE A-continued
Structures
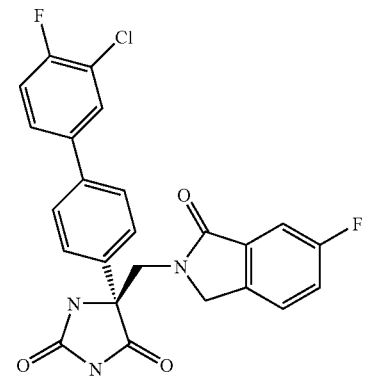
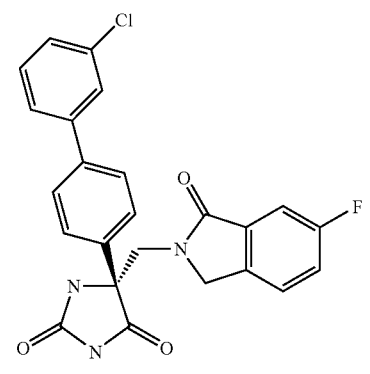
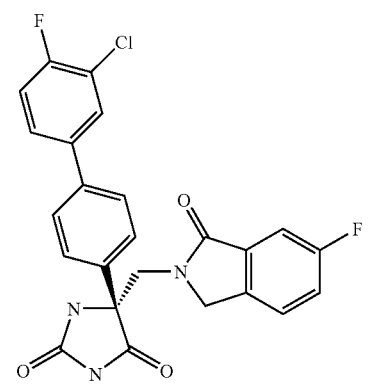
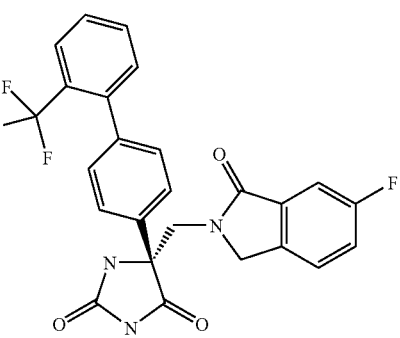
TABLE A-continued
Structures
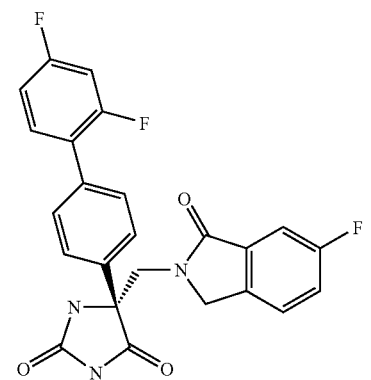
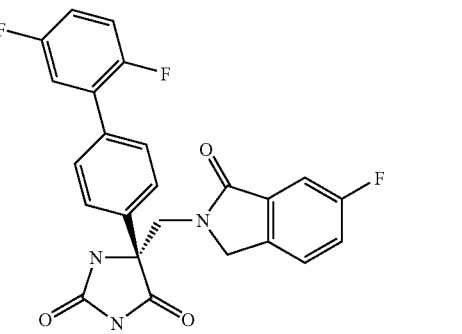
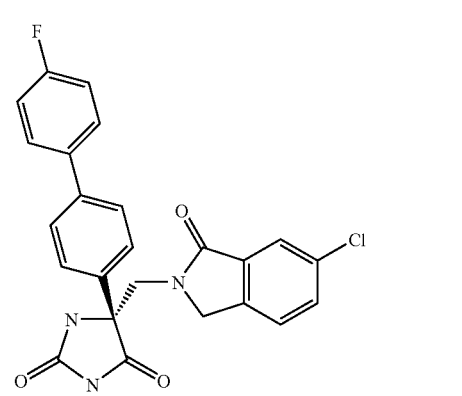
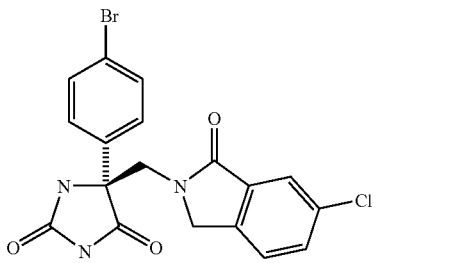

TABLE A-continued
Structures
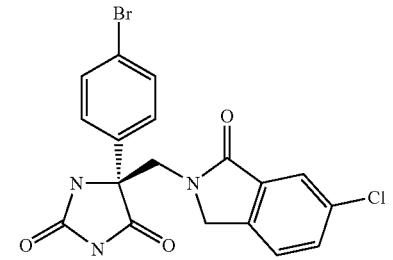
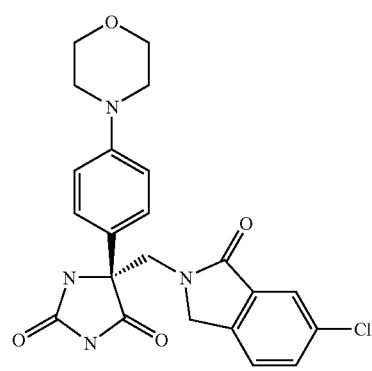
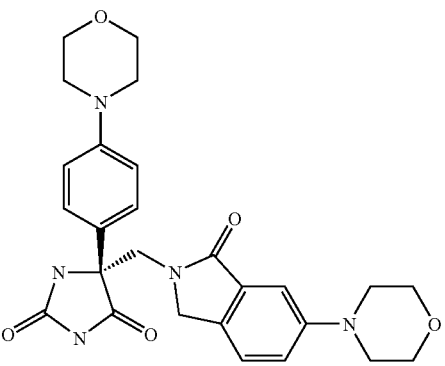
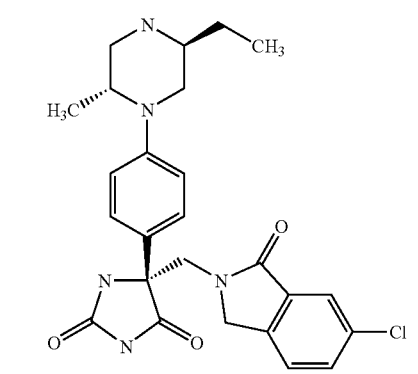
TABLE A-continued
Structures
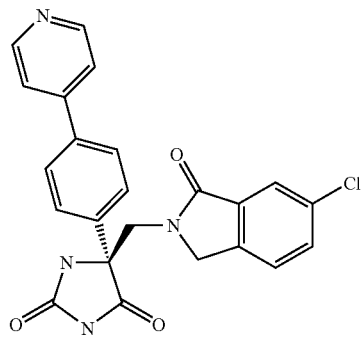
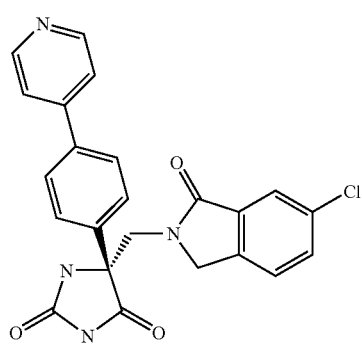
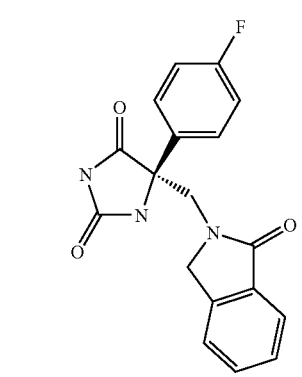
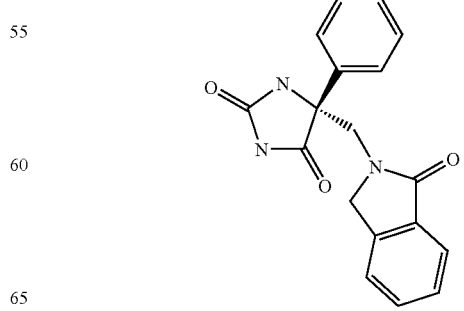

TABLE A-continued

Structures

TABLE A-continued
Structures
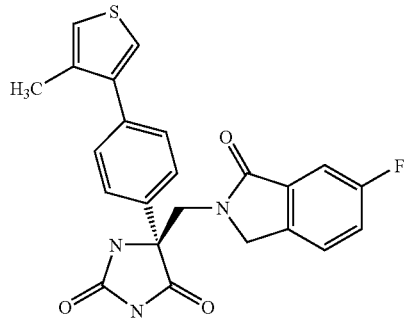
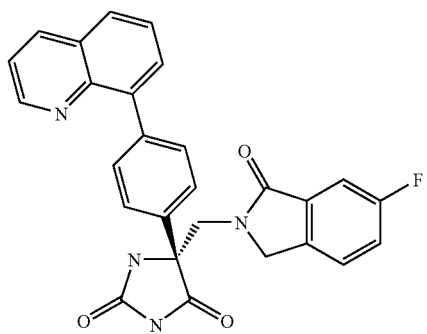
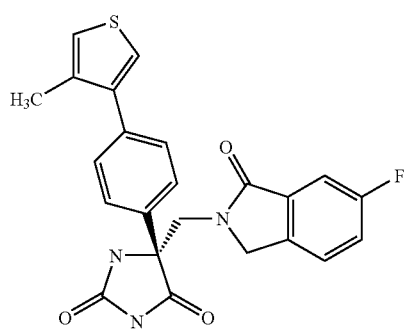
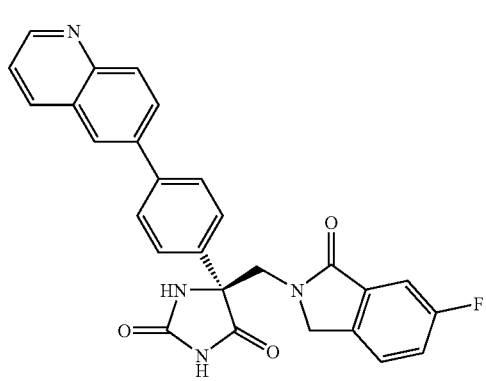
TABLE A-continued
Structures
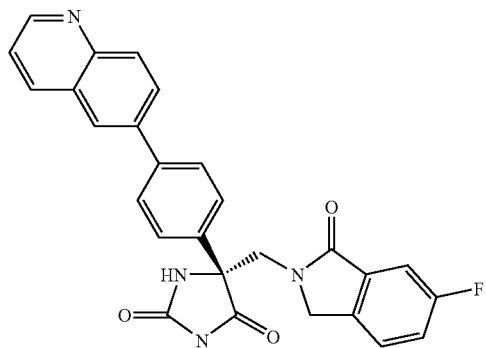
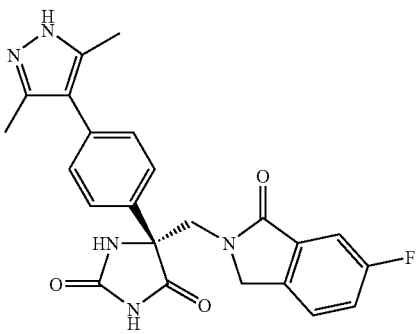
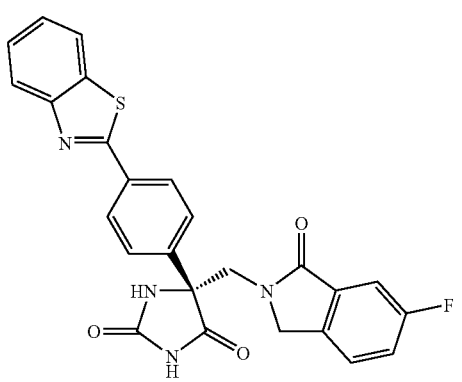
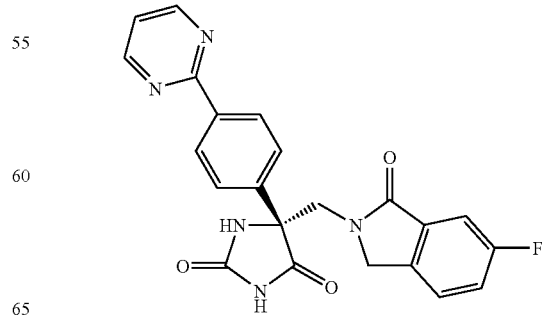

TABLE A-continued
Structures
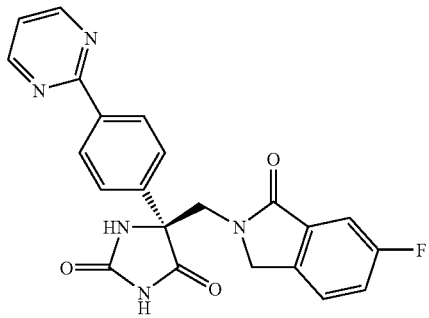
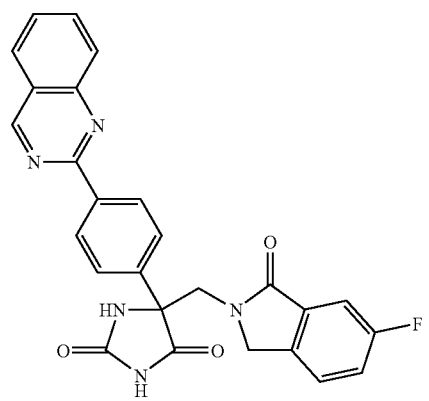
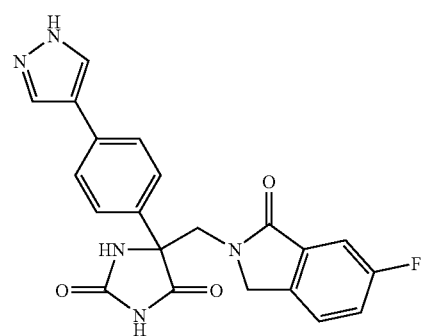
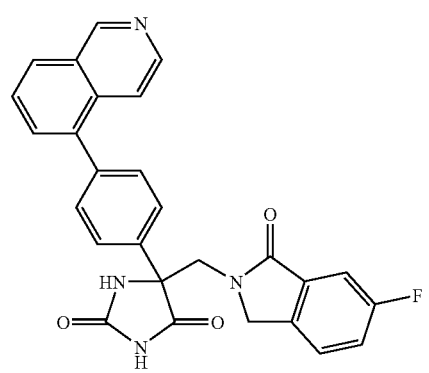
TABLE A-continued
Structures
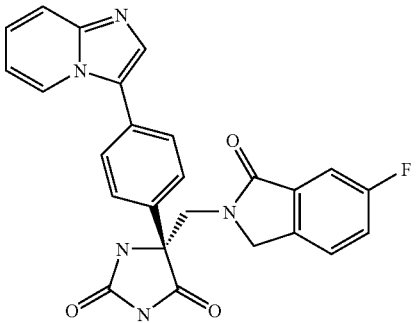
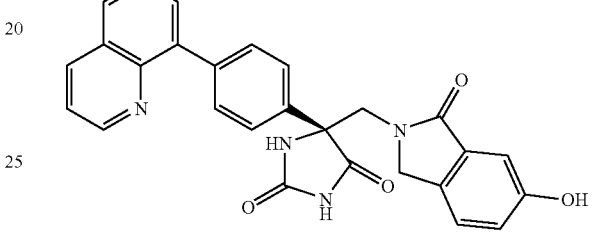
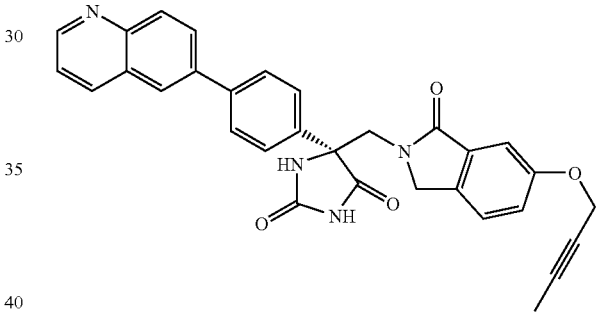
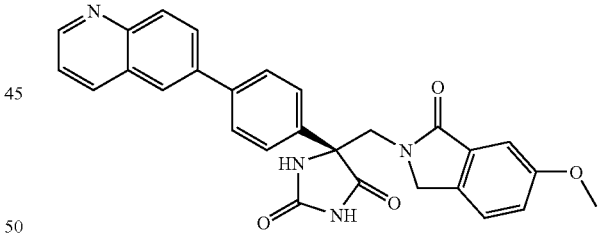
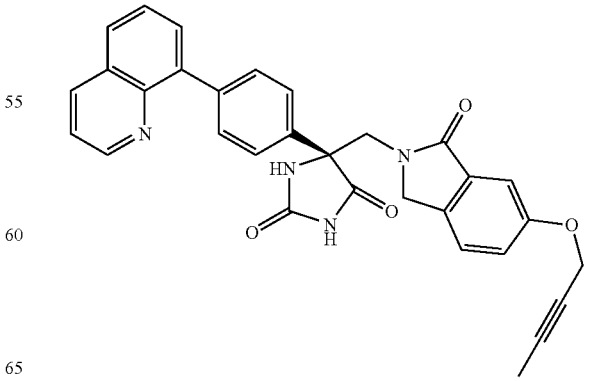

TABLE A-continued

Structures

TABLE A-continued
Structures
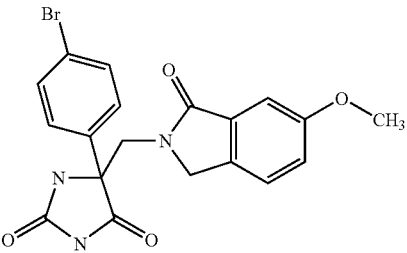

TABLE A-continued
Structures
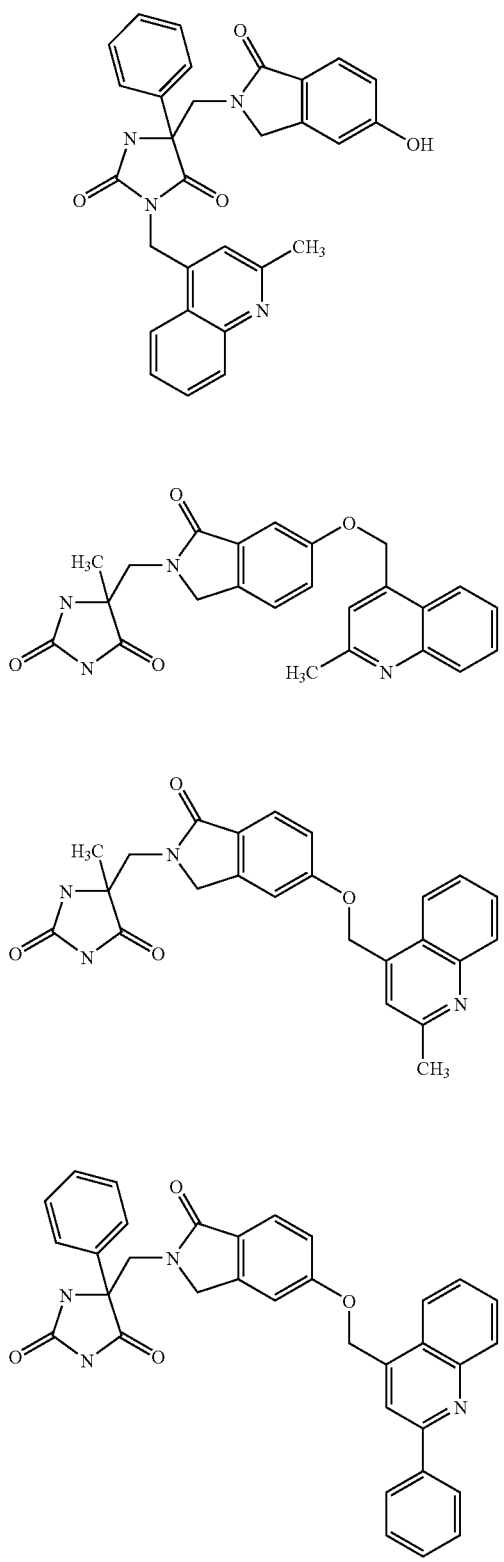
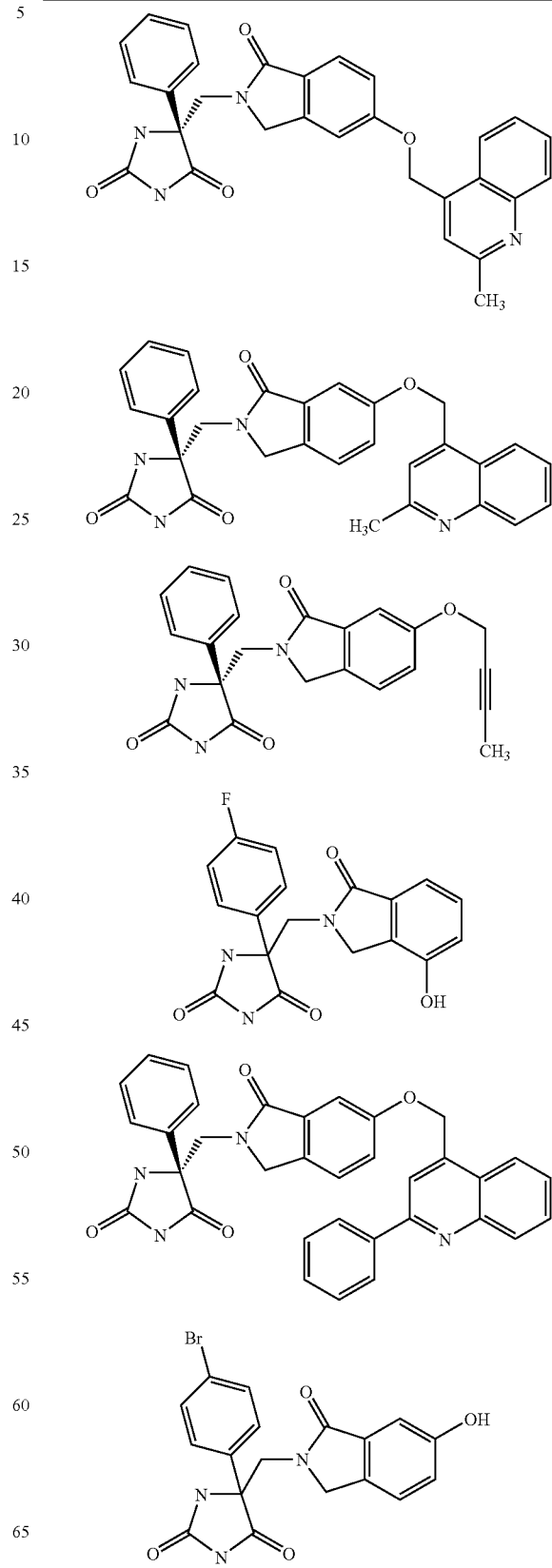

TABLE A-continued
Structures
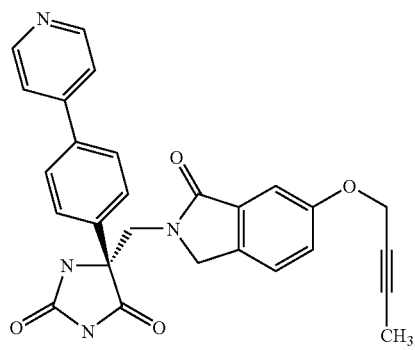
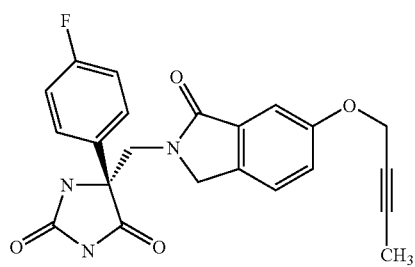
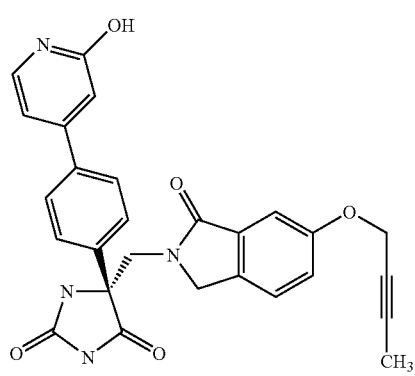
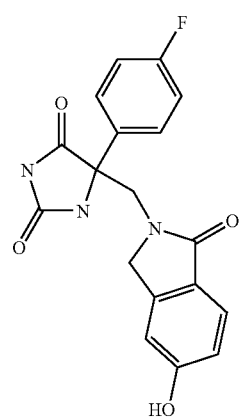
TABLE A-continued
Structures
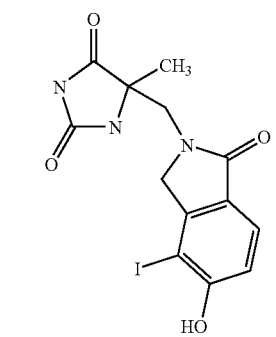
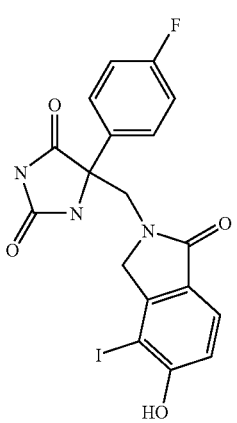
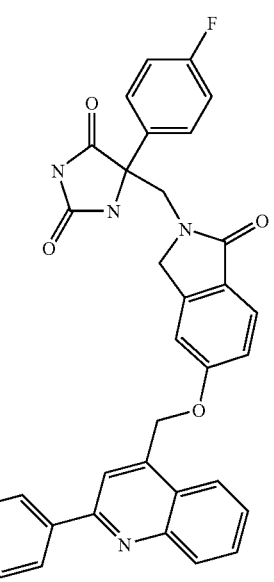

TABLE A-continued
Structures
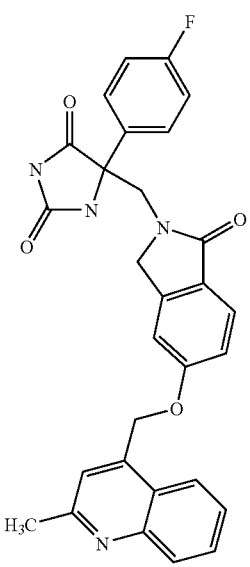
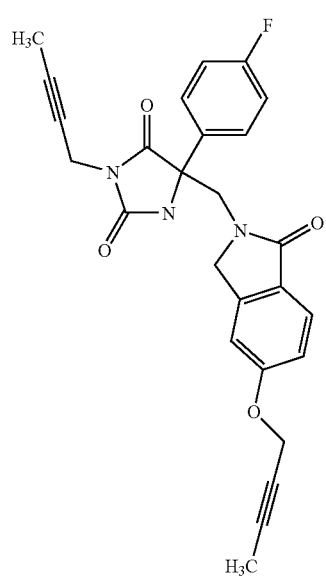
TABLE A-continued
Structures
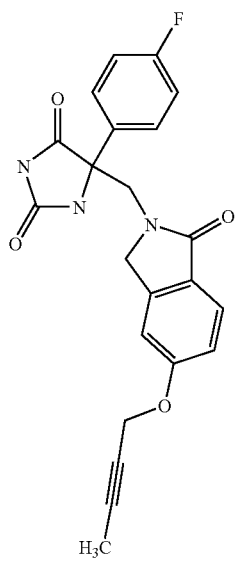
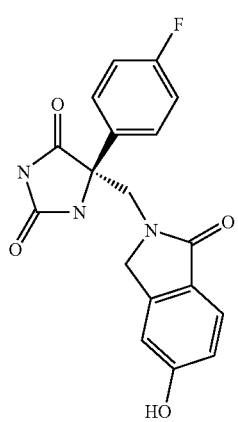
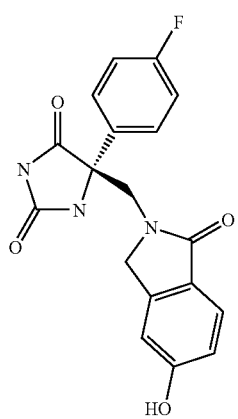

TABLE A-continued
Structures
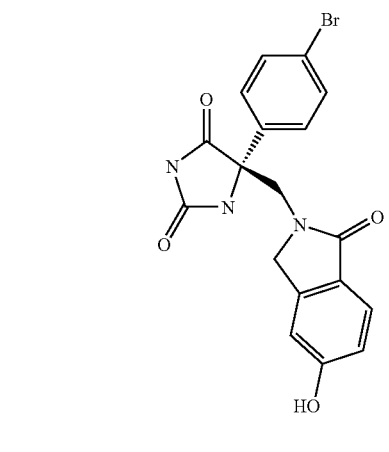
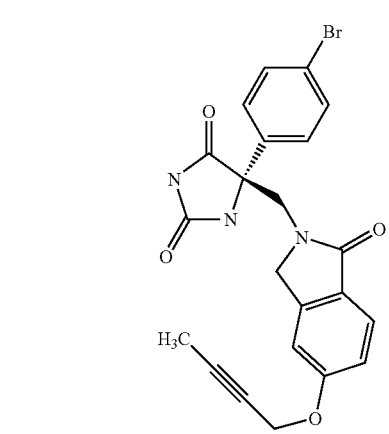
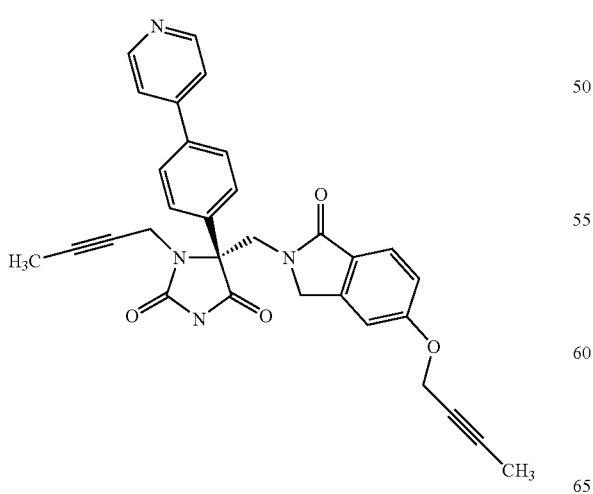
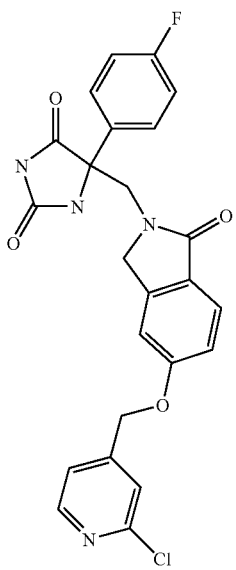
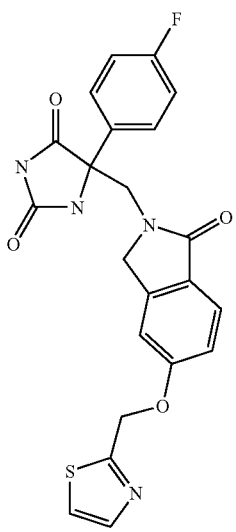
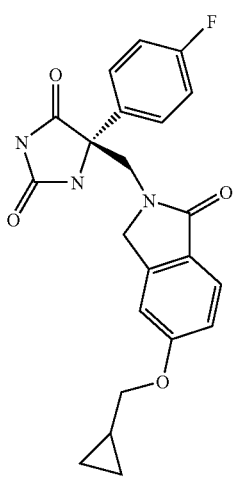

TABLE A-continued
Structures
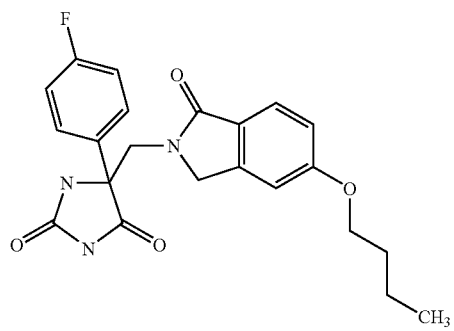
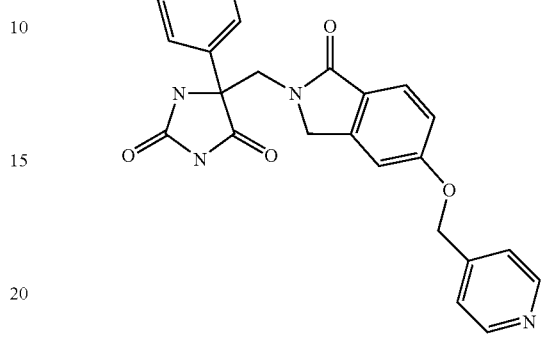
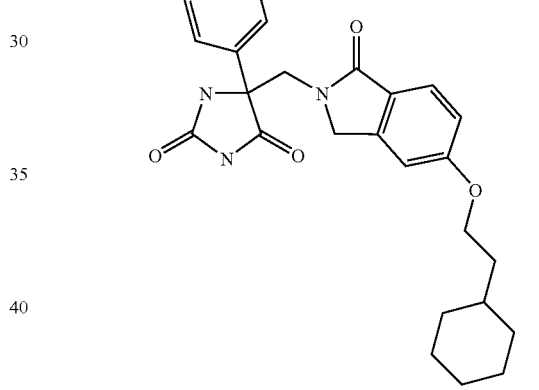
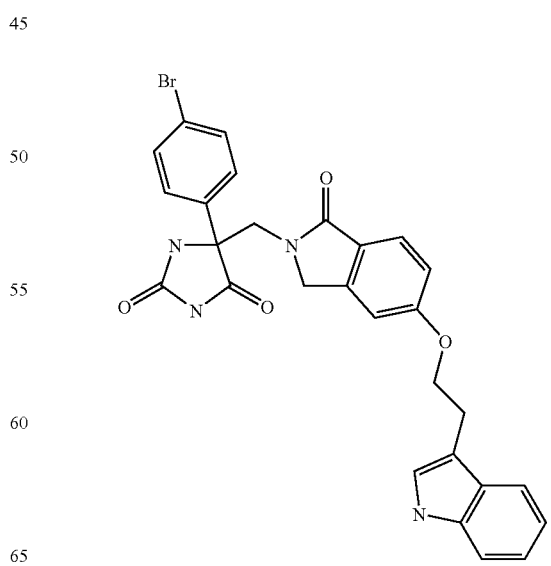

TABLE A-continued
Structures
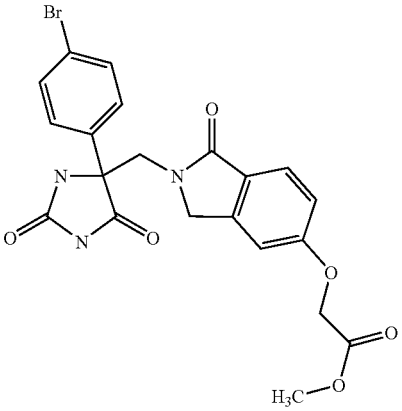
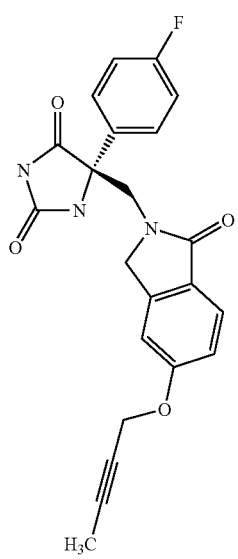
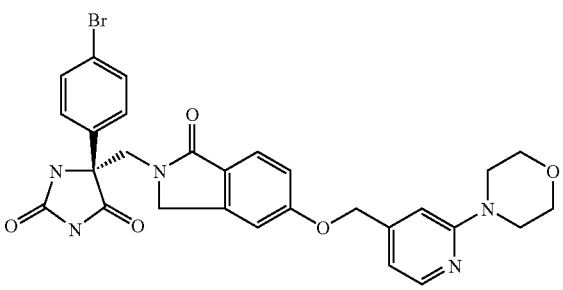
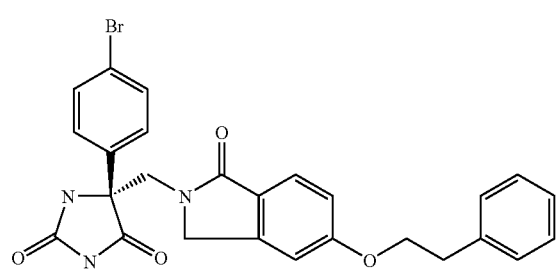
TABLE A-continued
Structures
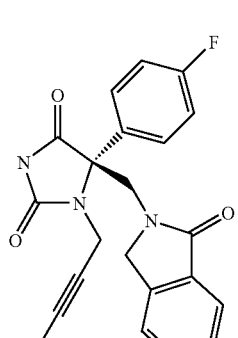
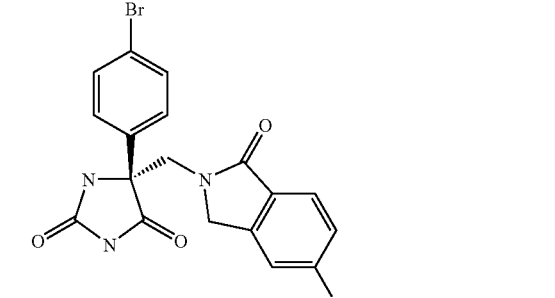

TABLE A-continued
Structures
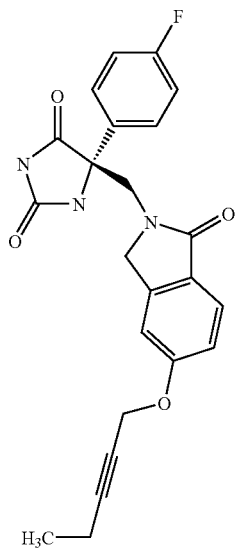
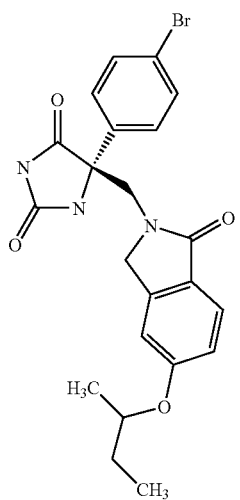
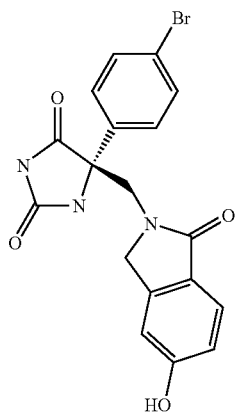
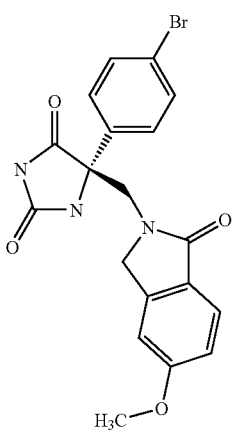
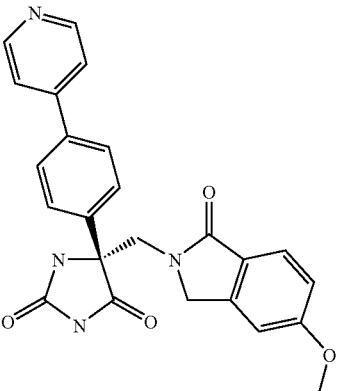
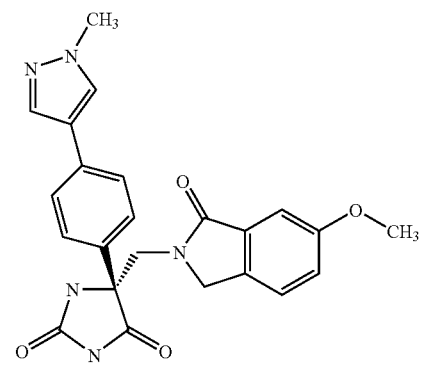

TABLE A-continued
Structures
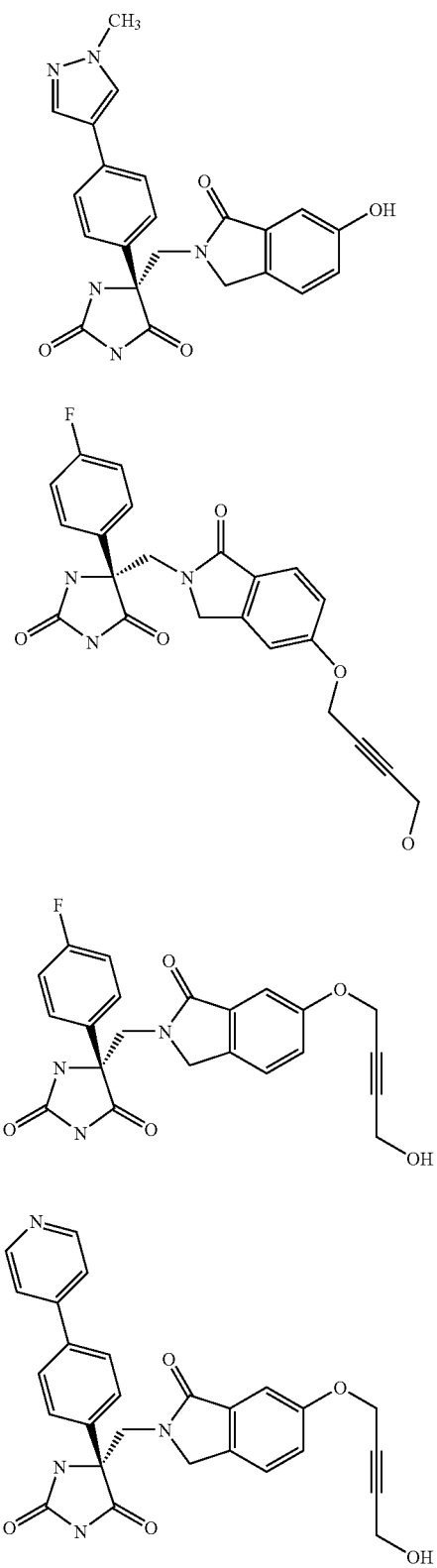
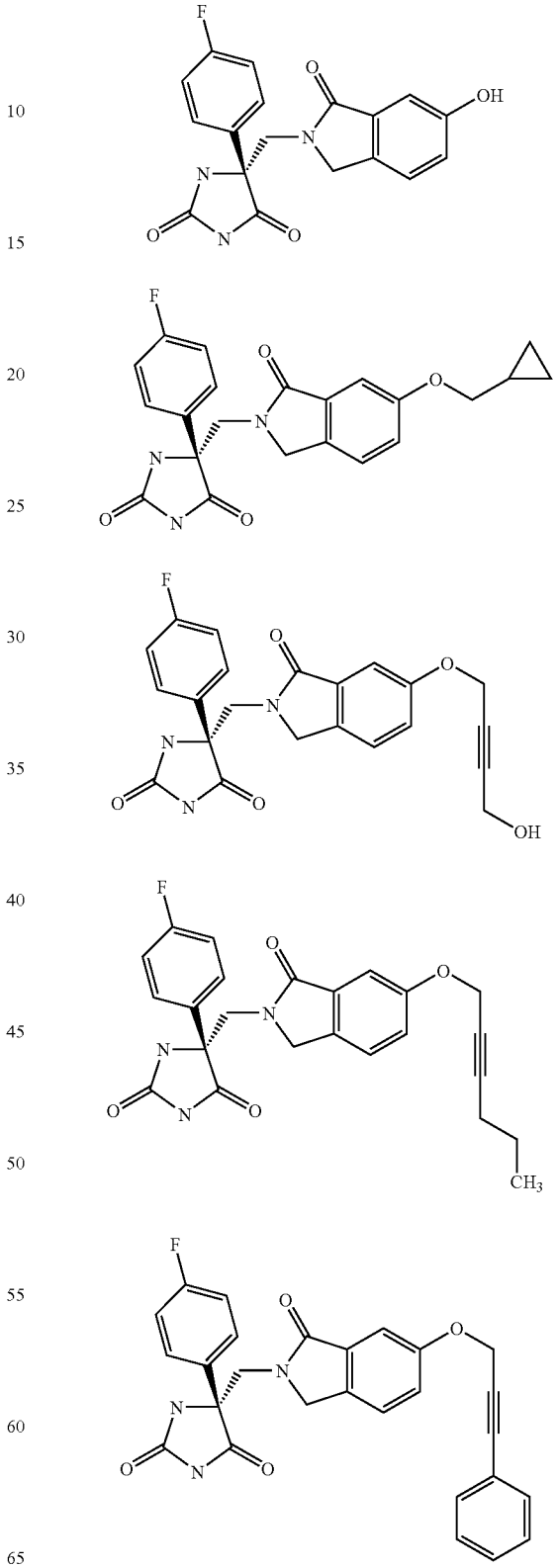

TABLE A-continued
Structures
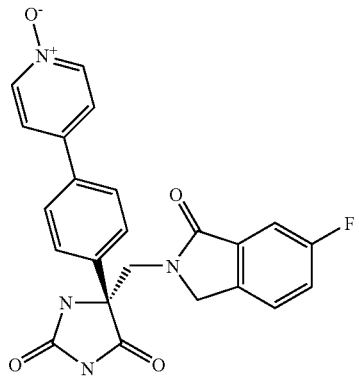
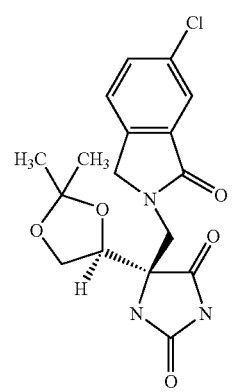
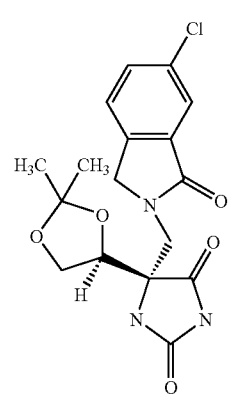
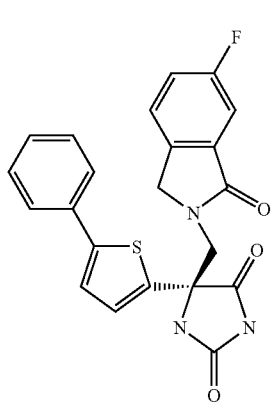
TABLE A-continued
Structures
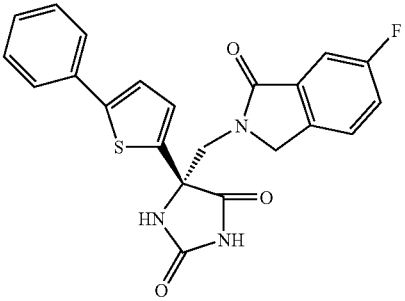
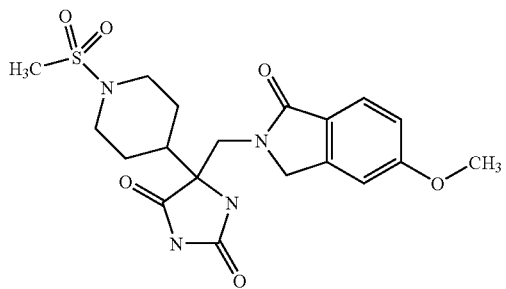
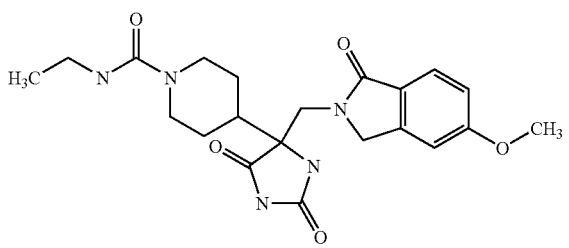
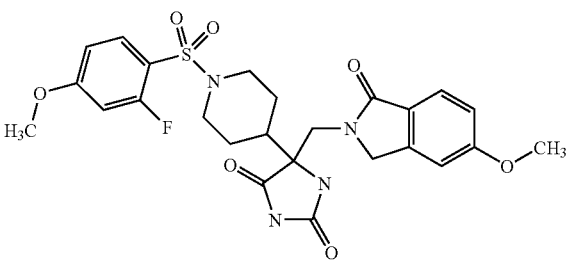
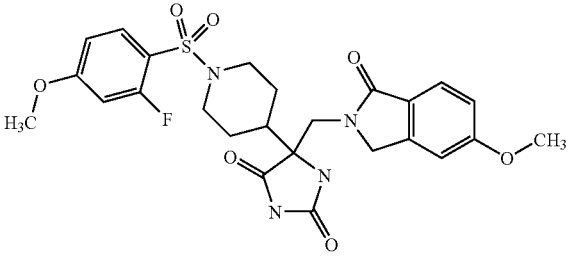

TABLE A-continued
Structures
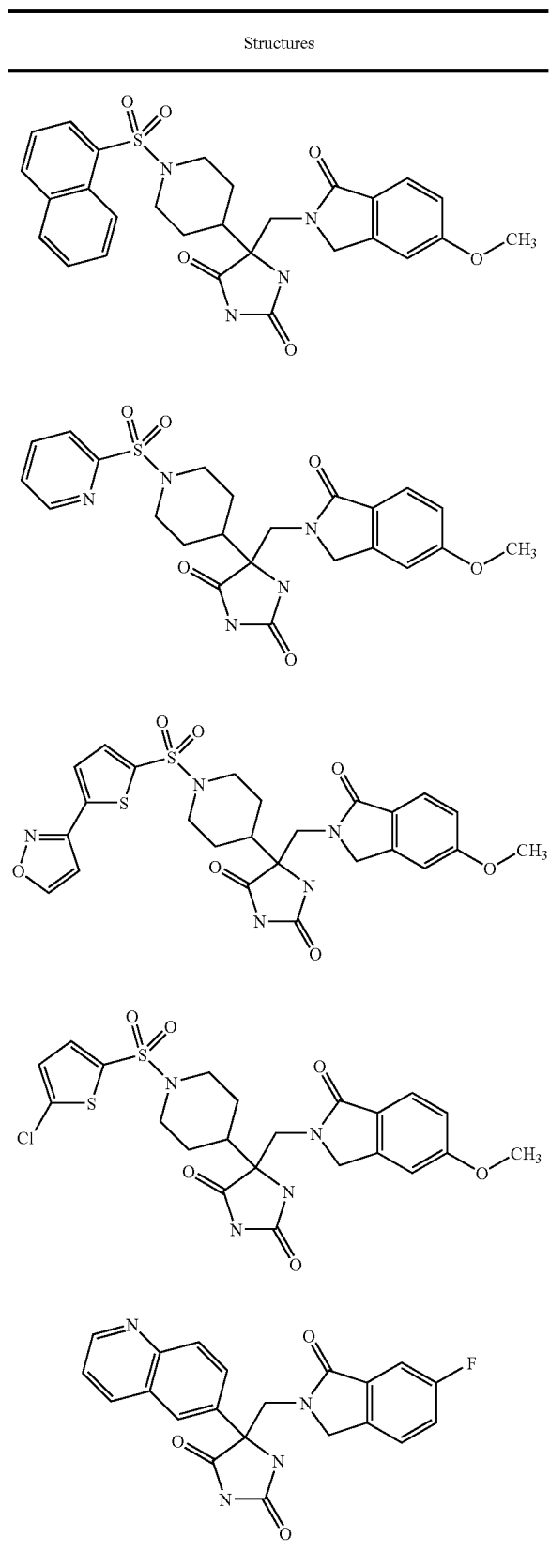
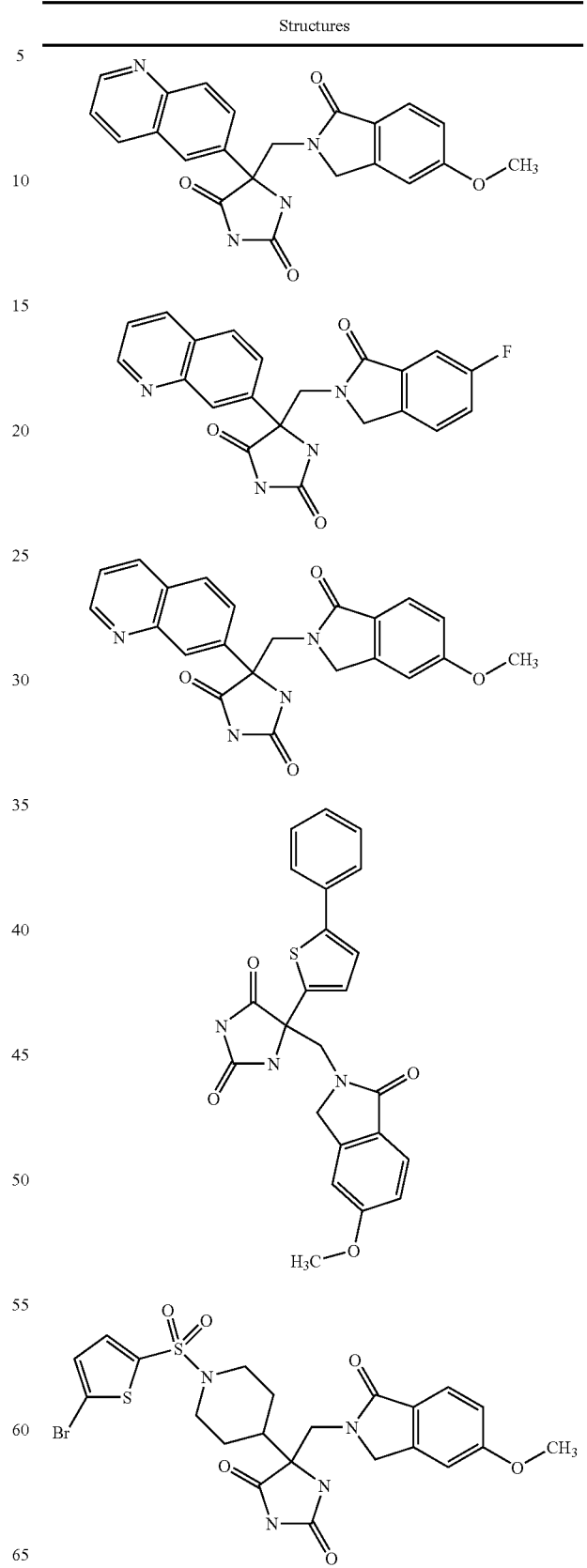

TABLE A-continued
Structures
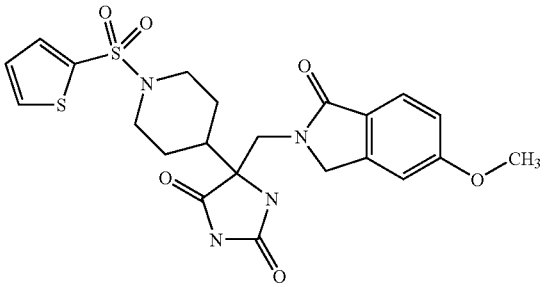
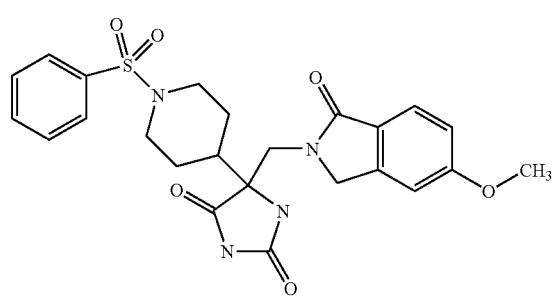
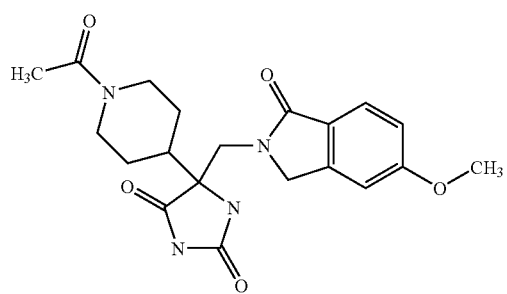
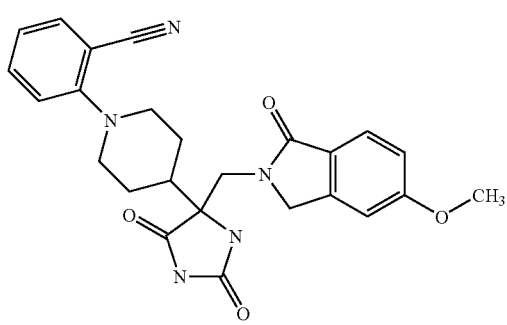
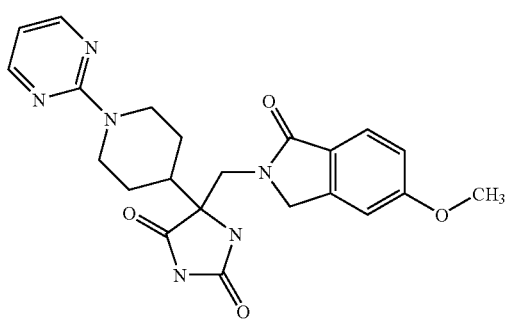
TABLE A-continued
Structures
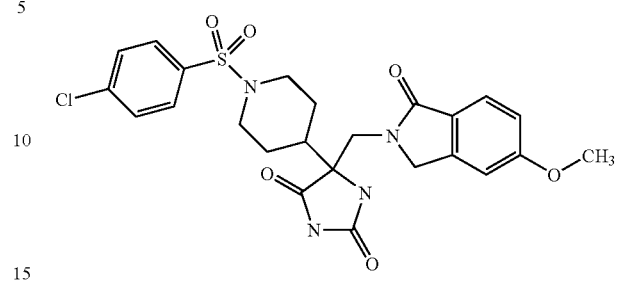
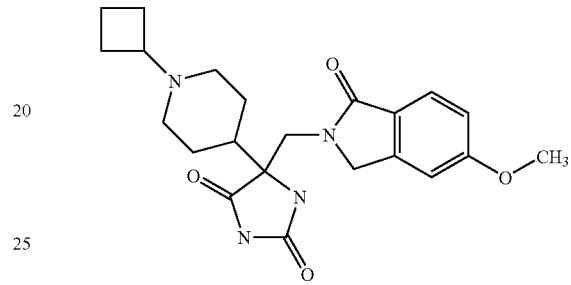
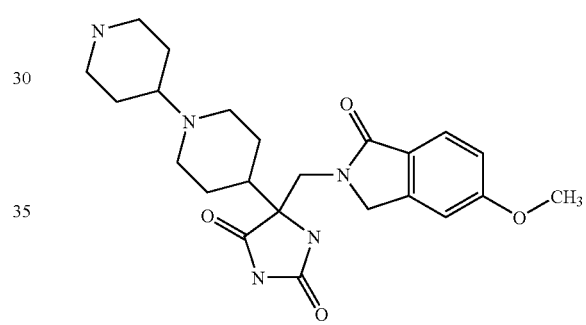
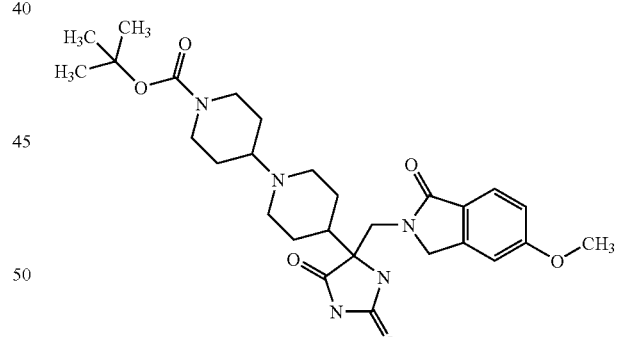
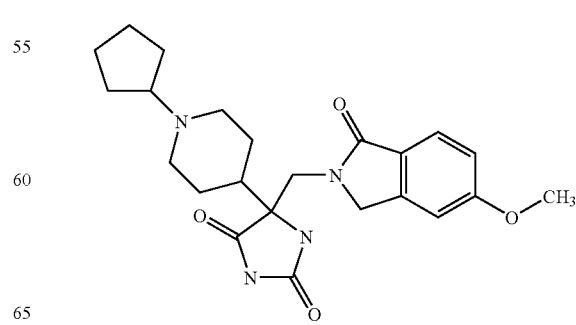

TABLE A-continued
Structures
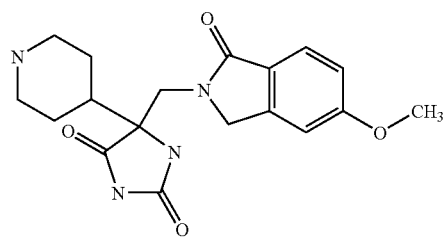
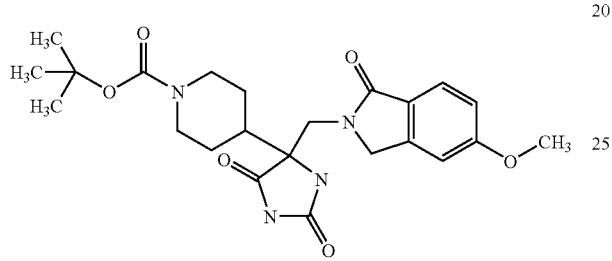
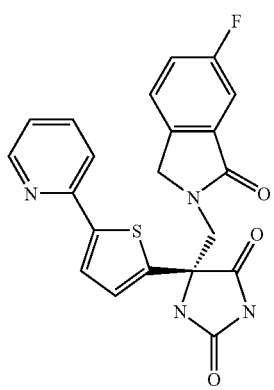
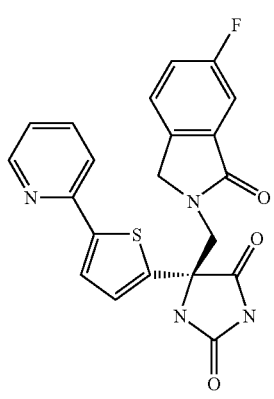
TABLE A-continued
Structures
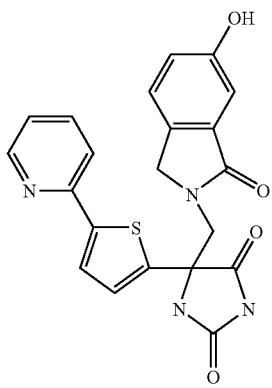
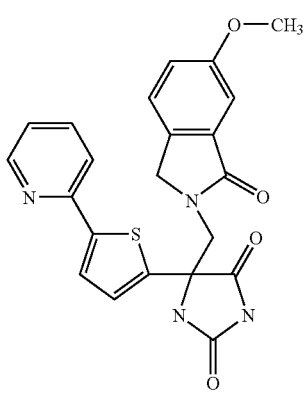
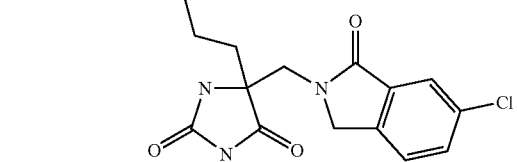
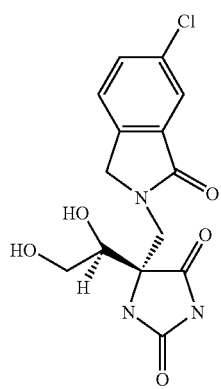

TABLE A-continued
Structures
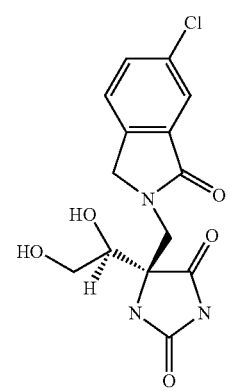
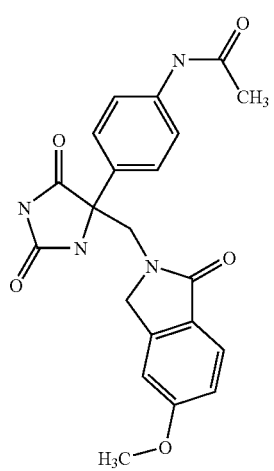
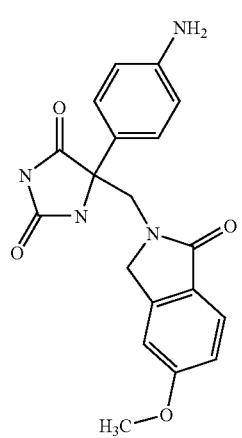
TABLE A-continued
Structures
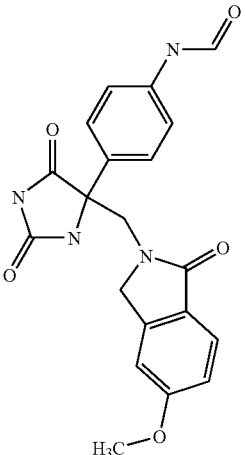
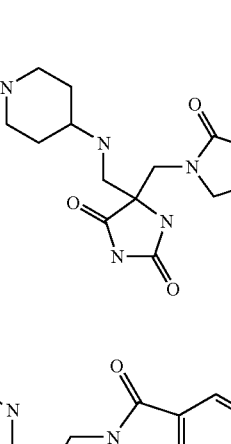
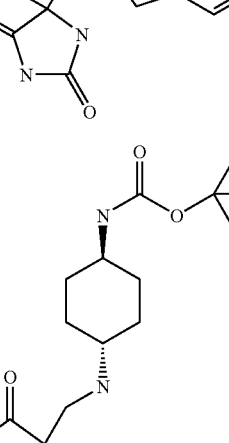
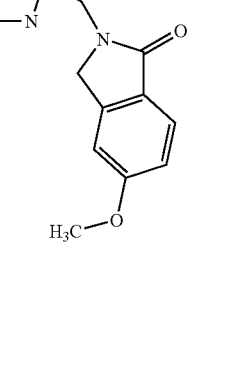

TABLE A-continued
Structures
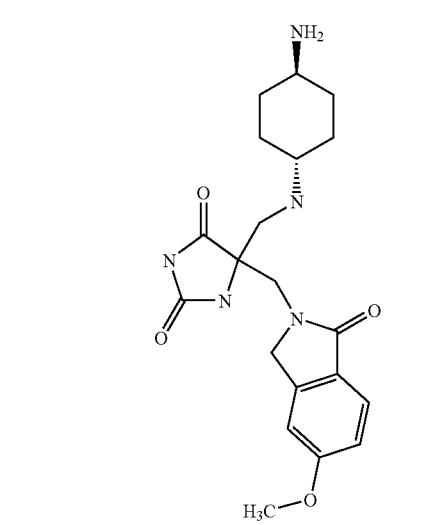
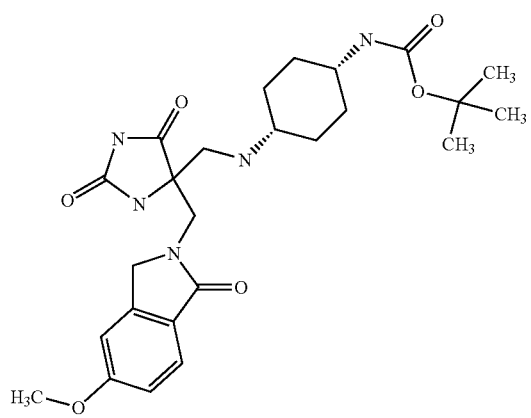
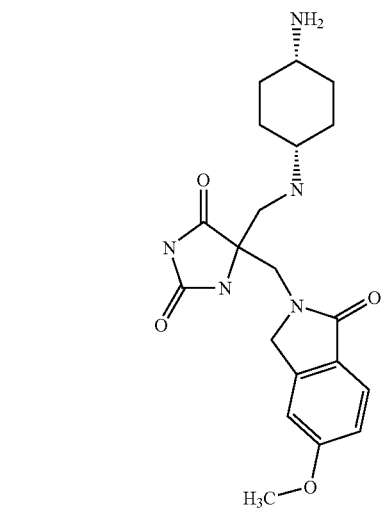
TABLE A-continued
Structures
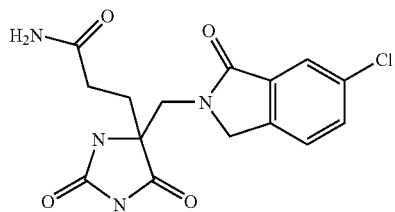
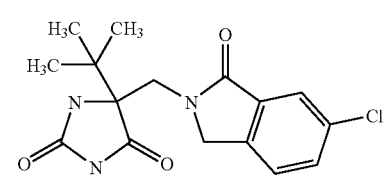
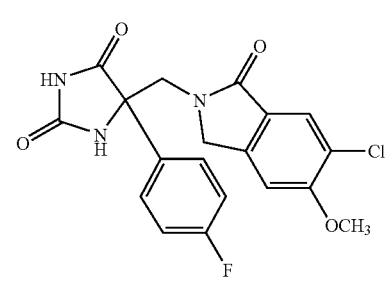
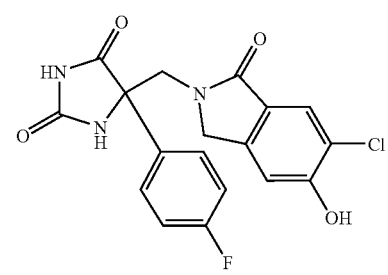
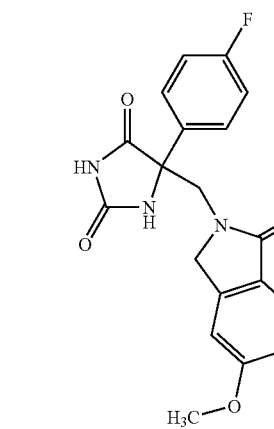

TABLE A-continued
Structures
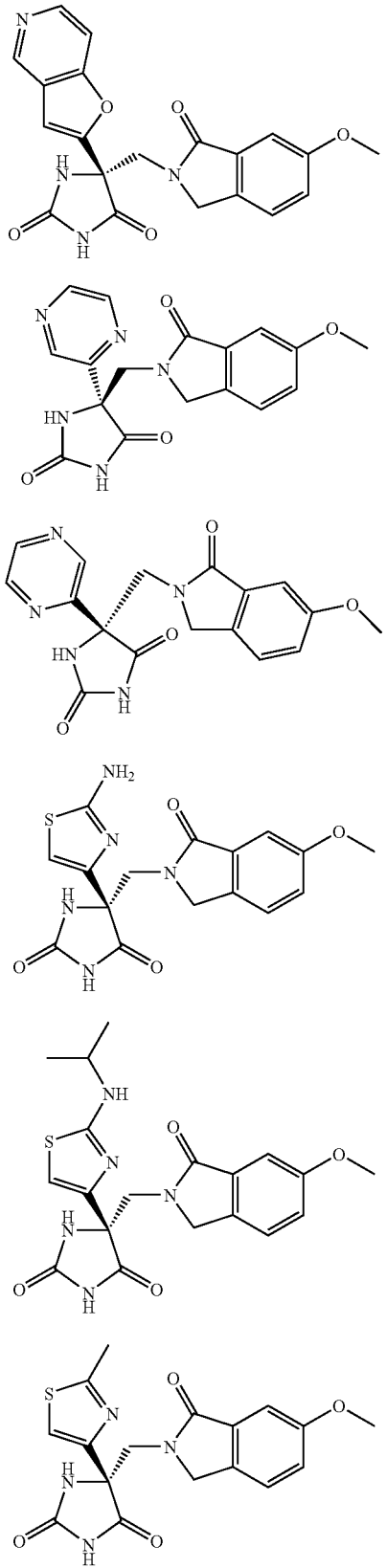
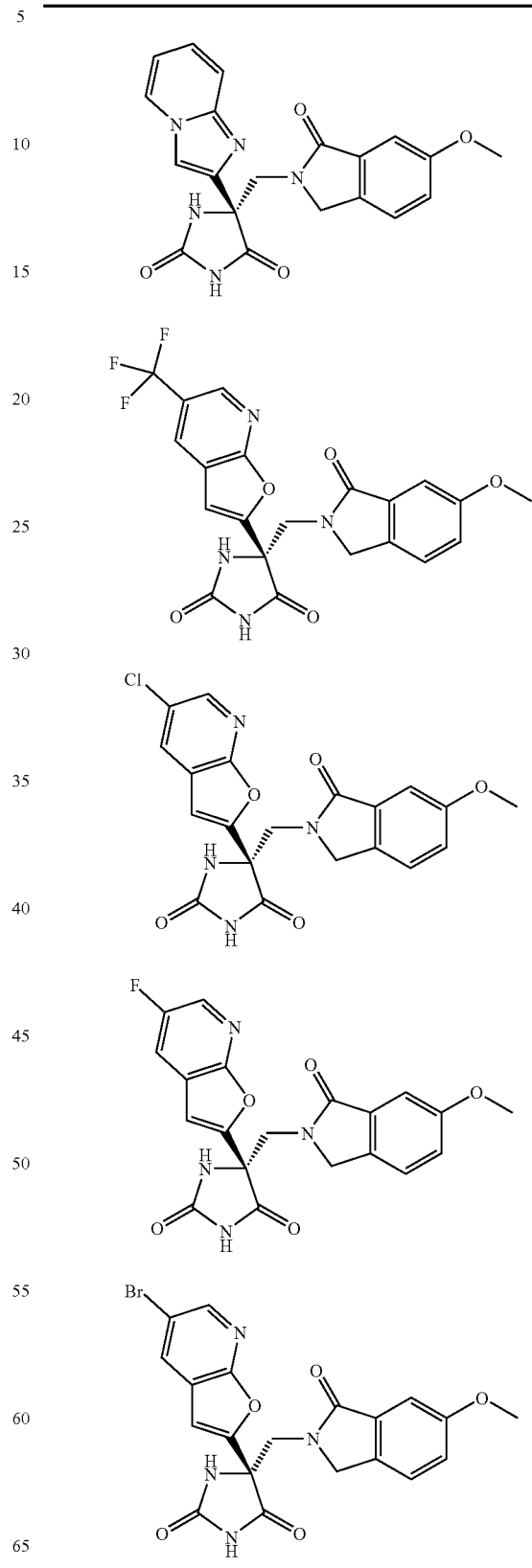

TABLE A-continued
Structures
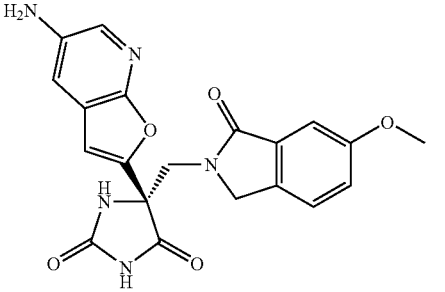
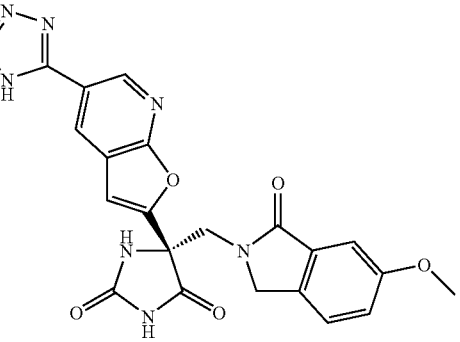
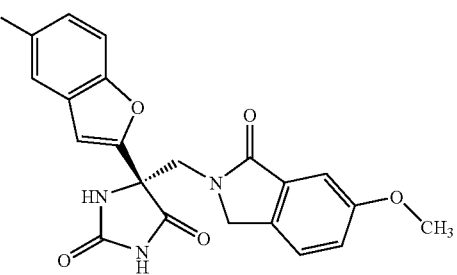
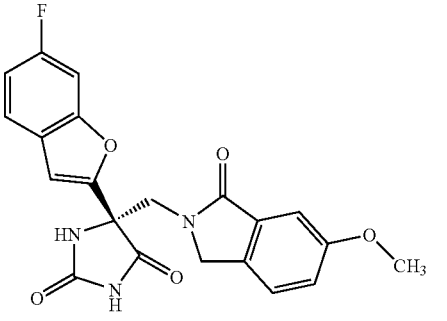
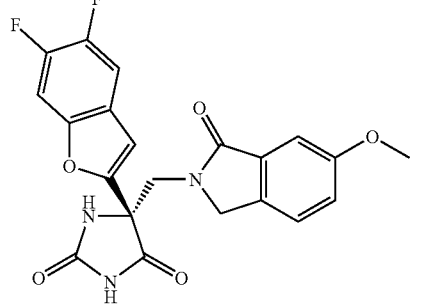
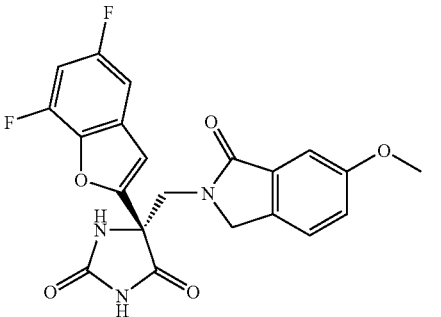
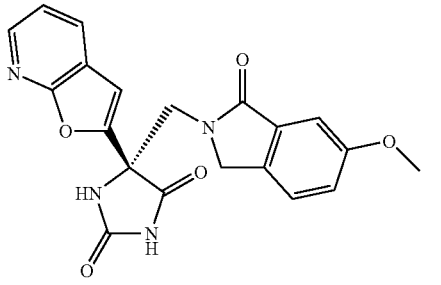
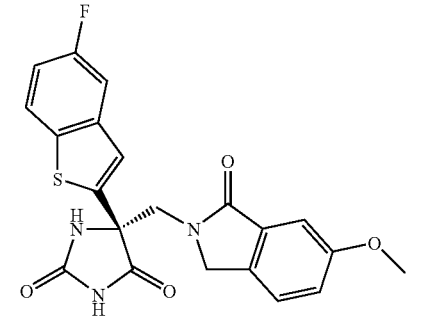

TABLE A-continued
Structures
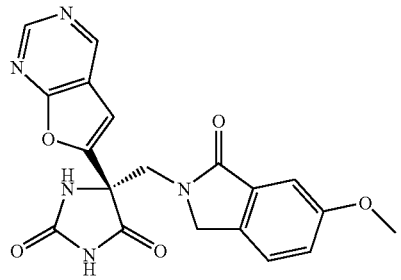
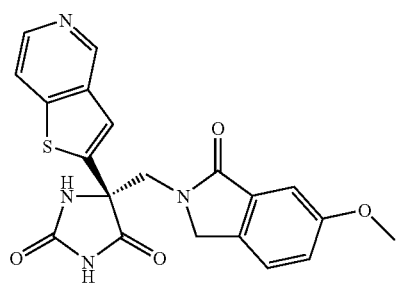
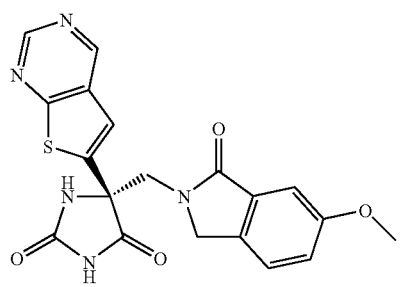
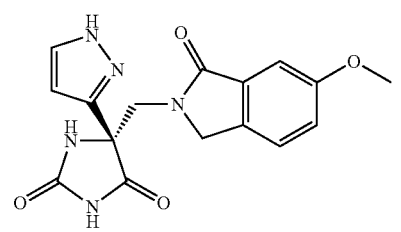
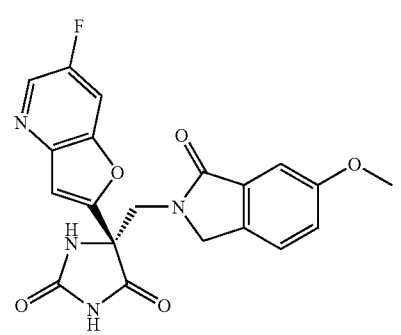
TABLE A-continued
Structures
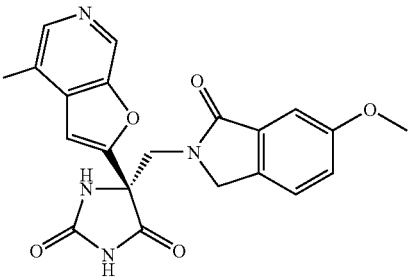
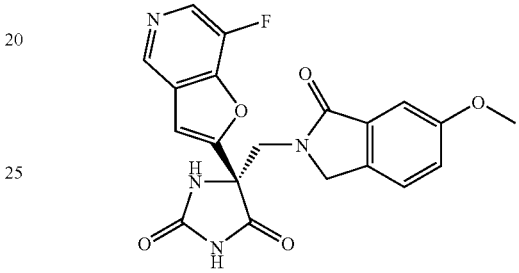
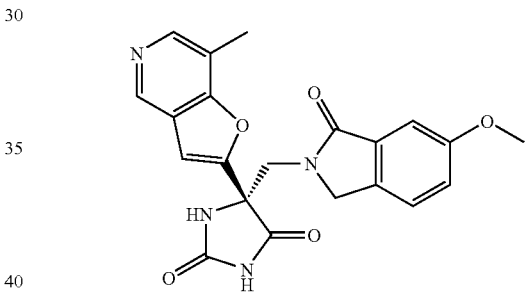
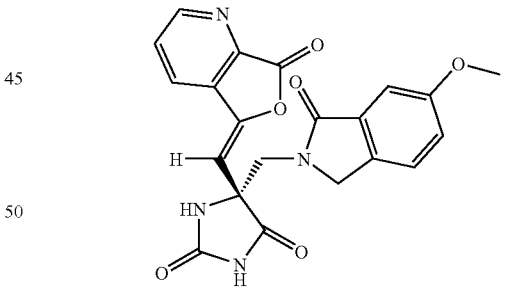
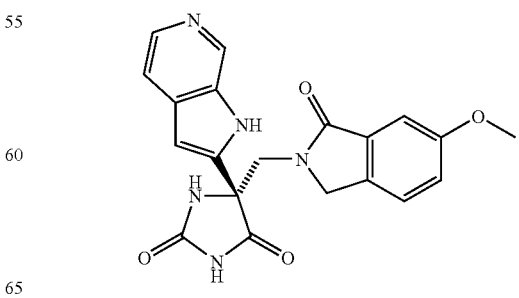

TABLE A-continued
Structures
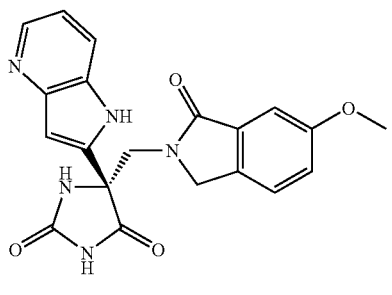
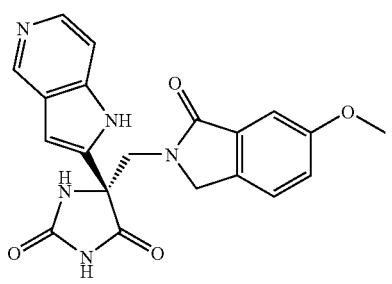
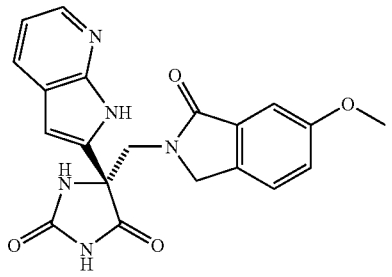
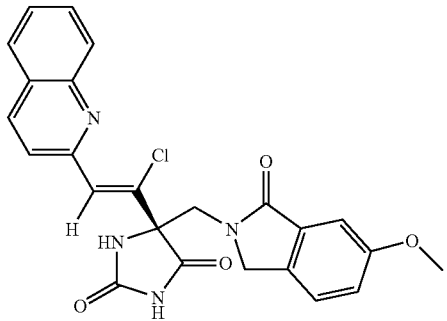
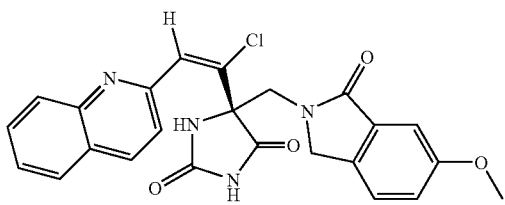
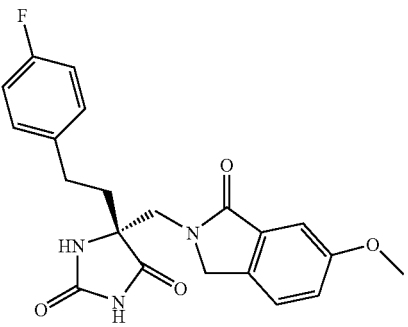
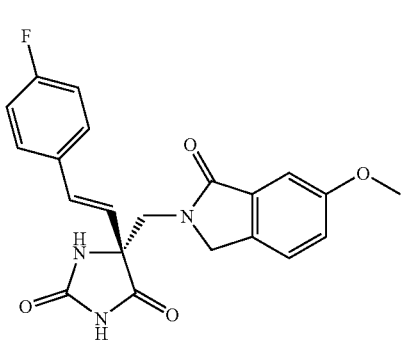
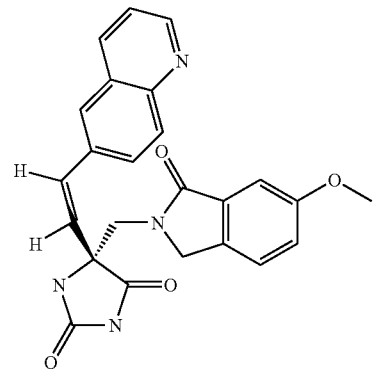
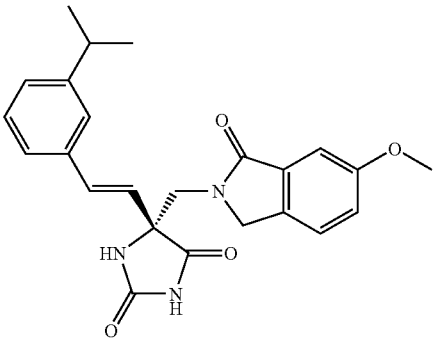

TABLE A-continued
Structures
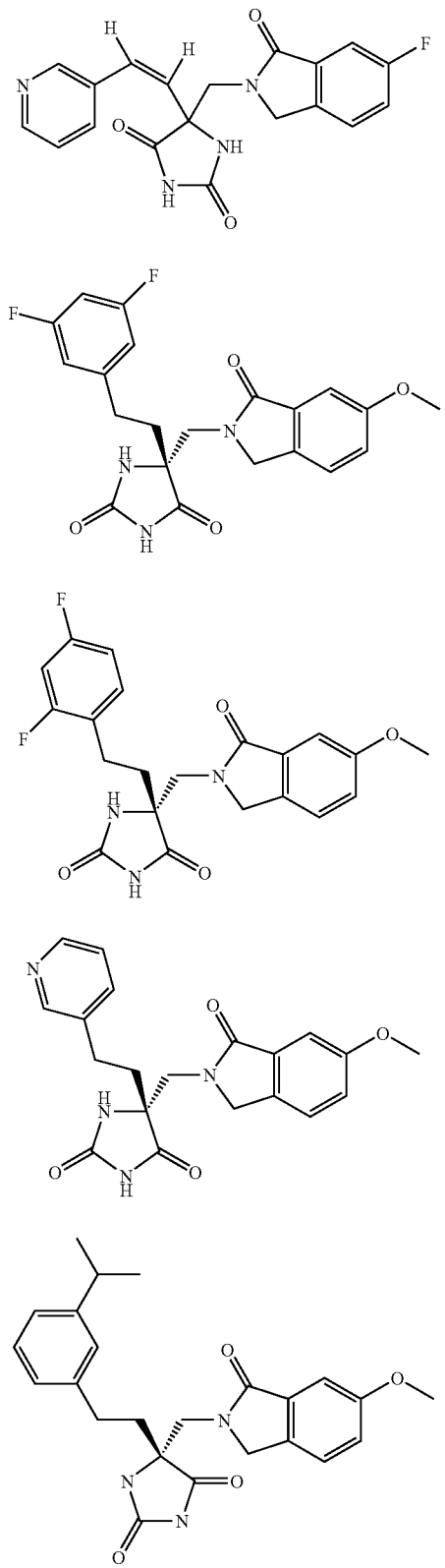
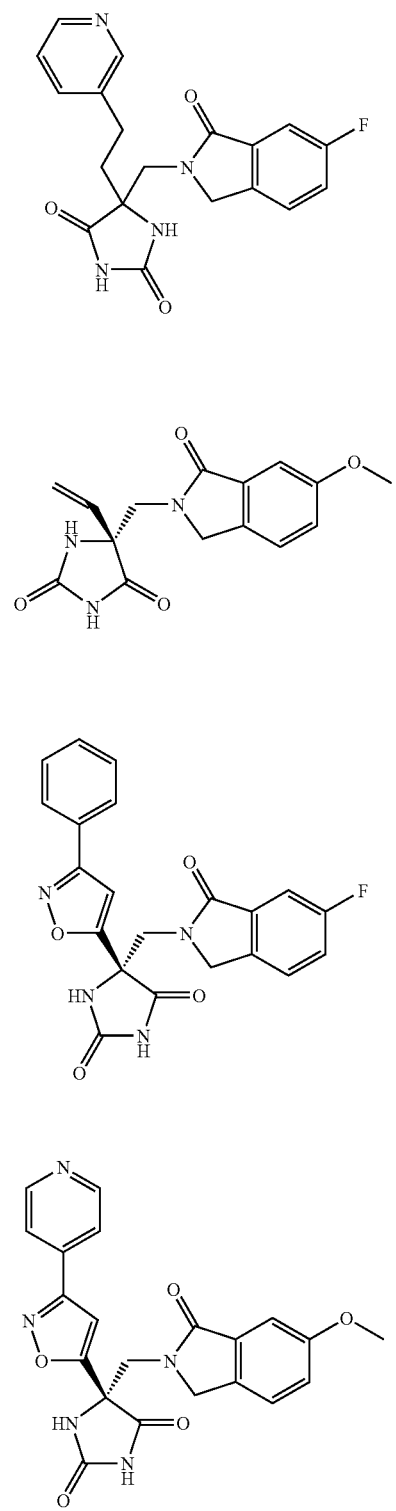

TABLE A-continued
Structures
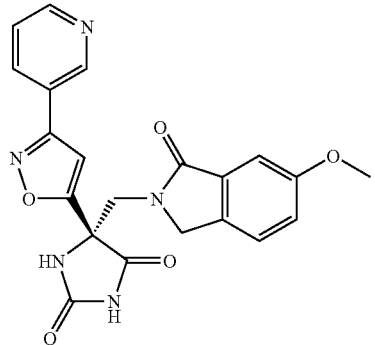
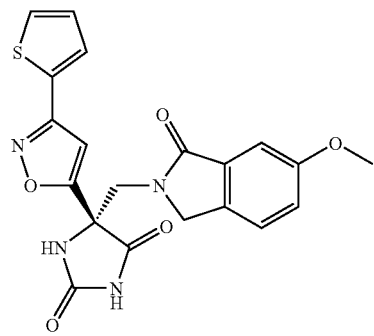
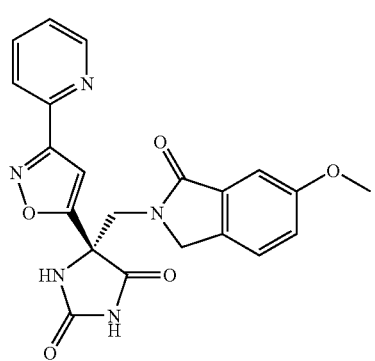
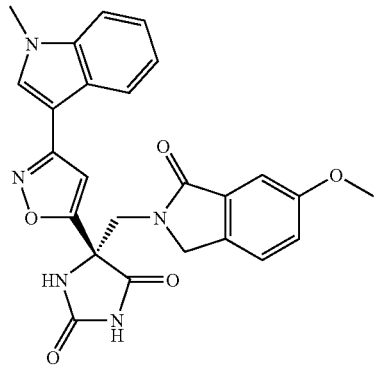
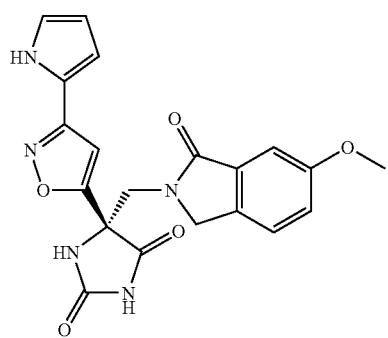
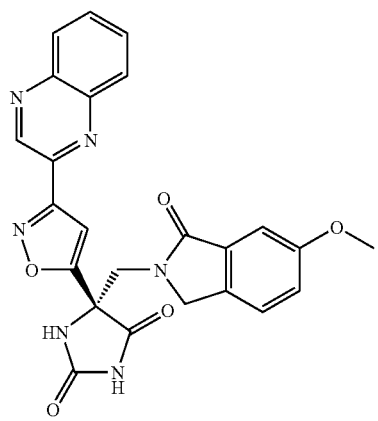
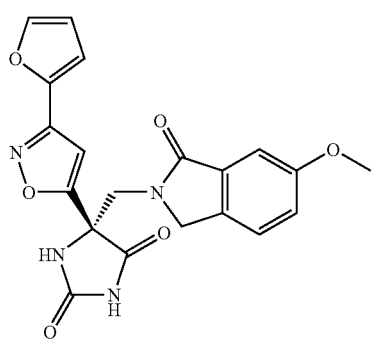
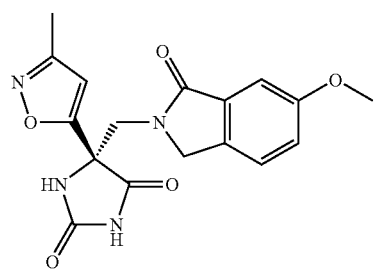

TABLE A-continued
Structures
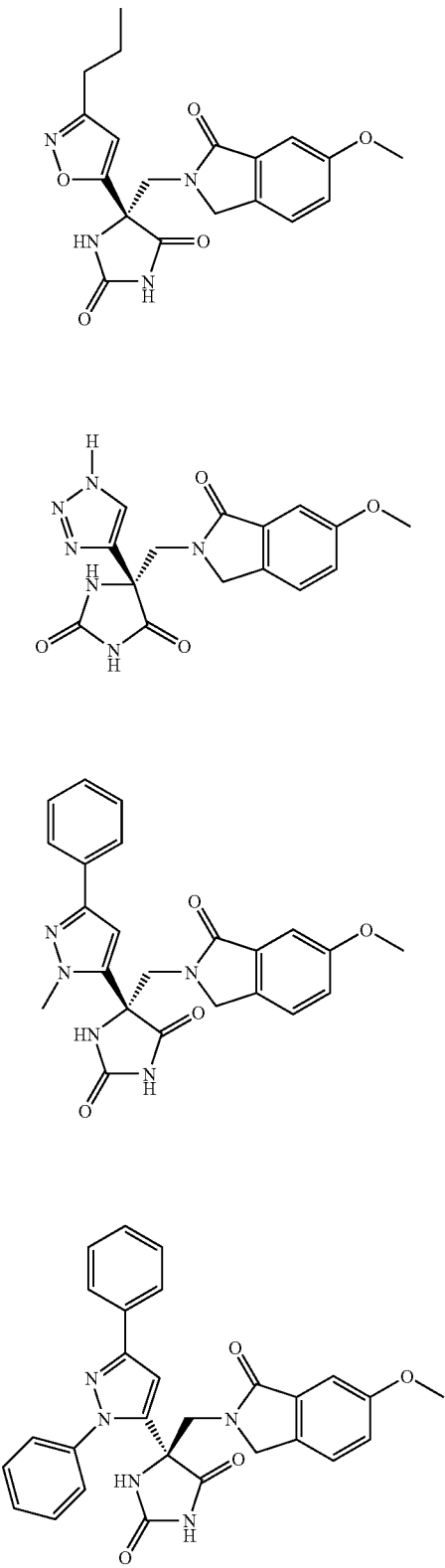
TABLE A-continued
Structures
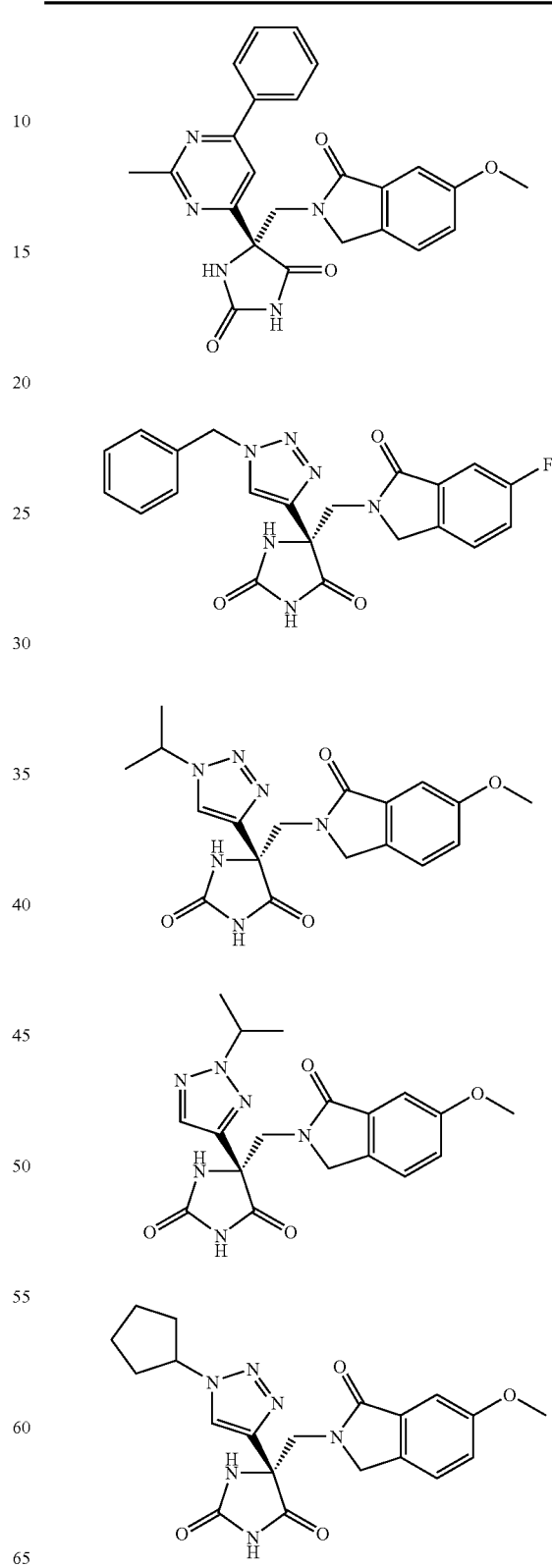

TABLE A-continued
Structures
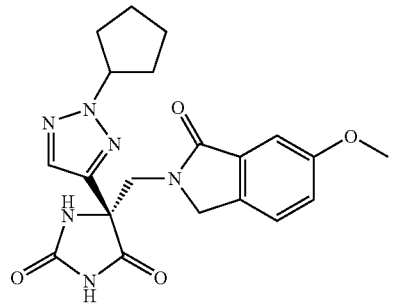
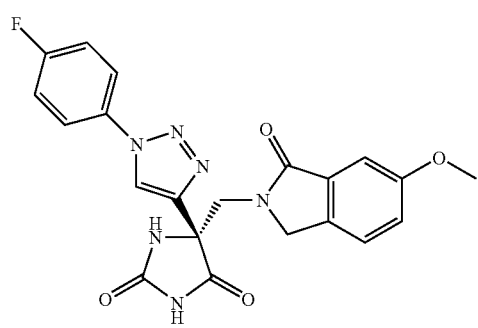
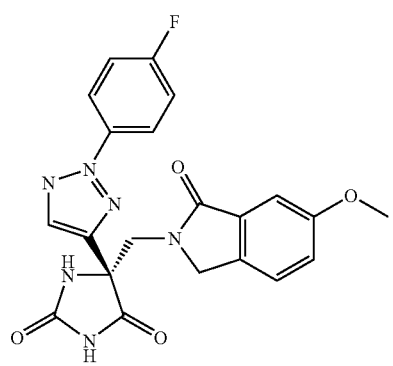
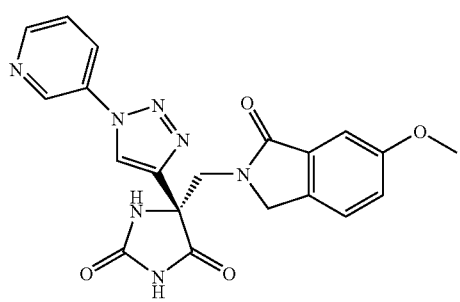
TABLE A-continued
Structures
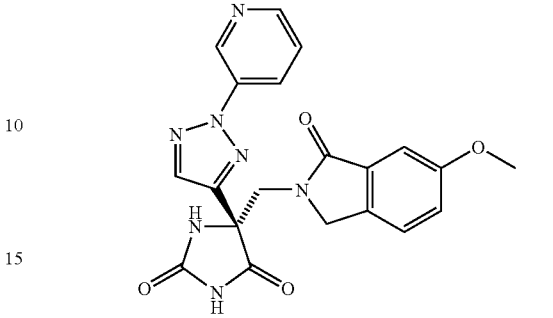
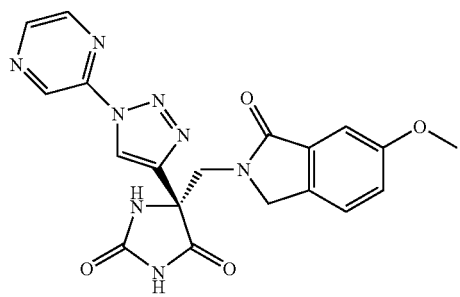
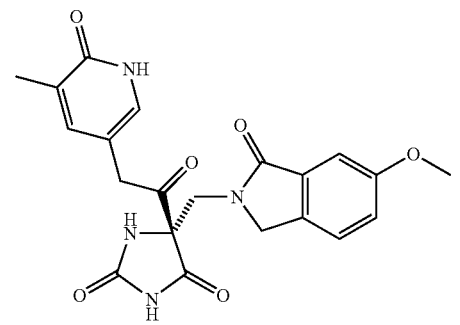
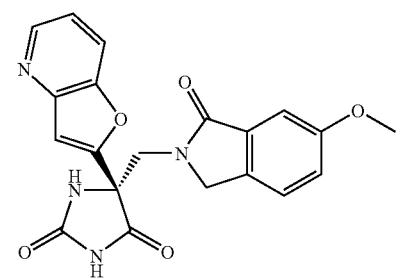
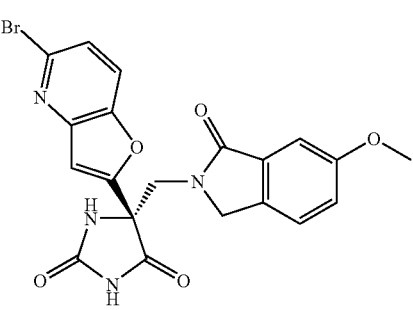

TABLE A-continued
Structures
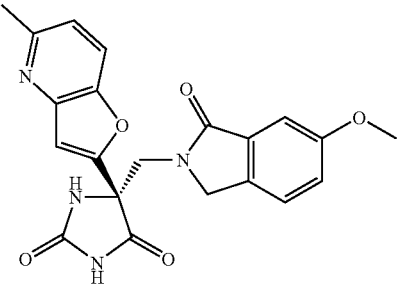
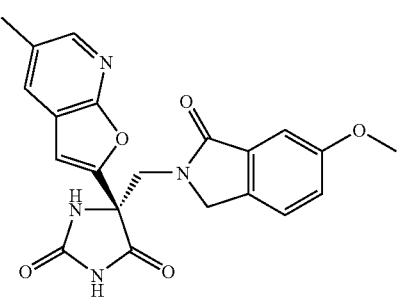
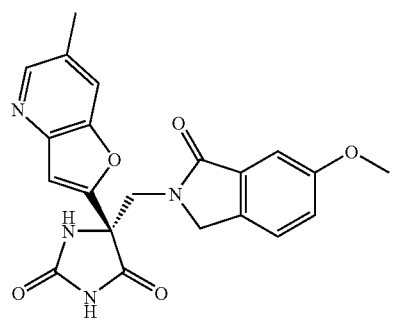
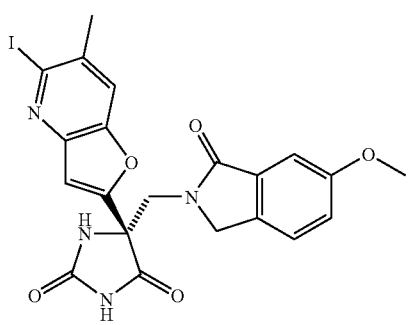
TABLE A-continued
Structures
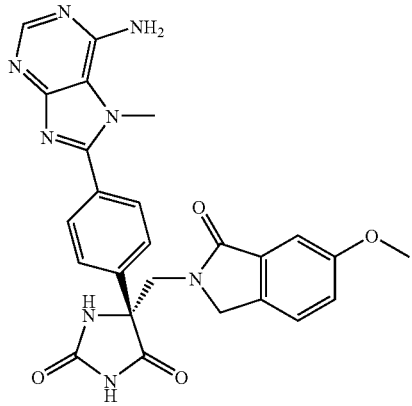
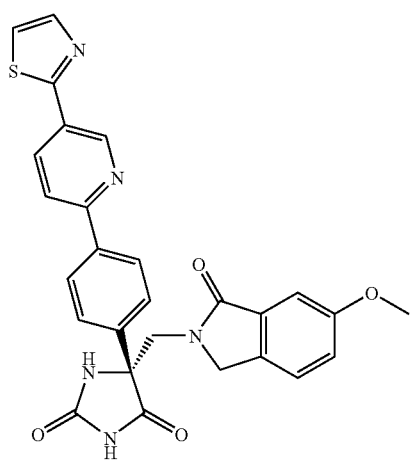
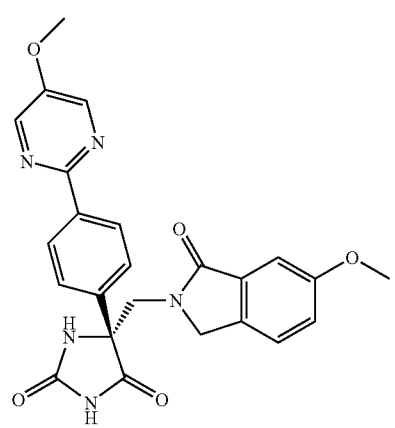

TABLE A-continued

Structures

TABLE A-continued
Structures
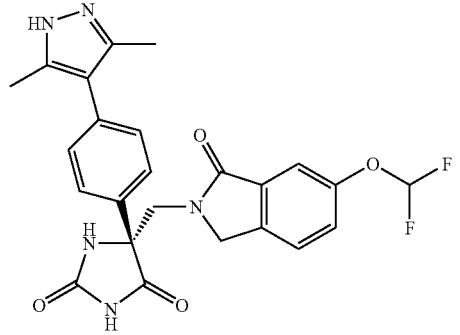
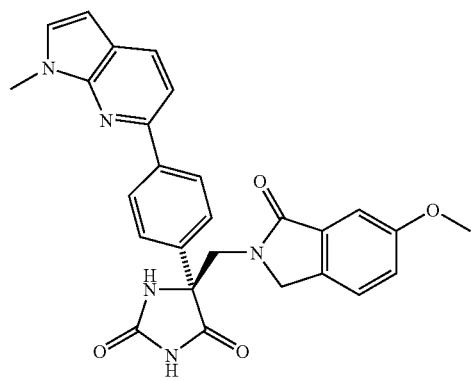
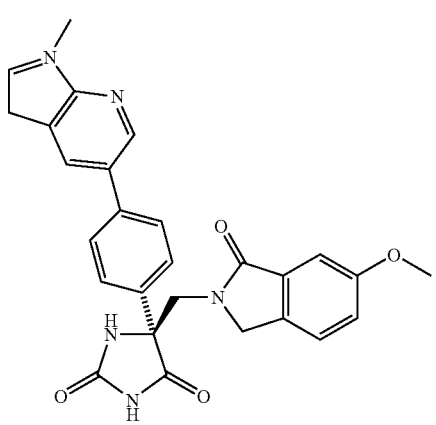
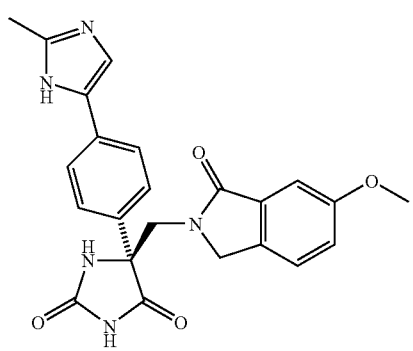
TABLE A-continued
Structures
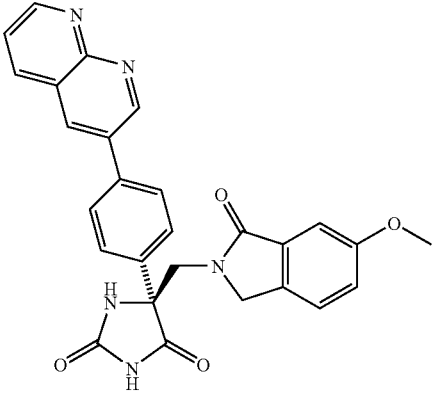
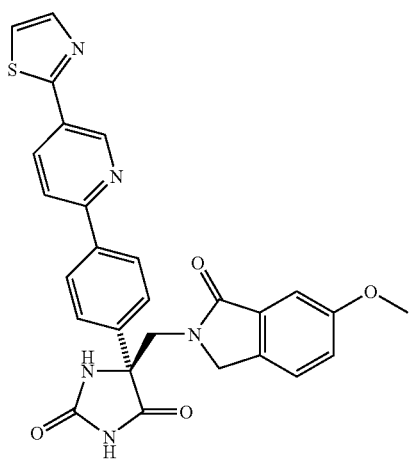
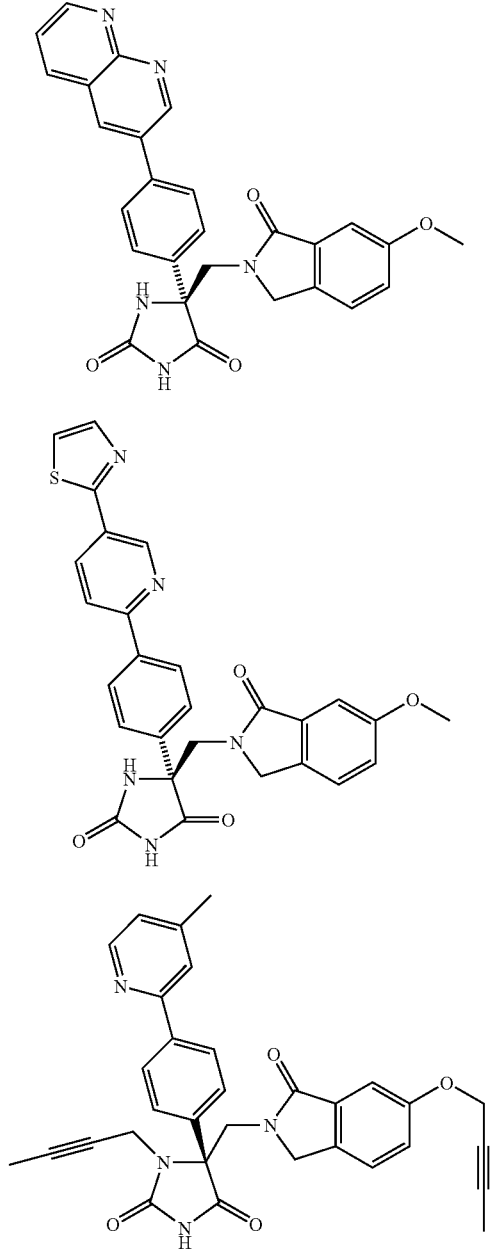
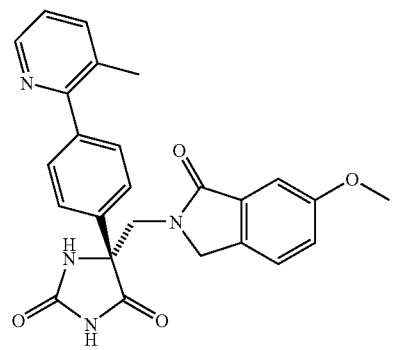

TABLE A-continued
Structures
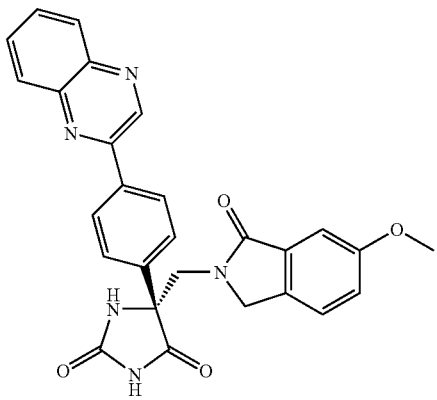
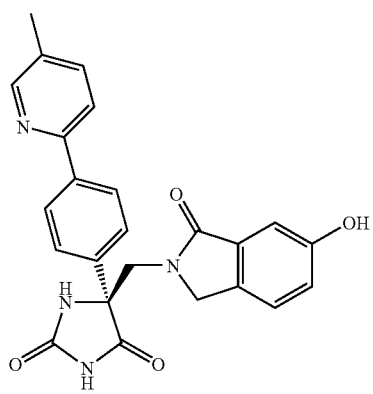
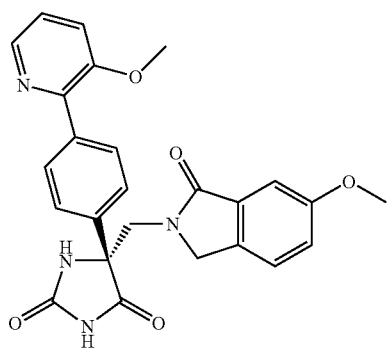
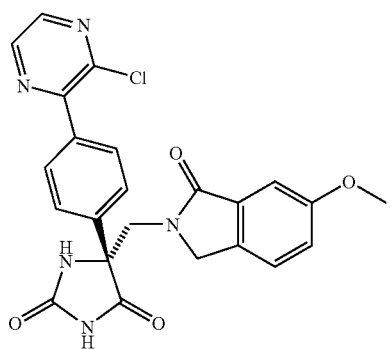
TABLE A-continued
Structures
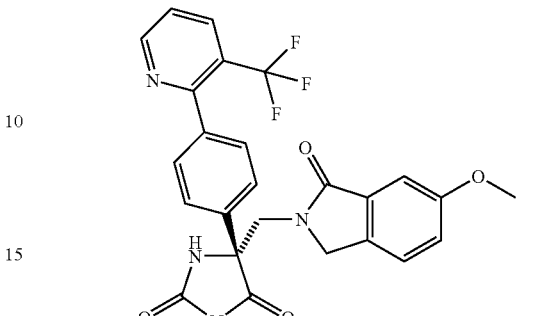
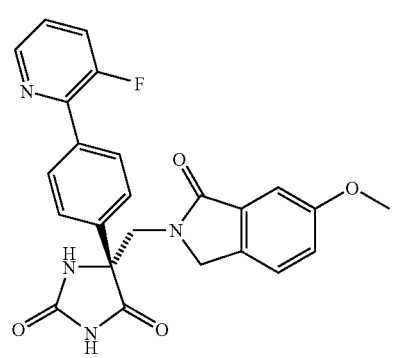
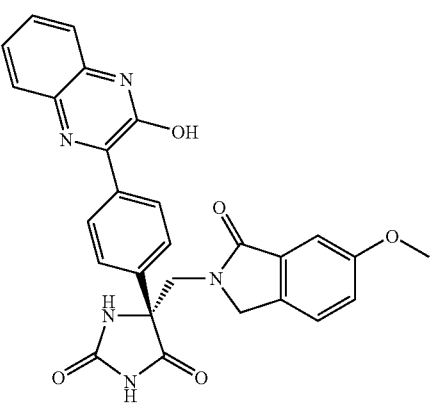
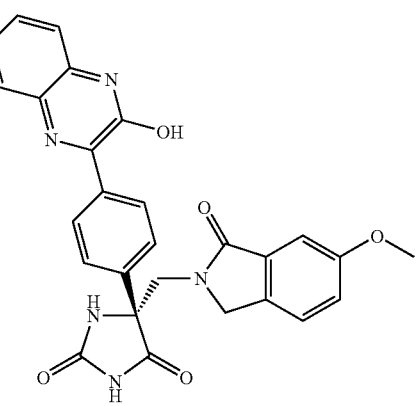

TABLE A-continued
Structures
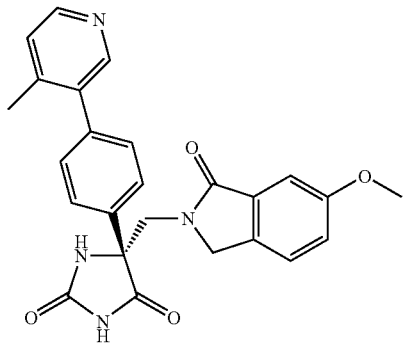
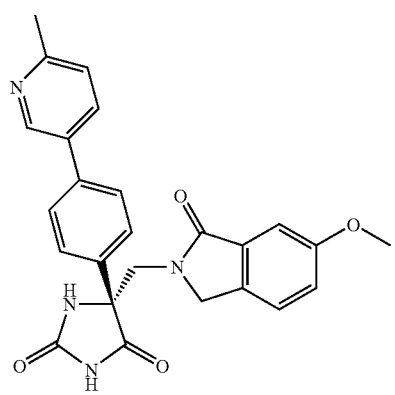
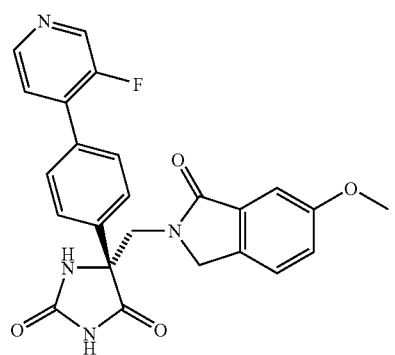
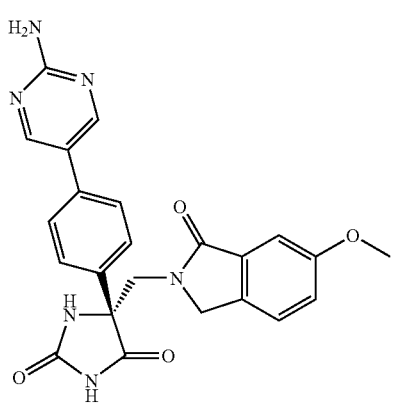
TABLE A-continued
Structures
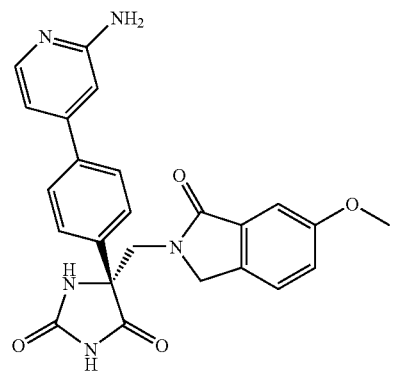
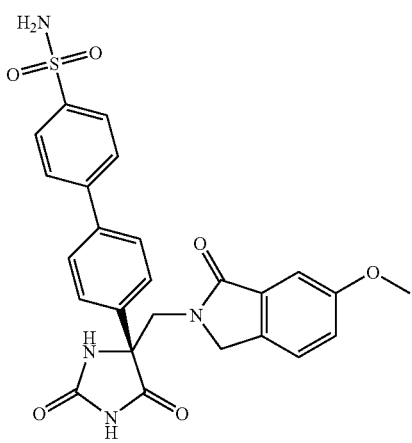
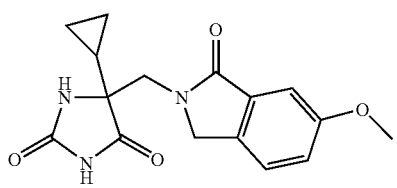
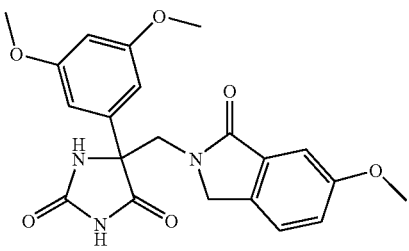

TABLE A-continued
Structures
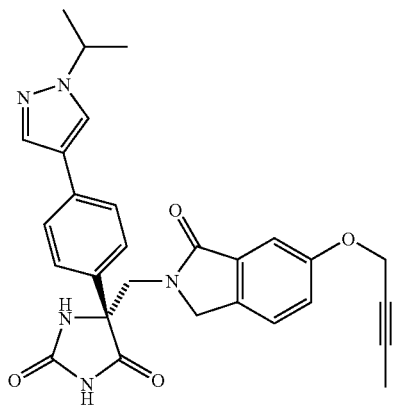
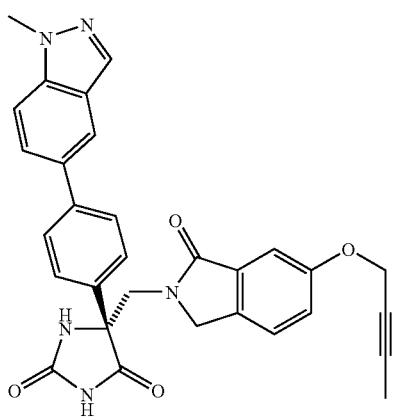
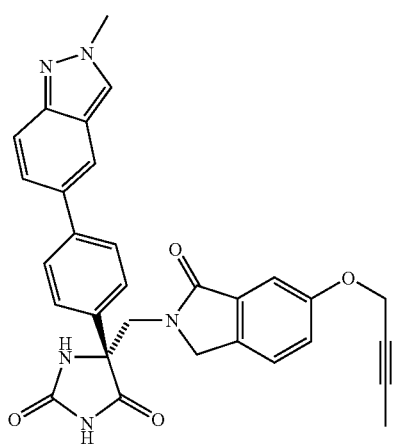
TABLE A-continued
Structures
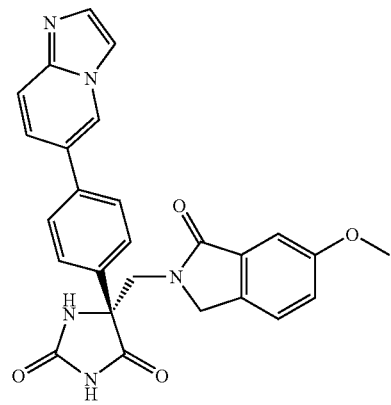
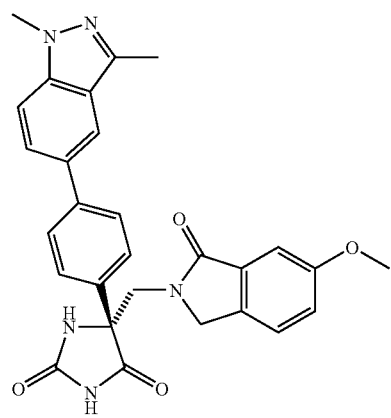
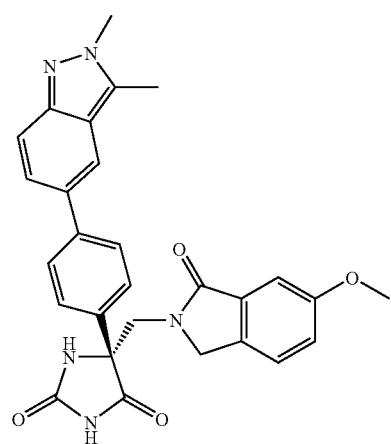

TABLE A-continued

Structures

TABLE A-continued
Structures
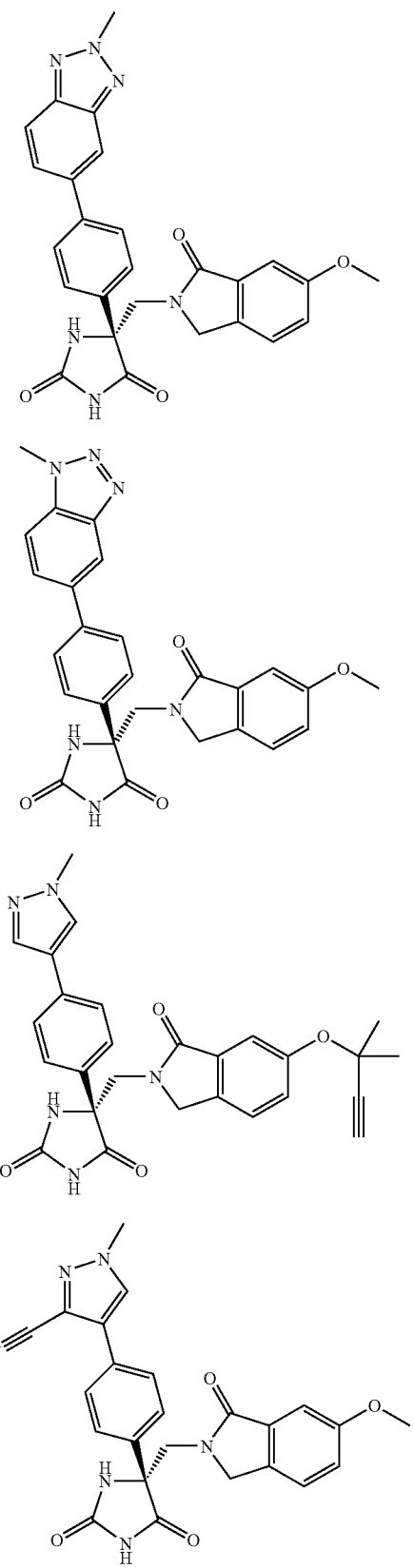
TABLE A-continued
Structures
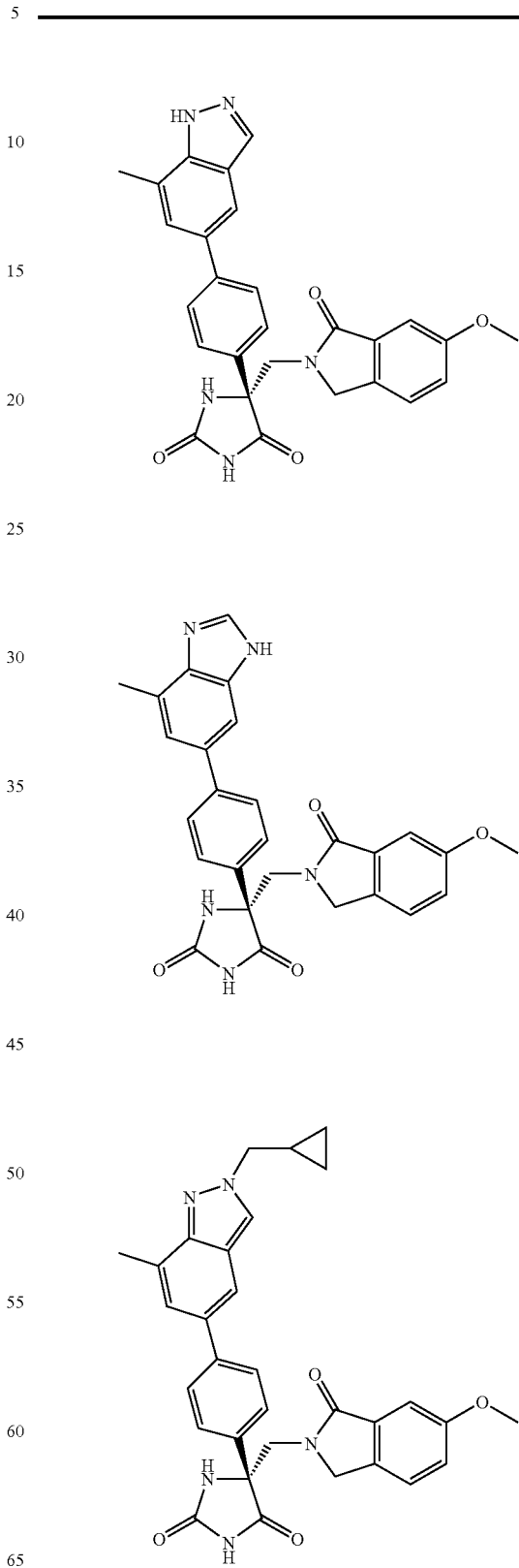

TABLE A-continued
Structures
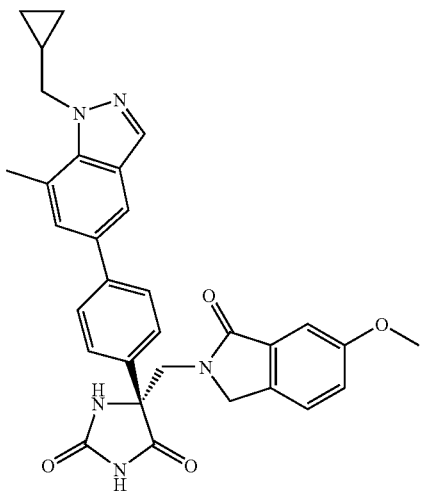
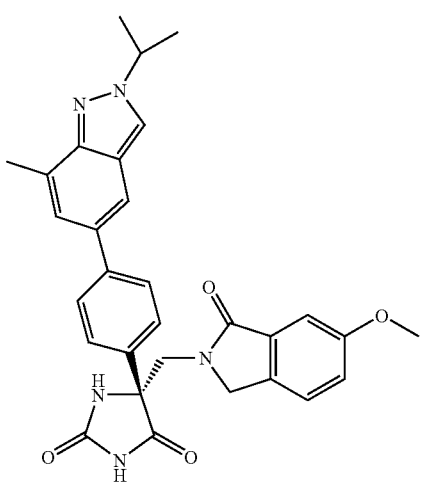
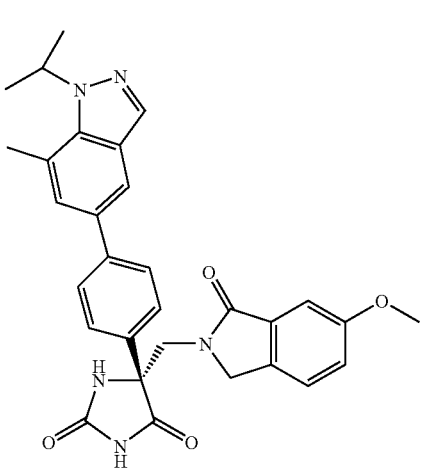
TABLE A-continued
Structures
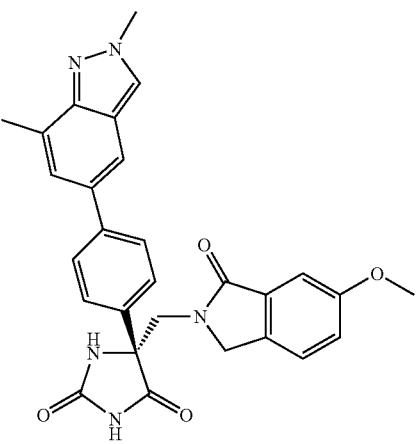
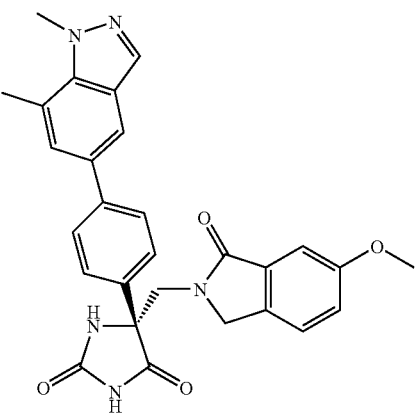
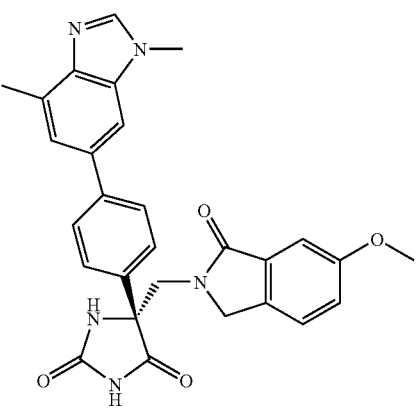

TABLE A-continued
| Structures |
|---|
| 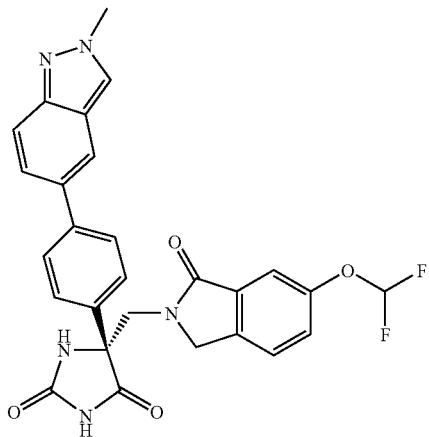 |
| 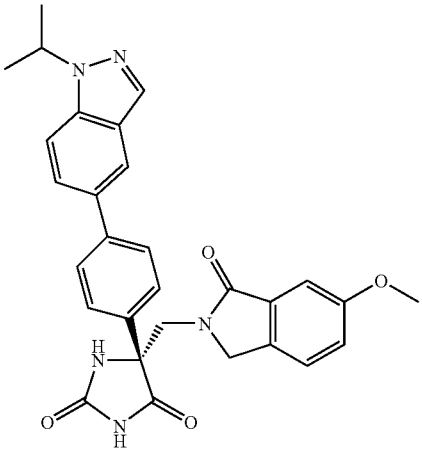 |
| 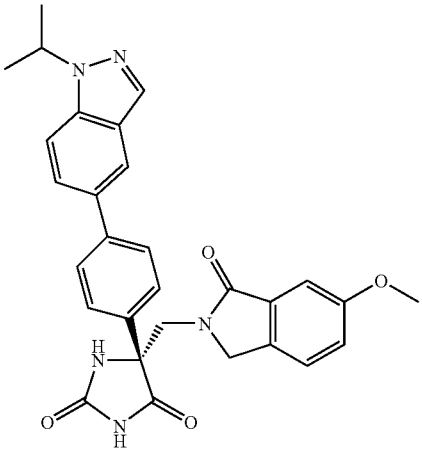 |
| 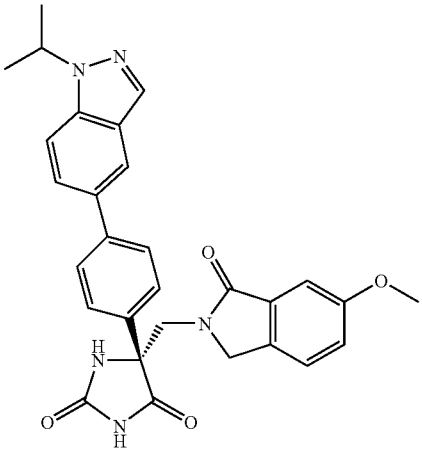 |
| 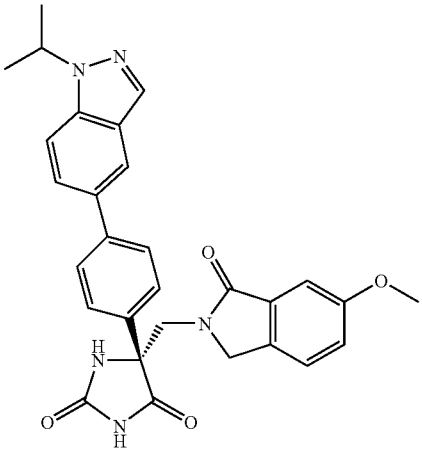 |
| 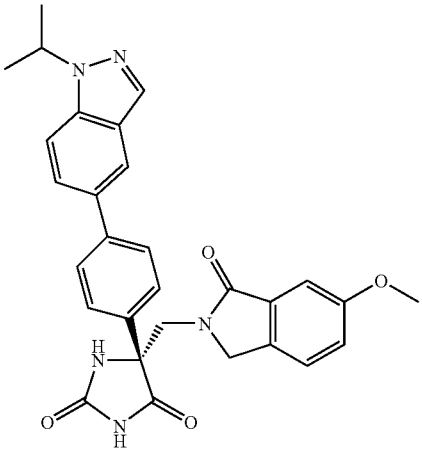 |
| 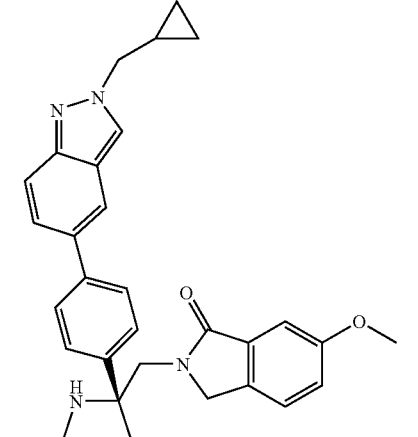 |
| 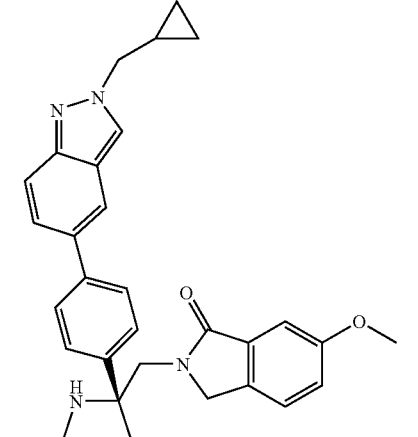 |
| 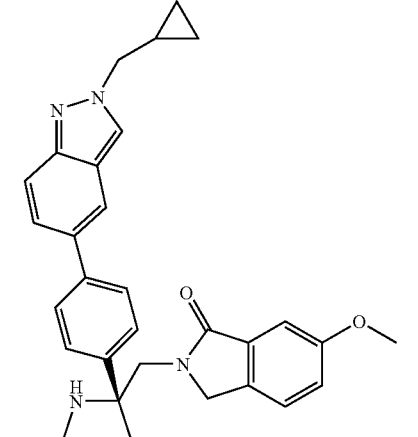 |
| 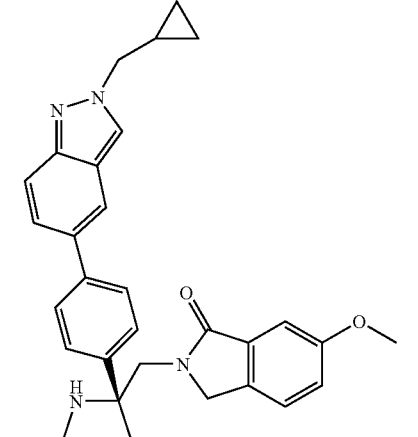 |
| 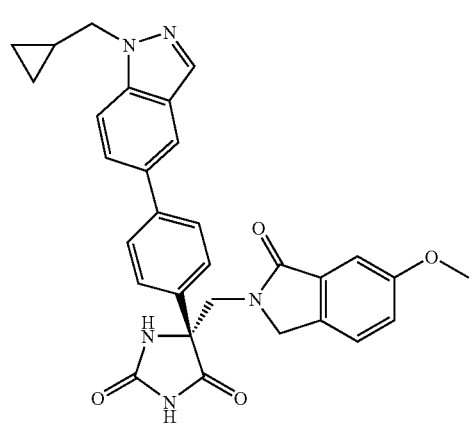 |
| 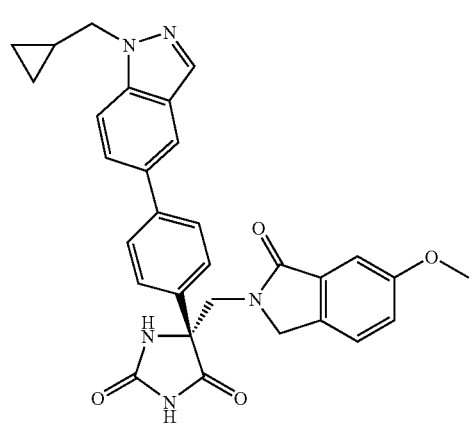 |
| 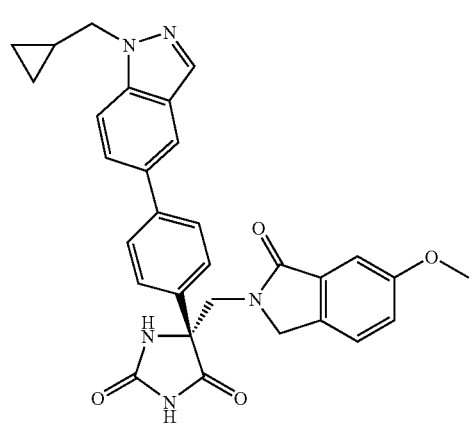 |
| 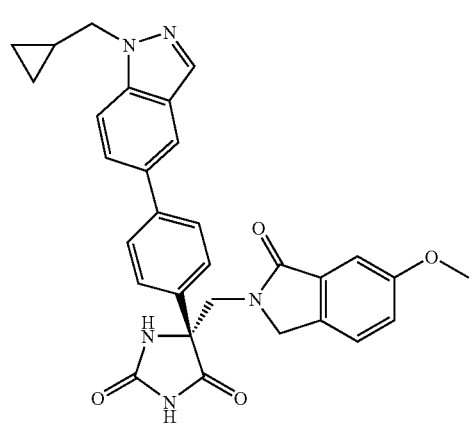 |

TABLE A-continued
Structures
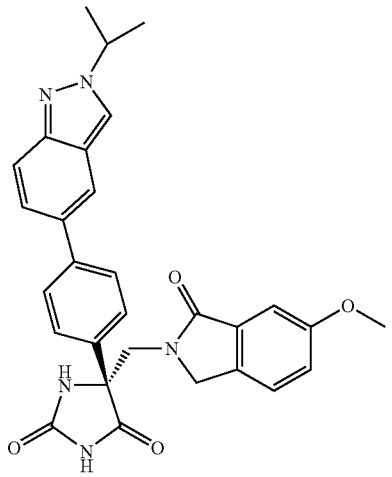
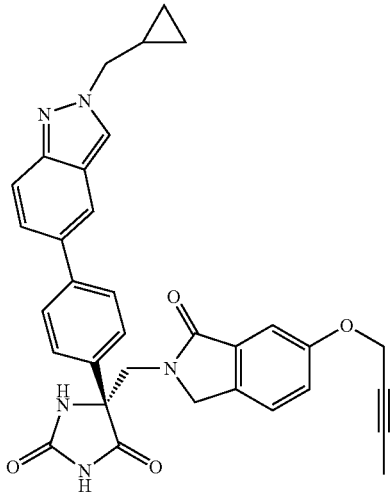
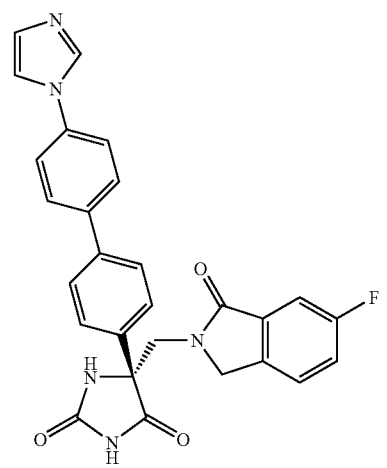
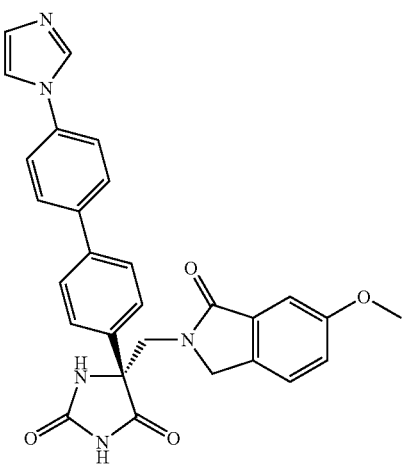
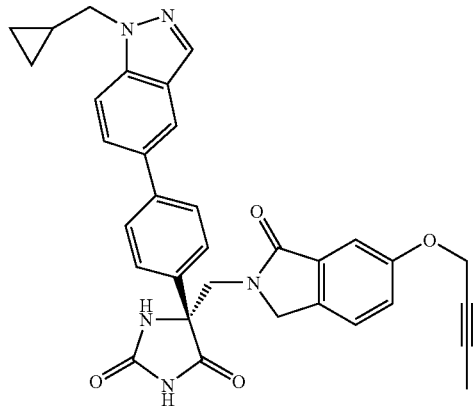
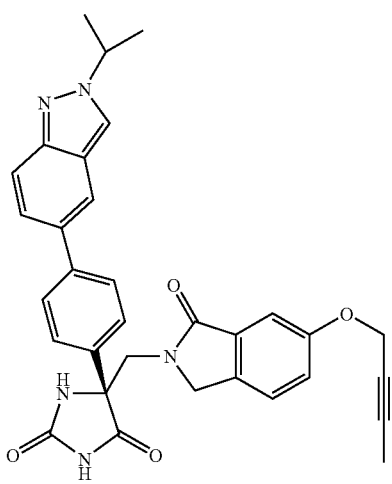

TABLE A-continued
Structures
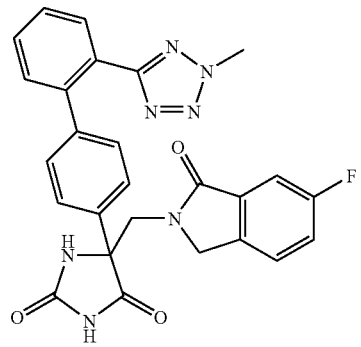
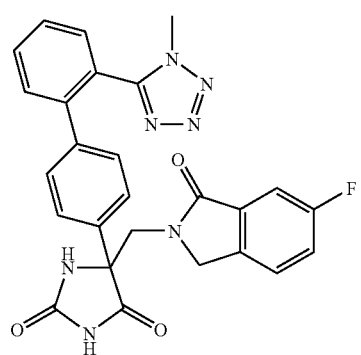
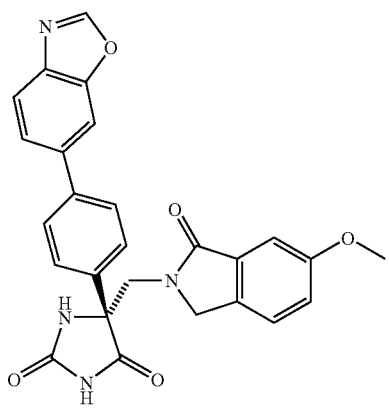
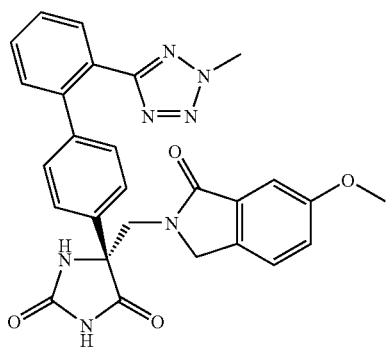
TABLE A-continued
Structures
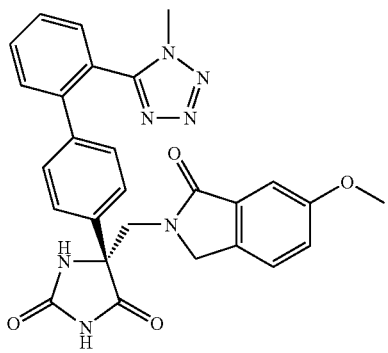
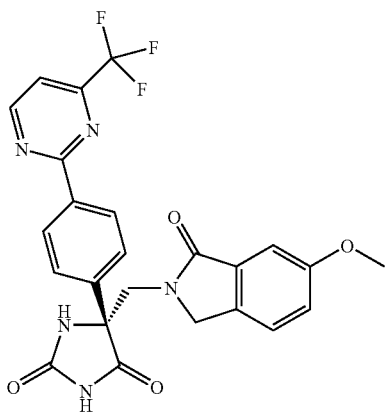
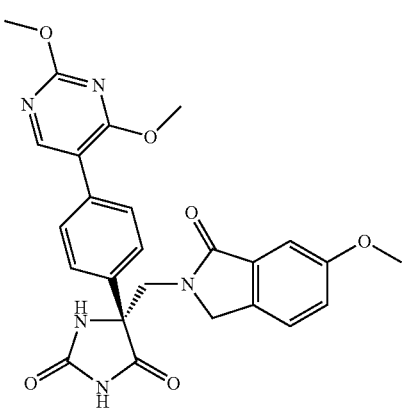

TABLE A-continued
Structures
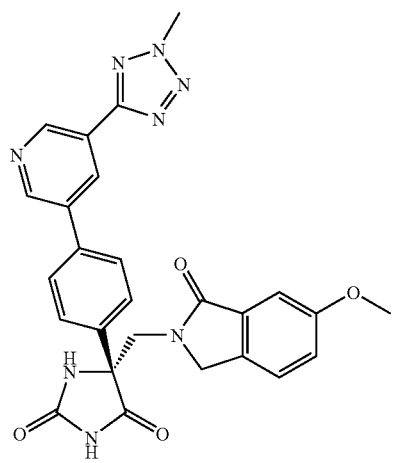
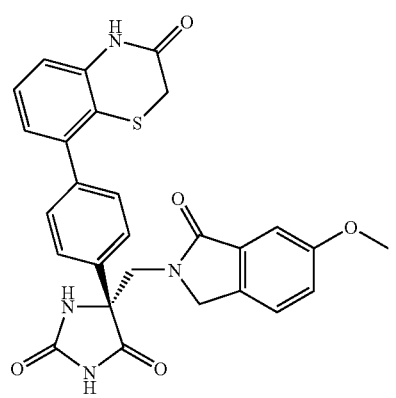
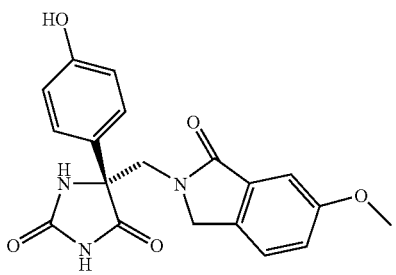
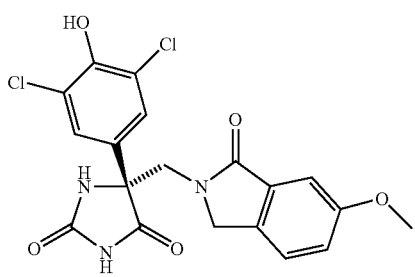
TABLE A-continued
Structures
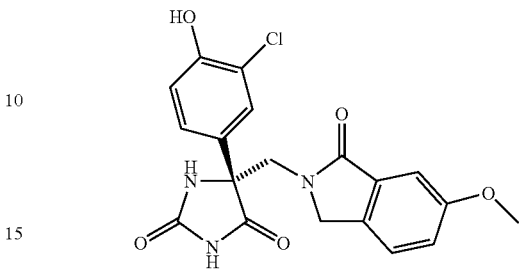
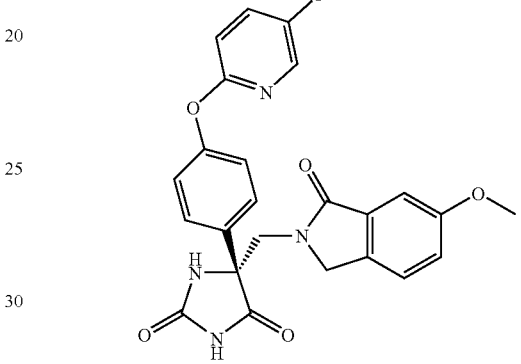
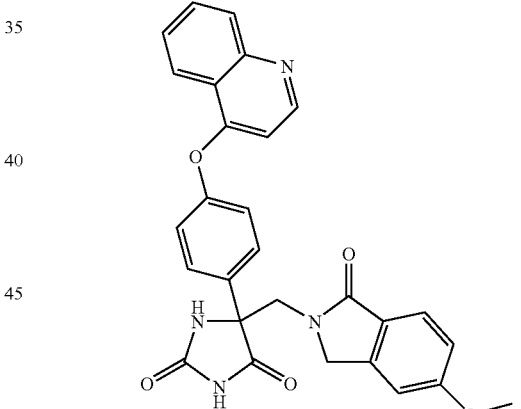
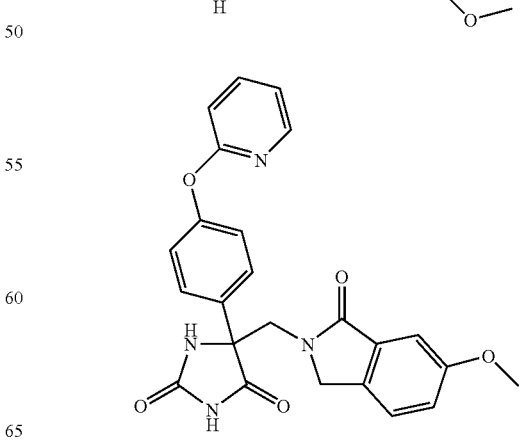

TABLE A-continued
Structures
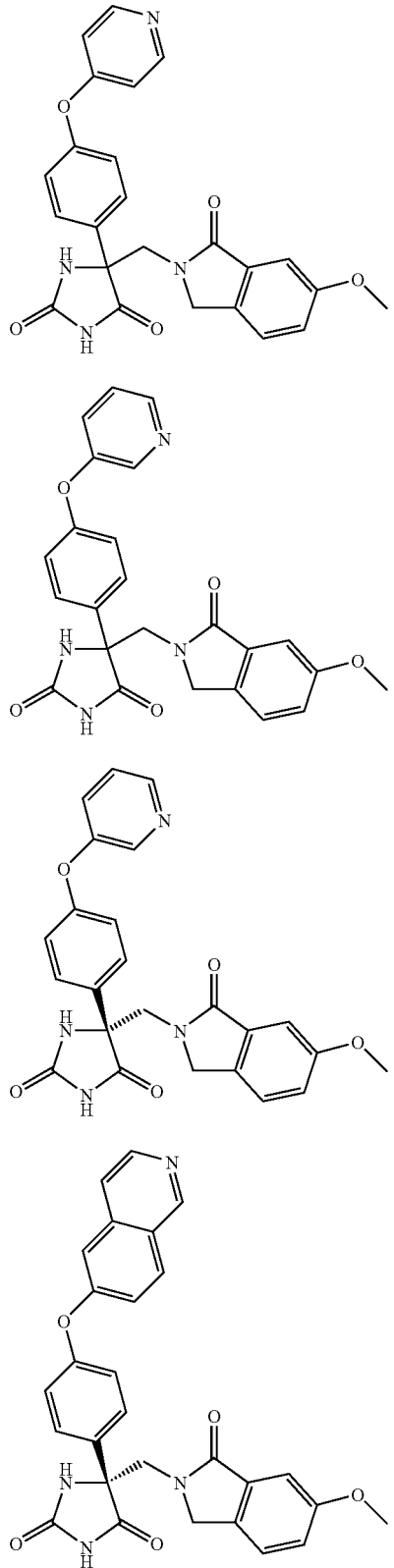
TABLE A-continued
Structures
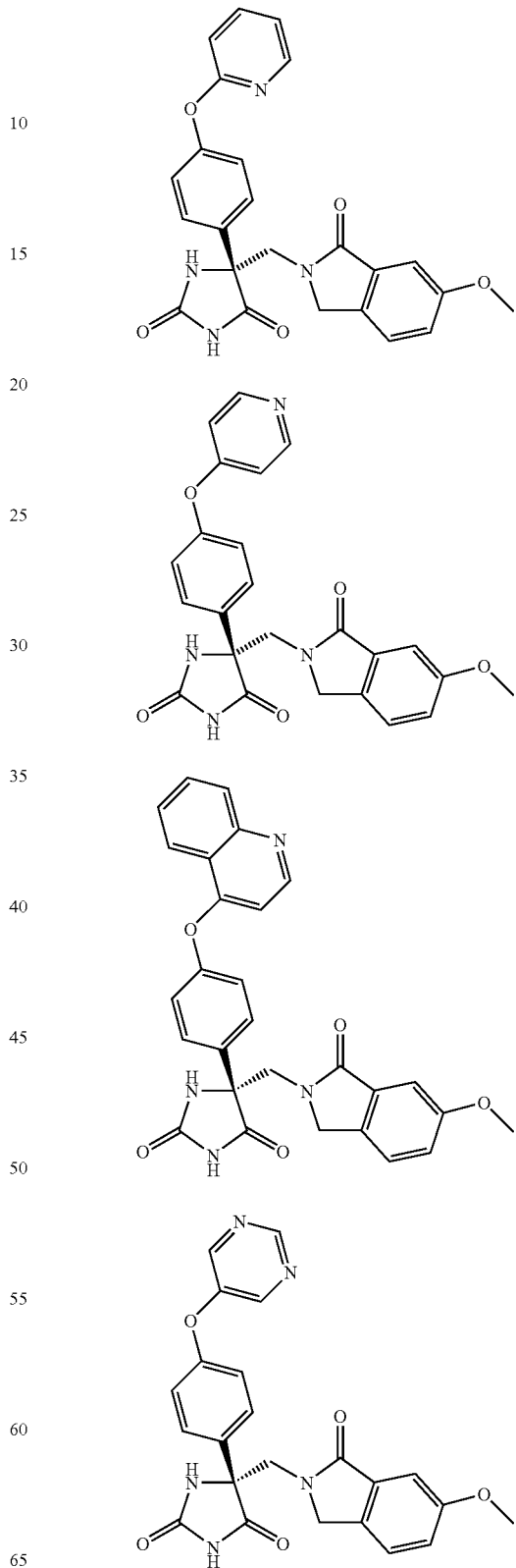

TABLE A-continued
Structures
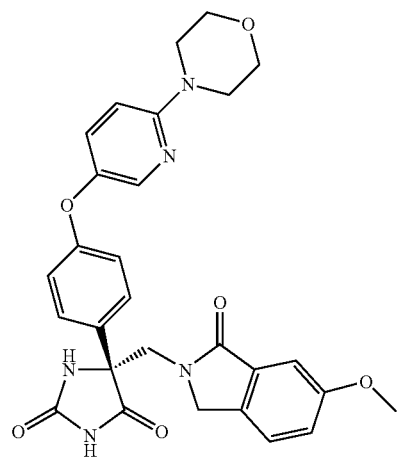
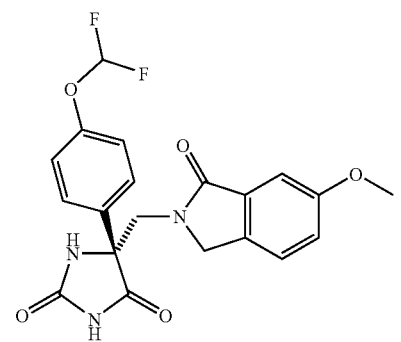
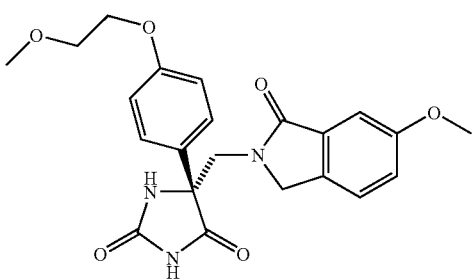
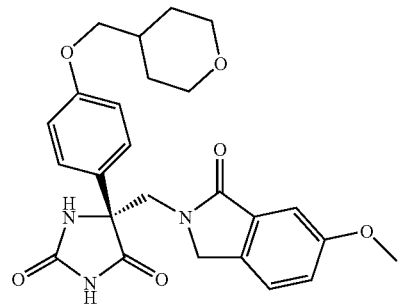
TABLE A-continued
Structures
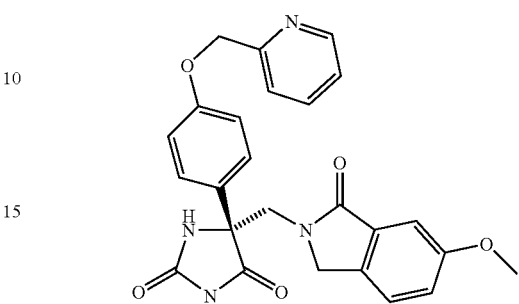
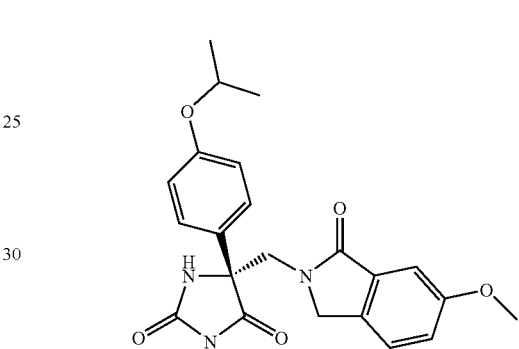
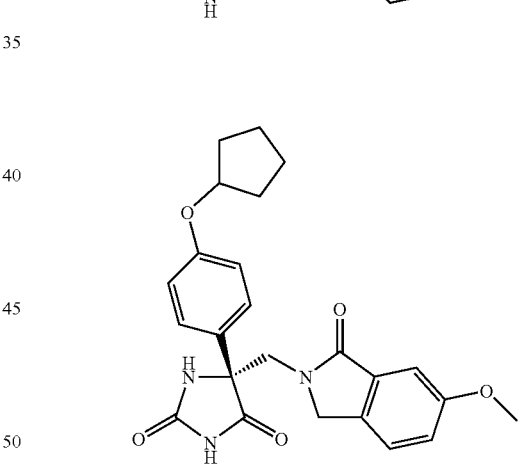
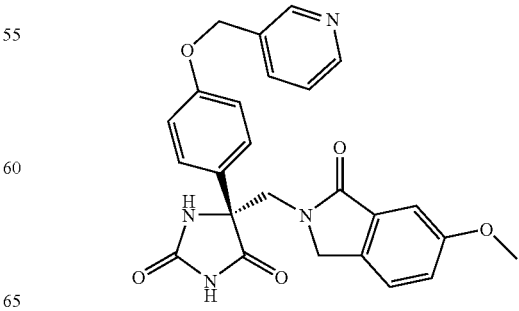

TABLE A-continued
Structures
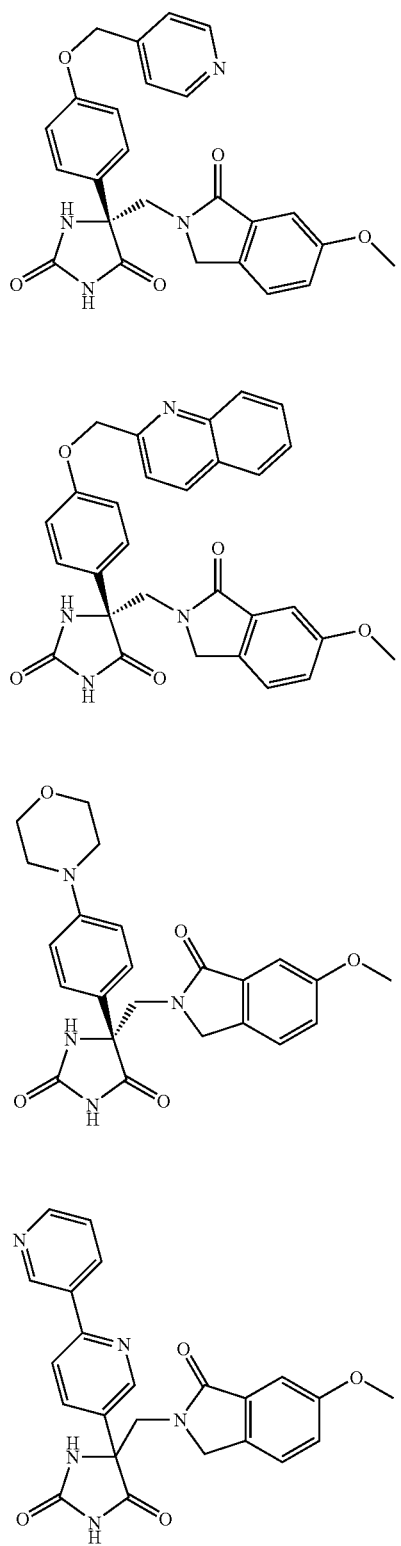
TABLE A-continued
Structures
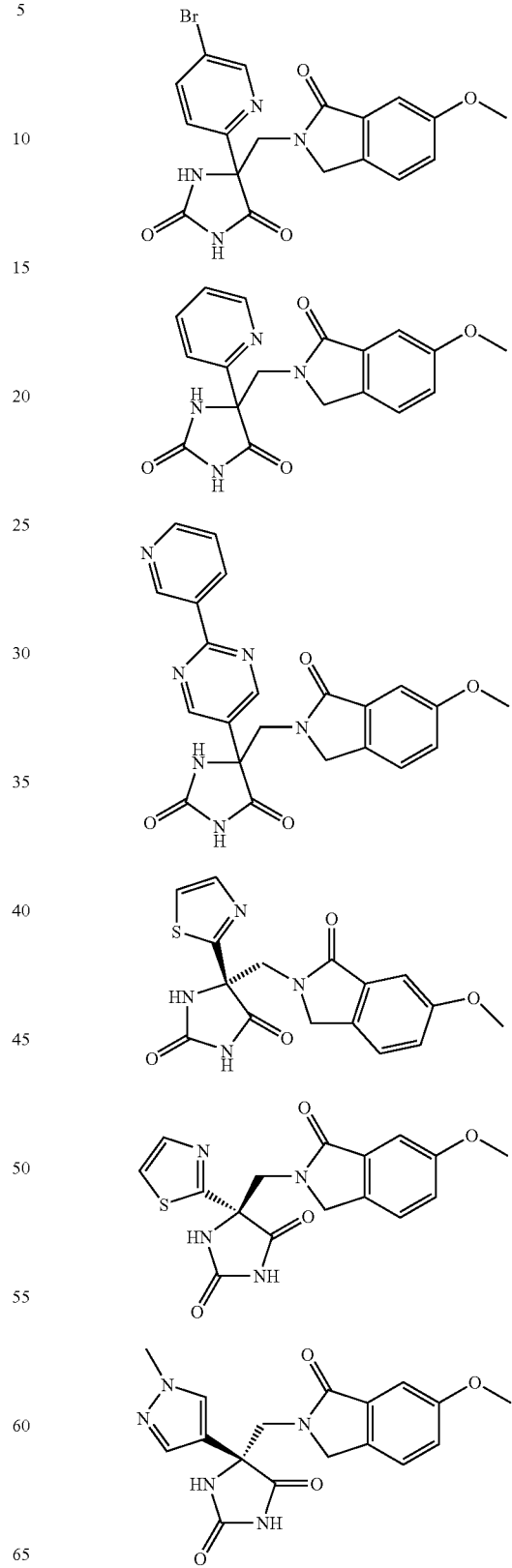

TABLE A-continued

Structures

TABLE A-continued
Structures
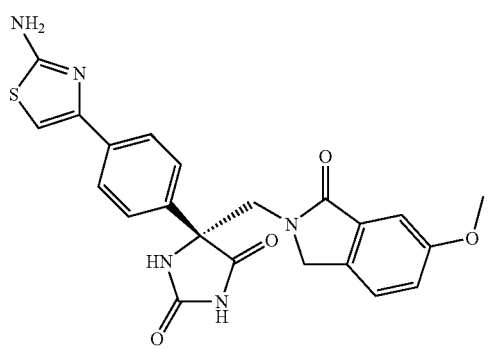
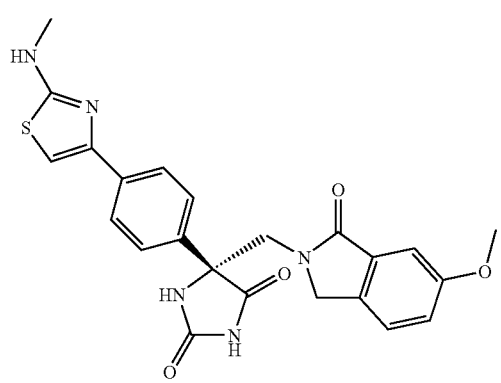
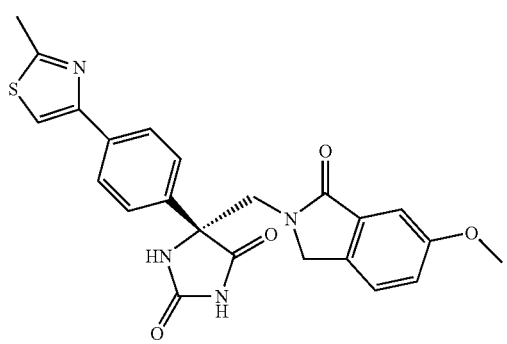
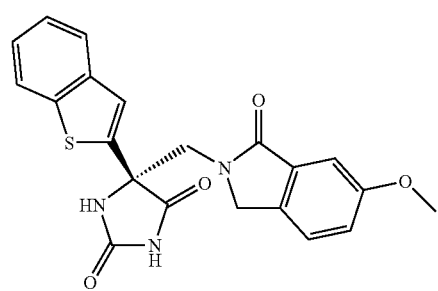
TABLE A-continued
Structures
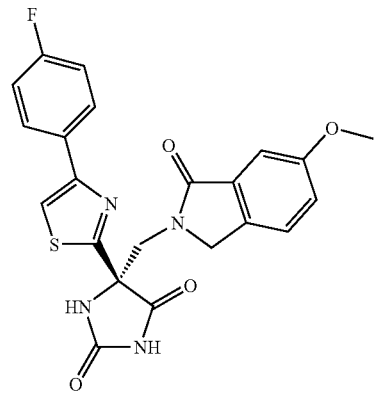
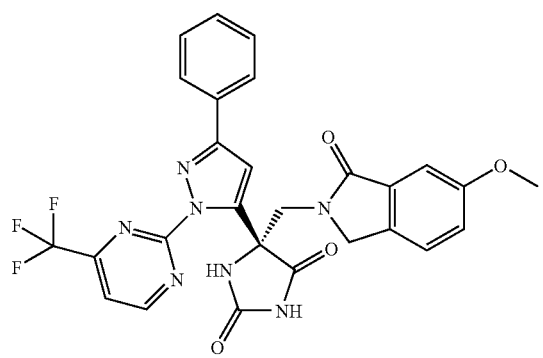
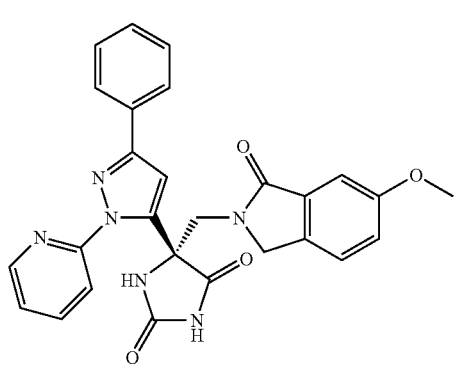
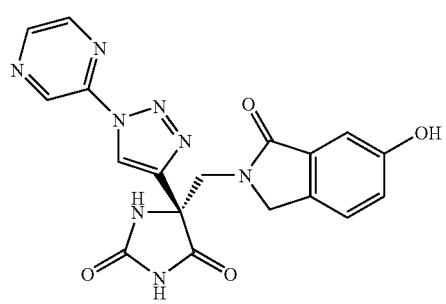

TABLE A-continued
| Structures |
|---|
| 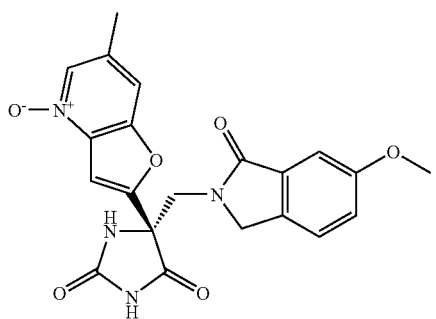 |
| 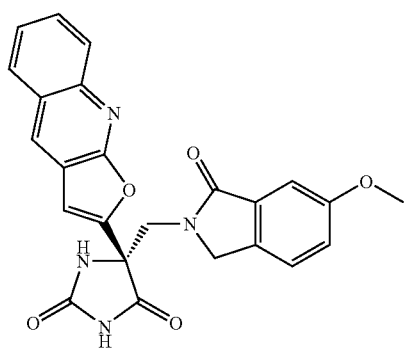 |
| 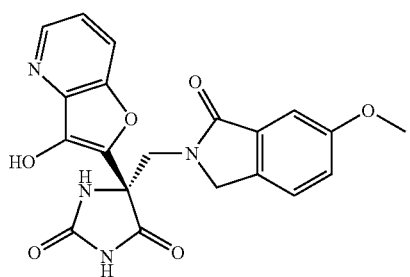 |
| 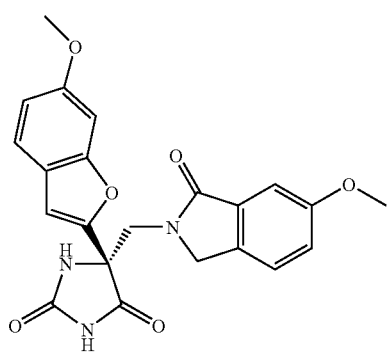 |
TABLE A-continued
| Structures |
|---|
| 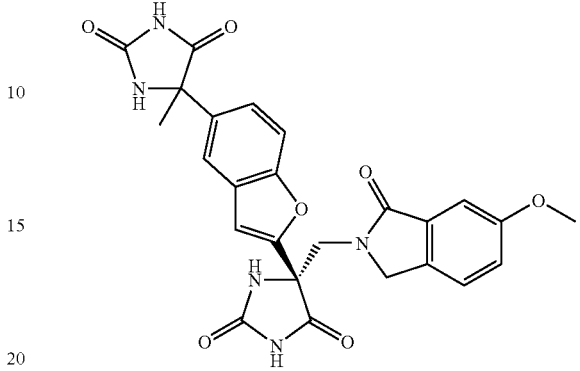 |
| 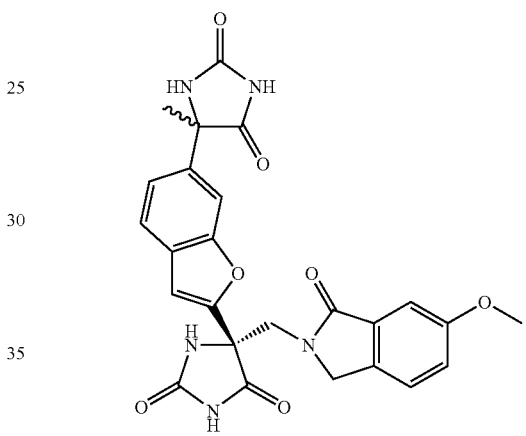 |
| 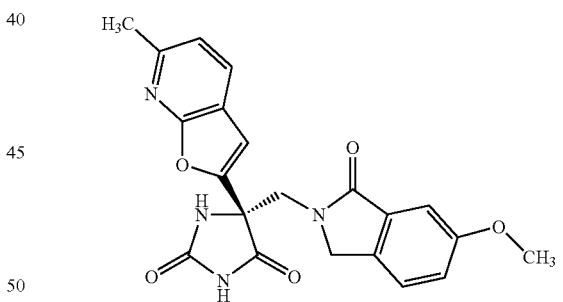 |
| 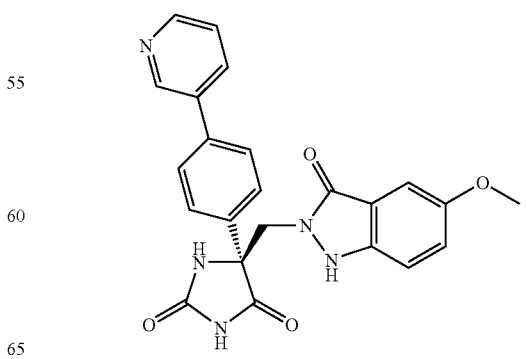 |

TABLE A-continued
Structures
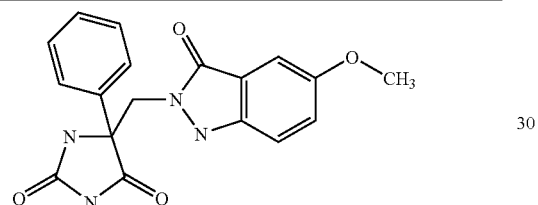
Another embodiment of the invention discloses the compounds shown in Table B below or a pharmaceutically acceptable salt, solvate, or ester thereof:
TABLE B
Structure
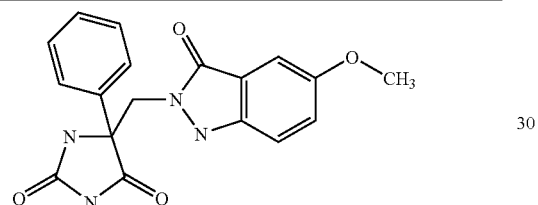
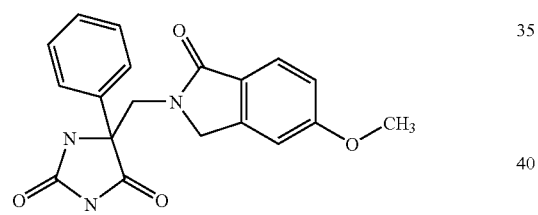
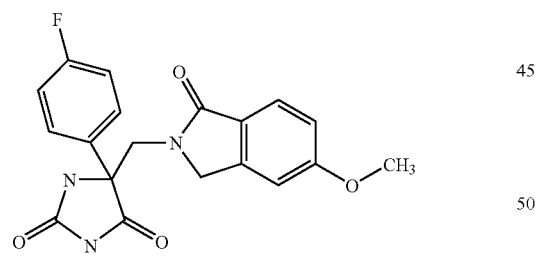
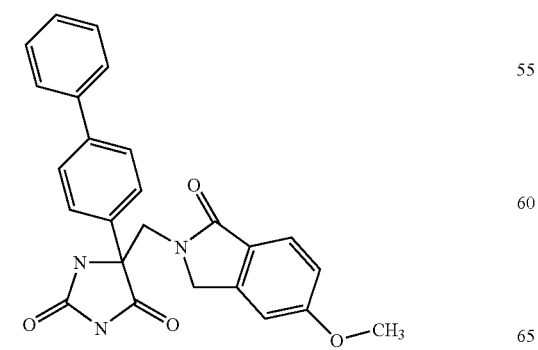
TABLE B-continued
Structure
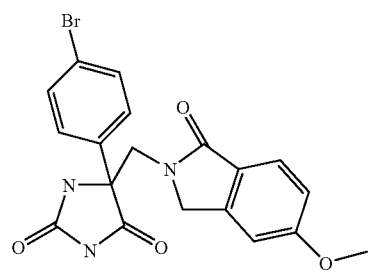
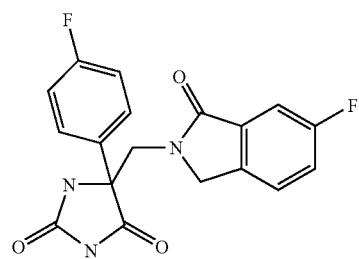
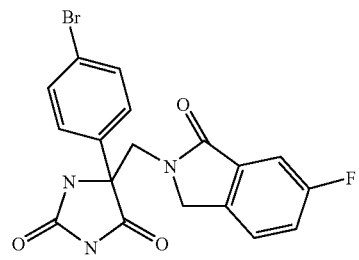
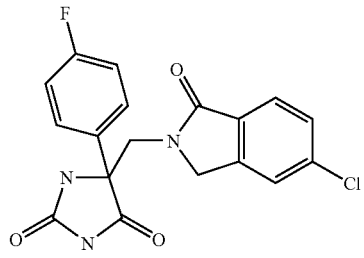
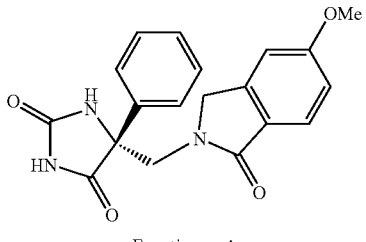
Enantiomer A

TABLE B-continued
| Structure |
|---|
| 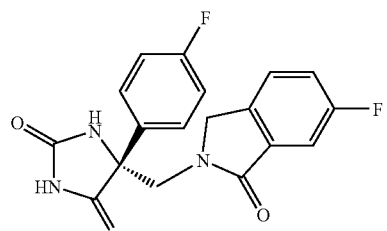<br>Enantiomer B |
| 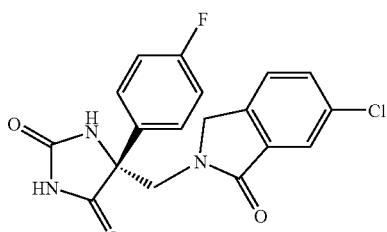<br>Enantiomer B |
| 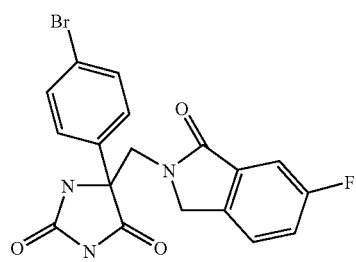 |
| 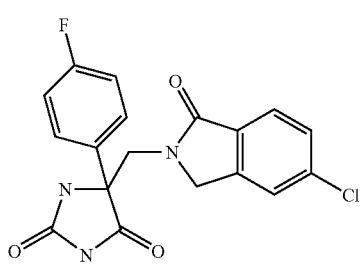 |
| 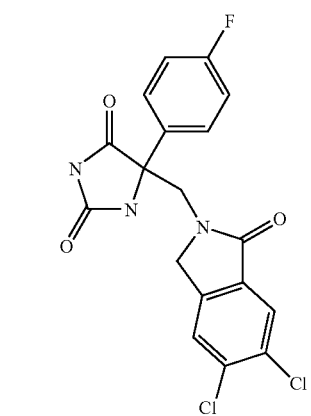 |
| 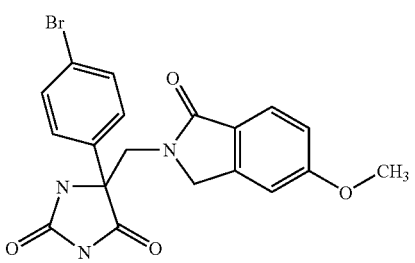 |
| 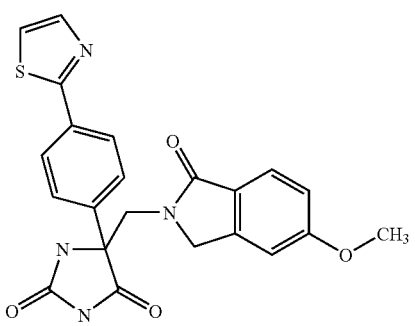 |
| 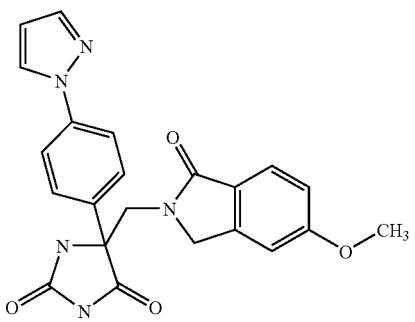 |
| 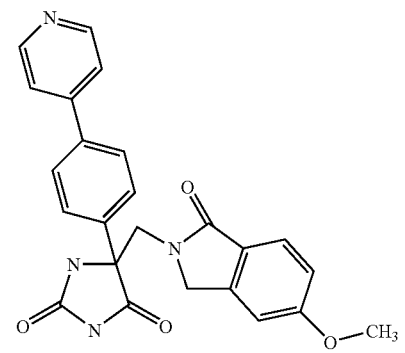 |

TABLE B-continued
Structure
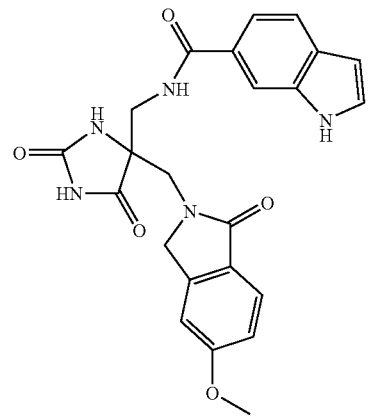
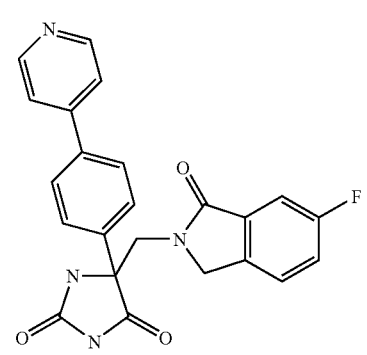
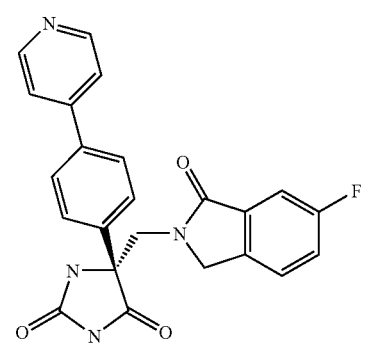
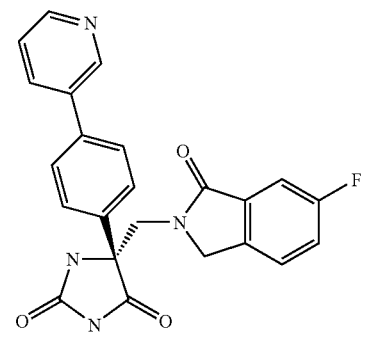
TABLE B-continued
Structure
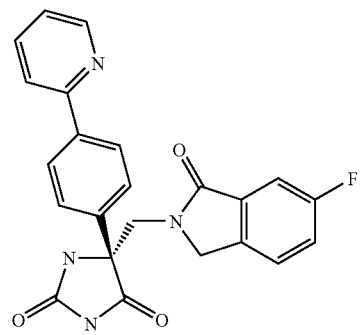
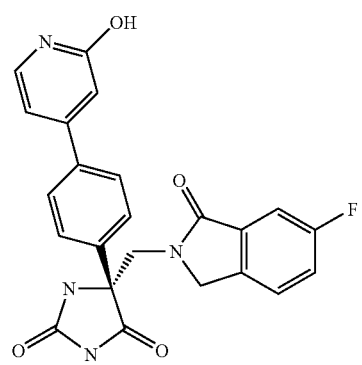
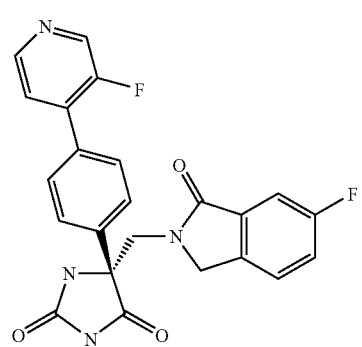
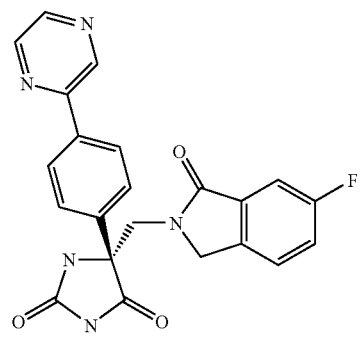

TABLE B-continued
Structure
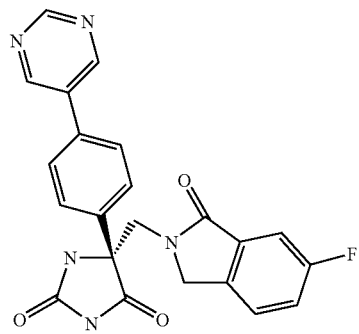
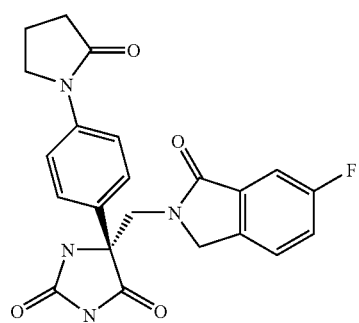
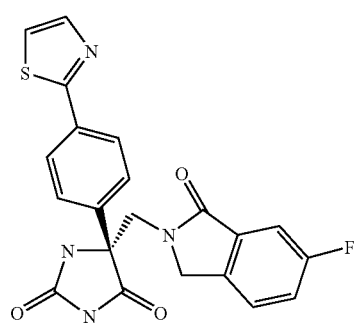
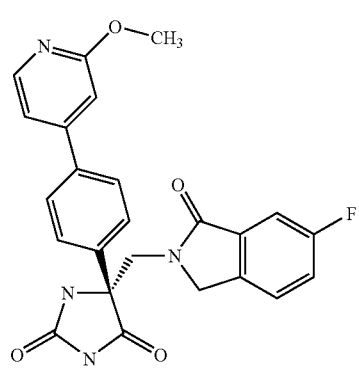
TABLE B-continued
Structure
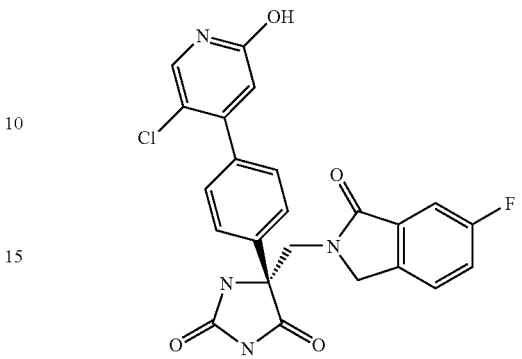
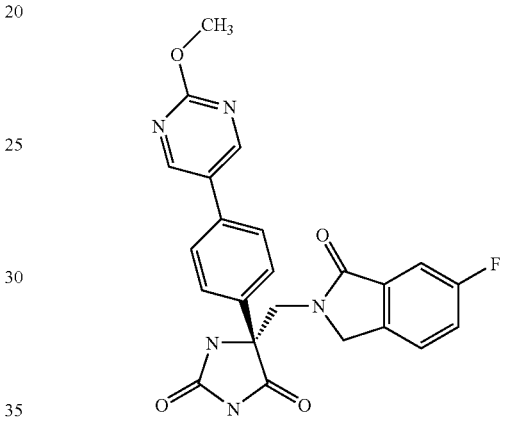
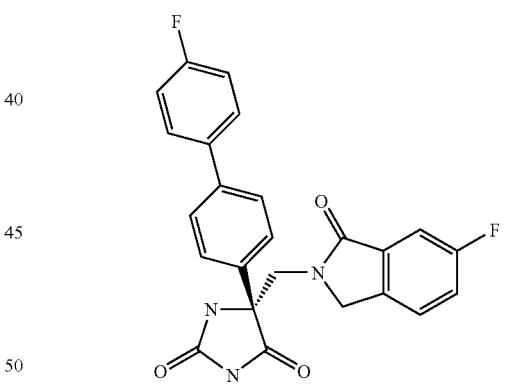
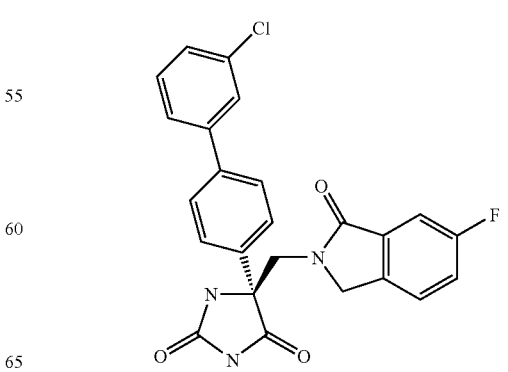

TABLE B-continued
Structure
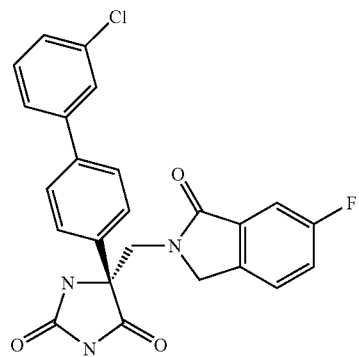
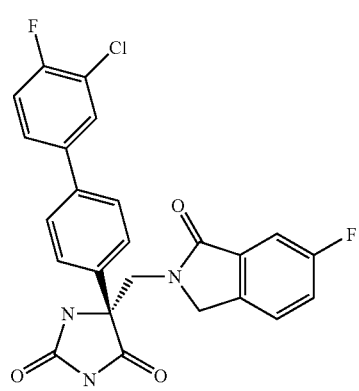
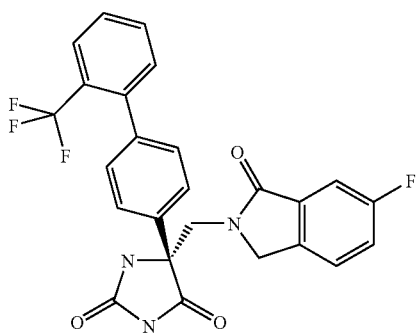
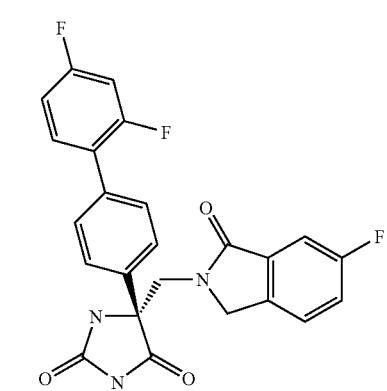
TABLE B-continued
Structure
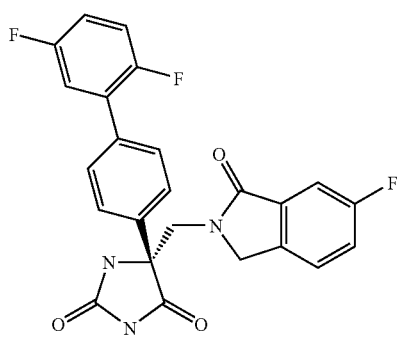
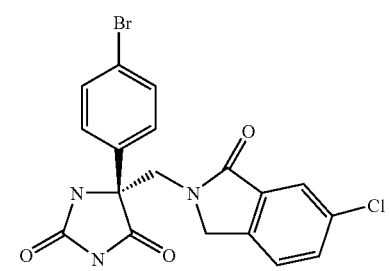
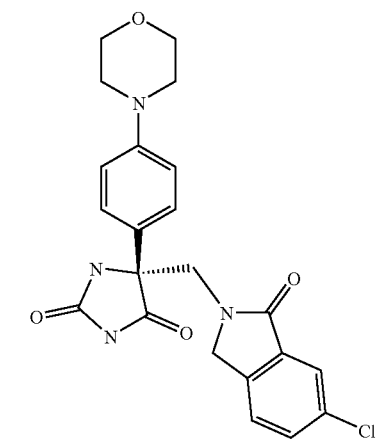
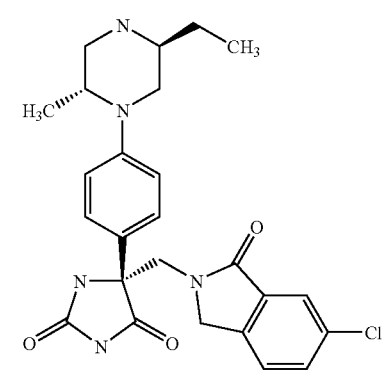

131
TABLE B-continued
Structure
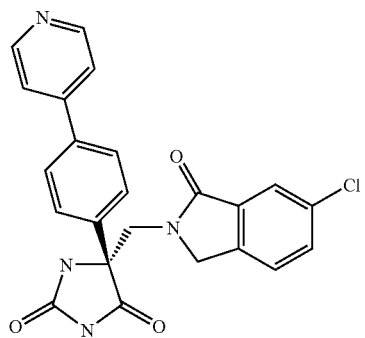
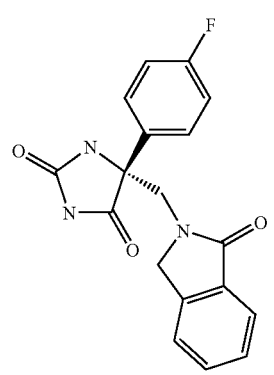
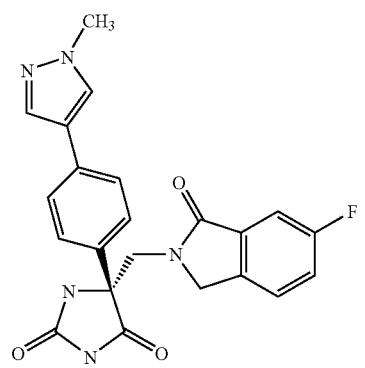
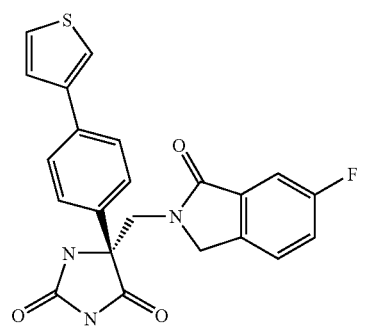
132
TABLE B-continued
Structure
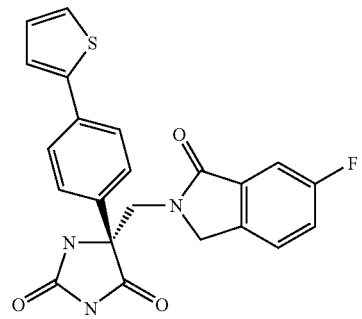
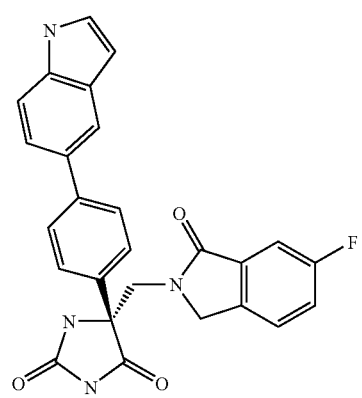
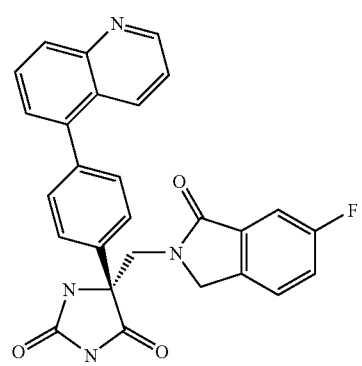
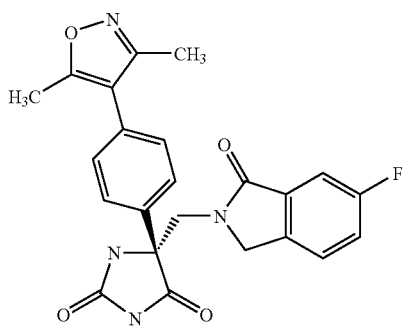

TABLE B-continued
Structure
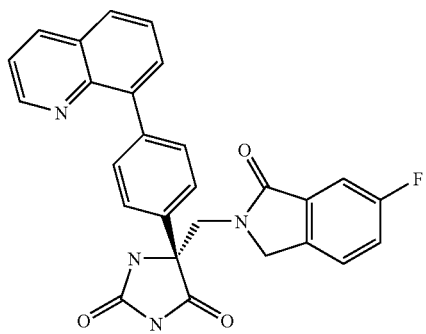
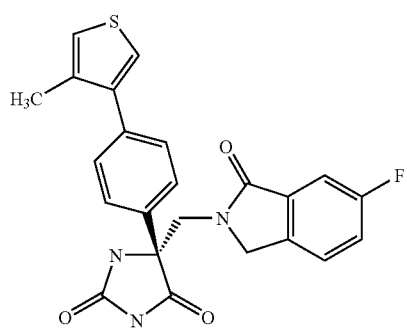
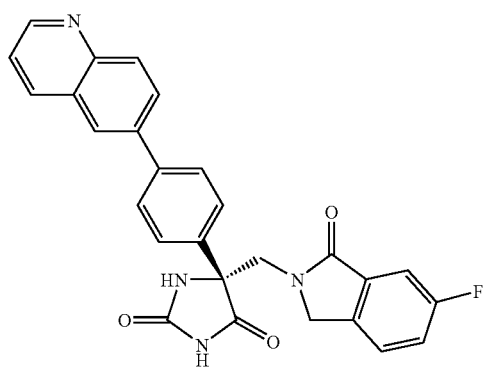
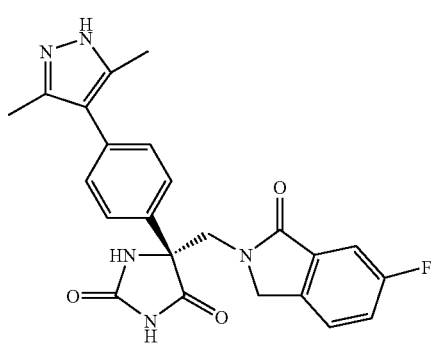
TABLE B-continued
Structure
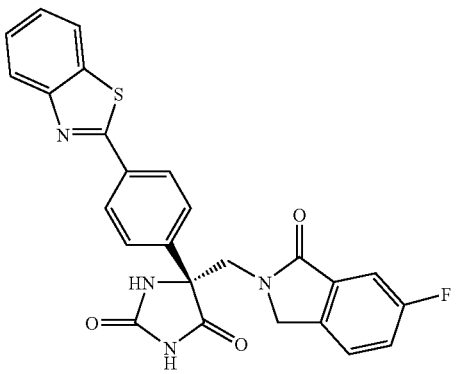
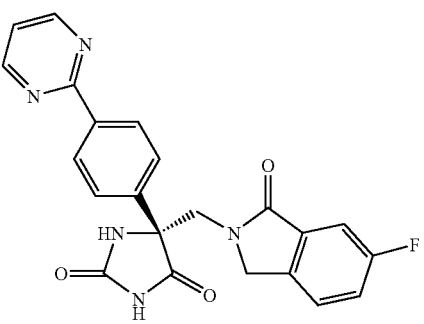
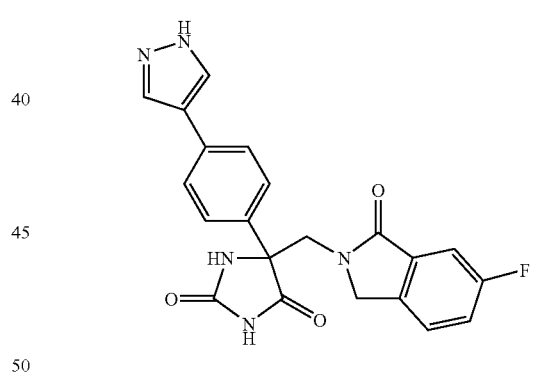
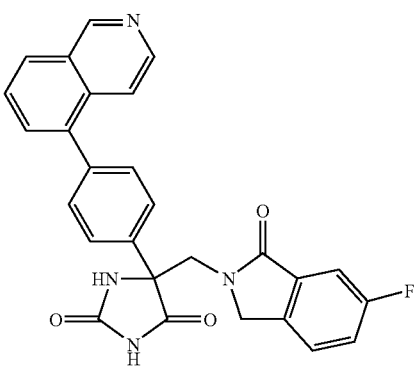

TABLE B-continued

Structure

TABLE B-continued
Structure
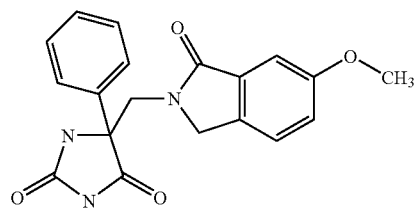
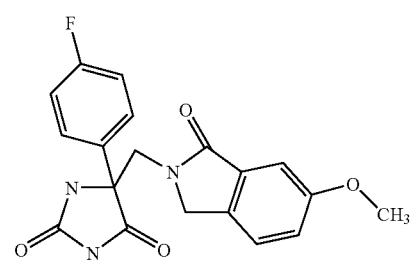
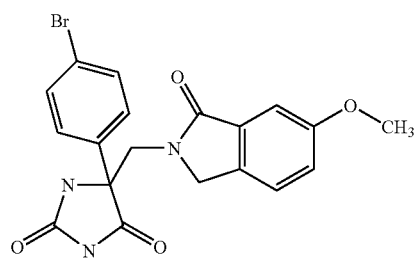
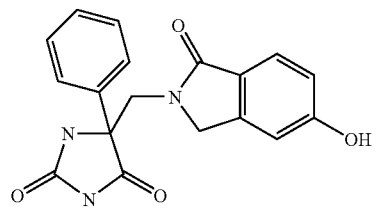
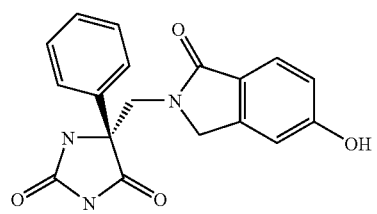
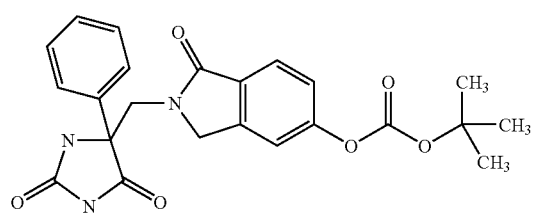
TABLE B-continued
Structure
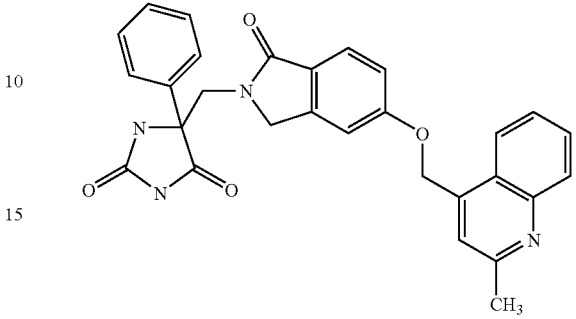
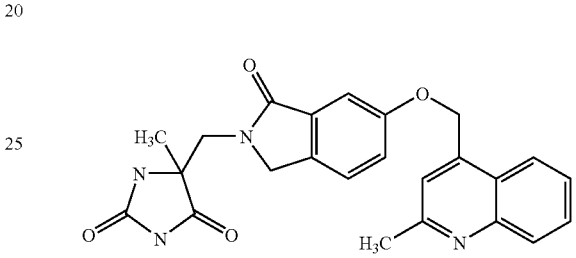
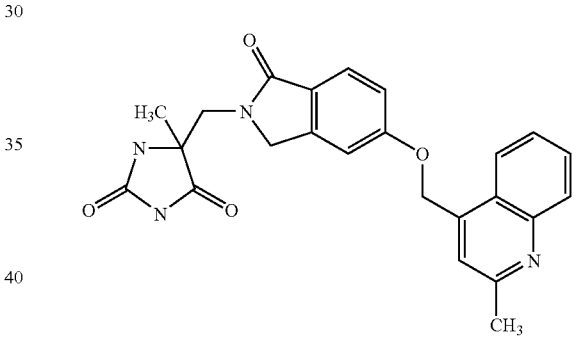
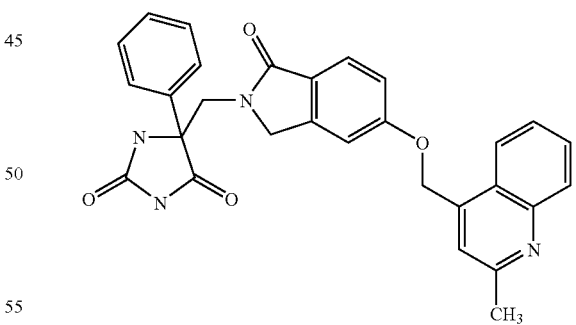
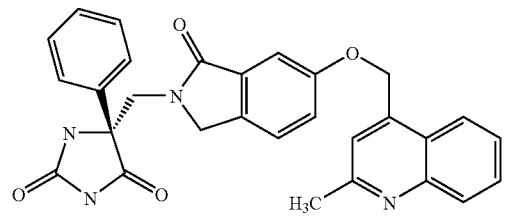

TABLE B-continued
Structure
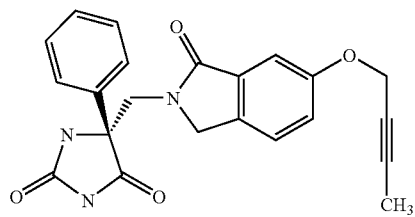
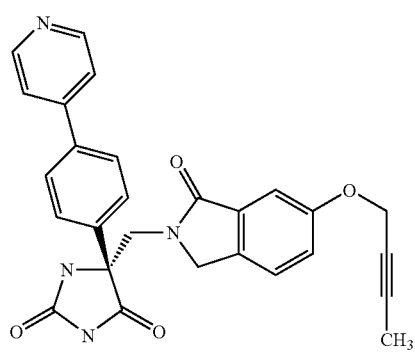
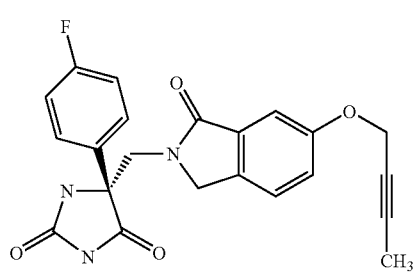
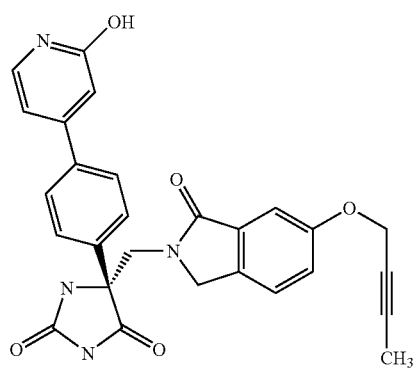
TABLE B-continued
Structure
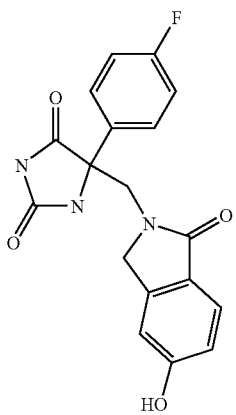
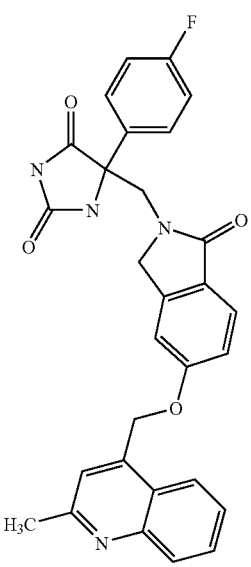
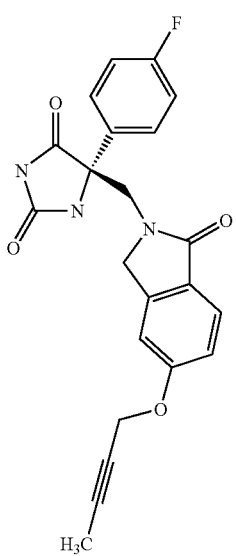

TABLE B-continued
Structure
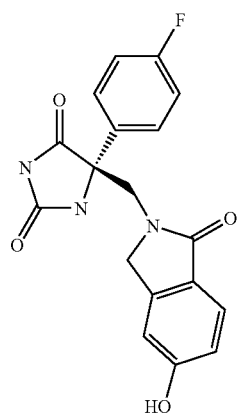
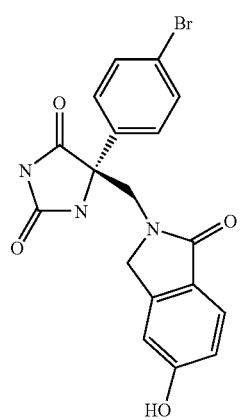
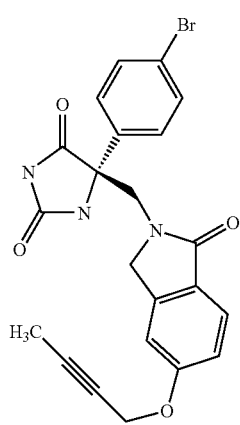
TABLE B-continued
Structure
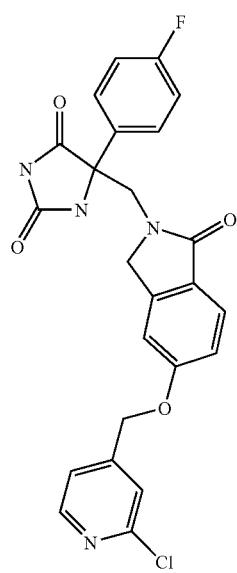
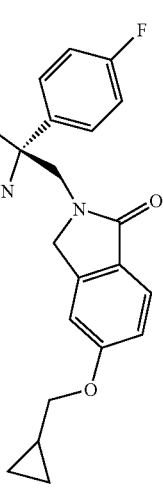
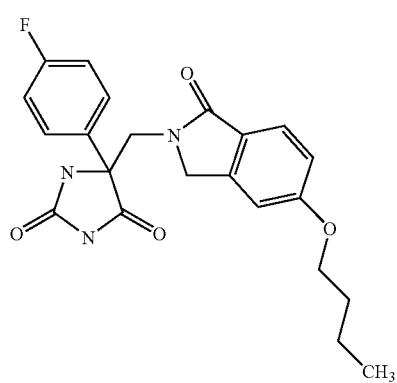

TABLE B-continued
Structure
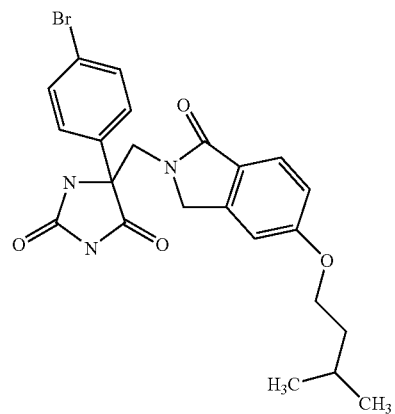
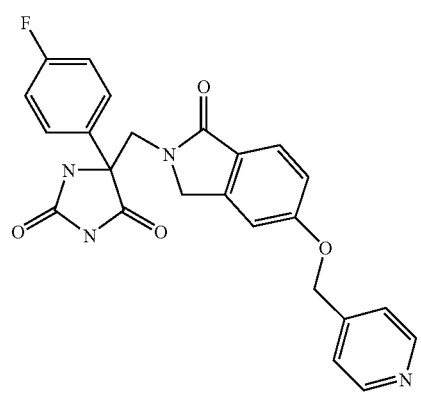
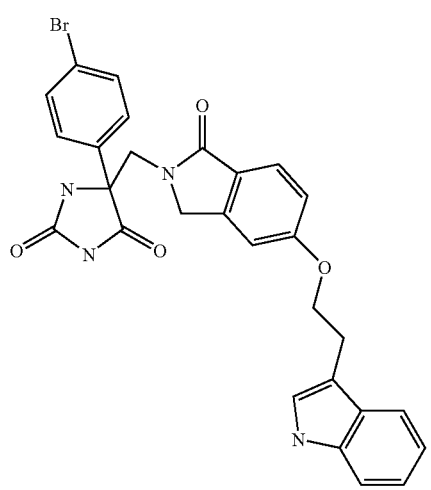
TABLE B-continued
Structure
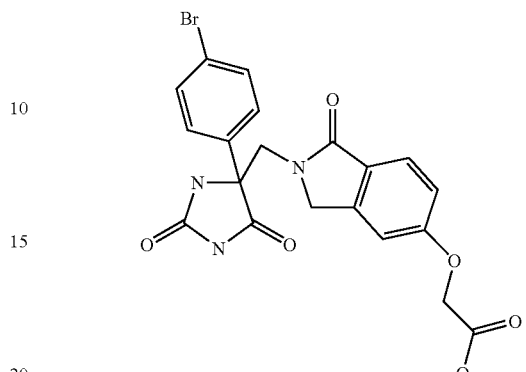
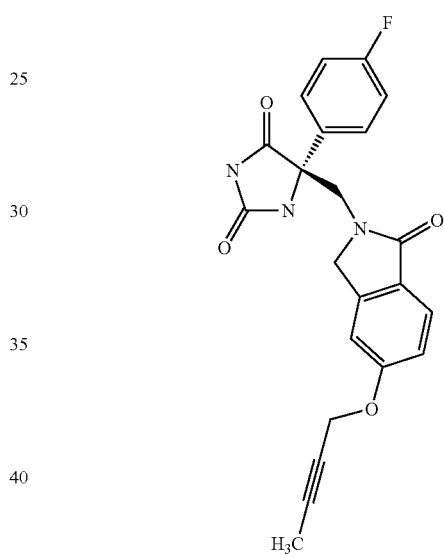
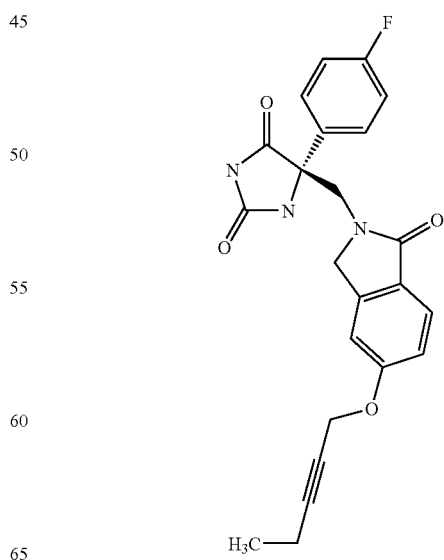

TABLE B-continued
Structure
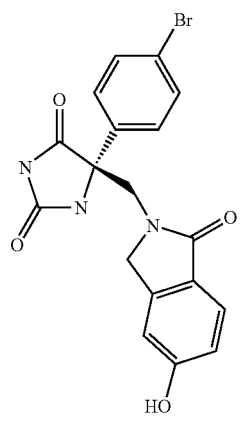
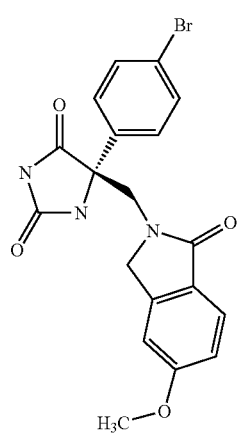
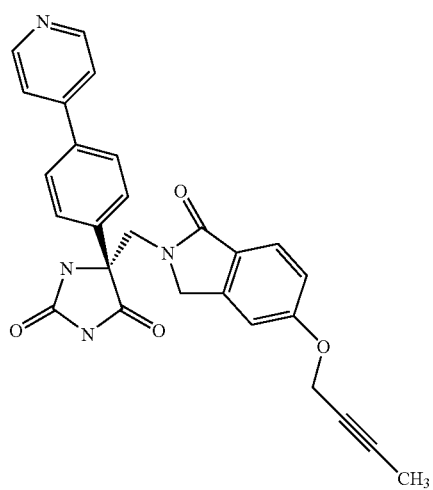
TABLE B-continued
Structure
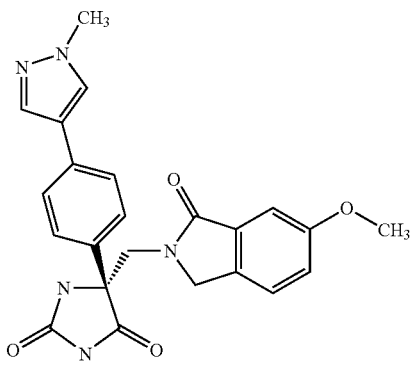
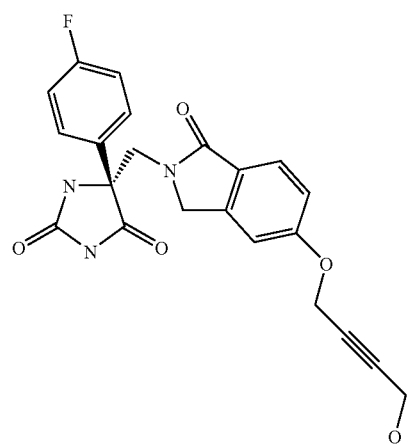
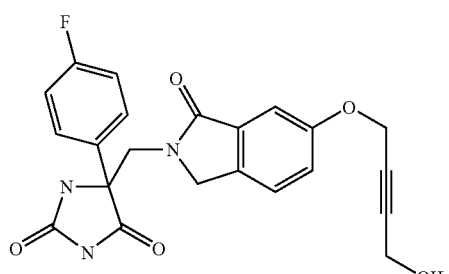
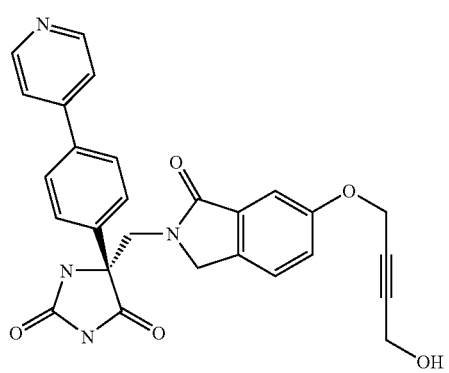

TABLE B-continued
Structure
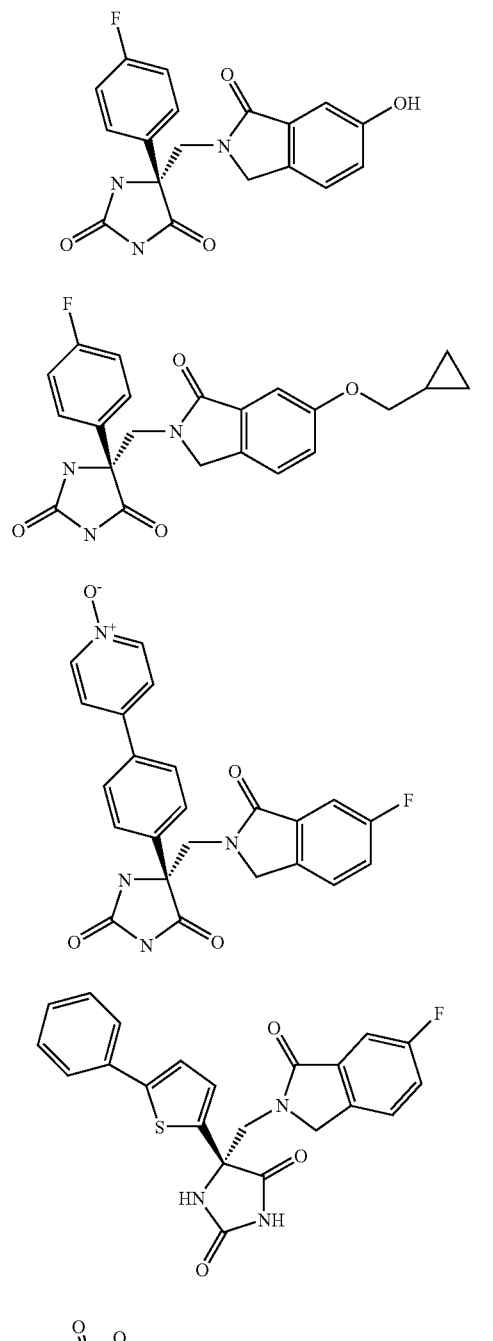
TABLE B-continued
Structure
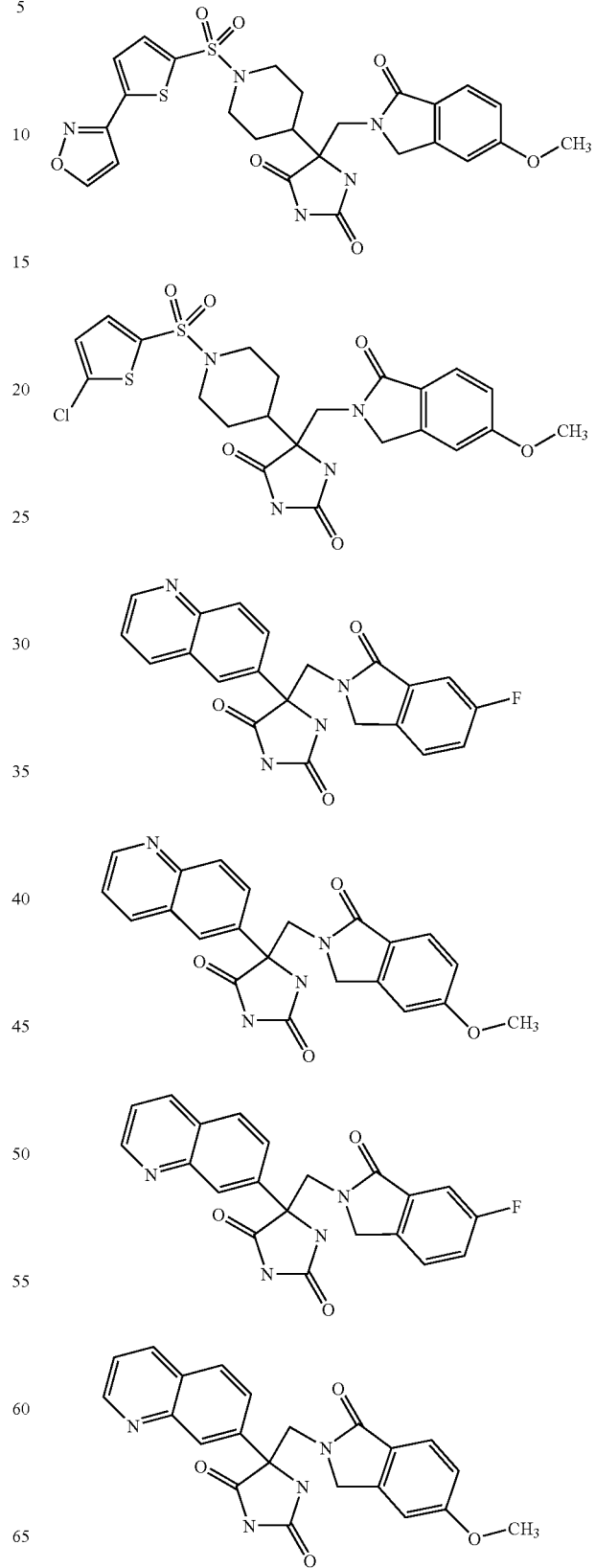

TABLE B-continued
| Structure |
|---|
| 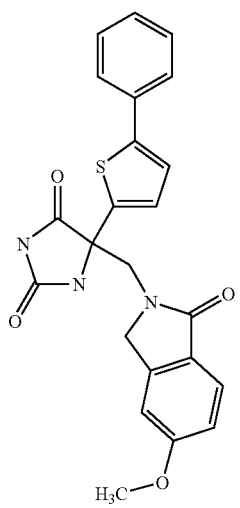 |
| 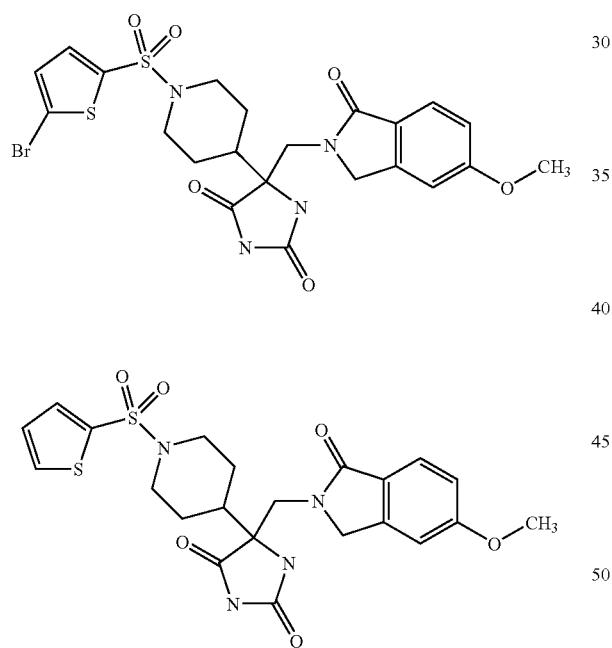 |
| 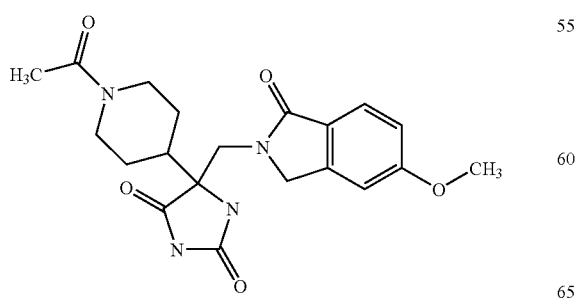 |
TABLE B-continued
| Structure |
|---|
| 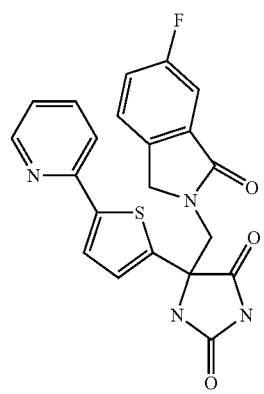 |
| 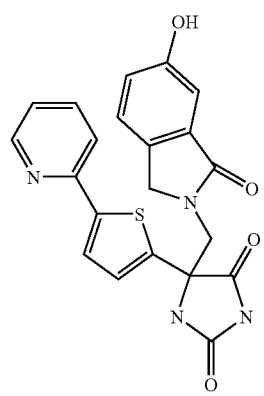 |
| 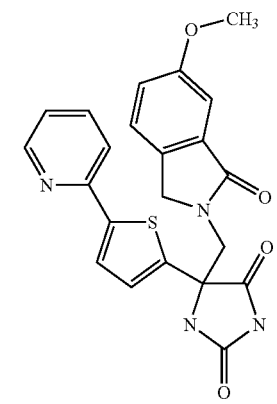 |

TABLE B-continued
Structure
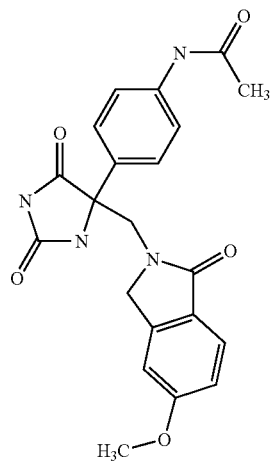
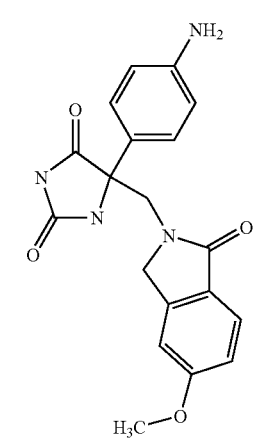
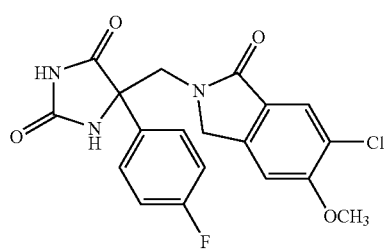
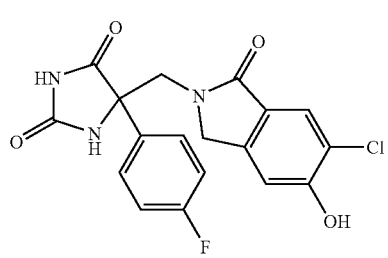
TABLE B-continued
Structure
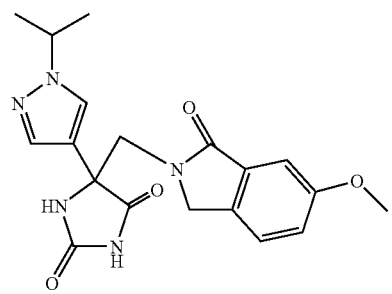
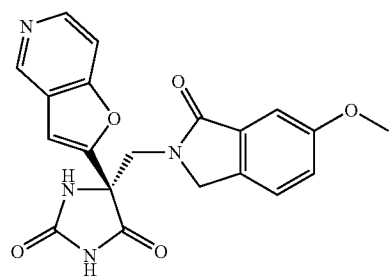
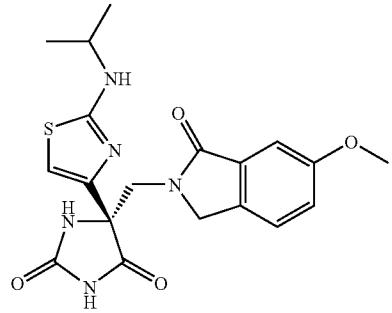
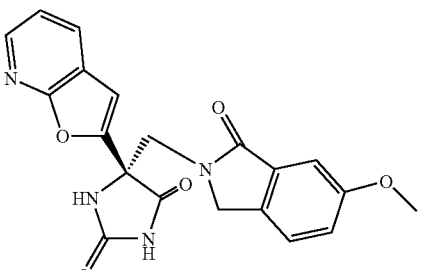
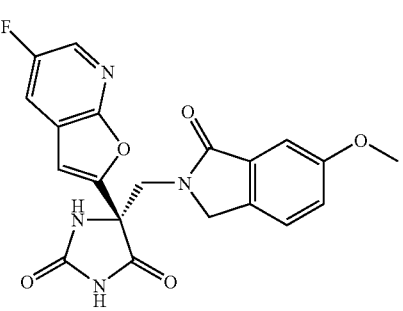

TABLE B-continued
| Structure |
|---|
| 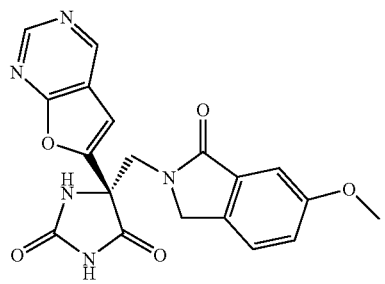 |
| 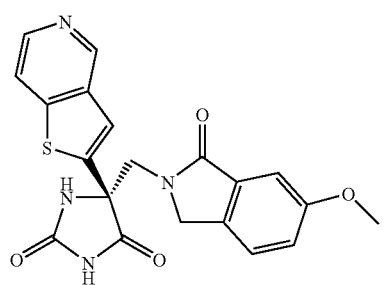 |
| 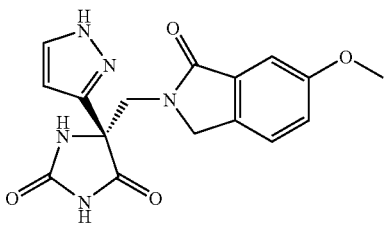 |
| 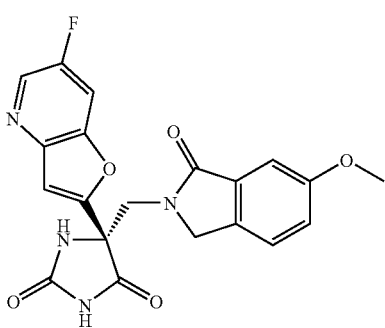 |
| 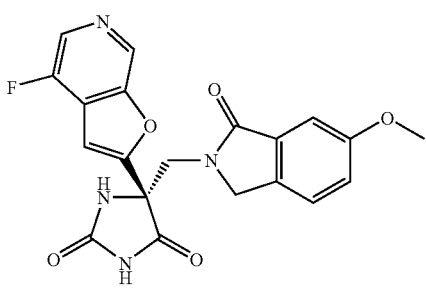 |
TABLE B-continued
| Structure |
|---|
| 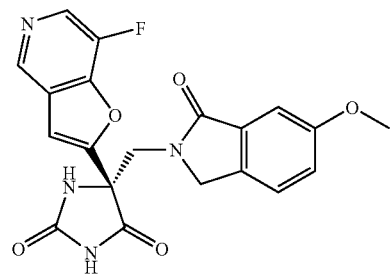 |
| 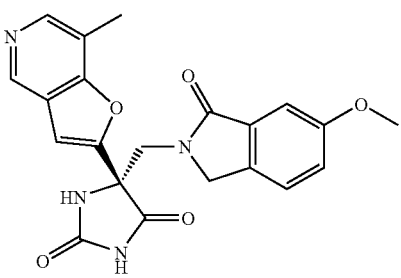 |
| 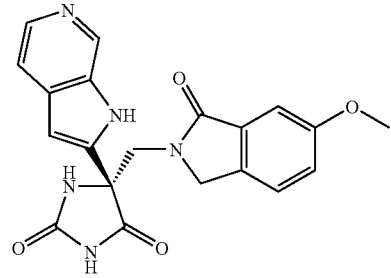 |
| 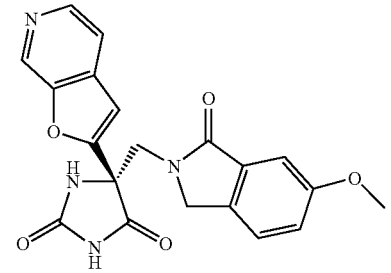 |
| 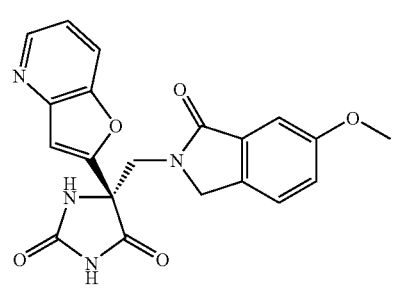 |

TABLE B-continued
Structure
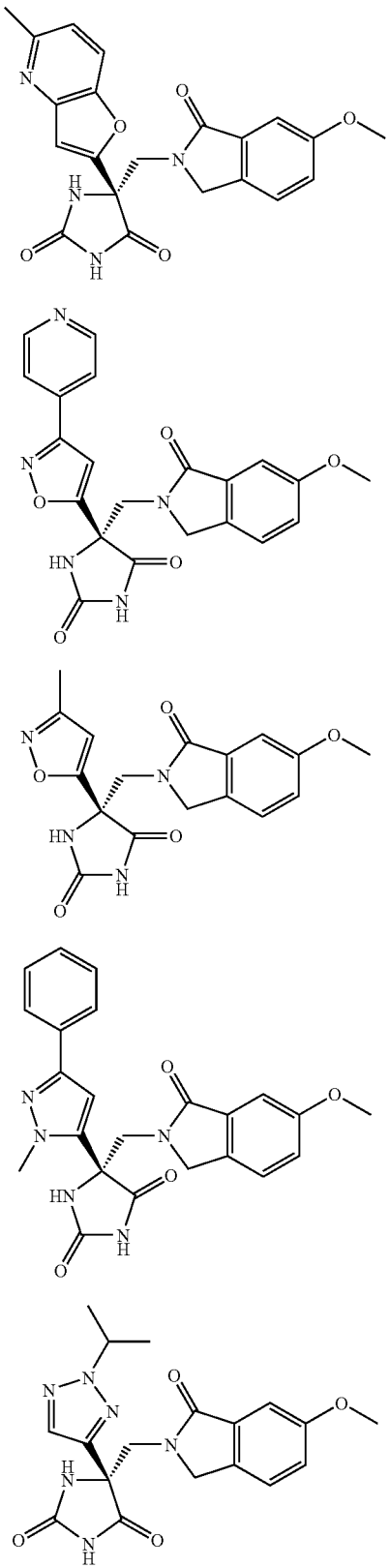
TABLE B-continued
Structure
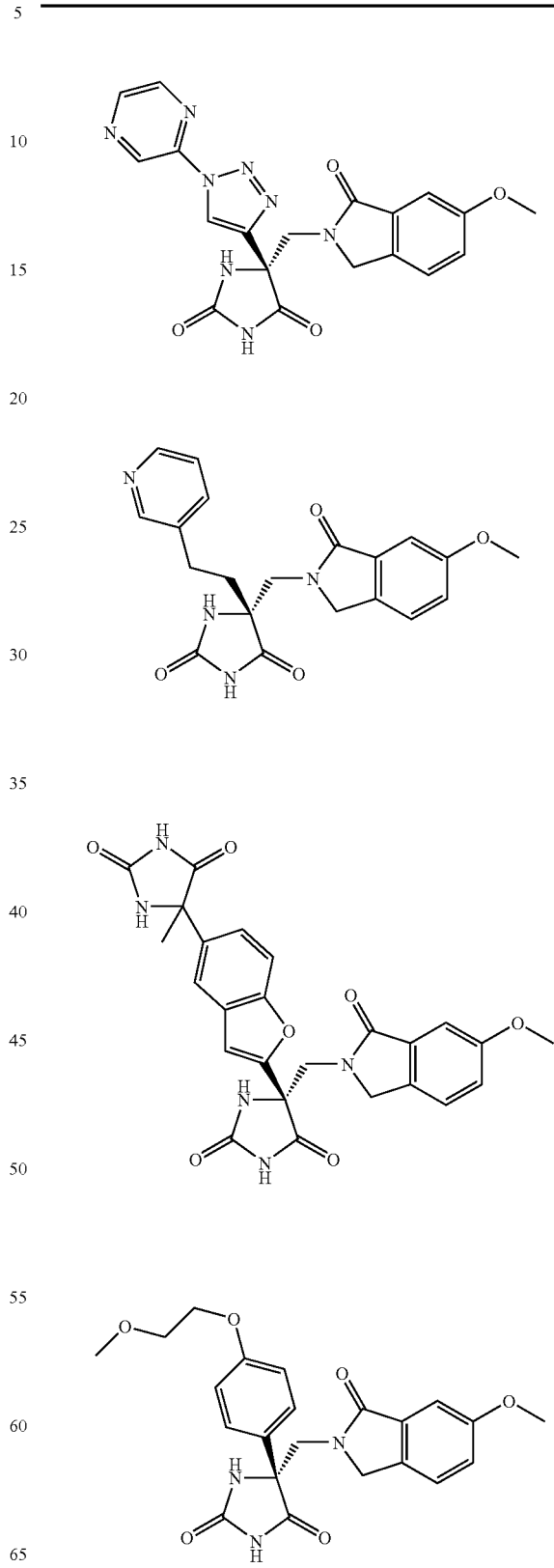

TABLE B-continued
Structure
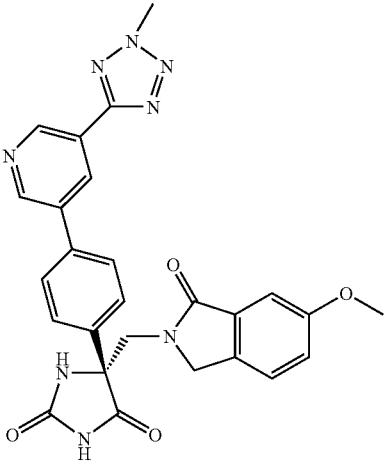
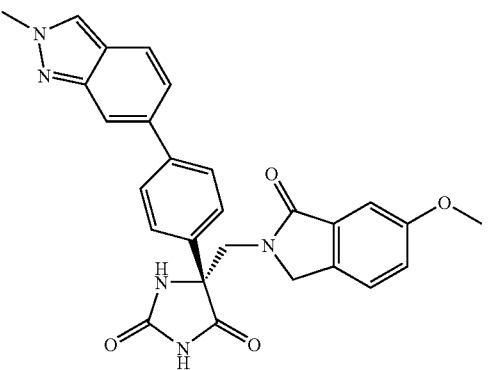
Another embodiment of the invention discloses the compounds shown in Table C below or a pharmaceutically acceptable salt, solvate, or ester thereof.
TABLE C
Structure
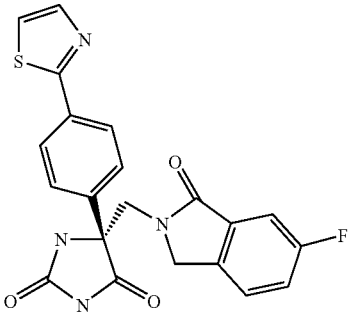
TABLE C-continued
Structure
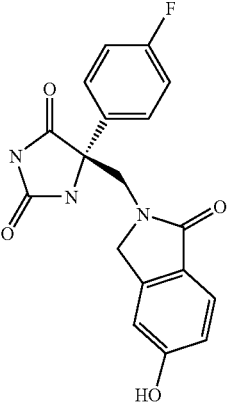
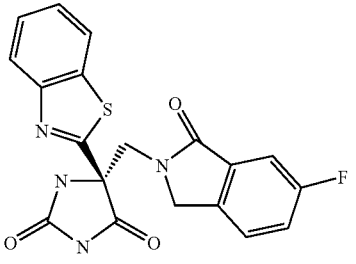
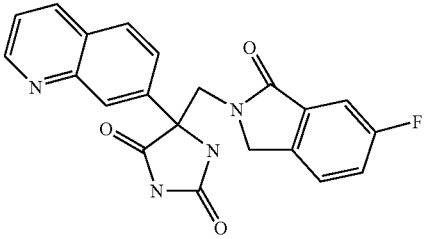
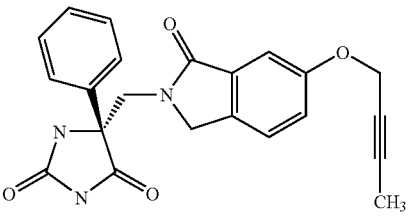
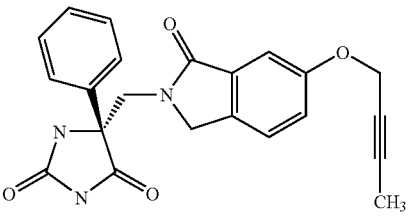

TABLE C-continued
Structure
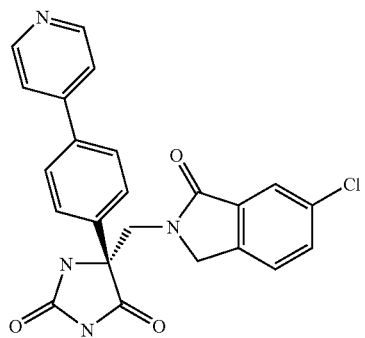
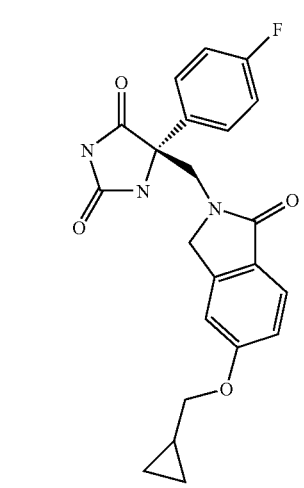
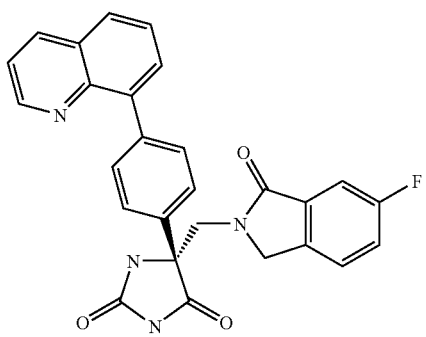
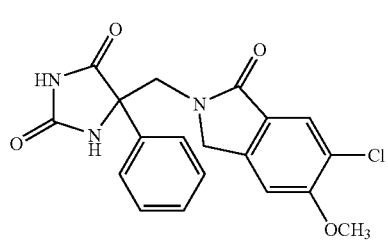
TABLE C-continued
Structure
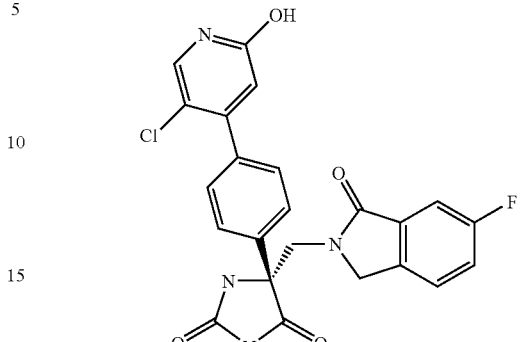
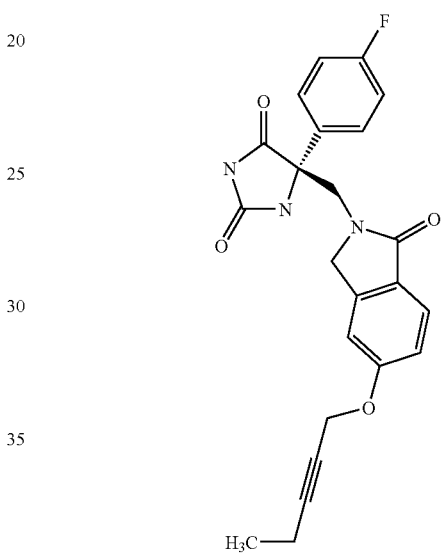
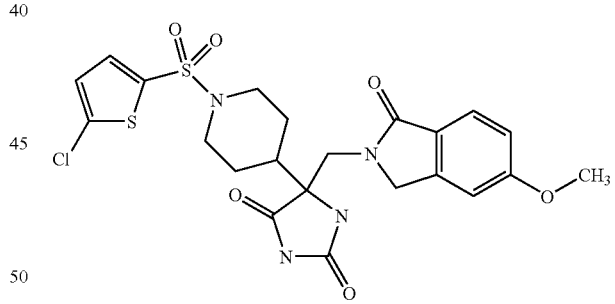
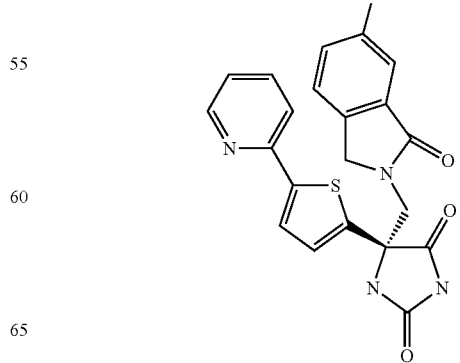

TABLE C-continued
Structure
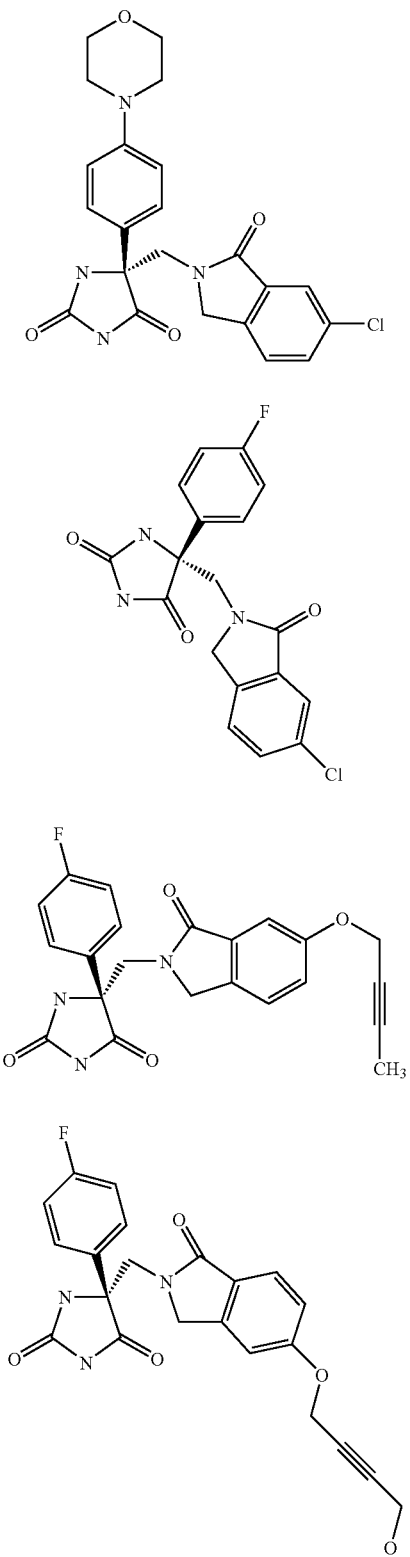
TABLE C-continued
Structure
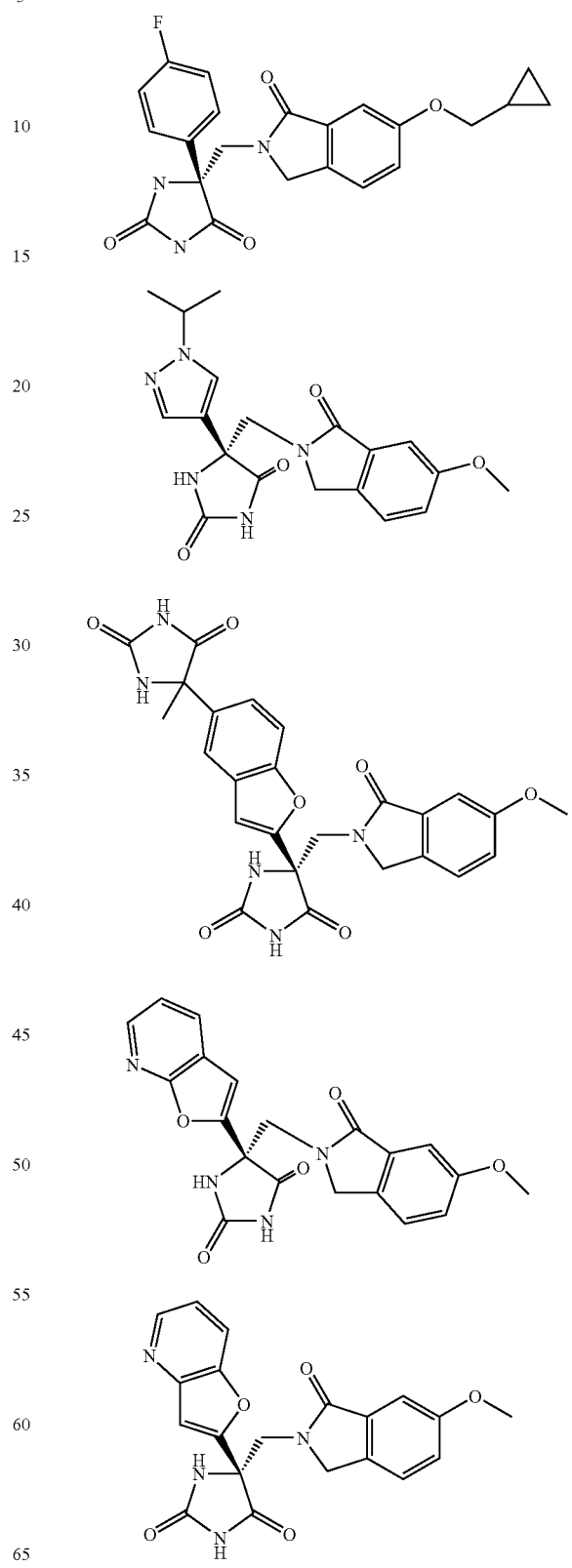

TABLE C-continued

Structure

[Chemical structure]

[Chemical structure]

[Chemical structure]

[Chemical structure]

[Chemical structure]

TABLE C-continued

Structure

[Chemical structure]

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), G$_1$G$_2$N—, G$_1$G$_2$N-alkyl-, G$_1$G$_2$NC(O)—, G$_1$G$_2$NSO$_2$— and —SO$_2$NG$_1$G$_2$, wherein G$_1$ and G$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

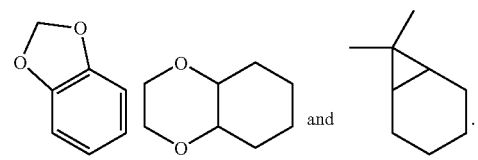

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes a ring system wherein a single moiety (e.g., carbonyl) simultaneously replaces two available hydrogens on the same carbon atom on the ring system. Examples of such moieties are pyrrolidone:

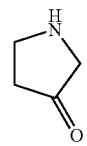

and thiomorpholinone:

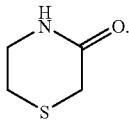

It should be noted that tautomeric forms such as, for example, the moieties:

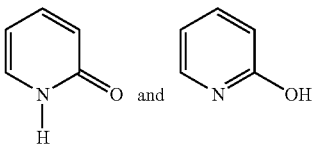

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$) alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —$C(OH)C(O)OY^1$ wherein $Y^1$ is H, ($C_1$-$C_6$)alkyl or benzyl, —$C(OY^2)Y^3$ wherein $Y^2$ is ($C_1$-$C_4$) alkyl and $Y^3$ is ($C_1$-$C_6$)alkyl, carboxy($C_1$-$C_6$)alkyl, amino ($C_1$-$C_4$)alkyl or mono-N— or di-N,N—($C_1$-$C_6$)alkylaminoalkyl, —$C(Y^4)Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting TACE, the production of TNF-α, MMPs, ADAMS or any combination thereof and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I, and of the salts, solvates and prodrugs of the compounds of Formula I, are intended to be included in the present invention.

The compounds according to the invention have pharmacological properties; in particular, the compounds of Formula I can be inhibitors of TACE, TNF-α and/or MMP activity.

In one aspect, the invention provides a pharmaceutical composition comprising as an active ingredient at least one compound of formula (I).

In another aspect, the invention provides a pharmaceutical composition of formula (I) additionally comprising at least one pharmaceutically acceptable carrier.

In another aspect, the invention provides a method of treating disorders associated with TACE, TNF-α, MMPs, ADAMs or any combination thereof, said method comprising administering to a patient in need of such treatment a pharmaceutical composition which comprises therapeutically effective amounts of at least one compound of formula (I).

In another aspect, the invention provides a use of a compound of formula (I) for the manufacture of a medicament to treat disorders associated with TACE, TNF-α, MMPs, ADAMs or any combination thereof.

The compounds of Formula I can have anti-inflammatory activity and/or immunomodulatory activity and can be useful in the treatment of diseases including but not limited to septic shock, hemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, OA and RA, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. It is contemplated that a compound of this invention may be useful in treating one or more of the diseases listed.

In another aspect, the invention provides a method of preparing a pharmaceutical composition for treating the disorders associated with TACE, TNF-α, MMPs, ADAMs or any combination thereof, said method comprising bringing into intimate contact at least one compound of formula (I) and at least one pharmaceutically acceptable carrier.

In another aspect, the invention provides a compound of formula (I) exhibiting TACE, TNF-α, MMPs, ADAMs or any combination thereof inhibitory activity, including enantiomers, stereoisomers and tautomers of said compound, and pharmaceutically acceptable salts, esters, or solvates of said compound, said compound being selected from the compounds of structures listed in Table A set forth above.

In another aspect, the invention provides a pharmaceutical composition for treating disorders associated with TACE, TNF-α, MMP, ADAM or any combination thereof in a subject comprising, administering to the subject in need of such treatment a therapeutically effective amount of at least one compound of formula (I) or a pharmaceutically acceptable salt, solvate, ester or isomer thereof.

In another aspect, the invention provides a compound of formula (I) in purified form.

In another aspect, the invention provides a method of treating a condition or disease mediated by TACE, MMPs, TNF-α, aggrecanase, or any combination thereof in a subject comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one compound of formula (I) or a pharmaceutically acceptable salt, solvate, ester, or isomer thereof.

In another aspect, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease and HIV infection in a subject comprising administering to the subject in need of such treatment a therapeutically effective amount of at least one compound of formula (I) or a pharmaceutically acceptable salt, solvate, ester, or isomer thereof.

In another aspect, the invention provides a method of treating a condition or disease selected from the group consisting of septic shock, hemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with COPD, comprising: administering to the subject in need of such treatment a therapeutically effective amount of at least one compound of formula (I) or a pharmaceutically acceptable salt, solvate, ester, or isomer thereof.

In another aspect, the invention provides a method of treating a condition or disease associated with rheumatoid arthritis, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with Crohn's disease, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with psoriasis, comprising: administering to the subject in need of such treatment a therapeutically effective amount of at least one compound of formula (I) or a pharmaceutically acceptable salt, solvate, ester, or isomer thereof.

In another aspect, the invention provides a method of treating a condition or disease associated with ankylosing spondylitis, comprising: administering to the subject in need of such treatment a therapeutically effective amount of at least one compound of formula (I) or a pharmaceutically acceptable salt, solvate, ester, or isomer thereof.

In another aspect, the invention provides a method of treating a condition or disease associated with sciatica, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with complex regional pain syndrome, comprising: administering to the subject in need of such treatment a therapeutically effective amount of at least one compound of formula (I) or a pharmaceutically acceptable salt, ester, solvate or isomer thereof.

In another aspect, the invention provides a method of treating a condition or disease associated with psoriatic arthritis, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with multiple sclerosis, comprising: administering to the subject in need of such treatment a therapeutically effective amount of at least one compound of formula (I) or a pharmaceutically acceptable salt, solvate, ester or isomer thereof, in combination with a compound selected from the group consisting of Avonex®, Betaseron, Copaxone or other compounds indicated for the treatment of multiple sclerosis.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with non-steroidal anti-inflammatory drugs (NSAIDs) such as piroxicam, naproxen, indomethacin, ibuprofen and the like; cycloxygenase-2 selective (COX-2) inhibitors such as Vioxx® and Celebrex®; immunosuppressives such as steroids, cyclosporin, Tacrolimus, rapamycin and the like; biological response modifiers (BRMs) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, other chemically different TACE inhibitors, chemokine receptor antagonists, Thalidomide and other small molecule inhibitors of pro-inflammatory cytokine production.

Also, a compound of the present invention may be co-administered or used in combination with an H1 antagonist for the treatment of seasonal allergic rhinitis and/or asthma. Suitable H1 antagonists may be, for example, Claritin®, Clarinex®, Allegra®, or Zyrtec®.

In another aspect, the invention provides a method of treating a condition or disease mediated by TACE, MMPs, TNF-α, aggrecanase, or any combination thereof in a subject comprising: administering to the subject in need of such treatment a therapeutically effective amount of at least one compound of formula (I) or a pharmaceutically acceptable salt, solvate, ester or isomer thereof in combination with a therapeutically effective amount of at least one medicament selected from the group consisting of disease modifying anti-rheumatic drugs (DMARDS), NSAIDs, COX-2 inhibitors, COX-1 inhibitors, immunosuppressives, biological response modifiers (BRMs), anti-inflammatory agents and H1 antagonists.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one compound of formula (I) or a pharmaceutically acceptable salt, solvate, ester or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another aspect, the invention provides a method of treating a condition or disease selected from the group consisting of septic shock, hemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one compound of formula (I) or a pharmaceutically acceptable salt, solvate, ester or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another aspect, the invention provides a method for treating RA comprising administering a compound of the formula I in combination with compound selected from the class consisting of a COX-2 inhibitor e.g. Celebrex® or Vioxx®; a COX-1 inhibitor e.g. Feldene®; an immunosuppressive e.g. methotrexate or cyclosporin; a steroid e.g. β-methasone; and anti-TNF-α compound, e.g. Enbrel® or Remicade®; a PDE IV inhibitor, or other classes of compounds indicated for the treatment of RA.

In another aspect, the invention provides a method for treating multiple sclerosis comprising administering a compound of the formula I in combination with a compound selected from the group consisting of Avonex®, Betaseron, Copaxone or other compounds indicated for the treatment of multiple sclerosis.

TACE activity is determined by a kinetic assay measuring the rate of increase in fluorescent intensity generated by TACE catalyzed cleavage of an internally quenched peptide substrate (SPDL-3). The purified catalytic domain of recombinant human TACE (rhTACEc, Residue 215 to 477 with two mutation (S266A and N452Q) and a 6×His tail) is used in the assay. It is purified from the baculovirus/Hi5 cells expression system using affinity chromatography. The substrate SPDL-3 is an internally quenched peptide (MCA-Pro-Leu-Ala-Gln-Ala-Val-Arg-Ser-Ser-Ser-Dpa-Arg-NH2), with its sequence derived from the pro-TNFα cleavage site. MCA is (7-Methoxycoumarin-4-yl)acetyl. Dpa is N-3-(2,4-Dinitrophenyl)-L-2,3-diaminopropionyl.

A 50 μl assay mixture contains 20 mM HEPES, pH 7.3, 5 mM $CaCl_2$, 100 μM $ZnCl_2$, 2% DMSO, 0.04% Methylcellulose, 30 μM SPDL-3, 70 pM rhTACEc and a test compound. RhTACEc is pre-incubated with the testing compound for 90 min. at 25° C. Reaction is started by addition of the substrate. The fluorescent intensity (excitation at 320 nm, emission at 405 nm) was measured every 45 seconds for 30 min. using a fluorospectrometer (GEMINI XS, Molecular Devices). Rate of enzymatic reaction is shown as Units per second. Effect of a test compound is shown as % of TACE activity in the absence of the compound.

Useful compounds for TACE inhibitory activity can exhibit $K_i$ values of less than about 1000 nm, preferably about 0.01 nm to about 1000 nm, more preferably about 0.1 nm to about 100 nm, and most preferably less than about 15 nm. The TACE inhibitory activity (Ki values) of some representative compounds of the present invention are listed in the "EXAMPLES" section hereinbelow.

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for controlled release.

The term pharmaceutical composition is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsion. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of Formula I useful in the method of the present invention range from 0.01 to 1000 mg per day. More preferably, dosages range from 0.1 to 1000 mg/day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The compounds of the invention may be produced by processes known to those skilled in the art and as shown in the following reaction schemes and in the preparations and examples described below.

EXAMPLES

The following abbreviations may be used in the procedures and schemes:
ACN Acetonitrile
AcOH Acetic acid
Aq Aqueous
BOC tert-Butoxycarbonyl BOC₂O BOC Anhydride
C degrees Celsius
CBZCl Benzyl chloroformate
DBU 1,8-Diazabicyclo[5.4.0]undec-7-ene
DCM Dichloromethane
DEAD Diethyl azodicarboxylate
(DHQ)2PHAL Hydroquinine 1,4-phthalazinediyl diether
DIAD Diisopropylazodicarboxylate
DIPEA Diisopropylethylamine
DMA N,N-Dimethylacetamide
DMAP 4-Dimethylaminopyridine
DME Dimethoxyethane
DMF Dimethylformamide
DMPU 1,3-Dimethyl-3,4,5,6-tetrahydro-2(1h)-pyrimidinone
DMSO Dimethyl sulfoxide
EDCl 1-(3-Dimethylaminopropyl)-3-ethylcarbodiimide hydrochloride
EI Electron ionization
Eq Equivalents
EtOAc Ethyl acetate
EtOH Ethanol
g grams
h hours
hr hours
$^1$H proton
HATU N,N,N',N'-Tetramethyl-O-(7-Azabenzotriazol-1-yl) Uronium hexafluorophosphate
Hex hexanes
HOBT 1-Hydroxybenzotriazole
HPLC High pressure liquid chromatography
LAH Lithium aluminum hydride
LDA Lithium diisopropylamide
M Molar
mmol millimolar
mCPBA meta-Chloroperoxybenzoic acid
Me Methyl
MeCN Acetonitrile
MeOH Methanol
min Minutes
mg Milligrams
MHZ Megahertz
mL Milliliter
MPLC Medium Pressure Liquid Chromatography
NMR Nuclear Magnetic Resonance
MS Mass Spectroscopy
NBS N-Bromosuccinimide
NMM N-Methylmorpholine
NMP 1-methyl-2-pyrrolidone
ON Overnight
PCC Pyridinium Chlorochromate
PTLC Preparative thin layer chromatography
PyBrOP Bromo-tris-pyrrolidino-phosphonium hexafluorophosphate
Pyr Pyridine
RT Room temperature
sgc Silica gel 60 chromatography
tBOC tert-Butoxycarbonyl
TACE TNF-alpha converting enzyme
TEA Triethylamine
TFA Trifluoroacetic acid
THF Tetrahydrofuran
TLC Thin layer chromatography NMR spectra were acquired on the following instruments: 400 MHZ NMR (Bruker), 500 MHZ NMR (Bruker), 400 MHz NMR (Varian), 300 MHZ NMR (Varian) using CD₃OD, CDCl₃ or DMSO-d₆ as solvents. LC-MS data were obtained using a PESciex API 150EX quadropole mass spectrometer using electroscopy ionization.

Purification via reverse phase chromatography (Gilson) was accomplished using a C18 reverse phase column with a gradient of (0.1% formic acid) 5:95 to 90:10 acetonitrile:water, at a flow rate of 14 mL/min. Samples were collected using UV detection. Alternatively an ISCO Companion with (0.1% formic acid) 5:95 to 95:5 acetonitrile:water, at a flow rate=10–55 mL/min.

Normal phase silica gel chromatography was either accomplished on a Biotage instrument using a 60 Å 12/M, 25/M, or 40/M flash cartridges, or on a Jones Flash Master Personal instrument using Isolute flash Si 5 g, 10 g, 20 g, 50 g, or 70 g cartridges.

The compounds of formula (I) may be produced by processes known to those skilled in the art and as shown in the following reaction schemes and in the preparations and examples described below. These preparations and examples should not be construed to limit the scope of the disclosure. Alternate mechanistic pathways and analogous structures may be apparent to those skilled in the art. Some of the compounds made by these processes are listed in the tables below. All kinds of isomeric forms of the compounds are considered to be within the scope of this invention.

Synthetic Routes and Examples

Example 1

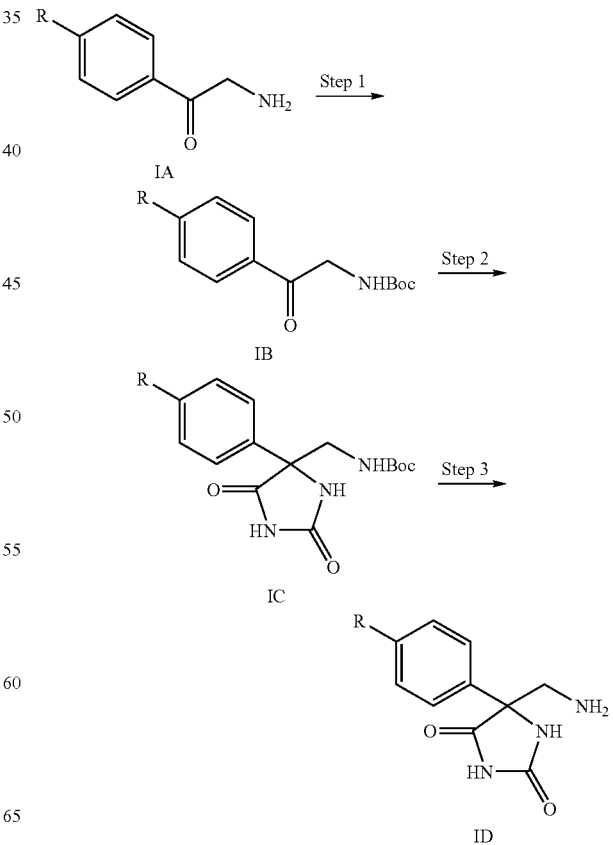

General Procedures for Example 1:

In step 1, Compound 1A (either commercially available, or prepared by a procedure similar to that described by Abdalla, G. M. and Sowell, J. W. *Journal of Heterocyclic Chemistry*, 1987, 24(2), 297-301) was treated with one equivalent of Di-tert-butyl dicarbonate in polar solvent, such as DMF, for 30 minutes to 12 hours. The solvent was removed and compound 1B could be used without further purification or purified by silica gel chromatography.

In step 2, compound 1B was reacted with potassium cyanide and ammonium carbonate in appropriated alcohol and water solution, at 50° C. to 90° C., for 5 hours to 48 hours. After cooling down, water was added and compound 1C could be collected by filtration.

In step 3, compound 1C was stirred with 2 to 20 equivalents of hydrogen chloride in methanol for 5 to 48 hours. After ethyl ether was added, Compound 1D could be collected by filtration.

Example 2

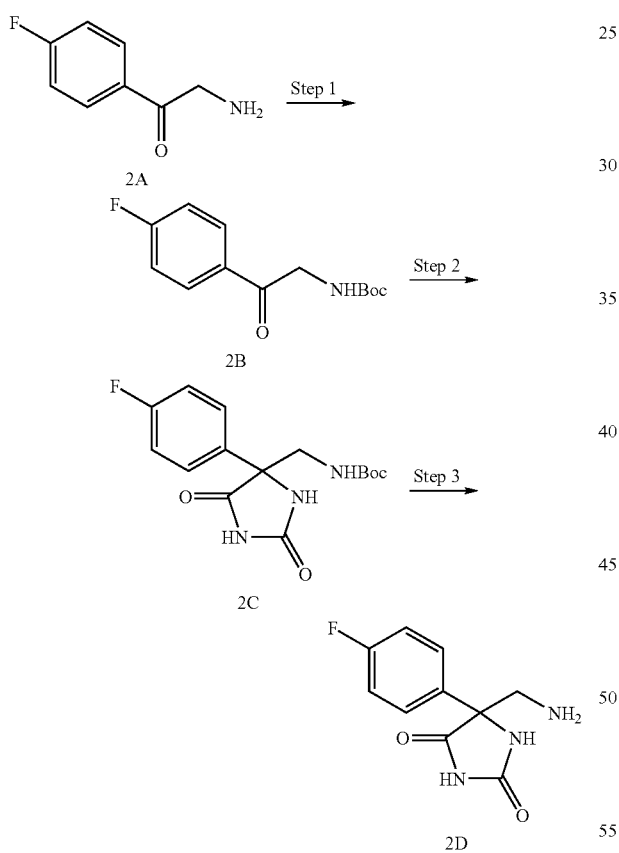

over $Na_2SO_4$. The solvent was removed by rotary evaporator to give compound 2B which was used without further purification.

Step 2

Compound 2B (9.06 g, 35.8 mmol), KCN (3.49 g, 53.7 mmol), and $(NH_4)_2CO_3$ (12.0 g, 125.2 mmol) were suspended in a mixture of EtOH (35 mL) and water (35 mL). The solution was stirred at 70° C. for three days. After cooling down, water (35 mL) was added. The solid was filtered and washed with water three times. The solid was dried under vacuum at 40° C. for 16 hours to give Compound 2C (7.9 g, 68%).

Step 3

Compound 2C (4.0 g) was suspended in methanol (50 mL) and HCl (4M in dioxane, 20 mL) was added. The solution was stirred at 25° C. for 3 hours. Ethyl ether (50 ml) was added. The solid was filtered, washed with ethyl ether twice, and dried under vacuum for 12 hours to give compound 2D (2.7 g, 84%).

The following intermediates were prepared as described in Examples 1 and 2.

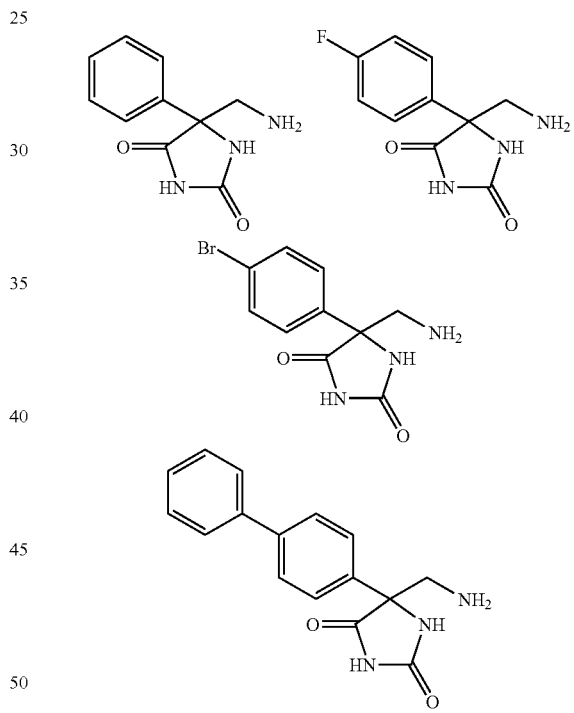

Example 3

Step 1

Compound 2A (Abdalla, G. M. and Sowell, J. W. *Journal of Heterocyclic Chemistry*, 1987, 24(2), 297-301) (Hydrochloride salt, 8.60 g, 45.4 mmol), triethyl amine (19.0 mL, 136 mmol), and di-tert-butyl dicarbonate (11.9 g, 54.4 mmol) were stirred in methylene chloride (100 mL) at 25° C. for 16 hours. Saturated aqueous $NaHCO_3$ (150 mL) was added. The aqueous layer was extracted with $CH_2Cl_2$ (100 mL) twice. The organic phase was washed with brine (100 mL) and dried

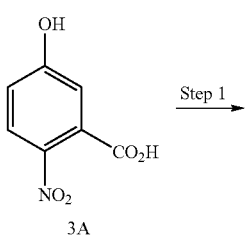

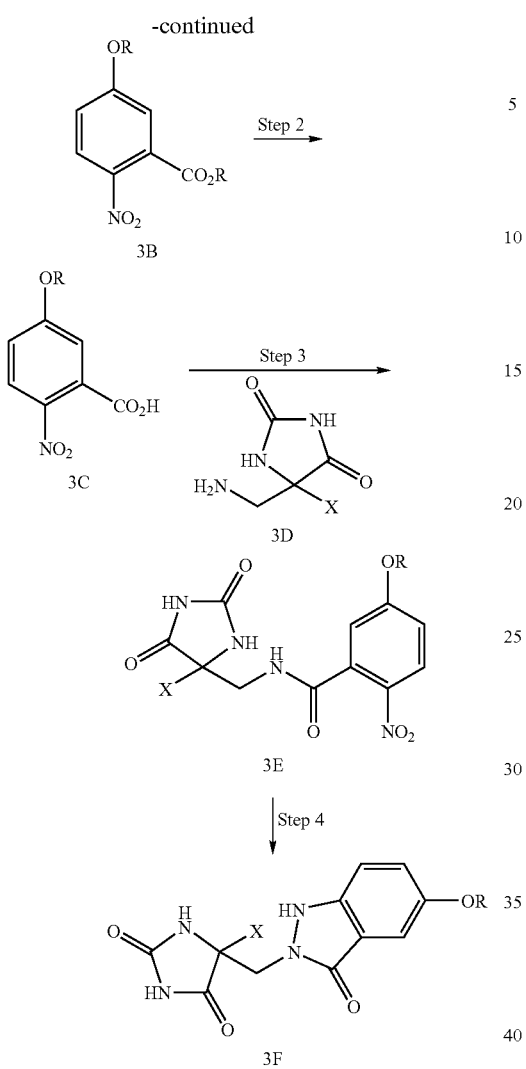

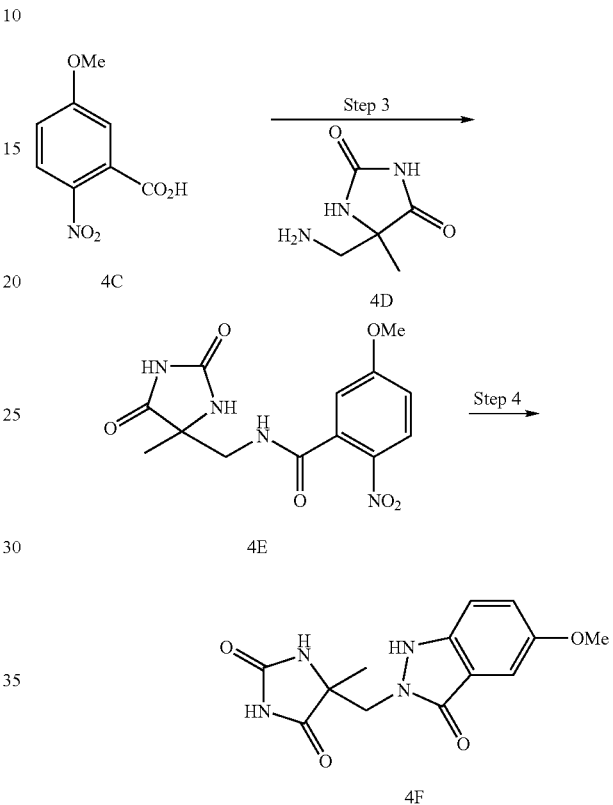

Example 4

Step 3

A 25 mL flask was charged with compound 4C (331 mg, 1.68 mmol), Compound 4D (Strafford, E. S, and Curley, R. W. Jr, *J. Med. Chem.* 1983, 26, 1463-1469) (200 mg, 1.4 mmol), EDCl (403 mg, 2.1 mmol), HOBT (227 mg, 1.68 mmol), NMM (0.46 mL, 4.2 mmol), and DMF (7 mL). The solution was stirred at room temperature overnight. Saturated aqueous $NaHCO_3$ (30 mL) and EtOAc (50 mL) were added. The organic phase was separated and washed with water (20 mL) and brine (20 mL), then dried over $Na_2SO_4$. The solvent was evaporated and the crude product was isolated by silica gel chromatography ($CH_2Cl_2$/MeOH/$NH_4OH$ 20:1:0.1 to 10:1:0.1) to give Compound 4E (201 mg, 45%).

Step 4

To a 10 mL flask was added compound 4E (50 mg, 0.155 mmol), NaOH (25 mg, 0.62 mmol), Zinc powder (62 mg, 0.47 mmol), MeOH (0.5 mL), and water (0.5 mL). The solution was stirred at 75° C. for 16 hours. After cooling to room temperature, solid was removed by filtration. The filtrate was adjusted to pH=5 by adding 2N HCl. The aqueous phase was extracted by EtOAc (10 mL). The organic solution was dried over $Na_2SO_4$ and concentrated. The product was isolated by General Procedures for Example 3

In step 1, 5-Hydroxy-2-nitro-benzoic acid (compound 3A) was dissolved in a suitable solvent, such as DMF, and reacted with an alkyl chloride or alkyl bromide in the presence of cesium carbonate at room temperature for 2 to 16 hours. Water and EtOAc were added. The organic phase was washed by water 1 to 5 times to remove DMF. The organic phase was washed with brine, dried, concentrated to give the crude product (compound 3B) which was used without further purification.

In step 2, compound 3B was dissolved in dioxane/water (3:1) and treated with lithium hydroxide at room temperature for 3 to 6 hours. The solution was made acidic by addition of 1N HCl solution and extracted with EtOAc. The products (compound 3C) were either used without further purification or purified by chromatography depending on the boiling point of the alcohol side products.

In step 3, compound 3C was dissolved in a suitable solvent, such as DMF, and coupled with compound 3D using EDCl and HOBT at room temperature overnight. After an aqueous/EtOAc work up, the product (compound 3E) was isolated by chromatography.

In step 4, compound 3E was suspended in MeOH/water (1:1) under $N_2$ atmosphere. NaOH and Zinc powder were added and the reaction mixture was stirred at 70° C. to 80° C. for 8 to 24 hours. After cooling to room temperature, the solution was adjusted to pH=6~7 with 1N HCl solution. The product (compound 3F) was extracted with EtOAc and purified by reverse phase HPLC.

silica gel chromatography (CH$_2$Cl$_2$/MeOH/NH$_4$OH, 40:1:0.1 to 20:1:0.1 to 10:1:0.1) to give compound 4F 6.5 mg (14%).

Example 5

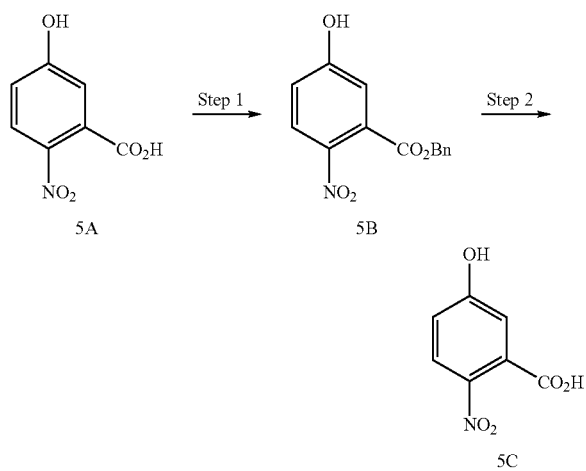

Step 1

Compound 5A (1.33 g, 7.26 mmol), benzyl bromide (2.73 g, 16.0 mmol), and Cs$_2$CO$_3$ (7.1 g, 22.0 mmol) were mixed in DMF (30 mL) and stirred at room temperature overnight. Saturated aqueous NaHCO$_3$ (100 mL) was added and the aqueous phase was extracted with EtOAc (100 mL) twice. The combined organic phases were washed with brine (50 mL), dried over Na$_2$SO$_4$, filtered, and concentrated by rotary evaporator. The product was isolated by silica gel chromatography (Hexane/EtOAc: 10:1 to 5:1) to give compound 5B (2.25 g, 89%).

Step 2

Compound 5B (2.25 g, 6.44 mmol) was dissolved in dioxane/water (3:1, 35 mL) and LiOH (810 mg, 19.3 mmol) was added. The solution was stirred at room temperature for 3 hours. Water (30 mL) was added followed by addition of 2N HCl (30 mL). The aqueous phase was extracted with EtOAc (50 mL) three times. The organic phase was washed with brine, dried over Na$_2$SO$_4$, filtered, and concentrated by rotary evaporator. The crude product was purified by silica gel chromatography (CH$_2$Cl$_2$/MeOH/HCO$_2$H: 40:1:0.1 to 20:1:0.1) to give compound 5C (1.6 g, 91%).

The following compounds were prepared as described in Examples 3-5.

In each of the tables below, those compounds having a Ki value of less than 10 nM (<10 nM) are designated with letter "A"; those with a Ki value of from 10 to less than 100 nM (10-<100 nM) are designated with letter "B"; those with a Ki value of from 100 to 1000 nM are designated with letter "C"; and those with a Ki value of more than 1000 nM (>1000 nM) are designated with letter "D".

TABLE 1

| Compound # | Structure | Exact Mass | Mass Obsvd | Ki (nM) |
|---|---|---|---|---|
| 1 | 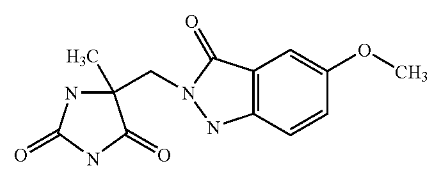 | 290.27 | 291.1 [M + H]$^+$ | B |
| 2 | 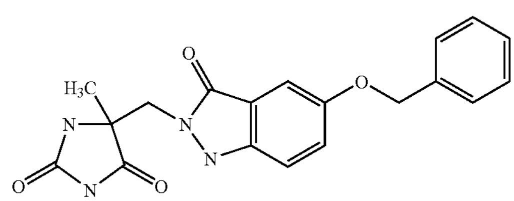 | 366.13 | 367.1 [M + H]$^+$ | C |
| 3 | 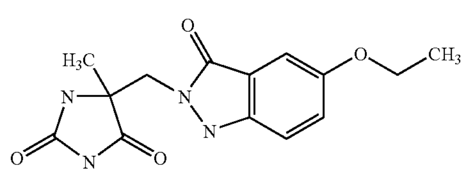 | 304.12 | 305.0 [M + H]$^+$ | C |
| 4 | 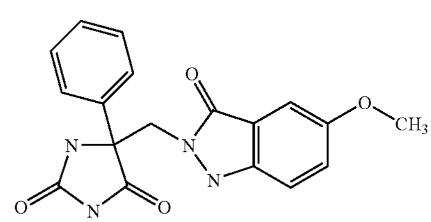 | 352.12 | 353.1 [M + H]$^+$ | A |

TABLE 1-continued

| Compound # | Structure | Exact Mass | Mass Obsvd | Ki (nM) |
|---|---|---|---|---|
| 5 | 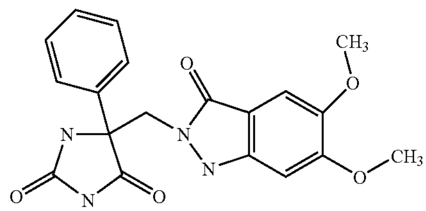 | 382.13 | 383.1 [M + H]+ | B |

Example 6

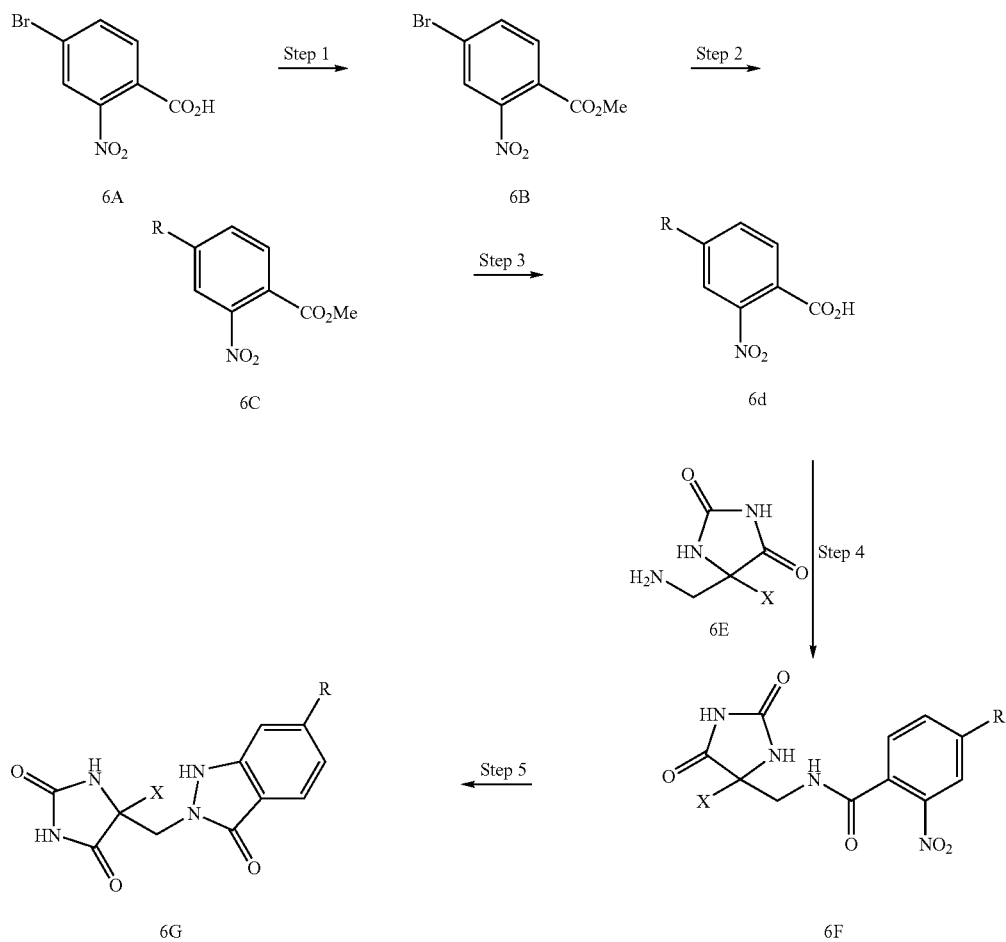

General Procedures for Example 6

In step 1, 4-Bromo-2-nitro-benzoic acid (compound 6A) was dissolved in a suitable solvent, such as DMF, and reacted with methyl iodide in the presence of cesium carbonate at room temperature for 2-16 hours. Water and EtOAc were added and the organic phase was washed by water 1-5 times to remove DMF. The organic phase was washed with brine, dried, concentrated, and dried to give the crude product (compound 6B) which used without further purification.

In step 2, the methyl ester (compound 6B) was mixed with $Pd(OAc)_2$, $Cs_2CO_3$, and an appropriate ligand, such as racemic-2-(Di-t-butylphosphino)-1,1'-binaphthyl. The mixture was placed under vacuum for 1 to 10 minutes to remove oxygen, and refilled with $N_2$. An alcohol and toluene were added and the solution was stirred at 50° C. to reflux temperature for 12 to 72 hours. After cooling to room temperature, the solid was removed by filtration and the solvent was removed. The product could be purified by chromatography. During this reaction, the methyl ester may be partially converted to the ester of the alcohol used. This side product was also collected and hydrolyzed in the next step.

In step 3, compound 6C was dissolved in Dioxane/water (3:1) and treated with lithium hydroxide at room temperature for 3-6 hours. The solution was made acidic by addition of 1N HCl solution and subjected to aqueous/EtOAc work up. The products (compound 6D) were either used without further purification or purified by chromatography depending on the boiling point of the alcohol side products.

In step 4, compound 6D was dissolved in a suitable solvent, such as DMF, and coupled with compound 6E under EDCl and HOBT conditions at room temperature overnight. After an aqueous/EtOAc work up, the product (compound 6F) could be isolated by chromatography.

In step 5, compound 6F was suspended in MeOH/water (1:1) under $N_2$ atmosphere. NaOH and zinc powder were added and the reaction mixture was stirred at 70° C. to 80° C. for 8 to 24 hours. After cooling to room temperature, the solution was adjusted to pH=6~7 with 1N HCl solution. Compound 6G was extracted with EtOAc and isolated by reverse phase HPLC.

Example 7

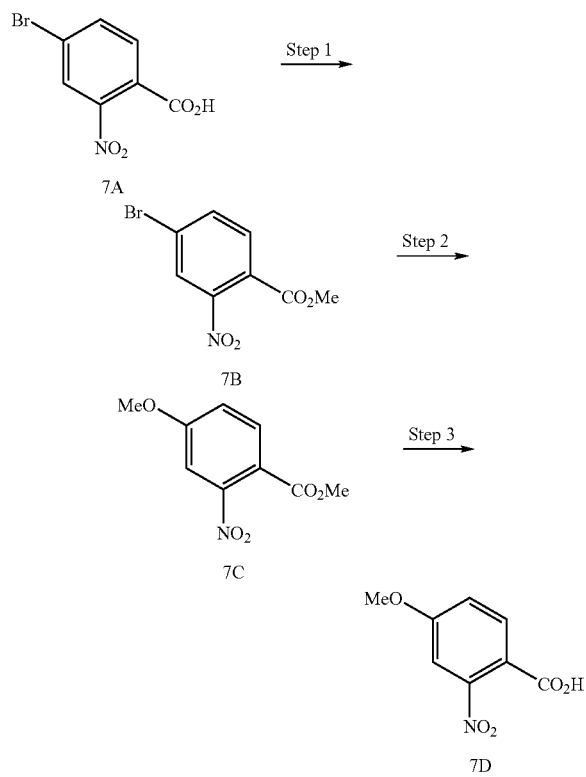

Step 1

Compound 7A (10.0 g, 40.7 mmol) was dissolved in DMF (100 mL). $Cs_2CO_3$ (27.0 g, 81.3 mmol) and methyl iodide (7.60 mL, 122.0 mmol) were added. The solution was stirred at room temperature overnight. EtOAc (250 mL) and water (100 mL) were added. The organic phase was separated and washed with water (100 mL) three times and brine (50 mL), then dried over $Na_2SO_4$, filtered, and concentrated using a rotary evaporator. The product was dried under vacuum to give compound 7B (10.3 g, 97%).

Step 2

Pd(OAc)2 (43 mg, 0.19 mmol), racemic-2-(di-t-butylphosphino)-1,1'-binaphthyl (92 mg, 0.23 mmol), and $Cs_2CO_3$ (1.88 g, 5.76 mmol) were placed in a 50 mL flask. The flask was placed under vacuum for 2 minutes and refilled with $N_2$. Compound 7B (1.00 g, 3.84 mmol) and MeOH (0.311 mL, 7.69 mmol) were dissolved in toluene (10 mL). The resulting solution was added to the above flask by pipette. The reaction mixture was stirred at 70° C. oil bath for 48 hours. After cooling to room temperature, the solid was filtered and the solvent was removed using a rotary evaporator. The product was isolated by silica gel chromatography (Hexane/EtOAc 20:1 to 10:1) to give compound 7C (380 mg, 47%).

Step 3

Compound 7C (380 mg, 1.80 mmol) was dissolved in dioxane/water (3:1, 8 mL) and LiOH (378 mg, 9.0 mmol) was added. The solution was stirred at room temperature for 3 hours. Water (5 mL) was added followed by addition of 2N HCl to adjust the pH=2~4. The aqueous phase was extracted with EtOAc (10 mL) three times. The organic phase was washed with brine, dried over $Na_2SO_4$, filtered, and concentrated. The crude product was dried under vacuum to give compound 7D which was used without further purification.

The following compounds were prepared as described in Examples 6-7

TABLE 2

| Compound # | Structure | Exact Mass | Mass Obsvd | Ki (nM) |
|---|---|---|---|---|
| 6 | 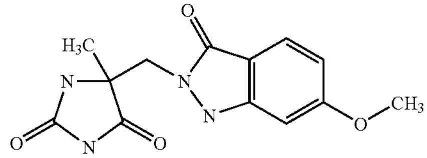 | 289.11 | 291.1 [M + H]+ | B |

TABLE 2-continued

| Compound # | Structure | Exact Mass | Mass Obsvd | Ki (nM) |
|---|---|---|---|---|
| 7 | 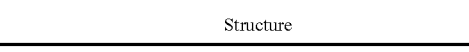 | 366.13 | 367.1 [M + H]⁺ | C |

Example 8

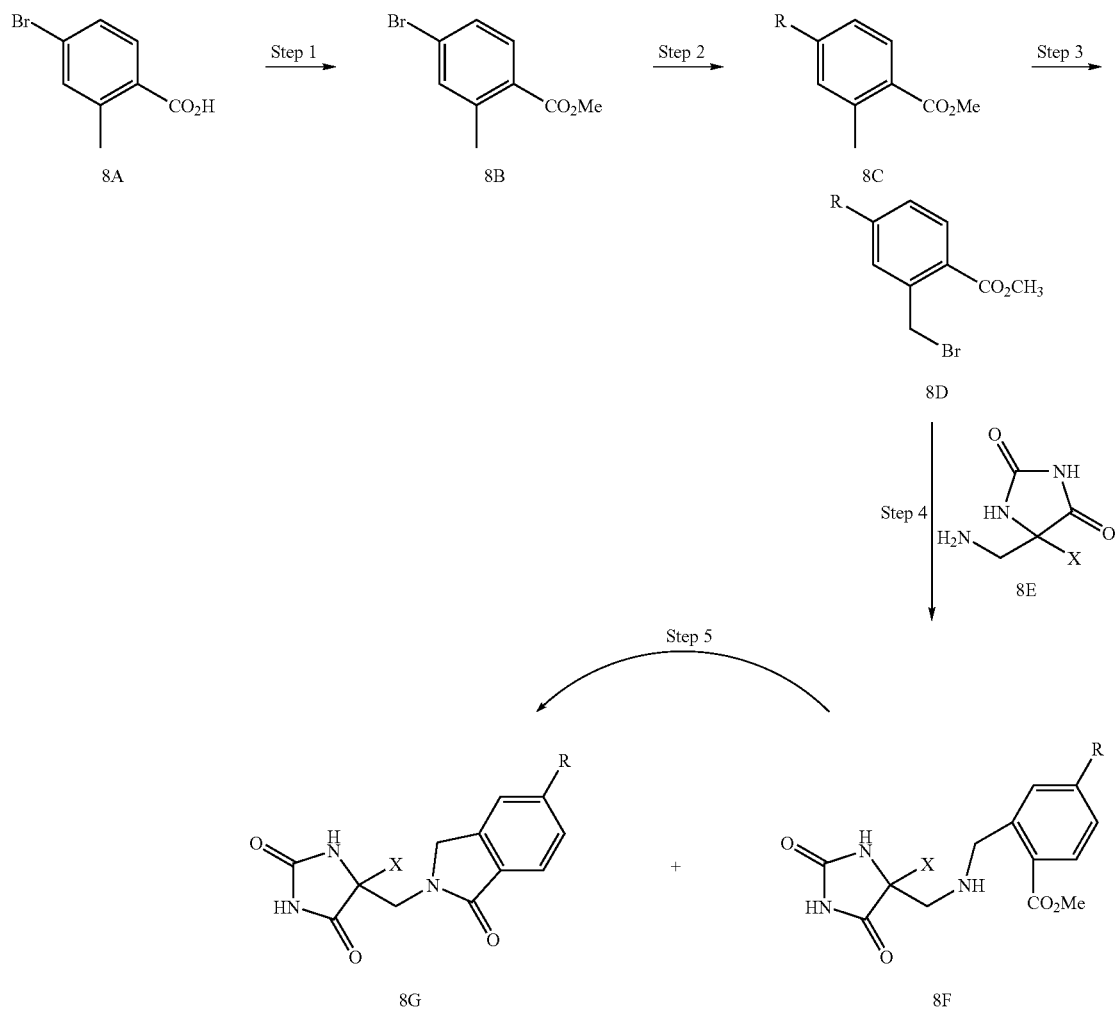

General Procedure for Example 8

In step 1, Compound 8A was dissolved in a suitable solvent, such as DMF, and reacted with methyl iodide in the presence of cesium carbonate at room temperature for 2-16 hours. Water and EtOAc were added and the organic phase was washed by water 1-5 times to remove DMF. The organic phase was washed with brine, dried, concentrated, and dried to give the crude product (compound 8B) which was used without further purification.

In step 2, when alcohol was used, the reaction was operated in a similar manner as step 2 in example 6. When an aromatic or heterocyclic stannane was used, the reaction was operated in the following manner. The aromatic or heterocyclic stannane was added into a dry flask, followed by addition of the 4-Bromo-2-methyl-benzoic acid methyl ester (compound 8B), a base, such as $Cs_2CO_3$, $K_3PO_4$, and a palladium catalyst, such as $Pd(PPh_3)_2Cl_2$. The flask was placed under vacuum for 1 to 10 minutes to remove oxygen and was refilled with $N_2$. An appropriate solvent, such as dry $CH_3CN$, was added and the solution was stirred at 60° C. to reflux temperature overnight to 3 days. The solid was removed by filtration and the solvent was removed. Compound 8C was isolated by chromatography.

In step 3, compound 8C was dissolved in a suitable inert solvent, such as benzene, $CCl_4$ or α,α,α-Trifluorotoluene. NBS and benzoyl peroxide were added and the solution was stirred at 50° C. to 90° C. for 1 to 24 hours. The solid was filtered and the solvent was removed. The residue was dissolved in ether and washed by water. The ether was removed to afford the compound 8D which was used without further purification.

In step 4, the benzyl bromide (compound 8D) was mixed with hydantoin methyl amine 8E, $K_2CO_3$, and DMF. The solution was stirred at room temperature for 12 to 24 hours. Then the solid was removed by filtration. The product could be purified by reverse phase HPLC. Compounds 8F and 8G could be obtained in a variable ratio.

Step 5 is used when the compound 8F was isolated in step 4. Compound 8F was dissolved in an appropriate solvent, such as MeOH, and stirred at 50° C. to reflux temperature for 1 to 12 hours. The product could be obtained by removing the solvent by rotary evaporator or purifying via reverse phase chromatography.

Example 9

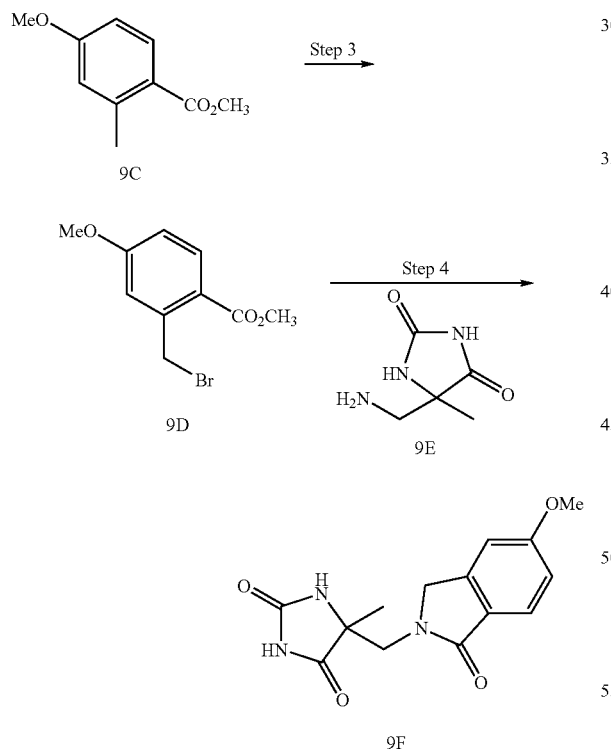

Step 3

Compound 9C (prepared according to the procedure described by Wyrick, S. D. et al. *Journal of Medicinal Chemistry*, 1987, 30(10), 1798-806) (3.33 g, 18.5 mmol) was dissolved in dry benzene (40 mL). NBS (3.45 g, 19.4 mmol) and benzoyl peroxide (134 mg, 0.55 mmol) were added. The solution was stirred in a 75° C. oil bath for about 2 hours. After cooling down, the solid was filtered and washed with $Et_2O$ (150 mL). The organic solution was then washed with water (50 mL) twice, dried over $Na_2SO_4$ or $MgSO_4$, filtered, and concentrated by rotary evaporator. The crude product was dried under vacuum to give Compound 9D which was used without further purification. $^1$H-NMR appeared to indicate that approximately 75% of this material was compound 9D.

Step 4

Compound 9D (4.62 mmol), Compound 9E (824 mg, 4.62 mmol), and $K_2CO_3$ (1.28 g, 9.24 mmol) were mixed in DMF (30 mL). The solution was stirred at room temperature for 20 hours. DMF (15 mL) was added and the solid was filtered and washed with DMF. All the DMF solution was combined and concentrated to 25 mL. The resulting solution was applied to reverse phase MPLC($CH_3CN$/water, 5% to 90%, containing 0.1% $HCO_2H$) to give compound 9F (198 mg, 15%).

Example 10

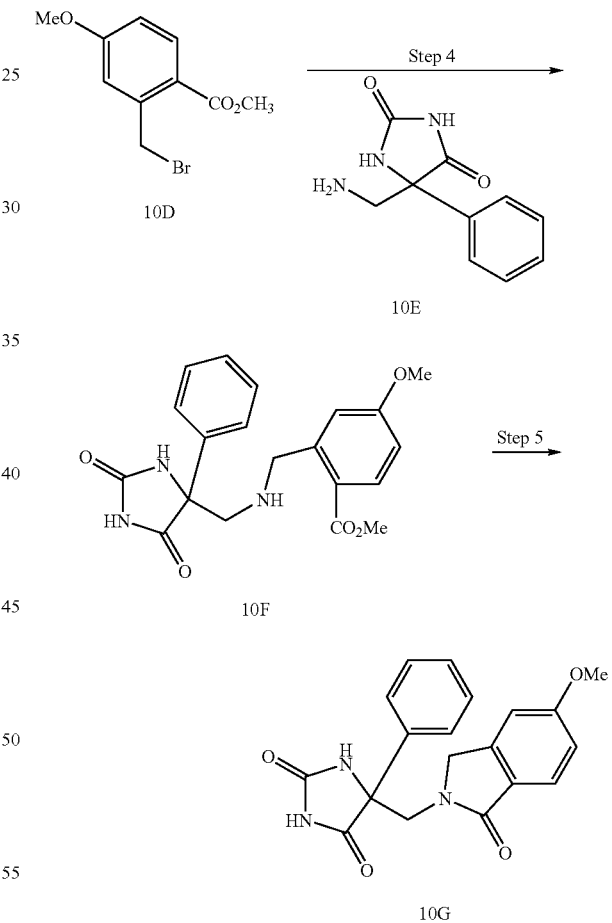

Step 4

Compound 10D (prepared in example 9) (902 mg, 2.07 mmol, factor=0.75), Compound 10E (prepared as described in Example 1, 500 mg, 2.07 mmol), and $K_2CO_3$ (629 mg, 4.56 mmol) were mixed in DMF (15 mL). The solution was stirred at room temperature for 20 hours. DMF (15 mL) was added and the solid was filtered and washed with DMF. All the DMF solution was combined and concentrated to 20 mL. It was applied to reverse phase MPLC (CH₃CN/water: 5% to 90%, containing 0.1% HCO₂H) to give compound 10F.

Step 5

Compound 10F (prepared in step 4) was dissolved in MeOH (5 mL), stirred at 65° C. for 5 hours, then concentrated to dryness. The compound was suspended in water and dried with lyophilizer to give compound 10G (68.3 mg, 9.4%).

Example 11

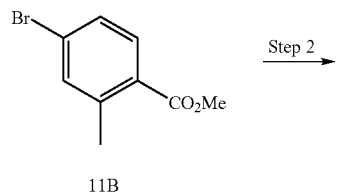

11B

-continued

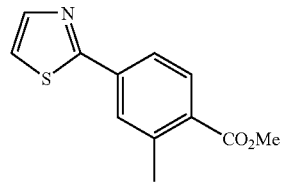

11C

Step 2

Compound 11B (500 mg, 2.18 mmol), 2-tributylstannylthiazole (0.97 mL, 2.84 mmol), Pd(PPh₃)₂Cl₂, and dry CH₃CN were stirred under nitrogen at reflux temperature overnight. After cooling to room temperature, the solid was filtered. The product was isolated by silica gel chromatography (Hexane/EtOAc: 20:1 to 10:1 to 5:1) to give compound 11C (480 mg, 94%).

The following compounds were prepared as described in Examples 8-11.

TABLE 3

| Compound # | Structure | Exact Mass | Mass Obsvd | $K_i$ (nM) |
|---|---|---|---|---|
| 8 | 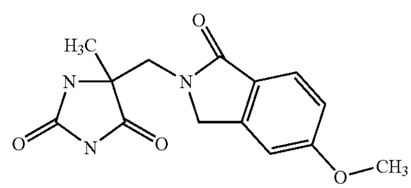 | 289.11 | 290.1 [M + H]⁺ | B |
| 9 | 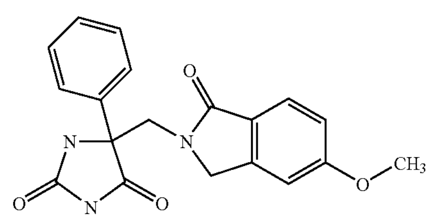 | 351.12 | 352.1 [M + H]⁺ | A |
| 10 | 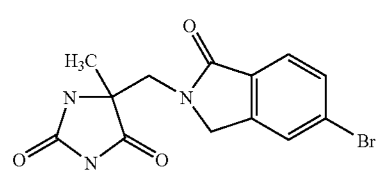 | 337.01 | 338 [M + H]⁺ | C |
| 11 | 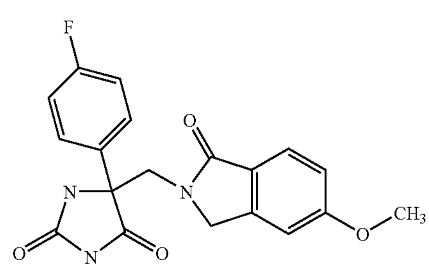 | 369.11 | 370.1 [M + H]⁺ | A |

TABLE 3-continued
| Compound # | Structure | Exact Mass | Mass Obsvd | Ki (nM) |
|---|---|---|---|---|
| 12 | 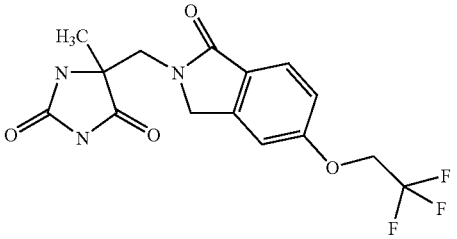 | 357.09 | 358.1 [M + H]+ | B |
| 13 | 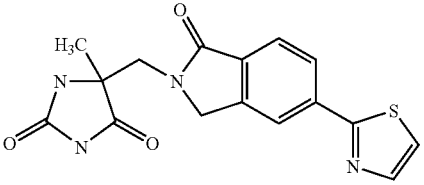 | 342.08 | 343.1 [M + H]+ | C |
| 14 | 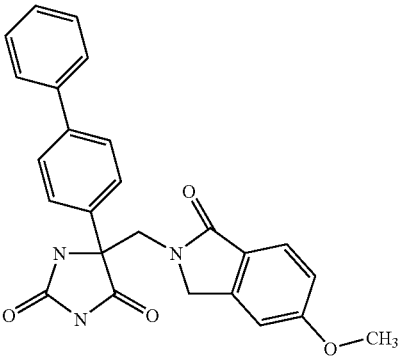 | 427.2 | 428.2 [M + H]+ | A |
| 15 | 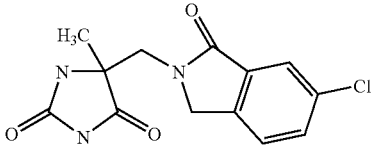 | 293.06 | 294.1 [M + H]+ | B |
| 16 | 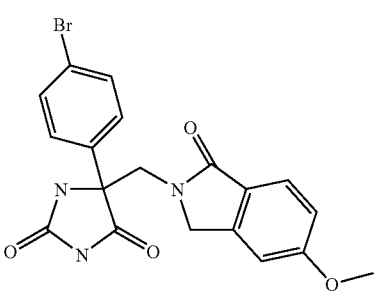 | 431.0 | 432.1 [M + H]+ | A |

TABLE 3-continued

| Compound # | Structure | Exact Mass | Mass Obsvd | Ki (nM) |
| --- | --- | --- | --- | --- |
| 17 | 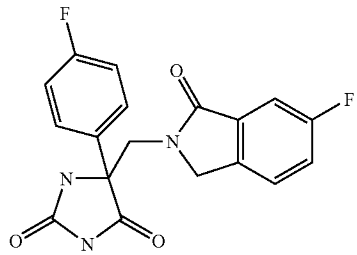 | 357.1 | 358.1 [M + H]$^+$ | A |
| 18 | 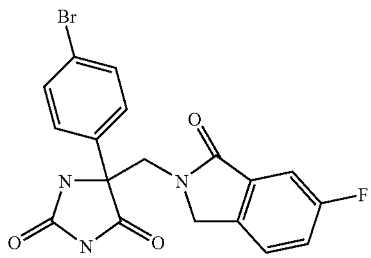 | 417.0 | 418.1 [M + H]$^+$ | A |
| 19 | 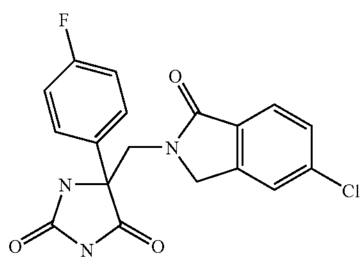 | 373.1 | 374.2 [M + H]$^+$ | A |

The following additional compounds were prepared as described in Examples 8 to 11.

TABLE 4

| Compound # | Structures | Exact Mass | Mass Obsvd | Ki (nM) |
| --- | --- | --- | --- | --- |
| 294 | 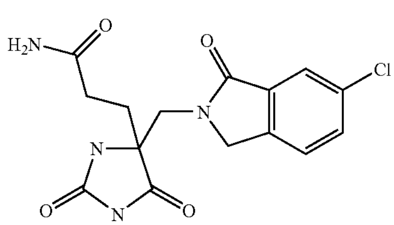 | 350.08 | 351.1 [M + H]$^+$ | B |
| 295 | 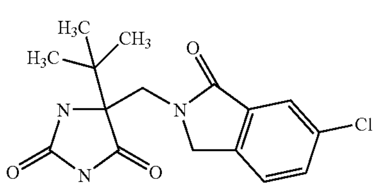 | 335.10 | 336.1 [M + H]$^+$ | B |

Example 12

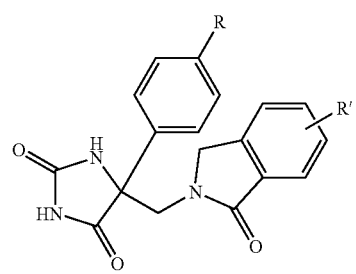

12A

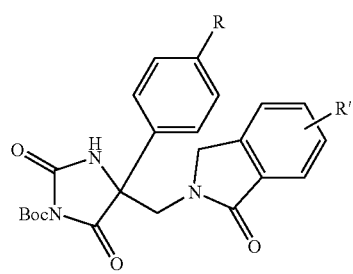

12B

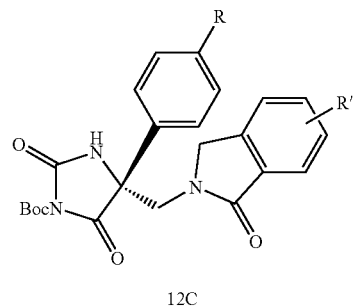

12C

+

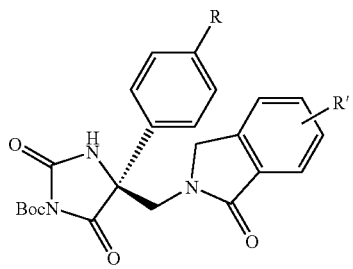

12D

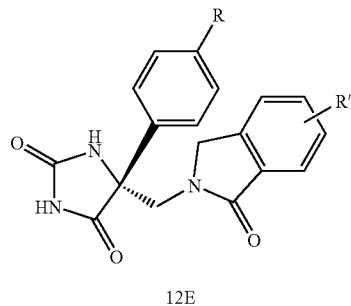

12E

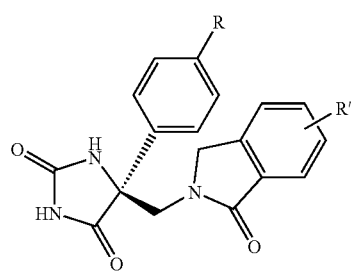

12F

General Procedures for Example 12:

In step 1, racemic compound 12A was treated with one equivalent of di-tert-butyl dicarbonate and 4-N,N-dimethylaminopyridine in polar solvent, such as DMF, for 30 minutes to 12 hours. The solvent was removed and the product (compound 12B) was isolated by silica gel (pretreated with 1% triethylamine in Hexane) chromatography.

In step 2, compound 12B was dissolved in proper solvents allowed by HPLC column, and resolved by HPLC using a preparative Chiralpak AD or Chiralcel OD column to give compound 12C and 12D.

In step 3, compound 12C and 12D were treated with excess HCl in methanol at 25° C. to 60° C. for one hour to 12 hours. The solvent was concentrated to give compound 12E and 12F.

Example 13

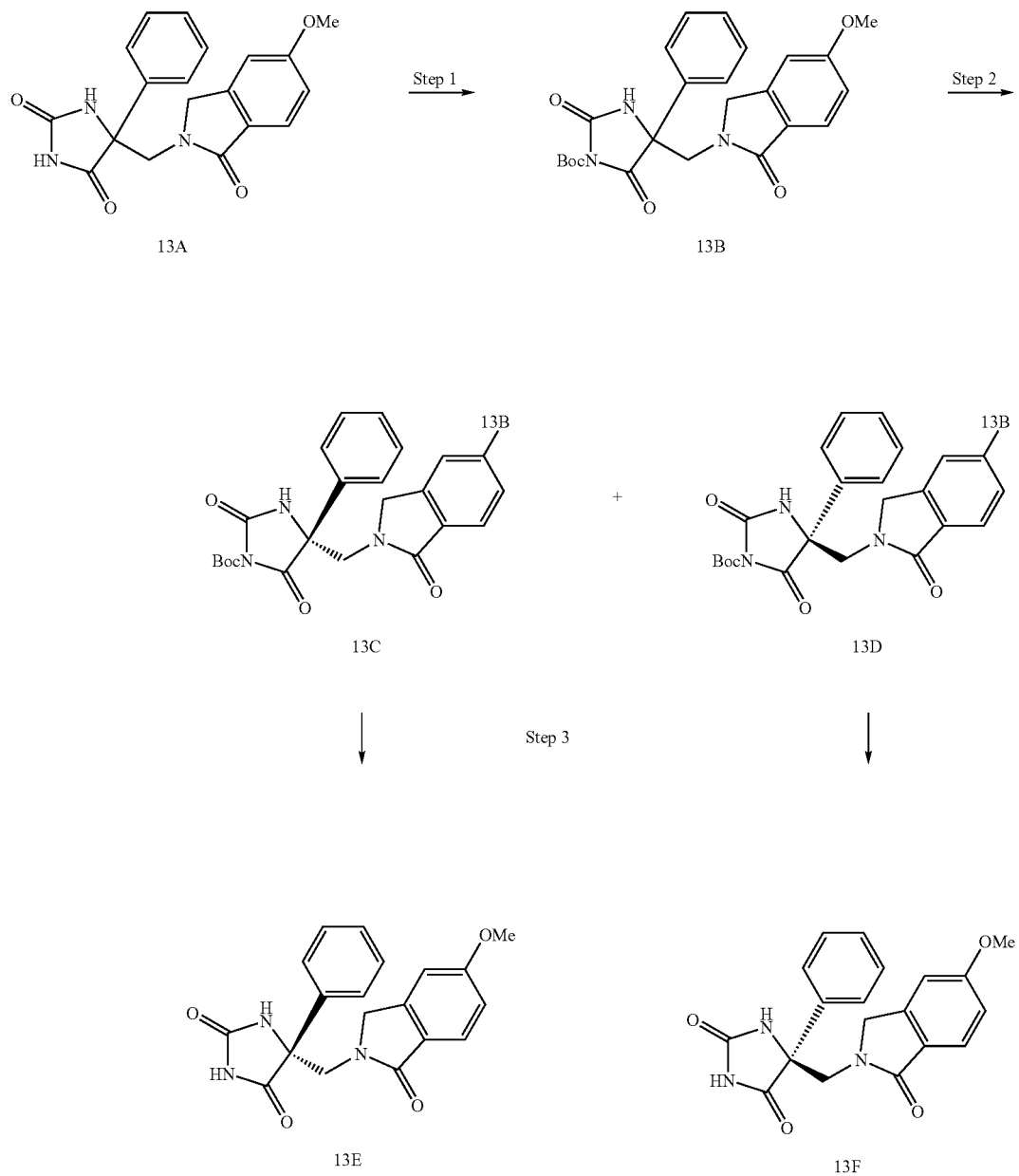

Step 1

Compound 13A (810 mg, 2.07 mmol), di-tert-butyl dicarbonate (429 mg, 1.97 mmol), and 4-dimethylaminopyridine (20 mg) were dissolved in a mixture of DMF (10 mL) and THF (20 mL). The solution was stirred at 25° C. overnight. Solvents were removed by rotary evaporator. The product was isolated by C18 chromatography (CH₃CN/water: 5% to 90%) to give product 13B (650 mg, 70%).

Step 2

Compound 13B (600 mg) was dissolved in a mixture of iso-propanol (6 mL) and CHCl₃ (4 mL). 2.5 mL was separated via HPLC with preparative chiralcel OD column (Mobile phase: iso-propanol/Hexane: 1:4). Fractions for each peak were collected and concentrated by rotary evaporator to give compound 13C (First peak, 197 mg) and compound 13D (second peak, 178 mg).

Step 3

Compound 13C (197 mg) was dissolved in methanol (3 mL). HCl (4M in Dioxane, 0.5 mL) was added. The solution was stirred in a 60° C. oil bath for three hours. Methanol was removed by rotary evaporator to give compound 13E.

Compound 13F was prepared in the same way as compound 13D (178 mg).

The following compounds were prepared as described in Examples 12-13

TABLE 5

| Compound # | Structures | Exact Mass | Mass Obsvd | Ki (nM) |
|---|---|---|---|---|
| 20 | Enantiomer A | 351.1 | 352.2 [M + H]+ | A |
| 21 | Enantiomer B | 351.1 | 352.2 [M + H]+ | C |
| 22 | Enantiomer A | 357.1 | 358.1 [M + H]+ | C |
| 23 | Enantiomer B | 357.1 | 358.1 [M + H]+ | A |
| 24 | Enantiomer A | 373.06 | 374.2 [M + H]+ | C |

TABLE 5-continued

| Compound # | Structures | Exact Mass | Mass Obsvd | Ki (nM) |
|---|---|---|---|---|
| 25 | 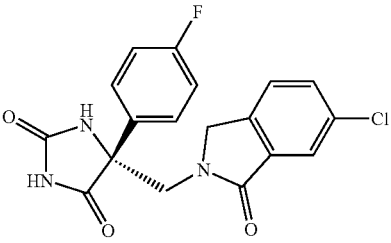<br>Enantiomer B | 373.06 | 374.2 [M + H]⁺ | A |

Proton NMR Spectral Data for Selected Compounds in Table 5.

Compound 25. ¹H NMR (500 Hz, DMSO-$d_6$) δ4.06 (d, J=14 Hz, 1H), 4.20 (d, J=14 Hz, 1H), 4.32 (d, J=18 Hz, 1H), 4.38 (d, J=18 Hz, 1H), 7.19-7.39 (m, 2H), 7.55-7.80 (m, 5H), 8.93 (s, 1H), 10.96 (s, 1H).

Example 14

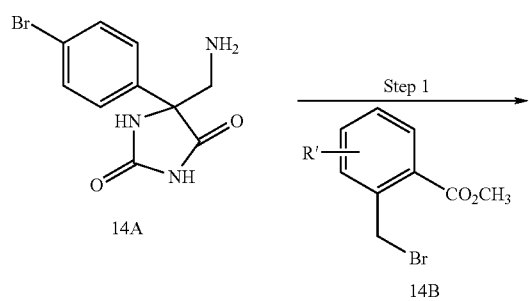

General Procedure for Example 14

In step 1, compound 14A (prepared as described in Example 1) was treated with a benzyl bromide (Compound 14B) and DIPEA base in DMF at 25° C. to 60° C. for 12 to 24 hours. The reaction solution was purified via C18 reverse phase chromatography to give compound 14C.

In step 2, compound 14C was treated with one equivalent di-tert-butyl dicarbonate in polar solvent, such as DMF, for 30 minutes to 12 hours. The solvent was removed and the product (compound 14D) was isolated by silica gel (pretreated with 1% triethylamine in Hexane) chromatography.

In step 3, compound 14D was subjected to either a Pd catalyzed reaction with a heterocyclic boronic acid or a heterocyclic stannane, or a copper catalyzed reaction with a heterocyclic amine. The reaction were heated in appropriate solvents, such as DMF and acetonitrile, at 60° C. to 150° C., for 5 minutes to 12 hours. In some cases, a microwave reactor was used. The product was purified by silica gel chromatography to give compound 14E or compound 14F.

In step 4, compound 14E was dissolved in methanol and was stirred with HCl for 1 hour to 12 hours at 25° C. to 60° C. The solvent was removed to give Compound 14F.

The following compounds were prepared as described in step 1 of Example 14 above.

TABLE 6

| Compound # | Structure | Exact Mass | Mass Obsvd | Ki (nM) |
|---|---|---|---|---|
| 100 | 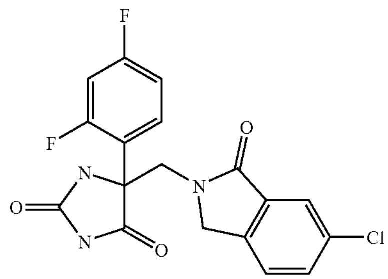 | 391.05 | 392.07 [M + H]+ | n/a |
| 101 | 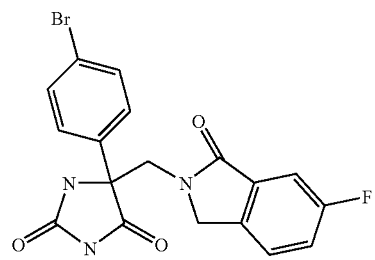 | 417.01 | 418.1 [M + H]+ | A |
| 102 | 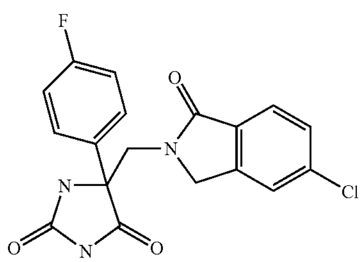 | 373.06 | 374.2 [M + H]+ | A |
| 103 | 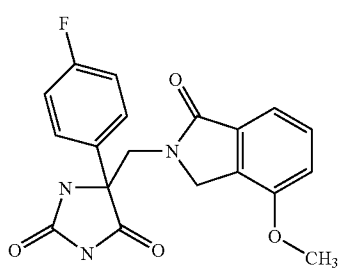 | 369.11 | 370.1 [M + H]+ | D |
| 104 | 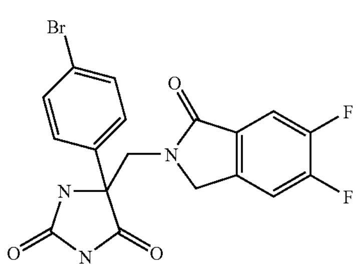 | 435.00 | 436.1 [M + H]+ | B |

TABLE 6-continued

| Compound # | Structure | Exact Mass | Mass Obsvd | Ki (nM) |
|---|---|---|---|---|
| 105 | 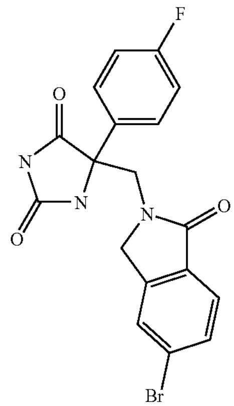 | 417.01 | 418.420 [M + H]⁺ | B |
| 106 | 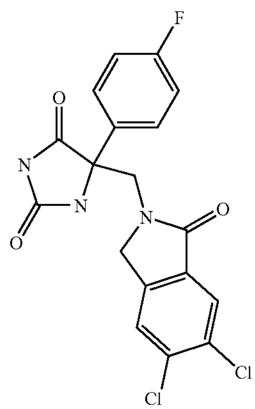 | 407.0 | 408 [M + H]⁺ | A |
| 107 | 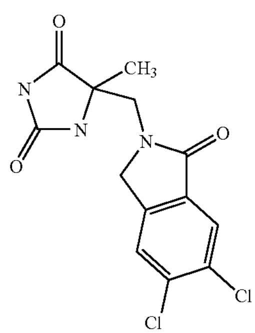 | 327.0 | 328 [M + H]⁺ | B |
| 108 | 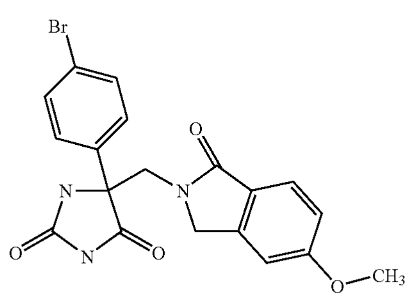 | 429.03 | 430.432 [M + H]⁺ | B |

TABLE 6-continued

| Compound # | Structure | Exact Mass | Mass Obsvd | Ki (nM) |
|---|---|---|---|---|
| 109 | 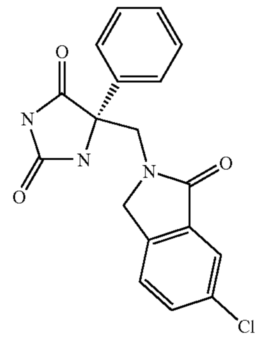 | 355.07 | 378.2 [M + Na]+ | B |

Example 15

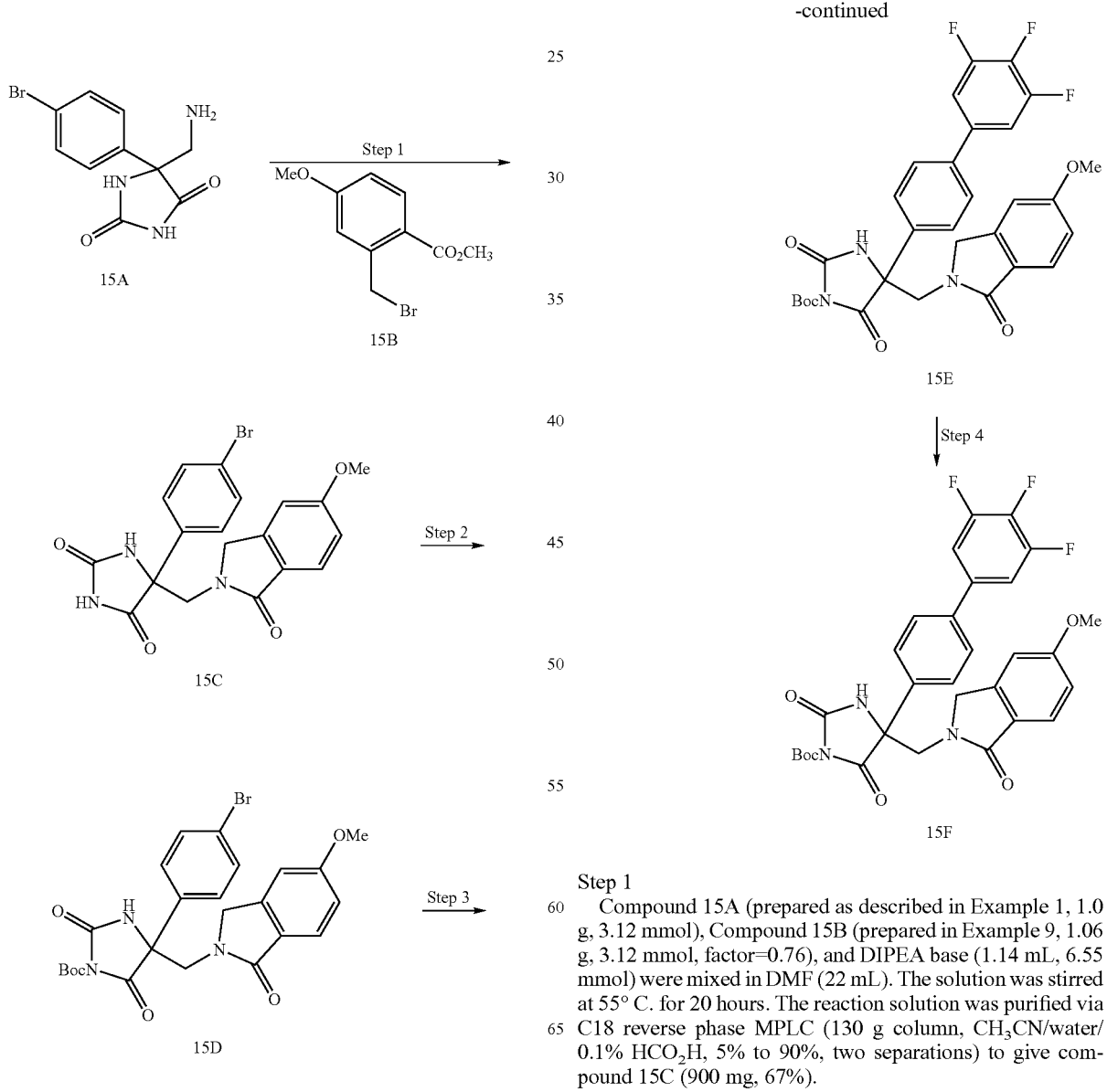

Step 1

Compound 15A (prepared as described in Example 1, 1.0 g, 3.12 mmol), Compound 15B (prepared in Example 9, 1.06 g, 3.12 mmol, factor=0.76), and DIPEA base (1.14 mL, 6.55 mmol) were mixed in DMF (22 mL). The solution was stirred at 55° C. for 20 hours. The reaction solution was purified via C18 reverse phase MPLC (130 g column, CH$_3$CN/water/ 0.1% HCO$_2$H, 5% to 90%, two separations) to give compound 15C (900 mg, 67%).

Step 2

Compound 15C (2.7 g, 6.28 mmol) was suspended in a mixture of DMF (20 mL) and THF (40 mL). Di-tert-butyl dicarbonate (1.51 g, 6.91 mmol) and 4-dimethylaminopyridine (38 mg, 0.31 mmol) were added. The solution was stirred at 25° C. for 16 hours. The solvents were removed by rotary evaporator. The residue was subjected to silica gel chromatography (Hexane/EtOAc: 2:1 to 1:1) to give compound 15D (2.36 g, 71%).

Step 3

Compound 15D (100 mg, 0.19 mmol), 3,4,5-trifluorophenyl boronic acid (40 mg, 0.23 mmol), 1,1'-bis(triphenylphosphino)ferrocene palladium (II) chloride (15 mg, 0.02 mmol), potassium carbonate (1M in water, 1 mL) and acetonitrile (1 mL) were added to a microwave reactor tube. The tube was sealed and reacted in the microwave reactor at 150° C. for 10 minutes. After cooling down, the aqueous layer was removed and the organic layer was concentrated. The crude product was purified by silica gel chromatography ($CH_2Cl_2$/MeOH/$NH_3$: 40:1:0.1) to give compound 15E.

Step 4

Compound 15E obtained from step 3 was suspended in MeOH HCl (2M in ethyl ether, 0.5 mL) was added. The reaction mixture was stirred at 50° C. for five hours. The solvent was removed. The product was purified via C18 reverse phase chromatography ($CH_3CN$/water/0.1% $HCO_2H$, 5% to 90%) to give compound 15F (8 mg, 8.8% from compound 15D).

Example 16

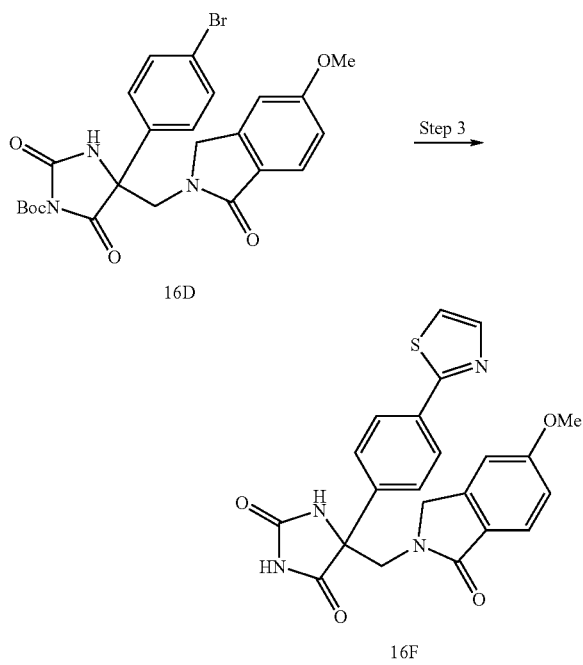

Step 3

Compound 16D (50 mg, 0.094 mmol, prepared in example 13), 2-tributylstannylthiazole (53 mg, 0.14 mmol), dichlorobis(triphenylphosphine) palladium (II) (7 mg, 0.01 mmol), and acetonitrile (1 mL) were added to a microwave reactor tube. The tube was sealed and reacted in a microwave reactor at 150° C. for 10 minutes. The solvent was evaporated and the product was purified by silica gel chromatography ($CH_2Cl_2$/MeOH/$NH_3$: 40:1:0.1 to 20:1:0.1) to give compound 16F (15 mg, 37%).

Example 17

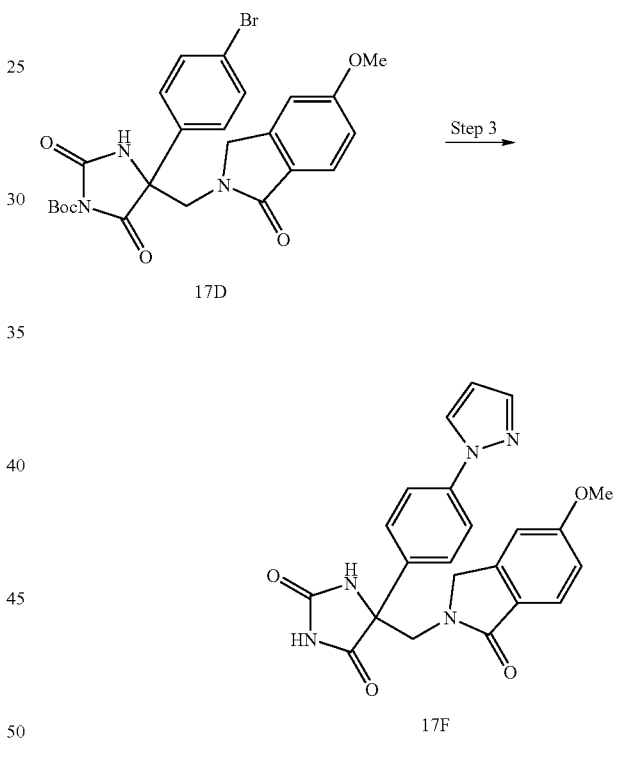

Step 3

Compound 17D (100 mg, 0.19 mmol, prepared in example 13), pyrazole (15.4 mg, 0.23 mmol), cesium carbonate (124 mg, 0.38 mmol), copper iodide (7.2 mg, 0.038 mmol), 1,10-phenanthroline (14 mg, 0.076 mmol), and N,N-dimethylacetamide (0.5 mL) were added to a dry reaction tube and filled with nitrogen. The reaction tube was sealed and heated in a 120° C. oil bath for two days. After cooling down, the reaction solution was purified by C18 chromatography ($CH_3CN$/water/0.1% $HCO_2H$, 5% to 90%) to give compound 17F (5 mg, 6.4%).

The following compounds were prepared as described in Examples 14-17

TABLE 7

| Compound # | Structure | Exact Mass | Mass Obsvd | Ki (nM) |
| --- | --- | --- | --- | --- |
| 26 | 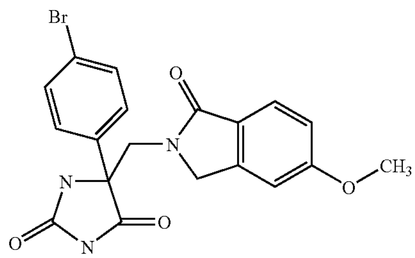 | 429.0 | 430.1 [M + H]+ | A |
| 27 | 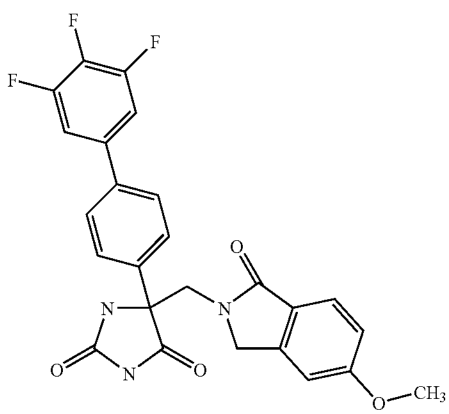 | 481.1 | 482.3 [M + H]+ | B |
| 28 | 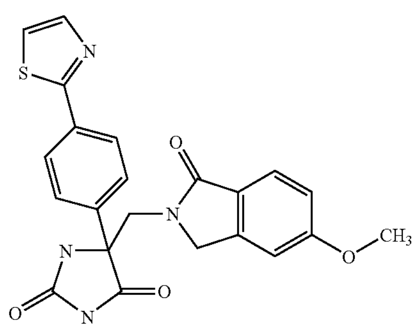 | 434.1 | 435.1 [M + H]+ | A |
| 29 | 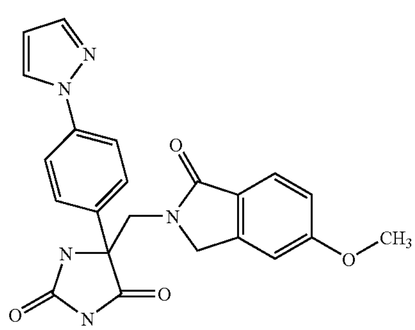 | 417.1 | 418.2 [M + H]+ | A |

TABLE 7-continued

| Compound # | Structure | Exact Mass | Mass Obsvd | Ki (nM) |
|---|---|---|---|---|
| 30 | 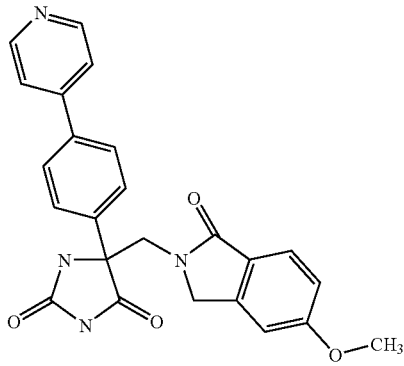 | 428.2 | 429.1 [M + H]+ | A |

Example 18

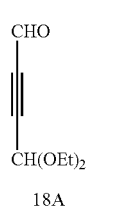 + 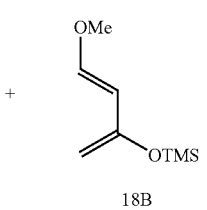 →<sup>Step 1</sup>

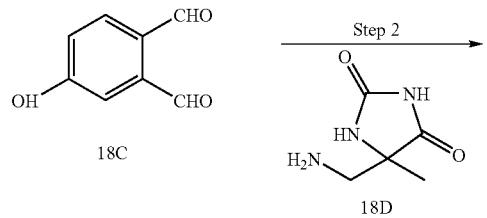

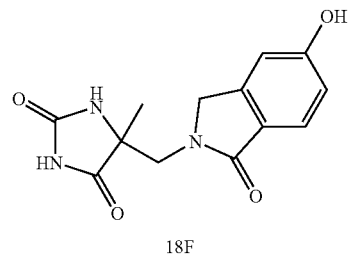

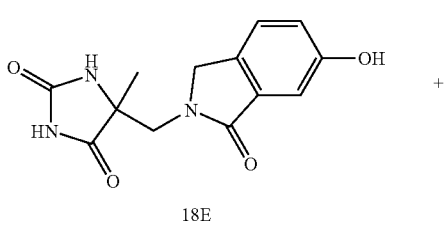

Step 1:

Compound 18A (1.0 g, 6.4 mmol) and compound 18B (1.324 g, 7.68 mmol) were dissolved in toluene (4 mL) and stirred at 80° C. for 24 hours. After cooling to room temperature, the solvent was removed by rotary evaporator. Half of the crude product was dissolved in THF/1N HCl (1:1, 14 mL) and stirred at room temperature for 2 hours. EtOAc (15 mL) and water (5 mL) were added. The organic phase was separated and the aqueous phase was extracted with EtOAc (15 mL) twice. The combined organic phase was dried over $Na_2SO_4$ and concentrated by rotary evaporator to give compound 18C which was used without further purification.

Step 2

Compound 18C (prepared in step 1) was dissolved in DMF (15 mL) and was cooled to 0° C. in an ice-water bath. Compound 18D (571 mg, 3.2 mmol) was added in one portion. The solution was allowed to warm up to room temperature over 2 hours, and stirred at room temperature for 3 days. A 2N HCl solution (20 mL) was added and the aqueous phase was extracted with EtOAc (50 mL) three times. The organic phases were combined, dried over $Na_2SO_4$, and concentrated to dryness. The product was isolated by reverse phase LC ($CH_3CN$/water/0.1% $HCO_2H$: 5% to 90%) to give compound 18E (65 mg, 7.4% from step 1) and Compound 18F (16 mg, 1.8% from step 1).

The following compounds were prepared as described in Example 18

TABLE 8

| Compound # | Structure | Exact Mass | Mass Obsvd | Ki (nM) |
|---|---|---|---|---|
| 31 | 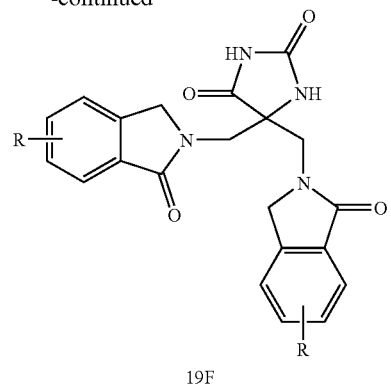 | 275.09 | 276.0 [M + H]+ | B |
| 32 | 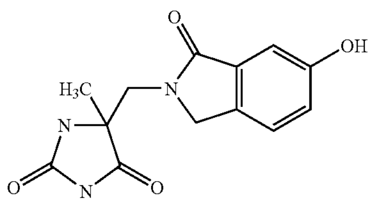 | 275.09 | 276.0 [M + H]+ | C |

Example 19

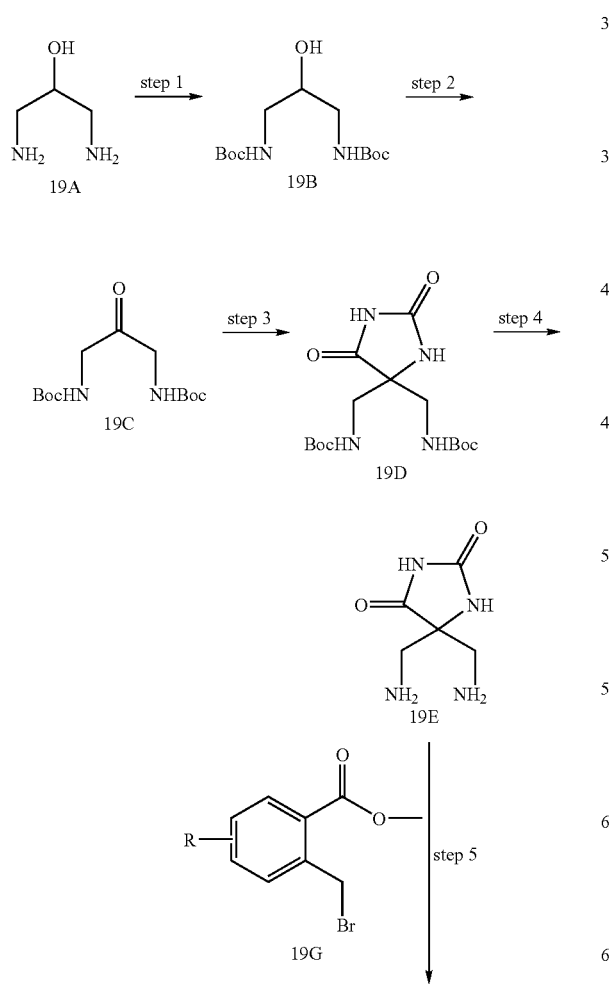

General Procedures for Example 19:

In step 1, compound 19A was treated with two equivalent of $Boc_2O$ in a suitable solvent, such as dichloromethane, for 30 min. to 12 h. The solvent was removed and the compound 19B could be used without further purification or purified by silica gel chromatography.

In step 2, compound 19B was treated with PCC and celite in a suitable solvent such as dichloromethane, for 2 hr to 12 hr. Compound 19C was purified by silica gel chromatography.

In step 3, compound 19C was reacted with potassium cyanide and ammonium carbonate in appropriated alcohol and water solution, at 50° C. to 90° C., for 5 hours to 48 hours. After cooling down, water was added and Compound 19D could be collected by filtration.

In step 4, compound 19D was stirred with 2 to 20 equivalents of hydrogen chloride in methanol for 5 to 48 hours. The solvent was removed and the Compound 19E could be used without further purification.

In step 5, the benzyl bromide (compound 19G) was mixed with hydantoin methyl amine 19E, DIPEA, and DMF. The solution was stirred at room temperature for 12 to 24 hours. The product (19F) was either removed by filtration or purified by silica gel chromatography.

Example 20

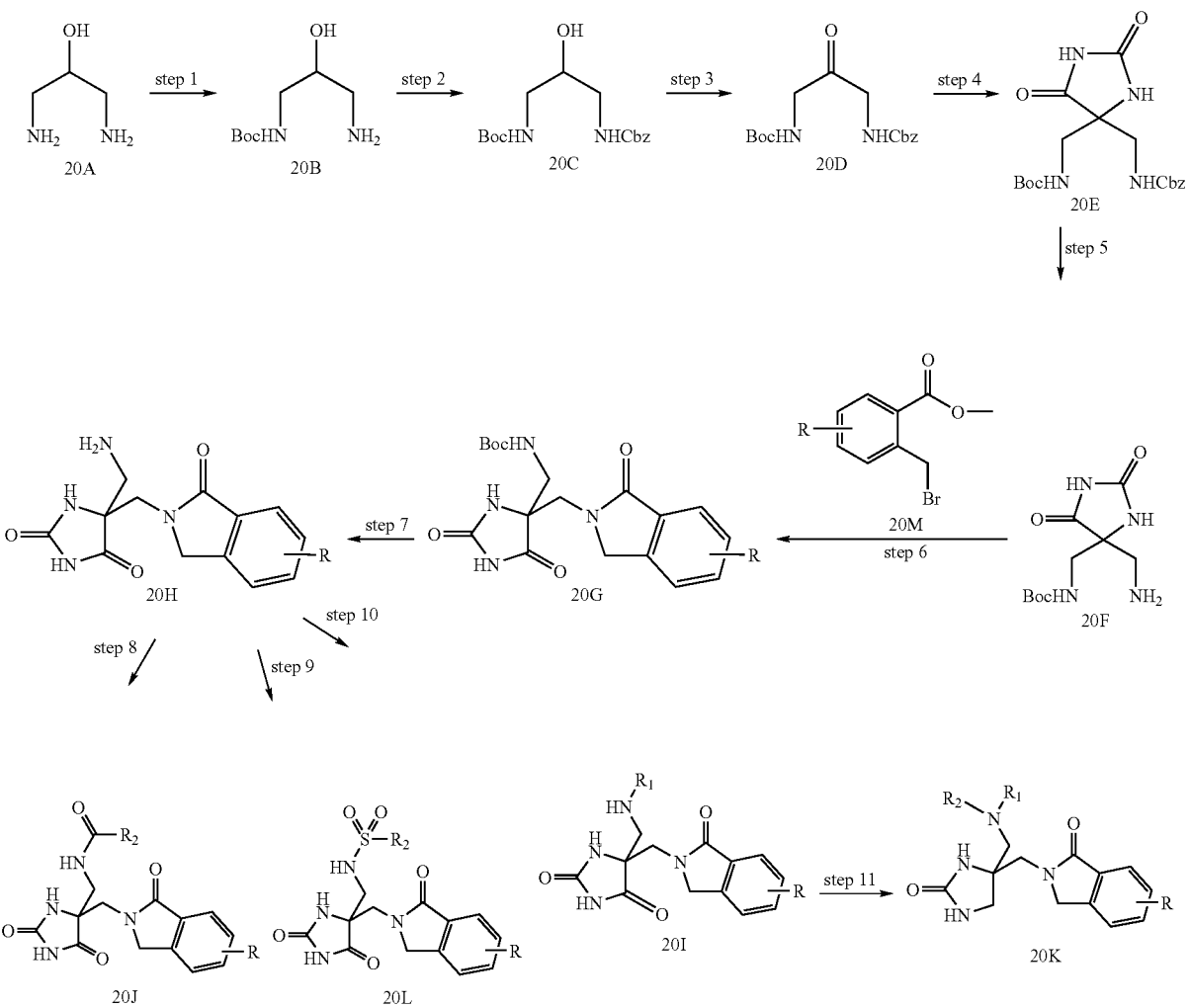

General Procedures for Example 20:

In step 1, Compound 20A was treated with BOC-ON in a suitable solvent such as dichloromethane, for 2 hr to 12 hr. Compound 20B was purified by silica gel chromatography.

In step 2, Compound 20B was treated with CbzCl and a base such as DIPEA, in a suitable solvent, such as dichloromethane, for 2 hr to 12 hr. Compound 20C was purified by silica gel chromatography.

In step 3, compound 20C was treated with PCC and celite in a suitable solvent such as dichloromethane, for 2 hr to 12 hr. Compound 20D was purified by silica gel chromatography.

In step 4, compound 20D was reacted with potassium cyanide and ammonium carbonate in appropriated alcohol and water solution, at 50° C. to 90° C., for 1 hour to 48 hours. After cooling down, water was added and Compound 20E could be collected by filtration.

In step 5, Compound 20E was treated with Pd/C in a suitable solvent such as methanol, in a par shaker under $H_2$ atmosphere. After filtering off the catalyst and concentration of solvent, the product was used without further purification.

In step 6, the benzyl bromide (compound 20M) was mixed with hydantoin methyl amine 20F, DIPEA, and DMF. The solution was stirred at room temperature to 80° C. for 12 to 24 hours. The product was either removed by filtration or purified by silica gel chromatography.

In step 7, compound 20G was stirred with 2 to 20 equivalents of hydrogen chloride in dioxane for 1 to 12 hours. The solvent was removed and the Compound 20H was used without further purification.

In step 8, Compound 20H was coupling with carboxylic acid to give compound 20J which was purified by silica gel chromatography.

In step 9, Compound 20H was coupling with sulphonyl chloride compound to give compound 20L which was purified by silica gel chromatography.

In step 10, Compound 20H was reacted with carbonyl compound under reductive amination condition to give compound 20I. Alternatively, compound 20H was treated with a suitable electrophile and a base to give the product 20I, which was purified by silica gel chromatography.

In step 11, compound 20I was reacted with carbonyl compound under reductive amination condition to give product 20K. Alternatively, compound 20I was treated with a suitable electrophile and a base to give the product 20K, which was purified by silica gel chromatography.

Example 21

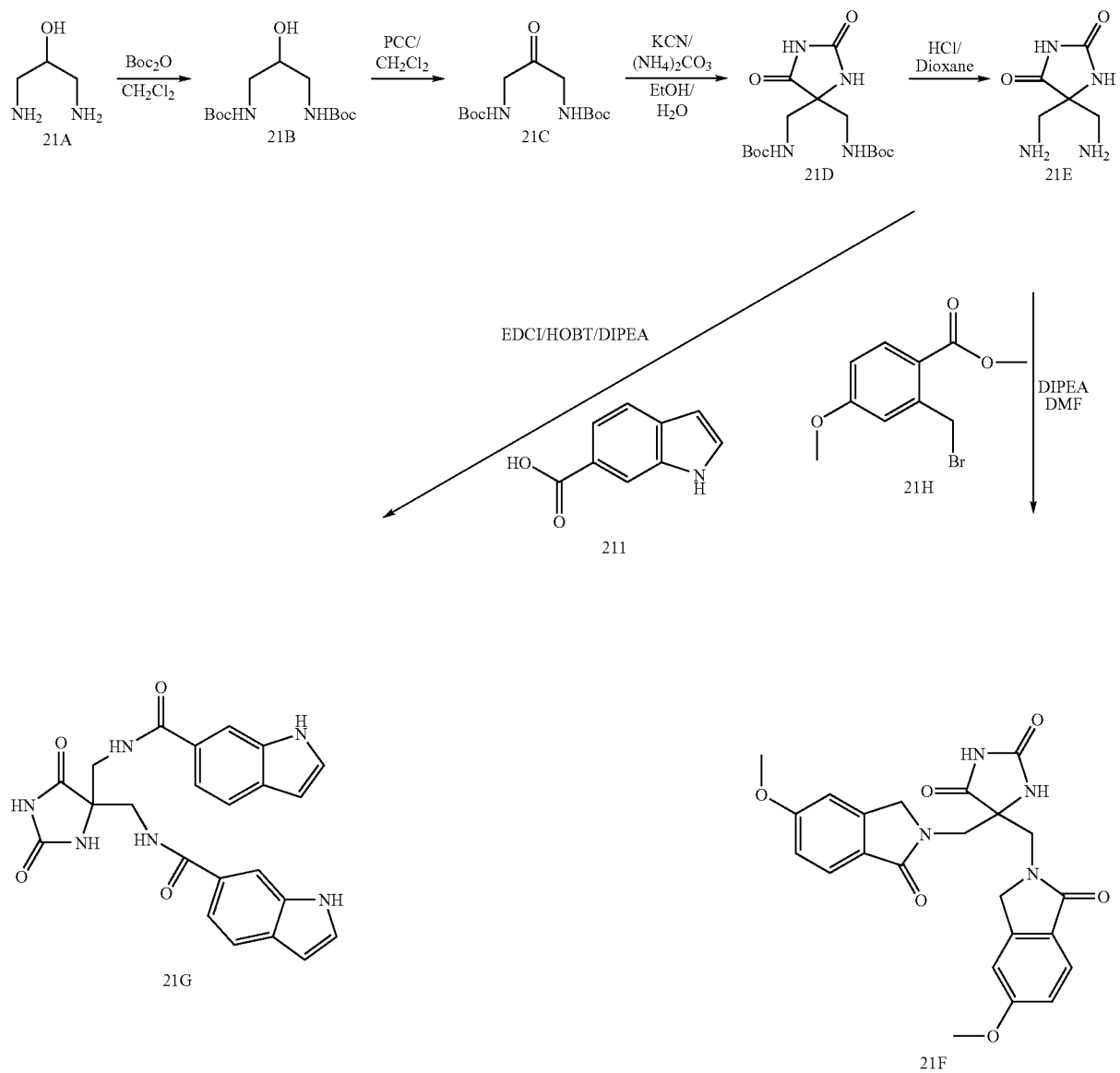

Compound 21B: Compound 21A (7 g, 77.7 mmol), and di-tert-butyl dicarbonate (35.6 g, 163 mmol) were stirred in methylene chloride (100 mL) at 25° C. for 2 hr. Saturated aqueous NaCl (150 mL) was added. The aqueous layer was extracted with $CH_2Cl_2$ (100 mL) twice. The organic phase was washed with brine (100 mL), dried over $Na_2SO_4$. The solvent was removed by rotary evaporator to give compound 21B (17 g, 76%) which was used without further purification.

Compound 21C: compound 21B (17 g, 58.6 mmol) was dissolved in methylene chloride (100 mL). PCC (25.2 g, 117 mmol) and celite (15 g) were added and the reaction mixture was stirred at 25° C. overnight. The solid was filtered off and the resulting solution was concentrated and purified via sgc (40% EtOAc/Hexanes) to give 3.62 g (22%) of compound 21C.

Compound 21D: Compound 21C (3.62, 12.6 mmol), KCN (1.23 g, 18.9 mmol), and $(NH_4)_2CO_3$ (3.62 g, 37.7 mmol) were suspended in a mixture of EtOH (30 mL) and water (30 mL). The solution was stirred at 80° C. overnight. After cooling down, water (35 mL) was added. The solid was filtered and washed with water three times. The solid was dried under vacuum to give compound 21D (3 g, 67%).

Compound 21E: Compound 21D (3.0 g) was suspended in methanol (50 mL) and HCl (4M in dioxane, 20 mL) was added. The solution was stirred at 25° C. for 3 hours. Ethyl ether (50 ml) was added. The solid was filtered, washed by ethyl ether twice, and dried under vacuum compound 21E (1.34 g, 70%).

Compound 21F: Compound 21E (130 mg, 0.82 mmol), compound 21H (0.27 g, 1 mmol) and DIPEA (0.55 mL, 2 mmol) were mixed in DMF (5 mL). The solution was stirred at room temperature overnight. Solvent was removed and the crude material was and purified via sgc (5% $NH_3.MeOH/CH_2Cl_2$) to give 129 mg (35%) of compound 21E.

Example 22

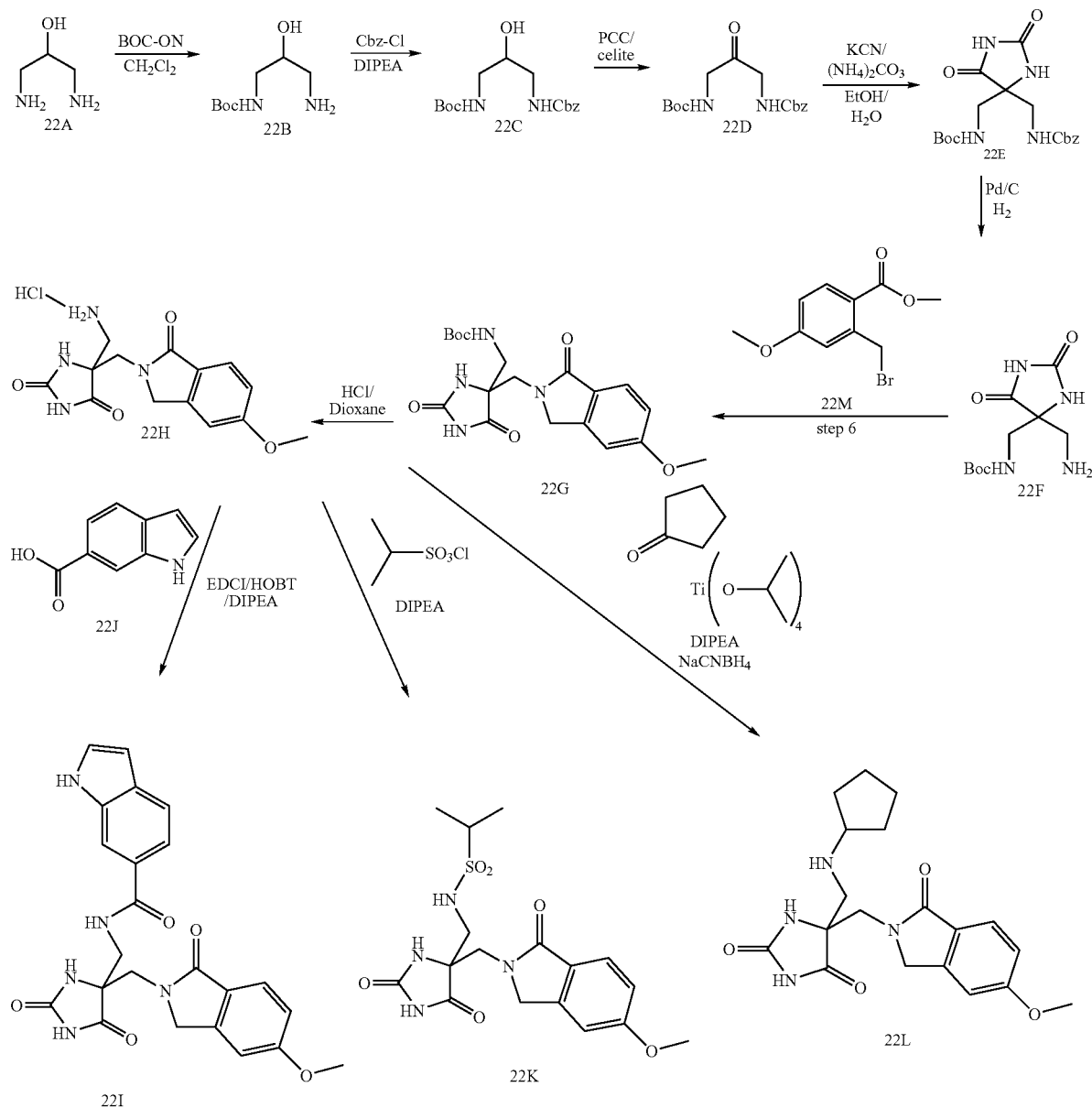

Compound 22B: Compound 22A (7.3 g, 81 mmol) was treated with BOC-ON (21.9 g, 89 mmol) in dichloromethane for 3 hr. Solvent was removed and the crude material was purified via sgc (10% $NH_3.MeOH/CH_2Cl_2$) to give 6.5 (42%) of compound 22B.

Compound 22C: Compound 22B (1.5 g, 7.9 mmol) was dissolved in dichloromethane (50 mL) at 0° C. CbzCl (1.24 ml, 8.7 mmol) and DIPEA (1.52 ml, 8.7 mmol) were added and the reaction was stirred at 0° C. for 30 min. The reaction mixture was washed by HCl (1N, 50 mL) and brine (50 mL). The organic layer was dried and concentrated to give crude compound 22C (2.6 g, 99%) which was used without further purification.

Compound 22D: Compound 22C (2.78 g, 8.57 mmol) was dissolved in methylene chloride (100 mL). PCC (4.62 g, 21.4 mmol) and celite (4.6 g) were added and the reaction mixture was stirred at 25° C. overnight. Another 0.5 eq. of PCC (923 mg, 4.3 mmol) was added and it was stirred for 3 hr at room temperature. The solid was filtered off and the resulting solution was concentrated and purified via sgc (50% EtOAc/Hexanes) to give 1.86 g (73%) of compound 22D.

Compound 22E: Compound 22D (1.86, 5.8 mmol), KCN (0.56 g, 8.65 mmol), and $(NH_4)_2CO_3$ (1.66 g, 17.3 mmol) were suspended in a mixture of EtOH (20 mL) and water (20 mL). The solution was stirred at 80° C. overnight. After cooling down, EtOH was removed. The solid was filtered and washed with water three times. The solid was dried under vacuum to give compound 22E (1.45 g, 64%).

Compound 22F: Compound 22E (1.45 g, 3.68 mmol) was treated with Pd/C in methanol in a par shaker under $H_2$ atmosphere of 50 psi for 60 hr. After filtering off the catalyst and concentration of solvent, Compound 22E (0.95 g, 99%) was used without further purification.

Compound 22G: Compound 22F (150 mg, 0.58 mmol), compound 22M (170 mg, 0.64 mmol) and DIPEA (0.22 mL, 1.28 mmol) were mixed in DMF (5 mL). The solution was stirred at 70° C. overnight. Solvent was removed and the crude material was and purified via sgc (5% $NH_3.MeOH/CH_2Cl_2$) to give 166 mg (71%) of compound 22G.

Compound 22H: Compound 22G (166 mg) was suspended in methanol (10 mL) and HCl (4M in dioxane, 4 mL) was added. The solution was stirred at 25° C. for 2 hours. Ethyl ether (50 ml) was added. Solvent was removed and give compound 22H (0.14 g, 99%).

Compound 22I: Compound 22H (42 mg, 0.12 mmol) and compound 22J (26 mg, 0.16 mmol) were dissolved in DMF (20 mL). EDCl (30 mg, 0.16 mmol), HOBT (21 mg, 0.16 mmol) and DIPEA (0.05 mL, 0.28 mmol) were added and the reaction mixture was stirred at room temperature for 2 hr. Solvent was removed and the crude material was and purified via sgc (10% $NH_3.MeOH/CH_2Cl_2$) to give 7 mg (13%) of compound 22I.

Compound 22L: Compound 22H (25 mg, 0.073 mmol) and cyclopentanone (7.5 mg, 0.088 mmol) were stirred in methylene chloride (5 mL). Titanium tetraisopropoxide (0.043 mL, 0.15 mmol) was added followed by addition of DIPEA (0.015 mL, 0.088 mmol). The reaction mixture was stirred at room temperature for 2 h. Then, $Na(OAc)_3BH$ (31 mg, 0.15 mmol) was added and the mixture was stirred at rt overnight. Saturated $K_2CO_3$ aq. (20 mL) was added, and the mixture was stirred at rt briefly. The solid was filtered off through a celite pad. The filtrate was diluted with methylene chloride (30 mL), and it was extracted with brine. The organic layer was dried and concentrated to dryness. The crude material was purified via PTLC (10% $NH_3.MeOH/CH_2Cl_2$) to give 7 mg (26%) of compound 22L.

Compound 22K: Compound 22H (20 mg, 0.06 mmol) and isopropyl sulphonyl (27 mg, 0.18 mmol) were dissolved in methylene chloride (10 mL). DIPEA (0.04 mL, 0.26 mmol) were added and the reaction mixture was stirred at room temperature for 48 hr. Solvent was removed and the crude material was and purified via sgc (10% $NH_3.MeOH/CH_2Cl_2$) to give 2 mg (8%) of Compound 22K.

The following compounds were prepared as described in Examples 19-22.

TABLE 9

| Compound # | Structure | Exact Mass | Mass Obsvd | Ki (nM) |
| --- | --- | --- | --- | --- |
| 33 | 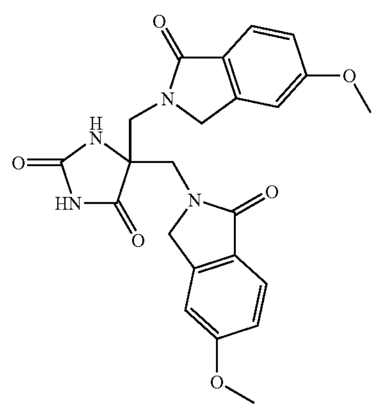 | 450.15 | 451.1 $[M + H]^+$ | B |
| 34 | 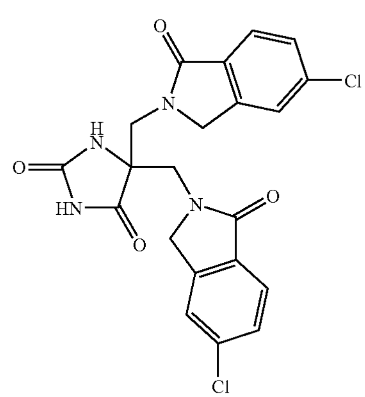 | 458.05 | 459.3 $[M + H]^+$ | B |

TABLE 9-continued

| Compound # | Structure | Exact Mass | Mass Obsvd | Ki (nM) |
|---|---|---|---|---|
| 35 | 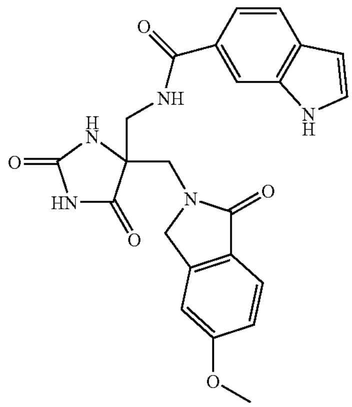 | 447.15 | 448.2 [M + H]$^+$ | A |
| 36 | 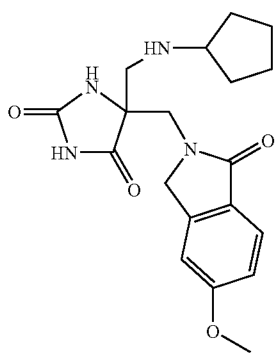 | 372.18 | 373.2 [M + H]$^+$ | B |
| 37 | 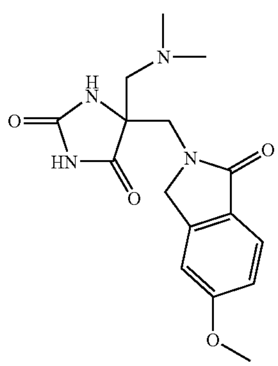 | 332.15 | 333.1 [M + H]$^+$ | C |
| 38 | 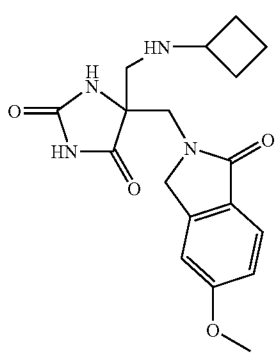 | 358.16 | 359.2 [M + H]$^+$ | B |

TABLE 9-continued
| Compound # | Structure | Exact Mass | Mass Obsvd | Ki (nM) |
|---|---|---|---|---|
| 39 | 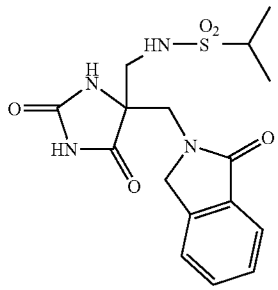 | 380.12 | 381.2 [M + H]+ | C |
| 40 | 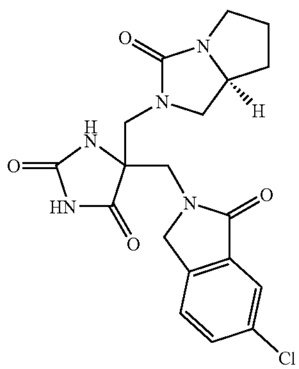 | 417.12 | 418.1 [M + H]+ | D |
| 41 | 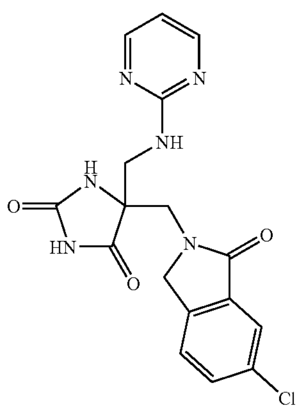 | 386.09 | 387.2 [M + H]+ | C |
Example 1001
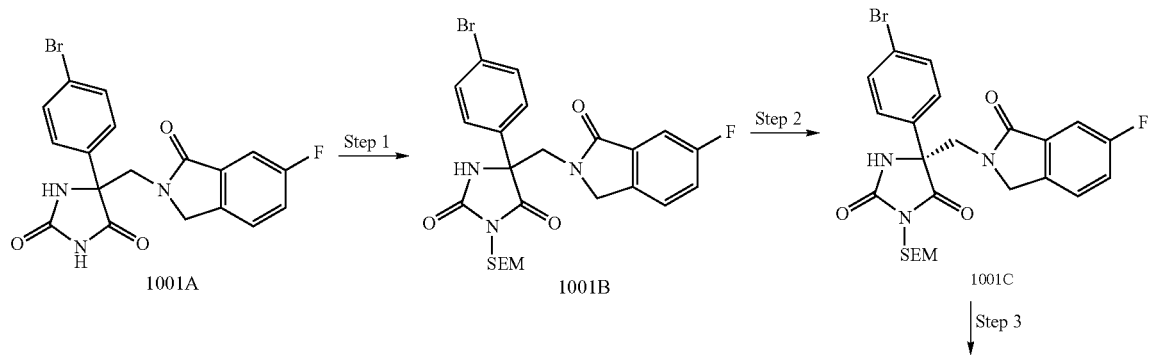

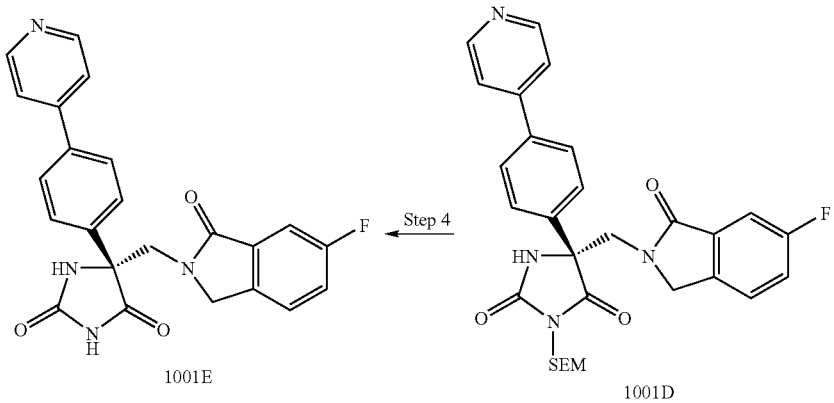

1001E            1001D

Step 1

To a solution of compound 1001A (1.65 g, 3.95 mmol) in anhydrous DMF (35 mL) was added 2-(trimethylsilyl) ethoxymethyl chloride (SEMCl, 0.93 mL, 4.73 mmol) and DIPEA (0.9 mL, 5.14 mmol). The solution was stirred at 25° C. for overnight. DMF was removed under vacuum. The product 1001B was purified by SGC (Hexane/EtOAc, 2:1. yield: 1.6 g, 74%).

Step 2

Compound 1001B was resolved by Chiralcel OD column (Mobile phase: Hexane/2-propanol 3:1). The first peak was collected and concentrated to give compound 1001C.

Step 3

To a dry flask was added compound 1001C (1.5 g, 2.73 mmol) and 4-pyridyl boronic acid (670 mg, 5.50 mmol). The flask was vacuumed and refilled with nitrogen three times. Pd(dppf)Cl$_2$ (220 mg, 0.30 mmol) was added and followed by addition of CH$_3$CN (20 mL) and aq. K$_2$CO$_3$ (1 M, 15 mL). The solution was stirred at 80° C. (oil bath) for 16 hours. After cooling down, CH$_3$CN (100 mL) was added and the solid was removed by filtration. The aqueous layer was separated and extracted with EtOAc (20 mL) once. The organic solution was combined and concentrated. The product was purified by SGC (CH$_2$Cl$_2$/MeOH/NH$_4$OH: 20:1:0.1) to give compound 1001D.

Step 4

Compound 1001D was dissolved in a mixture of methanol and HCl (4M in dioxane) (2:1, 30 mL) and was stirred overnight in a sealed pressure flask at 90° C. (oil bath). After the solution was cooled, the solution was transferred into a 250 mL round bottom flask. It was concentrated and dried under vacuum. The crude mixture was dissolved in methanol (50 mL) and Et$_3$N (0.5 mL) was added and stirred overnight at 25° C. The solvent was then removed and the product was purified by C18 reverse phase chromatography (CH$_3$CN/water 5% to 90%, with addition of 0.1% HCO$_2$H) to give compound 1001E (815 g, 71% from compound 1001C).

Example 1002

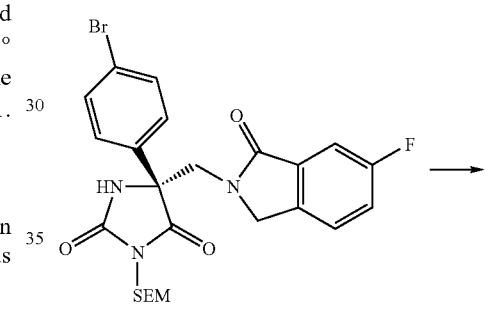

1003A

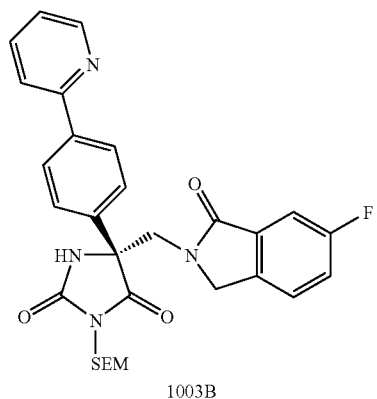

1003B

To a flamed dried flask was added compound 1003A (100 mg, 0.182 mmol), [1,4-bis(diphenylphosphino)butane]palladium(II) dichloride [Pd(dppb)Cl$_2$, 12 mg, 0.02 mmol], and copper (II) oxide (15 mg, 0.18 mmol). The flask was vacuumed and refilled with nitrogen. 2-Tri-n-butylstannylpyridine (0.076 mL, 0.237 mmol) and DMF (1 mL) were added. The solution was stirred at 100° C. oil bath for 5 hours. After cooling, the DMF was removed by rotary evaporator. The product was purified by SGC (Hexane/EtOAc 2:1) to give 1003B (84 mg, 84%).

Example 1003

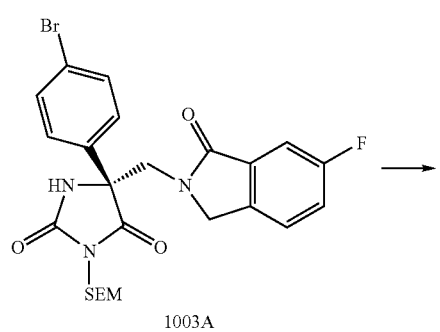

1003A

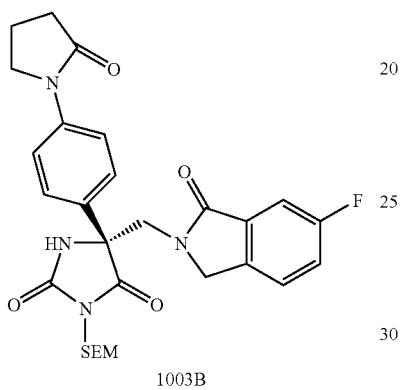

1003B

To a dry pressure tube was added compound 1003A (50 mg, 0.091 mmol), bis(dibenzylideneacetone) palladium [Pd(dba)$_2$, 1.6 mg, 0.0018 mmol], 9,9-dimethyl-4,5-bis(diphenylphosphino)xanthene (Xantphos, 3.0 mg, 0.0055 mmol) and Cs$_2$CO$_3$ (60 mg, 0.182 mmol). The pressure tube was vacuumed and refilled with nitrogen. Pyrrolidinone (14 mg, 0.16 mmol) and dioxane (0.5 mL) were added. The tube was sealed and stirred overnight at 100° C. (oil bath). After cooling, dioxane (2 mL) was added and the solid was removed by filtration. The solution was concentrated and purified by SGC (CH$_2$Cl$_2$/MeOH: 40:1) to give compound 1003B (27 mg).

Example 1004

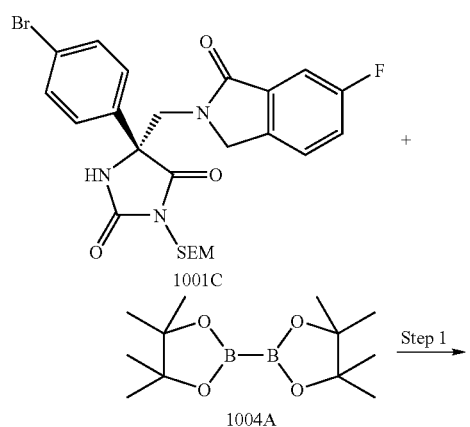

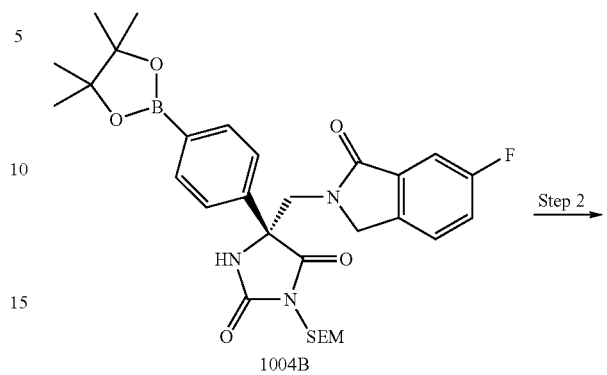

1004B

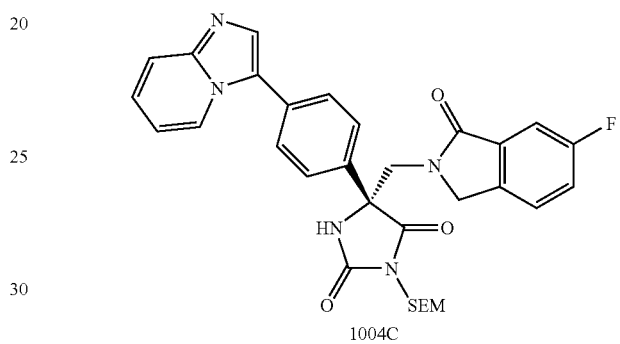

1004C

Step 1

Compound 1001C was prepared as described in Example 1001.

A mixture of compound 1001C (0.3 g, 0.55 mmol), bis(pinacolato)diboron (1004A; 170 mg, 0.65 mmol), potassium acetate (170 mg, 1.70 mmol), and [PdCl$_2$(dppf)]CH$_2$Cl$_2$ (50 mg, 0.05 mmol) in 1,4-dioxane (10 mL) was vacuumed and refilled with argon three times. The reaction mixture was stirred at 100° C. (oil bath) for 1.5 hours. After cooling down, the mixture was diluted in EtOAc (50 mL) and filtered through a Celite pad. The filtrate was concentrated in vacuo and the residual material was purified by silica gel column chromatography (2% MeOH in CH$_2$Cl$_2$) to afford compound 1004B (300 mg, 91% yield).

Step 2

A solution of compound 1004B (60 mg, 0.10 mmol), 3-bromoimidazo[1,2-a]pyridine (30 mg, 0.15 mmol), and [PdCl$_2$(dppf)]CH$_2$Cl$_2$ (8.2 mg, 0.01 mmol) in CH$_3$CN (3 mL) was treated with potassium carbonate (0.6 mL, 0.6 mmol, 1M in H$_2$O). The mixture was vacuumed and refilled with argon three times. The reaction mixture was stirred at 90° C. (oil bath) for 17 hours. After cooling, the mixture was diluted in EtOAc (20 mL) and filtered through a Celite pad. The filtrate was concentrated in vacuo and the residual material was purified by preparative TLC (10% MeOH in CH$_2$Cl$_2$) to afford compound 1004C (42 mg, 71% yield).

The following compounds were prepared as described in Examples 1001, 1002, 1003, or 1004.

TABLE 1000

| Compound # | Structure | Exact Mass | Mass Obsvd | Ki (nM) |
| --- | --- | --- | --- | --- |
| 110 | 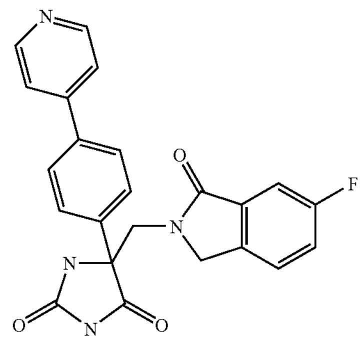 | 416.13 | 417.1 [M + H]+ | A |
| 111 | 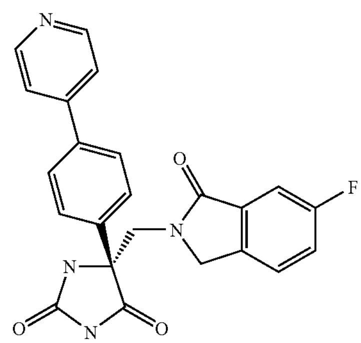 | 416.13 | 417.1 [M + H]+ | A |
| 112 | 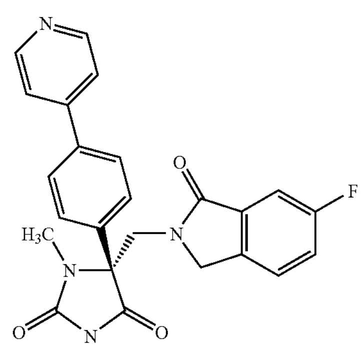 | 430.14 | 431.1 [M + H]+ | B |
| 113 | 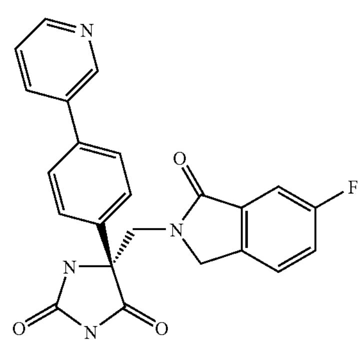 | 416.13 | 417.1 [M + H]+ | A |

TABLE 1000-continued

| Compound # | Structure | Exact Mass | Mass Obsvd | Ki (nM) |
|---|---|---|---|---|
| 114 | 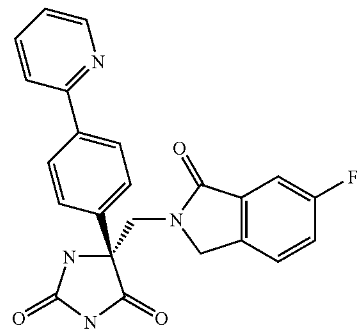 | 416.13 | 417.1 [M + H]+ | A |
| 115 | 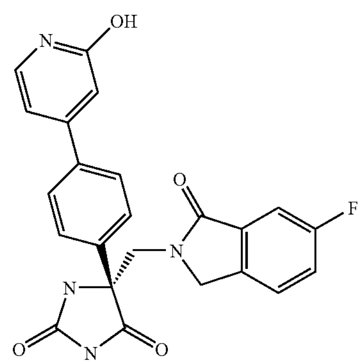 | 432.12 | 433.2 [M + H]+ | A |
| 116 | 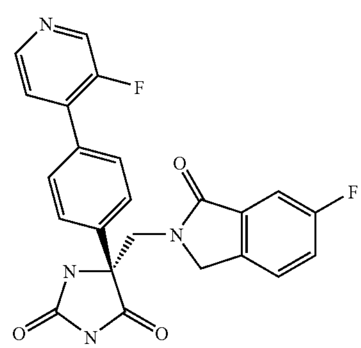 | 434.12 | 435.2 [M + H]+ | A |
| 117 | 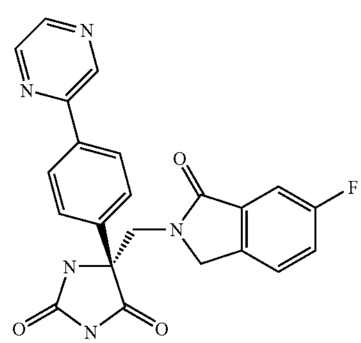 | 417.12 | 418.1 [M + H]+ | A |

TABLE 1000-continued

| Compound # | Structure | Exact Mass | Mass Obsvd | Ki (nM) |
|---|---|---|---|---|
| 118 | 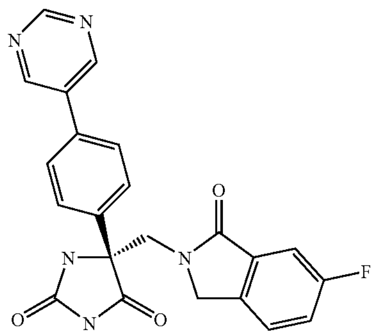 | 417.12 | 418.1 [M + H]+ | A |
| 119 | 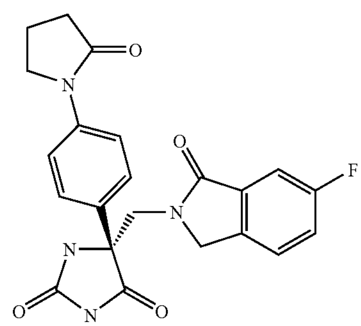 | 422.14 | 423.2 [M + H]+ | A |
| 120 | 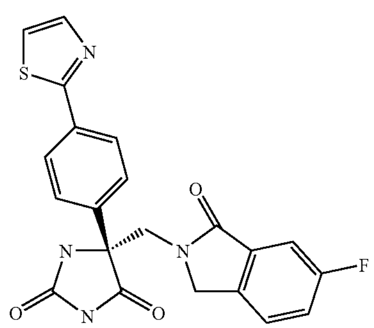 | 422.08 | 423.1 [M + H]+ | A |
| 121 | 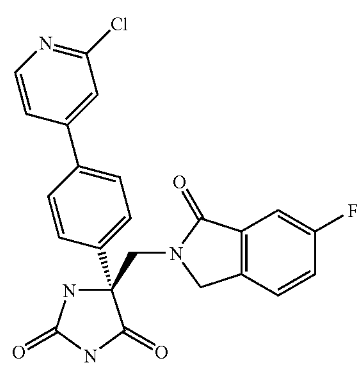 | 450.09 | 451.1 [M + H]+ | D |

TABLE 1000-continued

| Compound # | Structure | Exact Mass | Mass Obsvd | Ki (nM) |
|---|---|---|---|---|
| 122 | 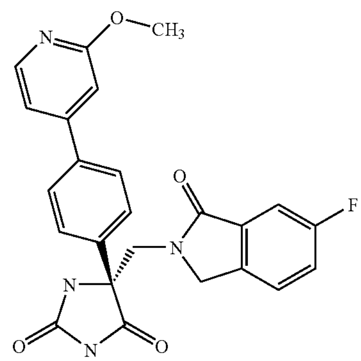 | 446.14 | 447.2 [M + H]+ | A |
| 123 | 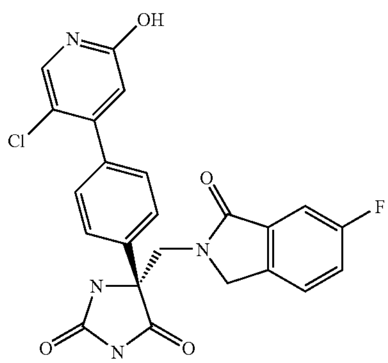 | 466.08 | 467.3 [M + H]+ | A |
| 124 | 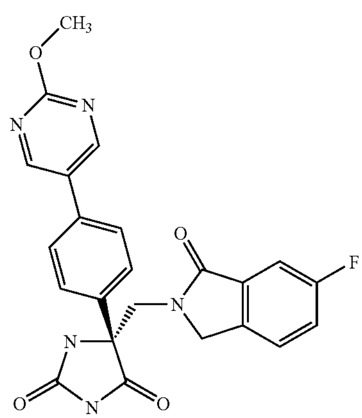 | 447.13 | 448.2 [M + H]+ | A |
| 125 | 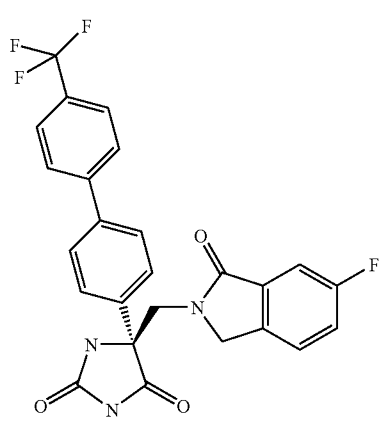 | 483.12 | 484.3 [M + H]+ | D |

TABLE 1000-continued
| Compound # | Structure | Exact Mass | Mass Obsvd | Ki (nM) |
|---|---|---|---|---|
| 126 | 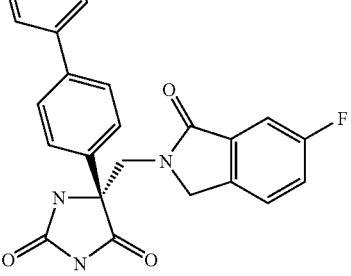 | 433.12 | 434.2 [M + H]+ | A |
| 127 | 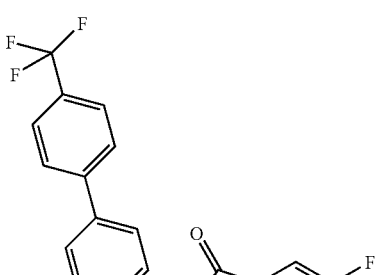 | 483.12 | 484.3 [M + H]+ | B |
| 128 | 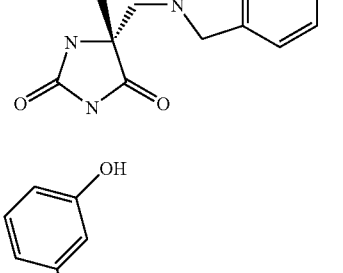 | 449.09 | 450.2 [M + H]+ | A |
| 129 | 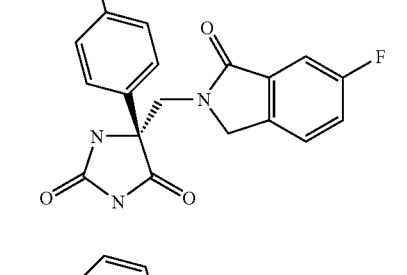 | 483.12 | 484.3 [M + H]+ | C |

TABLE 1000-continued

| Compound # | Structure | Exact Mass | Mass Obsvd | Ki (nM) |
|---|---|---|---|---|
| 130 | 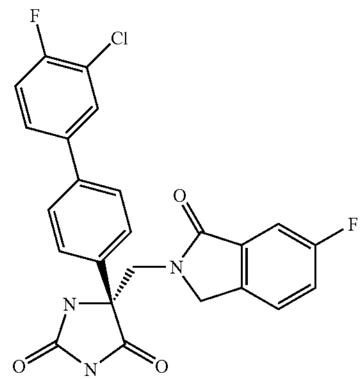 | 467.08 | 468.3 [M + H]+ | C |
| 131 | 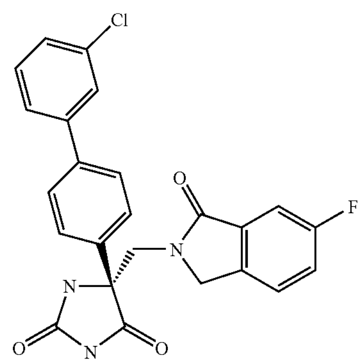 | 449.09 | 450.2 [M + H]+ | A |
| 132 | 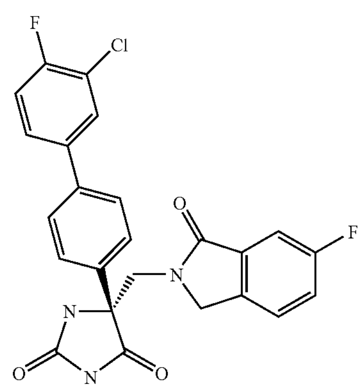 | 467.08 | 468.3 [M + H]+ | A |
| 133 | 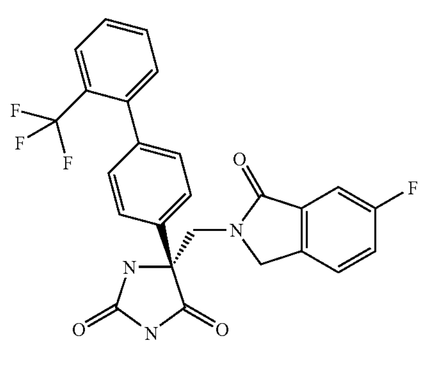 | 483.12 | 484.3 [M + H]+ | A |

TABLE 1000-continued

| Compound # | Structure | Exact Mass | Mass Obsvd | Ki (nM) |
| --- | --- | --- | --- | --- |
| 134 | 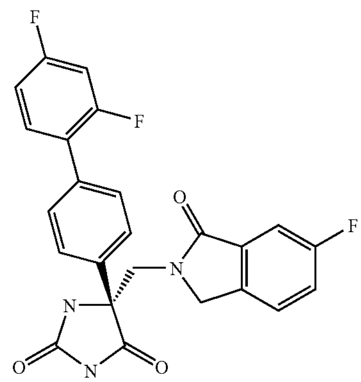 | 451.11 | 452.2 [M + H]+ | A |
| 135 | 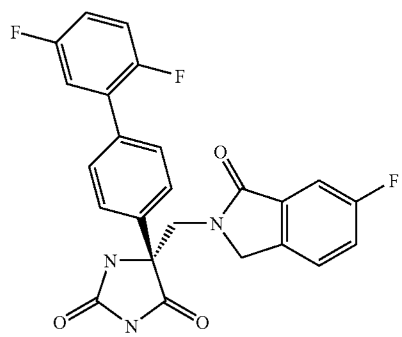 | 451.11 | 452.2 [M + H]+ | A |
| 136 | 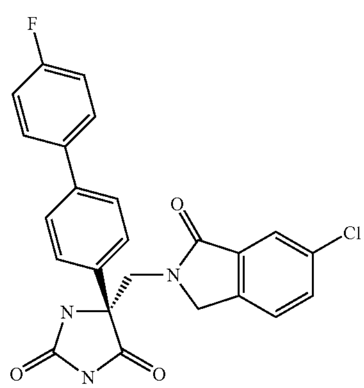 | 449.09 | 450.1 [M + H]+ | n/a |
| 137 | 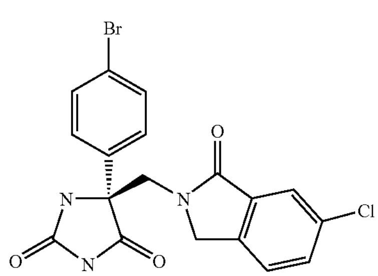 | 432.98 | 434.1 [M + H]+ | C |

TABLE 1000-continued

| Compound # | Structure | Exact Mass | Mass Obsvd | Ki (nM) |
| --- | --- | --- | --- | --- |
| 138 | 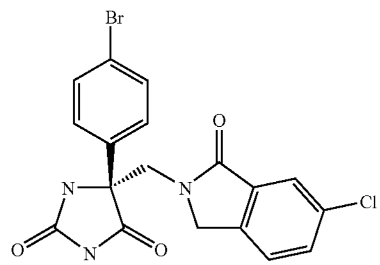 | 432.98 | 434.1 [M + H]+ | A |
| 139 | 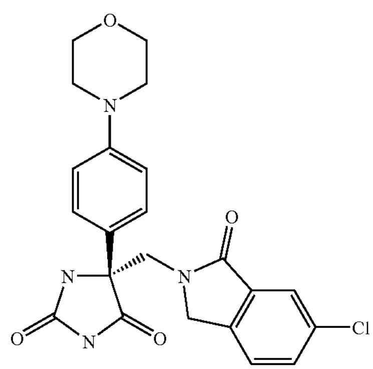 | 440.13 | 441.1 [M + H]+ | A |
| 140 | 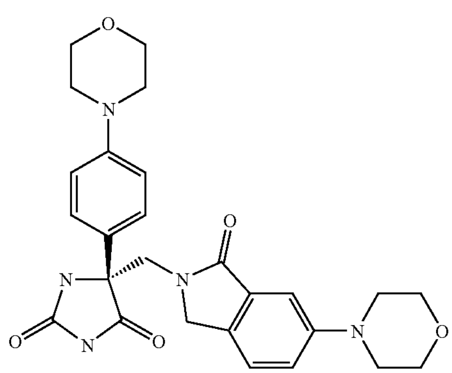 | 491.2 | 492.3 [M + H]+ | C |
| 141 | 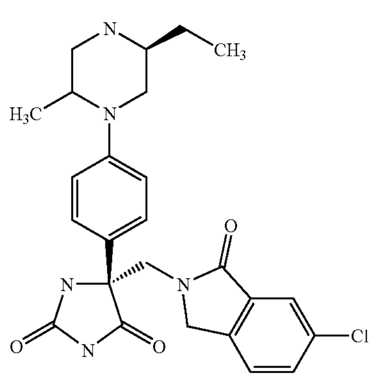 | 481.2 | 482.1 [M + H]+ | A |

TABLE 1000-continued
| Compound # | Structure | Exact Mass | Mass Obsvd | Ki (nM) |
|---|---|---|---|---|
| 142 | 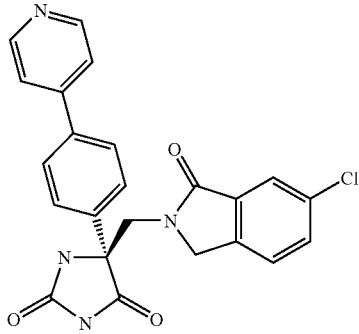 | 432.1 | 433.2 [M + H]+ | D |
| 143 | 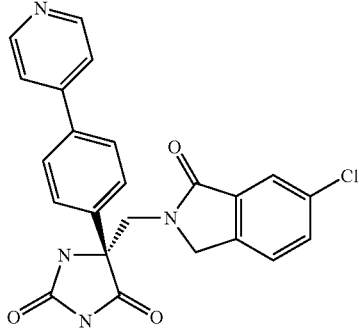 | 432.1 | 433.2 [M + H]+ | A |
| 144 | 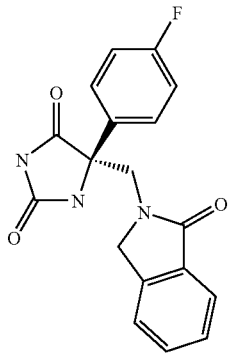 | 339.1 | 340 [M + H]+ | C |
| 145 | 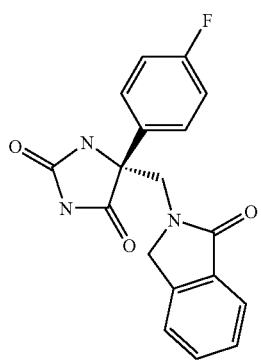 | 339.1 | 340 [M + H]+ | A |

TABLE 1000-continued
| Compound # | Structure | Exact Mass | Mass Obsvd | Ki (nM) |
|---|---|---|---|---|
| 146 | 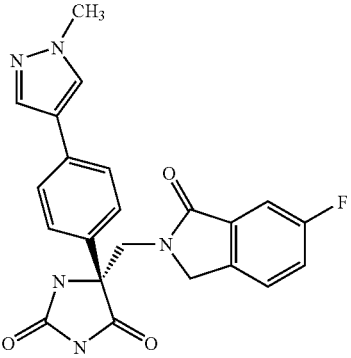 | 419.4 | 420.2 [M + H]+ | A |
| 147 | 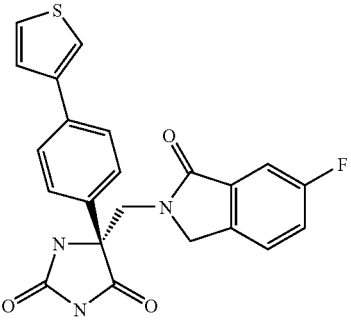 | 421.44 | 422.2 [M + H]+ | A |
| 148 | 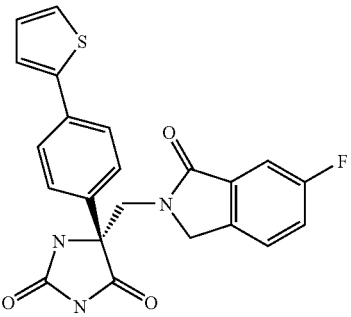 | 421.44 | 422.2 [M + H]+ | A |
| 149 | 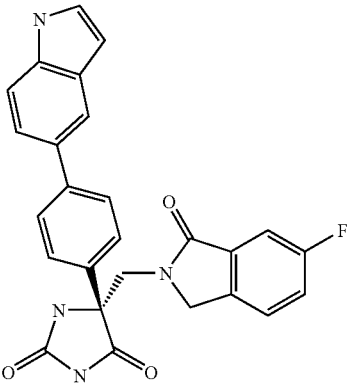 | 454.45 | 455.3 [M + H]+ | A |

TABLE 1000-continued

| Compound # | Structure | Exact Mass | Mass Obsvd | Ki (nM) |
|---|---|---|---|---|
| 150 | 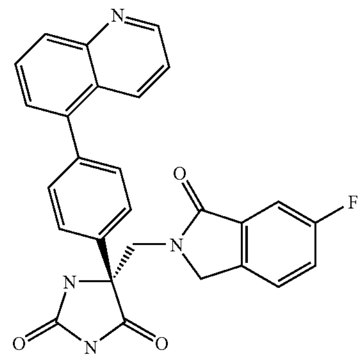 | 466.46 | 467.3 [M + H]+ | A |
| 151 | 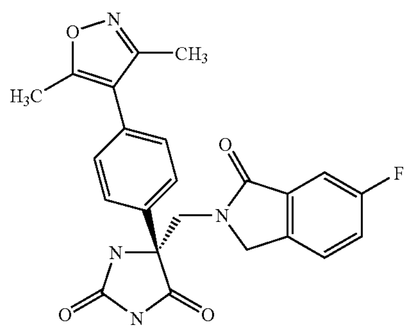 | 434.14 | 435.2 [M + H]+ | A |
| 152 | 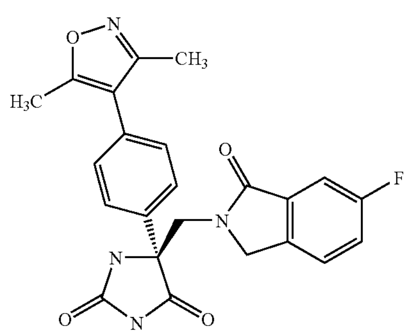 | 434.14 | 435.1 [M + H]+ | C |
| 153 | 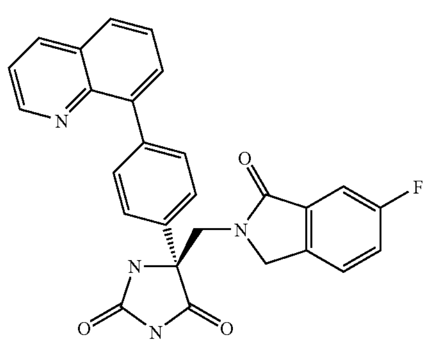 | 466.14 | 467.3 [M + H]+ | C |

TABLE 1000-continued

| Compound # | Structure | Exact Mass | Mass Obsvd | Ki (nM) |
|---|---|---|---|---|
| 154 | 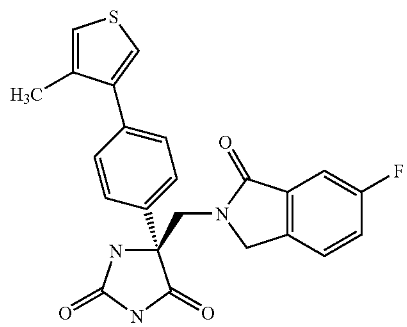 | 435.11 | 436.2 [M + H]+ | C |
| 155 | 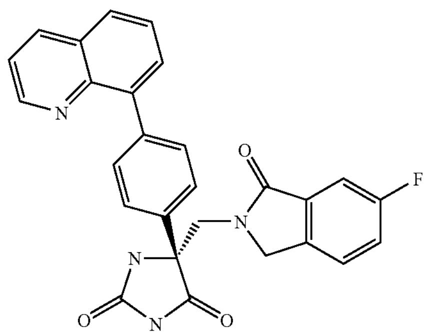 | 466.14 | 467.3 [M + H]+ | A |
| 156 | 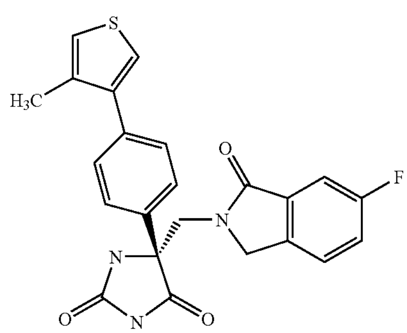 | 435.11 | 436.1 [M + H]+ | A |
| 157 | 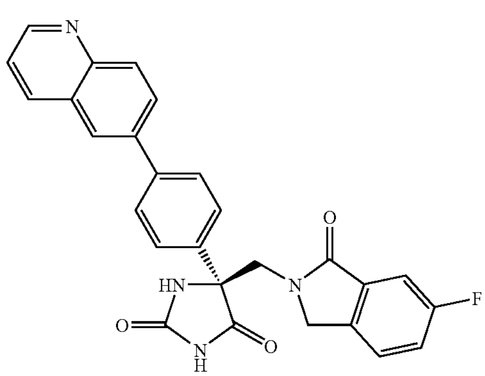 | 466.14 | 467.3 [M + H]+ | C |

TABLE 1000-continued
| Compound # | Structure | Exact Mass | Mass Obsvd | Ki (nM) |
|---|---|---|---|---|
| 158 | 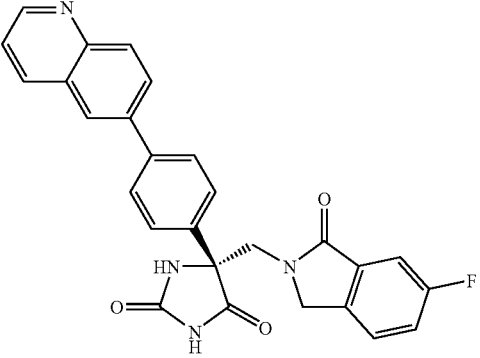 | 466.14 | 467.3 [M + H]+ | A |
| 159 | 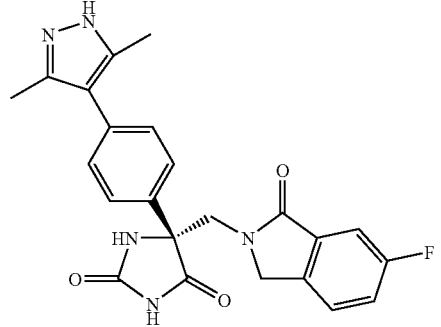 | 433.16 | 434.2 [M + H]+ | A |
| 160 | 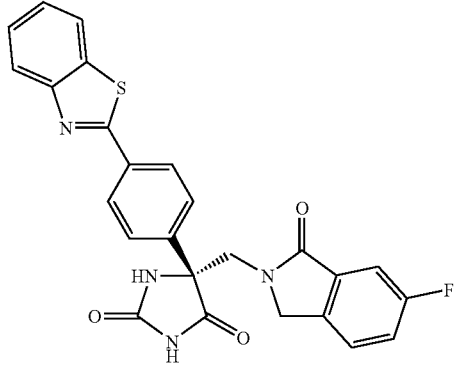 | 472.10 | 473.3 [M + H]+ | A |
| 161 | 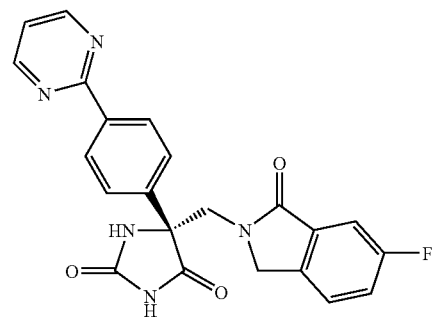 | 417.12 | 418.2 [M + H]+ | A |

TABLE 1000-continued
| Compound # | Structure | Exact Mass | Mass Obsvd | Ki (nM) |
|---|---|---|---|---|
| 162 | 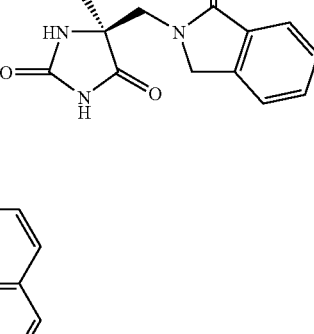 | 417.12 | 440.2 [M + Na]+ | C |
| 163 | 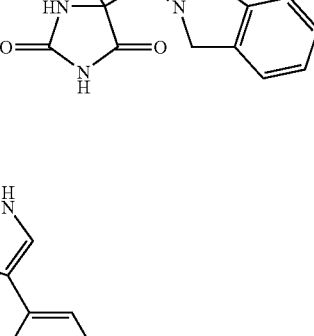 | 466.14 | 467.3 [M + H]+ | B |
| 164 | 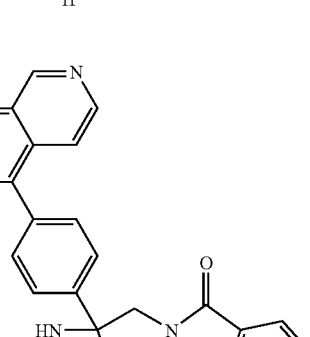 | 405.12 | 406.2 [M + H]+ | A |
| 165 | 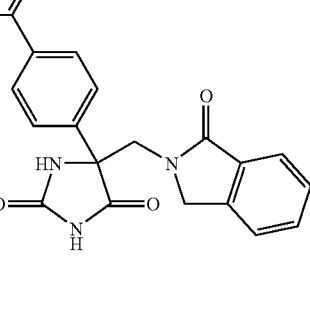 | 466.14 | 467.3 [M + H]+ | A |

TABLE 1000-continued

| Compound # | Structure | Exact Mass | Mass Obsvd | Ki (nM) |
|---|---|---|---|---|
| 166 | 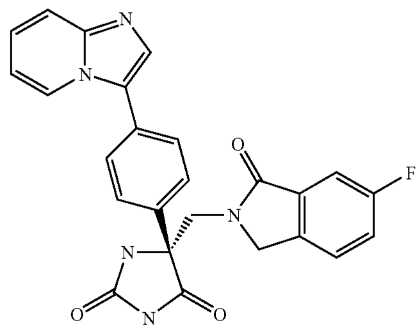 | 455.44 | 456.3 [M + H]+ | n/a |
| 167 | 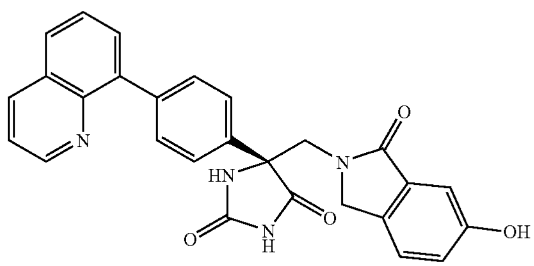 | 464.15 | 465.3 [M + H]+ | A |
| 168 | 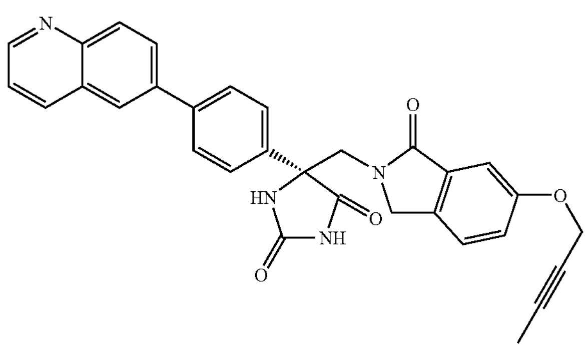 | 516.18 | 517.1 [M + H]+ | C |
| 169 | 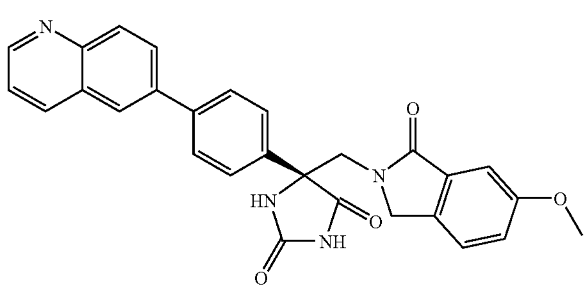 | 478.16 | 479.3 [M + H]+ | A |

TABLE 1000-continued

| Compound # | Structure | Exact Mass | Mass Obsvd | Ki (nM) |
|---|---|---|---|---|
| 170 | 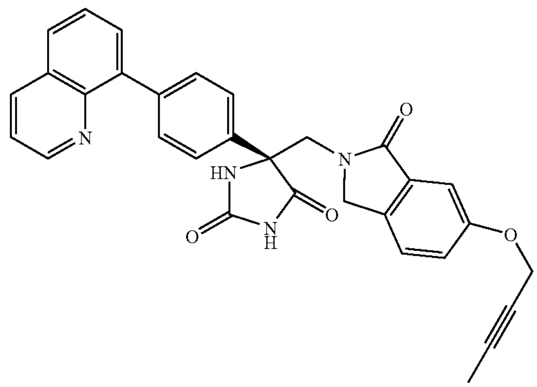 | 516.18 | 517.3 [M + H]⁺ | n/a |
| 171 | 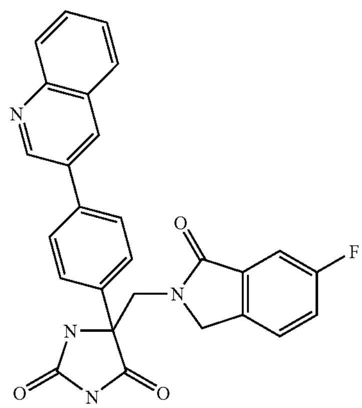 | 466.46 | 467.3 [M + H]⁺ | B |
| 172 | 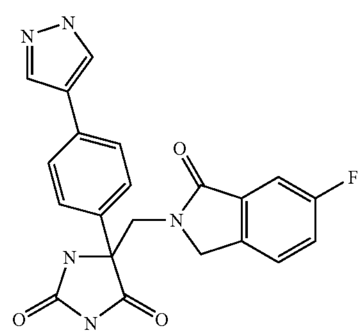 | 405.38 | 406.2 [M + H]⁺ | A |
| 173 | 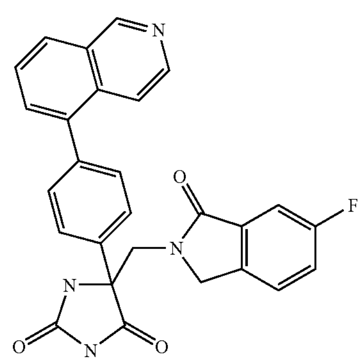 | 466.46 | 467.3 [M + H]⁺ | A |

TABLE 1000-continued

| Compound # | Structure | Exact Mass | Mass Obsvd | Ki (nM) |
|---|---|---|---|---|
| 174 | 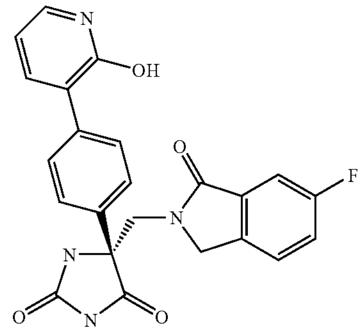 | 432.12 | 433.1 [M + H]+ | A |
| 175 | 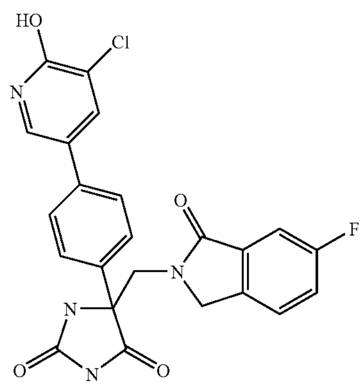 | 466.08 | 467.1 [M + H]+ | A |
| 176 | 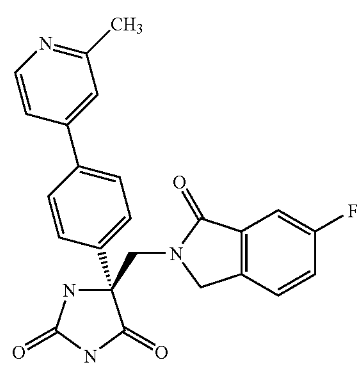 | 430.14 | 431.2 [M + H]+ | D |

Proton NMR Spectral Data for Selected Compounds in Table 1000.

Compound 111. $^1$H-NMR (500 MHz, DMSO-d$_6$) δ 9.0 (s, 1H), 8.79 (d, J=6.0 Hz, 2H), 7.92 (d, J=8.7 Hz, 2H), 7.79 (d, J=8.7 Hz, 2H), 7.76 (d, J=6.0 Hz, 2H), 7.65 (m, 1H), 7.48 (m, 2H), 4.40 (d, J=17.3H, 1H), 4.31 (d, J=17.3 Hz, 1H), 4.27 (d, J=14.2 Hz, 1H), 4.14 (d, J=14.2 Hz, 1H).

Compound 120. $^1$H-NMR (500 MHz, DMSO-d$_6$) δ8.99 (s, 1H), 8.03 (d, J=8.8 Hz, 2H), 7.96 (d, J=3.3 Hz, 1H), 7.84 (d, J=3.3 Hz, 1H), 7.77 (d, J=8.8 Hz, 2H), 7.65 (s, 1H), 7.47 (m, 2H), 4.38 (d, J=17.6 Hz, 1H), 4.28 (d, J=17.6 Hz, 1H), 4.27 (d, J=14.3 Hz, 1H), 4.13 (d, J=14.3 Hz, 1H).

Compound 123. $^1$H-NMR (500 MHz, DMSO-d$_6$) δ 8.99 (s, 1H), 7.84 (s, 1H), 7.74 (d, J=8.4 Hz, 2H), 7.66 (dd, J=8.5, 4.6 Hz, 1H), 7.54 (d, J=8.4 Hz, 2H), 7.49 (m, 2H), 6.65 (s, 1H), 4.40 (d, J=17.5 Hz, 1H), 4.31 (d, J=17.5 Hz, 1H), 4.29 (d, J=14.2 Hz, 1H), 4.10 9d, J=14.2 Hz, 1H).

Compound 139. $^1$H NMR (500 MHz, CD$_3$OD) δ3.17-3.21 (m, 4H), 3.83-3.88 (m, 4H), 4.14-4.52 (m, 4H), 7.01 (d, J=8.8 Hz, 2H), 7.47 (d, J=8 Hz, 1H), 7.46-7.48 (m, 3H), 7.75 (s, 1H).

Compound 143. ¹H NMR (400 MHz, CDCl₃) δ 4.21-4.50 (m, 4H), 7.498 (d, J=0.8 Hz, 1H), 7.52 (d, J=0.4 Hz, 1H), 7.73-7.76 (m, 3H), 7.76-7.87 (m, 4H), 8.60 (d, J=6 Hz, 2H).

Compound 155. ¹H NMR (500 MHz, CD₃OD) δ8.84 (dd, J=1.89, 4.1 Hz, 1H); 8.43 (dd, J=1.58, 8.2 Hz, 1H); 7.99 (dd, J=1.58, 8.2 Hz; 1H); 7.85 (m, 3H); 7.8 (dd, J=1.26 Hz, 6.94 Hz, 1H); 7.75 (m, 3H), 7.70 (dd, J=7.25 Hz, 0.95 Hz, 1H); 7.59 (dd, J=4.73 Hz, 7.57 Hz, 1H); 7.58 (dd, J=4.4 Hz, 8.2 Hz, 1H); 7.51 (dd, J=2.5 Hz, 7.8 Hz, 1H); 7.40 (m, 1H); 4.54 (d, J=17.0 Hz, 1H); 4.48 (d, J=17.0 Hz, 1H); 4.48 (d, J=14.5 Hz, 1H); 4.32 (1H, d, J=14.5 Hz, 1H).

Example 1005

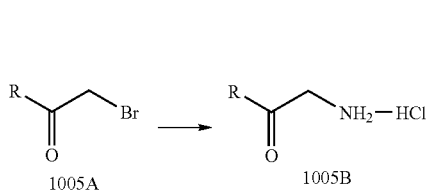

General Procedure for Example 1005

Compound 1005A was treated with one equivalent of hexamethylene tetramine in chloroform or other suitable solvent for about 5 hours. The product was collected by filtration and then treated with HCl in ethanol for one day to three days. The solid was then collected by filtration to give compound 1005B.

Example 1006

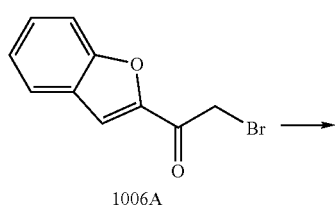

1-Benzofuran-2-yl-2-bromo-ethanone (1006A, 3.0 g, 12.55 mmol), hexamethylene tetramine (1.94 g, 13.80 mmol), and NaI (350 mg) were stirred in CHCl₃ (40 mL) for five hours. The solid was collected by filtration and dried under vacuum. The solid was then suspended in ethanol (30 mL) and HCl (conc, 36% in water, 10 mL) was added. The solution was stirred at 25° C. for 4 d. The solid was collected by filtration and washed by ethanol, dried under vacuum to give compound 1006B (3.05 g, contained NH₄Cl).

Example 1007

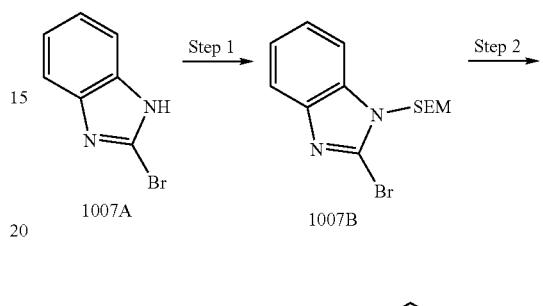

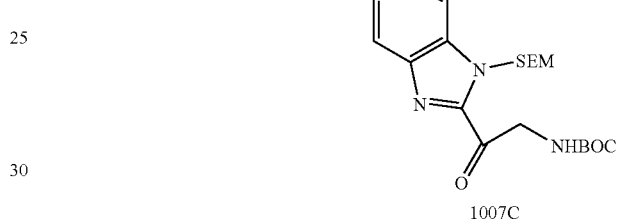

Step 1

To a flame dried flask was added 2-bromo-1H-benzimidazole (1007A, 2.94 g, 14.92 mmol), anhydrous THF (75 mL), and NaH (95%, 490 mg, 19.4 mmol). The solution was stirred at 25° C. for 45 minutes; SEMCl (3.17 mL, 17.9 mmol) was added. The solution was stirred at 25° C. for 2.5 hours. Water (50 mL) and EtOAc (100 mL) were added. The aqueous layer was separated and extracted with EtOAc (100 mL) once. The organic layers were combined and concentrated under vacuum. The product was purified by SGC (Hexane/EtOAc: 3:1) to give compound 1007B (3.6 g, 74%).

Step 2

To a flame dried flask was added compound 1007B (1.427 g, 4.35 mmol) and anhydrous ethyl ether/THF (2:1, 15 mL). The solution was cooled to −78° C. n-Butyllithium (1.6 M, 0.46 mL, 0.73 mmol) was added and stirred at −78° C. for 30 minutes. In another flamed dried pear shaped flask was added N-(tert-butoxycarbonyl)glycine-N'-methoxy-N'-methylamide (949 mg, 4.35 mmol) and anhydrous THF (2 mL). Isopropyl magnesium chloride (2 M, 2.5 mL, 5.0 mmol) was added at 0° C. The solution was stirred at 0° C. for 5 minutes and was added into the compound 1003C solution via cannula at −78° C. The solution was then gradually warmed up to −20° C. and stirred between −20° C. and 10° C. for 4 hours. Saturated NH₄Cl solution was added and the aqueous solution was extracted with EtOAc (50 mL) three times. The organic phases were combined and concentrated. The product was purified by SGC (Hexane/EtOAc: 3:1) to give compound 1007C (1.0 g, 57%).

The following compounds were prepared as described in Example 1, 14, 1005, 1006, and/or 1007.

TABLE 1001

| Compound # | Structure | Exact Mass | Mass Obsvd | Ki (nM) |
|---|---|---|---|---|
| 177 | 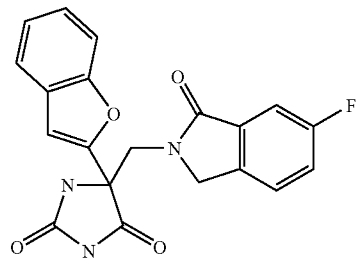 | 379.10 | 380.1 [M + H]+ | A |
| 178 | 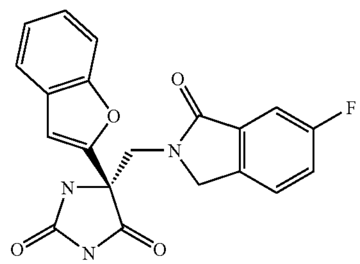 | 379.10 | 380.1 [M + H]+ | A |
| 179 | 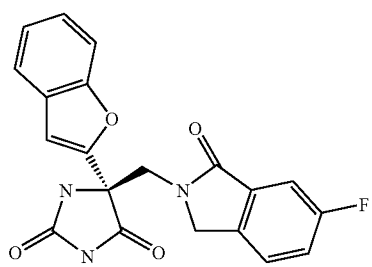 | 379.10 | 380.1 [M + H]+ | D |
| 180 | 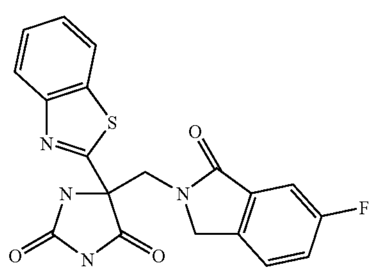 | 396.07 | 397.1 [M + H]+ | B |
| 181 | 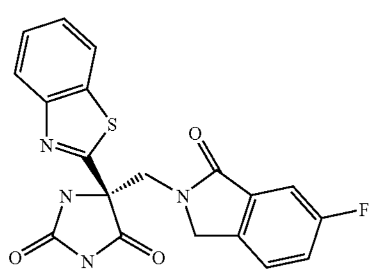 | 396.07 | 397.1 [M + H]+ | A |

TABLE 1001-continued

| Compound # | Structure | Exact Mass | Mass Obsvd | Ki (nM) |
|---|---|---|---|---|
| 182 | 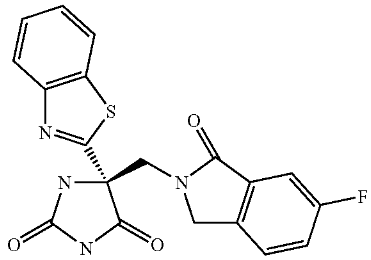 | 396.07 | 397.1 [M + H]⁺ | B |
| 183 | 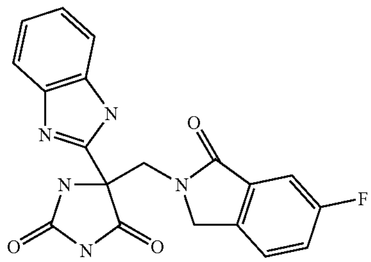 | 379.11 | 380.1 [M + H]⁺ | A |

Proton NMR Spectral Data for Selected Compounds in Table 1003.

Compound 181. $^1$H-NMR (500 MHz, DMSO-d$_6$) δ 11.3 (s, 1H), 9.34 (s, 1H), 8.18 (d, J=8.5 Hz, 1H), 8.12 (d, J=7.6 Hz, 1H), 7.67 (m, 1H), 7.61 (m, 1H), 7.50 (m, 3H), 4.65 (d, J=14.3 Hz, 1H), 4.44 (d, J=17.3 Hz, 1H), 4.38 (d, J=17.3 Hz, 1H), 4.34 (d, J=14.3 Hz, 1H).

Example 1008

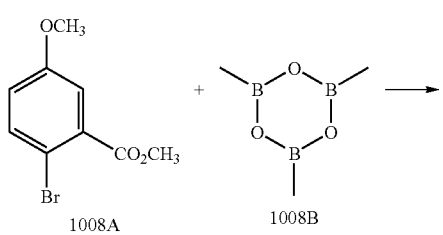

-continued

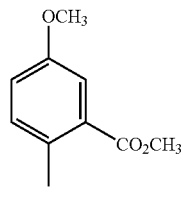

Compound 1008A (20 g, 81.61 mmol), 1008B (13.36 mL, 97.93 mmol), Pd(dppf)Cl$_2$ (1.0 g, 1.36 mmol), dioxane (350 mL), water (50 mL), and Cs$_2$CO$_3$ (22.5 g, 163 mmol) were stirred at 110° C. (oil bath) under nitrogen for 16 hours. After cooling, the solid was removed by filtration. The solution was concentrated and purified by SGC (Hexane/EtOAc, 10:1) to give 1008C (12.1 g, 80%).

The following compounds were prepared as described in Examples 14 and 1008 and 1009.

TABLE 1002

| Compound # | Structure | Exact Mass | Mass Obsvd | Ki (nM) |
|---|---|---|---|---|
| 184 | 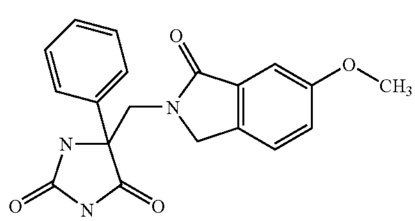 | 351.12 | 352.1 [M + H]⁺ | A |

TABLE 1002-continued
| Compound # | Structure | Exact Mass | Mass Obsvd | Ki (nM) |
|---|---|---|---|---|
| 185 | 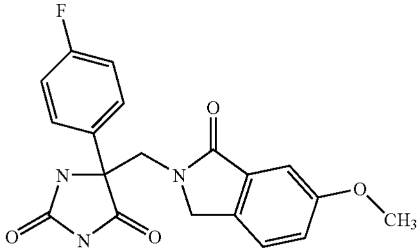 | 369.11 | 370.1 [M + H]+ | A |
| 186 | 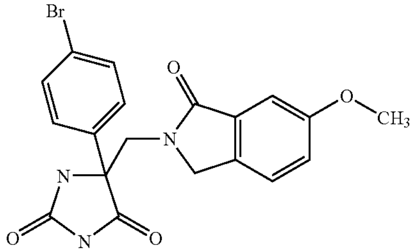 | 429.03 | 430.2 [M + H]+ 432.2 [M + Na]+ | A |
Example 1009
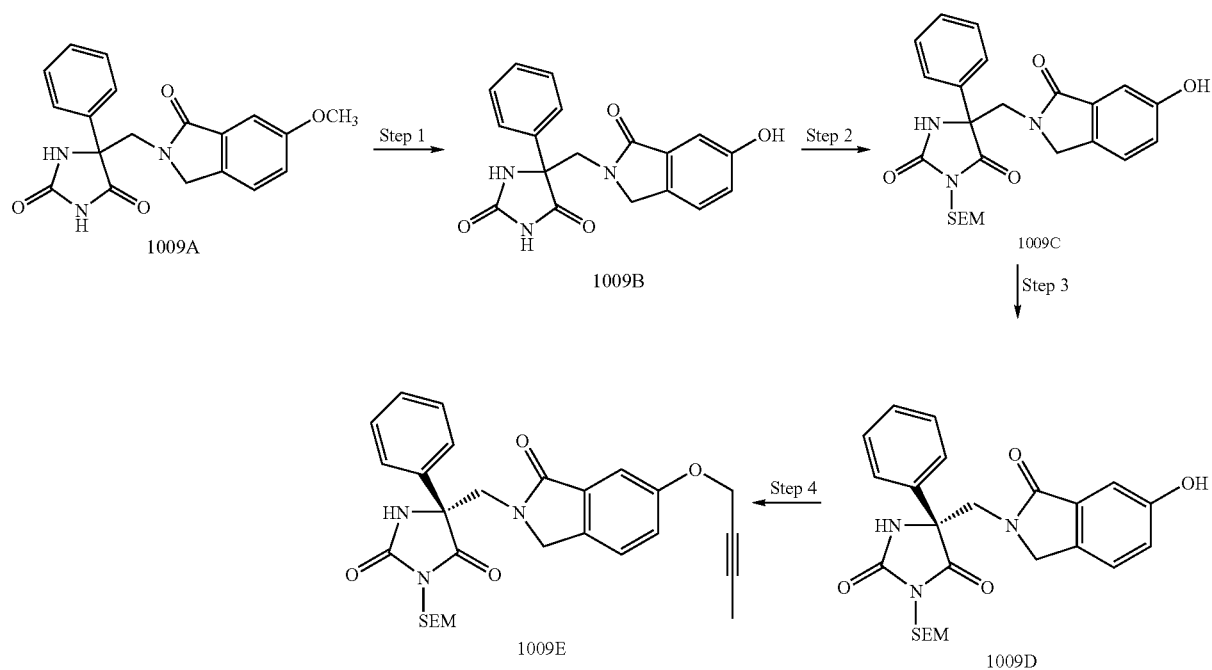

Step 1

Compound 1009A (1.18 g, 3.36 mmol) and pyridine hydrochloride (2.33 g, 20.17 mmol) were added into a 20 mL microwave reactor tube and reacted at 200° C. for 1 hour. After cooling down, the solid was dissolved in DMF and purified by C18 chromatography (CH$_3$CN/water 5% to 90%, with 0.1% HCO$_2$H) to give compound 1009B (0.87 g, 77%).

Step 2

Compound 1009B (0.75 g, 2.22 mmol) was dissolved in DMF (12 mL). SEMCl (0.48 mL, 2.44 mmol) and DIPEA (0.775 mL, 4.44 mmol) were added and the solution was stirred at 25° C. for 4 hours. DMF was removed under vacuum and the product was purified by SGC (Hexane/EtOAc: 3:1 to 1:1) to give compound 1009C (0.81 g, 78%).

Step 3

Compound 1009C was resolved on Chiralcel OD column by using Hexane and 2-propanol as mobile phase. The first peak was collected and concentrated to give compound 1009D.

Step 4

Compound 1009D (100 mg, 0.214 mmol), 1-bromo-2-butyne (34 mg, 0.257 mmol), and Cs$_2$CO$_3$ (140 mg, 0.428 mmol) were stirred in DMF (2 mL) at 0° C. for 2 hours, then at 25° C. for overnight. Water (5 mL) was added and the aqueous solution was extracted with EtOAc (10 mL) three times. The organic phases were combined and concentrated. The product was purified by SGC (Hexane/EtOAc: 3:1) to give compound 1009E (81 mg).

Example 1010

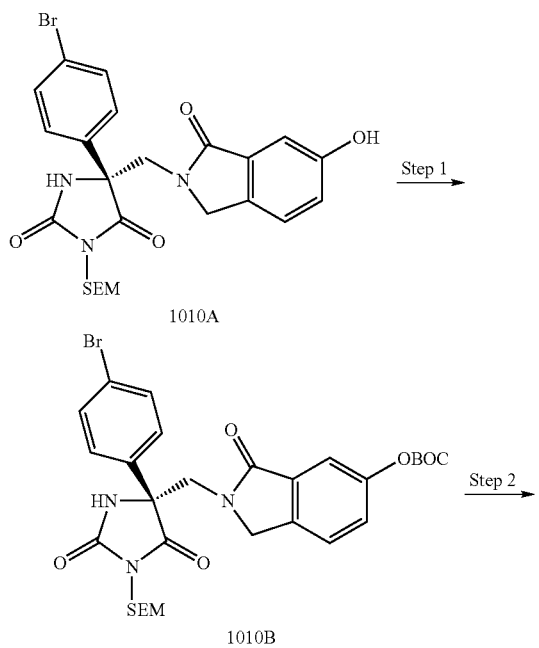

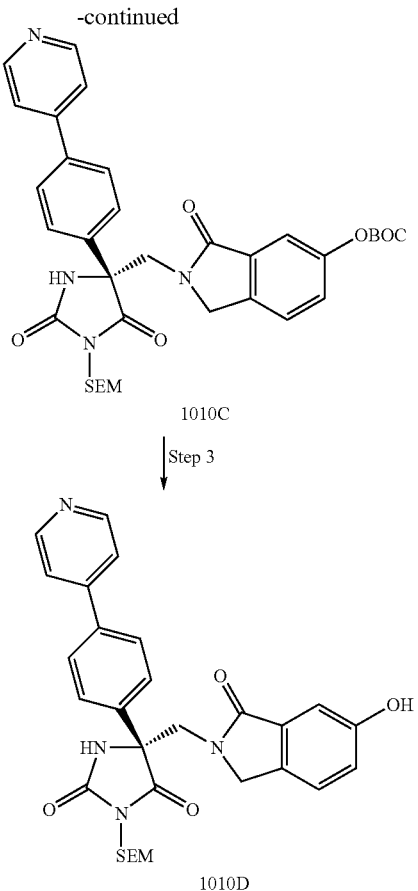

Step 1

Compound 1010A (1.03 g, 1.88 mmol), (BOC)$_2$O (493 mg, 2.26 mmol), and Cs$_2$CO$_3$ (741 mg, 2.26 mmol) were stirred overnight in CHCl$_3$ (20 mL). Water was added. The aqueous layer was extracted with EtOAc (3×50 mL). The combined organic layers were concentrated and purified by SGC (Hexane/EtOAc 5% to 90%) to give compound 1010B (1.01 g, 83%).

Step 2

To a dry flask was added compound 1010B (500 mg, 0.77 mmol) and 4-pyridyl boronic acid (190 mg, 1.55 mmol). The flask was vacuumed and refilled with nitrogen three times. Pd(dppf)Cl$_2$ (28 mg, 0.04 mmol) was added and followed by addition of CH$_3$CN (5 mL) and K$_2$CO$_3$ (1 M, 4 mL). The solution was stirred at 80° C. (oil bath) for 16 hours. After cooling down, CH$_3$CN (100 mL) was added and the solid was removed by filtration. The aqueous layer was separated and extracted once with EtOAc (20 mL). The organic solution was combined and concentrated. The product was purified by SGC (CH$_2$Cl$_2$/MeOH/NH$_4$OH: 20:1:0.1) to give compound 1010C.

Step 3

Compound 1010C obtained in step 2 was dissolved in MeOH (10 mL) and HCl (4M in dioxane, 3 mL) was added and stirred overnight at 25° C. MeOH was then removed and the product was dried under vacuum to give Compound 1010D (315 mg, 75% from compound 1010B).

The following compounds were prepared as described in Examples 14 and 1009 or 1010.

TABLE 1003

| Compound # | Structure | Exact Mass | Mass Obsvd | Ki (nM) |
|---|---|---|---|---|
| 187 | 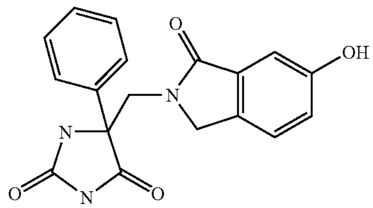 | 337.11 | 338.1 [M + H]⁺ | B |
| 188 | 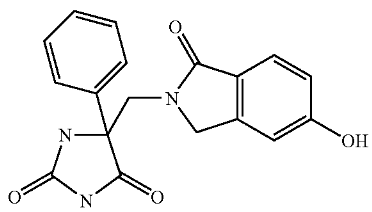 | 337.11 | 338.1 [M + H]⁺ 360.1 [M + Na]⁺ | A |
| 189 | 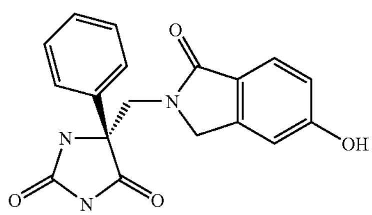 | 337.11 | 338.2 [M + H]⁺ 360.2 [M + Na]⁺ | A |
| 190 | 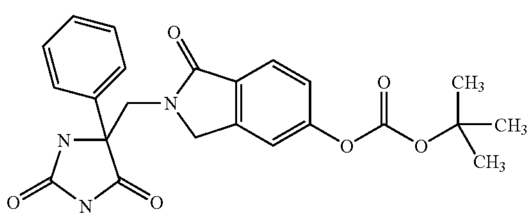 | 437.16 | 438.2 [M + H]⁺ | A |
| 191 | 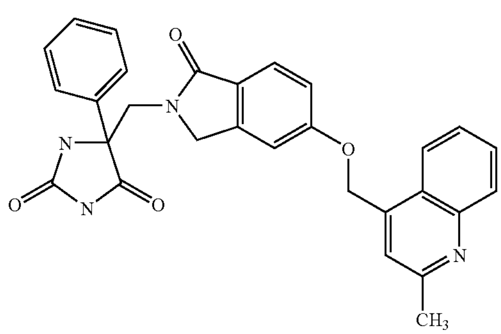 | 492.18 | 493.3 [M + H]⁺ | A |

TABLE 1003-continued

| Compound # | Structure | Exact Mass | Mass Obsvd | Ki (nM) |
|---|---|---|---|---|
| 192 | 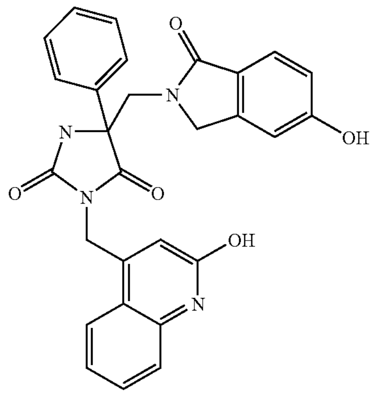 | 492.18 | 493.3 [M + H]+ | C |
| 193 | 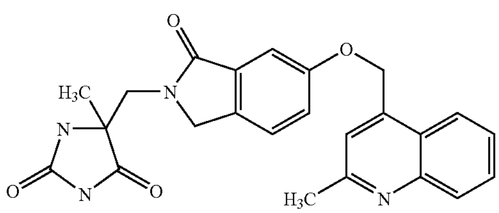 | 430.16 | 431.1 [M + H]+ | A |
| 194 | 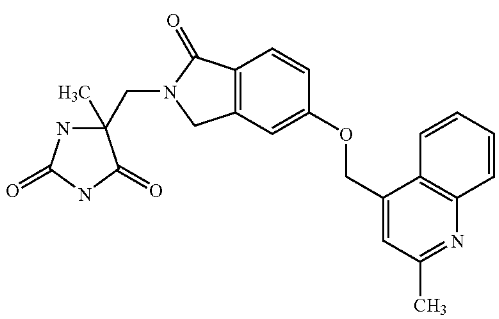 | 430.16 | 431.1 [M + H]+ | A |
| 195 | 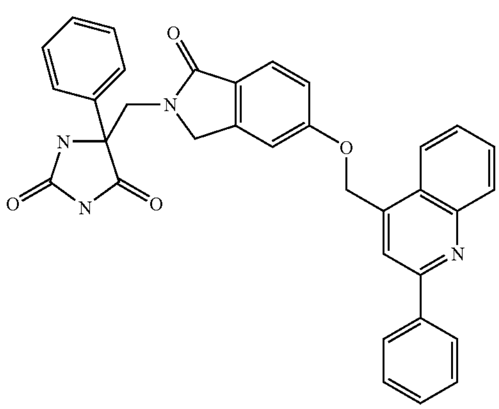 | 554.20 | 555.1 [M + H]+ | B |

TABLE 1003-continued

| Compound # | Structure | Exact Mass | Mass Obsvd | Ki (nM) |
|---|---|---|---|---|
| 196 | 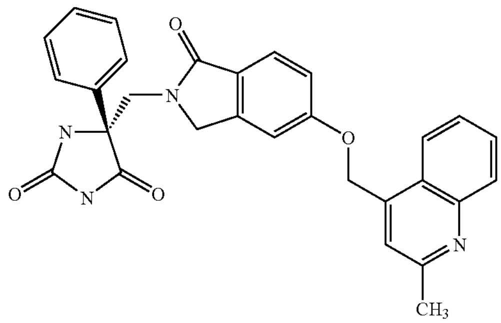 | 492.16 | 493.1 [M + H]+ | A |
| 197 | 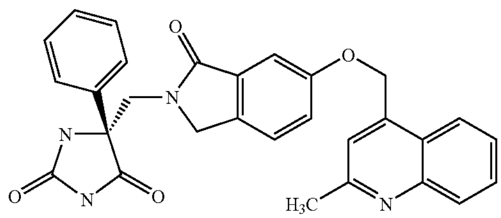 | 492.16 | 493.1 [M + H]+ | A |
| 198 | 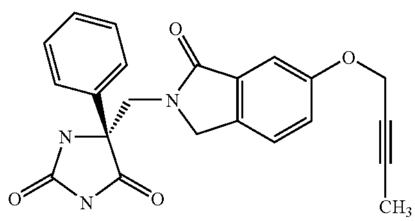 | 389.14 | 390.1 [M + H]+ | A |
| 199 | 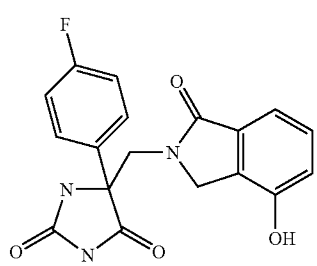 | 355.10 | 356.1 [M + H]+ | C |
| 200 | 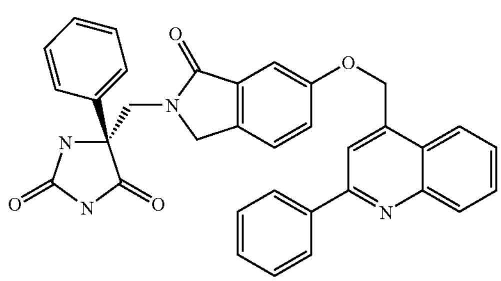 | 554.20 | 555.1 [M + H]+ | B |

TABLE 1003-continued

| Compound # | Structure | Exact Mass | Mass Obsvd | Ki (nM) |
|---|---|---|---|---|
| 201 | 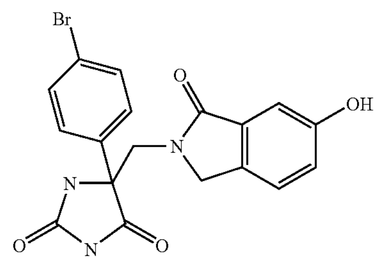 | 415.02 | 416.2 [M + H]+ | B |
| 202 | 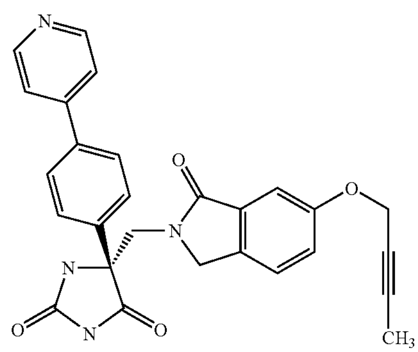 | 466.16 | 467.1 [M + H]+ | A |
| 203 | 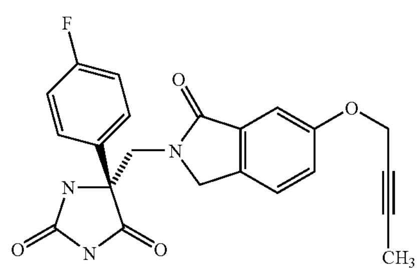 | 407.13 | 408.2 [M + H]+ | A |
| 204 | 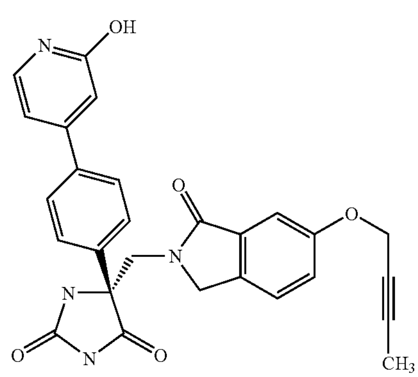 | 482.16 | 483.3 [M + H]+ | A |

TABLE 1003-continued

| Compound # | Structure | Exact Mass | Mass Obsvd | Ki (nM) |
|---|---|---|---|---|
| 205 | 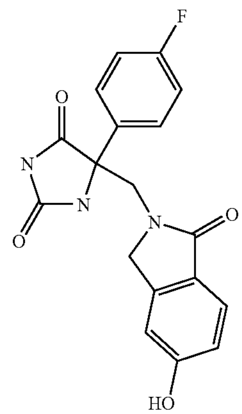 | 355.1 | 356 [M + H]⁺ | A |
| 206 | 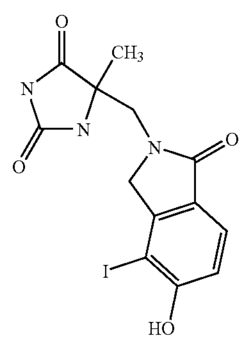 | 400.99 | 402 [M + H]⁺ | C |
| 207 | 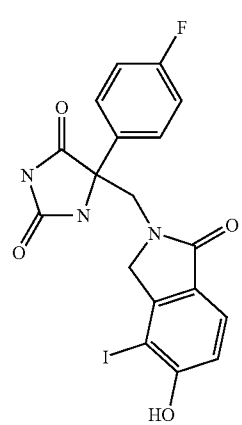 | 480.99 | 482 [M + H]⁺ | D |

TABLE 1003-continued
| Compound # | Structure | Exact Mass | Mass Obsvd | Ki (nM) |
|---|---|---|---|---|
| 208 | 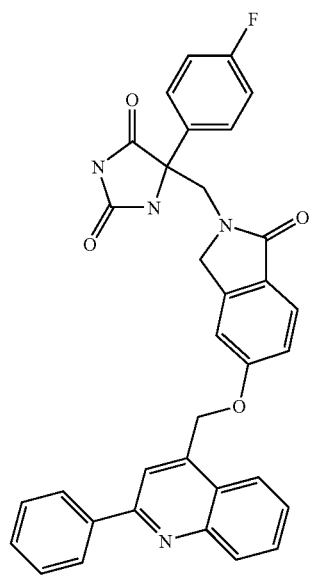 | 572.19 | 573 [M + H]+ | B |
| 209 | 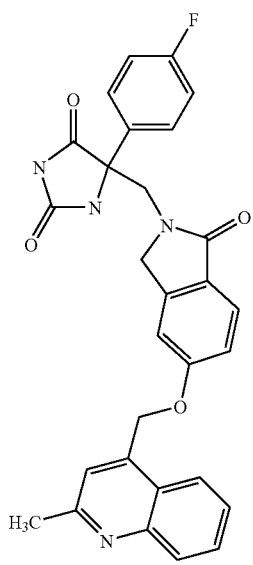 | 510.17 | 511 [M + H]+ | A |

TABLE 1003-continued

| Compound # | Structure | Exact Mass | Mass Obsvd | Ki (nM) |
|---|---|---|---|---|
| 210 | 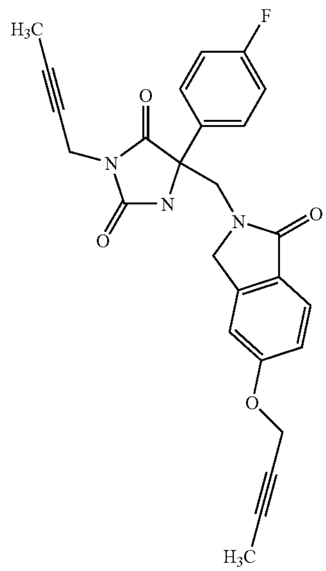 | 459.16 | 460 [M + H]+ | D |
| 211 | 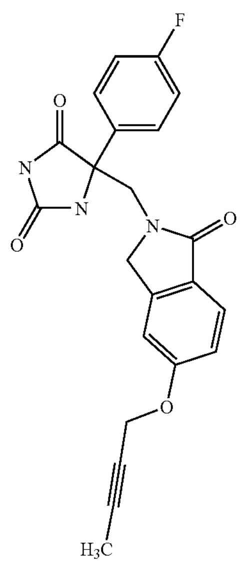 | 407.13 | 408 [M + H]+ | A |
| 212 | 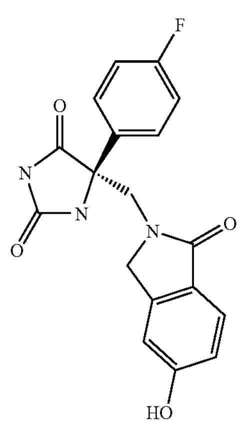 | 355.1 | 356 [M + H]+ | C |

TABLE 1003-continued

| Compound # | Structure | Exact Mass | Mass Obsvd | Ki (nM) |
| --- | --- | --- | --- | --- |
| 213 | 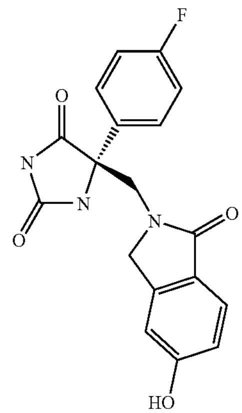 | 355.1 | 356 [M + H]⁺ | A |
| 214 | 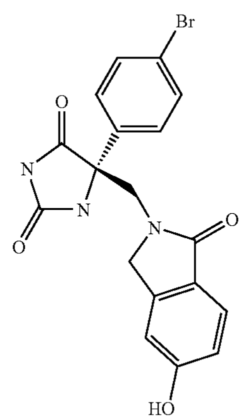 | 415.02 | 416.418 [M + H]⁺ | A |
| 215 | 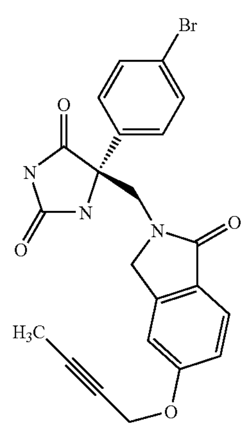 | 467.05 | 468.470 [M + H]⁺ | A |

TABLE 1003-continued
| Compound # | Structure | Exact Mass | Mass Obsvd | Ki (nM) |
|---|---|---|---|---|
| 216 | 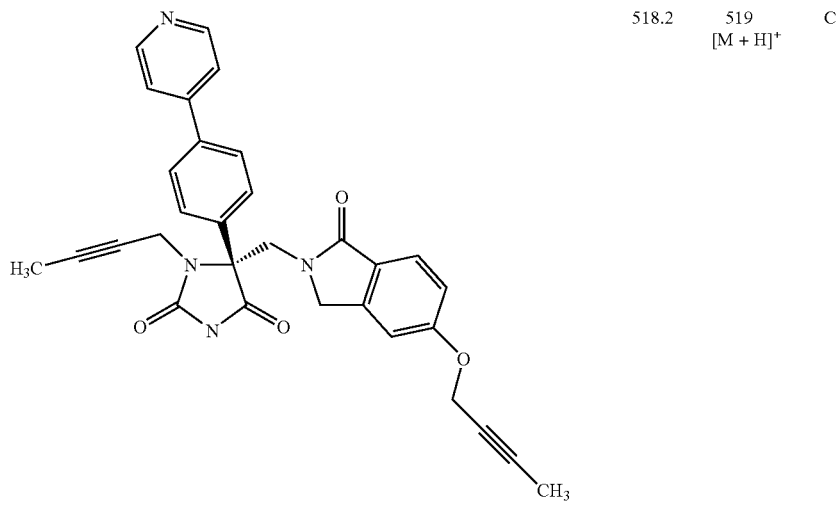 | 518.2 | 519 [M + H]⁺ | C |
| 217 | 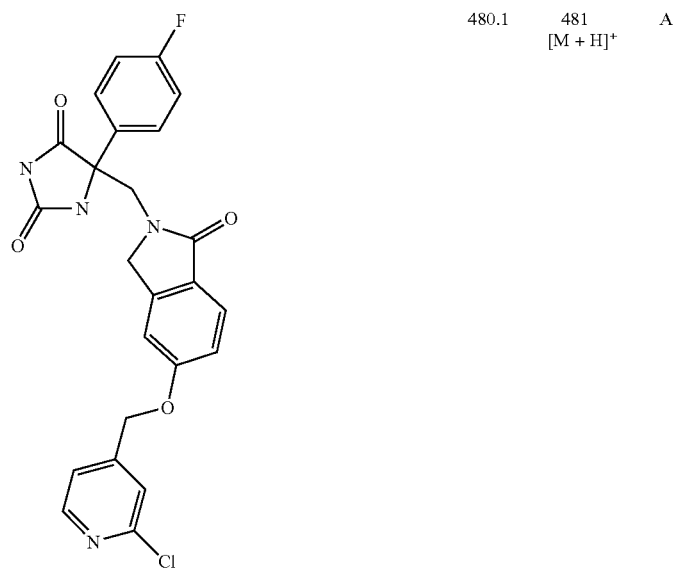 | 480.1 | 481 [M + H]⁺ | A |

TABLE 1003-continued

| Compound # | Structure | Exact Mass | Mass Obsvd | Ki (nM) |
|---|---|---|---|---|
| 218 | 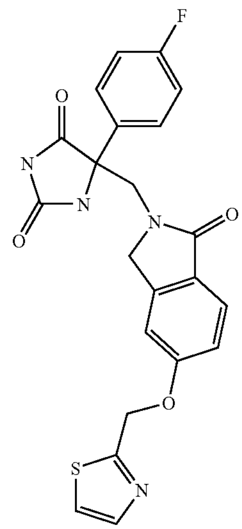 | 452.1 | 453 [M + H]+ | B |
| 219 | 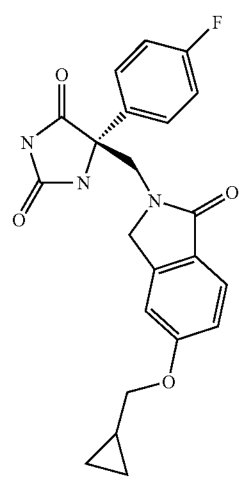 | 409.14 | 410 [M + H]+ | A |
| 220 | 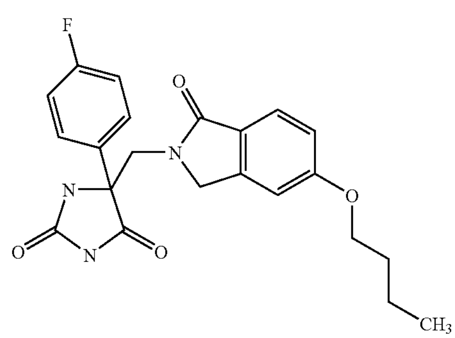 | 411.16 | 412 [M + H]+ | A |

TABLE 1003-continued
| Compound # | Structure | Exact Mass | Mass Obsvd | Ki (nM) |
|---|---|---|---|---|
| 221 | 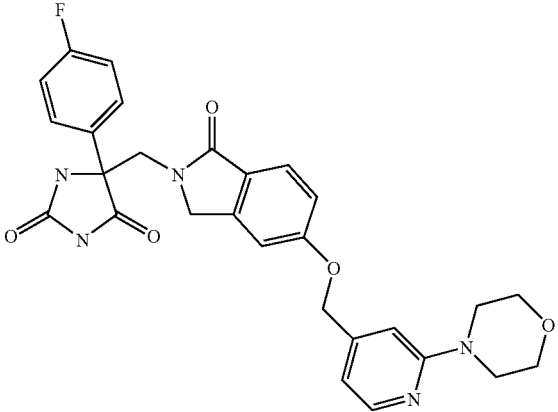 | 531.19 | 532 [M + H]+ | B |
| 222 | 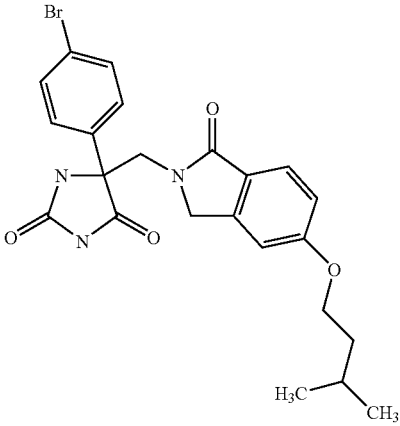 | 485.1 | 486.488 [M + H]+ | A |
| 223 | 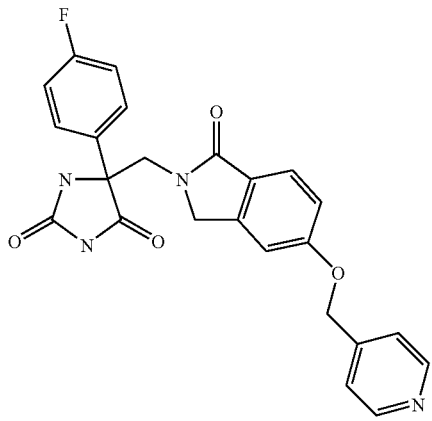 | 446.14 | 447 [M + H]+ | A |

TABLE 1003-continued
| Compound # | Structure | Exact Mass | Mass Obsvd | Ki (nM) |
|---|---|---|---|---|
| 224 | 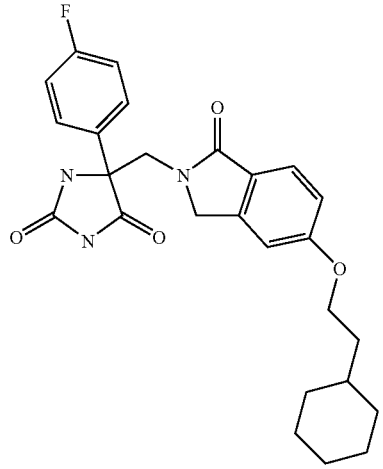 | 465.21 | 466 [M + H]⁺ | C |
| 225 | 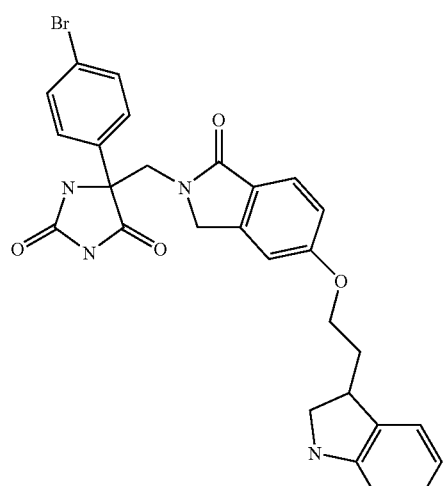 | 558.09 | 559.561 [M + H]⁺ | A |
| 226 | 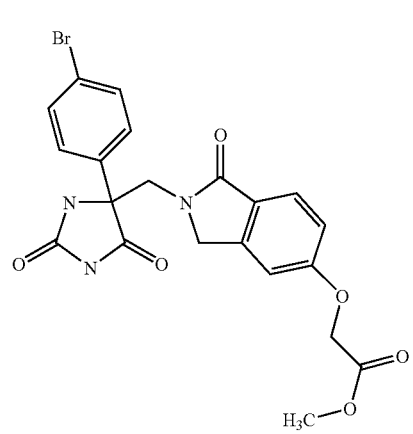 | 487.04 | 488.490 [M + H]⁺ | A |

TABLE 1003-continued

| Compound # | Structure | Exact Mass | Mass Obsvd | Ki (nM) |
|---|---|---|---|---|
| 227 | 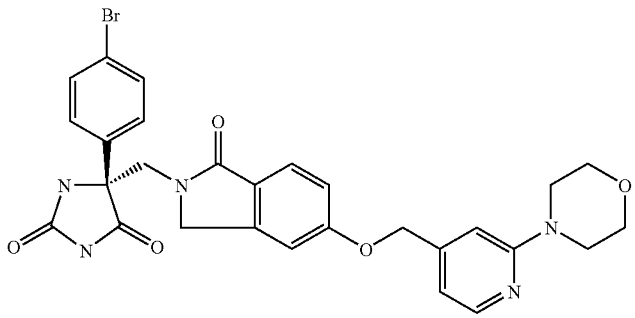 | 591.11 | 592.1 [M + H]+ | B |
| 228 | 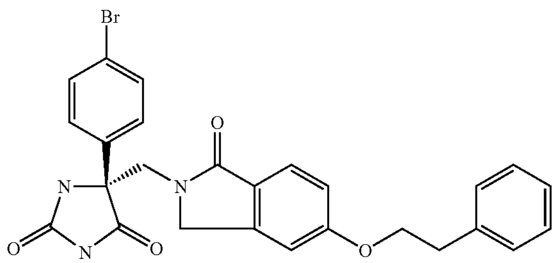 | 519.1 | 520.1 [M + H]+ | C |
| 229 | 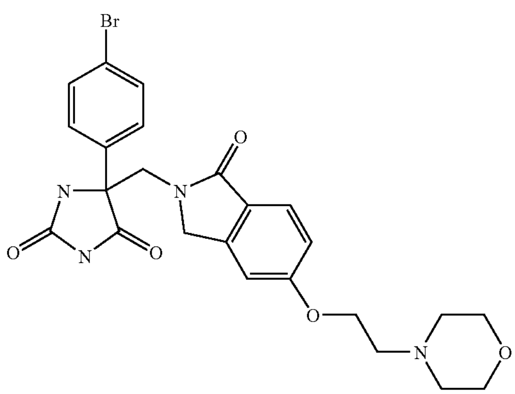 | 528.1 | 529.4 [M + H]+ | B |
| 230 | 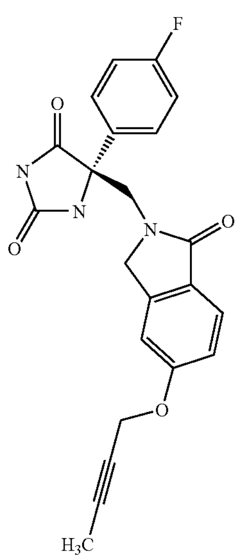 | 407.13 | 408 [M + H]+ | A |

TABLE 1003-continued
| Compound # | Structure | Exact Mass | Mass Obsvd | Ki (nM) |
|---|---|---|---|---|
| 231 | 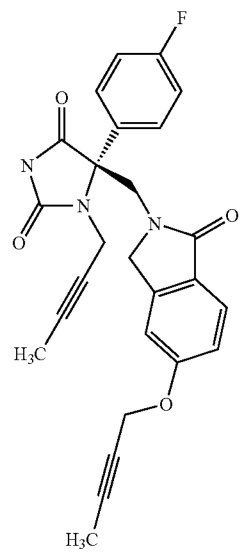 | 459.16 | 460 [M + H]⁺ | C |
| 232 | 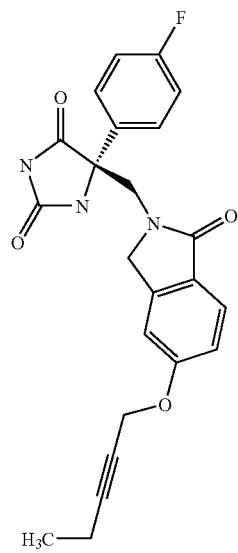 | 421.14 | 422 [M + H]⁺ | A |

TABLE 1003-continued

| Compound # | Structure | Exact Mass | Mass Obsvd | Ki (nM) |
|---|---|---|---|---|
| 233 | 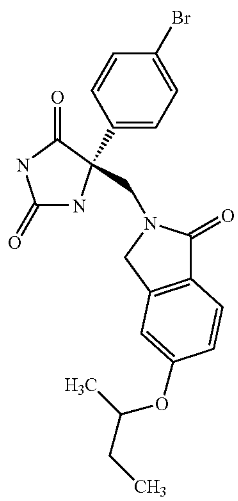 | 471.08 | 472.474 [M + H]+ | C |
| 234 | 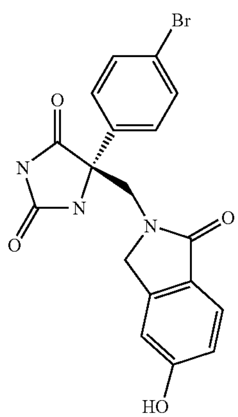 | 415.02 | 416.418 [M + H]+ | A |
| 235 | 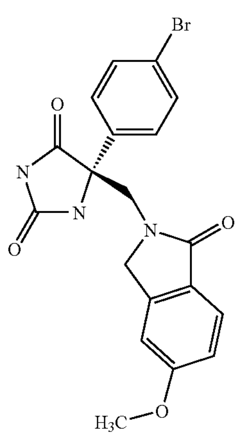 | 429.03 | 430.432 [M + H]+ | A |

TABLE 1003-continued

| Compound # | Structure | Exact Mass | Mass Obsvd | Ki (nM) |
|---|---|---|---|---|
| 236 | 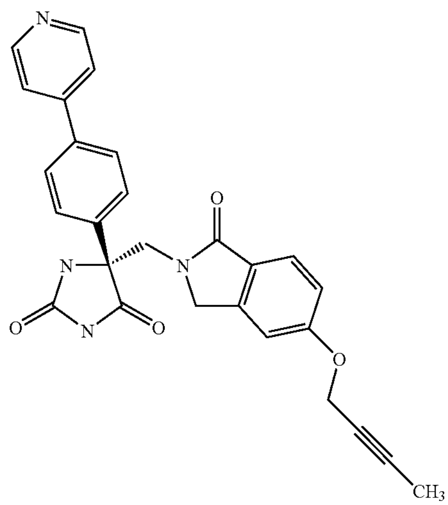 | 466.16 | 467 [M + H]⁺ | A |
| 237 | 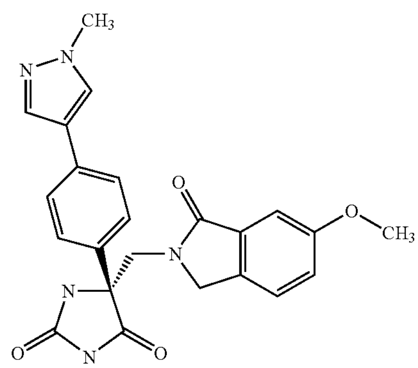 | 431.44 | 432.2 [M + H]⁺ | A |
| 238 | 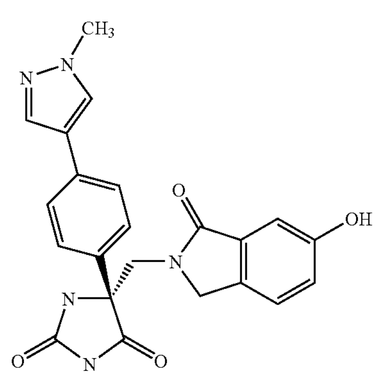 | 417.41 | 418.2 [M + H]⁺ | n/a |

TABLE 1003-continued

| Compound # | Structure | Exact Mass | Mass Obsvd | Ki (nM) |
|---|---|---|---|---|
| 239 | 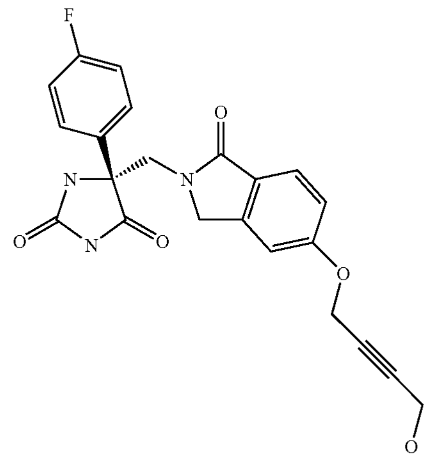 | 423.12 | 424.2 [M + H]⁺ | A |
| 240 | 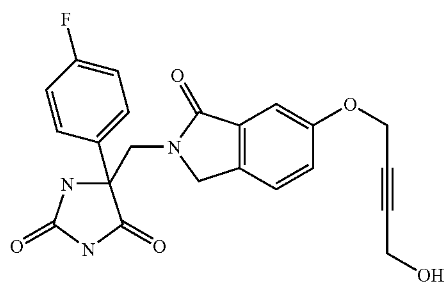 | 423.12 | 424.2 [M + H]⁺ | A |
| 241 | 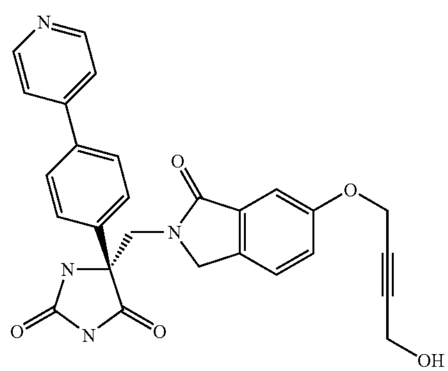 | 482.16 | 483.3 [M + H]⁺ | A |
| 242 | 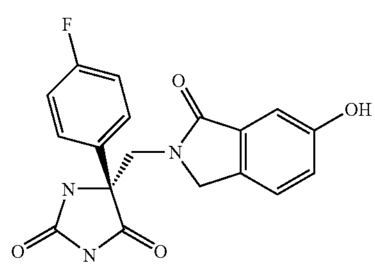 | 355.10 | 356.2 [M + H]⁺ | A |

TABLE 1003-continued

| Compound # | Structure | Exact Mass | Mass Obsvd | Ki (nM) |
|---|---|---|---|---|
| 243 | 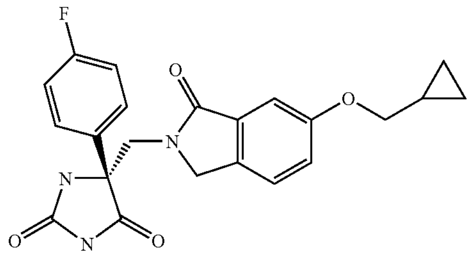 | 409.14 | 410.2 [M + H]+ | A |
| 244 | 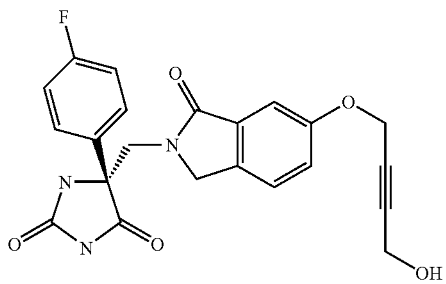 | 423.12 | 424.1 [M + H]+ | n/a |
| 245 | 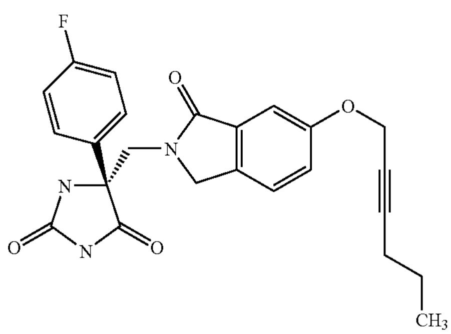 | 435.16 | 436.2 [M + H]+ | n/a |
| 246 | 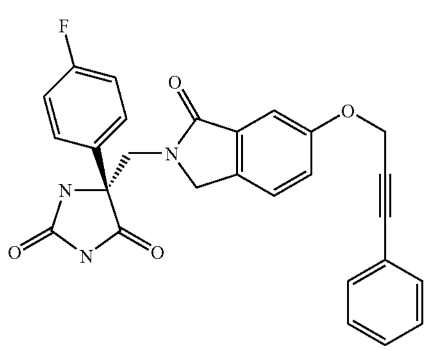 | 469.14 | 470.3 [M + H]+ | n/a |

Proton NMR Spectral Data for Selected Compounds in Table 1003.

Compound 198. $^1$H-NMR (400 MHz, DMSO-$d_6$) δ 9.22 (s, 1H), 7.64 (m, 2H). 7.43 (m, 4H), 7.22 (t, J=2.2 Hz, 1H), 7.16 (dd, J=9.6, 1.2 Hz, 1H). 4.82 (d, J=2.0 Hz, 2H), 4.16 (m, 4H), 3.33 (s, 3H).

Compound 203. $^1$H-NMR (400 MHz, DMSO-$d_6$) δ 7.63 (dd, J=8.8, 5.6 Hz, 2H), 7.43 (d, J=8.4 Hz, 1H), 7.13 (m, 4H), 4.80 (d, J=0.8 Hz, 1H), 4.39 (d, J=17.6 Hz, 1H), 4.17 (d, J=17.6 Hz, 1H), 4.13 (d, J=13.6 Hz, 1H), 3.71 (d, J=13.6 Hz, 1H) 3.34 (s, 3H).

Compound 213. $^1$H NMR (500 Hz, CD$_3$OD) δ 4.11 (d, J=15 Hz, 1H), 4.27 (d, J=15 Hz, 1H), 4.29 (d, J=17 Hz, 1H), 4.38 (d, J=17 Hz, 1H), 6.84-6.89 (m, 2H), 7.16-7.21 (m, 2H), 7.56-7.60 (m, 1H), 7.71-7.76 (m, 2H)

Compound 219. $^1$H NMR (500 Hz, CD$_3$OD) δ 0.36-0.40 (m, 2H), 0.61-0.68 (m, 2H), 1.25-1.35 (m, 1H), 3.91 (d, J=7 Hz, 2H), 4.14 (d, J=15 Hz, 1H), 4.30 (d, J=15 Hz, 1H), 4.34 (d, J=17 Hz, 1H), 4.43 (d, J=17 Hz, 1H), 7.01-7.05 (m, 2H), 7.17-7.23 (m, 2H), 7.65-7.69 (m, 1H), 7.72-7.77 (m, 2H)

Compound 232. $^1$H NMR (500 Hz, CD$_3$OD) δ 1.13 (t, J=8 Hz, 3H), 2.21-2.27 (m, 2H), 4.15 (d, J=14 Hz, 1H), 4.31 (d, J=14 Hz, 1H), 4.36 (d, J=17 Hz, 1H), 4.45 (d, J=17 Hz, 1H), 4.79 (t, J=2 Hz, 2H), 7.04-7.14 (m, 2H), 7.16-7.25 (m, 2H), 7.64-7.79 (m, 3H).

Compound 233. $^1$H NMR (500 Hz, CD$_3$OD) δ7.678 (d, J=8.5 Hz, 1H); 7.455 (d, J=4.1 Hz, 1H), 7.817 (d, J=4.1 Hz, 1H); 7.099 (s, 1H); 7.052 (dd, J=2.207, 6.305 Hz, 1H); 4.515 (d, J=17.3 Hz, 1H), 4.450 (d, J=17.3 Hz, 1H); 4.065 (d, J=14.5 Hz, 1H); 3.89 (s, 3H); 3.87 (d, J=14.5 Hz, 1H); 3.85 (m, 1H); 2.46 (m. 2H); 2.09 (m, 1H) 1.89 (m, 1H); 1.76 (m, 1H); 1.67 (m, 1H); 1.54 (m, 1H); 1.32 (m, 1H).

Compound 239. $^1$H NMR (500 Hz, DMSO-$d_6$) δ4.11 (d, J=15 Hz, 1H), 4.27 (d, J=15 Hz, 1H), 4.29 (d, J=17 Hz, 1H), 4.38 (d, J=17 Hz, 1H), 6.84-6.89 (m, 2H), 7.16-7.21 (m, 2H), 7.56-7.60 (m, 1H), 7.71-7.76 (m, 2H)

Compound 243. $^1$H-NMR (500 MHz, CD$_3$OD) δ 8.53 (s, 1H), 7.67 (dd, J=8.5, 5 Hz, 2H), 7.46 (d, J=8 Hz, 1H), 7.27 (t, J=8.5 Hz, 2H), 7.15 (m, 2H), 4.31 9d, J=17.0 Hz, 1H), 4.22 (d, J=17 Hz, 1H), 4.13 (d, J=14.2 Hz, 1H), 4.06 (d, J=14.2 Hz, 1H), 3.88 9d, J=6.5 Hz, 2H), 3.35 9m, 2H), 1.22 (m, 1H), 0.57 (d, J=8 Hz, 1H), 0.33 (d, J=5 Hz, 1H).

Example 1011

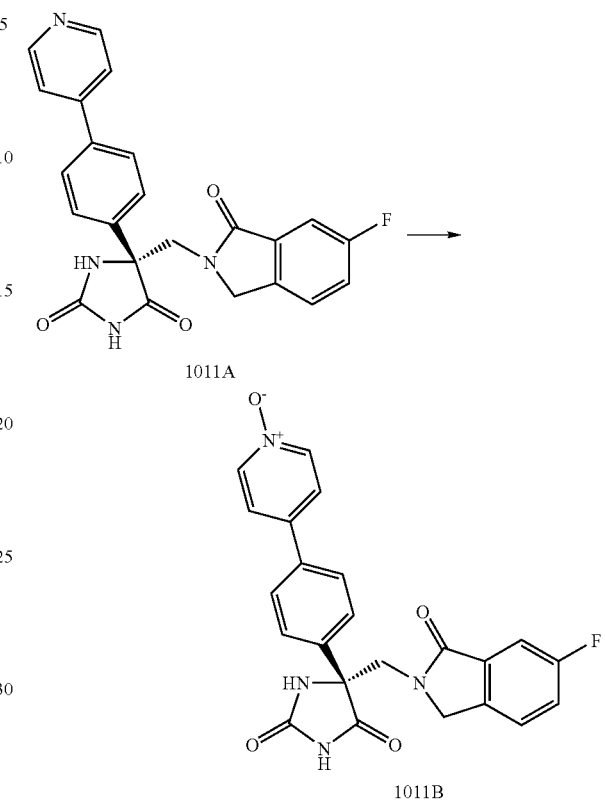

To a solution of compound 1011A (100 mg) in DMF (5 mL) was added m-chlorobenzoyl peroxide (MCPBA, 100 mg). The solution was stirred overnight at 25° C. The product was purified by C18 reverse phase chromatography (CH$_3$CN/water 5% to 90%, with 0.1% HCO$_2$H) to give compound 1011B (73 mg).

The following compounds were prepared as described in Examples 1010 and 1011.

TABLE 1004

| Compound # | Structure | Exact Mass | Mass Obsvd | Ki (nM) |
|---|---|---|---|---|
| 247 | 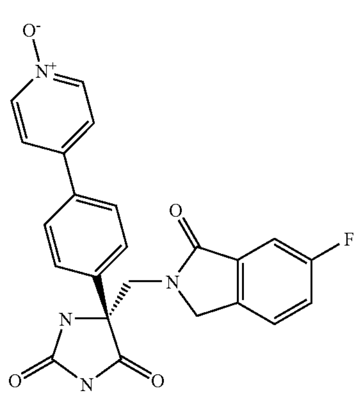 | 432.12 | 433.1 [M + H]$^+$ | A |

Example 1012

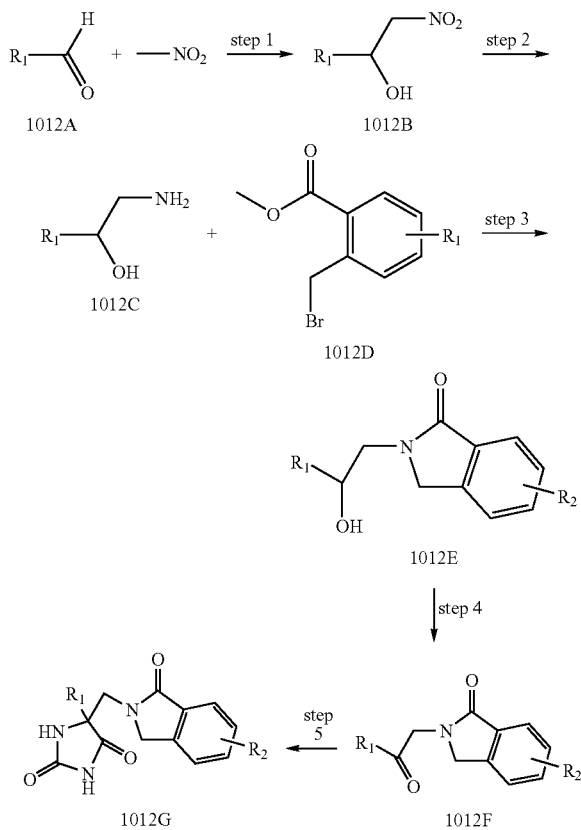

In step 1, Compound 1012A was treated with nitromethane and KO'Bu in a mixture of THF and t-BuOH for 2 to 12 h. Alternatively, compound 1012A was treated with nitromethane and TBAF in a suitable solvent such as THF for 2 to 12 h. Compound 1012B was purified by silica gel chromatography.

In step 2, Compound 1012B was treated with Pd/C in a suitable solvent such as methanol, in a Parr shaker under $H_2$ atmosphere. After filtering off the catalyst and concentration of solvent, the product was used without further purification.

In step 3, the benzyl bromide (compound 1012D) was mixed with compound 1012C, DIPEA, and DMF. The solution was stirred at 0° C. to room temperature for 12 to 24 hours. The product was either removed by filtration or purified by silica gel chromatography.

In step 4, compound 1012E was treated with PCC and Celite in a suitable solvent such as dichloromethane for 2 to 12 h. Compound 1012F was purified by silica gel chromatography.

In step 5, compound 1012F was reacted with potassium cyanide and ammonium carbonate in an appropriate alcohol and water solution, at 50° C. to 90° C., for 5 to 48 hours. After cooling, water was added and compound 1012G was collected by filtration.

Example 1013

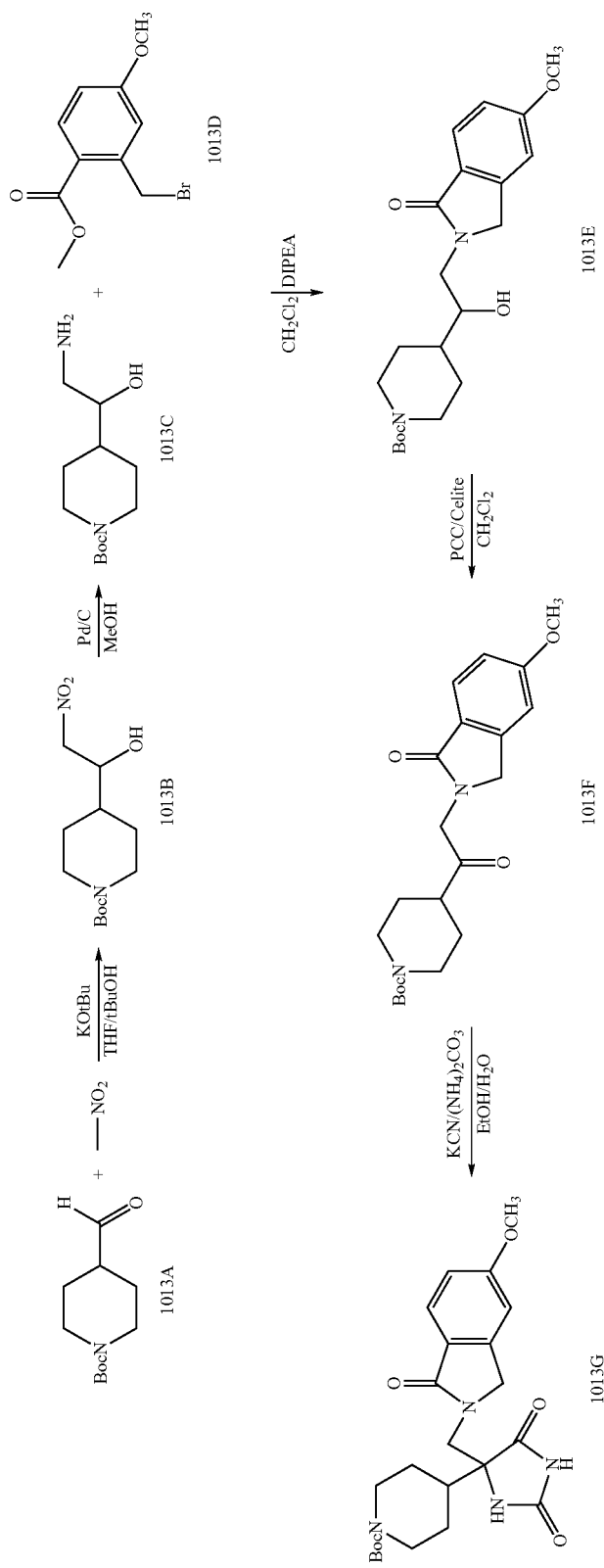

Compound 1013B: To a solution of THF (15 mL) and t-BuOH (15 mL) was added compound 1013A (1.2 g, 5.6 mmol) and nitromethane (0.61 mL, 11.2 mmol) followed by addition of KOtBu (0.63 g, 5.6 mmol). The reaction mixture was stirred at room temperature for 2 h. The reaction mixture was adjusted to pH 6 using HOAc. The reaction mixture was diluted with EtOAc (30 mL), and was extracted with brine. The aqueous layer was extracted with EtOAc (30 mL×2) The combined organic layers were washed with brine, dried, and concentrated to dryness. The crude material was purified via PTLC (25% EtOAc/Hexanes) to give 1.24 g (81%) of compound 1013B.

Compound 1013C: Compound 1013B (1.24 g, 4.5 mmol) was treated with Pd/C in methanol in a Parr shaker under $H_2$ atmosphere (50 psi) overnight. After filtering off the catalyst and concentration of solvent, compound 1013C (1.1 g, 99%) was used without further purification.

Compound 1013E: Compound 1013C (1.02 g, 4.2 mmol) was dissolved in dichloromethane (30 mL) at 0° C. Compound 1013D (1.13 g, 4.2 mmol) and DIPEA (0.73 mL, 4.2 mmol) were added and the reaction was stirred at 0° C. and slowly warmed up to rt overnight. The reaction mixture was washed with HCl (1N, 50 mL) and brine (50 mL). The organic layer was dried and concentrated to dryness. The crude material was purified via PTLC (50% EtOAc/Hexanes) to give 0.88 g (54%) of compound 1013E.

Compound 1013F: Compound 1013E (0.88 g, 2.25 mmol) was dissolved in methylene chloride (30 mL). PCC (1.22 g, 5.63 mmol) and Celite (1.22 g) were added and the reaction mixture was stirred at 25° C. overnight. The solid was filtered off and the resulting solution was concentrated and purified via sgc (90% EtOAc/Hexanes) to give 0.62 g (71%) of compound 1013F.

Compound 1013G: Compound 1013F (1.01 g, 2.6 mmol), KCN (0.25 g, 3.9 mmol), and $(NH_4)_2CO_3$ (0.75 g, 7.8 mmol) were suspended in a mixture of $NH_3$ in Methanol (7 N, 10 mL) and water (10 mL). The solution was stirred at 90° C. overnight. After cooling, water (20 mL) was added. The solid was filtered and washed with water three times. The solid was dried under vacuum to give compound 1013G (0.86 g, 72%).

Example 1014

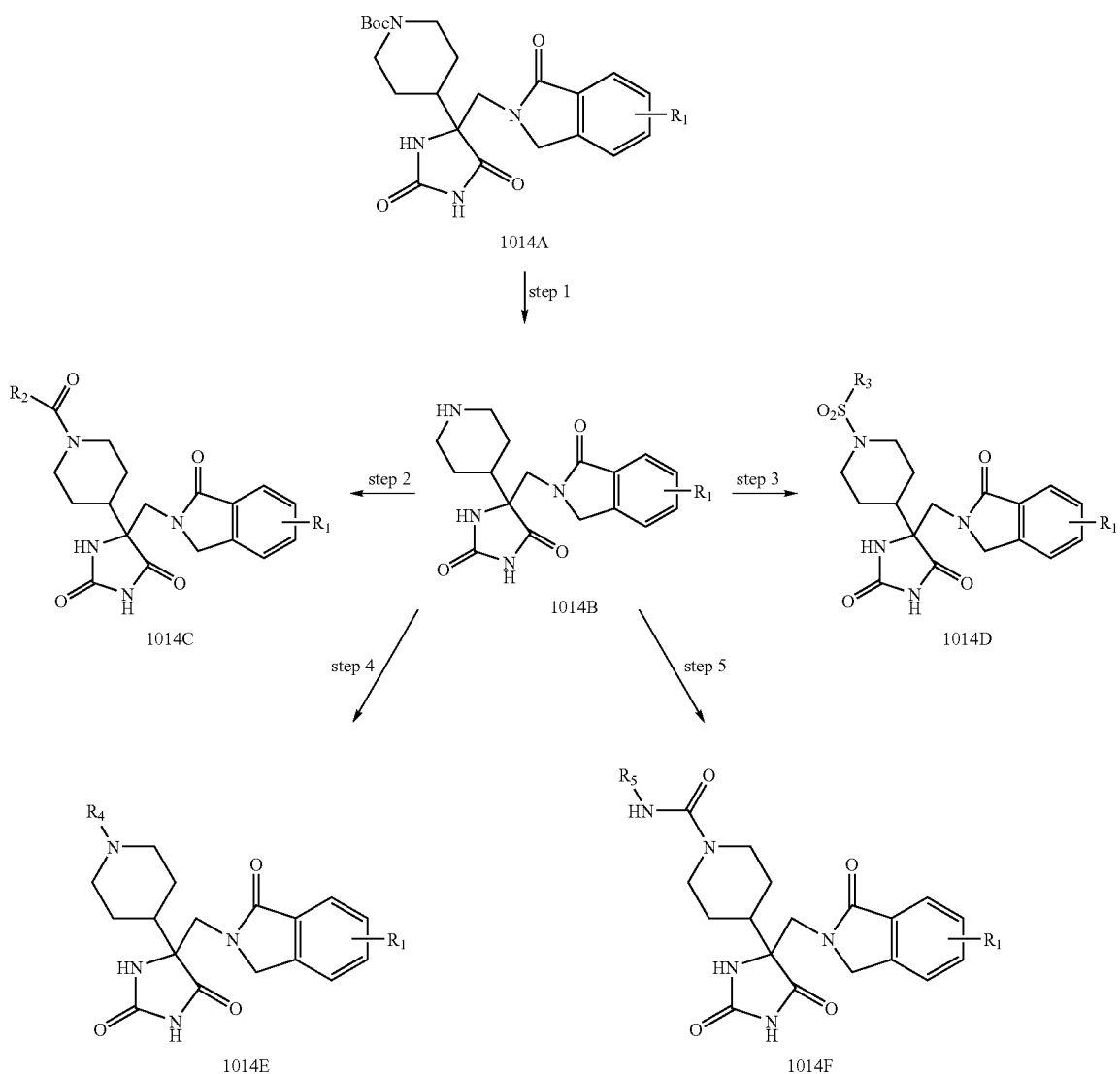

Step 1.

Compound 1014A was stirred with 2 to 20 equivalents of hydrogen chloride in methanol for 5 to 48 hours. The solvent was removed and the compound 1014B could be used without further purification.

Step 2.

Compound 1014B was treated with carboxylic anhydride and DIPEA to give Compound 1014C which was purified by silica gel chromatography.

Step 3.

Compound 1014B was coupled with sulphonyl chloride compound to give Compound 1014D, which was purified by silica gel chromatography.

Step 4.

Compound 1014B was reacted with carbonyl compound under reductive amination conditions to give compound 1014E. Alternatively, compound 1014B was treated with a suitable electrophile and a base to give compound 1014E, which was purified by silica gel chromatography.

Step 5.

Compound 1014B was reacted with isocyanate compound and DIPEA to give Compound 1014F, which was purified by silica gel chromatography.

Example 1015

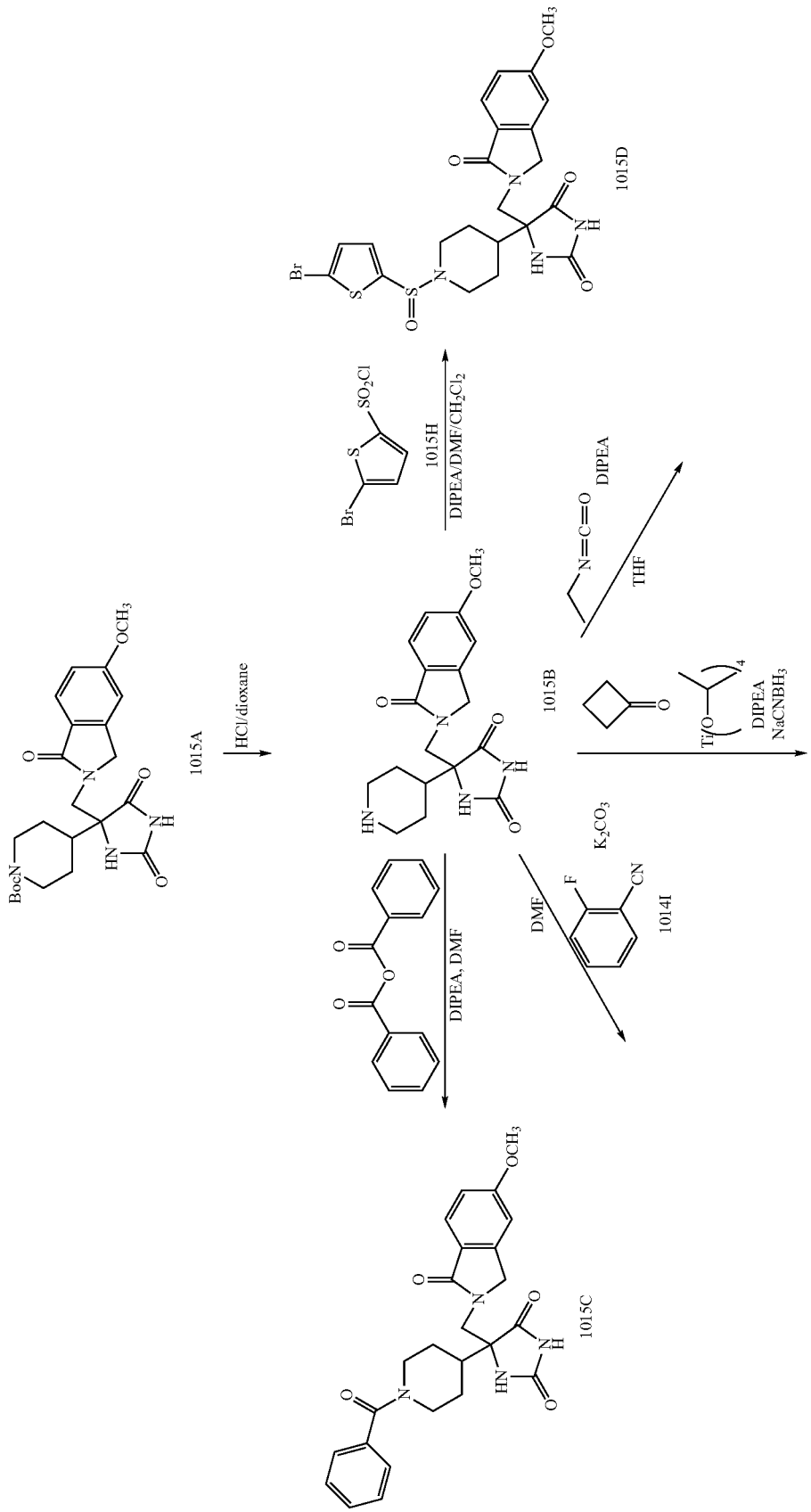

-continued
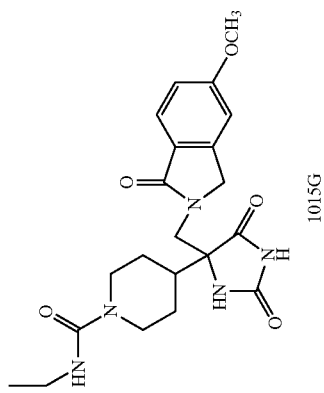
1015G
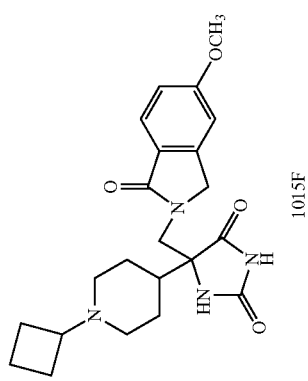
1015F
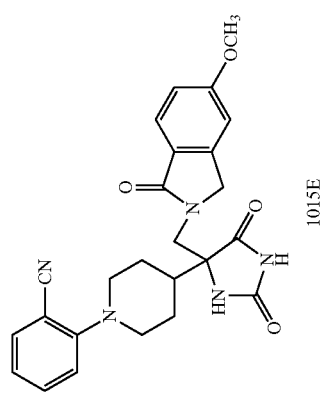
1015E

Compound 1015B: Compound 1015A (0.86 g) was suspended in methanol (10 mL) and HCl (4M in dioxane, 10 mL) was added. The solution was stirred at 25° C. for 3 hours. Solvent was removed and the material was dried under vacuum to give compound 1015B (0.74 g, 99%).

Compound 1015C: Compound 1015B (40 mg, 0.11 mmol) and benzoic acid anhydride (25 mg, 0.11 mmol) were dissolved in DMF (1 mL). DIPEA (0.06 mL, 0.33 mmol) was added and the reaction mixture was stirred at room temperature overnight. Solvent was removed and the crude material was purified via sgc (5% NH$_3$.MeOH/CH$_2$Cl$_2$) to give 3.7 mg (7%) of compound 1015C.

Compound 1015D: Compound 1015B (40 mg, 0.11 mmol) and compound 1015H (30 mg, 0.11 mmol) were dissolved in DMF (1 mL). DIPEA (0.25 mL, 1.4 mmol) was added and the reaction mixture was stirred at room temperature overnight. Solvent was removed and the crude material was purified via sgc (5% NH$_3$.MeOH/CH$_2$Cl$_2$) to give 2.2 mg (3%) of compound 1015D.

Compound 1015E: Compound 1015B (40 mg, 0.11 mmol) and compound 1015I (0.024 mL, 0.22 mmol) were dissolved in DMF (1 mL). K$_2$CO$_3$ (46 mg, 0.33 mmol) was added and the reaction mixture was stirred at 90° C. overnight. Solvent was removed and the crude material was purified via sgc (5% NH$_3$.MeOH/CH$_2$Cl$_2$) to give 2.6 mg (5%) of compound 1015E.

Compound 1015F: Compound 1015B (46 mg, 0.13 mmol) and cyclobutanone (0.2 mL) were stirred in methylene chloride (1 mL). Titanium tetraisopropoxide (0.045 mL, 0.15 mmol) was added followed by addition of DIPEA (0.027 mL, 0.16 mmol). The reaction mixture was stirred at room temperature for 2 h. Then, NaCNBH$_3$ (41 mg, 0.65 mmol) was added and the mixture was stirred at rt overnight. The solvent was removed. The crude material was purified via PTLC (10% NH$_3$.MeOH/CH$_2$Cl$_2$) to give 3.1 mg (6%) of compound 1015F.

Compound 1015G: Compound 1015B (80 mg, 0.24 mmol) and ethyl isocyanate (0.018 mL, 0.24 mmol) were dissolved in DMF (1 mL). DIPEA (0.17 mL, 0.97 mmol) was added and the reaction mixture was stirred at room temperature overnight. Solvent was removed and the crude material was purified via sgc (9% NH$_3$.MeOH/CH$_2$Cl$_2$) to give 11 mg (11%) of compound 1015G.

The following compounds were prepared as described in Examples 1012 to 1015.

TABLE 1005

| Compound # | Structure | Exact Mass | Mass Obsvd | Ki (nM) |
| --- | --- | --- | --- | --- |
| 248 | 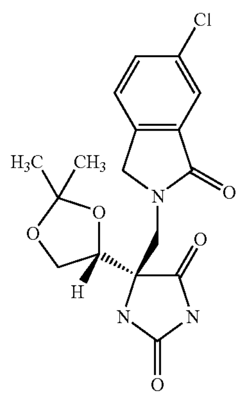 | 379.09 | 380.1 [M + H]$^+$ | C |
| 249 | 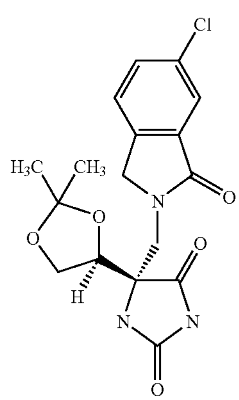 | 379.09 | 380.1 [M + H]$^+$ | C |

TABLE 1005-continued
| Compound # | Structure | Exact Mass | Mass Obsvd | Ki (nM) |
|---|---|---|---|---|
| 250 | 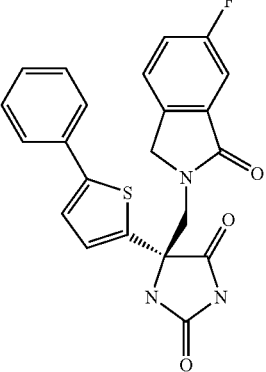 | 421.09 | 422.1 [M + H]+ | B |
| 251 | 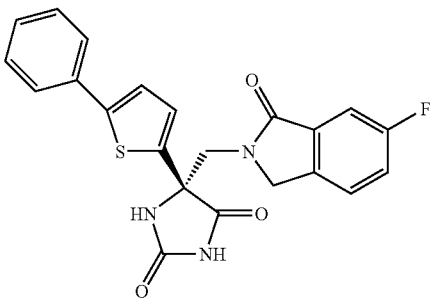 | 421.09 | 422.1 [M + H]+ | A |
| 252 | 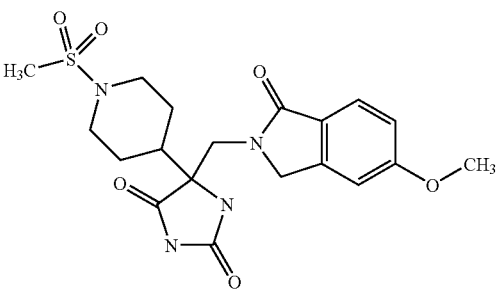 | 436.14 | 437.1 [M + H]+ | B |
| 253 | 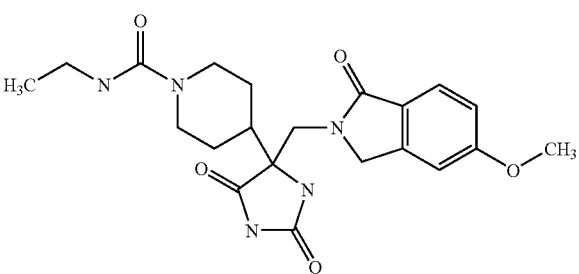 | 429.2 | 430.1 [M + H]+ | B |
| 254 | 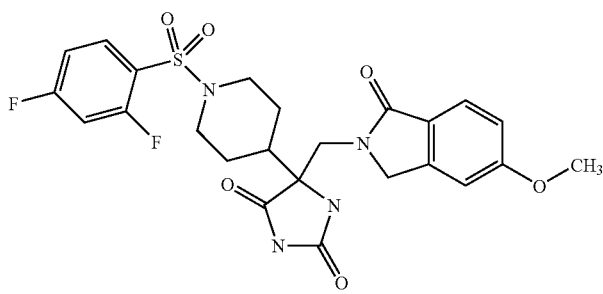 | 534.14 | 535.1 [M + H]+ | B |

TABLE 1005-continued

| Compound # | Structure | Exact Mass | Mass Obsvd | Ki (nM) |
| --- | --- | --- | --- | --- |
| 255 | 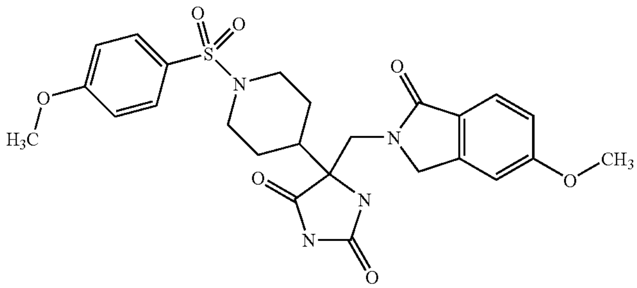 | 528.17 | 529.3 [M + H]⁺ | B |
| 256 | 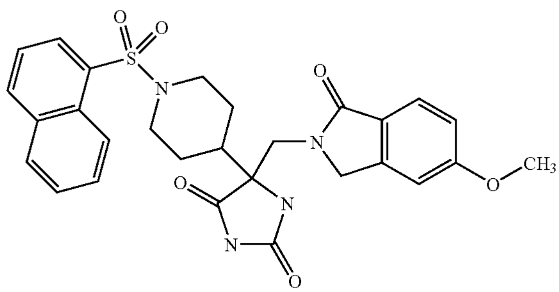 | 548.17 | 549.3 [M + H]⁺ | A |
| 257 | 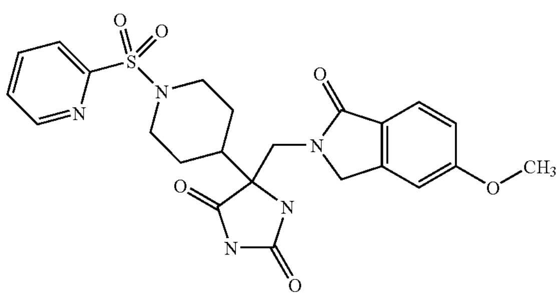 | 499.15 | 500.3 [M + H]⁺ | B |
| 258 | 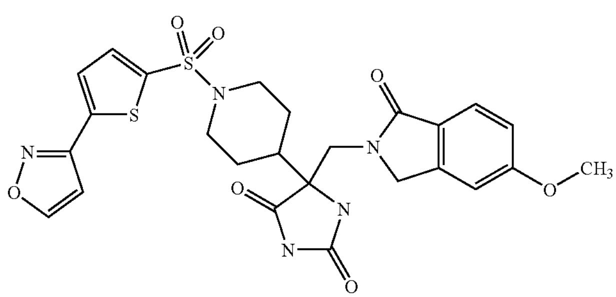 | 571.12 | 572.1 [M + H]⁺ | A |
| 259 | 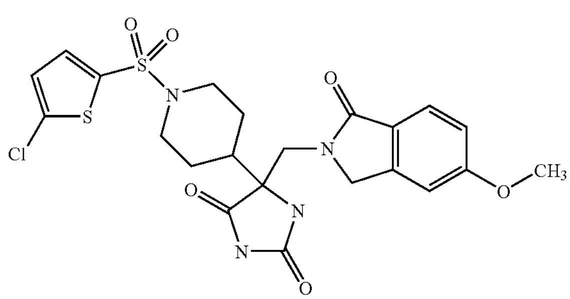 | 538.07 | 539.1 [M + H]⁺ | A |

TABLE 1005-continued

| Compound # | Structure | Exact Mass | Mass Obsvd | Ki (nM) |
| --- | --- | --- | --- | --- |
| 260 | 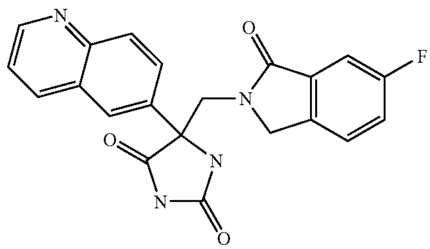 | 390.11 | 391.1 [M + H]+ | A |
| 261 | 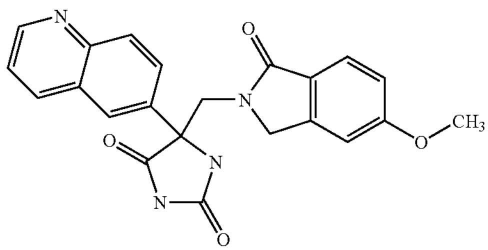 | 402.13 | 403.2 [M + H]+ | A |
| 262 | 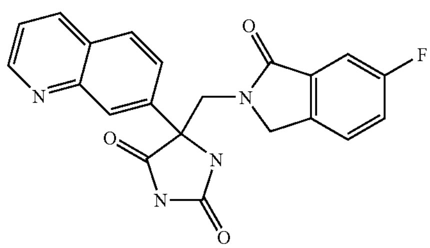 | 390.11 | 391.1 [M + H]+ | A |
| 263 | 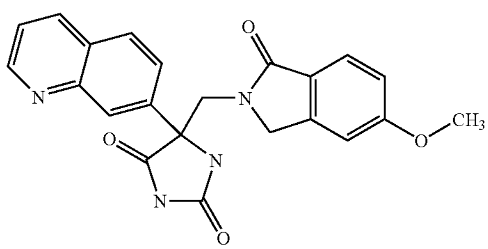 | 402.13 | 403.1 [M + H]+ | A |
| 264 | 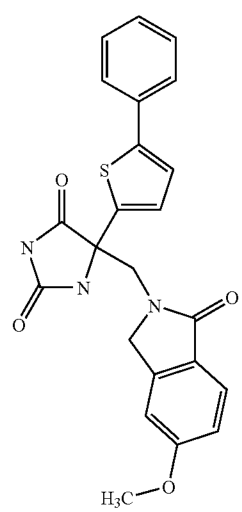 | 433.11 | 434.1 [M + H]+ | A |

TABLE 1005-continued

| Compound # | Structure | Exact Mass | Mass Obsvd | Ki (nM) |
|---|---|---|---|---|
| 265 | 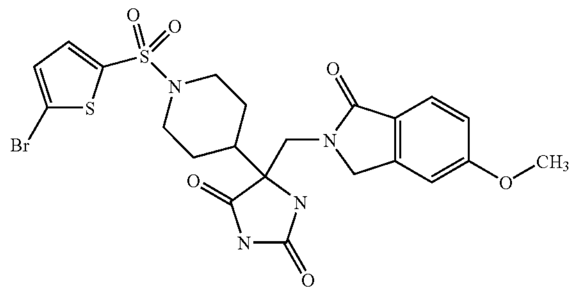 | 582.02 | 585.1 [M + H]⁺ | A |
| 266 | 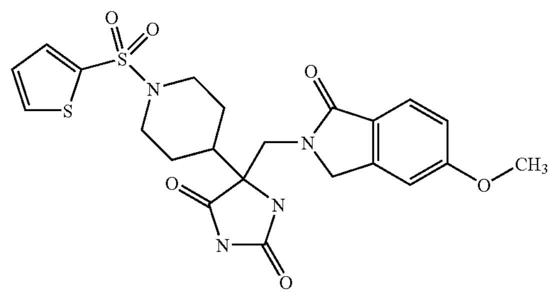 | 504.11 | 505.1 [M + H]⁺ | A |
| 267 | 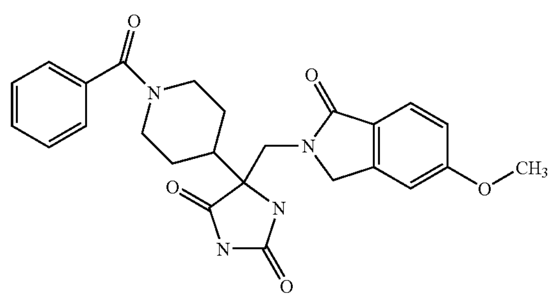 | 462.19 | 463.1 [M + H]⁺ | B |
| 268 | 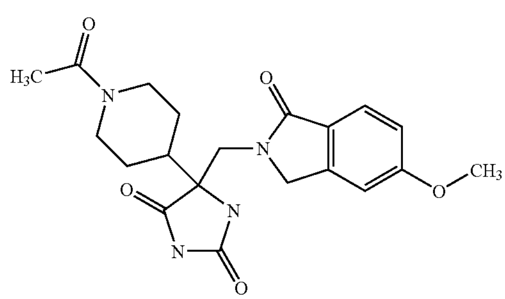 | 400.17 | 401.1 [M + H]⁺ | A |
| 269 | 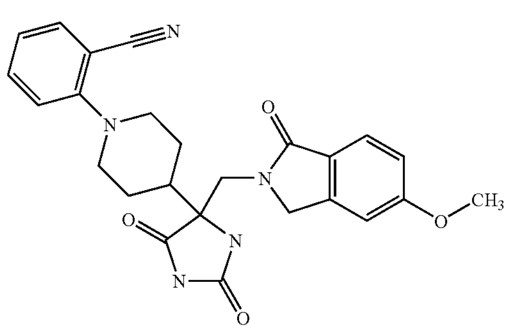 | 459.19 | 460.1 [M + H]⁺ | B |

TABLE 1005-continued

| Compound # | Structure | Exact Mass | Mass Obsvd | Ki (nM) |
|---|---|---|---|---|
| 270 | 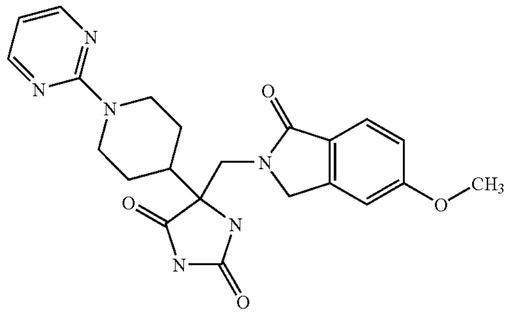 | 436.19 | 437.2 [M + H]⁺ | B |
| 271 | 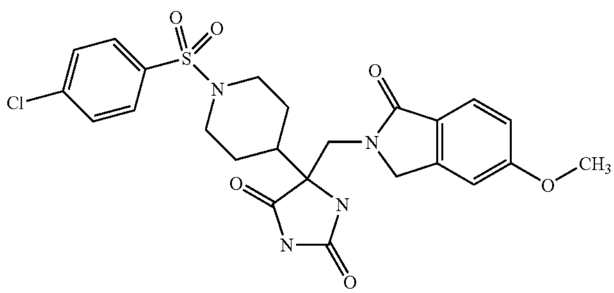 | 532.12 | 533.3 [M + H]⁺ | B |
| 272 | 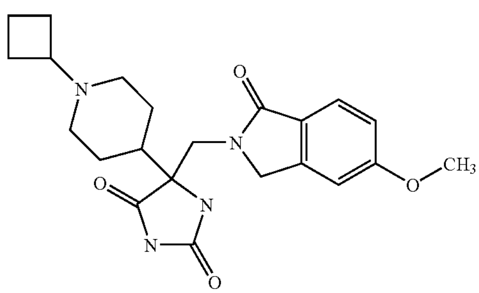 | 412.21 | 413.2 [M + H]⁺ | C |
| 273 | 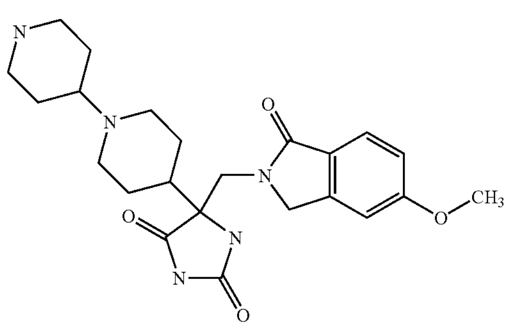 | 441.24 | 442.1 [M + H]⁺ | C |

TABLE 1005-continued

| Compound # | Structure | Exact Mass | Mass Obsvd | Ki (nM) |
|---|---|---|---|---|
| 274 | 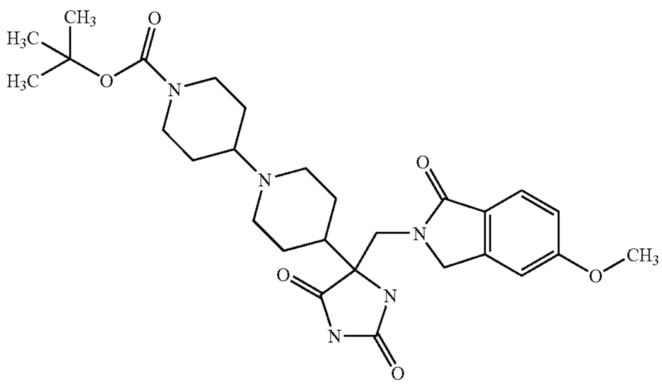 | 541.29 | 542.3 [M + H]+ | C |
| 275 | 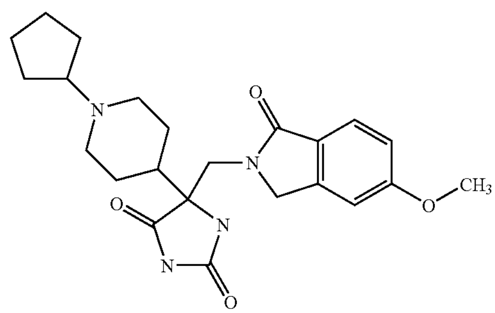 | 426.23 | 427.2 [M + H]+ | C |
| 276 | 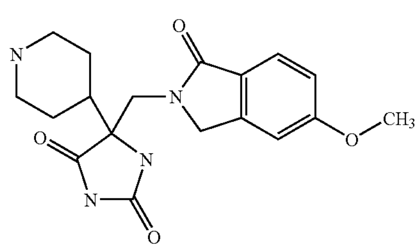 | 358.16 | 359.1 [M + H]+ | C |
| 277 | 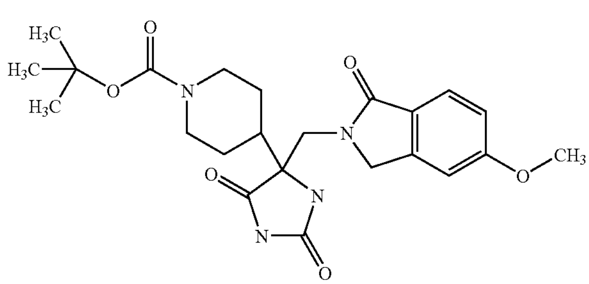 | 458.22 | 459.1 [M + H]+ | B |

Proton NMR Spectral Data for Selected Compounds in Table 1005.

Compound 262. $^1$H NMR (500 Hz, CD$_3$OD) δ8.921 (m, 1H); 8.433 (d, J=8.6 Hz, 1H); 8.357 (s, 1H); 8.072 (m, 4H); 7.622 (m, 1H); 7.545 (m, 1H); 7.476 (m, 1H); 7.369 (m, 1H); 4.522 (d, J=17 Hz, 1H); 4.510 (d, J=14.5 Hz, 1H); 4.425 (d, J=17 Hz, 1H), 4.350 (d, J=14.5 Hz, 1H).

Example 1016

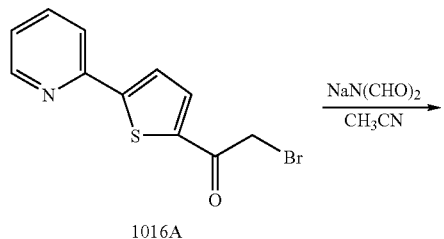
1016A

NaN(CHO)$_2$ / CH$_3$CN

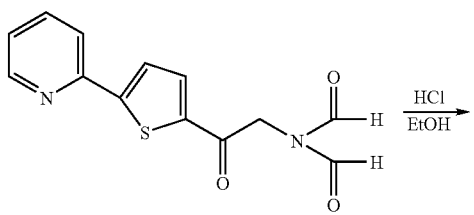
1016B

HCl / EtOH

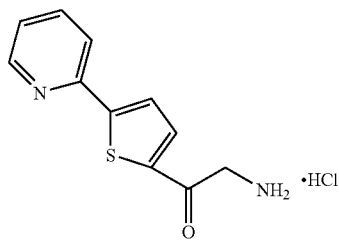
1016C

Compound 1016B: Compound 1016A (500 mg, 1.77 mmol) was suspended in CH$_3$CN (5 mL) followed by addition of NaN(CHO)$_2$ (202 mg, 2.12 mmol). The reaction mixture was stirred at rt for 30 min before warmed up to 70° C. and stirred for 2 h. Solid was collected by suction filtration and washed with acetonitrile to give 1016B (380 mg, 78%) as brown solid.

Compound 1016C: Compound 1016B (380 mg, 1.38 mmol) was stirred with HCl (36% aq., 1 mL) and EtOH (10 mL) at rt for 2 days. It was then heated to 60° C. for 2 hr. Solvent was removed and it was dried under vacuum to give 1016C (345 mg, 98%). The material was used without further purification.

The following compounds were prepared as described in Example 1016, Example 2 and Example 8.

TABLE 1006

| Compound # | Structure | Exact Mass | Mass Obsvd | Ki (nM) |
|---|---|---|---|---|
| 278 | 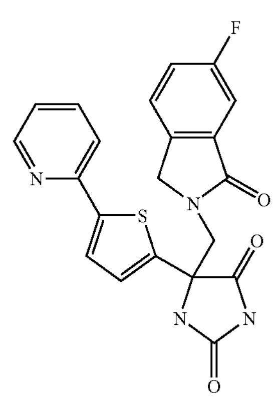 | 422.08 | 423.1 [M + H]$^+$ | A |

TABLE 1006-continued

| Compound # | Structure | Exact Mass | Mass Obsvd | Ki (nM) |
|---|---|---|---|---|
| 279 | 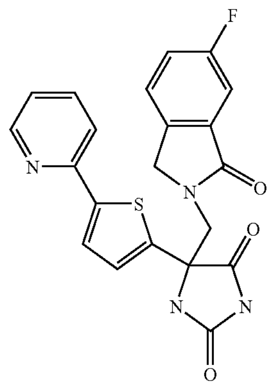 | 422.08 | 423.1 [M + H]⁺ | C |
| 280 | 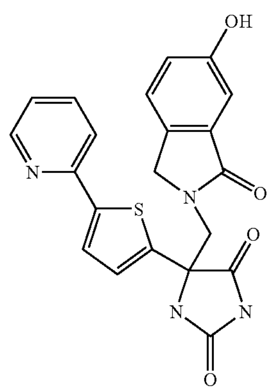 | 420.9 | 421.1 [M + H]⁺ | A |
| 281 | 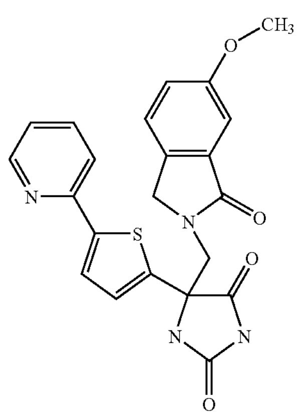 | 434.1 | 435.2 [M + H]⁺ | A |

Proton NMR Spectral Data for Selected Compounds in Table 1006.

Compound 278. $^1$H NMR (500 Hz, CD$_3$OD) δ8.503 (d, J=4.73 Hz, 1H); 7.84 (m, 2H); 7.67 (d, J=3.8 Hz, 1H); 7.56 (dd, J=4.4 Hz, 8.5 Hz, 1H); 7.50 (dd, J=2.5 Hz, 7.8 Hz, 1H); 7.38 (m, 1H); 7.33 (d, J=4.1 Hz, 2H); 7.3 (m, 1H); 4.52 (d, J=17 Hz, 1H); 4.45 (d, J=17 Hz, 1H); 4.43 (d, J=14.2 Hz, 1H); 4.28 (d, J=14.2 Hz, 1H).

Example 1017

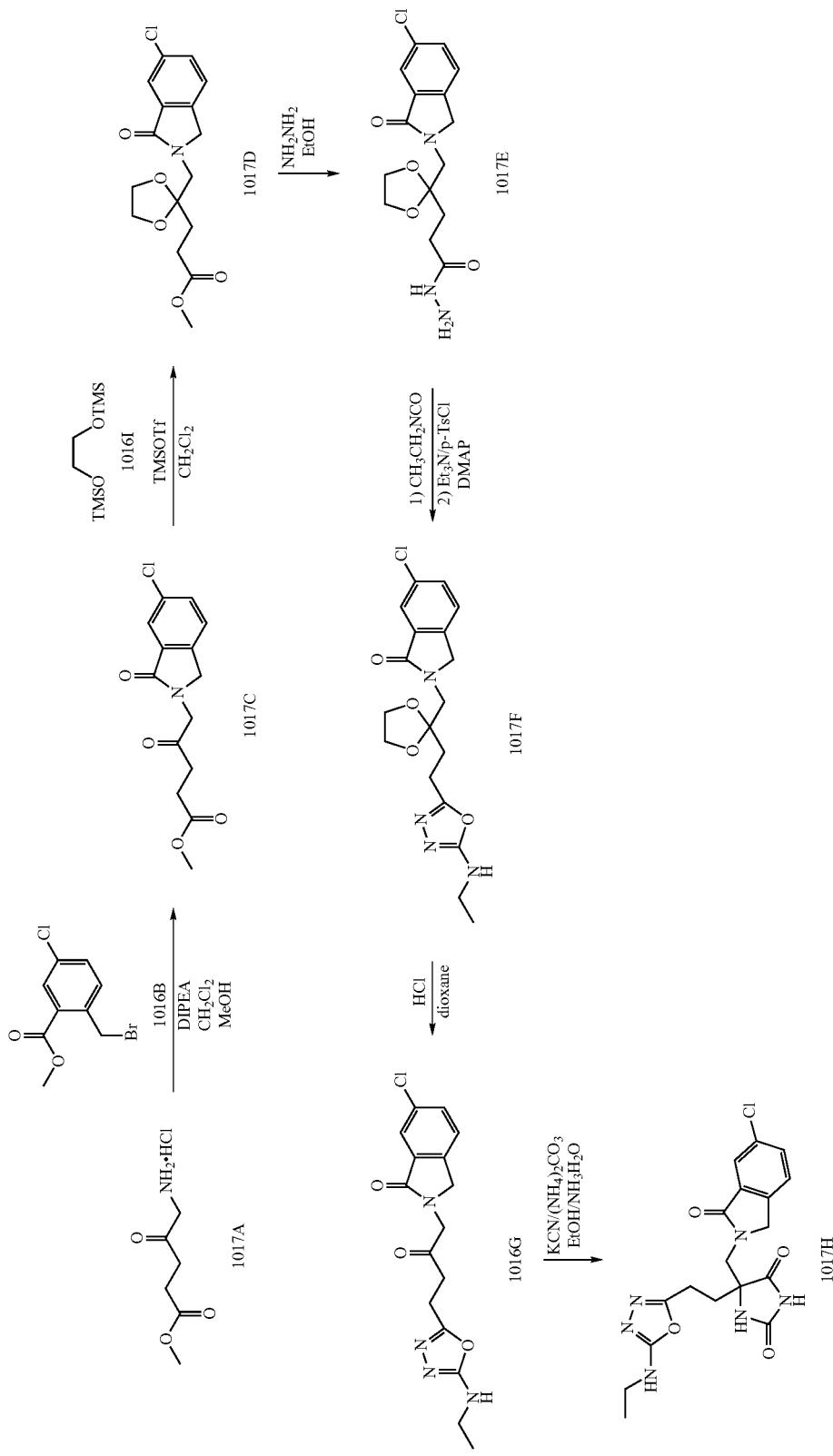

Compound 1017C: Compound 1017A (1.5 g, 8.26 mmol) was dissolved in dichloromethane (20 mL) and methanol (10 mL) at 0° C. Compound 1017B (2.64 g, 10 mmol) and DIPEA (2.9 mL, 16.5 mmol) were added and the reaction was stirred at 0° C. and slowly warmed up to rt overnight. The reaction mixture was then heated to 50° C. and stirred for 2 h. The reaction mixture was washed with brine (50 mL). The organic layer was dried and concentrated to dryness. The crude material was purified via PTLC (50% EtOAc/hexanes) to give 0.7 g (29%) of compound 1017C.

Compound 1017D: Compound 1017C (200 mg, 0.68 mmol) was stirred in CH$_2$Cl$_2$ (15 mL) at 0° C. followed by addition of compound 1017I (0.5 mL, 2.04 mmol) and TMS-OTf (13 □L, 0.07 mmol). The reaction mixture was stirred at 0° C. to 5° C. for 6 hr before warmed up to rt and stirred overnight. The solvent was removed and the crude material was purified via PTLC (EtOAc) to give 0.21 g (91%) of compound 1017D.

Compound 1017E: Compound 1017D (210 mg, 0.62 mmol) was heated in a sealed tube with NH$_2$NH$_2$ (0.2 mL, 6.2 mmol) and EtOH (2 mL) at 60° C. overnight. Solvent was removed and gave crude material 1017E (210 mg, 99%) which was used without further purification.

Compound 1017F: Compound 1017E (210 mg, 0.62 mmol) and ethyl isocyanate (59 µL, 0.74 mmol) were dissolved in CH$_2$Cl$_2$ (10 mL). The reaction mixture was stirred at room temperature overnight. To this mixture was added Et$_3$N (0.43 mL, 3.1 mmol), DMAP (15 mg, cat.) and p-TsCl (141 mg, 0.74 mmol). The reaction was stirred at rt overnight. Solvent was removed and the crude material was purified via sgc (10% NH$_3$.MeOH/CH$_2$Cl$_2$) to give 60 mg (25%) of compound 1017F.

Compound 1017G: Compound 1017F (60 mg, 0.15 mmol) was heated in a sealed tube with HCl (3 mL, 4N in dioxane) at 65° C. for 48 hr. Solvent was removed and the crude material was purified via sgc (5% NH$_3$.MeOH/CH$_2$Cl$_2$) to give 35 mg (66%) of compound 1017G.

Compound 1017H: Compound 1017G (34 mg, 0.1 mmol), KCN (10 mg, 0.15 mmol), and (NH$_4$)$_2$CO$_3$ (30 mg, 0.3 mmol) were suspended in a mixture of NH$_3$.H$_2$O (1 mL) and ethanol (1 mL). The solution was stirred at 90° C. overnight. Solvent was removed and the crude material was purified via sgc (10% NH$_3$.MeOH/CH$_2$Cl$_2$) to give 6 mg (15%) of compound 1017H.

The following compounds were prepared as described in Example 1017

Example 1018

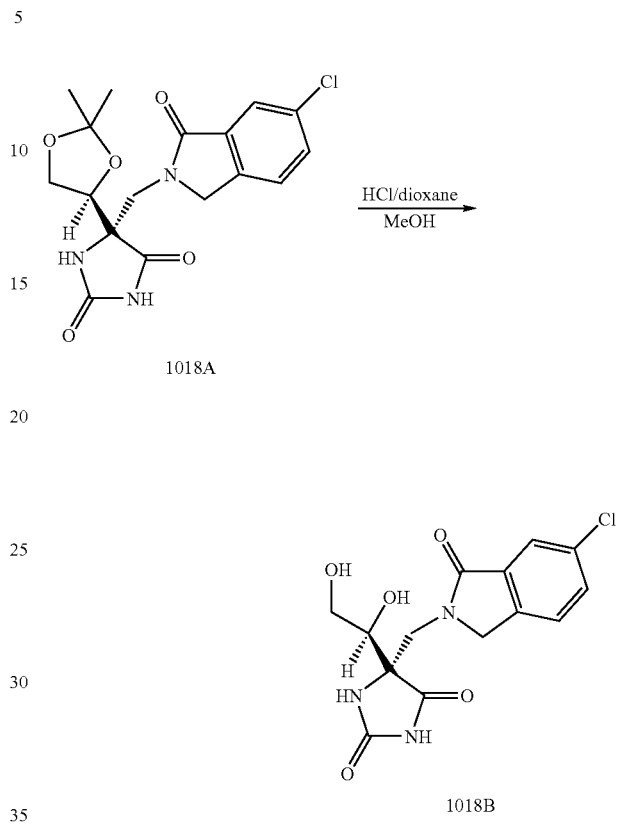

Compound 1018A: Compound 1018A was synthesized following procedures in Example 1012.

Compound 1018B: Compound 1018A (180 mg, 047 mmol) was stirred in MeOH (1 mL) at rt. HCl (3 mL, 4N in dioxane) was added and the reaction mixture was heated to 70° C. overnight. Solvent was evaporated. The crude material was taken up in water and the solid was collected by suction filtration to give 1018B (115 mg, 71%).

TABLE 1007

| Compound # | Structure | Exact Mass | Mass Obsvd | Ki (nM) |
|---|---|---|---|---|
| 282 | 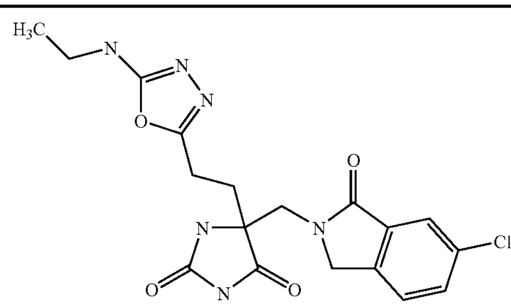 | 418.12 | 419.1 [M + H]$^+$ | B |

Example 1019

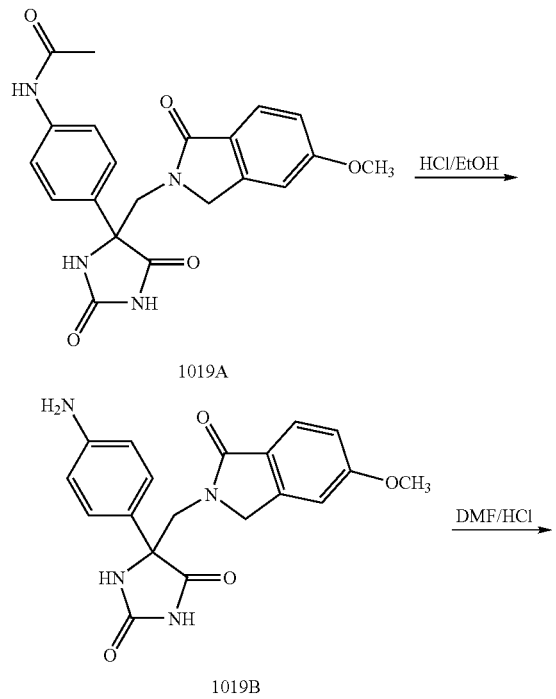

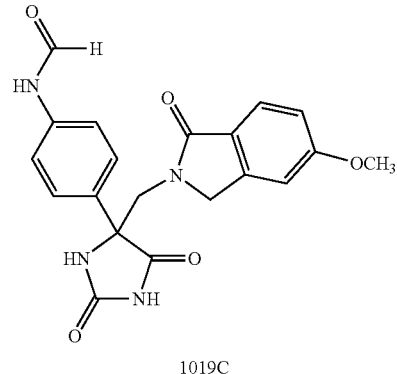

Compound 1019A: Compound 1019A was synthesized following procedures described in Example 1012.

Compound 1019B: Compound 1019A (74 mg, 0.18 mmol) was dissolved in EtOH (2 mL) and HCl (0.4 mL, aq. 36%) was added and the reaction mixture was heated to 70° C. overnight. Solvent was removed and gave 1019B as a light yellow solid (74 mg, 99%).

Compound 1019C: Compound 1019B (20 mg, 0.05 mmol) was stirred in DMF (1 mL) and HCl (cat., 4 N in dioxane) at 120° C. overnight. Solvent was removed and the crude material was purified via PTLC (9% $NH_3$.MeOH/$CH_2Cl_2$) to give 8 mg (37%) of Compound 1019C.

The following compounds were prepared as described in Example 1012, 1018 and 1019.

TABLE 1008

| Compound # | Structure | Exact Mass | Mass Obsvd | Ki (nM) |
|---|---|---|---|---|
| 283 | 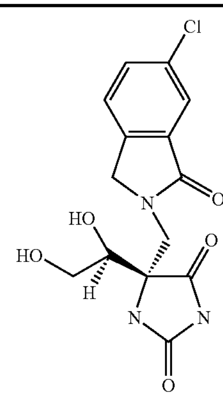 | 339.06 | 340.2 [M + H]$^+$ | B |
| 284 | 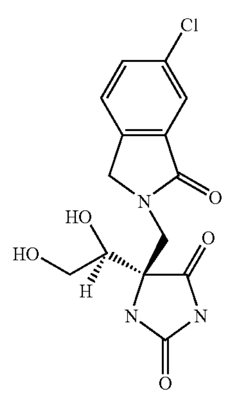 | 339.06 | 340.2 [M + H]$^+$ | D |

TABLE 1008-continued

| Compound # | Structure | Exact Mass | Mass Obsvd | Ki (nM) |
|---|---|---|---|---|
| 285 | 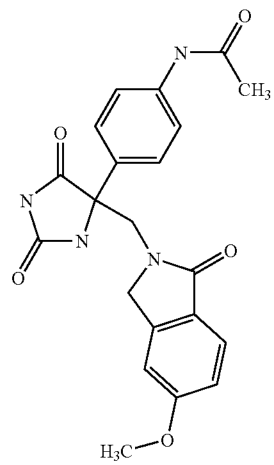 | 408.14 | 409.2 [M + H]⁺ | A |
| 286 | 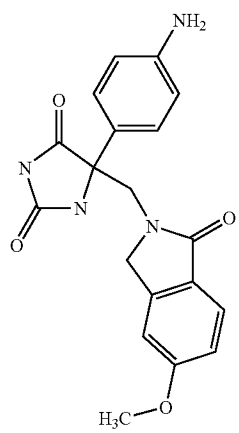 | 366.13 | 367.1 [M + H]⁺ | A |
| 287 | 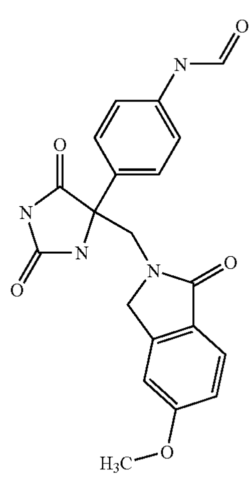 | 394.13 | 395.2 [M + H]⁺ | B |

Example 1020

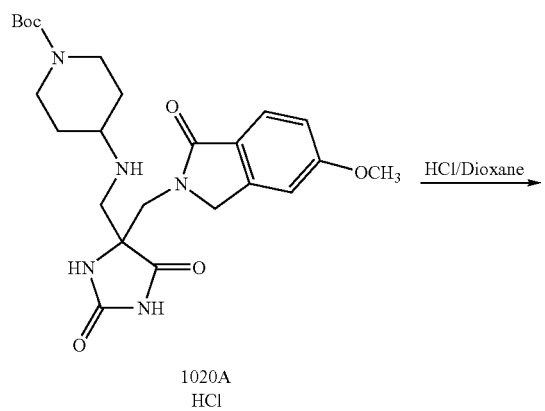

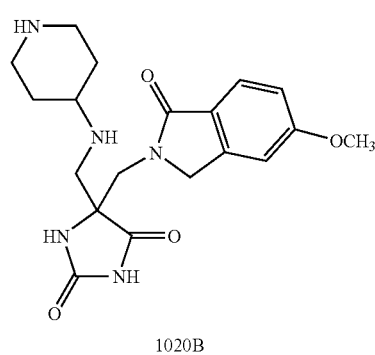

Compound 1020A: Compound 1020A was synthesized following the procedures described in Example 22.

Compound 1020B: Compound 1020A (855 mg, 1.86 mmol) was stirred in MeOH (10 mL) and HCl (10 mL, 4N in dioxane) at rt for 2 hr. Solvent was removed and the material was dried to give 1020B (735 mg, 99%).

The following compounds were prepared as described in Example 22 and Example 1020.

TABLE 1009

| Compound # | Structure | Exact Mass | Mass Obsvd | Ki (nM) |
|---|---|---|---|---|
| 288 | 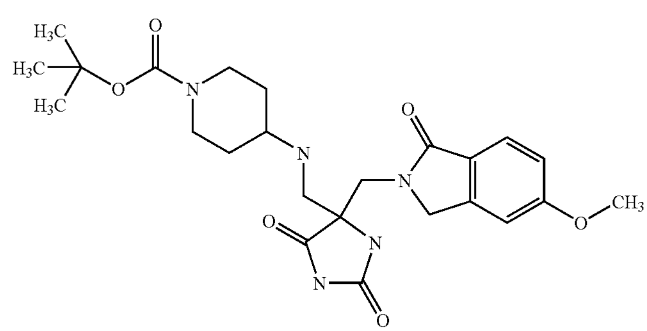 | 487.24 | 488.3 [M + H]$^+$ | B |
| 289 | 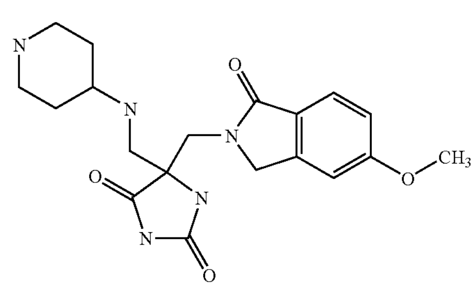 | 387.19 | 388.1 [M + H]$^+$ | C |

TABLE 1009-continued
| Compound # | Structure | Exact Mass | Mass Obsvd | Ki (nM) |
|---|---|---|---|---|
| 290 | 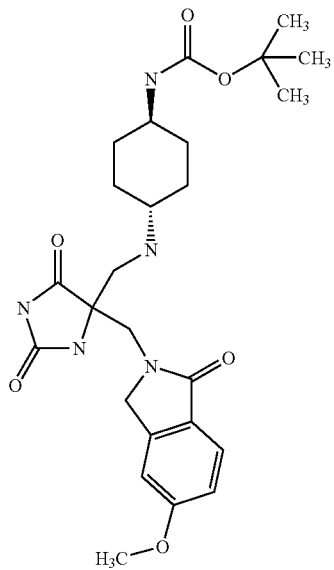 | 501.26 | 502.3 [M + H]+ | B |
| 291 | 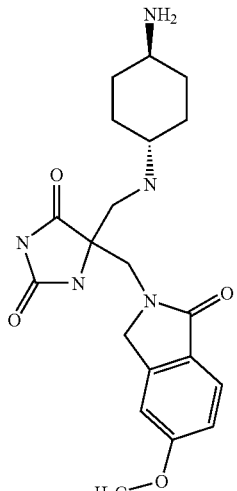 | 401.21 | 402.2 [M + H]+ | C |
| 292 | 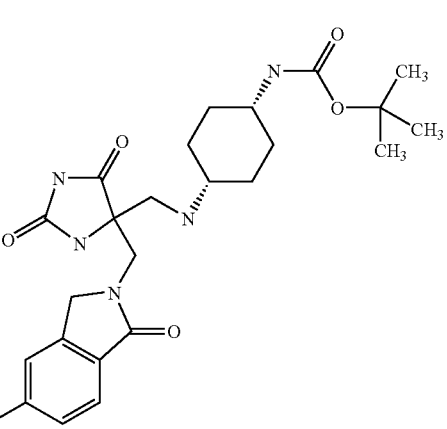 | 501.26 | 502.3 [M + H]+ | B |

TABLE 1009-continued

| Compound # | Structure | Exact Mass | Mass Obsvd | Ki (nM) |
|---|---|---|---|---|
| 293 | 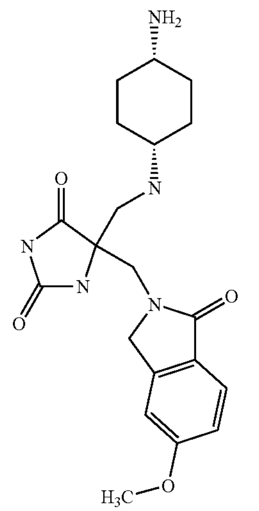 | 401.21 | 402.1 [M + H]+ | B |

Example 1021

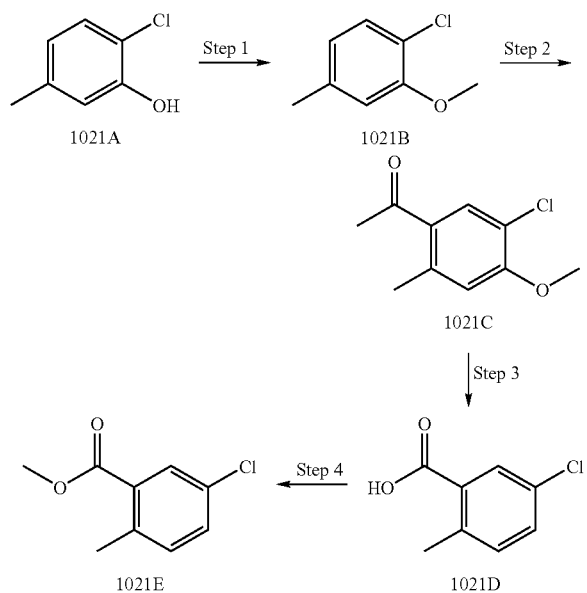

Step 1

DMF (100 mL), cesium carbonate (41.13 g, 126 mmol), and 2-chloro-5-methylphenol (1021A) (15.0 g, 105 mmol) were added to a flask. Methyl iodide (17.92 g, 126 mmol) was added dropwise via addition funnel. The reaction mixture was stirred overnight at room temperature. The reaction mixture was diluted with EtOAc, washed with water and brine, and dried with $Na_2SO_4$. The resulting material was filtered, and concentrated to dryness. The crude product was purified via flash sgc using 1:4 EtOAc:hexanes as the mobile phase to give 15.93 g of 1021B.

Step 2

A flask containing $AlCl_3$ (2.55 g, 19.1 mmol), and LiCl (0.41 g, 9.6 mmol) was placed in a −30° C. cold bath. A solution of 1021B (1.0 g, 6.38 mmol) and acetyl chloride (0.75 g, 9.5 mmol) in 20 mL of $CH_2Cl_2$ was added dropwise. The reaction mixture was stirred for 1 h at −30° C., then allowed to warm to rt and stirred overnight at rt. The reaction mixture was poured into a mixture of ice and EtOAc. The organic layer was washed with water, saturated aq $NaHCO_3$, and water, then dried with $Na_2SO_4$, and concentrated to dryness to give 1.18 g of Compound 1021C.

Step 3

Sodium hydroxide (58 g, 1.45 mol) was dissolved in water (260 mL) and the flask was cooled in an ice-water bath. Bromine (19 mL) was added dropwise to the flask with stirring. The reaction mixture was stirred for 0.5 h after the addition was complete. The resulting solution was added dropwise to an ice-water cooled flask containing Compound 1021C (18.5 g, 93.1 mmol). After the addition was complete, the reaction mixture was allowed to warm to rt and left stirring overnight. The reaction mixture was heated at 40° C. for 2 h. $NaHSO_3$ (55 g) was added. The reaction mixture was stirred for 1 h. The resulting material was diluted with 10% aq NaOH and extracted with EtOAc to remove starting material. The aqueous layer was adjusted to pH 1 and extracted with additional EtOAc. The organic layer was dried with $Na_2SO_4$, filtered, and concentrated to dryness to give 12.31 g of 1021D.

Step 4

DMF (10 mL), Compound 1021D (0.50 g, 2.49 mmol), and $K_2CO_3$ (0.41 g, 2.96 mmol) were added to a flask. Methyl iodide (0.42 g, 2.96 mmol) was added dropwise. The reaction mixture was stirred overnight at room temperature. The reaction mixture was concentrated to dryness to give 0.52 g of 1021E.

The following compounds were prepared as described in step 1 in Example 14 and Example 1021.

TABLE 1010

| Compound # | Structure | Exact Mass | Mass Obsvd | Ki (nM) |
|---|---|---|---|---|
| 296 | 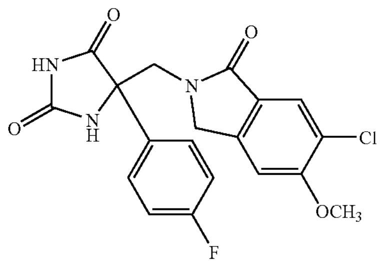 | 403.07 | 404.2 [M + H]⁺ | A |
| 297 | 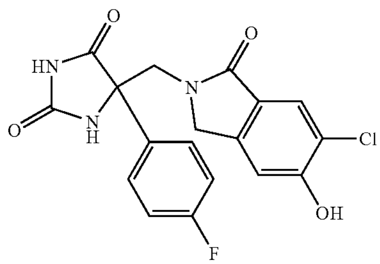 | 389.06 | 390.2 [M + H]⁺ | A |
| 298 | 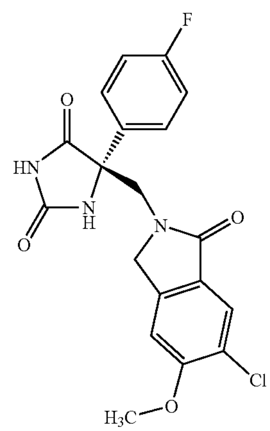 | 403.07 | 404.1 [M + H]⁺ | n/a |

Proton NMR Spectral Data for Selected Compounds in Table 1010.

Compound 296. $^1$H NMR (500 Hz, DMSO-$d_6$) $\delta$3.93 (s, 3H), 4.00 (d, J=14 Hz, 1H), 4.19 (d, J=14 Hz, 1H), 4.23 (d, J=18 Hz, 1H), 4.34 (d, J=18 Hz, 1H), 7.24-7.34 (m, 2H), 7.42 (s, 1H), 7.62-7.73 (m, 3H), 8.92 (s, 1H), 10.95 (s, 1H).

Specific TACE inhibitory activity (Ki values) of some representative compounds of the present invention are set forth below.

TABLE 1011

| Compound # | Structure | Ki (nM) |
|---|---|---|
| 111 | 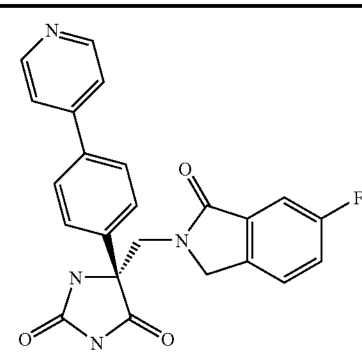 | 0.48 |

TABLE 1011-continued
| Compound # | Structure | Ki (nM) |
|---|---|---|
| 120 | 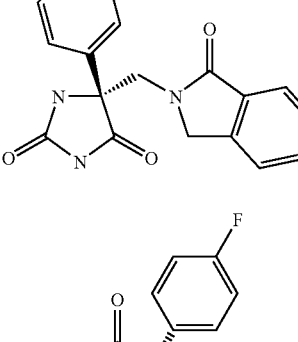 | 4 |
| 213 | 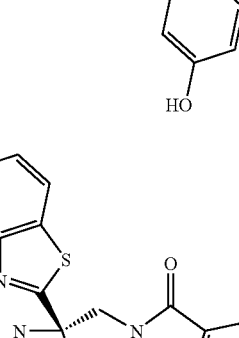 | 0.8 |
| 181 | 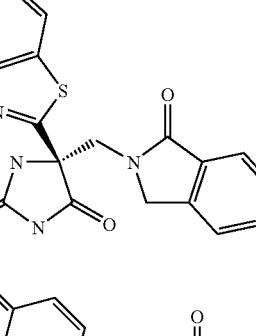 | 3.17 |
| 262 | 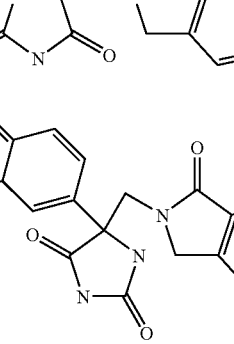 | 4.91 |
| 198 | 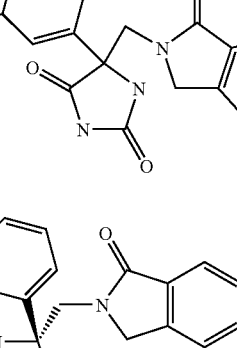 | 1.29 |

TABLE 1011-continued

| Compound # | Structure | Ki (nM) |
|---|---|---|
| 143 | 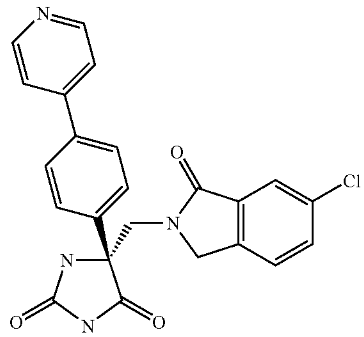 | 1.87 |
| 219 | 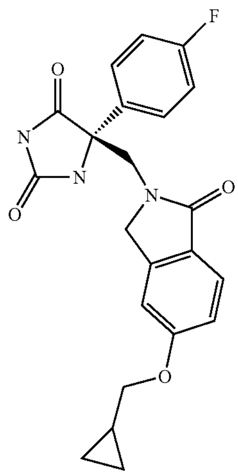 | 2.4 |
| 155 | 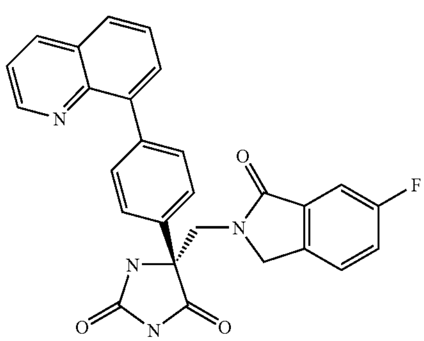 | 1.05 |
| 296 | 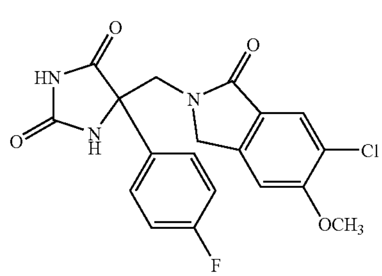 | 1.01 |

TABLE 1011-continued
| Compound # | Structure | Ki (nM) |
|---|---|---|
| 123 | 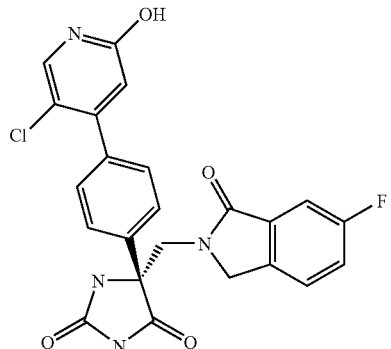 | 1.2 |
| 232 | 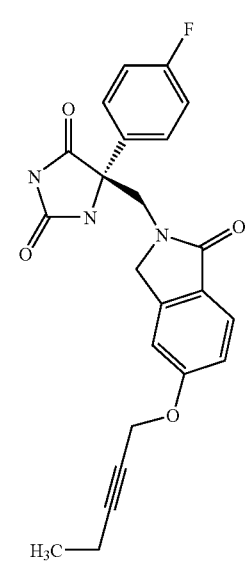 | 1.0 |
| 233 | 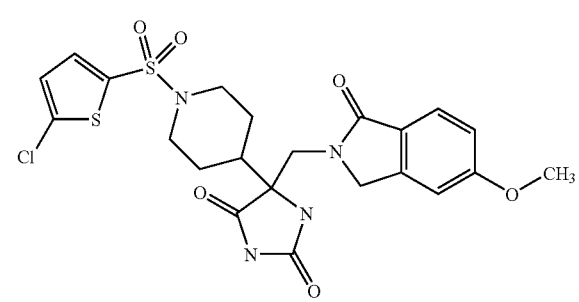 | 2.35 |
| 278 | 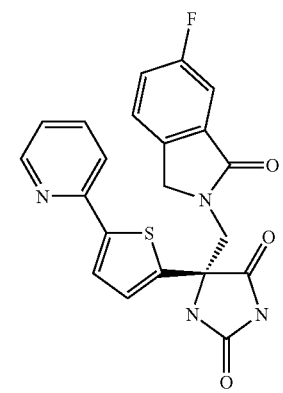 | 2.2 |

TABLE 1011-continued

| Compound # | Structure | Ki (nM) |
|---|---|---|
| 139 | 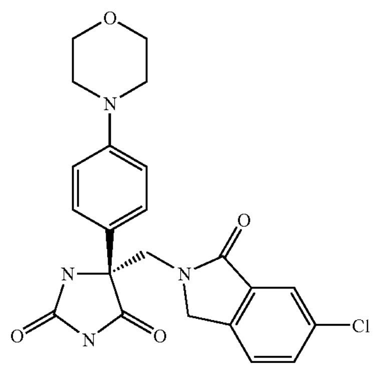 | 2.8 |
| 25 | 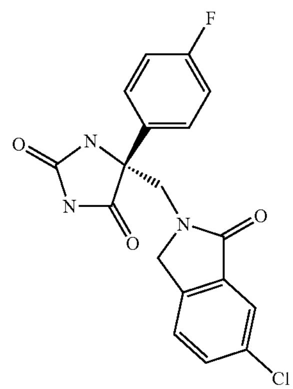 | 0.43 |
| 203 | 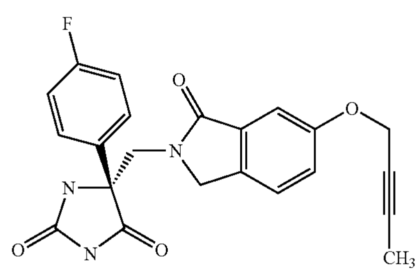 | 0.23 |
| 239 | 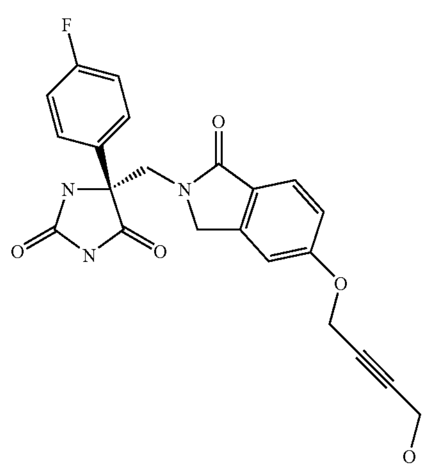 | 0.11 |

TABLE 1011-continued

| Compound # | Structure | Ki (nM) |
|---|---|---|
| 243 | 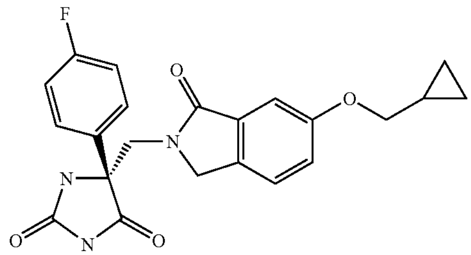 | 3.00 |

The following additional compounds were also prepared by procedures described above as well as in the description discussed later.

TABLE 3000

| Compound ID | Structures | Exact Mass | Mass Obsvd | Ki Rating |
|---|---|---|---|---|
| 3000 | 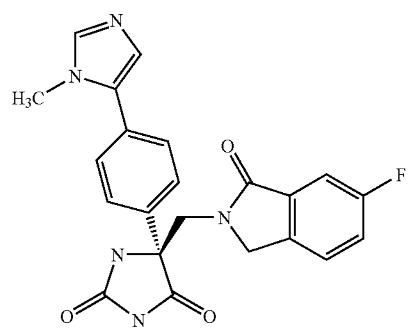 | 419.14 | 420.1 [M + H]+ | C |
| 3001 | 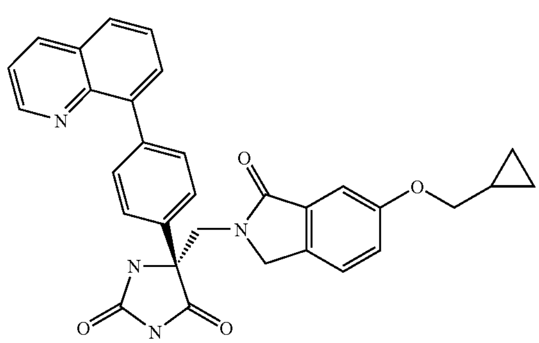 | 518.20 | 519.1 [M + H]+ | B |
| 3002 | 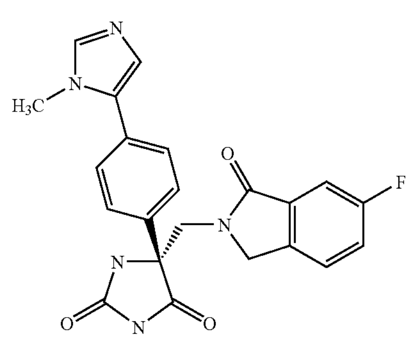 | 419.14 | 420.1 [M + H]+ | A |

| Compound ID | Structures | Exact Mass | Mass Obsvd | Ki Rating |
|---|---|---|---|---|
| 3003 | 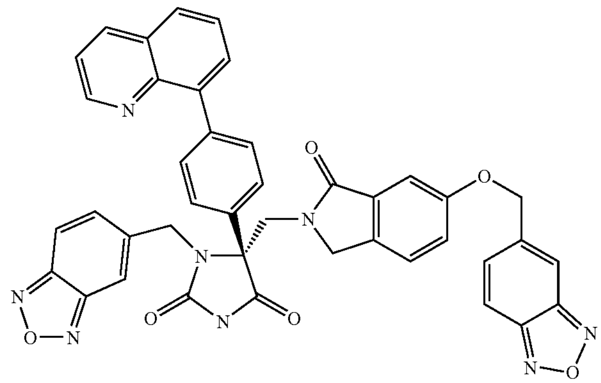 | 728.71 | 729.2 [M + H]+ | D |
| 3004 | 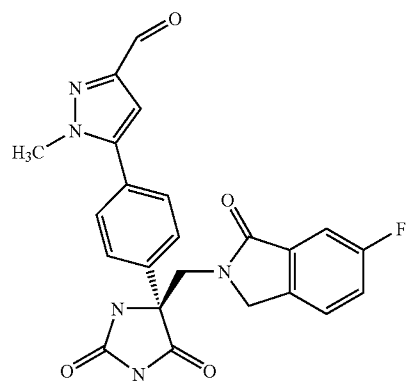 | 447.13 | 448.2 [M + H]+ | C |
| 3005 | 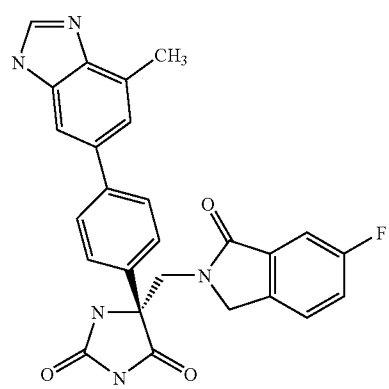 | 469.16 | 470.3 [M + H]+ | A |
| 3006 | 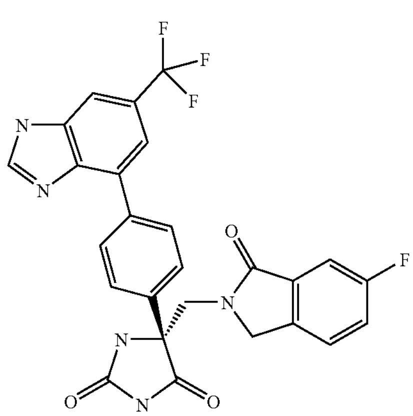 | 523.13 | 524.3 [M + H]+ | A |

TABLE 3000-continued
| Compound ID | Structures | Exact Mass | Mass Obsvd | Ki Rating |
|---|---|---|---|---|
| 3007 | 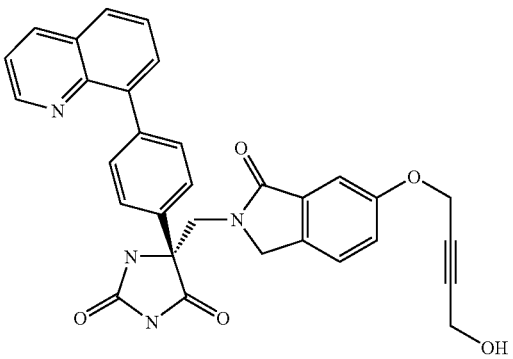 | 532.20 | 533.3 [M + H]+ | A |
| 3008 | 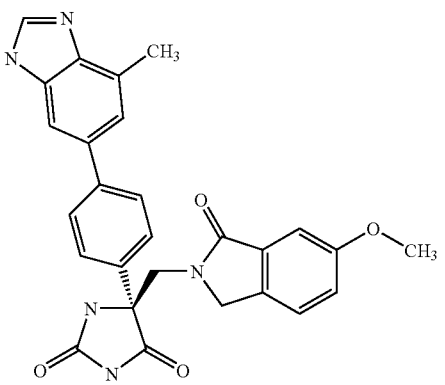 | 481.20 | 482.3 [M + H]+ | B |
| 3009 | 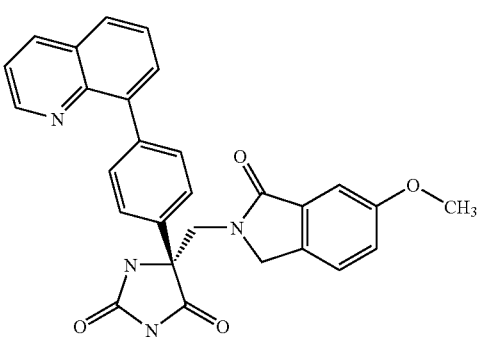 | 478.16 | 479.3 [M + H]+ | A |
| 3010 | 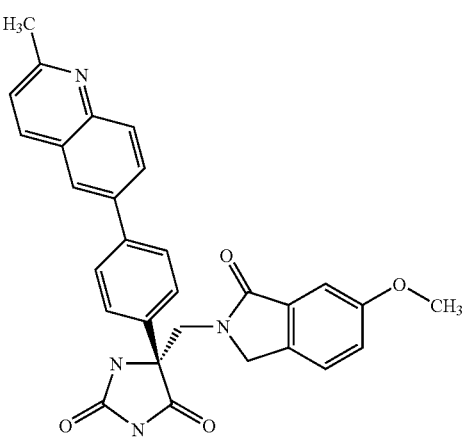 | 492.20 | 493.3 [M + H]+ | A |

TABLE 3000-continued
| Compound ID | Structures | Exact Mass | Mass Obsvd | Ki Rating |
|---|---|---|---|---|
| 3011 | 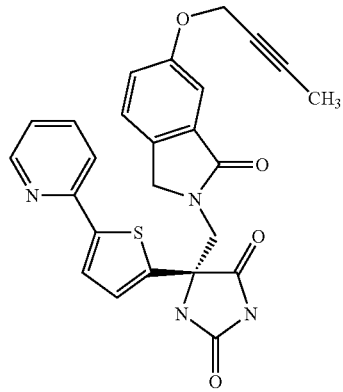 | 472.10 | 473.3 [M + H]+ | A |
| 3012 | 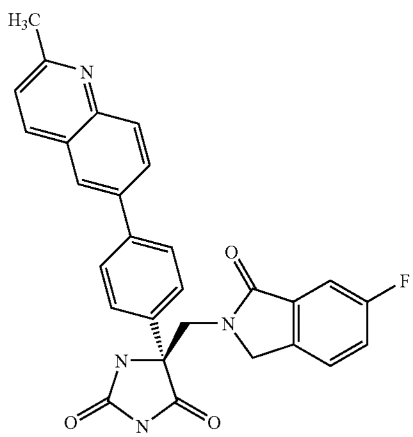 | 480.20 | 481.3 [M + H]+ | D |
| 3013 | 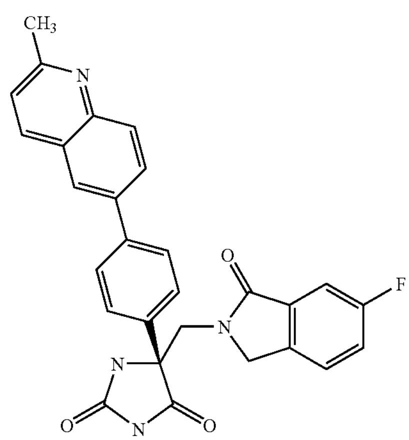 | 480.20 | 481.3 [M + H]+ | A |

TABLE 3000-continued
| Compound ID | Structures | Exact Mass | Mass Obsvd | Ki Rating |
|---|---|---|---|---|
| 3014 | 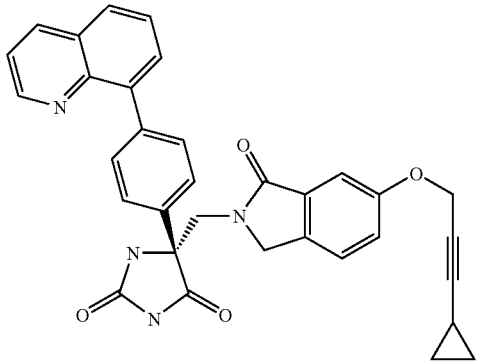 | 542.20 | 543.3 [M + H]+ | B |
| 3015 | 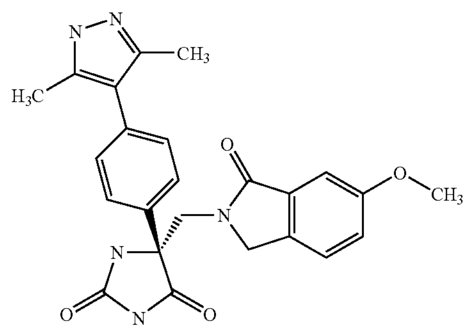 | 445.20 | 446.2 [M + H]+ | A |
| 3016 | 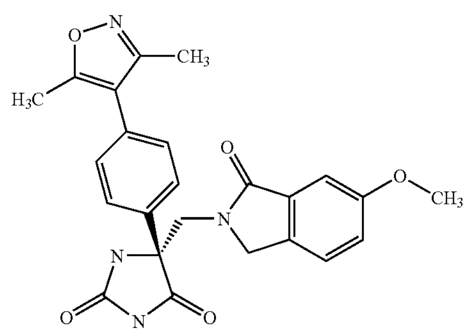 | 446.20 | 447.2 [M + H]+ | A |
| 3017 | 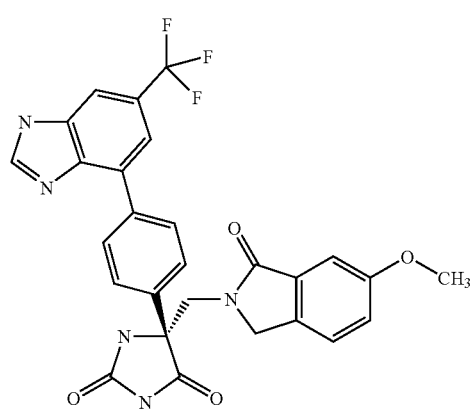 | 535.15 | 536.3 [M + H]+ | B |

TABLE 3000-continued

| Compound ID | Structures | Exact Mass | Mass Obsvd | Ki Rating |
|---|---|---|---|---|
| 3018 | 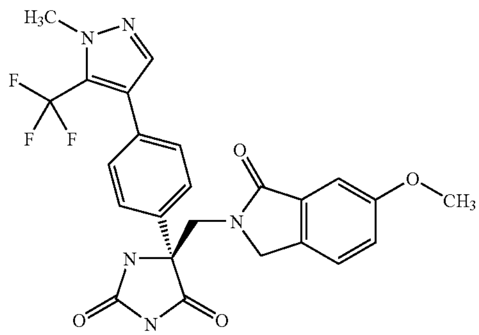 | 499.10 | 500.3 [M + H]+ | B |
| 3019 | 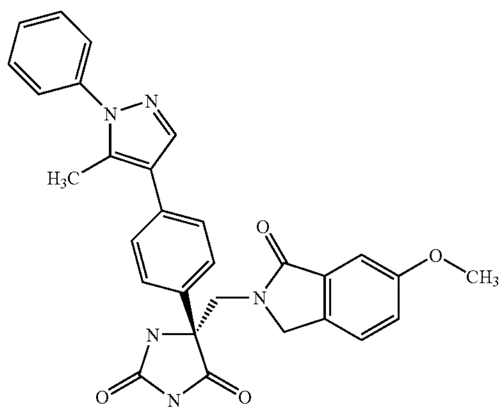 | 507.20 | 508.3 [M + H]+ | A |
| 3020 | 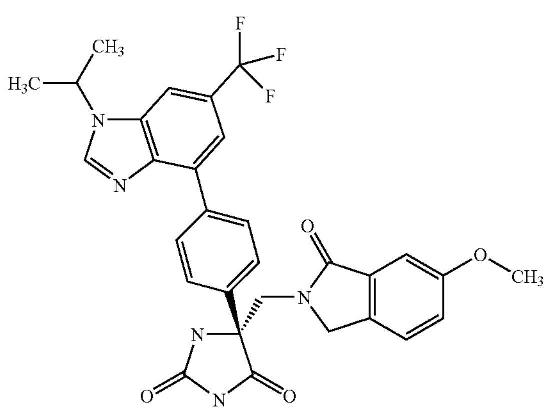 | 577.19 | 578.3 [M + H]+ | B |
| 3021 | 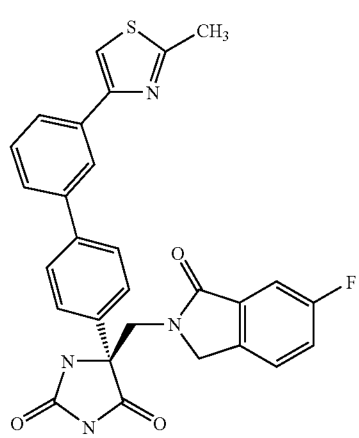 | 512.13 | 513.3 [M + H]+ | D |

TABLE 3000-continued

| Compound ID | Structures | Exact Mass | Mass Obsvd | Ki Rating |
|---|---|---|---|---|
| 3022 | 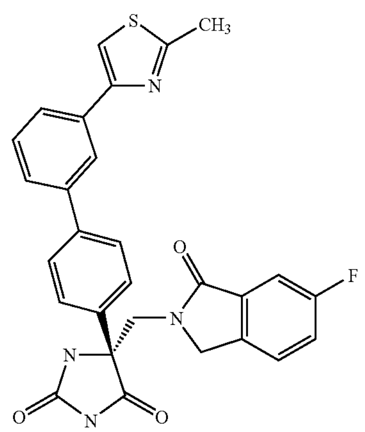 | 512.13 | 513.3 [M + H]⁺ | B |
| 3023 | 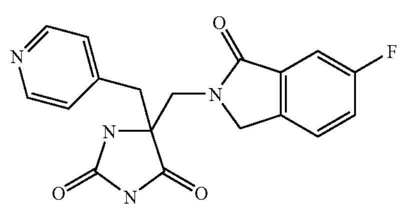 | 354.34 | 355.2 [M + H]⁺ | D |
| 3024 | 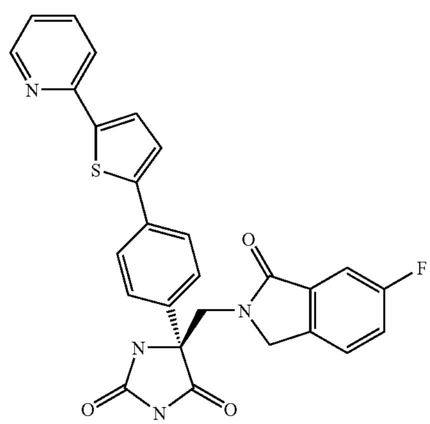 | 498.12 | 499.3 [M + H]⁺ | C |
| 3025 | 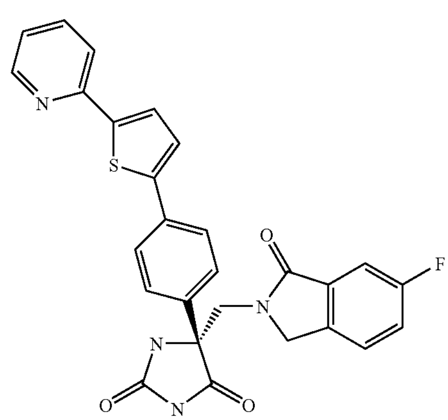 | 498.12 | 499.3 [M + H]⁺ | B |

TABLE 3000-continued

| Compound ID | Structures | Exact Mass | Mass Obsvd | Ki Rating |
|---|---|---|---|---|
| 3026 | 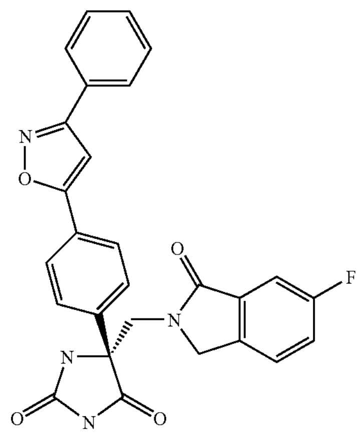 | 482.14 | 483.3 [M + H]+ | B |
| 3027 | 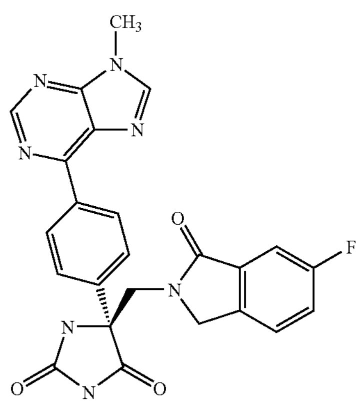 | 471.15 | 472.3 [M + H]+ | D |
| 3028 | 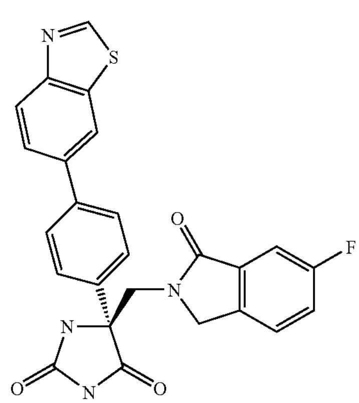 | 472.10 | 473.3 [M + H]+ | C |

TABLE 3000-continued

| Compound ID | Structures | Exact Mass | Mass Obsvd | Ki Rating |
|---|---|---|---|---|
| 3029 | 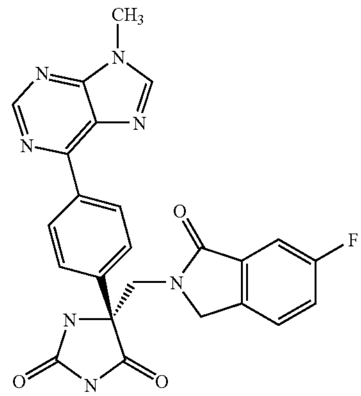 | 471.15 | 472.3 [M + H]+ | A |
| 3030 | 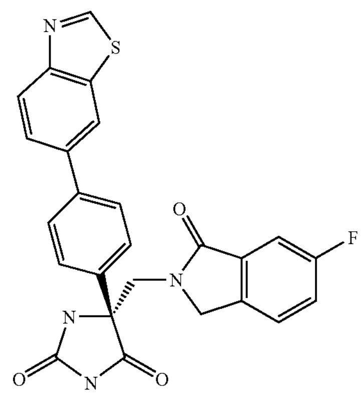 | 472.10 | 473.3 [M + H]+ | A |
| 3031 | 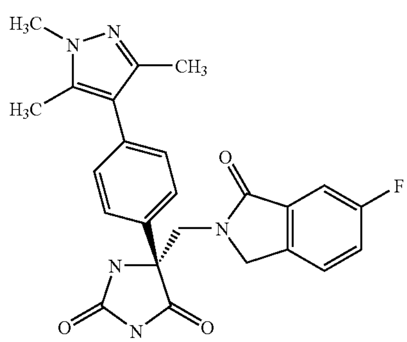 | 447.17 | 448.2 [M + H]+ | A |
| 3032 | 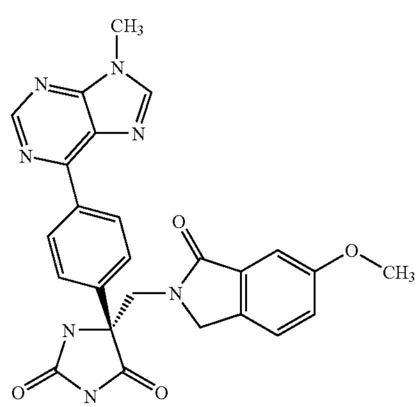 | 483.17 | 484.3 [M + H]+ | A |

TABLE 3000-continued

| Compound ID | Structures | Exact Mass | Mass Obsvd | Ki Rating |
|---|---|---|---|---|
| 3033 | 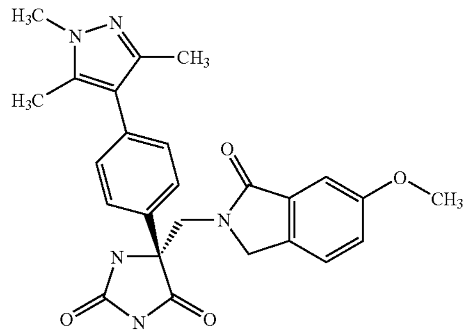 | 459.19 | 460.3 [M + H]+ | A |
| 3034 | 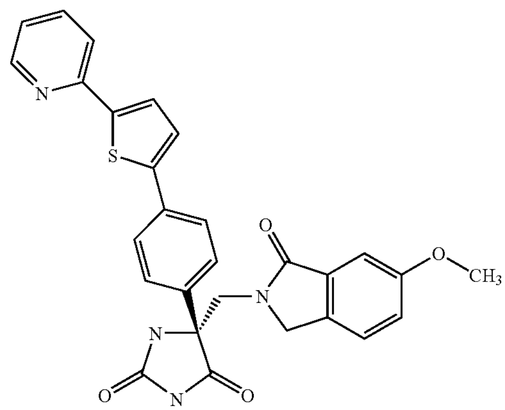 | 510.14 | 511.3 [M + H]+ | A |
| 3035 | 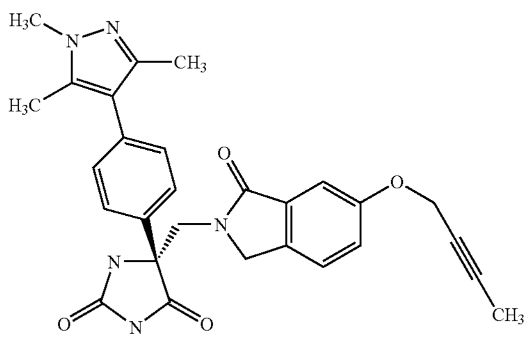 | 497.21 | 498.3 [M + H]+ | A |
| 3003 | 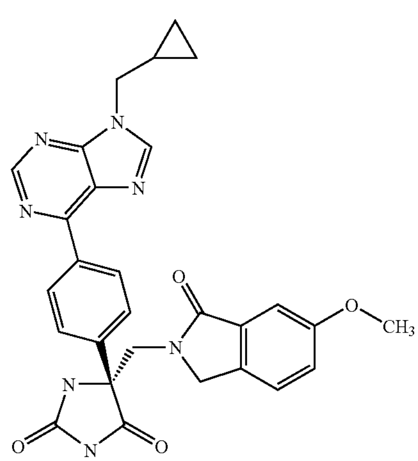 | 523.20 | 524.3 [M + H]+ | A |

TABLE 3000-continued

| Compound ID | Structures | Exact Mass | Mass Obsvd | Ki Rating |
|---|---|---|---|---|
| 3037 | 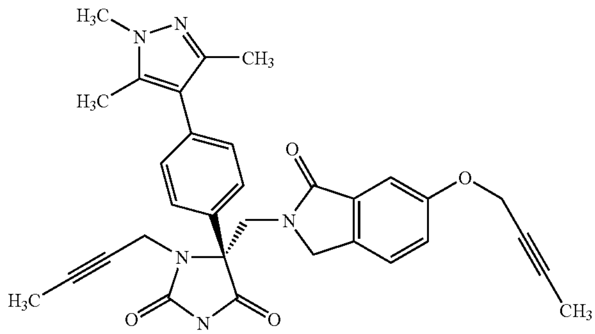 | 549.24 | 550.3 [M + H]+ | A |
| 3038 | 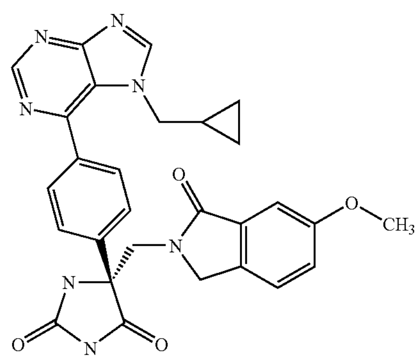 | 523.20 | 524.3 [M + H]+ | A |
| 3039 | 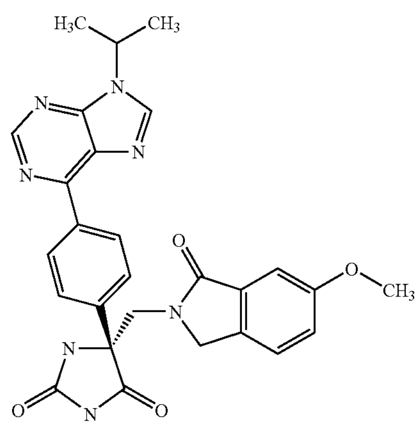 | 511.20 | 512.3 [M + H]+ | A |
| 3040 | 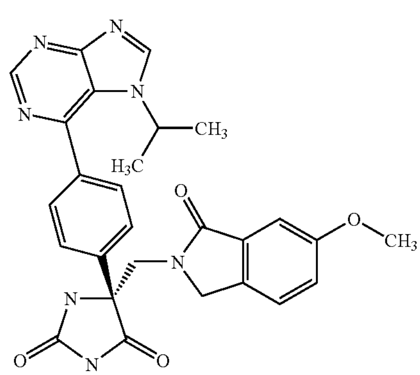 | 511.20 | 512.3 [M + H]+ | A |

TABLE 3000-continued
| Compound ID | Structures | Exact Mass | Mass Obsvd | Ki Rating |
|---|---|---|---|---|
| 3041 | 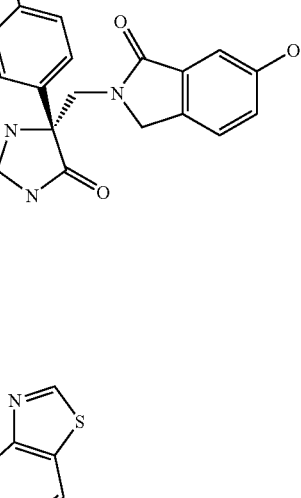 | 513.20 | 514.3 [M + H]+ | A |
| 3042 | 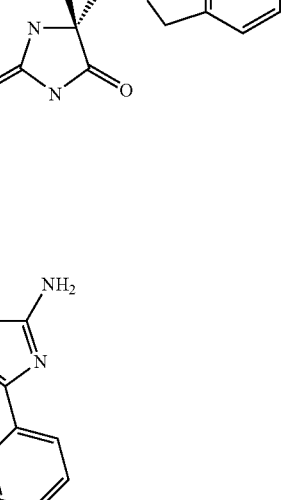 | 584.12 | 585.3 [M + H]+ | A |
| 3043 | 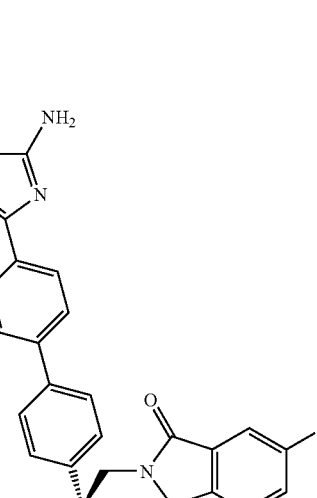 | 525.14 | 526.3 [M + H]+ | C |

| Compound ID | Structures | Exact Mass | Mass Obsvd | Ki Rating |
|---|---|---|---|---|
| 3044 | 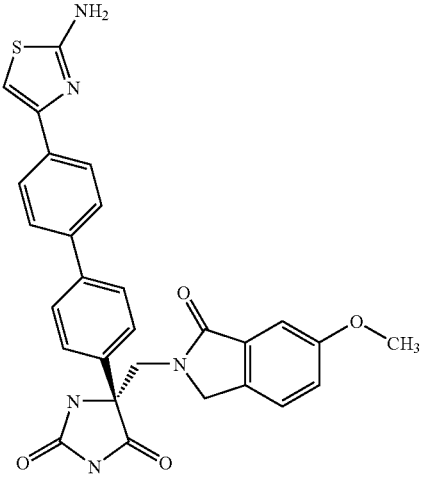 | 525.14 | 526.3 [M + H]+ | A |
| 3045 | 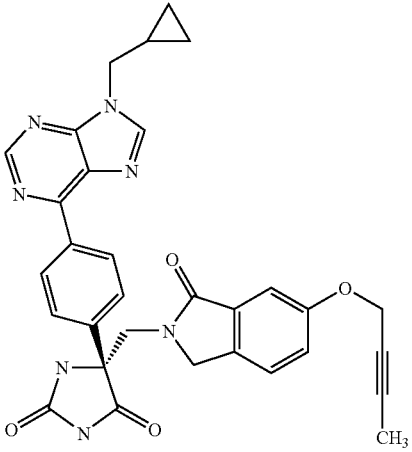 | 561.21 | 562.3 [M + H]+ | A |
| 3046 | 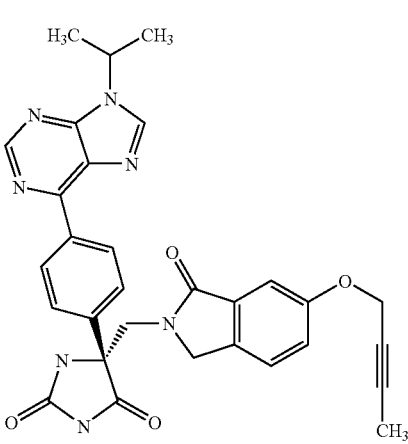 | 549.21 | 550.3 [M + H]+ | A |

TABLE 3000-continued
| Compound ID | Structures | Exact Mass | Mass Obsvd | Ki Rating |
|---|---|---|---|---|
| 3047 | 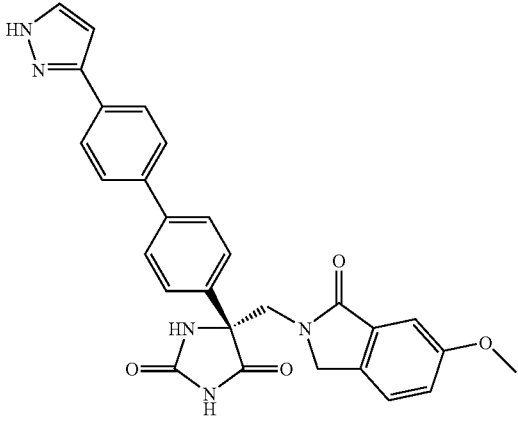 | 493.18 | 494.3 [M + H]⁺ | A |
| 3048 | 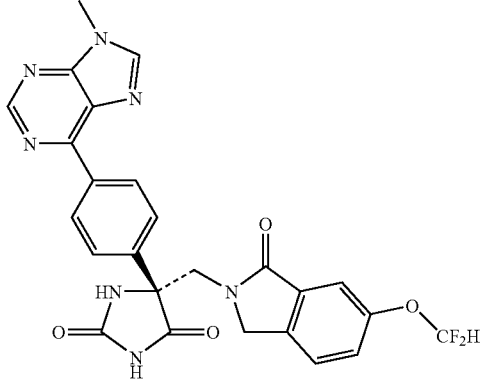 | 519.15 | 520.3 [M + H]⁺ | A |
| 4001 | 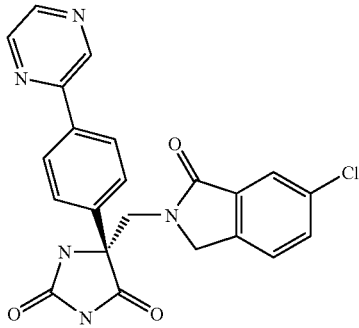 | 433.1 | 434.2 [M + H]⁺ | A |
| 4002 | 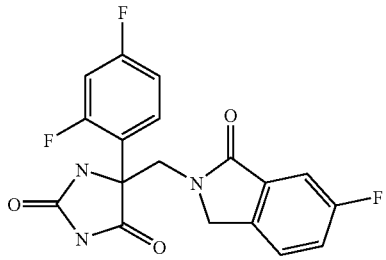 | 375.1 | 376.1 [M + H]⁺ | A |

TABLE 3000-continued
| Compound ID | Structures | Exact Mass | Mass Obsvd | Ki Rating |
|---|---|---|---|---|
| 4003 | 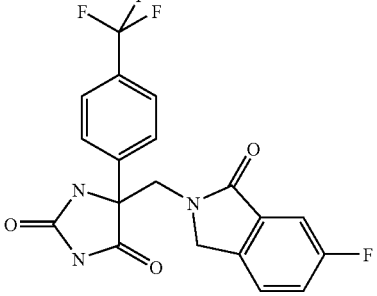 | 407.1 | 408.2 [M + H]+ | A |
| 4004 | 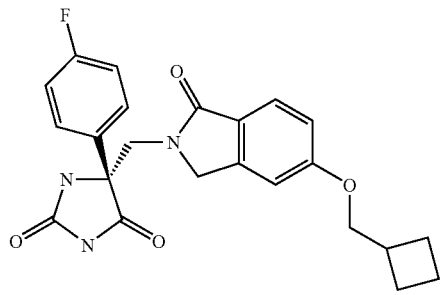 | 423.2 | 424.2 [M + H]+ | A |
| 4005 | 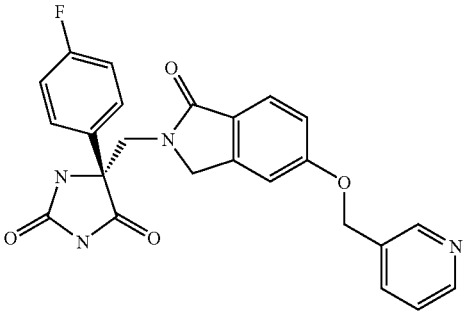 | 446.1 | 447.2 [M + H]+ | A |
| 4006 | 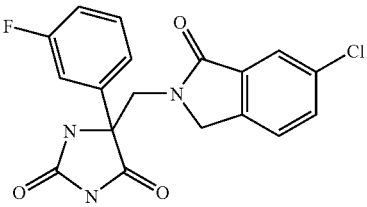 | 373.1 | 374.2 [M + H]+ | C |
| 4007 | 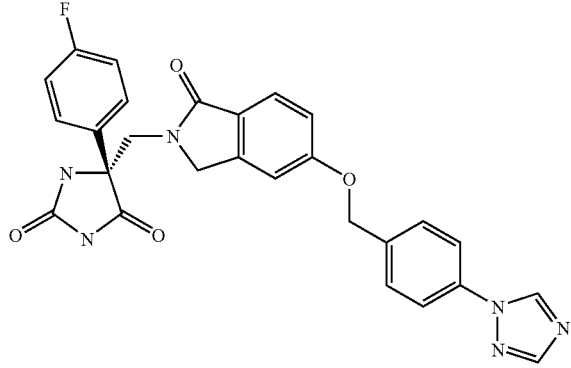 | 512.2 | 513.3 [M + H]+ | A |

TABLE 3000-continued

| Compound ID | Structures | Exact Mass | Mass Obsvd | Ki Rating |
|---|---|---|---|---|
| 4008 | 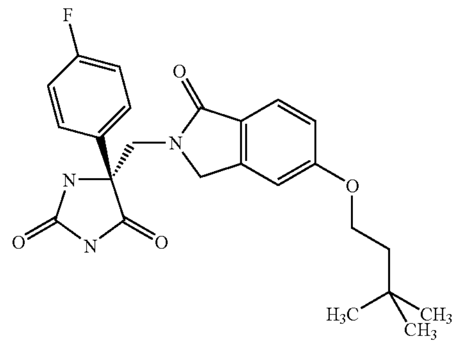 | 439.2 | 440.2 [M + H]+ | B |
| 4009 | 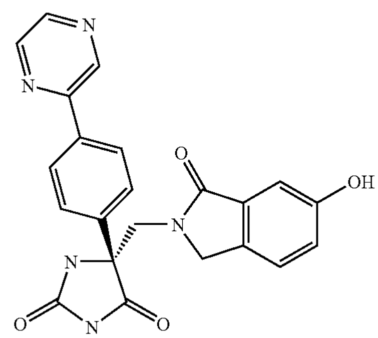 | 415.1 | 416.2 [M + H]+ | B |
| 4010 | 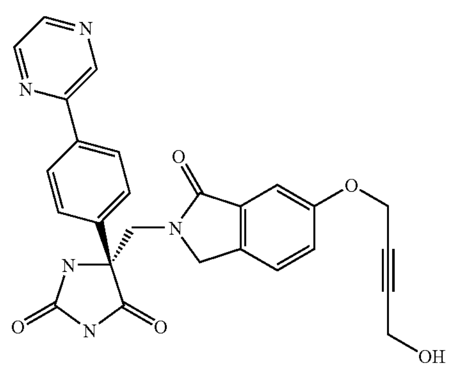 | 483.2 | 484.3 [M + H]+ | A |
| 4011 | 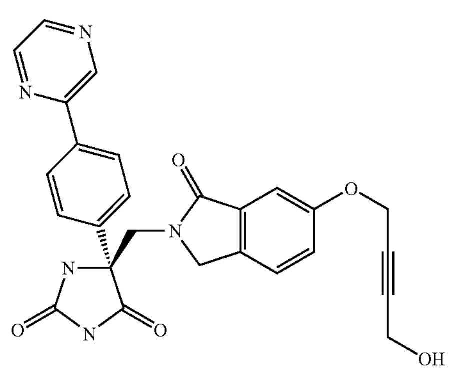 | 483.2 | 484.3 [M + H]+ | C |

TABLE 3000-continued

| Compound ID | Structures | Exact Mass | Mass Obsvd | Ki Rating |
|---|---|---|---|---|
| 4012 | 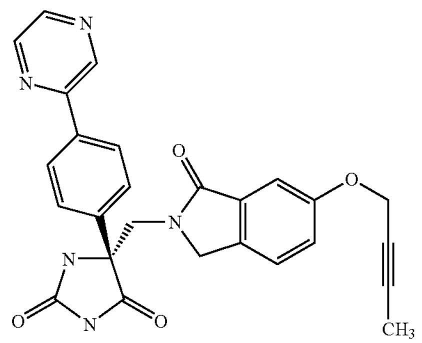 | 467.2 | 468.3 [M + H]+ | A |
| 4013 | 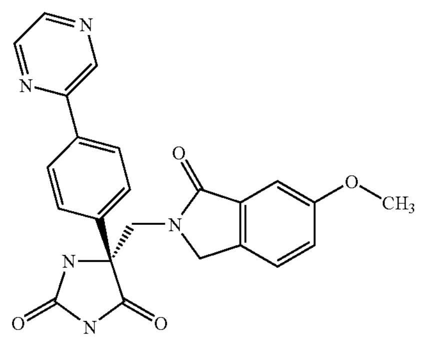 | 429.2 | 430.2 [M + H]+ | A |
| 4014 | 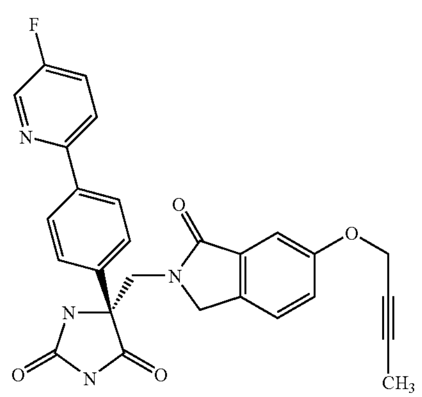 | 484.2 | 485.3 [M + H]+ | A |
| 4015 | 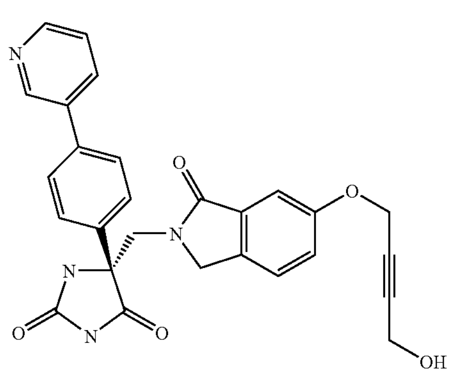 | 482.2 | 483.3 [M + H]+ | A |

TABLE 3000-continued

| Compound ID | Structures | Exact Mass | Mass Obsvd | Ki Rating |
|---|---|---|---|---|
| 4016 | 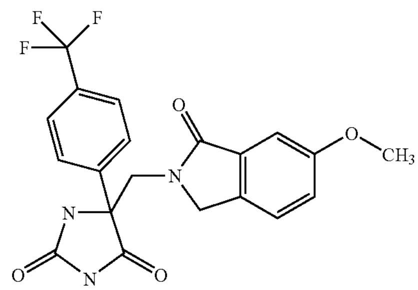 | 419.1 | 420.0 [M + H]+ | A |
| 4017 | 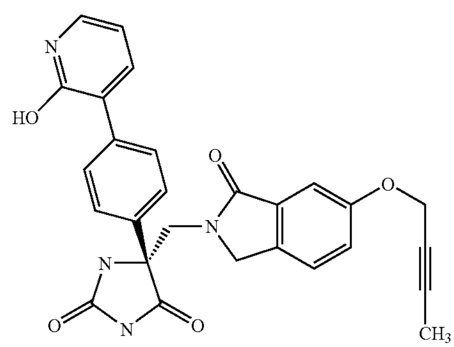 | 482.2 | 483.3 [M + H]+ | A |
| 4018 | 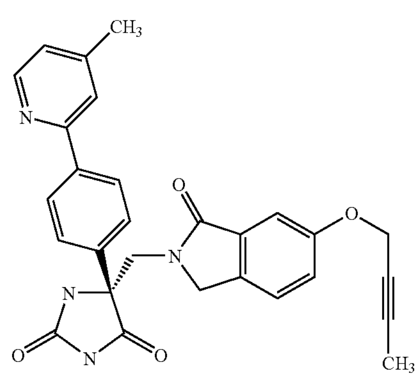 | 480.2 | 481.3 [M + H]+ | A |
| 4019 | 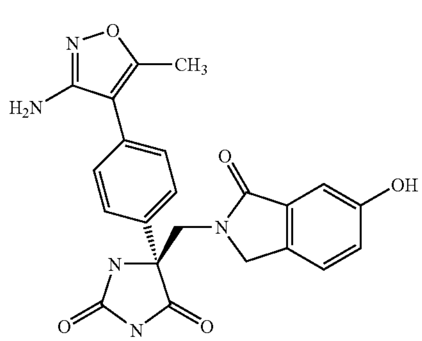 | 433.1 | 434.2 [M + H]+ | C |

TABLE 3000-continued

| Compound ID | Structures | Exact Mass | Mass Obsvd | Ki Rating |
|---|---|---|---|---|
| 4020 | 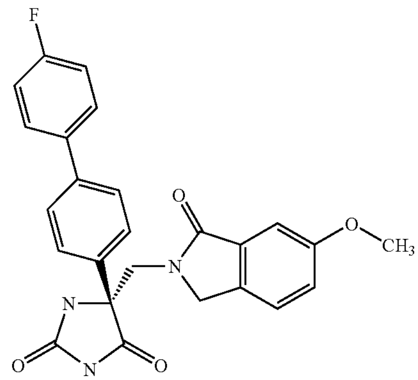 | 445.1 | 446.2 [M + H]⁺ | A |
| 4021 | 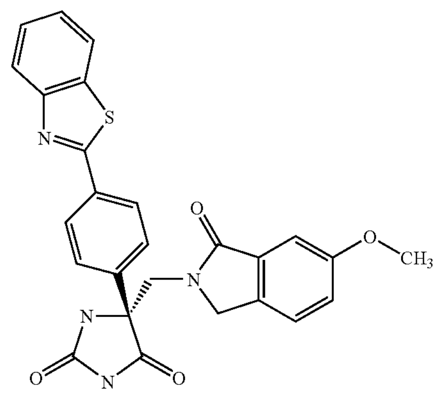 | 484.1 | 485.3 [M + H]⁺ | A |
| 4022 | 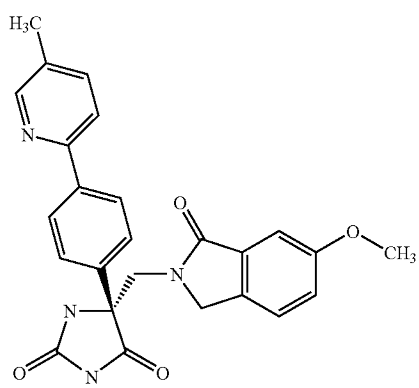 | 442.2 | 443.2 [M + H]⁺ | A |
| 4023 | 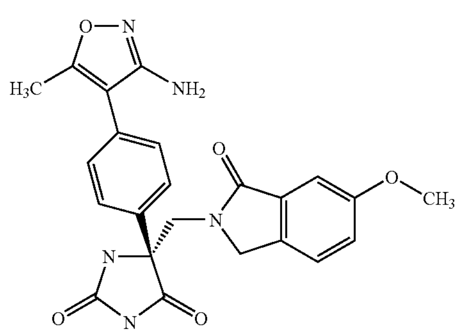 | 447.2 | 448.2 [M + H]⁺ | A |

TABLE 3000-continued

| Compound ID | Structures | Exact Mass | Mass Obsvd | Ki Rating |
|---|---|---|---|---|
| 4024 | 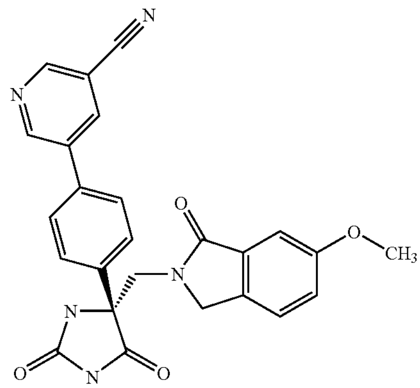 | 453.1 | 454.2 [M + H]+ | A |
| 4025 | 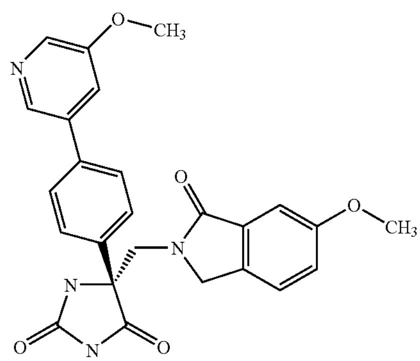 | 458.2 | 459.3 [M + H]+ | A |
| 4026 | 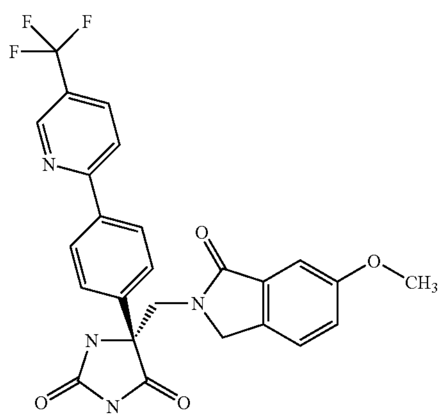 | 496.2 | 497.3 [M + H]+ | A |
| 4027 | 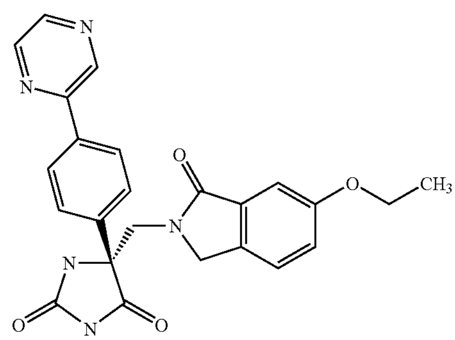 | 443.2 | 444.2 [M + H]+ | A |

TABLE 3000-continued

| Compound ID | Structures | Exact Mass | Mass Obsvd | Ki Rating |
|---|---|---|---|---|
| 4028 | 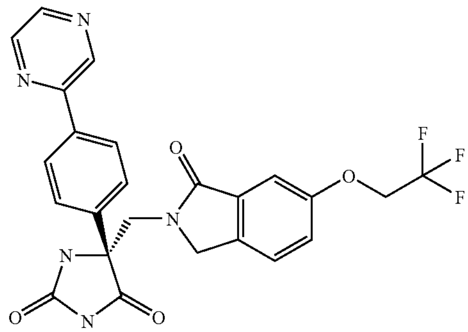 | 497.1 | 498.3 [M + H]$^+$ | B |
| 4029 | 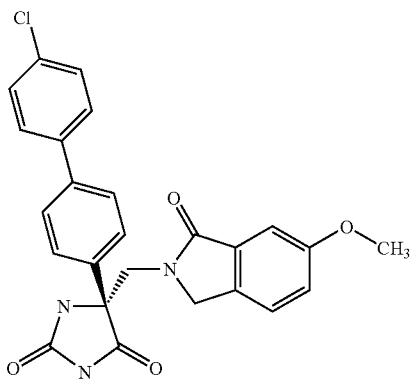 | 461.1 | 462.3 [M + H]$^+$ | A |
| 4030 | 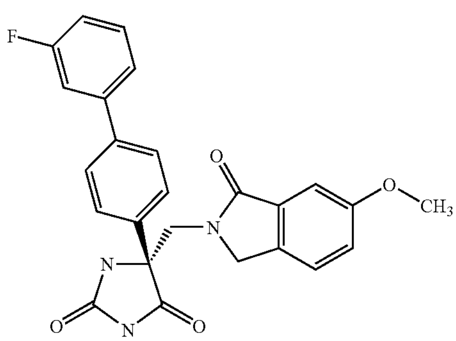 | 445.1 | 446.2 [M + H]$^+$ | A |
| 4031 | 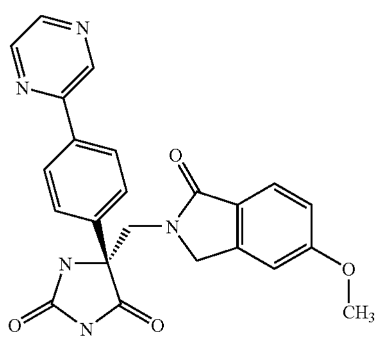 | 429.1 | 430.2 [M + H]$^+$ | A |

TABLE 3000-continued

| Compound ID | Structures | Exact Mass | Mass Obsvd | Ki Rating |
|---|---|---|---|---|
| 4032 | 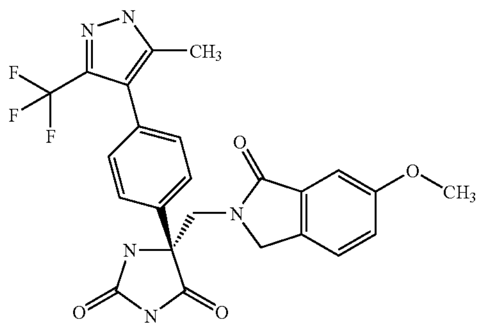 | 499.1 | 500.3 [M + H]+ | A |
| 4033 | 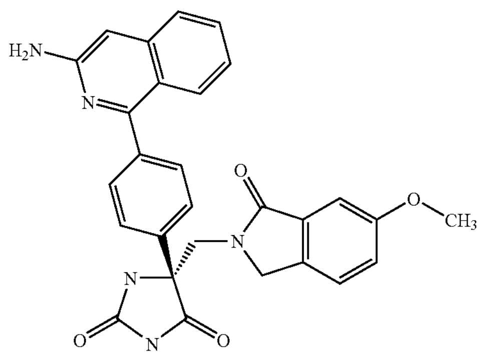 | 493.2 | 494.3 [M + H]+ | A |
| 4034 | 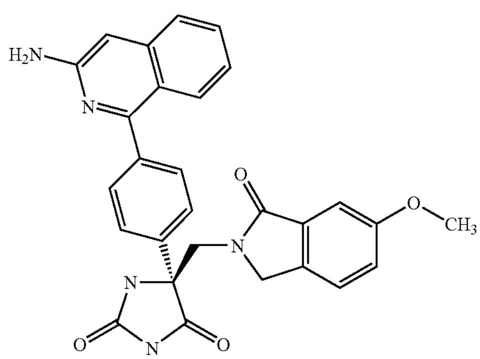 | 493.2 | 494.3 [M + H]+ | B |
| 4035 | 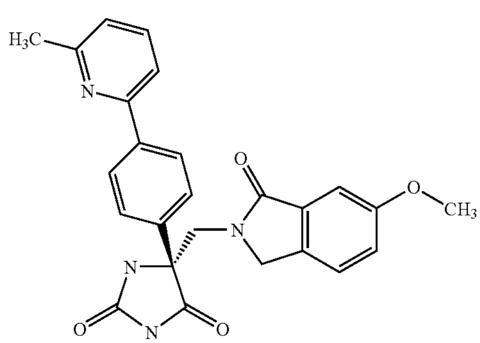 | 442.2 | 443.2 [M + H]+ | A |

TABLE 3000-continued

| Compound ID | Structures | Exact Mass | Mass Obsvd | Ki Rating |
|---|---|---|---|---|
| 4036 | 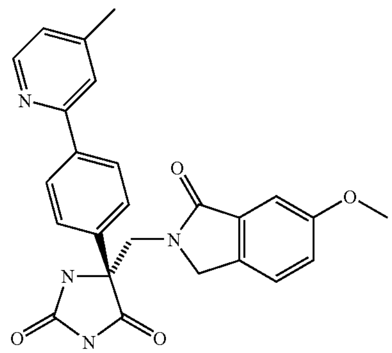 | 442.2 | 443.2 [M + H]⁺ | n/a |
| 4037 | 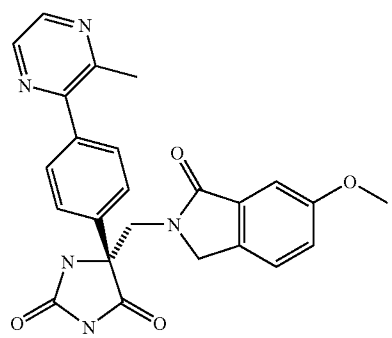 | 443.2 | 444.2 [M + H]⁺ | n/a |
| 4038 | 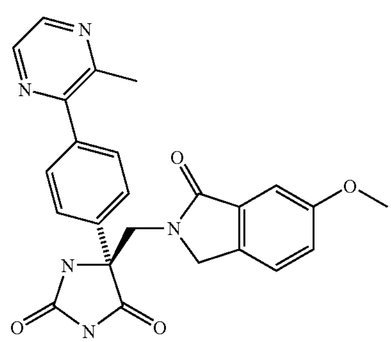 | 443.2 | 444.2 [M + H]⁺ | n/a |
| 4039 | 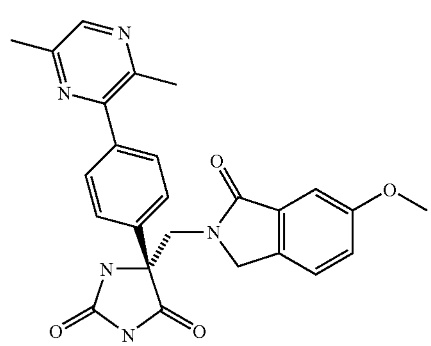 | 457.2 | 458.3 [M + H]⁺ | n/a |

TABLE 3000-continued

| Compound ID | Structures | Exact Mass | Mass Obsvd | Ki Rating |
|---|---|---|---|---|
| 4040 | 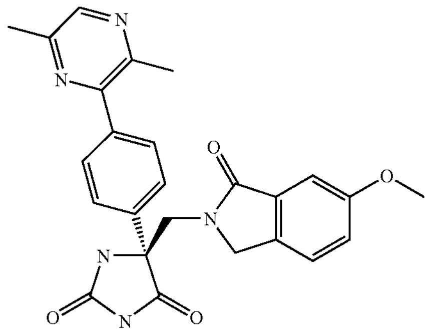 | 457.2 | 458.3 [M + H]+ | n/a |
| 4041 | 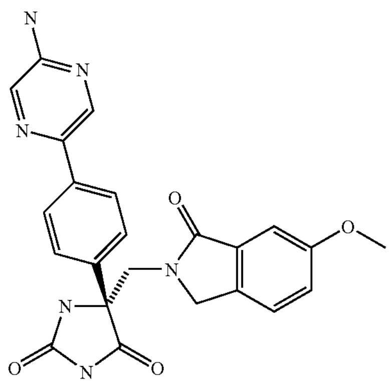 | 444.1 | 445.2 [M + H]+ | n/a |
| 4042 | 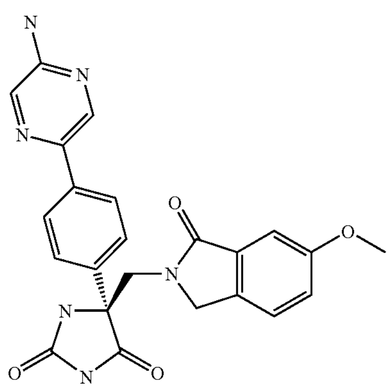 | 444.1 | 445.2 [M + H]+ | n/a |
| 5000 | 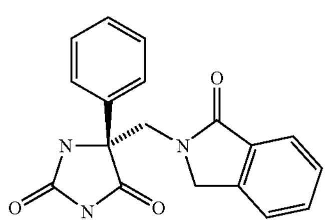 | 321.1 | 322.2 [M + H]+ | |

TABLE 3000-continued

| Compound ID | Structures | Exact Mass | Mass Obsvd | Ki Rating |
|---|---|---|---|---|
| 5001 | 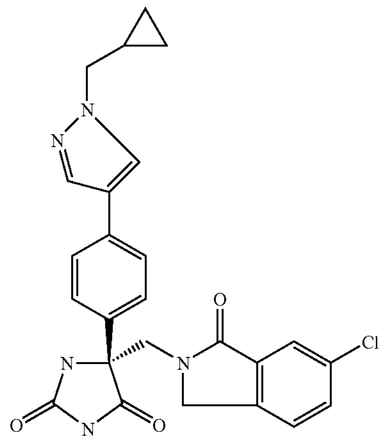 | 475.1 | 476.3 [M + H]+ | |
| 5003 | 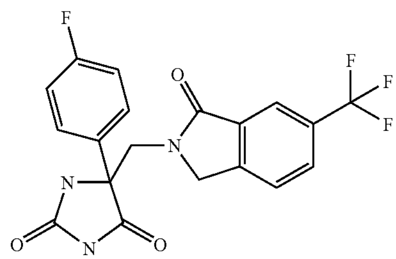 | 407.1 | 408.2 [M + H]+ | B |
| 5004 | 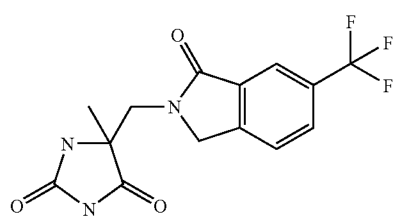 | 327.1 | 328.2 [M + H]+ | C |
| 5005 | 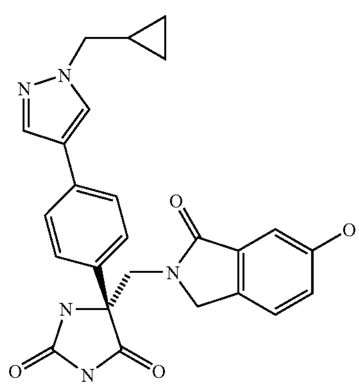 | 457.2 | 458.3 [M + H]+ | A |

TABLE 3000-continued

| Compound ID | Structures | Exact Mass | Mass Obsvd | Ki Rating |
|---|---|---|---|---|
| 5006 | 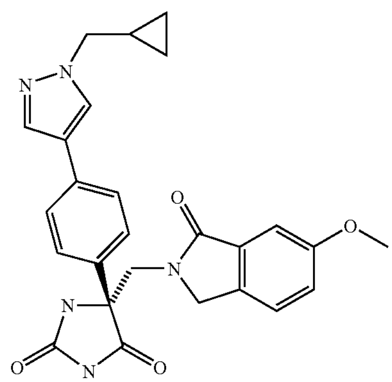 | 471.2 | 472.1 [M + H]+ | A |
| 5007 1338095 | 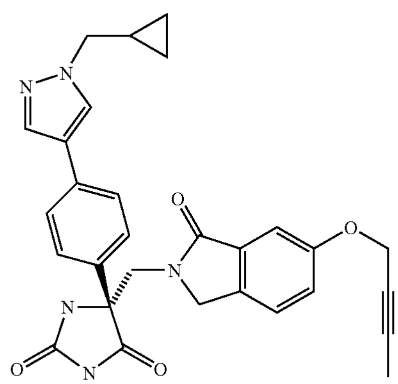 | 509.2 | 510.3 [M + H]+ | A |
| 5008 | 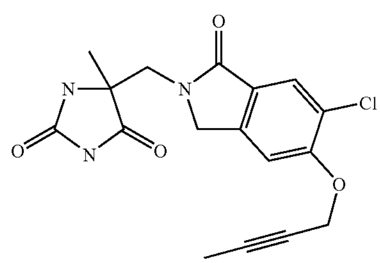 | 361.08 | 362.2 [M + H]+ | B |
| 5009 | 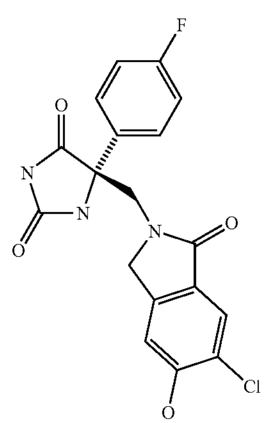 | 389.1 | 390.2 [M + H]+ | A |

TABLE 3000-continued
| Compound ID | Structures | Exact Mass | Mass Obsvd | Ki Rating |
|---|---|---|---|---|
| 5010 | 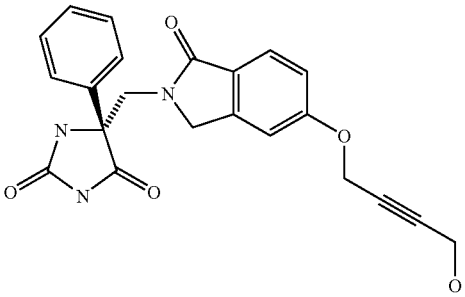 | 405.1 | 406.2 [M + H]$^+$ | A |
| 5011 | 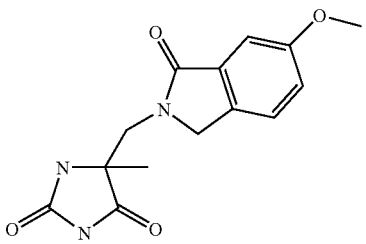 | 289.1 | 290.2 [M + H]$^+$ | B |
| 5012 | 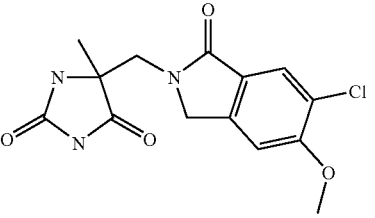 | 323.1 | 324.2 [M + H]$^+$ | B |
| 5013 | 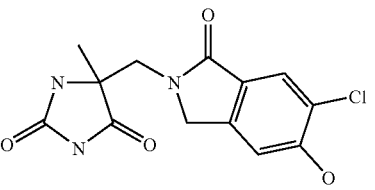 | 309.1 | 310.2 [M + H]$^+$ | C |
| 5014 | 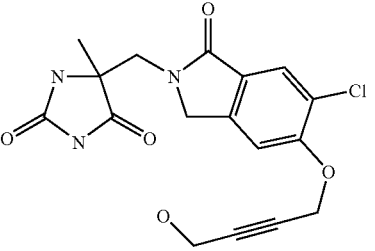 | 377.1 | 378.2 [M + H]$^+$ | C |
| 5015 | 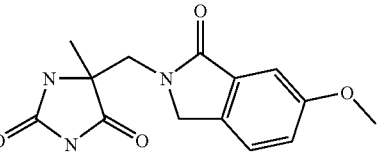 | 289.1 | 290.2 [M + H]$^+$ | B |

TABLE 3000-continued

| Compound ID | Structures | Exact Mass | Mass Obsvd | Ki Rating |
|---|---|---|---|---|
| 5016 | 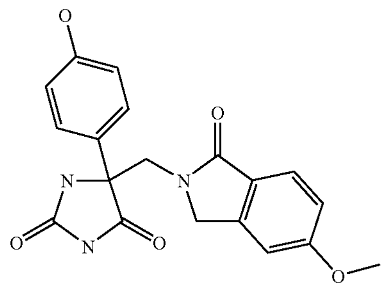 | 367.1 | 368.2 [M + H]+ | B |
| 5017 | 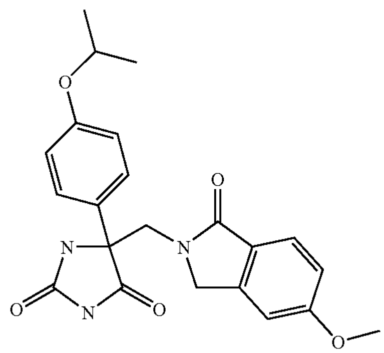 | 409.2 | 410.2 [M + H]+ | A |
| 5018 | 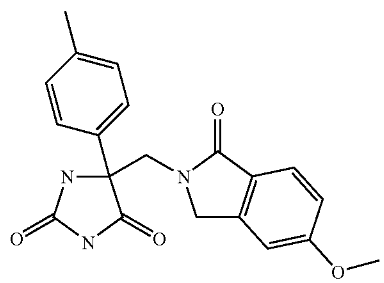 | 365.14 | 366.2 [M + H]+ | A |
| 5019 | 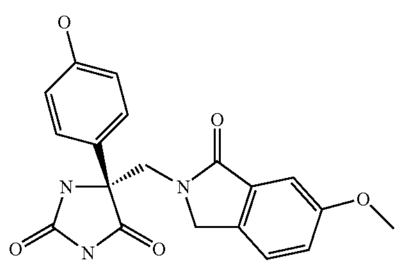 | 367.12 | 368.2 [M + H]+ | A |
| 5020 | 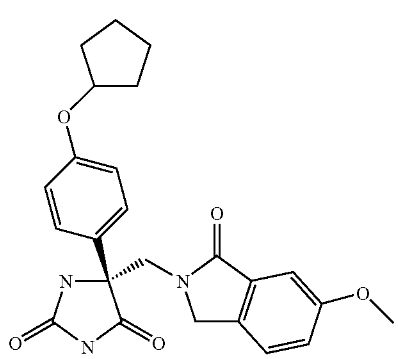 | 435.2 | 436.2 [M + H]+ | A |

TABLE 3000-continued

| Compound ID | Structures | Exact Mass | Mass Obsvd | Ki Rating |
|---|---|---|---|---|
| 5021 | 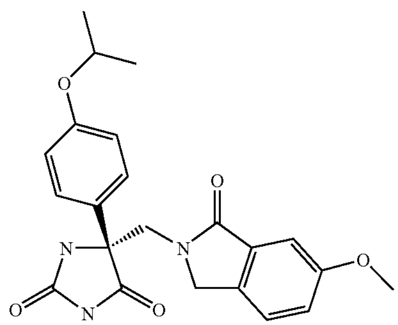 | 409.2 | 410.2 [M + H]⁺ | A |
| 5022 | 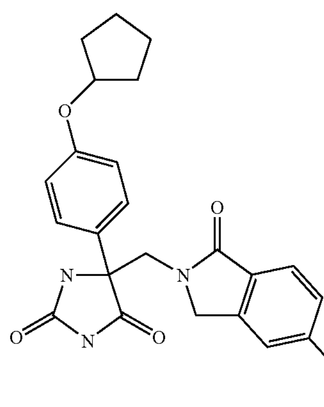 | 435.2 | 436.2 [M + H]⁺ | A |
| 5023 | 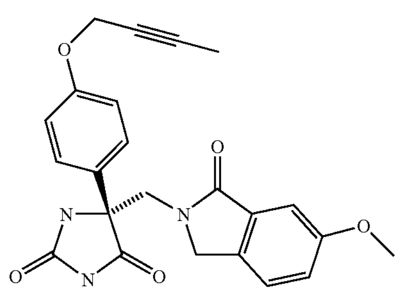 | 419.2 | 420.2 [M + H]⁺ | A |
| 5024 | 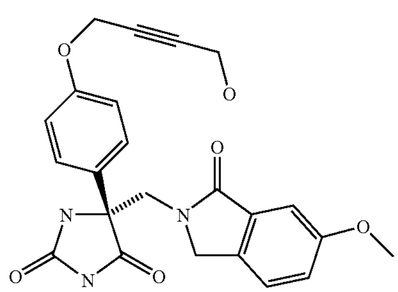 | 435.1 | 436.2 [M + H]⁺ | A |

TABLE 3000-continued

| Compound ID | Structures | Exact Mass | Mass Obsvd | Ki Rating |
|---|---|---|---|---|
| 5025 | 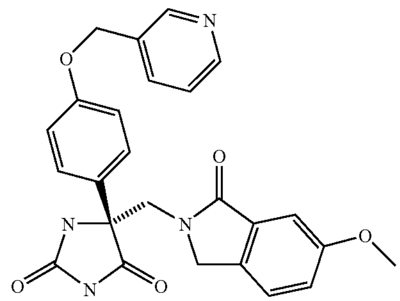 | 458.2 | 459.3 [M + H]+ | A |
| 6000 | 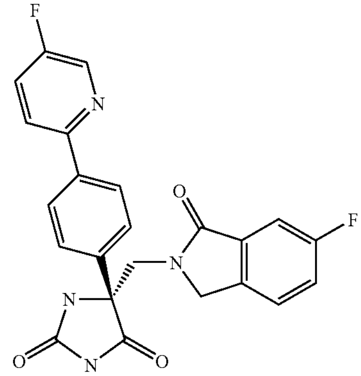 | 434.39 | 435.4 [M + H]+ | A |
| 6001 | 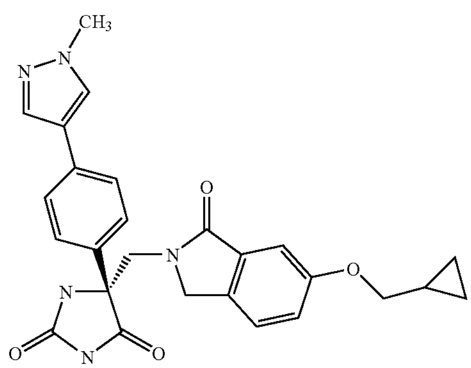 | 471.50 | 472.5 [M + H]+ | A |
| 6002 | 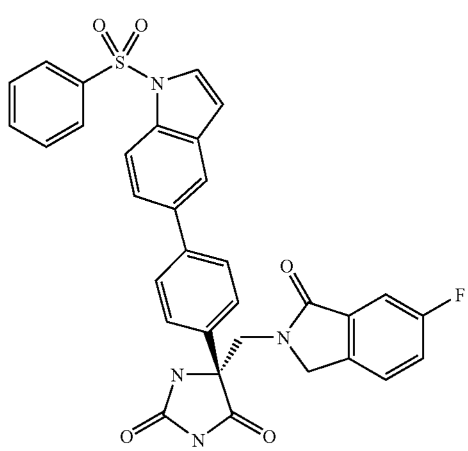 | 594.61 | 595.7 [M + H]+ | B |

TABLE 3000-continued

| Compound ID | Structures | Exact Mass | Mass Obsvd | Ki Rating |
|---|---|---|---|---|
| 6003 | 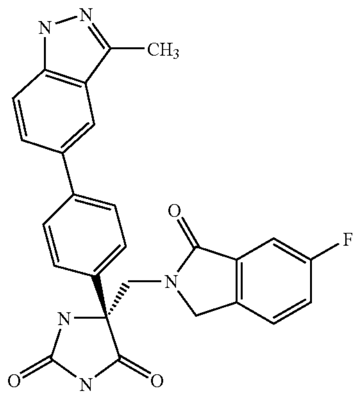 | 469.46 | 470.5 [M + H]+ | A |
| 6004 | 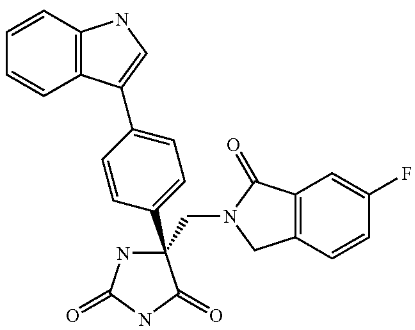 | 454.45 | 455.5 [M + H]+ | A |
| 6005 | 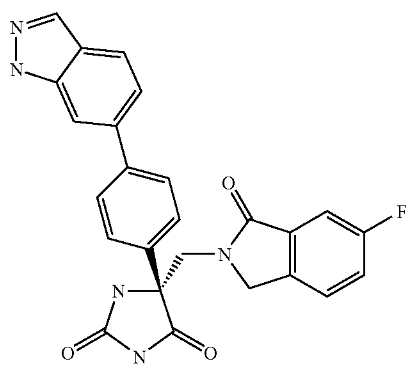 | 455.44 | 456.3 [M + H]+ | A |
| 6006 | 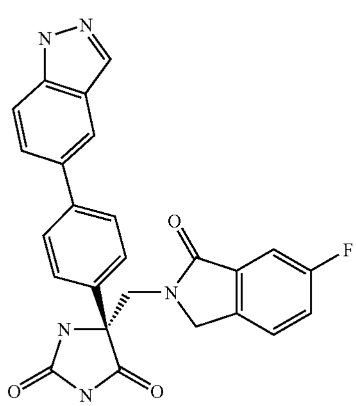 | 455.44 | 456.3 [M + H]+ | A |

TABLE 3000-continued

| Compound ID | Structures | Exact Mass | Mass Obsvd | Ki Rating |
|---|---|---|---|---|
| 6007 | 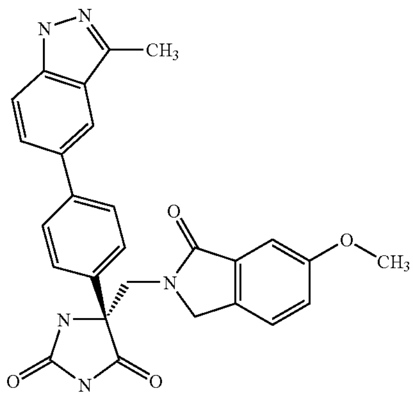 | 481.50 | 482.6 [M + H]+ | A |
| 6008 | 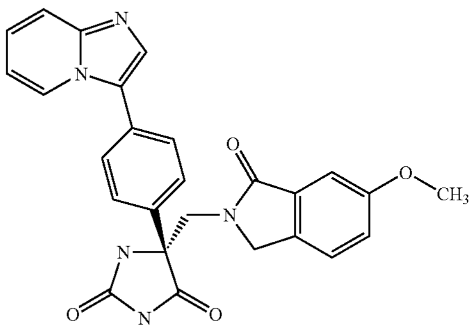 | 467.47 | 468.5 [M + H]+ | A |
| 6009 | 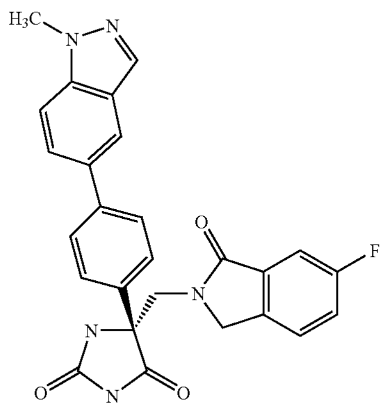 | 469.46 | 470.5 [M + H]+ | A |
| 6010 | 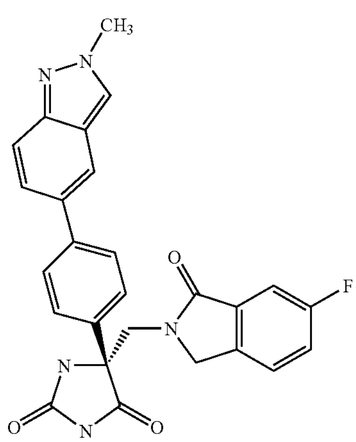 | 469.46 | 470.5 [M + H]+ | A |

TABLE 3000-continued

| Compound ID | Structures | Exact Mass | Mass Obsvd | Ki Rating |
|---|---|---|---|---|
| 6011 | 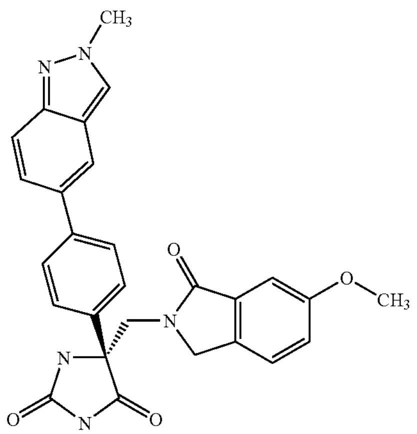 | 481.50 | 482.4 [M + H]+ | A |
| 6012 | 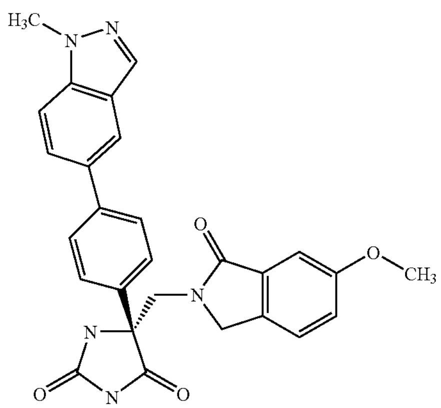 | 481.50 | 482.4 [M + H]+ | A |
| 6013 | 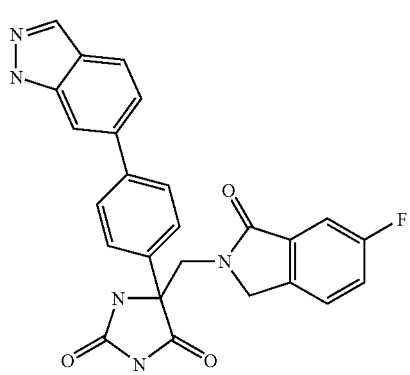 | 455.44 | 456.3 [M + H]+ | A |

TABLE 3000-continued

| Compound ID | Structures | Exact Mass | Mass Obsvd | Ki Rating |
|---|---|---|---|---|
| 6014 | 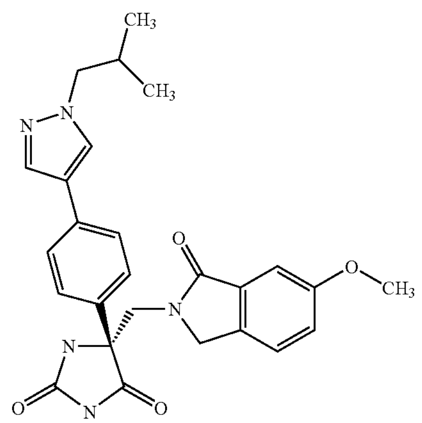 | 473.52 | 474.5 [M + H]⁺ | A |
| 6015 | 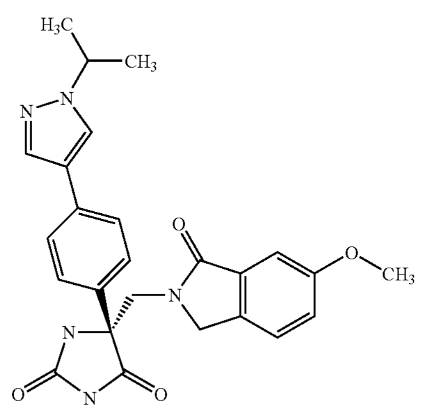 | 459.49 | 460.5 [M + H]⁺ | A |
| 6016 | 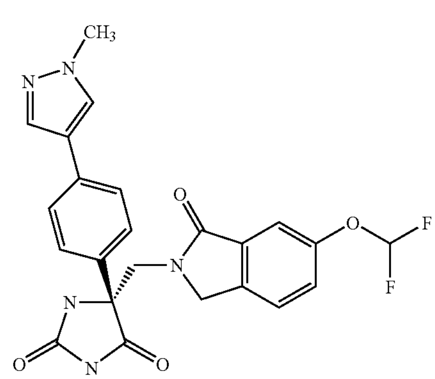 | 503.89 | 504.9 [M + H]⁺ | A |

TABLE 3000-continued
| Compound ID | Structures | Exact Mass | Mass Obsvd | Ki Rating |
|---|---|---|---|---|
| 6017 | 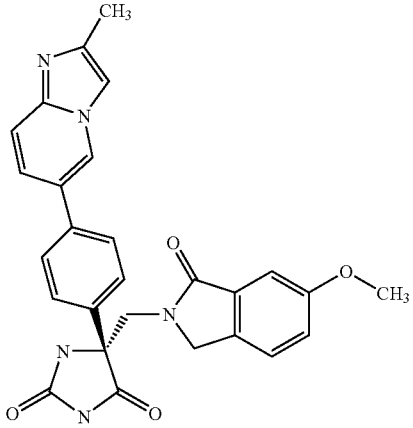 | 481.50 | 482.5 [M + H]$^+$ | A |
| 6018 | 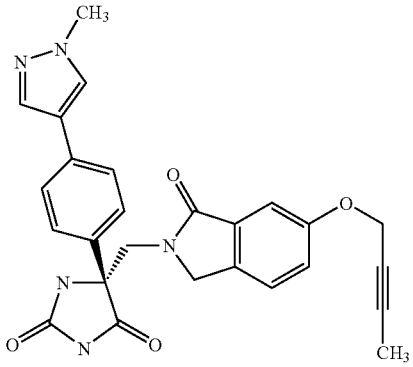 | 469.49 | 470.5 [M + H]$^+$ | A |
| 6019 | 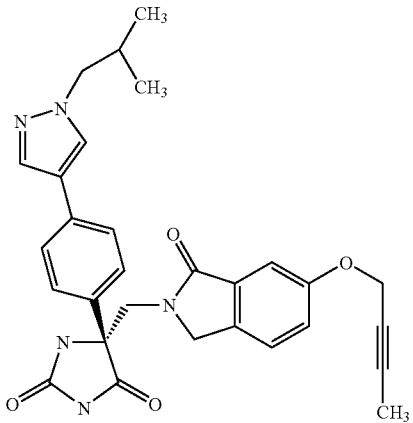 | 511.57 | 512.6 [M + H]$^+$ | A |

TABLE 3000-continued

| Compound ID | Structures | Exact Mass | Mass Obsvd | Ki Rating |
|---|---|---|---|---|
| 6020 | 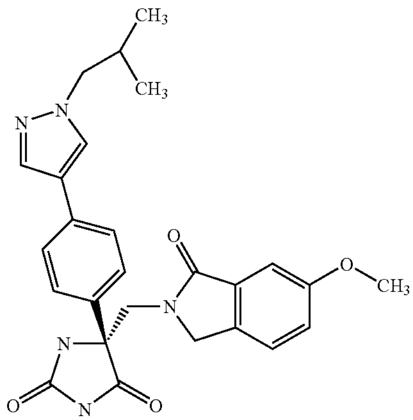 | 473.52 | 474.5 [M + H]+ | A |
| 6021 | 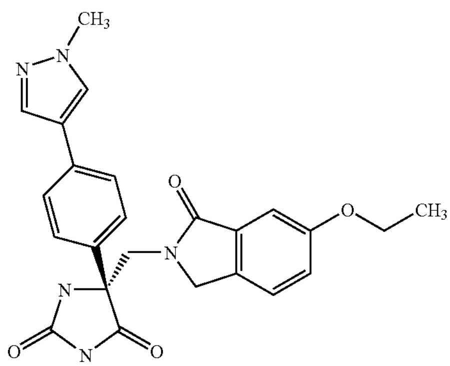 | 445.47 | 446.5 [M + H]+ | A |
| 6022 | 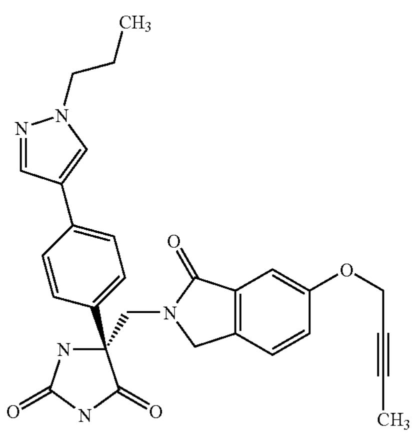 | 497.54 | 498.6 [M + H]+ | A |
| 6023 | 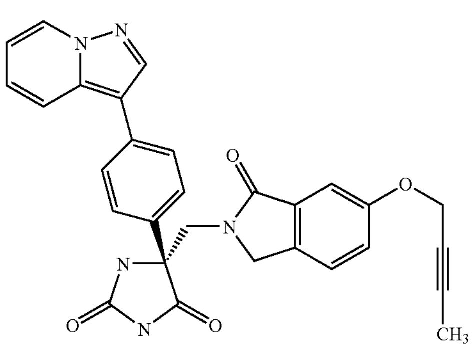 | 505.5 | 506.5 [M + H]+ | A |

TABLE 3000-continued

| Compound ID | Structures | Exact Mass | Mass Obsvd | Ki Rating |
|---|---|---|---|---|
| 6024 | 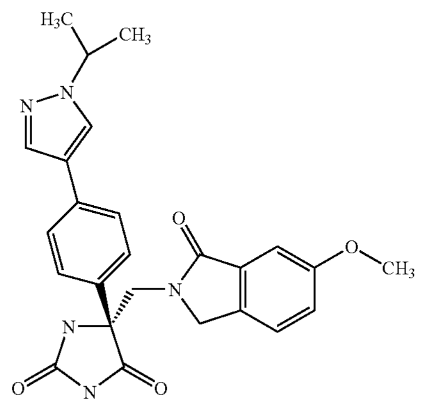 | 459.49 | 460.6 [M + H]+ | A |
| 6025 | 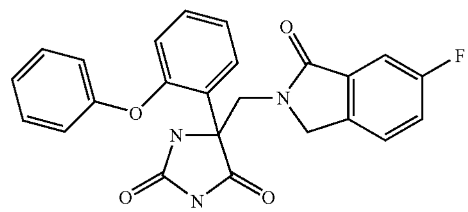 | 431.41 | 432.5 [M + H]+ | B |
| 6026 | 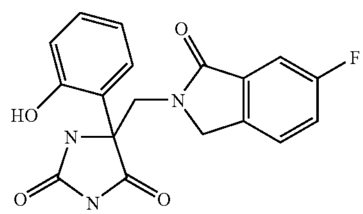 | 355.31 | 356.4 [M + H]+ | A |
| 6027 | 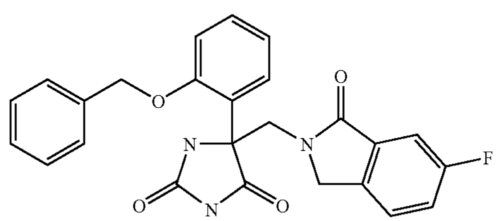 | 445.44 | 446.5 [M + H]+ | B |
| 6028 | 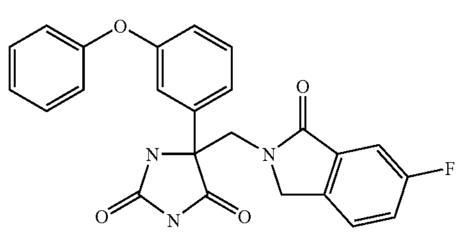 | 431.41 | 432.4 [M + H]+ | B |
| 6029 | 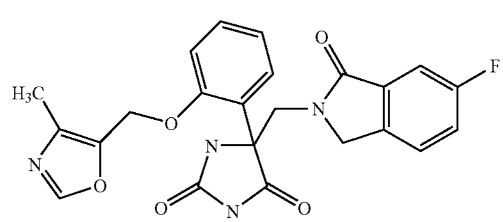 | 450.42 | 451.4 [M + H]+ | B |

TABLE 3000-continued

| Compound ID | Structures | Exact Mass | Mass Obsvd | Ki Rating |
|---|---|---|---|---|
| 7000 | 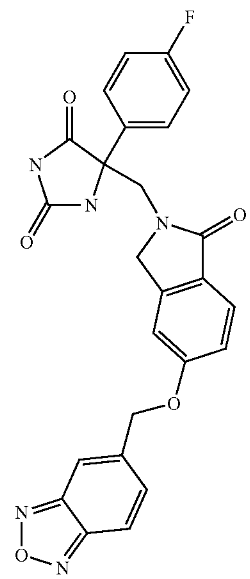 | 487.4393 | 488.3 [M + H]⁺ | C |
| 7001 | 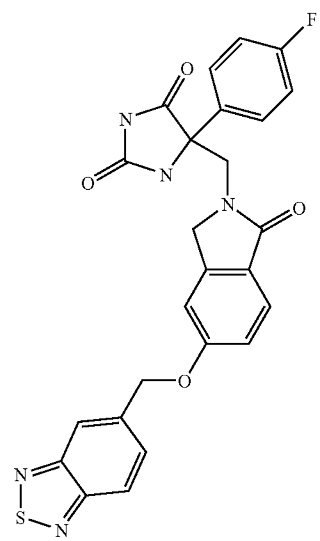 | 503.5049 | 504.3 [M + H]⁺ | C |
| 7002 | 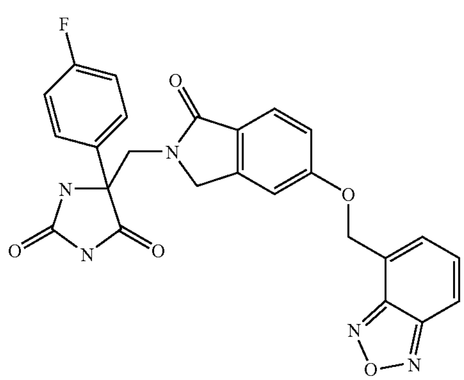 | 487.4393 | 488.3 [M + H]⁺ | B |

TABLE 3000-continued

| Compound ID | Structures | Exact Mass | Mass Obsvd | Ki Rating |
|---|---|---|---|---|
| 7003 | 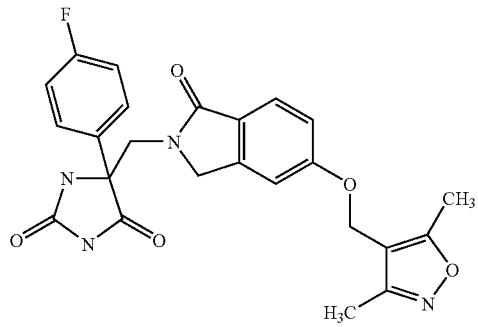 | 464.4457 | 465.3 [M + H]+ | C |
| 7004 | 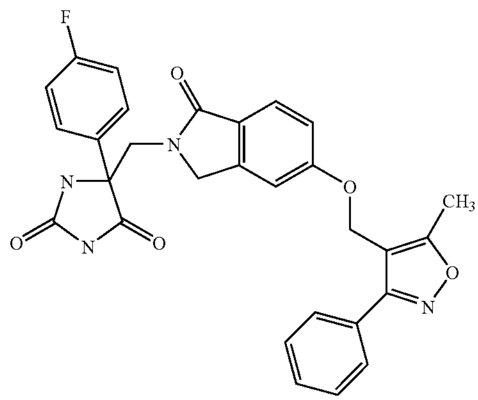 | 526.5151 | 527.3 [M + H]+ | D |
| 7005 | 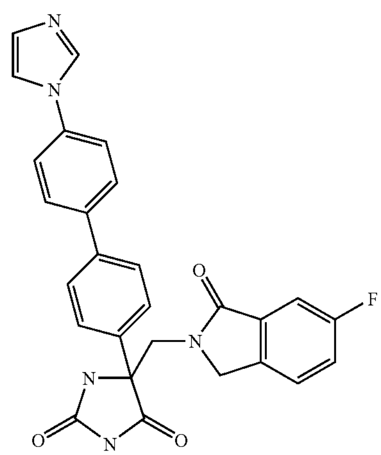 | 481.4778 | 482.3 [M + H]+ | B |
| 7006 | 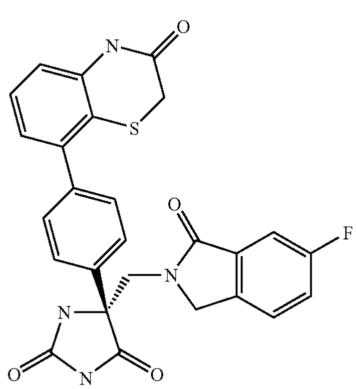 | 502.5169 | 503.3 [M + H]+ | A |

TABLE 3000-continued

| Compound ID | Structures | Exact Mass | Mass Obsvd | Ki Rating |
|---|---|---|---|---|
| 7007 | 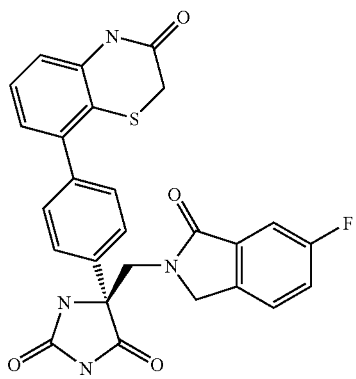 | 502.5169 | 503.3 [M + H]+ | C |
| 7008 | 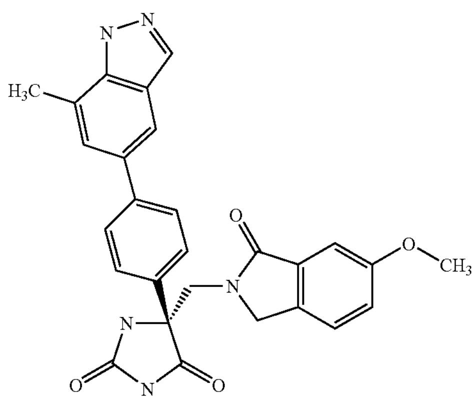 | 481.5026 | 482.3 [M + H]+ | A |
| 7009 | 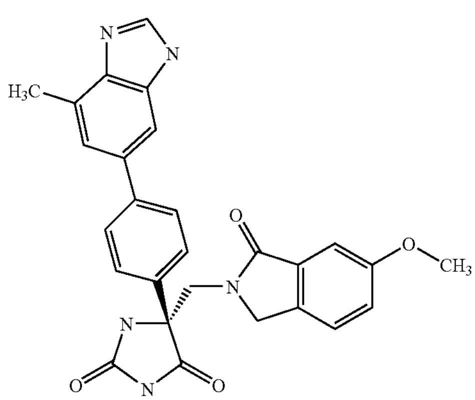 | 481.5026 | 482.3 [M + H]+ | A |

TABLE 3000-continued

| Compound ID | Structures | Exact Mass | Mass Obsvd | Ki Rating |
|---|---|---|---|---|
| 7010 | 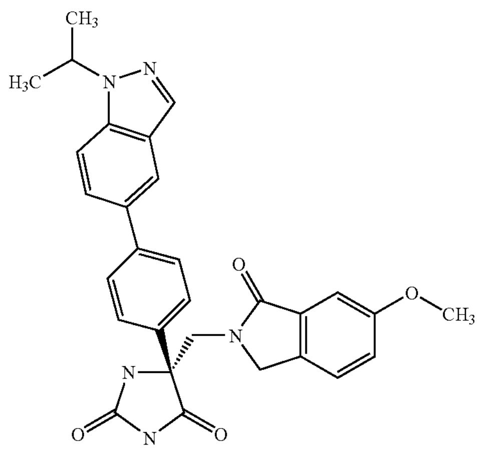 | 509.5558 | 510.3 [M + H]⁺ | A |
| 7011 | 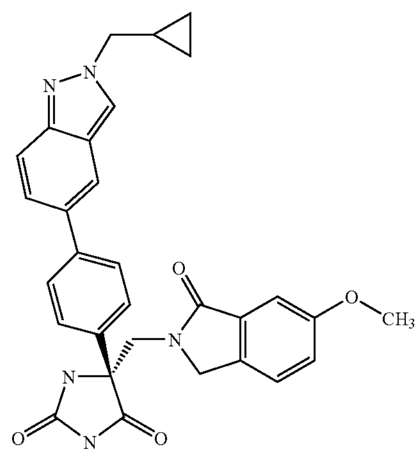 | 521.5665 | 522.3 [M + H]⁺ | A |
| 7012 | 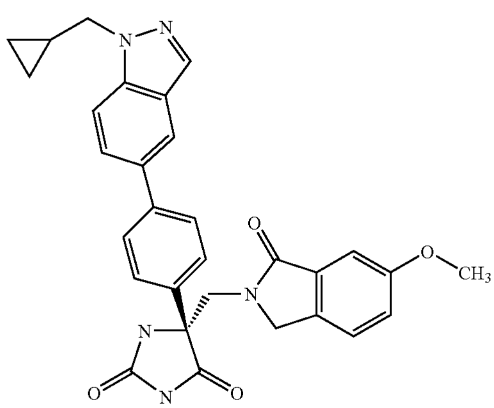 | 521.5665 | 522.3 [M + H]⁺ | A |

TABLE 3000-continued
| Compound ID | Structures | Exact Mass | Mass Obsvd | Ki Rating |
|---|---|---|---|---|
| 7013 | 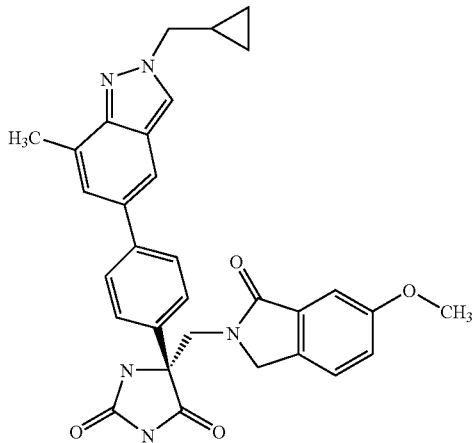 | 535.5931 | 536.3 [M + H]+ | A |
| 7014 | 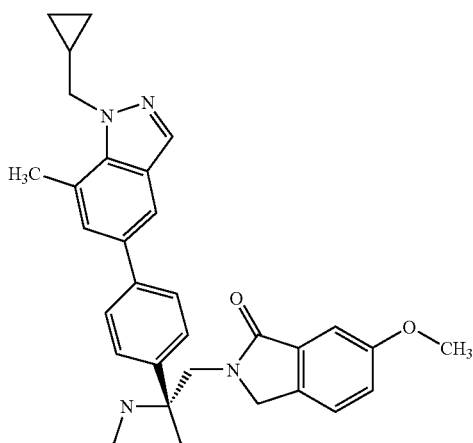 | 535.5931 | 536.3 [M + H]+ | B |
| 7015 | 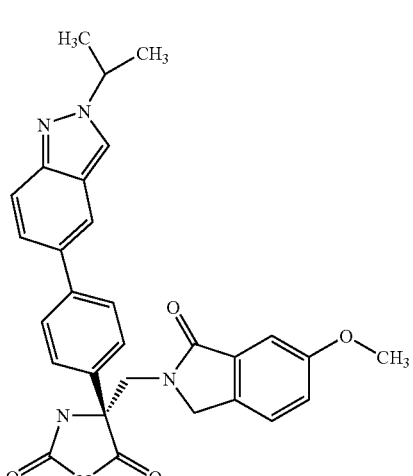 | 509.5558 | 510.3 [M + H]+ | A |

TABLE 3000-continued

| Compound ID | Structures | Exact Mass | Mass Obsvd | Ki Rating |
|---|---|---|---|---|
| 7016 | 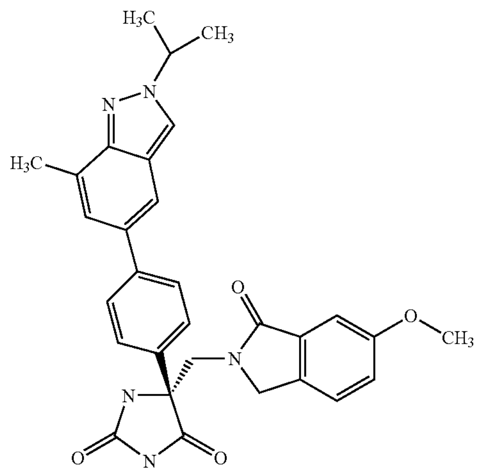 | 523.5824 | 524.3 [M + H]⁺ | A |
| 7017 | 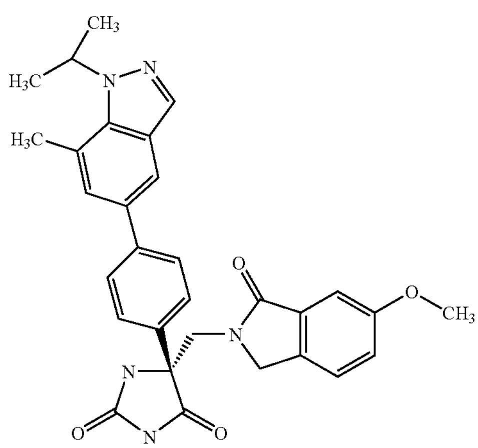 | 523.5824 | 524.3 [M + H]⁺ | A |
| 7018 | 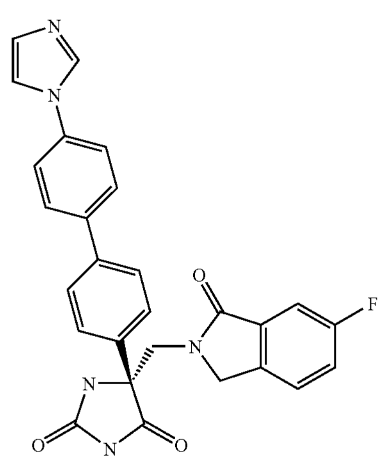 | 481.4778 | 482.3 [M + H]⁺ | A |

TABLE 3000-continued

| Compound ID | Structures | Exact Mass | Mass Obsvd | Ki Rating |
|---|---|---|---|---|
| 7019 | 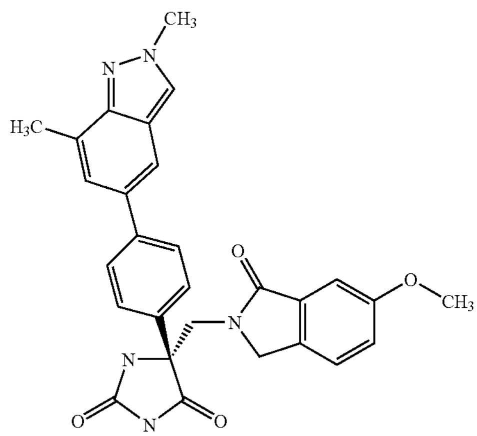 | 495.5292 | 496.3 [M + H]⁺ | A |
| 7020 | 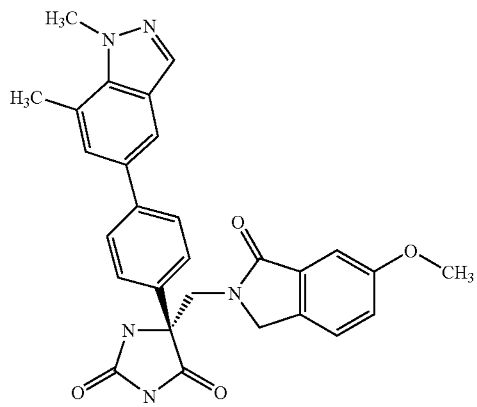 | 495.5292 | 496.3 [M + H]⁺ | A |
| 7021 | 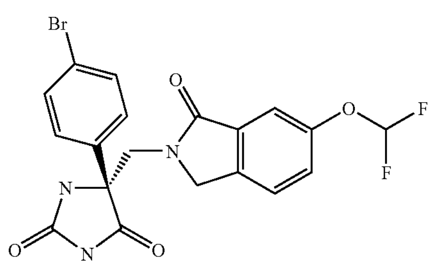 | 466.233 | 468.3 [M + H]⁺ | A |
| 7022 | 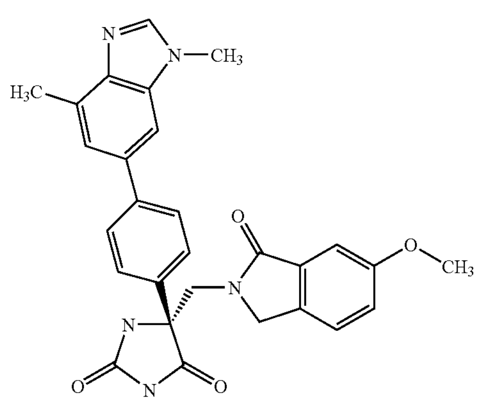 | 495.5292 | 496.3 [M + H]⁺ | A |

TABLE 3000-continued

| Compound ID | Structures | Exact Mass | Mass Obsvd | Ki Rating |
|---|---|---|---|---|
| 7023 | 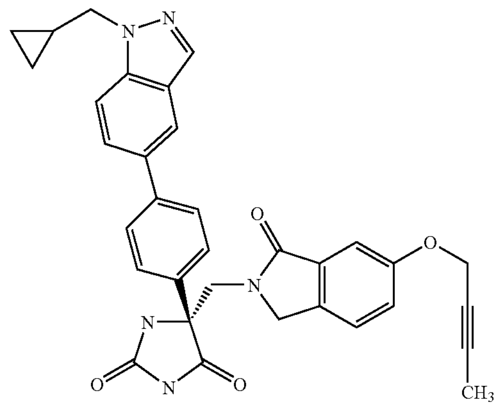 | 559.6145 | 560.3 [M + H]+ | B |
| 7024 | 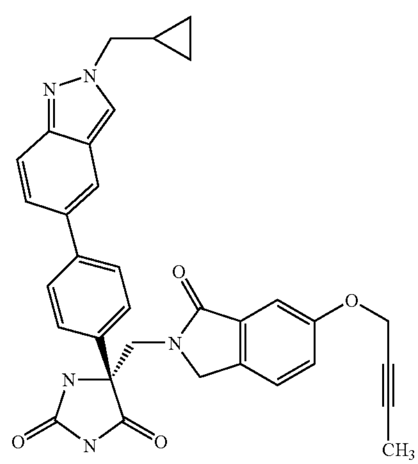 | 559.6145 | 560.3 [M + H]+ | A |
| 7025 | 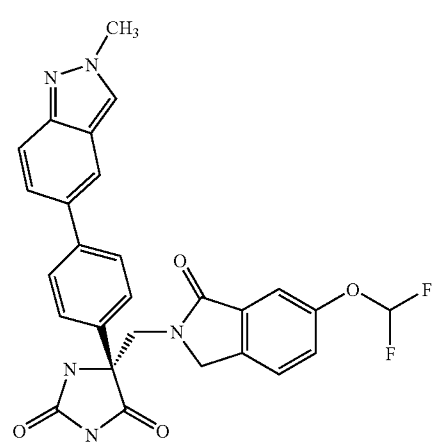 | 517.4835 | 518.3 [M + H]+ | A |

TABLE 3000-continued

| Compound ID | Structures | Exact Mass | Mass Obsvd | Ki Rating |
|---|---|---|---|---|
| 7026 | 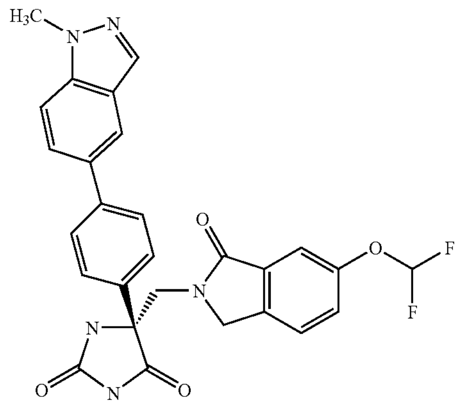 | 517.4835 | 518.3 [M + H]+ | A |
| 8001 | 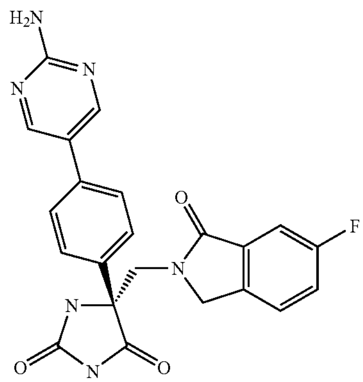 | 432.13 | 433.2 [M + H]+ | A |
| 8002 | 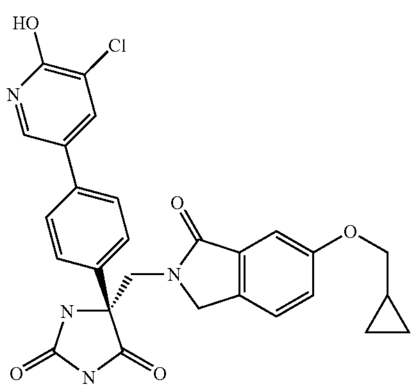 | 518.14 | 519.3 [M + H]+ | A |
| 8003 | 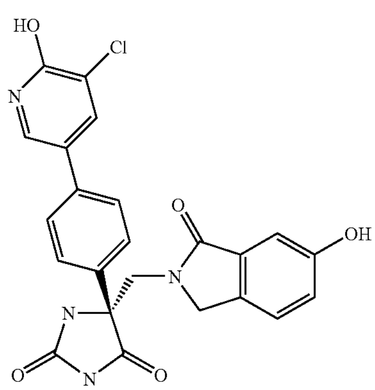 | 464.09 | 465.3 [M + H]+ | A |

TABLE 3000-continued
| Compound ID | Structures | Exact Mass | Mass Obsvd | Ki Rating |
|---|---|---|---|---|
| 8004 | 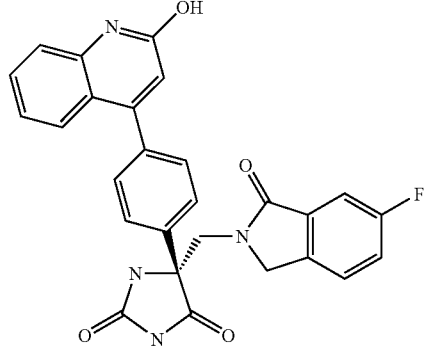 | 482.14 | 483.3 [M + H]+ | A |
| 8005 | 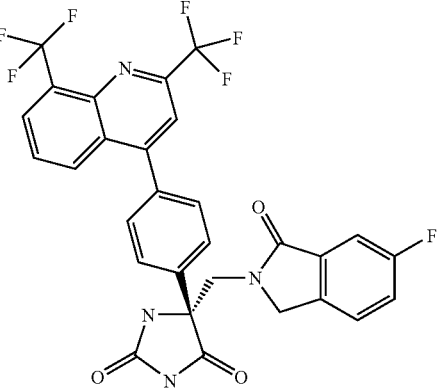 | 602.12 | 603.3 [M + H]+ | C |
| 8006 | 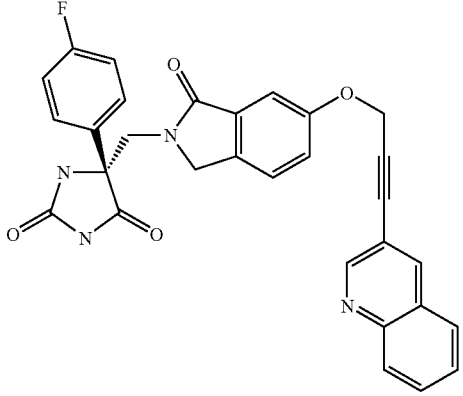 | 520.15 | 521.3 [M + H]+ | B |
| 8007 | 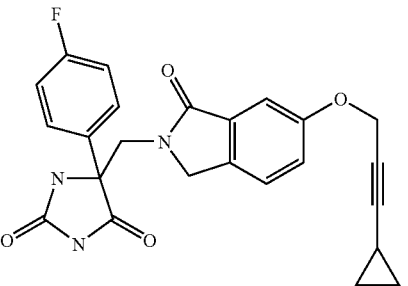 | 433.14 | 434.2 [M + H]+ | A |

TABLE 3000-continued

| Compound ID | Structures | Exact Mass | Mass Obsvd | Ki Rating |
|---|---|---|---|---|
| 8008 | 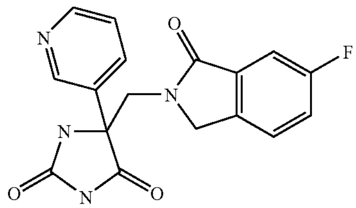 | 340.1 | 341.2 [M + H]⁺ | B |
| 8009 | 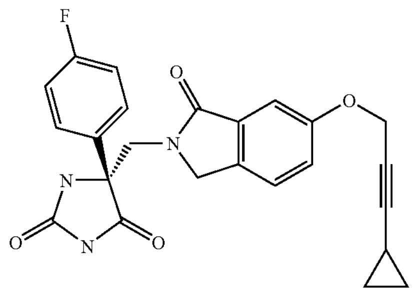 | 433.14 | 434.2 [M + H]⁺ | A |
| 8010 | 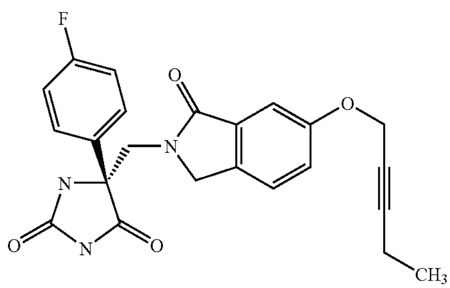 | 421.14 | 422.2 [M + H]⁺ | A |
| 8011 | 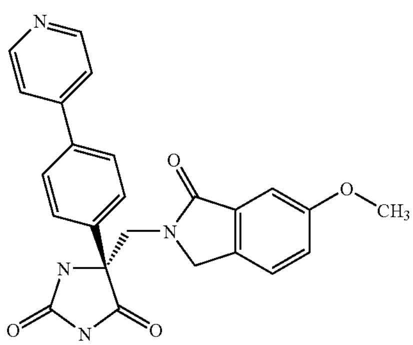 | 428.15 | 429.2 [M + H]⁺ | A |
| 8012 | 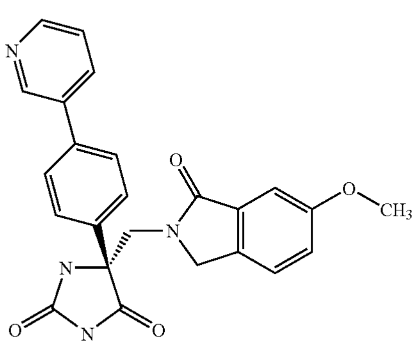 | 428.15 | 429.2 [M + H]⁺ | A |

TABLE 3000-continued

| Compound ID | Structures | Exact Mass | Mass Obsvd | Ki Rating |
|---|---|---|---|---|
| 8013 | 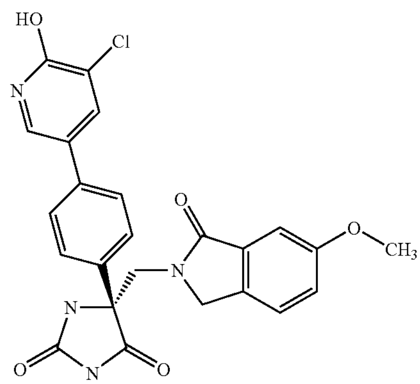 | 478.1 | 479.3 [M + H]+ | A |
| 8014 | 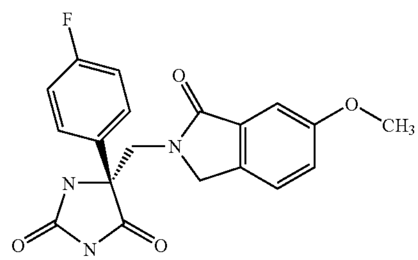 | 369.11 | 370.2 [M + H]+ | A |
| 8015 | 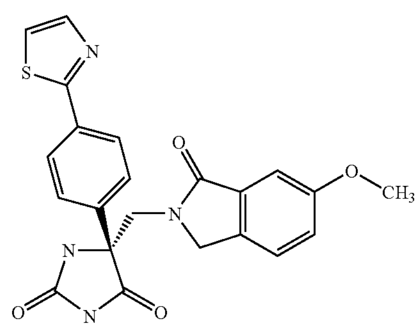 | 434.1 | 435.2 [M + H]+ | A |
| 8016 | 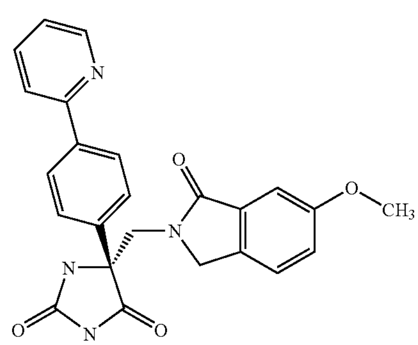 | 428.15 | 429.2 [M + H]+ | A |

TABLE 3000-continued
| Compound ID | Structures | Exact Mass | Mass Obsvd | Ki Rating |
|---|---|---|---|---|
| 8017 | 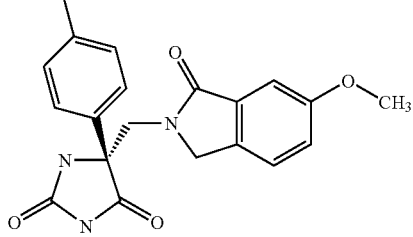 | 444.14 | 445.2 [M + H]+ | A |
| 8018 | 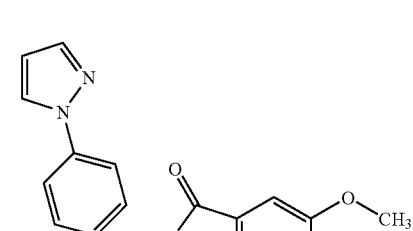 | 417.14 | 418.2 [M + H]+ | A |
| 8019 | 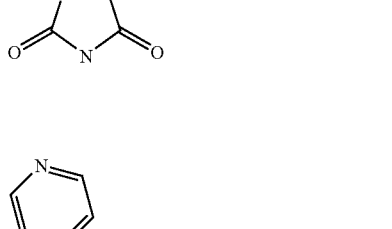 | 428.15 | 429.2 [M + H]+ | A |
| 8020 | 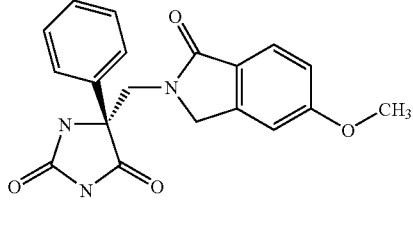 | 414.13 | 415.2 [M + H]+ | A |

TABLE 3000-continued

| Compound ID | Structures | Exact Mass | Mass Obsvd | Ki Rating |
|---|---|---|---|---|
| 8021 | 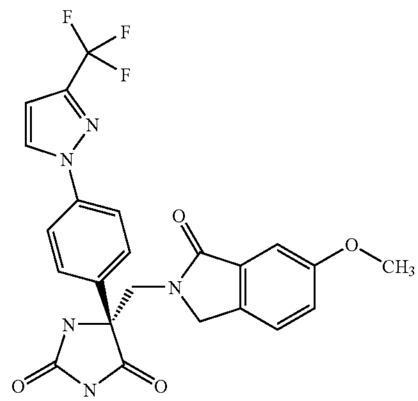 | 485.13 | 486.3 [M + H]+ | A |
| 8022 | 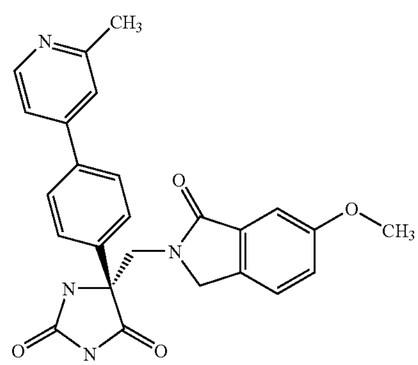 | 442.16 | 443.2 [M + H]+ | A |
| 8023 | 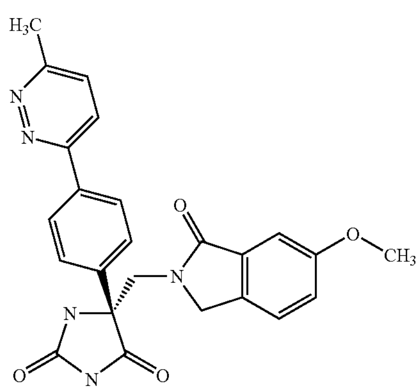 | 443.16 | 444.2 [M + H]+ | |
| 8024 | 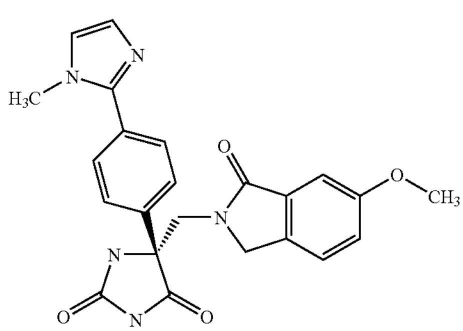 | 431.16 | 432.2 [M + H]+ | |

TABLE 3000-continued

| Compound ID | Structures | Exact Mass | Mass Obsvd | Ki Rating |
|---|---|---|---|---|
| 8025 | 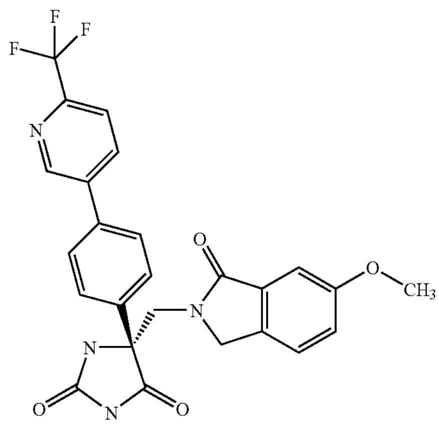 | 496.14 | 497.3 [M + H]+ | |
| 8027 | 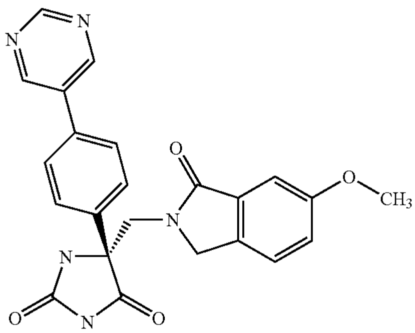 | 429.14 | 430.2 [M + H]+ | |
| 2021F | 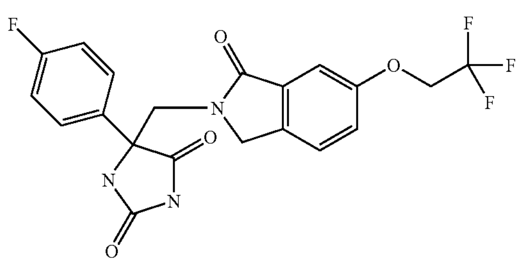 | 437.1 | 438.1 [M + H]+ | C |
| 2023C | 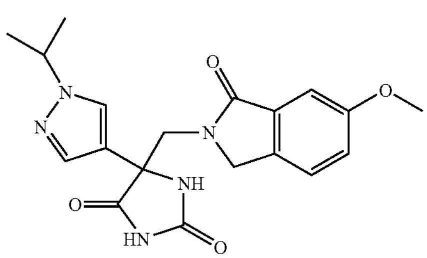 | 383.16 | 384.1 [M + H]+ | A |

TABLE 3000-continued

| Compound ID | Structures | Exact Mass | Mass Obsvd | Ki Rating |
|---|---|---|---|---|
| 2024D | 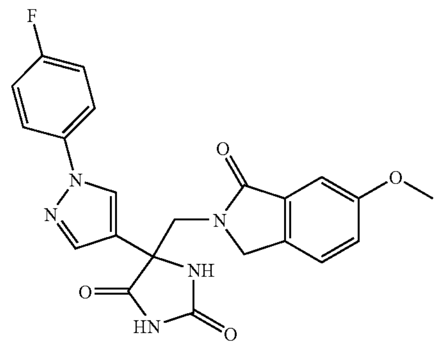 | 435.13 | 436.1 [M + H]+ | A |
| 2022G | 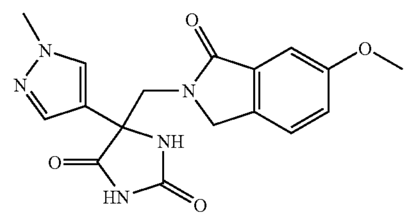 | 355.13 | 356.1 [M + H]+ | A |
| 2025C | 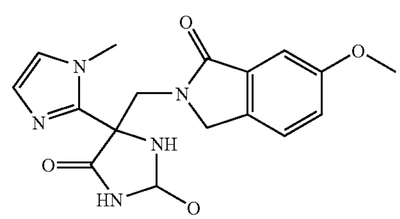 | 355.13 | 356.1 [M + H]+ | A |
| 2028 | 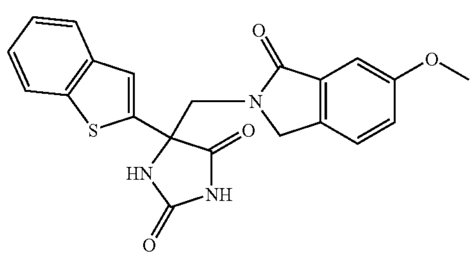 | 407.1 | 408.1 [M + H]+ | A |
| 2026H | 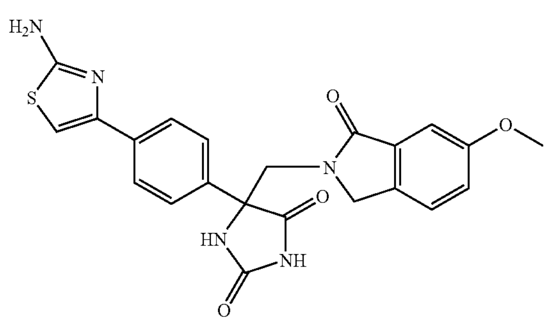 | 449.1 | 450.1 [M + H]+ | A |

TABLE 3000-continued

| Compound ID | Structures | Exact Mass | Mass Obsvd | Ki Rating |
|---|---|---|---|---|
| 2030A | 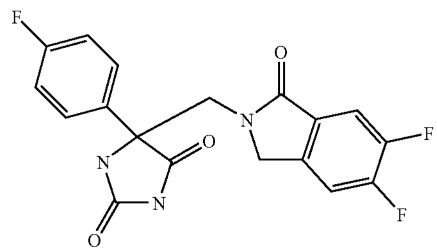 | 375.08 | 376.1 [M + H]+ | C |
| 2030C | 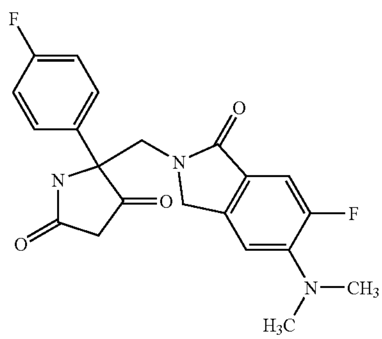 | 400.13 | 401.2 [M + H]+ | C |
| 2030B | 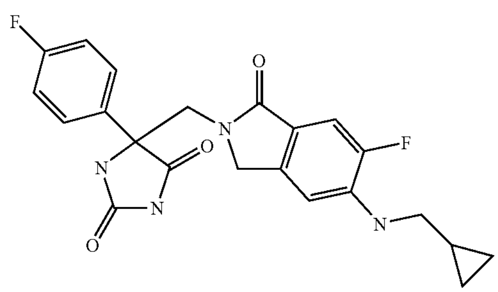 | 426.15 | 427.1 [M + H]+ | B |
| 2031C | 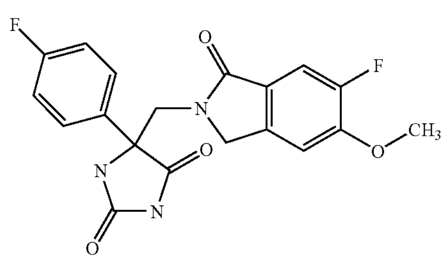 | 387.10 | 388.1 [M + H]+ | A |
| 2031D | 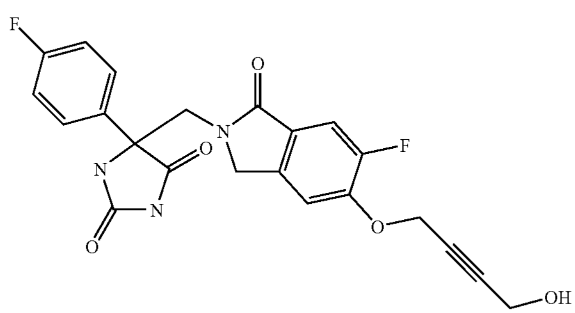 | 441.11 | 442.0 [M + H]+ | A |

TABLE 3000-continued

| Compound ID | Structures | Exact Mass | Mass Obsvd | Ki Rating |
|---|---|---|---|---|
| 2030D | 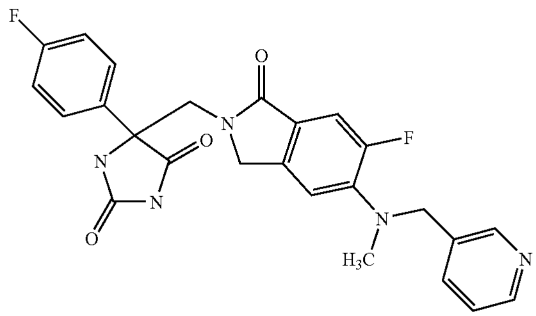 | 477.16 | 478.1 [M + H]⁺ | B |
| 2031A | 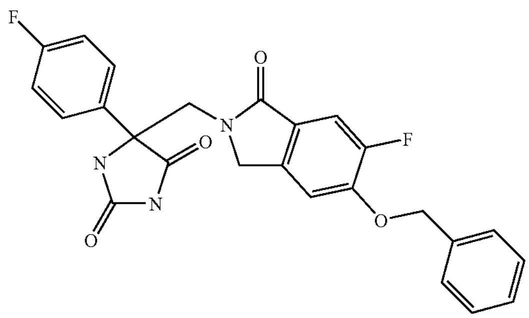 | 463.13 | 464.0 [M + H]⁺ | B |
| 2031B | 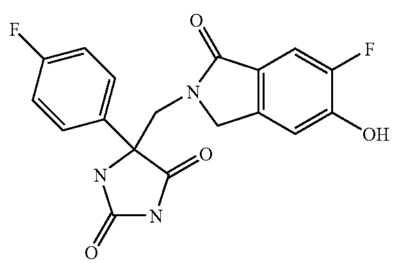 | 373.09 | 374.0 [M + H]⁺ | B |
| 2032B | 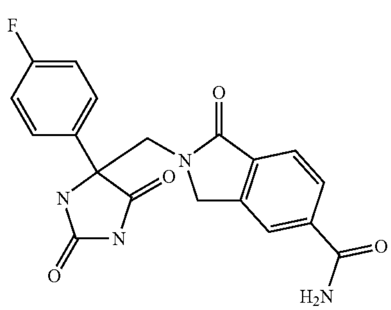 | 382.11 | 383.1 [M + H]⁺ | B |

TABLE 3000-continued

| Compound ID | Structures | Exact Mass | Mass Obsvd | Ki Rating |
|---|---|---|---|---|
| 2031E | 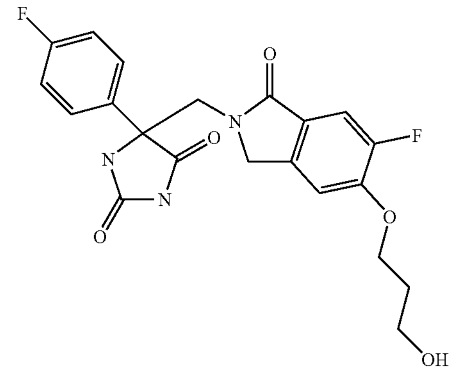 | 431.13 | 432.1 [M + H]+ | B |
| 2031F | 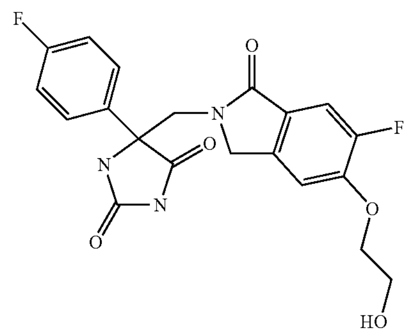 | 417.11 | 418.1 [M + H]+ | B |

Procedures

Example 4000

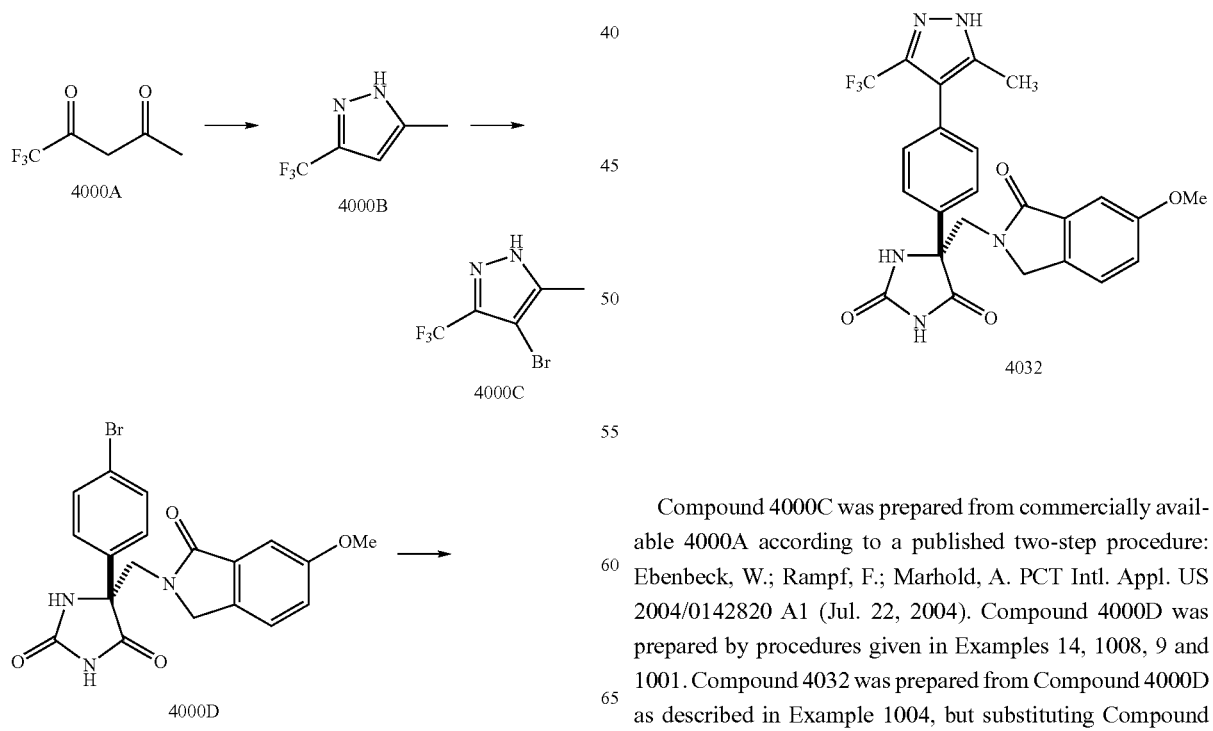

Compound 4000C was prepared from commercially available 4000A according to a published two-step procedure: Ebenbeck, W.; Rampf, F.; Marhold, A. PCT Intl. Appl. US 2004/0142820 A1 (Jul. 22, 2004). Compound 4000D was prepared by procedures given in Examples 14, 1008, 9 and 1001. Compound 4032 was prepared from Compound 4000D as described in Example 1004, but substituting Compound 4000C for 3-bromoimidazo[1,2-a]pyridine in Step 2.

Example 4100

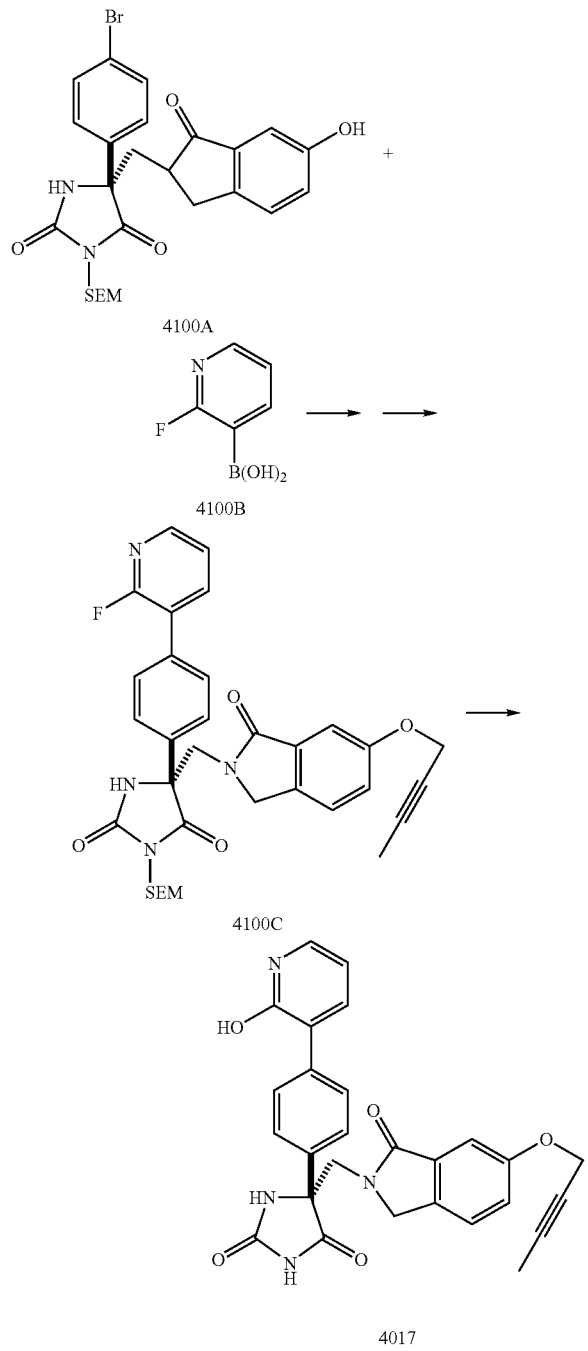

Compound 4100C was prepared from compound 4100A and commercially available Compound 4100B by procedures given in Example 14 and 1009. Subsequently, compound 4100C (123 mg, 0.2 mmol) was dissolved in methanol (1 mL) in a pressure tube and treated with HCl (0.4 mL, 4 M in dioxane). The tube was sealed and heated with stirring at 90° C. for 18 h. The reaction mixture was allowed to cool to rt and the solvent was then removed under reduced pressure. The residue was re-dissolved in methanol (1 mL) and DIPEA (0.27 mL, 0.20 mg, 1.6 mmol) was added. The reaction mixture was stirred overnight at rt. The volatile components were removed by evaporation and the residue was purified by PTLC (8% MeOH—CH$_2$Cl$_2$) to give Compound 4017 (59 mg, 61% yield) as a beige solid.

Example 1022

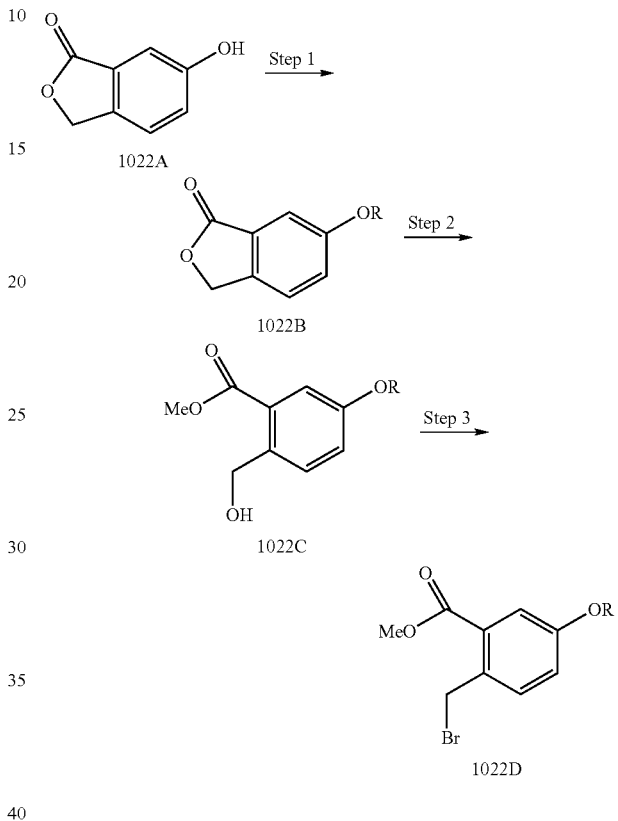

Step 1

To a solution of 1022A (500 mg, 3.33 mmol) in acetone (40 mL) were added potassium carbonate (920 mg, 6.7 mmol) and 1-bromo-2-butyne (0.32 mL, 3.7 mmol, in case of R=CH$_2$CCCH$_3$). The reaction mixture was heated to reflux for 2 h. After cooling to RT, the mixture was added to ice water/CH$_2$Cl$_2$. The organic layers were extracted with CH$_2$Cl$_2$ and the combined organic solution was washed with saturated aqueous NaCl solution, dried (Na$_2$SO$_4$), and concentrated in vacuo to afford 1022B (674 mg, quantitative yield).

Steps 2 and 3

A suspension of 1022B (100 mg, 0.5 mmol) in 1N NaOH solution (0.5 mL) was heated to 100° C. The reaction mixture was stirred for 1 h at the temperature and concentrated in vacuo. The residue was dried by azeotropic distillation with toluene and the resulting solid was dissolved in DMF (0.6 mL) followed by addition of xs. MeI (0.1 mL, 1.5 mmol). The mixture was stirred at RT for 2 h and diluted in EtOAc. The organic solution was washed with water, saturated aqueous NaCl solution, dried (Na$_2$SO$_4$), and concentrated in vacuo to give crude 1022C (117 mg). The crude 1022C (67 mg, 0.28 mmol) was dissolved in CH$_2$Cl$_2$ (2 mL) and the solution was treated with PPh$_3$ (150 mg, 0.57 mmol) and CBr$_4$ (189 mg, 0.57 mmol) at RT. The mixture was stirred at RT for 1 h and concentrated in vacuo. The residue was purified by preparative TLC (CH$_2$Cl$_2$) to afford 1022D (50 mg, 60% yield).

Example 1023

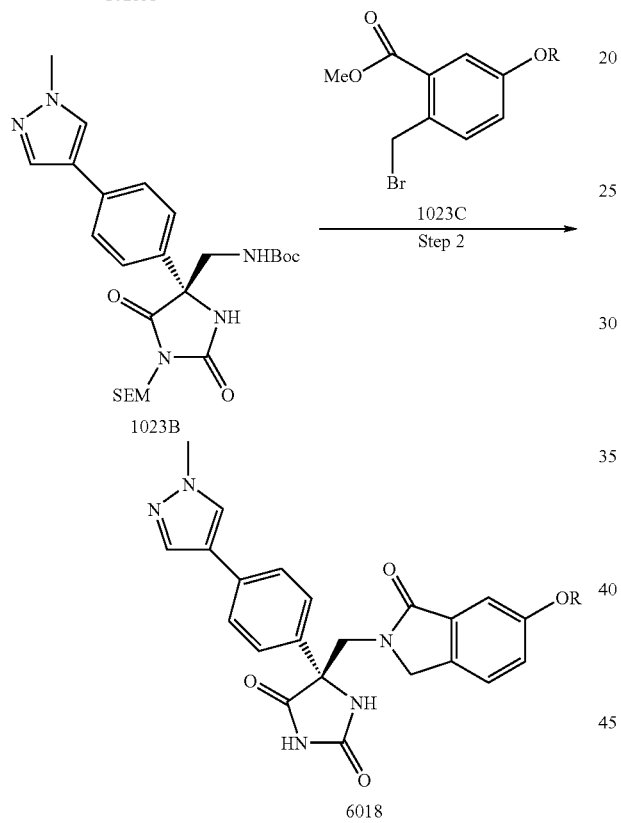

Step 1

A mixture of 1023A (370 mg, 0.72 mmol), 1-methyl-4-(4,4,5,5-tetramethyl-1,3,2-dioxaborolan-2-yl)-1H-pyrazole (225 mg, 1.08 mmol), potassium carbonate (1M aqueous solution, 2.9 mL, 2.9 mmol), and [PdCl$_2$(dppf)]CH$_2$Cl$_2$ (59 mg, 0.072 mmol) in acetonitrile (12 mL) was vacuumed and refilled with argon three times. The reaction mixture was stirred at 80° C. oil bath for 17 hours. After cooling down, the mixture was diluted in EtOAc (50 mL) and filtered through a celite pad. The filtrate was concentrated in vacuo and the residual material was purified by silica gel column chromatography (1% to 1.5% MeOH in CH$_2$Cl$_2$) to afford compound 1023B (369 mg, 99% yield).

Step 2

A solution of 1023B (109 mg, 0.21 mmol) in EtOAc/MeOH (4/1, 5 mL) was treated with 4N HCl in dioxane (2 mL). The reaction mixture was stirred at RT for 15 h and concentrated in vacuo. The residue was dissolved in DMF (1 mL) and treated with 1022D (75 mg, 0.25 mmol, R=CH$_2$CCCH$_3$) and diisopropylethyl amine (0.22 mL, 1.26 mmol). The mixture was stirred at 60° C. for 9.5 h and concentrated in vacuo. The residue was dissolved in MeOH (5 mL) and treated with 4N HCl in dioxane (1 mL) at 70° C. for 17 h in a pressure vessel. After cooling to RT, the mixture was concentrated and the residue was treated with ammonia in MeOH for 0.5 h. The precipitate was filtered off and the filtrate was concentrated. The residue was dissolved in DMF (3-4 mL) and purified by reverse phase column chromatography (0.01% HCO$_2$H in water-0.01% HCO$_2$H in acetonitrile) to afford 6018 (48 mg, 49% yield).

Example 1024

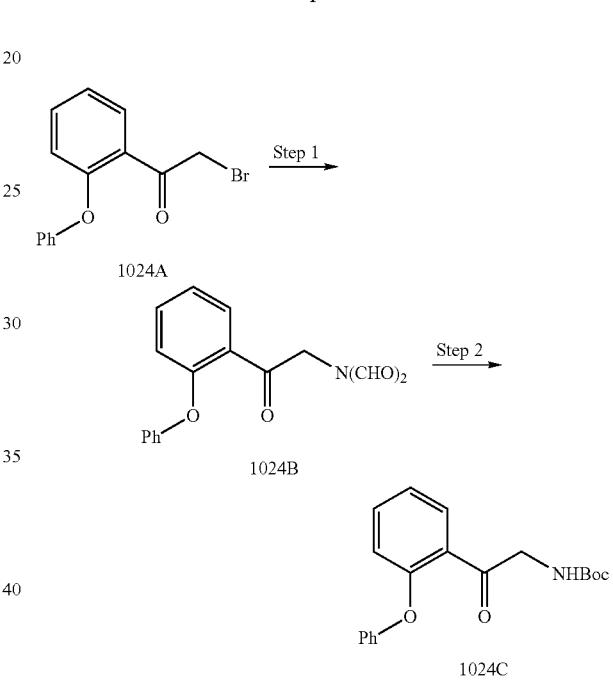

Step 1

A mixture of 1024A (811 mg, 2.8 mmol) and sodium diformyl amide (291 mg, 3.0 mmol) in acetonitrile (15 mL) was stirred at RT for 19 h. The resulting suspension was filtered through celite and the filtrate was concentrated in vacuo. The residue was purified by SiO$_2$ column chromatography (CH$_2$Cl$_2$) to give 1024B (611 mg, 77% yield).

Step 2

A solution of 1024B (611 mg, 2.16 mmol) in EtOH (40 mL) was treated with 4N HCl in dioxane (8 mL) at RT. The resulting solution was stirred at RT for 16 h and concentrated in vacuo. The residue was dissolved in dioxane/water (5/1, 24 mL) and the solution was stirred at RT for 2 h. The mixture was added to water and the organic layers were extracted with CH$_2$Cl$_2$ and the combined organic solution was washed with saturated aqueous NaCl solution, dried (Na$_2$SO$_4$), and concentrated in vacuo. The residue was purified by SiO$_2$ column chromatography (CH$_2$Cl$_2$/hexane=1/1 to CH$_2$Cl$_2$ only) to give 1024C (679 mg, 96% yield).

Example 1025

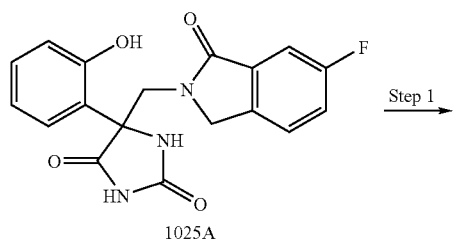

1025A

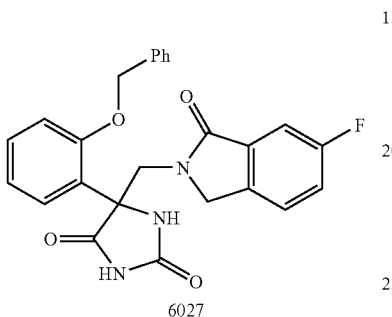

6027

Step 1

A mixture of 1025A (52 mg, 0.11 mmol), benzyl bromide (13 μL, 0.11 mmol), and cesium carbonate (108 mg, 0.33 mmol) in DMF (0.5 mL) was stirred at RT for 2 h. The mixture was diluted in EtOAc and the organic solution was washed with water, saturated aqueous NaCl solution, dried (Na$_2$SO$_4$), and concentrated in vacuo. The residue was purified by preparative TLC (5% MeOH in CH$_2$Cl$_2$) to give 6027 (34 mg, 54% yield).

Example 1026

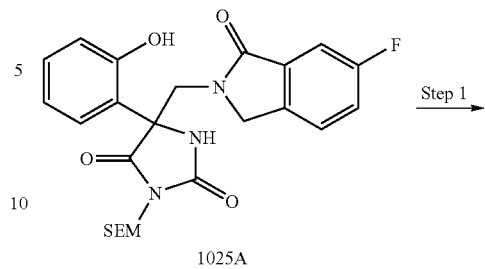

1025A

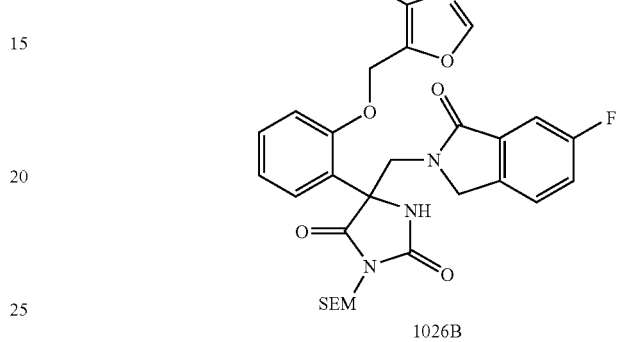

1026B

Step 1

To a solution of 1026A (41 mg, 0.084 mmol), 5-hydroxymethyl-4-methyl-1,3-oxazole (19 mg, 0.17 mmol), and PPh$_3$ (66 mg, 0.25 mmol) in THF (1 mL) was added diisopropyl azodicarboxylate (50 μL, 0.25 mmol) dropwisely at 0° C. The mixture was stirred at 0° C. for 10 min and was allowed to warm to RT. After stirring for 2 h at RT, the mixture was concentrated in vacuo and the residue was purified by preparative TLC (CH$_2$Cl$_2$) to afford 1026B (38 mg, 77% yield).

Example 5021

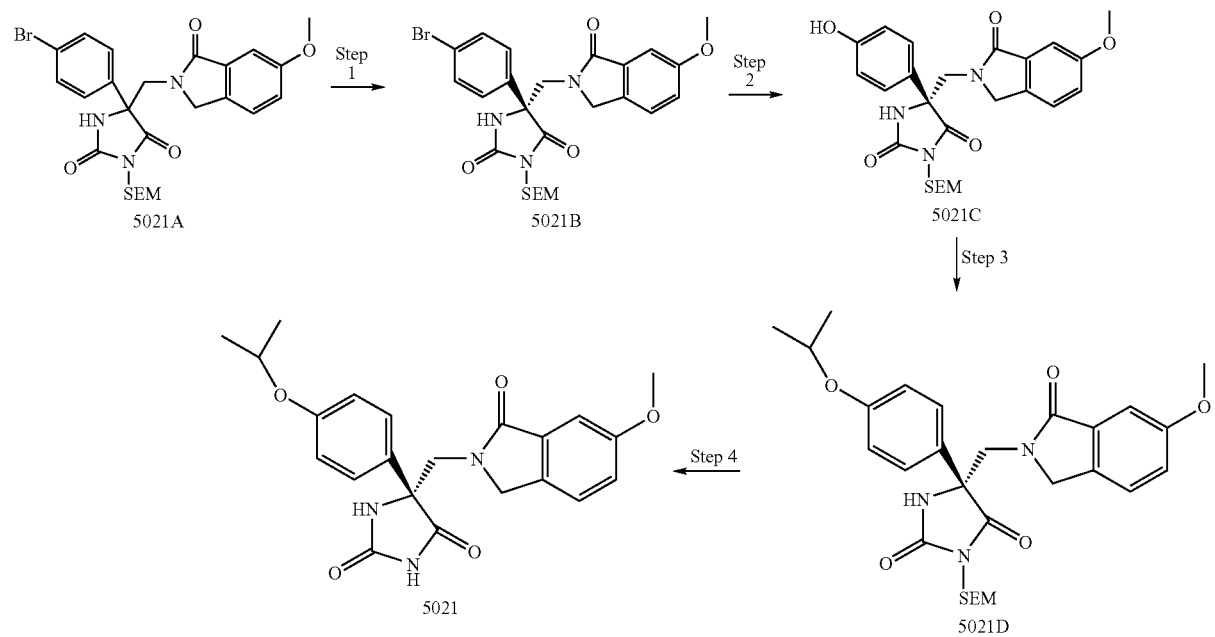

Compound 5021A was prepared using chemistry described in Examples 14, 1001, and 1008.

Step 1

Compound 5021A was resolved by Chiralcel OD column (Mobile phase: Hexane:2-propanol 4:1). The first peak was collected and concentrated to give compound 5021B.

Step 2

Compound 5021B (1.82 g, 3.25 mmol), bis(pinacolato)diboron (2.89 g, 11.4 mmol), potassium acetate (1.5 g, 15 mmol), and [PdCl$_2$(dppf)]CH$_2$Cl$_2$ (0.27 g, 0.3 mmol) were added to a roundbottomed flask and placed under N$_2$. The flask was cycled three times between vacuum and nitrogen. Dioxane (30 mL, Aldrich anhydrous) was added via syringe. The reaction mixture was stirred at 80° C. (oil bath) for 4 hours. The reaction mixture was allowed to cool to rt. Water (30 mL) was added, followed by sodium perborate-(5.0 g, 32 mmol). The reaction mixture was left stirring overnight at room temperature. The resulting mixture was diluted with EtOAc, washed with water and brine, dried with MgSO$_4$, and concentrated to dryness. The crude product was purified via flash silica gel chromatography using a 30% to 100% EtOAc-Hexanes gradient as the mobile phase. A white solid (1.28 g) was collected as product 5021C.

Step 3

Compound 5021C (40 mg, 0.12 mmol), cesium carbonate (59 mg, 1.5 eq), and DMF (1 mL) were added to a round bottomed flask. The flask was sonicated for 30 min. 2-bromopropane (18 mg, 1.2 eq) was added and the reaction mixture was stirred at rt overnight. The resulting mixture was diluted with EtOAc, washed with water, dried with MgSO$_4$, and concentrated to dryness. The crude product was purified via flash chromatography using a 10% to 100% EtOAc-Hexanes gradient as the mobile phase. Compound 5021D (28 mg) was obtained as product.

Step 4

Compound 5021D was converted to compound 5021 using procedures similar to those described in Example 1001.

Example 7000

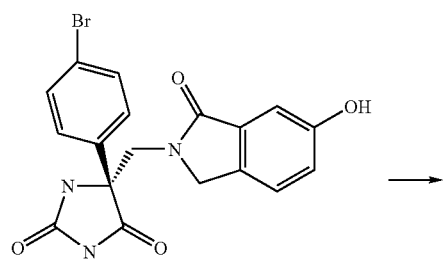

214

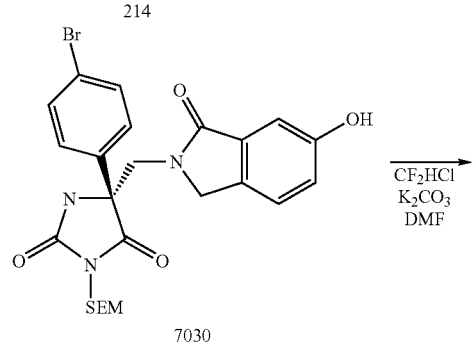

7030

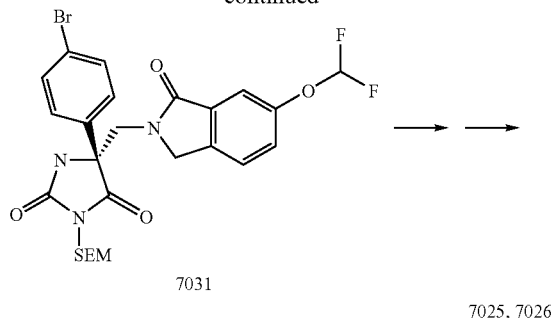

7031

7025, 7026

7025 was synthesized from 7031 using appropriate heterocyclic bromide using the procedure similar to synthesis of 169.

7031 was prepared from 7030 using the procedure described below:

7030 (0.273 g, 0.5 mmol) in 5 mL anhydrous DMF was treated with potassium carbonate (0.2 g, 0.15 mmol). The flask was equipped with a dry ice acetone trap and difluoro chloromethane gas was bubbled for 2 h. The bubbling was stopped and excess reagent was removed by bubbling nitrogen. The reaction was diluted with 50 mL ethyl acetate and washed with water (2×50 mL) and brine (1×25 mL). The organics were dried and concentrated to yield a crude which was purified by silica-gel prep plate chromatography using 1:1 ethyl acetate:hexane to yield 0.037 g of pure product.

7030 itself was prepared from 214, using standard procedure reported previously in this case.

Example 8001

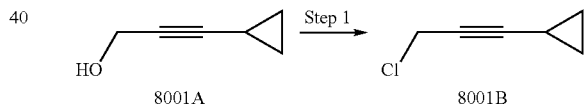

Compound 8001B was prepared according to a literature procedure (Munyemana, F.; Frisque-Hesbain, A.; Devos, A.; and Ghosez, L. *Tetrahedron Letters* 30(23), 3077-3080, 1989).

Example 8002

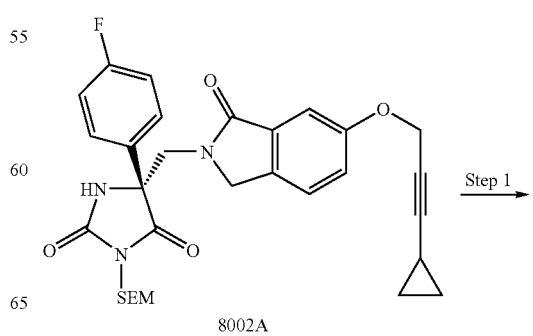

8002A

-continued

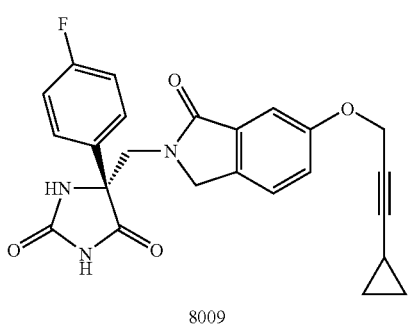

8009

Compound 8002A (746 mg, 1.32 mmol) was dissolved in anhydrous acetonitrile (10 mL) and the solution was coiled to 0° C. by ice water bath. $BF_3$-$Et_2O$ (0.84 mL, 6.62 mmol) was added dropwise via syringe. The solution was stirred at 0° C. for two hours. DIPEA (1 mL) was added followed by NaOH (1N, 1 mL). The solution was stirred at 25° C. for two hours. The solvent was removed and the product was purified by C18 reverse phase chromatography ($CH_3CN$/water, 5% to 90%, with 0.5% $HCO_2H$) to give 8009. 8009 was dissolved in methanol and NaOH (1N, 1.0 mL, 1.0 mmol, 0.95 equivalent) was added. The solution was stirred at 25° C. for 30 minutes. The solvent was removed to give the sodium salt form of 8009 (495 mg).

Example 2021

Step 1:

To a solution of compound 2021A (4 g, 26.8 mmol) in water (25 mL) and concentrated sulfuric acid (1 mL) was added sodium nitrite (2.2 g, 31.8 mmol) in water (10 mL) with ice bath cooling. The reaction mixture was diluted with concentrated sulfuric acid (20 mL). The reaction mixture was added to 50% sulfuric acid (50 mL) at reflux and boiled for 2 minutes. The reaction mixture was cooled to room temperature and diluted with water (250 mL). The mixture was extracted with diethyl ether (5×100 mL). The combined organic layers were washed with sodium bicarbonate solution and brine, dried over sodium sulfate and concentrated to afford 2021B (1.6 g) as a yellow solid.

Step 2:

A mixture of compound 2021B (790 mg, 5.3 mmol), cesium carbonate (1.90 g, 5.8 mmol) and 2,2,2-trifluoroethyl trifluoromethanesulfonate (1.47 g, 6.3 mmol) in NMP (15 mL) was stirred overnight at room temperature. The reaction mixture was filtered and the solids were washed with ethyl acetate. The filtrate was poured into water and extracted with ethyl acetate. The combined organic layers were dried over sodium sulfate and concentrated. Recrystallization from 30% ethyl acetate/hexane afford 2021C (728 mg) as a yellow solid. HPLC-MS $t_R$=1.54 min ($UV_{254\ nm}$); mass calculated for formula C10H7F3O3 232.03, observed LCMS m/z 233.1 (M+H).

Step 3:

A suspension of 2021C (168 mg, 0.72 mmol) and 1.0 N sodium hydroxide (0.72 mL, 0.72 mmol) in water (0.8 mL)

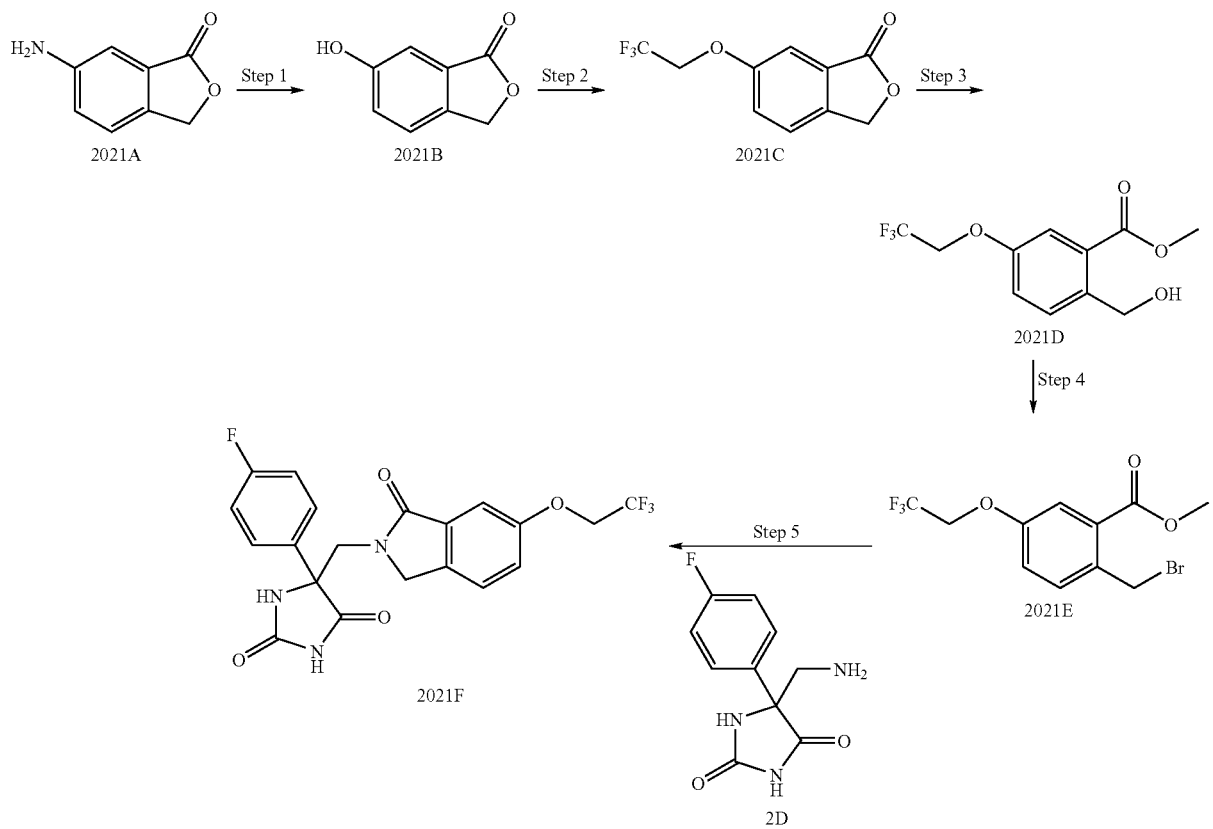

was heated at 100° C. for 1 hour. The reaction mixture was concentrated and the residue was azeotroped with toluene. The sodium salt was dissolved in DMF (1 mL) and methyl iodide (0.135 mL, 2.16 mmol) was added. The reaction mixture was stirred for 2 hours at room temperature. The reaction mixture was diluted with ethyl acetate and water. The layers were separated and the aqueous layer was extracted with ethyl acetate. The combined organic layers were washed with brine, dried over sodium sulfate and concentrated. Purification by chromatography (SiO$_2$, 30% ethyl acetate/hexane) afforded 2021D (149 mg) as a solid. HPLC-MS $t_R$=1.56 min (UV$_{254\ nm}$); mass calculated for formula C11H11F3O4 264.06, observed LCMS m/z 287.1 (M+Na).

Step 4:

A mixture of 2021D (149 mg, 0.56 mmol), carbon tetrabromide (371 mg, 1.12 mg), and triphenylphosphine (294 mg, 1.12 mmol) in dichloromethane (5 mL) was stirred for 40 minutes at room temperature. The mixture was concentrated and purified by chromatography (SiO$_2$, 5% to 10% ethyl acetate/hexane) to afford 2021E (153) mg as an oil. HPLC-MS $t_R$=2.04 min (UV$_{254\ nm}$); mass calculated for formula C11H10BrF3O3 325.98, observed LCMS m/z 349 (M+Na).

Step 5:

Compound 2021F (136 mg) was prepared from 2021E (151 mg, 0.46 mmol) and 2D (118 mg, 0.45 mmol) using previously described procedures. HPLC-MS $t_R$=1.60 min (UV$_{254\ nm}$); mass calculated for formula C20H15F4N3O4 437.1, observed LCMS m/z 438.1 (M+Na).

Example 2022

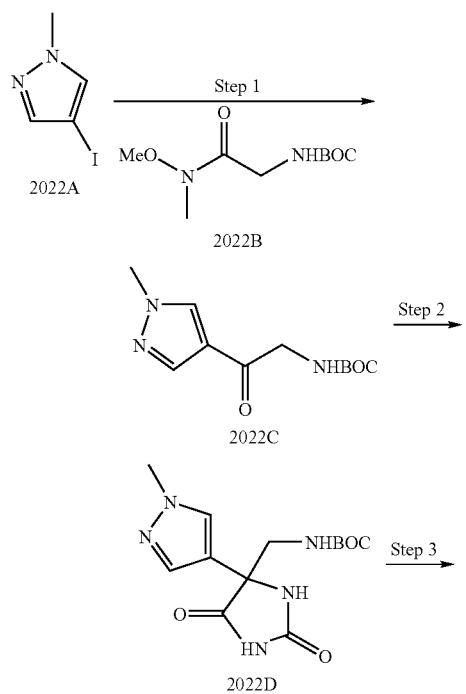

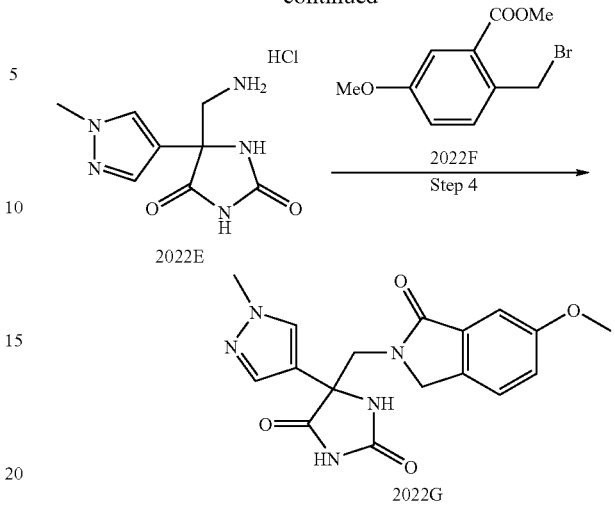

Step 1:

Compound 2022C was prepared according to a modification of a procedure by Felding, J. et al. (*J. Org. Chem.* 1999, 64, 4196-4198) using 4-Iodo-1-methyl-1H-pyrazole 2022A and Weinreb amide 2022B as starting materials. The crude reaction mixture was chromatographed (SiO$_2$, 60%-80% ethyl acetate/hexane) to give compound 2022C (62%). HPLC-MS $t_R$=1.18 min (UV$_{254\ nm}$); mass calculated for formula C11H17N3O3 239.1, observed LCMS m/z 184.1 (M-tBu+H).

Step 2:

BOCamino hydantoin 2022D was prepared using procedures described in Example 1, Step 2. (81%) HPLC-MS $t_R$=0.94 min (UV$_{254\ nm}$); mass calculated for formula C13H19N5O4 309.1, observed LCMS m/z 310.1 (M+H).

Step 3:

Amino hydantoin 2022E was prepared using procedures described in Example 1, Step 3. HPLC-MS $t_R$=0.18 min (UV$_{254\ nm}$); mass calculated for formula C8H11N5O2 209.1, observed LCMS m/z 210.1 (M+H).

Step 4:

Hydantoin 2022G was prepared using procedures described in Example 8. HPLC-MS $t_R$=2.23 min (UV$_{254\ nm}$; 10 min); mass calculated for formula C17H17N5O4 355.1, observed LCMS m/z 356.1 (M+H).

Example 2023

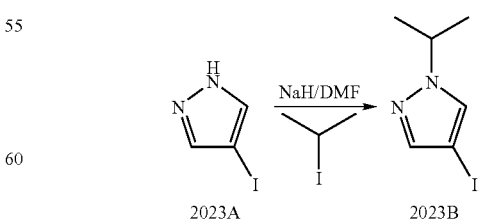

Step 1:

To a slurry of sodium hydride (95%, 0.58 g, 23 mmol) in DMF (20 mL) was added a solution of 4-Iodo-1H-pyrazole (2023A) (4.07 g, 21 mmol) in DMF (20 mL) and the resulting mixture was stirred at rt for 10 min. Then 2-iodopropane (2.52 mL, 25.2 mmol) was added dropwise and the resulting mixture was stirred at rt overnight. The reaction mixture was concentrated, diluted with ethyl acetate, washed with water (4 times), brine, dried and concentrated to give an oily residue which was chromatographed (SiO$_2$, 10%-20% ethyl acetate/hexane) to give 4-Iodo-1-isopropyl-1H-pyrazole 2023B (3.27 g, 66%). HPLC-MS $t_R$=1.66 min (UV$_{254\ nm}$); mass calculated for formula C6H9IN2 235.98, observed LCMS m/z 237.0 (M+H).

Example 2024

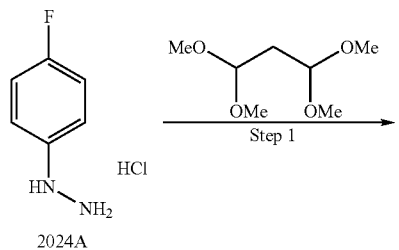

Step 1:
Compound 2024B was prepared according to a modification of a procedure by Roppe, J. et al. (*J. Med. Chem.* 2004, 47, 4645-4648) using 4-fluorophenylhydrazine hydrochloride 2024A and malondialdehyde-bis-(dimethylacetal) as starting materials (95% yield). HPLC-MS $t_R$=1.62 min (UV$_{254\ nm}$); mass calculated for formula C9H7FN2 162.1, observed LCMS m/z 163.1 (M+H).

Step 2:
Compound 2024C was prepared according to a modification of a procedure by Rodriguez-Franco, M. I. et al. (*Tetrahedron. Lett.* 2001, 42, 863-865) (85% yield). HPLC-MS $t_R$=1.98 min (UV$_{254\ nm}$); mass calculated for formula C9H6FIN2 287.96, observed LCMS m/z 288.9 (M+H).

Example 2025

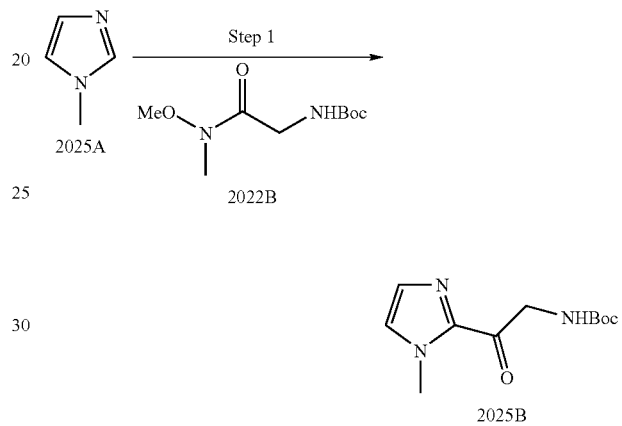

Step 1:
Compound 2025B was prepared according to a modification of a procedure by Evans, D. A. et al. (*J. Am. Chem. Soc.* 2005, 127, 8942-8943) using 1-Methyl-1H-imidazole 2025A and Weinreb amide 2022B as starting materials (42%). HPLC-MS $t_R$=1.24 min (UV$_{254\ nm}$); mass calculated for formula C11H17N3O3 239.1, observed LCMS m/z 240.1 (M+H).

The following compounds were prepared using procedures described in Examples 2021 to 2025.

| Compound # | Structure | Exact mass | MS m/e (M + H) |
|---|---|---|---|
| 2021F | 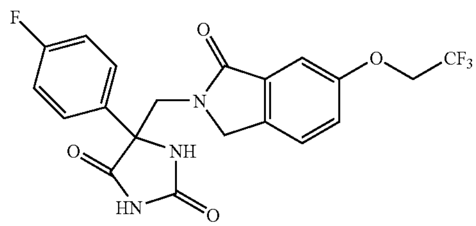 | 437.1 | 438.1 |

-continued
| Compound # | Structure | Exact mass | MS m/e (M + H) |
|---|---|---|---|
| 2023C | 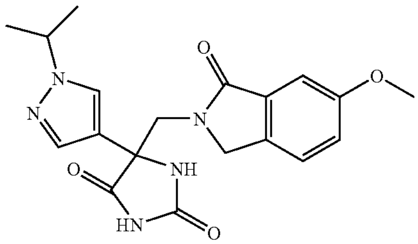 | 383.16 | 384.1 |
| 2024D | 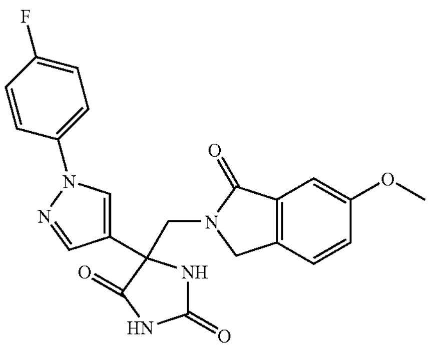 | 435.13 | 436.1 |
| 2022G | 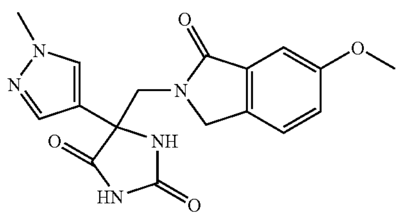 | 355.13 | 356.1 |
| 2025C | 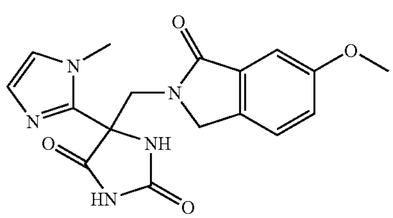 | 355.13 | 356.1 |
Example 2026
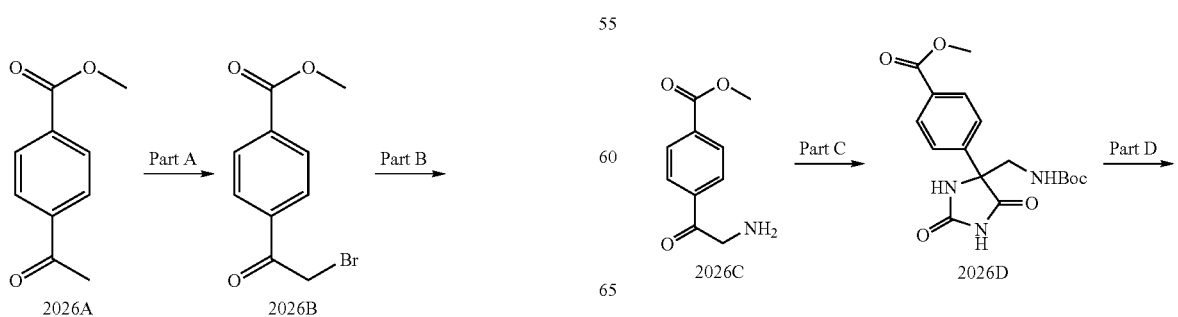

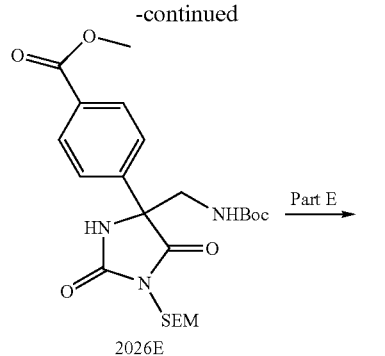

2026E

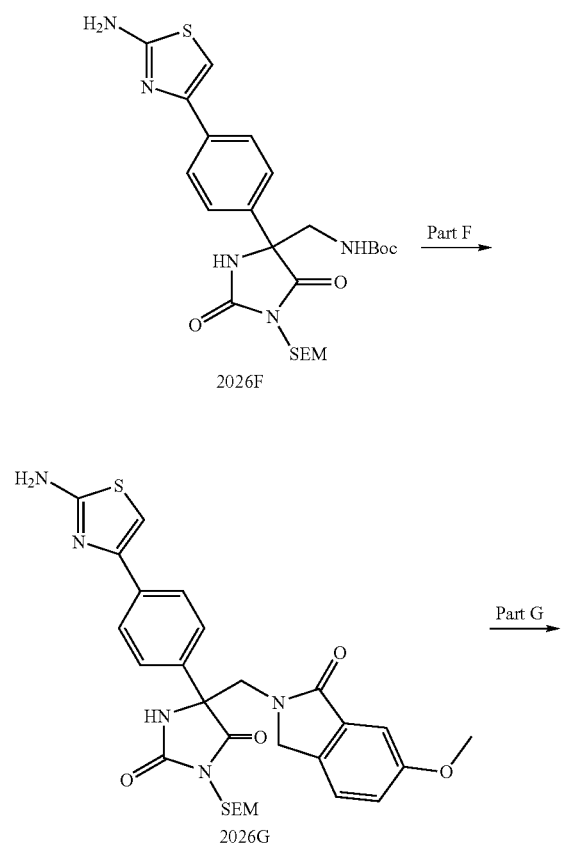

2026F

2026G

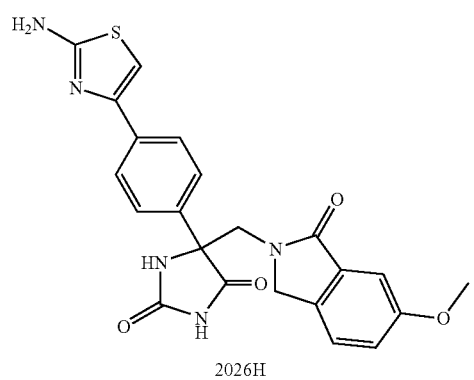

2026H

Part A

To a solution of methyl 4-acetylbenzoate (2026A) (1.9 g, 10.6 mmol) in acetic acid (10 mL) was added dropwise bromine (1.7 g, 21.3 mmol). The mixture was heated at 60° C. for 30 min, then stirred at room temperature for 1 hour, and poured into cold water (30 mL). The light yellow precipitate was collected, washed with water and dried (2.6 g, 96%).

Part B

Compound 2026C was prepared from compound 2026B following the procedure described in Example 1005.

Part C

Compound 2026D was prepared following the procedures described in Example 1 HPLC-MS $t_R$=1.36 min (UV$_{254\ nm}$); mass calculated for formula C17H21N3O6 363.1, observed LCMS m/z 386.0 (M+Na).

Part D

To a mixture of 2026D (7.87 g, 21.7 mmol) and diisopropylethylamine (7.5 mL, 43.4 mmol) in DMF (80 mL) was added 2-trimethylsilylethoxy methyl chloride (4.7 mL, 23.8 mmol). The mixture was stirred at room temperature overnight, diluted with water and extracted with ethyl acetate. The combined organic layers were washed with water, brine, dried over sodium sulfate and concentrated. The residue was purified by column chromatography (SiO$_2$, 15% EtOAc/hexane to 30% EtOAc/hexane) to afford 2026E as a white solid (10.2 g, 95%): HPLC-MS $t_R$=2.17 min (UV$_{254\ nm}$); mass calculated for formula C23H35N3O7Si 493.2, observed LCMS m/z 516.1 (M+Na).

Part E

Compound 2026F was prepared from ester 2026E following a procedure as described in Guo, Z. et. al (WO 2005/121130A2).

Part F

Compound 2026G was prepared following a previously described procedure. HPLC-MS $t_R$=1.67 min (UV$_{254\ nm}$); mass calculated for formula C28H33N5O5SSi 579.2, observed LCMS m/z 580.3 (M+H).

Part G

Compound 2026G (65 mg, 0.11 mmol) was heated in a sealed tube in MeOH (2 mL) and 4 N HCl in 1,4-dioxane (2 mL) overnight at 90° C. Solvent was evaporated and the residue was stirred in MeOH (2 mL) and triethylamine (2 mL) at room temperature for 4 hours. The solvent was removed and the residue was purified by reverse phase chromatography to give 2026H (11 mg, 20%): HPLC-MS $t_R$=1.00 min (UV$_{254\ nm}$); mass calculated for formula C22H19N5O4S 449.1, observed LCMS m/z 450.1 (M+H).

| Compound # | Structure | Exact mass | MS m/e (M + H) |
|---|---|---|---|
| 2026H | 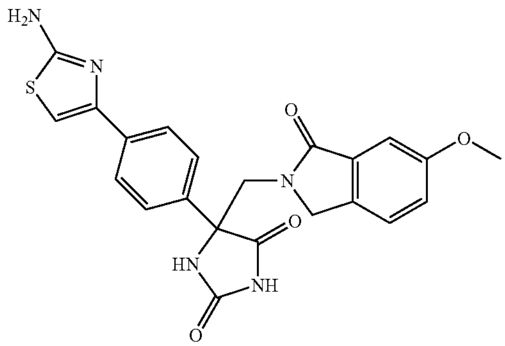 | 449.1 | 450.1 |

Example 2030

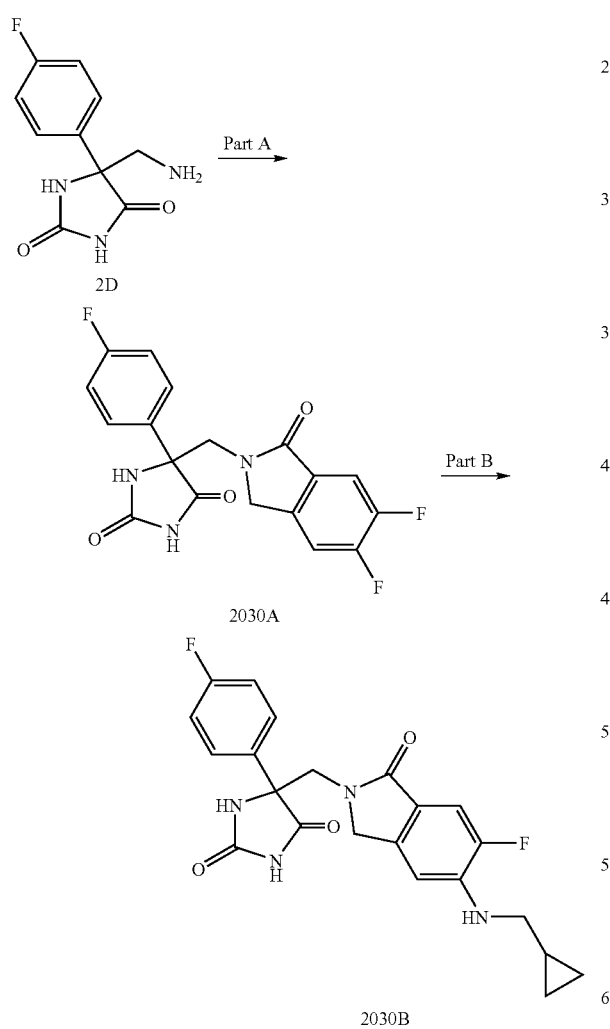

Part A:
Compound 2030A was prepared using previously described methods from 2D. HPLC-MS $t_R$=3.80 min (UV$_{254\ nm}$), Mass calculated for formula $C_{18}H_{12}F_3N_3O_3$ 375.1, observed LCMS m/z 376.1 (M+H).

Part B:
Compound 2030A (100 mg, 0.27 mmol) and cyclopropylmethylamine (0.140 mL) in NMP (0.5 mL) was heated at 100° C. for 12 h. After cooling to room temperature, the reaction mixture was diluted with EtOAc, washed with water and brine, dried over Na$_2$SO$_4$, and concentrated. Recrystallization from EtOAc/hexane yielded 2030B as a white solid (75 mg, 66%). HPLC-MS $t_R$=4.06 min (UV$_{254\ nm}$), Mass calculated for formula $C_{22}H_{20}F_2N_4O_3$ 426.2, observed LCMS m/z 427.1 (M+H).

Example 2031

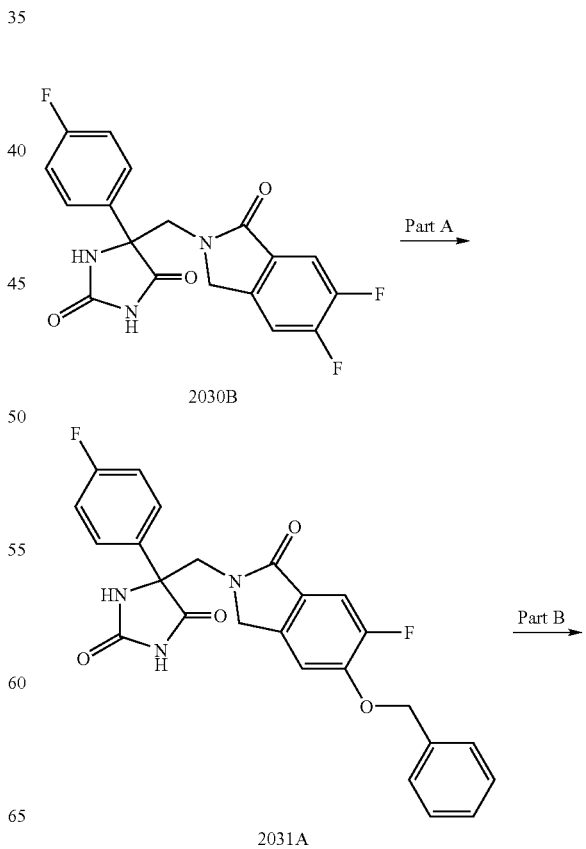

2031B

Part A:

Compound 2030B (250 mg, 0.67 mmol) in 1 mL of benzyl alcohol was added with powdered KOH (75 mg, 1.33 mmol). The reaction mixture was stirred at 100° C. for 2 h and cooled to room temperature. It was diluted with EtOAc, washed with 1N HCl, H$_2$O, and brine, dried over Na$_2$SO$_4$, and concentrated. Flash column chromatography with EtOAc afforded 2031A as a white solid (280 mg, 91%). HPLC-MS $t_R$=4.29 min (UV$_{254\ nm}$), Mass calculated for formula C$_{25}$H$_{19}$F$_2$N$_3$O$_4$ 463.1, observed LCMS m/z 464.0 (M+H).

Part B:

Compound 2031A (250 mg, 0.54 mmol) in EtOH (30 mL) was added with 10% palladium on carbon (100 mg). The reaction mixture was stirred at room temperature for 2 h under 1 atmosphere of hydrogen. It was then filtered through celite, washed with EtOH, and concentrated, affording 2031B as a white solid (120 mg, 60%). HPLC-MS $t_R$=2.66 min (UV$_{254\ nm}$), Mass calculated for formula C$_{18}$H$_{13}$F$_2$N$_3$O$_4$ 373.1, observed LCMS m/z 374.0 (M+H).

Example 2032

2D

2032A

2032B

Part A:

Compound 2032A was prepared using previously described method from 2D. HPLC-MS $t_R$=2.94 min (UV$_{254\ nm}$), Mass calculated for formula C$_{19}$H$_{13}$FN$_4$O$_3$ 364.1, observed LCMS m/z 365.0 (M+H).

Part B:

Compound 2032A (100 mg, 0.27 mmol) was dissolved in 2 mL of 90% H$_2$SO$_4$. After stirring at 60° C. for 10 h, the reaction mixture was poured into 50 g of ice, and white solid was precipitated. Filtration and drying under vacuum gave 2032B as a white solid (80 mg, 78%). HPLC-MS $t_R$=2.01 min (UV$_{254\ nm}$), Mass calculated for formula C$_{19}$H$_{15}$FN$_4$O$_6$ 382.1, observed LCMS m/z 383.1 (M+H).

The following compounds were prepared as described in Examples 2030 to 2032.

| Compound # | Structure | Exact mass | MS m/e (M + H) |
|---|---|---|---|
| 2030A | 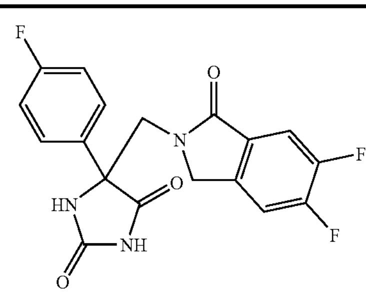 | 375.08 | 376.1 |

-continued

| Compound # | Structure | Exact mass | MS m/e (M + H) |
|---|---|---|---|
| 2030C | 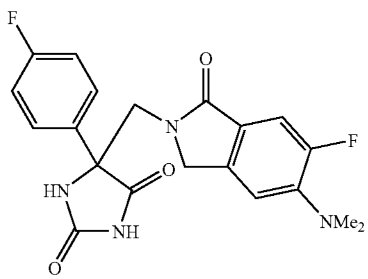 | 400.13 | 401.2 |
| 2030B | 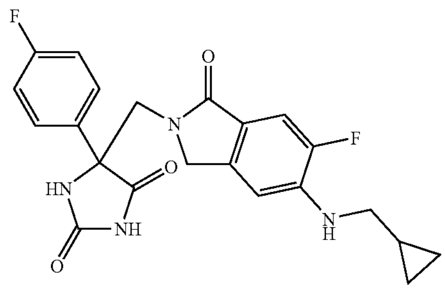 | 426.15 | 427.1 |
| 2031C | 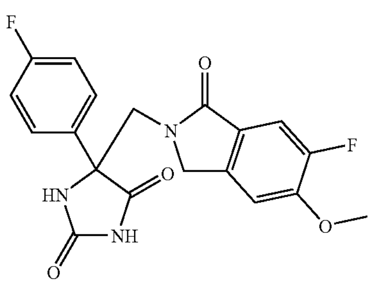 | 387.10 | 388.1 |
| 2031D | 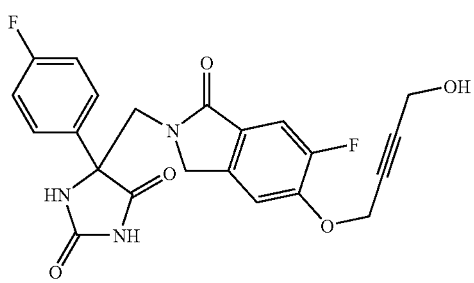 | 441.11 | 442.0 |
| 2030D | 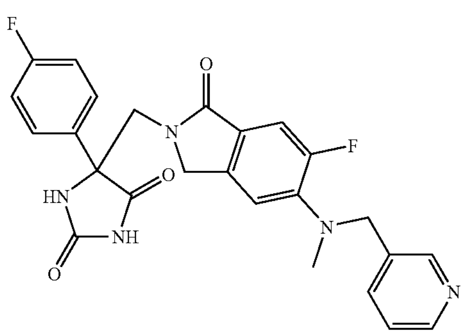 | 477.16 | 478.1 |

-continued

| Compound # | Structure | Exact mass | MS m/e (M + H) |
|---|---|---|---|
| 2031A | 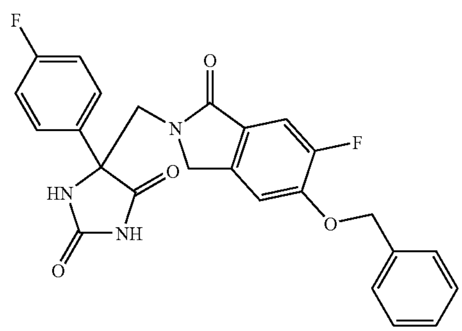 | 463.13 | 464.0 |
| 2031B | 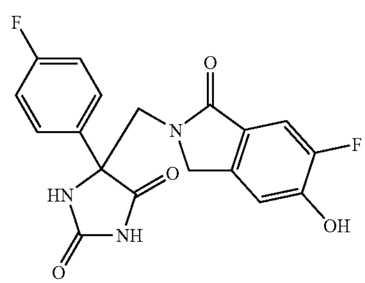 | 373.09 | 374.0 |
| 2032B | 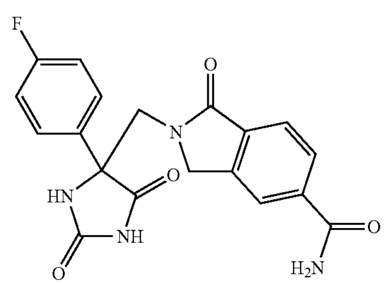 | 382.11 | 383.1 |
| 2031E | 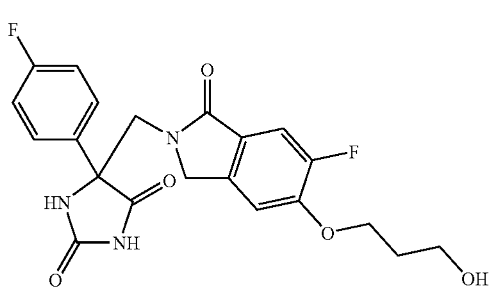 | 431.13 | 432.1 |
| 2031F | 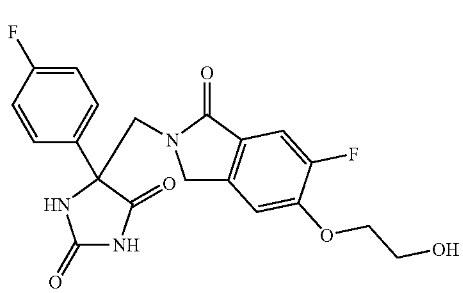 | 417.11 | 418.1 |

The Table below lists compounds prepared by the procedures set forth below:

TABLE 6000

| Compound ID | Structure | Exact Mass | Mass Obsvd | Ki (nM) |
|---|---|---|---|---|
| 96 | 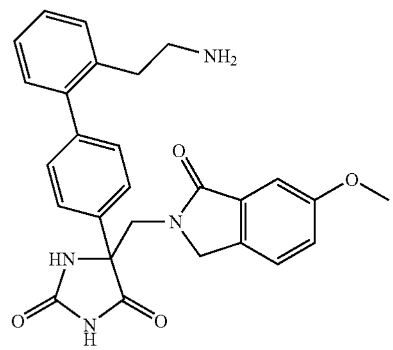 | 470.20 | 471.3[M + H]+ | B |
| 9200 | 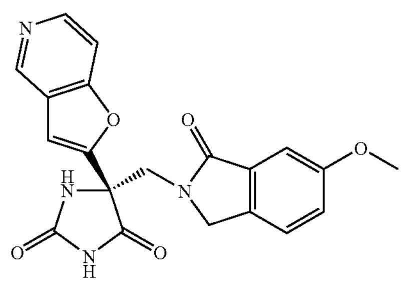 | 392.11 | 392.11 | A |
| 9201 | 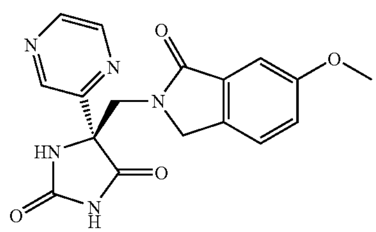 | 353.11 | 354.1[M + H]+ | D |
| 9202 | 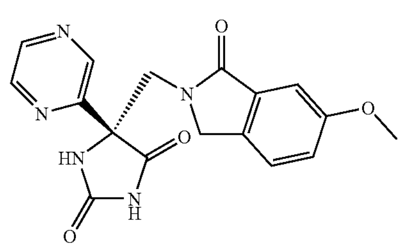 | 353.11 | 354.1[M + H]+ | A |
| 9203 | 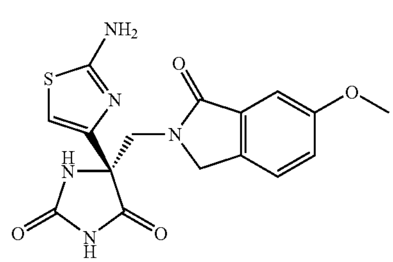 | 373.08 | 374.0[M + H]+ | A |

TABLE 6000-continued

| Compound ID | Structure | Exact Mass | Mass Obsvd | Ki (nM) |
|---|---|---|---|---|
| 9204 | 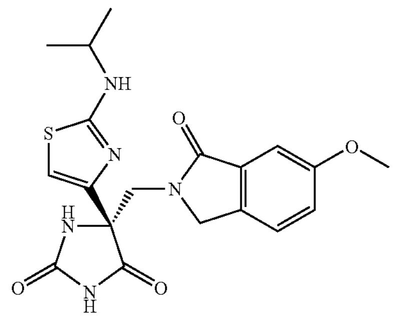 | 415.13 | 416.0[M + H]+ | A |
| 9205 | 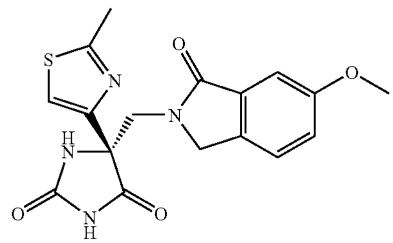 | 372.09 | 373.0[M + H]+ | A |
| 9206 | 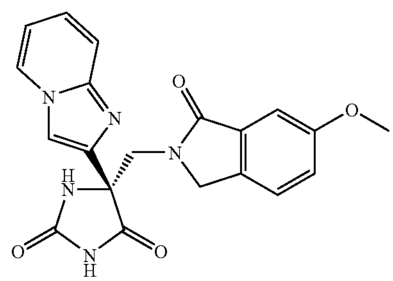 | 391.13 | 392.0[M + H]+ | A |
| 9207 | 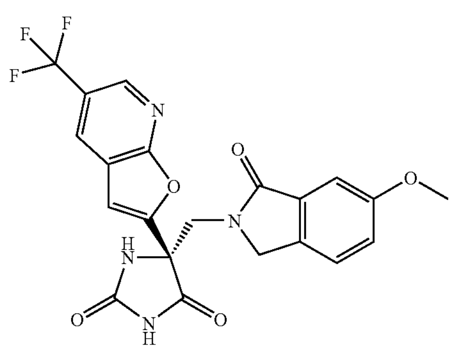 | 460.10 | 461.0[M + H]+ | A |
| 9208 | 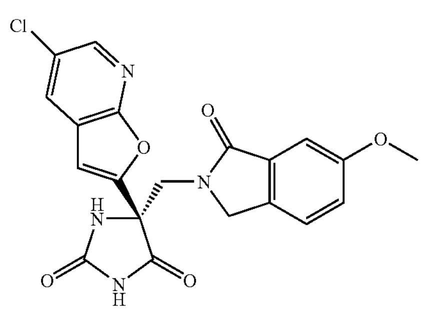 | 426.07 | 427.1[M + H]+ | A |

TABLE 6000-continued

| Compound ID | Structure | Exact Mass | Mass Obsvd | Ki (nM) |
|---|---|---|---|---|
| 9209 | 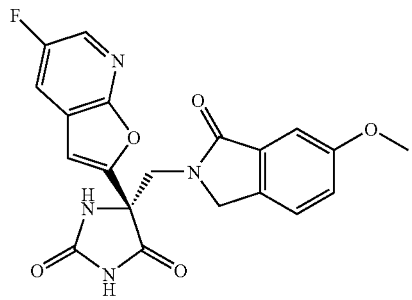 | 410.10 | 411.1[M + H]⁺ | A |
| 9210 | 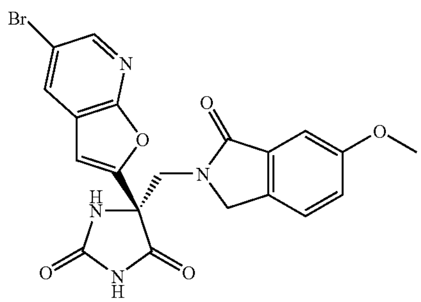 | 470.02 | 471.1[M + H]⁺ | A |
| 9211 | 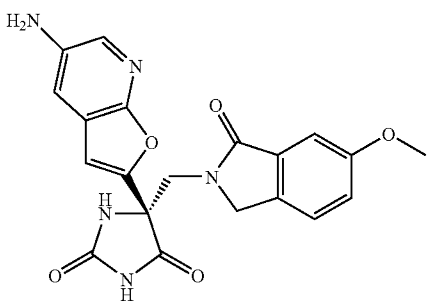 | 407.12 | 408.1[M + H]⁺ | A |
| 9212 | 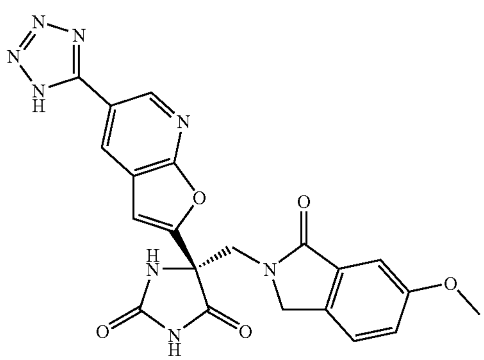 | 460.10 | 461.2[M + H]⁺ | A |
| 9213 | 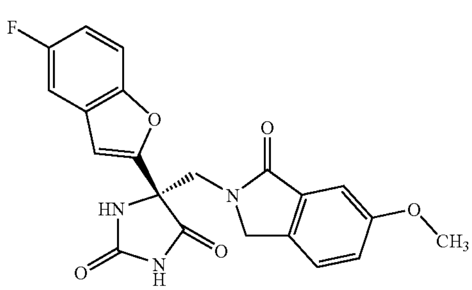 | 409.37 | 410.1[M + H]⁺ | A |

TABLE 6000-continued

| Compound ID | Structure | Exact Mass | Mass Obsvd | Ki (nM) |
|---|---|---|---|---|
| 9214 | 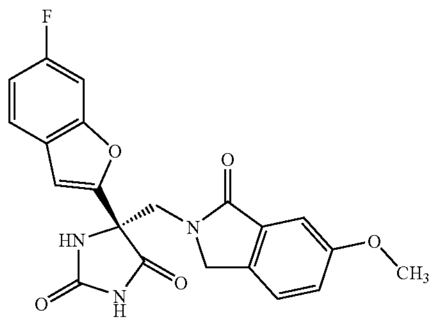 | 409.37 | 410.1[M + H]+ | A |
| 9215 | 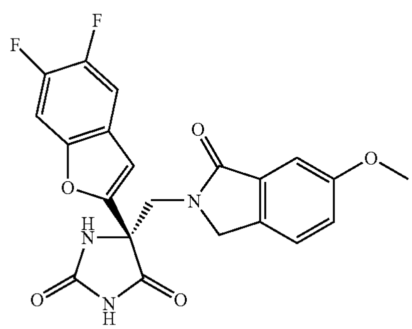 | 427.10 | 428.0[M + H]+ | A |
| 9216 | 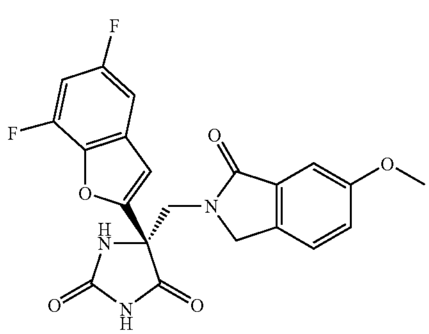 | 427.10 | 428.0[M + H]+ | A |
| 9217 | 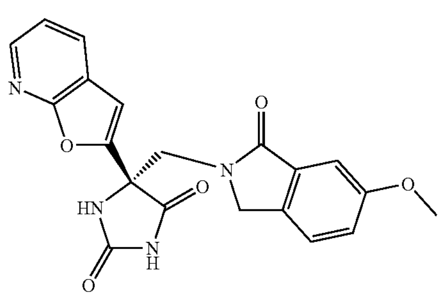 | 392.11 | 393.1[M + H]+ | A |

TABLE 6000-continued

| Compound ID | Structure | Exact Mass | Mass Obsvd | Ki (nM) |
|---|---|---|---|---|
| 9218 | 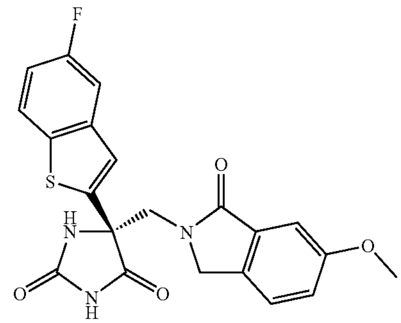 | 425.08 | 426.1[M + H]+ | A |
| 9219 | 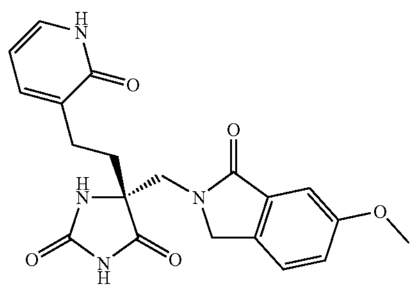 | 396.14 | 397.1[M + H]+ | A |
| 9220 | 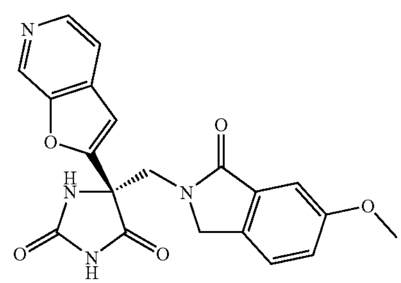 | 392.11 | 393.1[M + H]+ | A |
| 9221 | 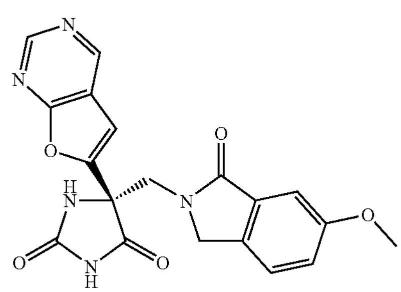 | 393.11 | 394.1[M + H]+ | A |
| 9222 | 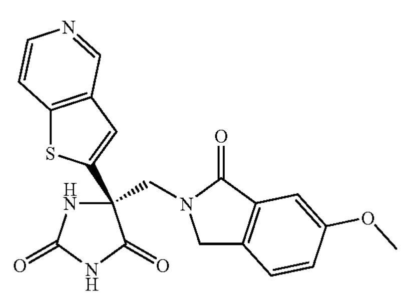 | 408.09 | 409.1[M + H]+ | A |

TABLE 6000-continued

| Compound ID | Structure | Exact Mass | Mass Obsvd | Ki (nM) |
|---|---|---|---|---|
| 9223 | 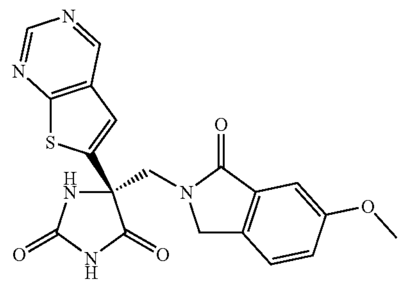 | 409.08 | 410.2[M + H]⁺ | A |
| 9224 | 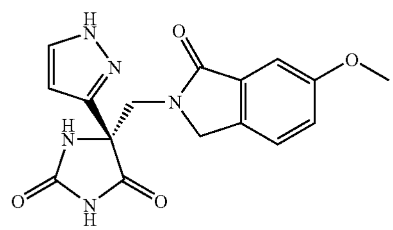 | 341.11 | 342.1[M + H]⁺ | A |
| 9225 | 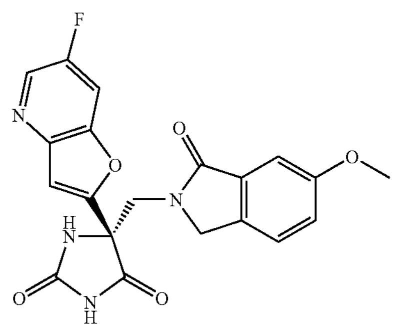 | 410.10 | 411.1[M + H]⁺ | A |
| 9226 | 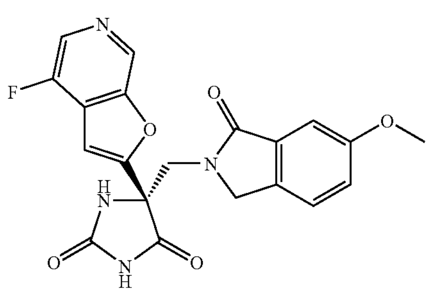 | 410.10 | 411.1[M + H]⁺ | A |
| 9227 | 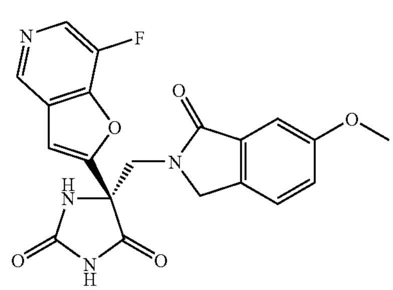 | 410.10 | 411.1[M + H]⁺ | A |

TABLE 6000-continued

| Compound ID | Structure | Exact Mass | Mass Obsvd | Ki (nM) |
|---|---|---|---|---|
| 9228 | 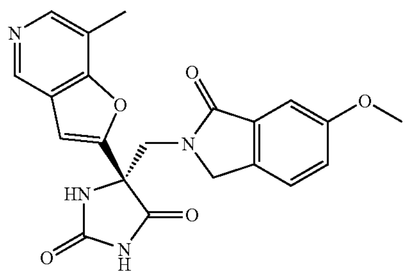 | 406.13 | 407.1[M + H]+ | A |
| 9229 | 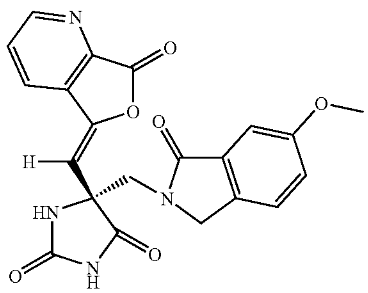 | 420.11 | 421.1[M + H]+ | B |
| 9230 | 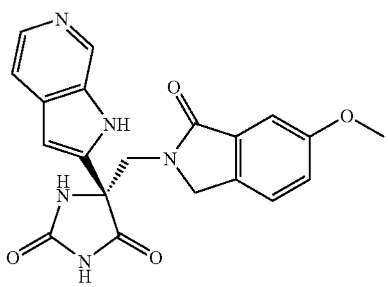 | 391.13 | 392.2[M + H]+ | A |
| 9231 | 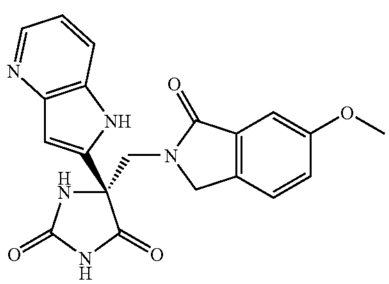 | 391.13 | 392.2[M + H]+ | A |
| 9232 | 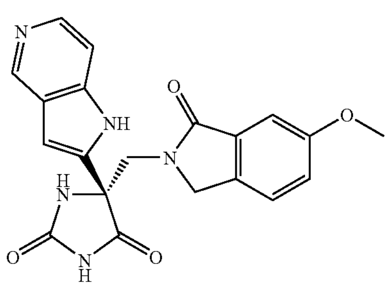 | 391.13 | 392.2[M + H]+ | A |

TABLE 6000-continued
| Compound ID | Structure | Exact Mass | Mass Obsvd | Ki (nM) |
|---|---|---|---|---|
| 9233 | 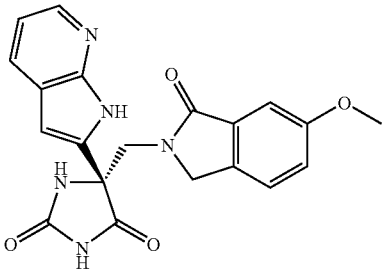 | 391.13 | 392.2[M + H]+ | A |
| 9234 | 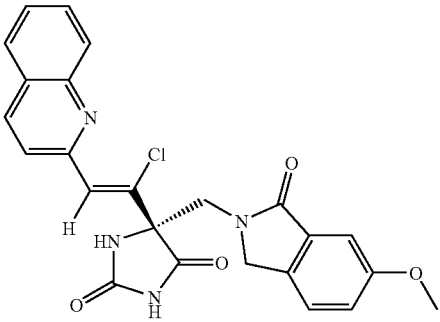 | 462.11 | 463.1[M + H]+ | A |
| 9235 | 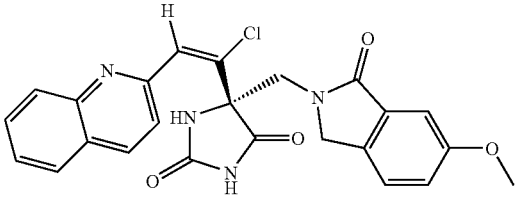 | 462.11 | 463.1[M + H]+ | A |
| 9236 | 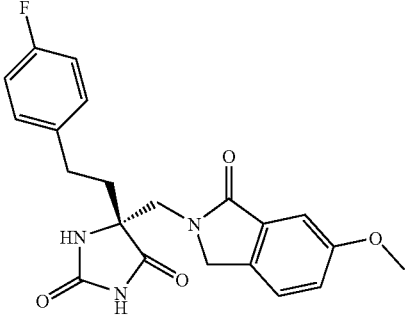 | 397.40 | 398.1[M + H]+ | A |
| 9237 | 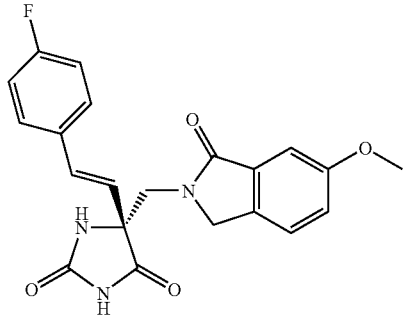 | 395.13 | 396.2[M + H]+ | A |

TABLE 6000-continued

| Compound ID | Structure | Exact Mass | Mass Obsvd | Ki (nM) |
|---|---|---|---|---|
| 9238 | 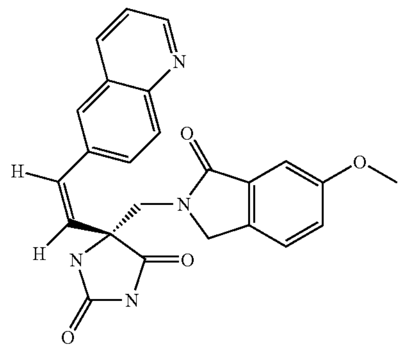 | 419.19 | 420.2[M + H]⁺ | A |
| 9239 | 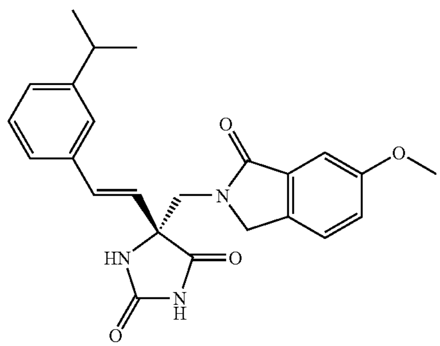 | 419.18 | 420.2[M + H]⁺ | A |
| 9240 | 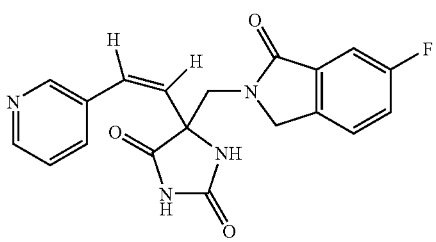 | 366.3 | 367.2[M + H]⁺ | B |
| 9241 | 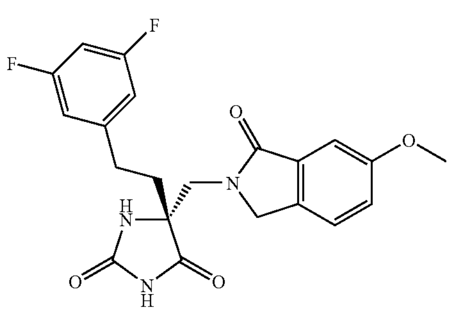 | 415.13 | 416.2[M + H]⁺ | A |
| 9242 | 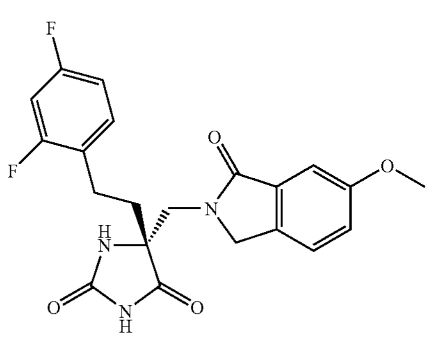 | 415.13 | 416.2[M + H]⁺ | A |

TABLE 6000-continued

| Compound ID | Structure | Exact Mass | Mass Obsvd | Ki (nM) |
|---|---|---|---|---|
| 9243 | 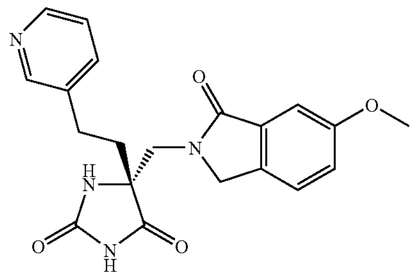 | 380.15 | 381.2[M + H]+ | A |
| 9244 | 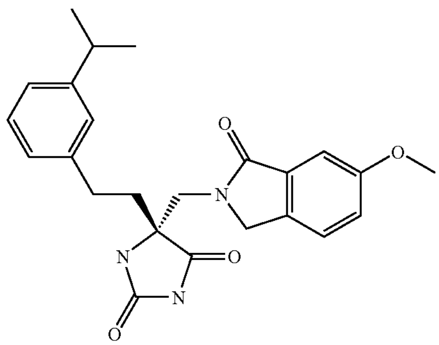 | 421.20 | 422.2[M + H]+ | A |
| 9245 | 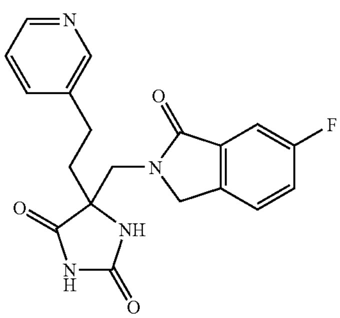 | 368.4 | 369.99[M + H]+ | B |
| 9246 | 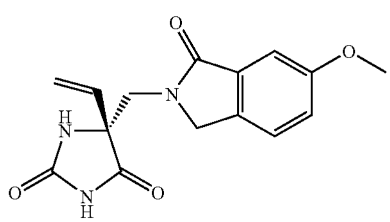 | 301.1 | 302.2 | B |
| 9247 | 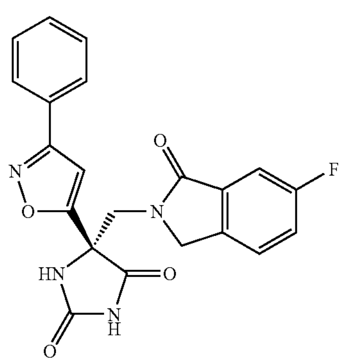 | 406.4 | 407.1[M + H]+ | A |

TABLE 6000-continued
| Compound ID | Structure | Exact Mass | Mass Obsvd | Ki (nM) |
|---|---|---|---|---|
| 9248 | 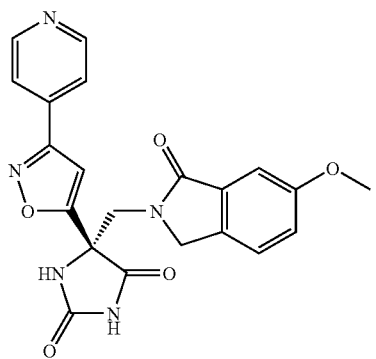 | 419.4 | 420.1[M + H]+ | A |
| 9249 | 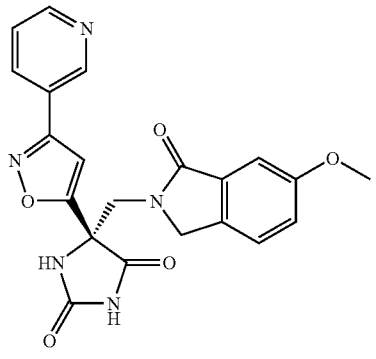 | 419.4 | 420.2[M + H]+ | A |
| 9250 | 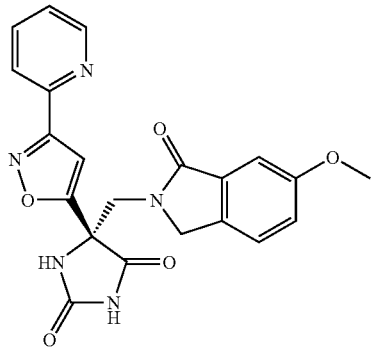 | 419.4 | 420.2[M + H]+ | A |
| 9251 | 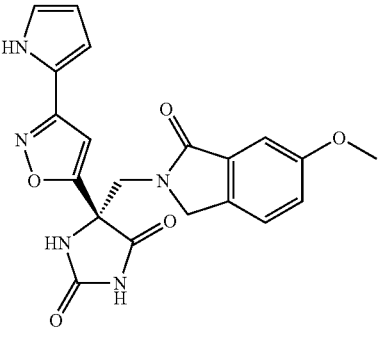 | 407.4 | 408.2[M + H]+ | A |

TABLE 6000-continued

| Compound ID | Structure | Exact Mass | Mass Obsvd | Ki (nM) |
|---|---|---|---|---|
| 9252 | 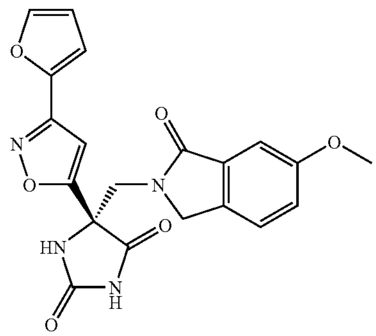 | 408.4 | 409.2[M + H]⁺ | A |
| 9253 | 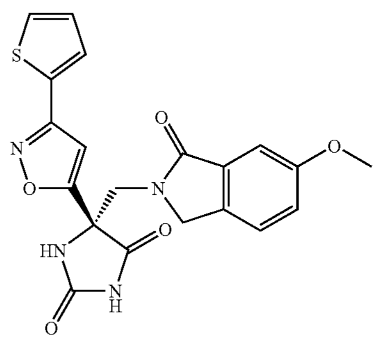 | 424.4 | 425.2[M + H]⁺ | A |
| 9254 | 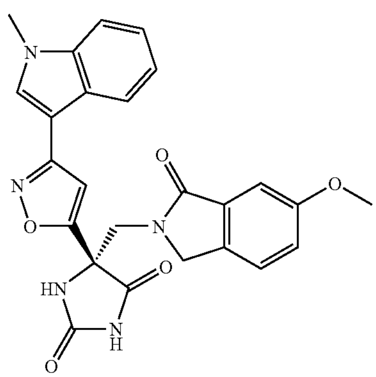 | 471.5 | 472.3[M + H]⁺ | A |
| 9255 | 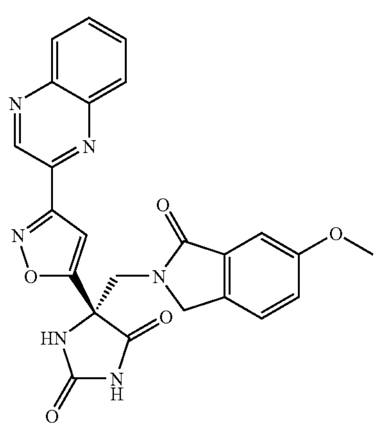 | 470.4 | 471.3[M + H]⁺ | A |

TABLE 6000-continued

| Compound ID | Structure | Exact Mass | Mass Obsvd | Ki (nM) |
|---|---|---|---|---|
| 9256 | 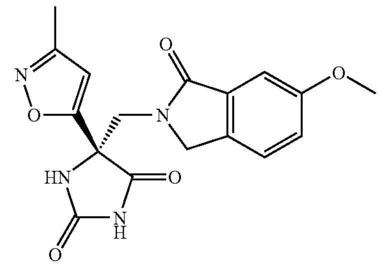 | 356.3 | 357.2[M + H]+ | A |
| 9257 | 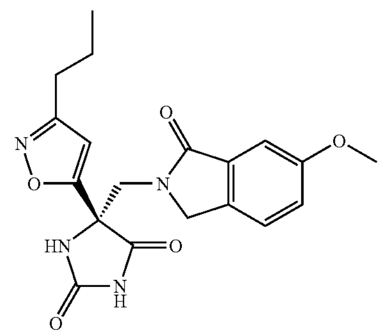 | 384.9 | 385.2[M + H]+ | A |
| 9258 | 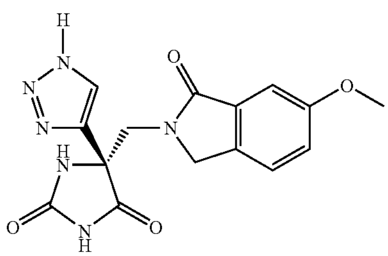 | 342.3 | 343.2[M + H]+ | B |
| 9259 | 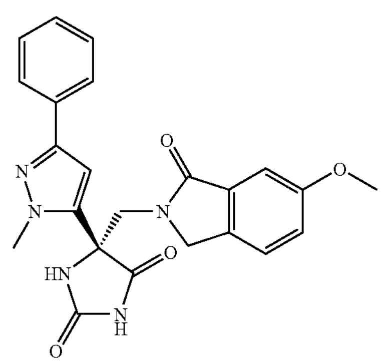 | 431.4 | 432.2[M + H]+ | A |

TABLE 6000-continued

| Compound ID | Structure | Exact Mass | Mass Obsvd | Ki (nM) |
|---|---|---|---|---|
| 9260 | 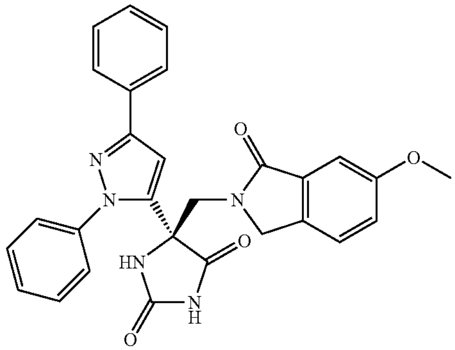 | 493.5 | 494.3[M + H]+ | B |
| 9261 | 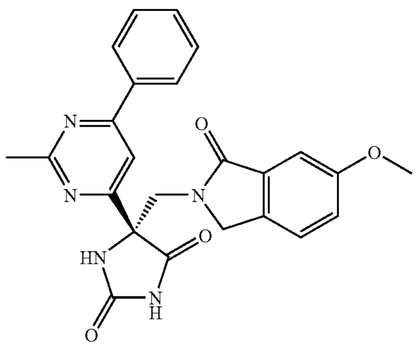 | 443.5 | 444.2[M + H]+ | A |
| 9262 | 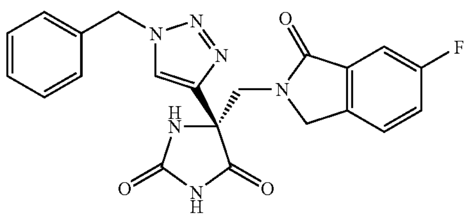 | 420.4 | 421.2[M + H]+ | B |
| 9263 | 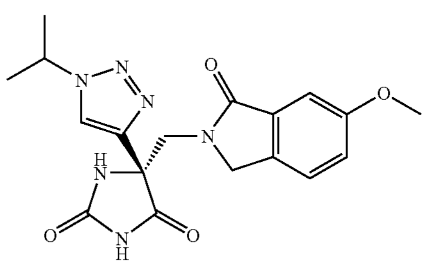 | 384.4 | 385.2[M + H]+ | A |
| 9264 | 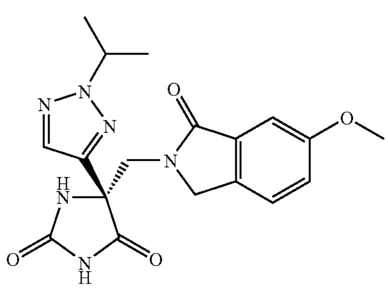 | 384.4 | 385.2[M + H]+ | A |

TABLE 6000-continued

| Compound ID | Structure | Exact Mass | Mass Obsvd | Ki (nM) |
|---|---|---|---|---|
| 9265 | 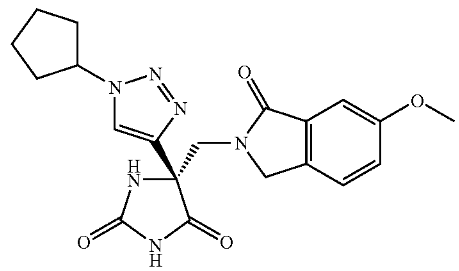 | 410.4 | 411.2[M + H]+ | A |
| 9266 | 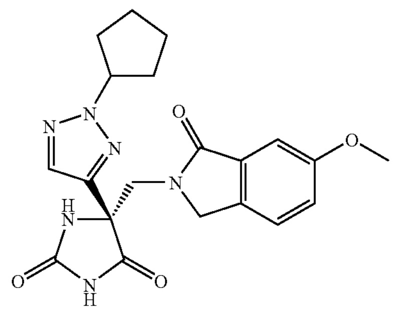 | 410.4 | 411.2[M + H]+ | A |
| 9267 | 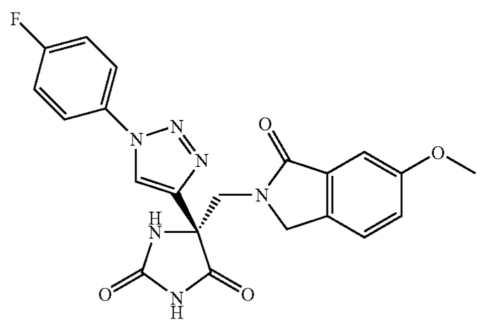 | 436.4 | 437.2[M + H]+ | A |
| 9268 | 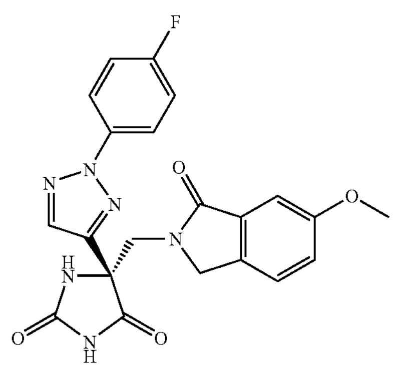 | 436.4 | 437.2[M + H]+ | A |
| 9269 | 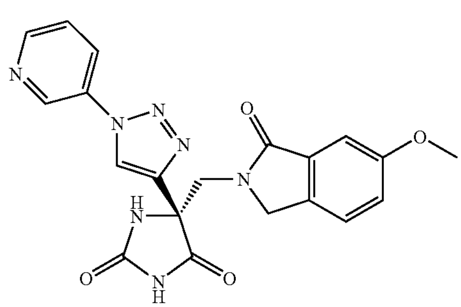 | 419.4 | 420.2[M + H]+ | A |

TABLE 6000-continued

| Compound ID | Structure | Exact Mass | Mass Obsvd | Ki (nM) |
|---|---|---|---|---|
| 9270 | 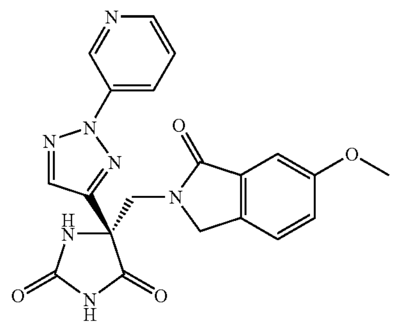 | 419.4 | 420.2[M + H]+ | A |
| 9271 | 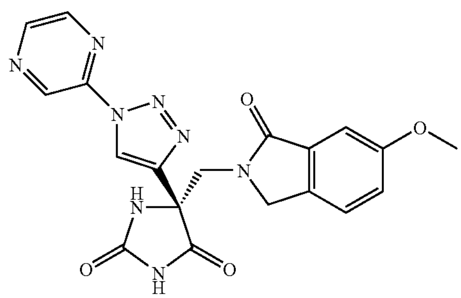 | 420.4 | 421.2[M + H]+ | A |
| 9272 | 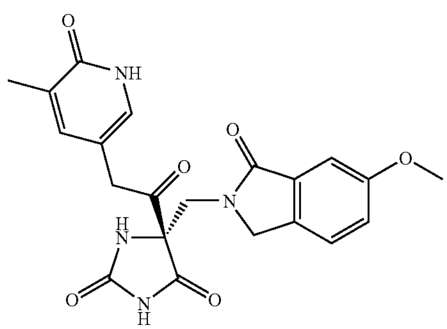 | 424.40 | 425.5[M + H]+ | A |
| 9273 | 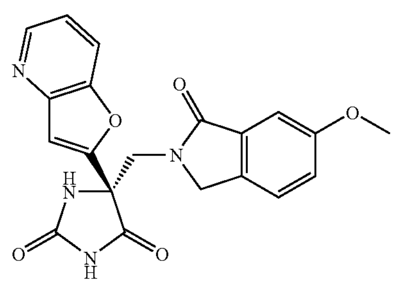 | 392.36 | 393.4[M + H]+ | A |
| 9274 | 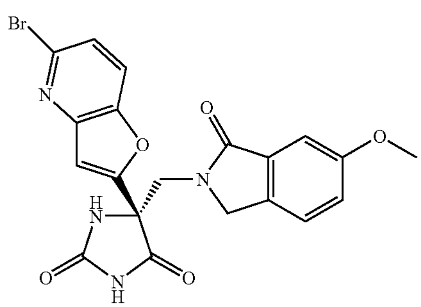 | 471.26 | 472.3[M + H]+ | A |

TABLE 6000-continued

| Compound ID | Structure | Exact Mass | Mass Obsvd | Ki (nM) |
|---|---|---|---|---|
| 9275 | 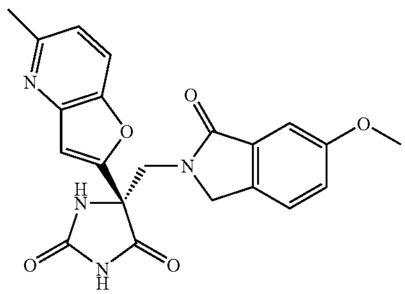 | 406.39 | 407.4[M + H]+ | A |
| 9276 | 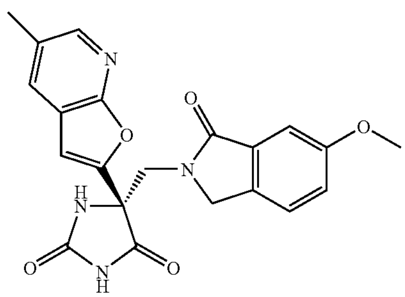 | 406.39 | 407.5[M + H]+ | A |
| 9277 | 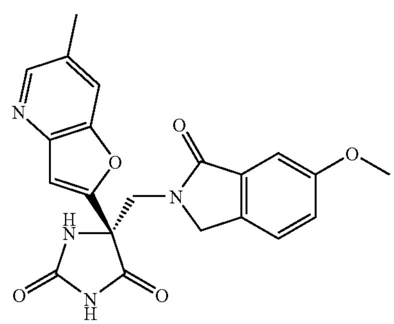 | 406.39 | 407.5[M + H]+ | A |
| 9278 | 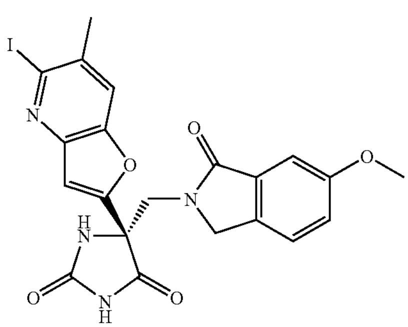 | 532.29 | 533.4[M + H]+ | A |

TABLE 6000-continued

| Compound ID | Structure | Exact Mass | Mass Obsvd | Ki (nM) |
|---|---|---|---|---|
| 9500 | 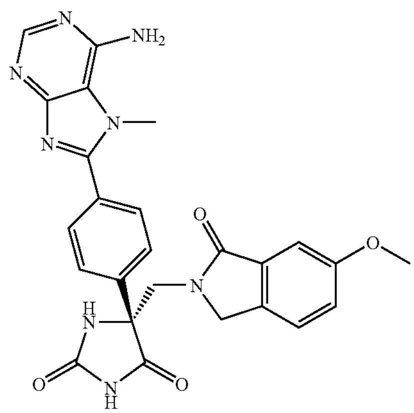 | 498.18 | 499.3[M + H]+ | A |
| 9501 | 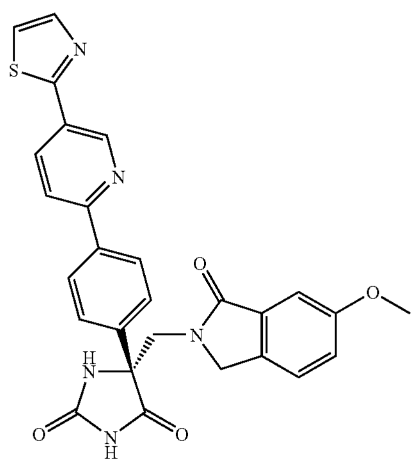 | 511.13 | 512.3[M + H]+ | A |
| 9502 | 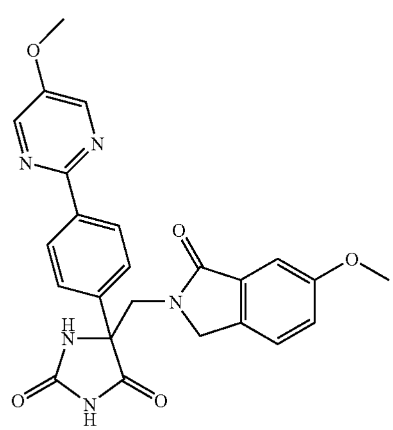 | 459.15 | 460.3[M + H]+ | A |

TABLE 6000-continued

| Compound ID | Structure | Exact Mass | Mass Obsvd | Ki (nM) |
|---|---|---|---|---|
| 9504 | 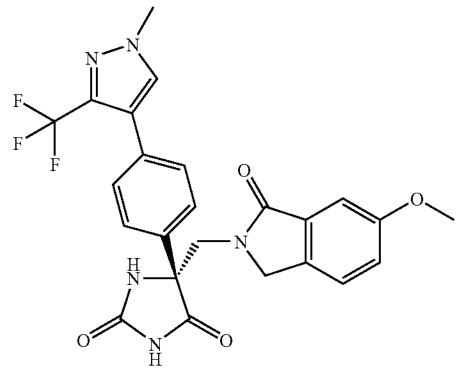 | 499.15 | 500.3[M + H]⁺ | A |
| 9505 | 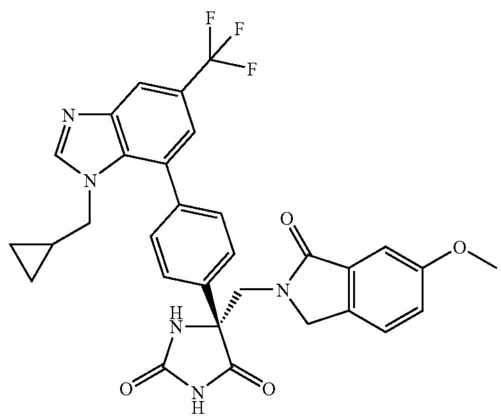 | 589.19 | 590.3[M + H]⁺ | A |
| 9506 | 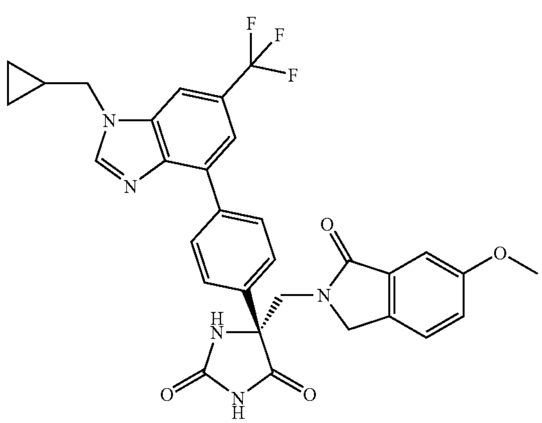 | 589.19 | 590.3[M + H]⁺ | A |
| 9507 | 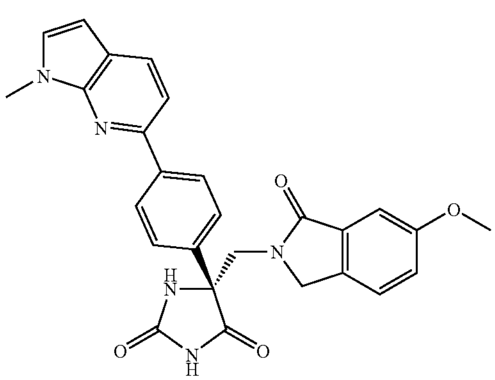 | 481.18 | 482.3[M + H]⁺ | A |

TABLE 6000-continued

| Compound ID | Structure | Exact Mass | Mass Obsvd | Ki (nM) |
|---|---|---|---|---|
| 9508 | 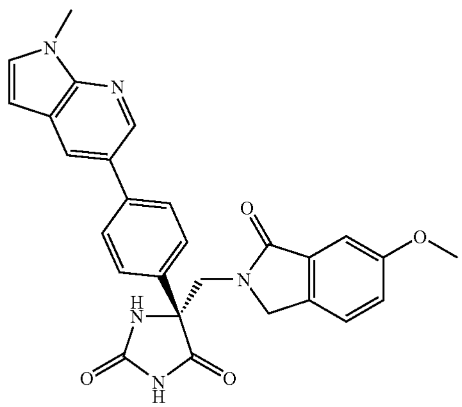 | 481.18 | 482.3[M + H]⁺ | A |
| 9509 | 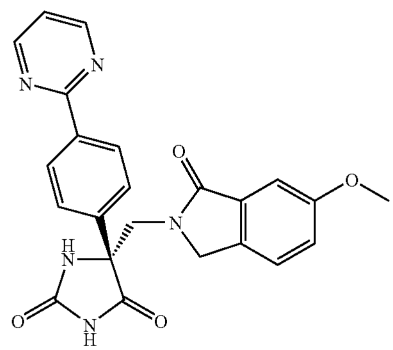 | 429.14 | 430.2[M + H]⁺ | A |
| 9510 | 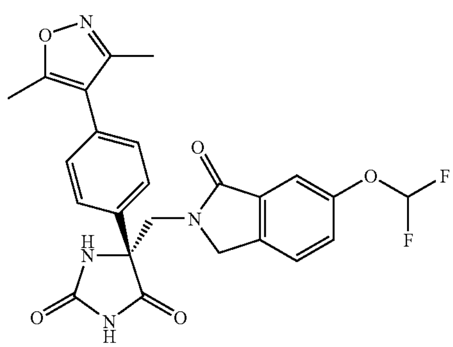 | 482.14 | 483.3[M + H]⁺ | A |
| 9511 | 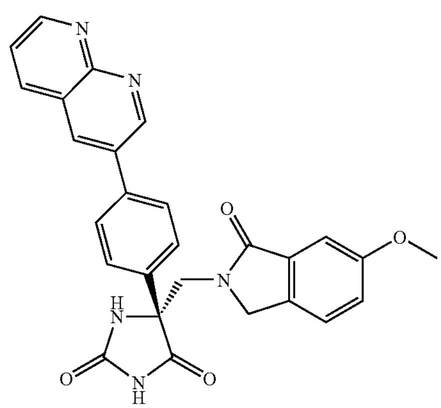 | 479.16 | 480.3 | A |

TABLE 6000-continued

| Compound ID | Structure | Exact Mass | Mass Obsvd | Ki (nM) |
|---|---|---|---|---|
| 9512 | 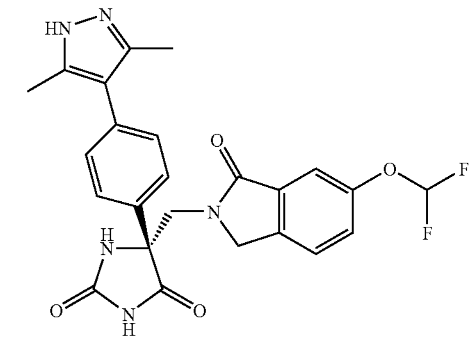 | 481.16 | 482.3[M + H]+ | A |
| 9513 | 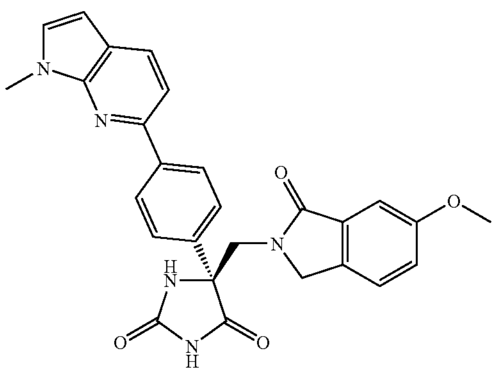 | 481.18 | 482.3[M + H]+ | B |
| 9514 | 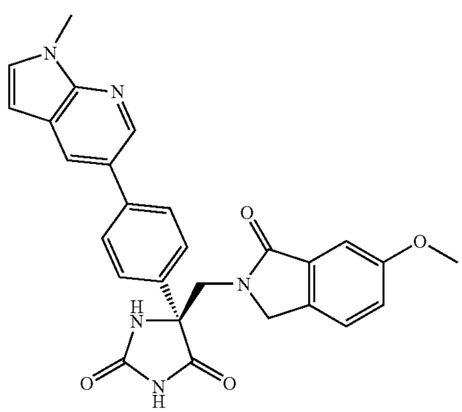 | 481.18 | 482.3[M + H]+ | B |
| 9515 | 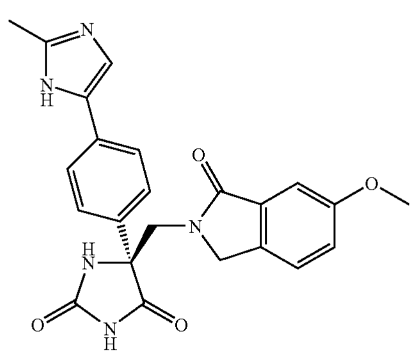 | 431.16 | 432.2[M + H]+ | C |

TABLE 6000-continued

| Compound ID | Structure | Exact Mass | Mass Obsvd | Ki (nM) |
|---|---|---|---|---|
| 9516 | 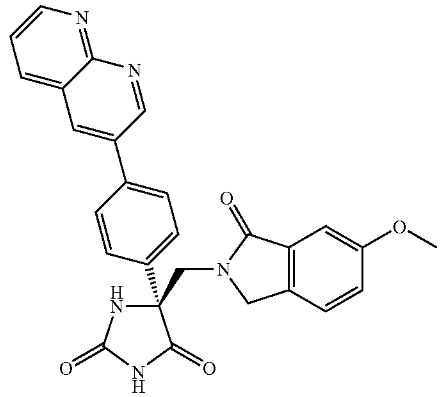 | 479.16 | 480.3[M + H]+ | N/A |
| 9517 | 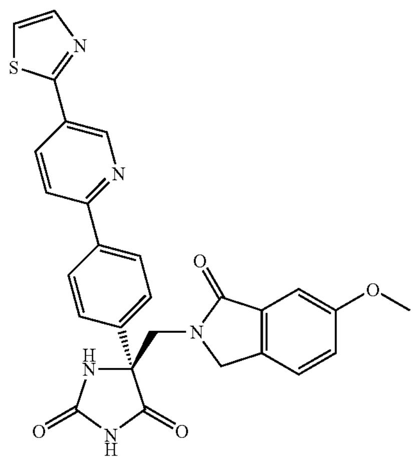 | 511.13 | 512.3[M + H]+ | C |
| 9901 | 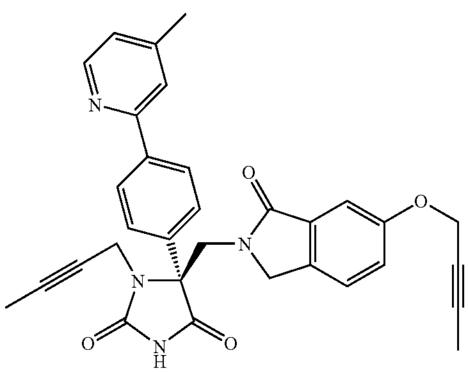 | 532.59 | 533.3[M + H]+ | C |
| 9902 | 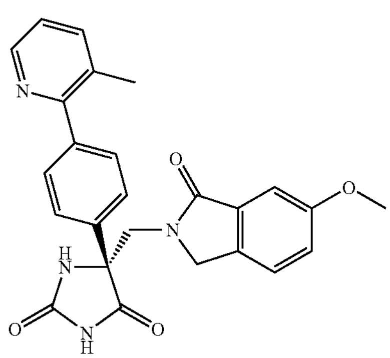 | 442.47 | 443.2[M + H]+ | A |

TABLE 6000-continued

| Compound ID | Structure | Exact Mass | Mass Obsvd | Ki (nM) |
|---|---|---|---|---|
| 9906 | 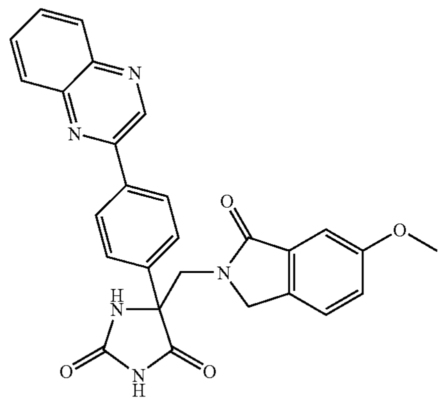 | 479.49 | 480.3[M + H]+ | A |
| 9908 | 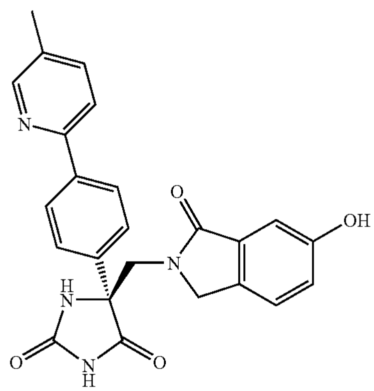 | 428.44 | 429.2[M + H]+ | C |
| 9909 | 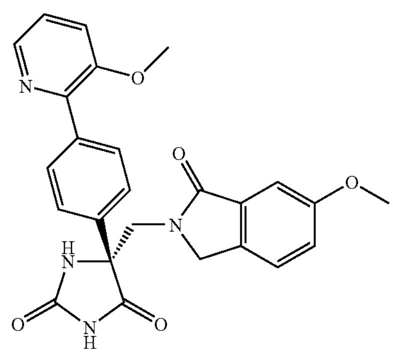 | 458.47 | 459.3[M + H]+ | A |
| 9913 | 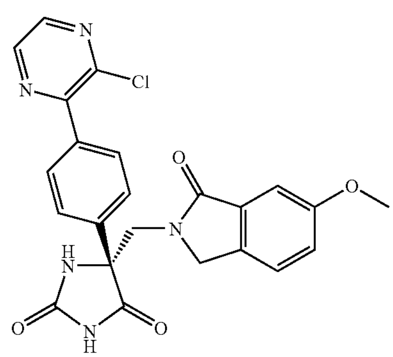 | 463.87 | 464.3[M + H]+ | A |

TABLE 6000-continued

| Compound ID | Structure | Exact Mass | Mass Obsvd | Ki (nM) |
|---|---|---|---|---|
| 9914 | 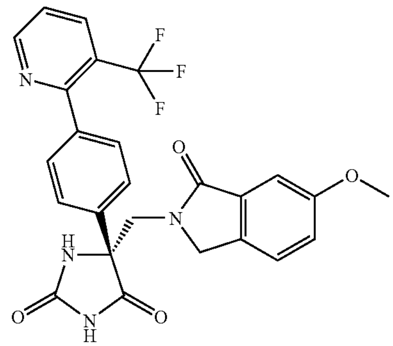 | 496.44 | 497.3[M + H]+ | A |
| 9915 | 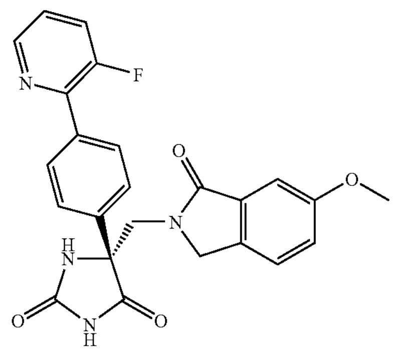 | 446.43 | 447.2[M + H]+ | A |
| 9916 | 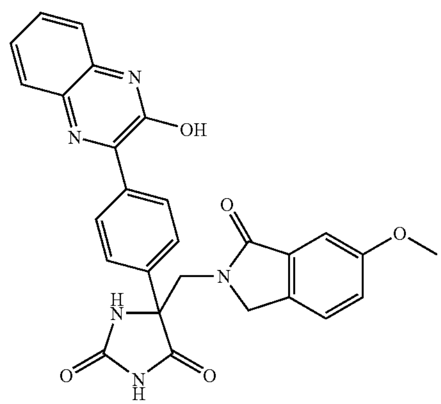 | 495.49 | 479.3 [(M-OH) + H]+ | A |
| 9923 | 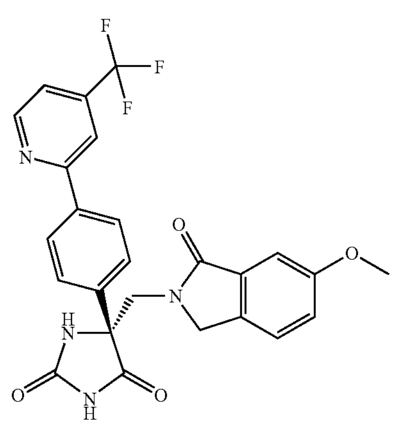 | 496.44 | 497.3[M + H]+ | A |

TABLE 6000-continued

| Compound ID | Structure | Exact Mass | Mass Obsvd | Ki (nM) |
|---|---|---|---|---|
| 9928 | 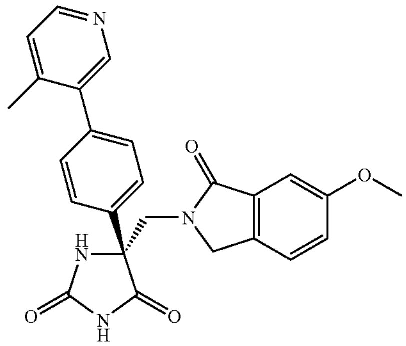 | 442.47 | 443.2[M + H]+ | A |
| 9520 | 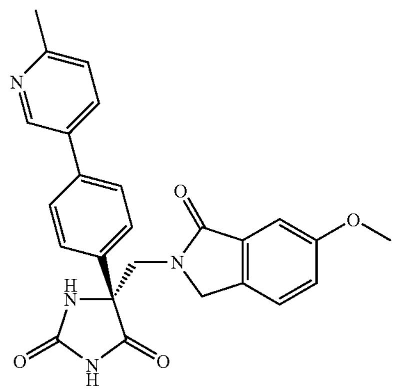 | 442.16 | 443.2[M + H]+ | A |
| 9521 | 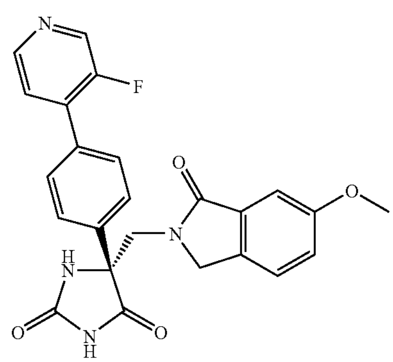 | 446.14 | 447.2[M + H]+ | A |
| 9522 | 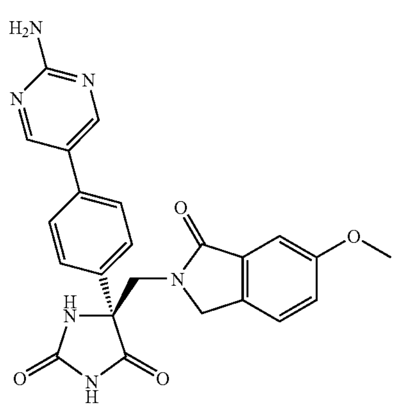 | 444.15 | 445.2[M + H]+ | A |

TABLE 6000-continued
| Compound ID | Structure | Exact Mass | Mass Obsvd | Ki (nM) |
|---|---|---|---|---|
| 9523 | 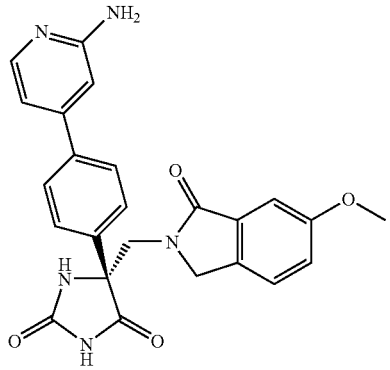 | 443.16 | 444.2[M + H]+ | A |
| 9636 | 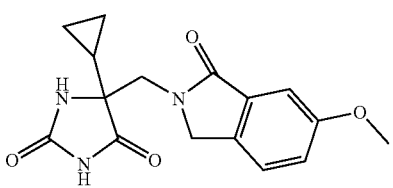 | 315.1 | 316.2[M + H]+ | B |
| 9637 | 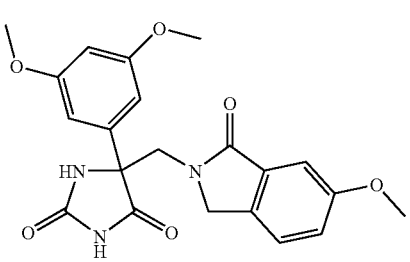 | 411.1 | 412.2[M + H]+ | A |
| 9700 | 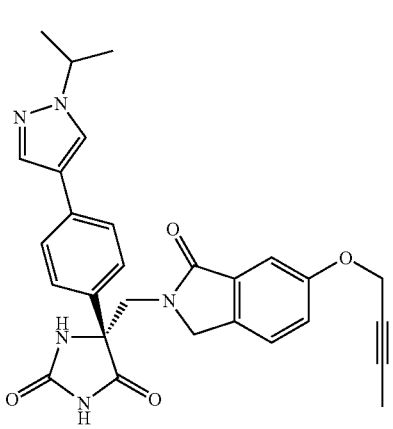 | 497.54 | 498.5[M + H]+ | A |

TABLE 6000-continued

| Compound ID | Structure | Exact Mass | Mass Obsvd | Ki (nM) |
|---|---|---|---|---|
| 9701 | 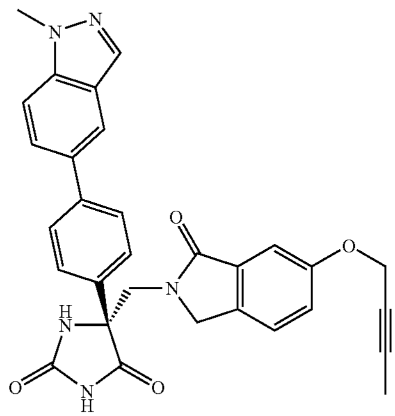 | 519.55 | 520.5[M + H]+ | A |
| 9702 | 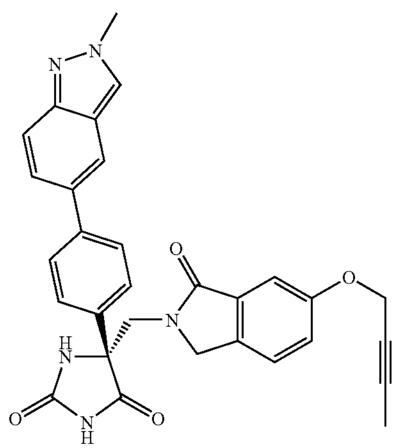 | 519.55 | 520.5[M + H]+ | A |
| 9703 | 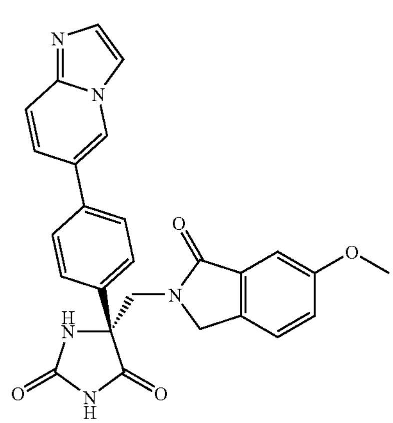 | 467.47 | 468.5[M + H]+ | A |

TABLE 6000-continued

| Compound ID | Structure | Exact Mass | Mass Obsvd | Ki (nM) |
|---|---|---|---|---|
| 9704 | 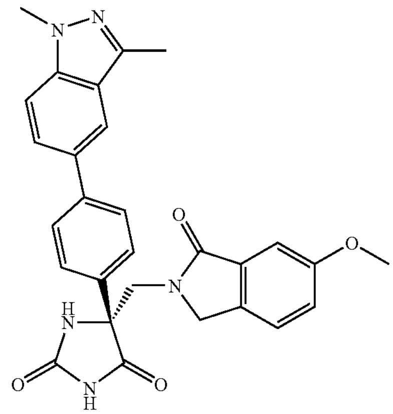 | 495.52 | 496.5[M + H]+ | A |
| 9705 | 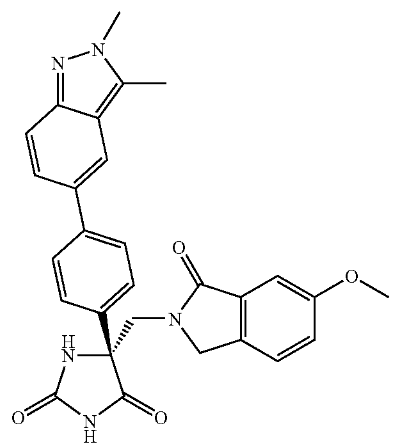 | 495.52 | 496.5[M + H]+ | A |
| 9706 | 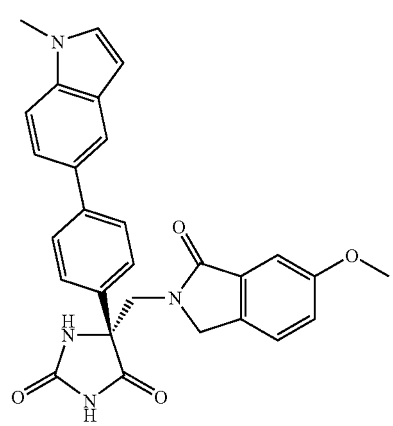 | 480.51 | 481.5[M + H]+ | A |

TABLE 6000-continued
| Compound ID | Structure | Exact Mass | Mass Obsvd | Ki (nM) |
|---|---|---|---|---|
| 9707 | 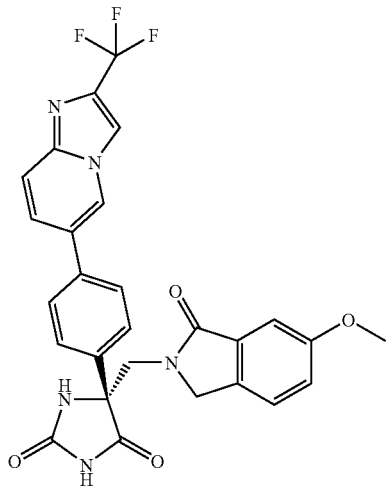 | 535.47 | 536.4[M + H]+ | A |
| 9708 | 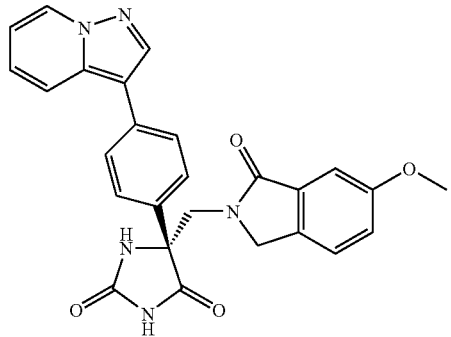 | 467.47 | 468.5[M + H]+ | A |
| 9709 | 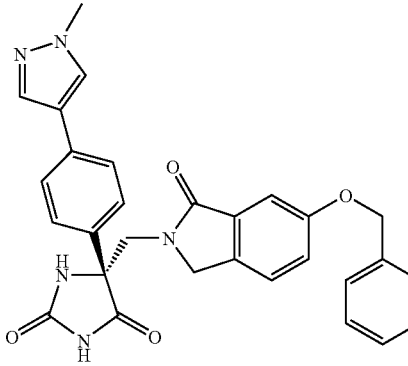 | 507.53 | 508.5[M + H]+ | A |

TABLE 6000-continued

| Compound ID | Structure | Exact Mass | Mass Obsvd | Ki (nM) |
|---|---|---|---|---|
| 9710 | 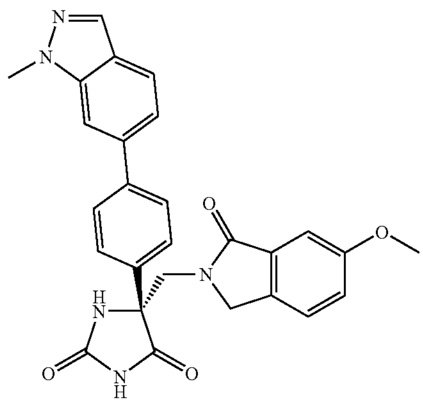 | 481.50 | 482.5[M + H]⁺ | A |
| 9711 | 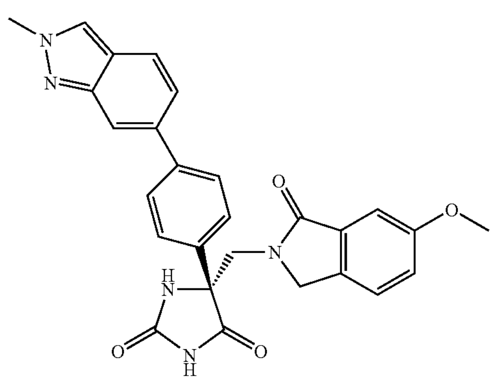 | 481.50 | 482.5[M + H]⁺ | A |
| 9712 | 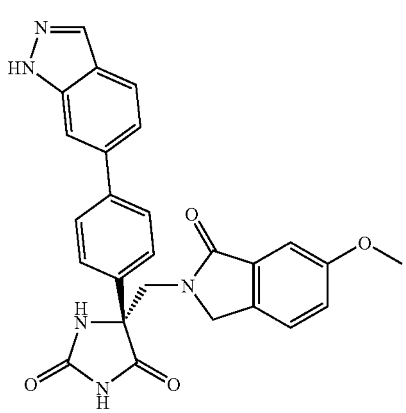 | 467.47 | 468.4[M + H]⁺ | A |

TABLE 6000-continued

| Compound ID | Structure | Exact Mass | Mass Obsvd | Ki (nM) |
|---|---|---|---|---|
| 9714 | 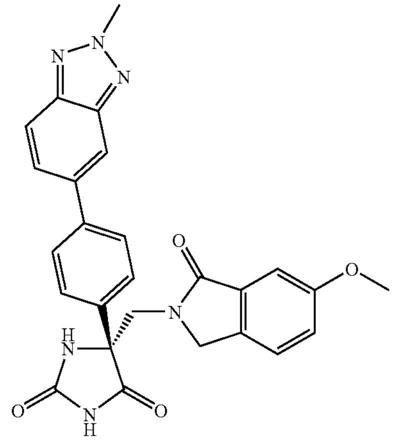 | 482.49 | 483.5[M + H]+ | A |
| 9715 | 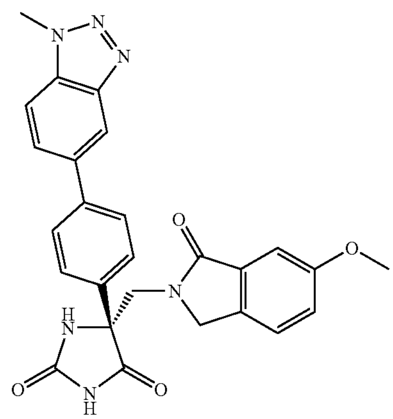 | 482.49 | 483.5[M + H]+ | A |
| 9716 | 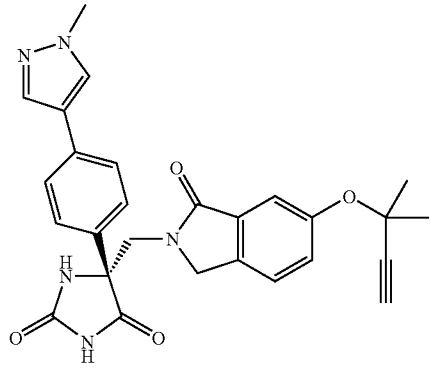 | 483.51 | 484.5[M + H]+ | C |

TABLE 6000-continued

| Compound ID | Structure | Exact Mass | Mass Obsvd | Ki (nM) |
|---|---|---|---|---|
| 9717 | 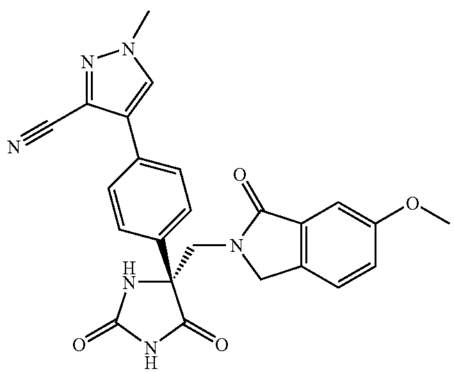 | 456.45 | 457.5[M + H]+ | A |
| 9730 | 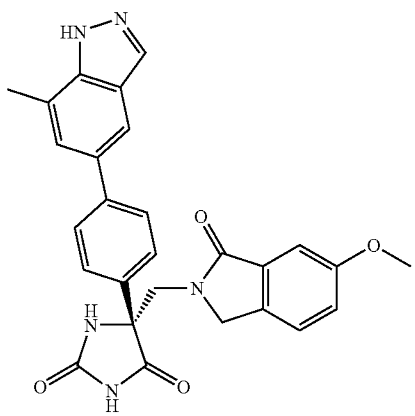 | 481.5 | 482.3[M + H]+ | A |
| 9731 | 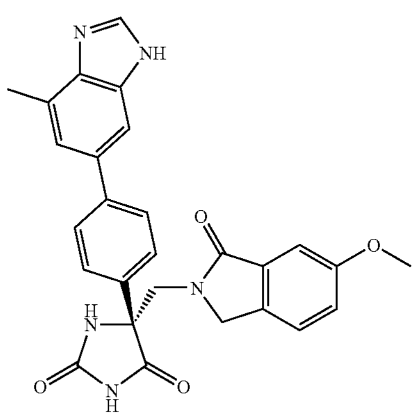 | 481.5 | 482.3[M + H]+ | A |

TABLE 6000-continued
| Compound ID | Structure | Exact Mass | Mass Obsvd | Ki (nM) |
|---|---|---|---|---|
| 9732 | 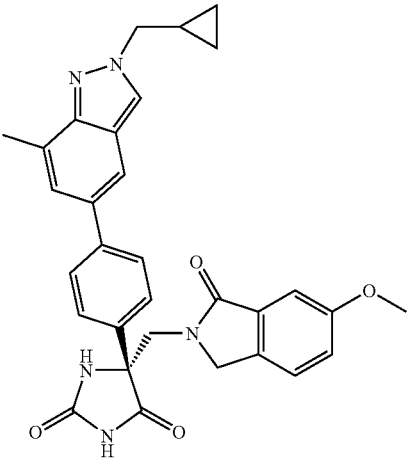 | 535.6 | 536.3[M + H]⁺ | A |
| 9733 | 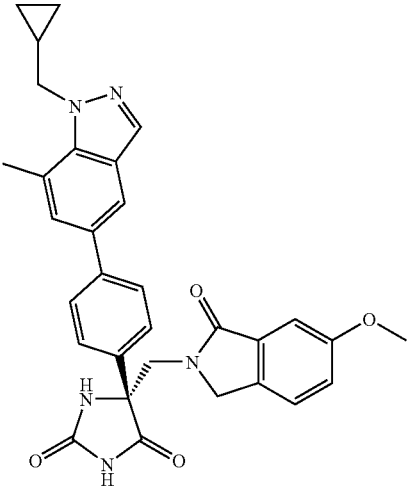 | 535.6 | 536.3[M + H]⁺ | B |
| 9734 | 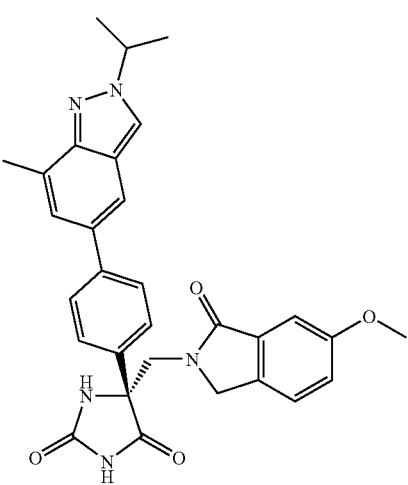 | 523.6 | 524.3[M + H]⁺ | A |

TABLE 6000-continued

| Compound ID | Structure | Exact Mass | Mass Obsvd | Ki (nM) |
|---|---|---|---|---|
| 9735 | 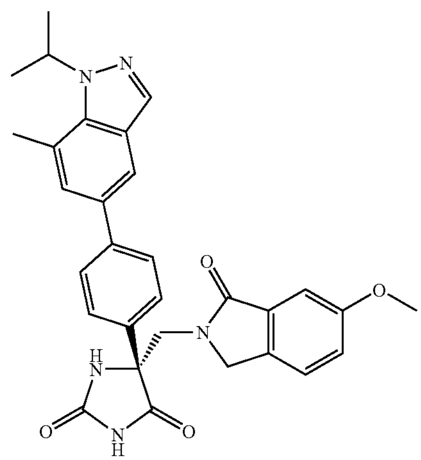 | 523.6 | 524.3[M + H]+ | A |
| 9736 | 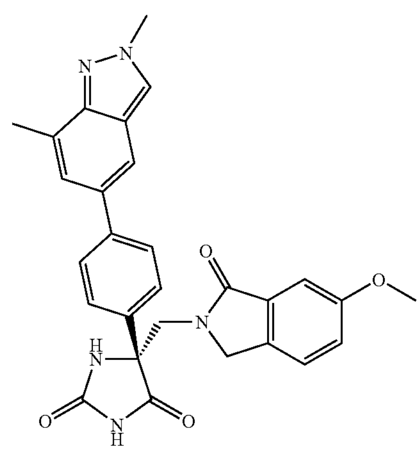 | 495.5 | 496.3[M + H]+ | A |
| 9737 | 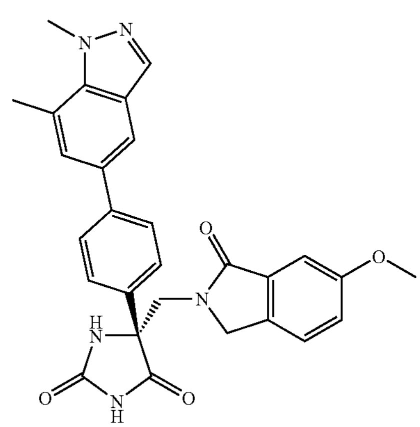 | 495.5 | 496.3[M + H]+ | A |

TABLE 6000-continued
| Compound ID | Structure | Exact Mass | Mass Obsvd | Ki (nM) |
|---|---|---|---|---|
| 9738 | 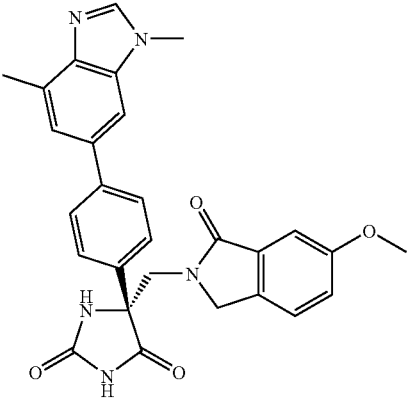 | 495.5 | 496.3[M + H]⁺ | A |
| 9739 | 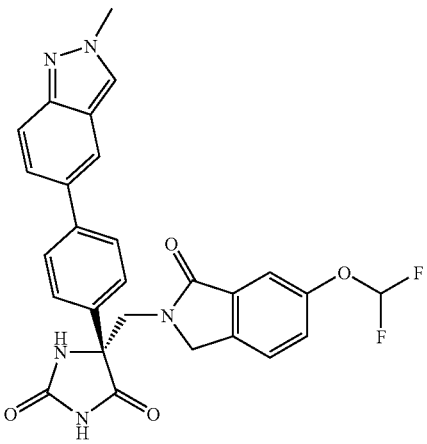 | 517.5 | 518.3[M + H]⁺ | A |
| 9740 | 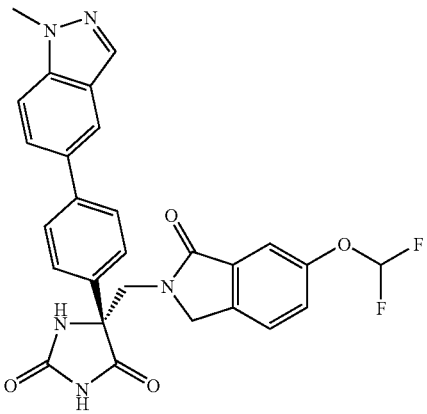 | 517.5 | 518.3[M + H]⁺ | A |

TABLE 6000-continued
| Compound ID | Structure | Exact Mass | Mass Obsvd | Ki (nM) |
|---|---|---|---|---|
| 9741 | 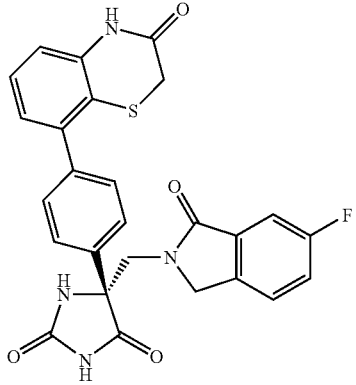 | 502.5 | 380.2[M + H]+ | A |
| 9742 | 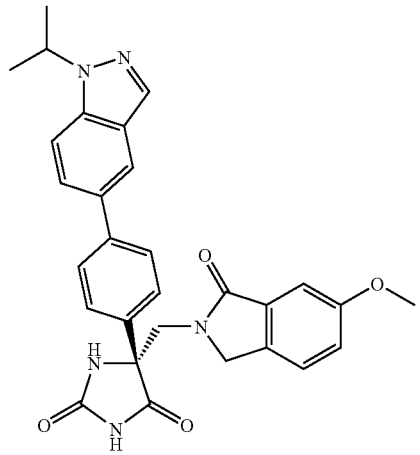 | 509.6 | 380.2[M + H]+ | A |
| 9743 | 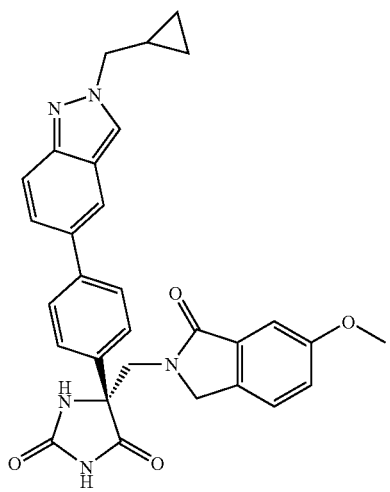 | 521.6 | 380.2[M + H]+ | A |

TABLE 6000-continued

| Compound ID | Structure | Exact Mass | Mass Obsvd | Ki (nM) |
|---|---|---|---|---|
| 9744 | 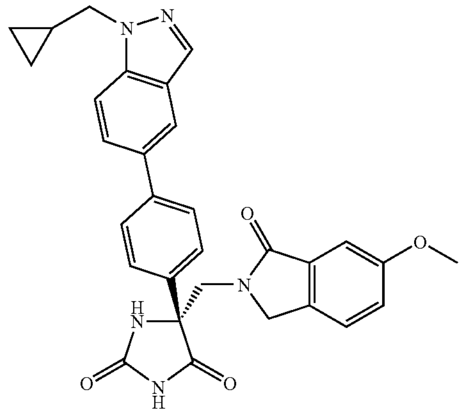 | 521.6 | 380.2[M + H]+ | A |
| 9745 | 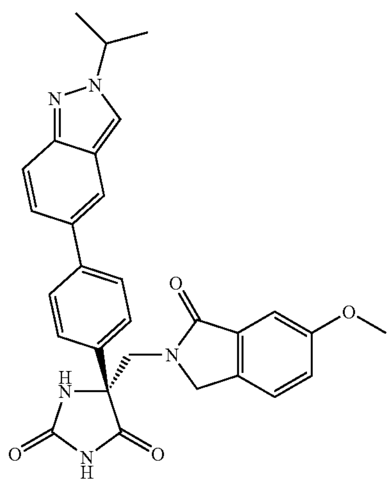 | 509.6 | 380.2[M + H]+ | A |
| 9746 | 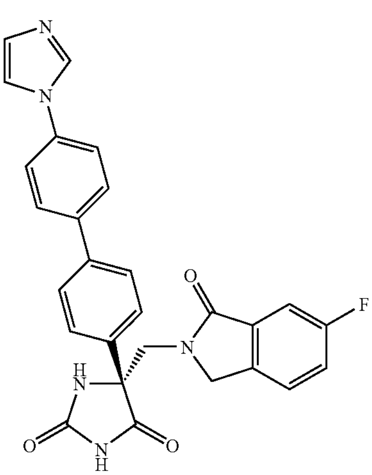 | 481.5 | 380.2[M + H]+ | A |

TABLE 6000-continued
| Compound ID | Structure | Exact Mass | Mass Obsvd | Ki (nM) |
|---|---|---|---|---|
| 9748 | 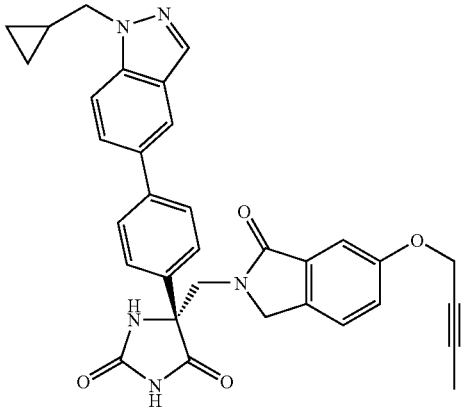 | 559.6 | 380.2[M + H]+ | B |
| 9749 | 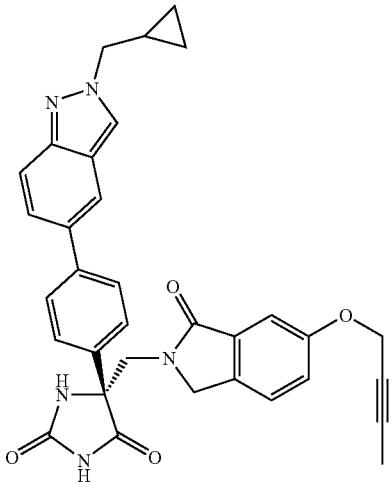 | 559.6 | 380.2[M + H]+ | A |
| 9750 | 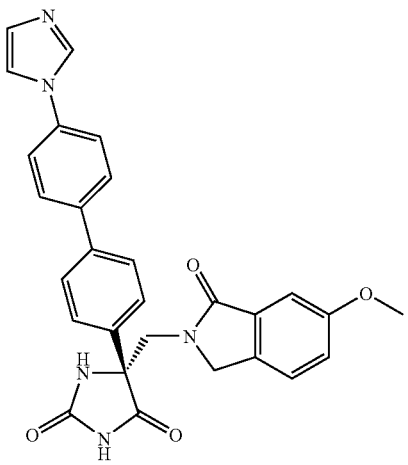 | 493.5 | 494.3[M + H]+ | A |

TABLE 6000-continued

| Compound ID | Structure | Exact Mass | Mass Obsvd | Ki (nM) |
|---|---|---|---|---|
| 9751 | 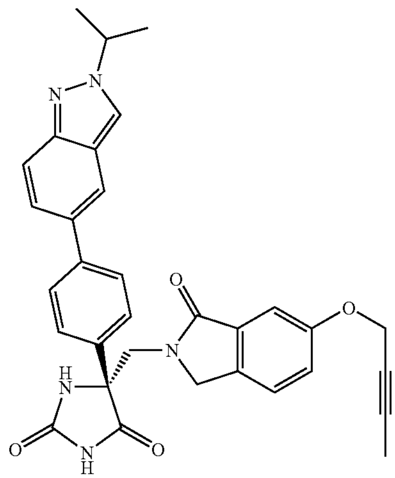 | 547.6 | 548.3[M + H]+ | A |
| 9752 | 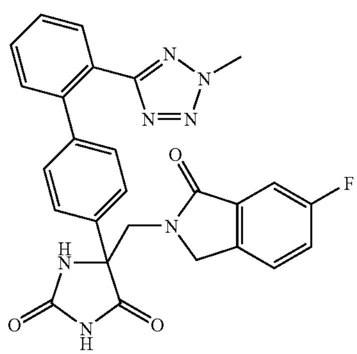 | 497.5 | 498.3[M + H]+ | A |
| 9753 | 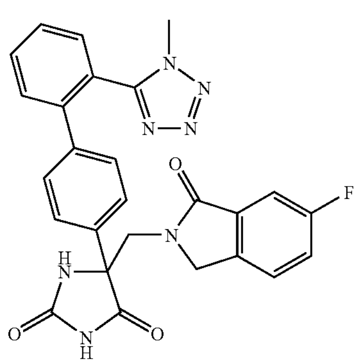 | 497.5 | 498.3[M + H]+ | B |

TABLE 6000-continued
| Compound ID | Structure | Exact Mass | Mass Obsvd | Ki (nM) |
|---|---|---|---|---|
| 9754 | 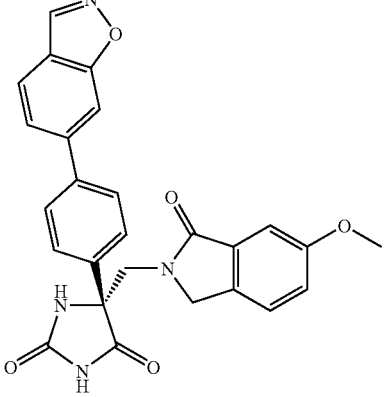 | 468.5 | 469.3[M + H]+ | A |
| 9755 | 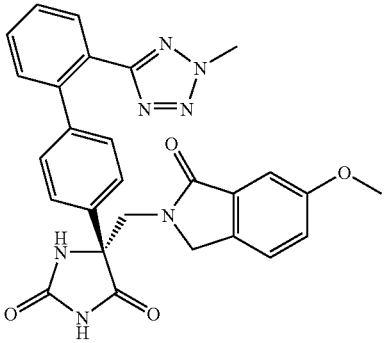 | 509.5 | 510.3[M + H]+ | A |
| 9756 | 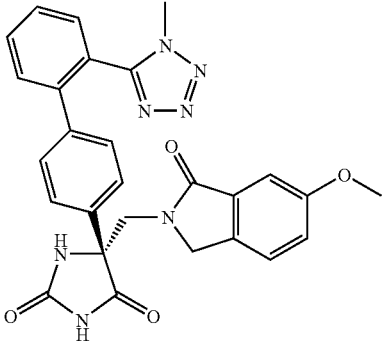 | 509.5 | 510.3[M + H]+ | A |
| 9757 | 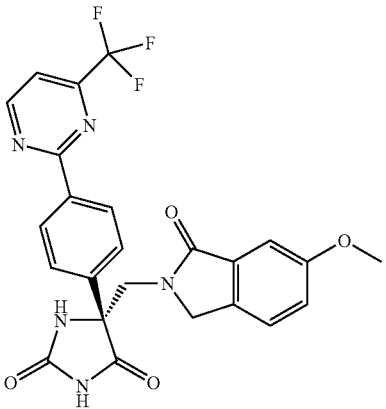 | 497.4 | 498.3[M + H]+ | A |

TABLE 6000-continued

| Compound ID | Structure | Exact Mass | Mass Obsvd | Ki (nM) |
|---|---|---|---|---|
| 9758 | 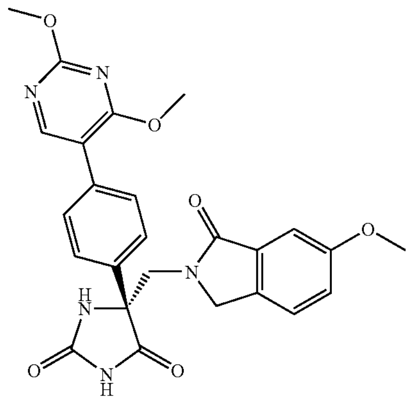 | 489.5 | 490.3[M + H]+ | A |
| 9759 | 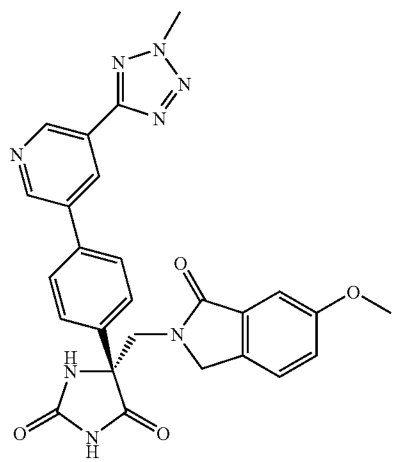 | 510.5 | 511.3[M + H]+ | A |
| 9760 | 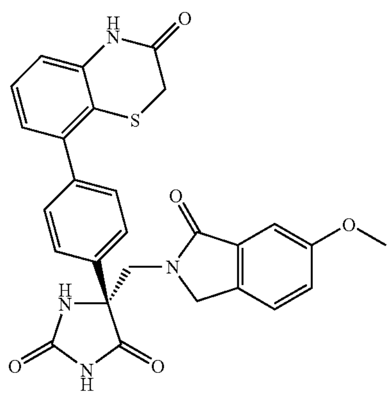 | 514.6 | 515.3[M + H]+ | A |
| 9600 | 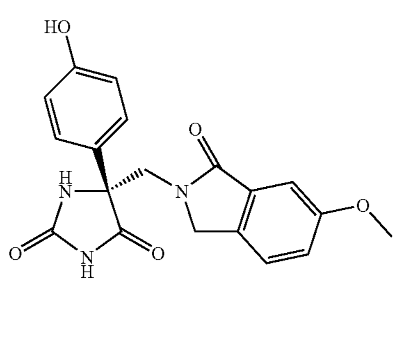 | 367.1 | 368.2[M + H]+ | A |

TABLE 6000-continued

| Compound ID | Structure | Exact Mass | Mass Obsvd | Ki (nM) |
|---|---|---|---|---|
| 9601 | 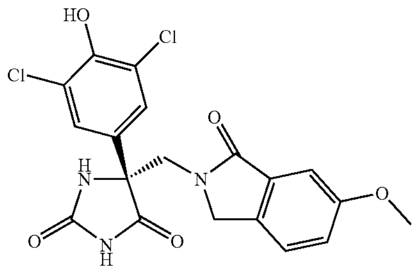 | 435.0 | 436.2[M + H]+ | A |
| 9602 | 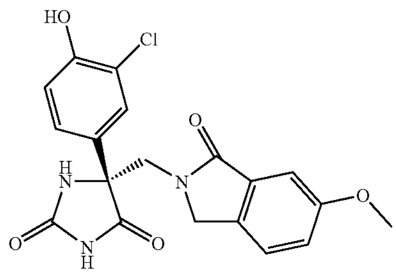 | 401.1 | 402.2[M + H]+ | A |
| 9603 | 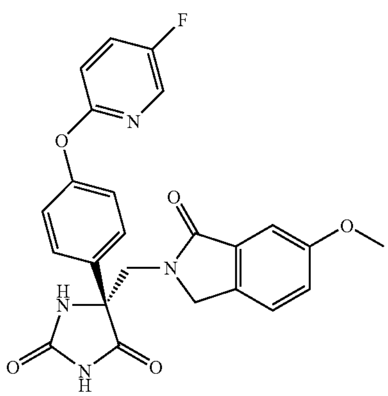 | 462.1 | 463.2[M + H]+ | A |
| 9607 | 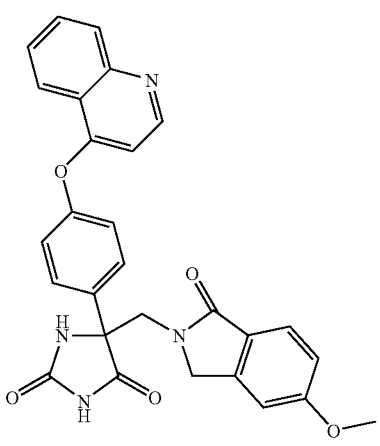 | 494.2 | 495.3[M + H]+ | A |

TABLE 6000-continued

| Compound ID | Structure | Exact Mass | Mass Obsvd | Ki (nM) |
|---|---|---|---|---|
| 9608 | 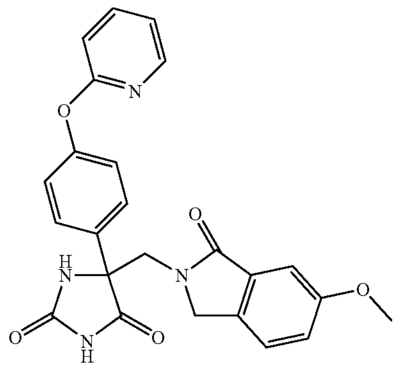 | 444.1 | 445.2[M + H]+ | B |
| 9609 | 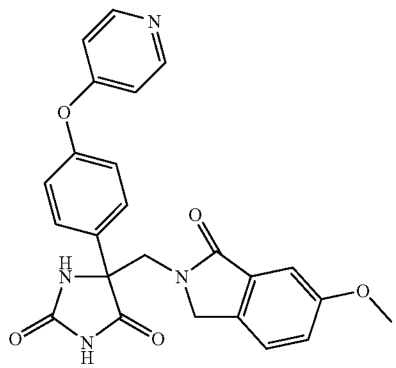 | 444.1 | 445.2[M + H]+ | C |
| 9610 | 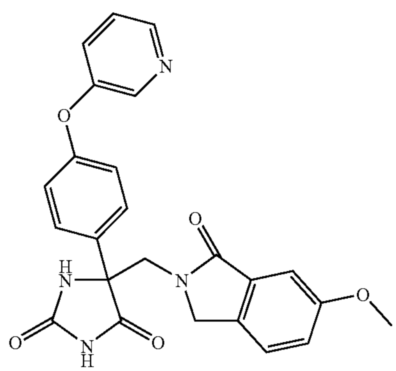 | 444.1 | 445.2[M + H]+ | A |
| 9611 | 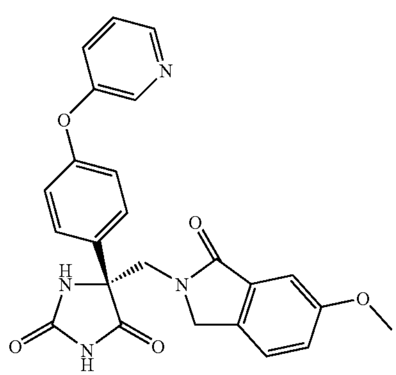 | 444.1 | 445.2[M + H]+ | A |

TABLE 6000-continued

| Compound ID | Structure | Exact Mass | Mass Obsvd | Ki (nM) |
| --- | --- | --- | --- | --- |
| 9612 | 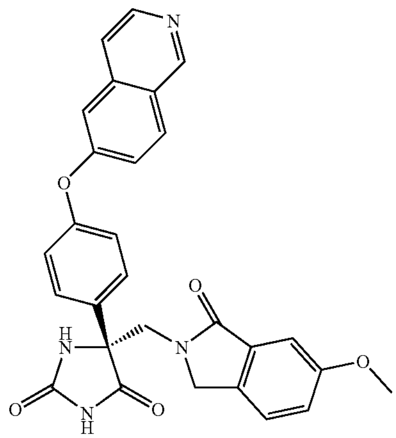 | 494.1 | 495.3[M + H]+ | A |
| 9613 | 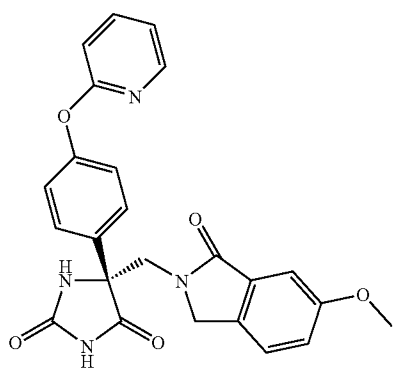 | 444.1 | 445.2[M + H]+ | A |
| 9614 | 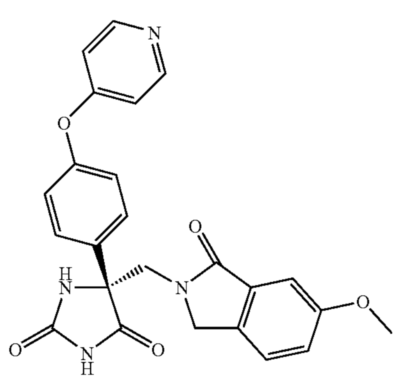 | 444.1 | 445.2[M + H]+ | A |

TABLE 6000-continued

| Compound ID | Structure | Exact Mass | Mass Obsvd | Ki (nM) |
|---|---|---|---|---|
| 9615 | 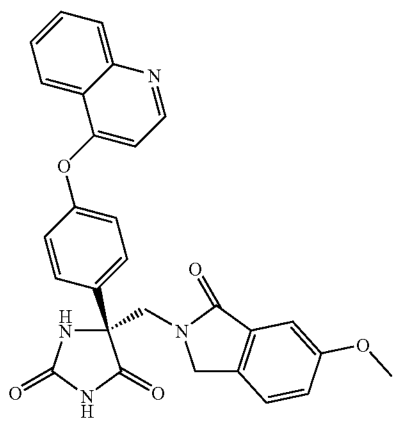 | 494.2 | 495.3[M + H]+ | A |
| 9618 | 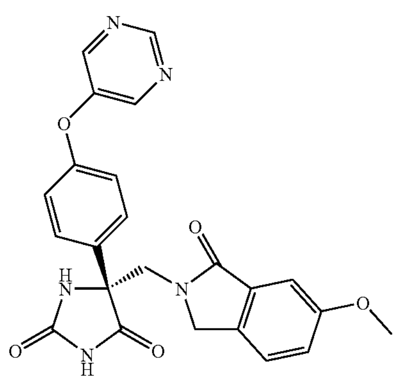 | 445.1 | 446.2[M + H]+ | A |
| 9619 | 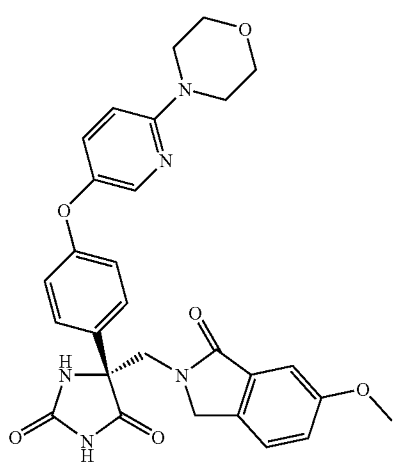 | 529.2 | 530.3[M + H]+ | A |

TABLE 6000-continued

| Compound ID | Structure | Exact Mass | Mass Obsvd | Ki (nM) |
|---|---|---|---|---|
| 9624 | 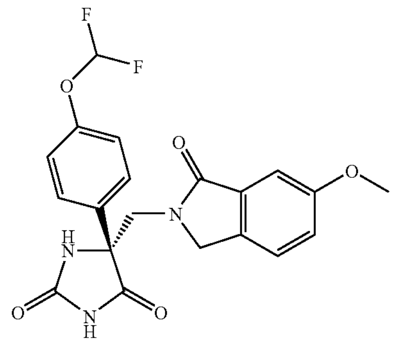 | 417.1 | 418.2[M + H]+ | A |
| 9625 | 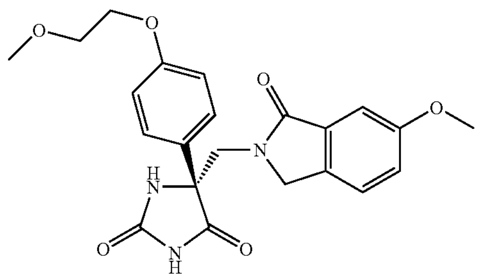 | 425.2 | 426.2[M + H]+ | A |
| 9626 | 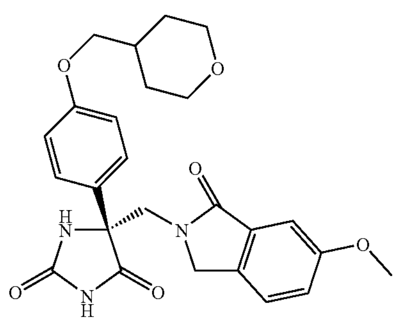 | 465.2 | 466.3[M + H]+ | A |
| 9627 | 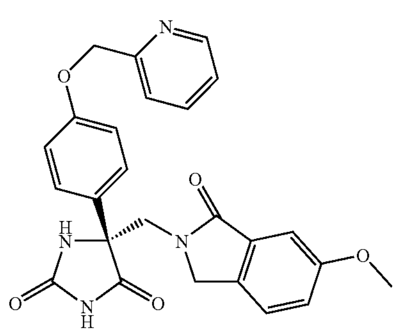 | 458.2 | 459.3[M + H]+ | A |

TABLE 6000-continued

| Compound ID | Structure | Exact Mass | Mass Obsvd | Ki (nM) |
|---|---|---|---|---|
| 9628 | 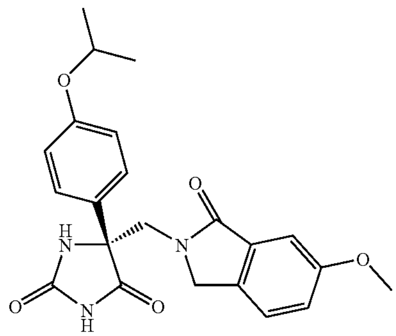 | 409.1 | 410.2[M + H]+ | A |
| 9629 | 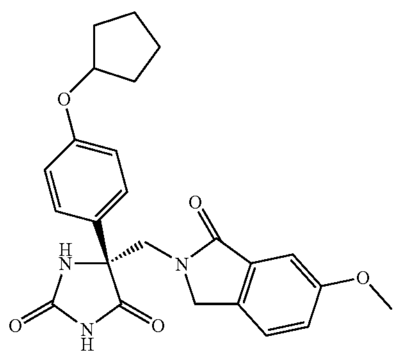 | 435.2 | 436.2[M + H]+ | A |
| 9632 | 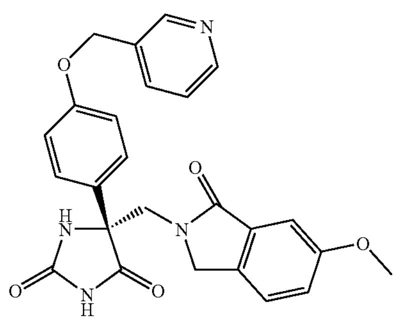 | 458.2 | 459.3[M + H]+ | A |
| 9633 | 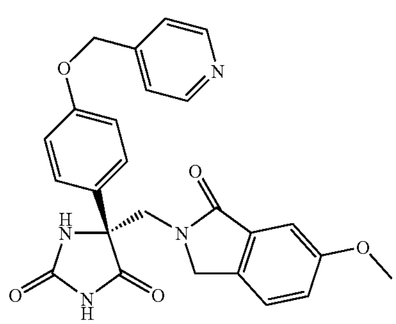 | 458.2 | 459.3[M + H]+ | A |

TABLE 6000-continued

| Compound ID | Structure | Exact Mass | Mass Obsvd | Ki (nM) |
|---|---|---|---|---|
| 9634 | 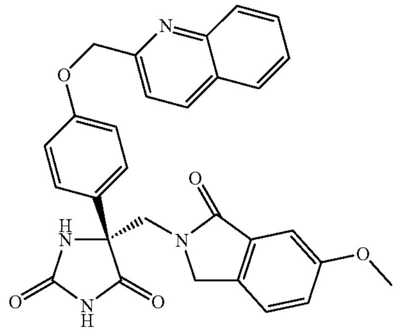 | 508.2 | 509.3[M + H]+ | A |
| 9638 | 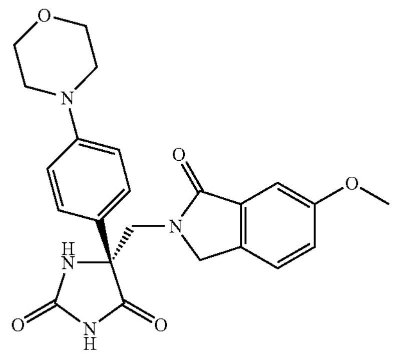 | 436.2 | 437.2[M + H]+ | A |
| 9650 | 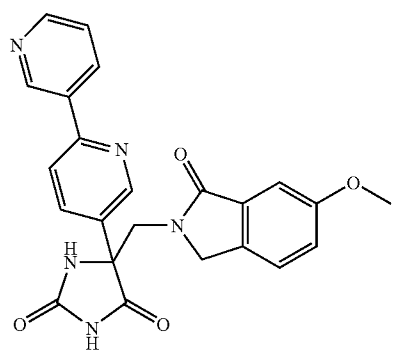 | 429.14 | 430.2[M + H]+ | A |
| 9651 | 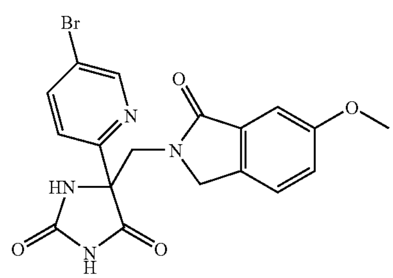 | 430.03 | 431.2[M + H]+ | A |
| 9652 | 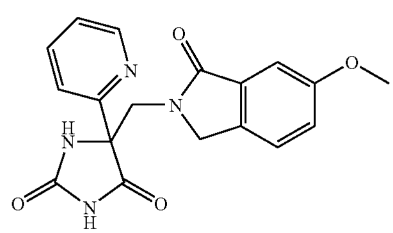 | 352.12 | 353.2[M + H]+ | A |

TABLE 6000-continued

| Compound ID | Structure | Exact Mass | Mass Obsvd | Ki (nM) |
|---|---|---|---|---|
| 9653 | 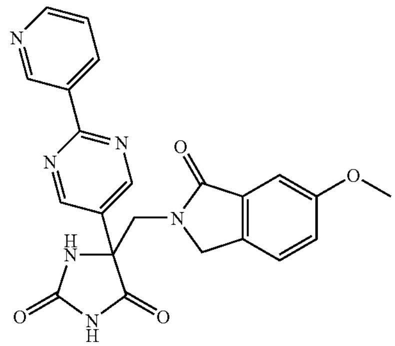 | 430.14 | 431.2[M + H]+ | A |
| 9002C | 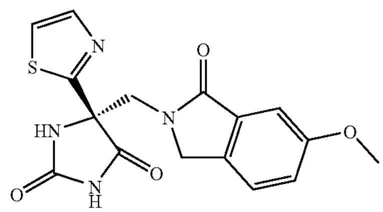 | 358.07 | 359.0[M + H]+ | A |
| 9002D | 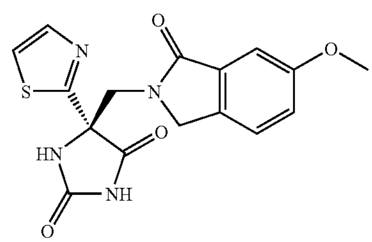 | 358.07 | 359.0[M + H]+ | B |
| 9003D | 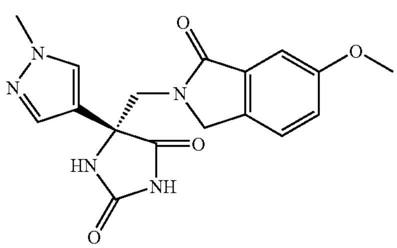 | 355.13 | 356.1[M + H]+ | A |
| 9003E | 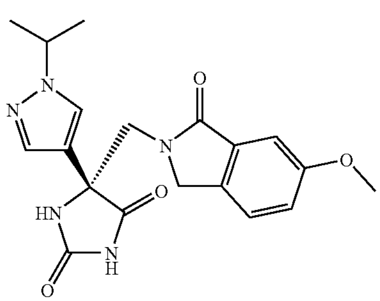 | 383.16 | 384.2[M + H]+ | A |

TABLE 6000-continued

| Compound ID | Structure | Exact Mass | Mass Obsvd | Ki (nM) |
|---|---|---|---|---|
| 9003F | 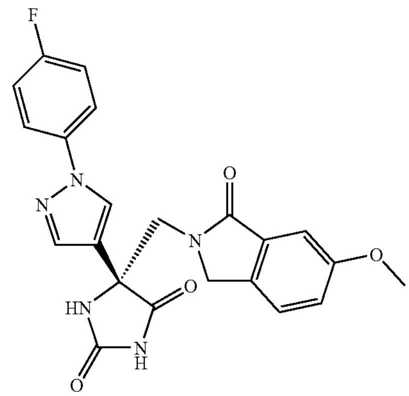 | 435.13 | 436.1[M + H]⁺ | A |
| 9003G | 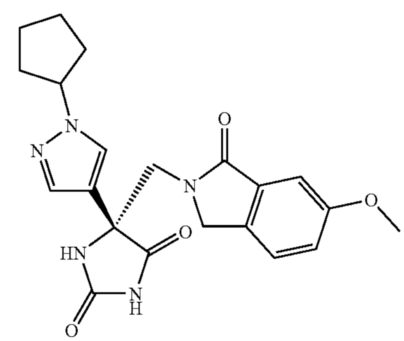 | 409.17 | 410.2[M + H]⁺ | A |
| 9003H | 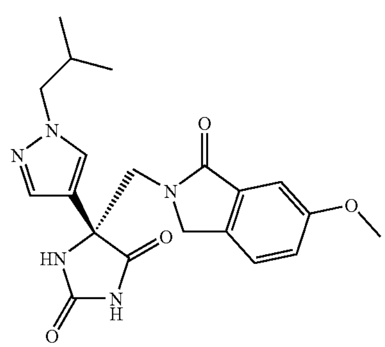 | 397.17 | 398.2[M + H]⁺ | A |
| 9003I | 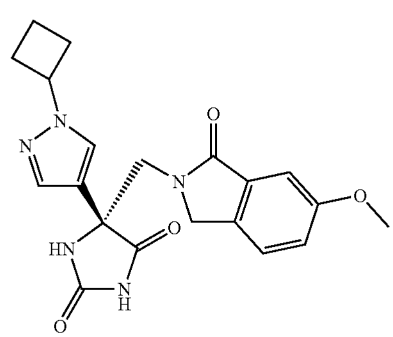 | 395.16 | 396.1[M + H]⁺ | A |

TABLE 6000-continued

| Compound ID | Structure | Exact Mass | Mass Obsvd | Ki (nM) |
|---|---|---|---|---|
| 9003J | 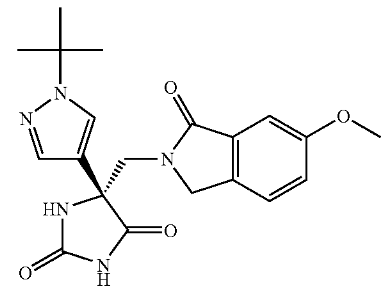 | 397.17 | 398.2[M + H]⁺ | A |
| 9003K | 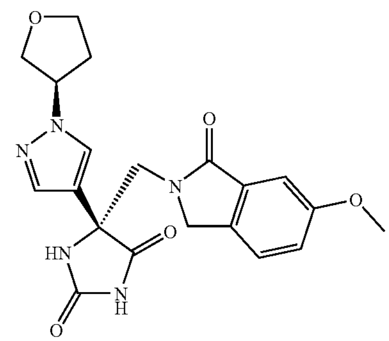 | 411.15 | 412.1[M + H]⁺ | A |
| 9003L | 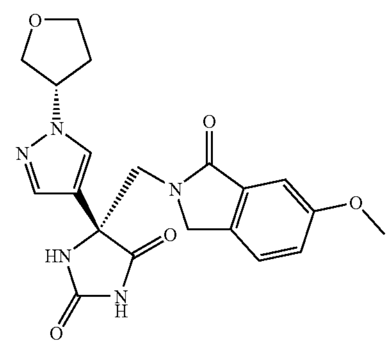 | 411.15 | 412.1[M + H]⁺ | A |
| 9003M | 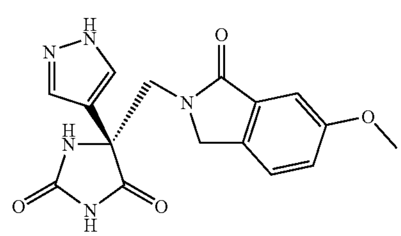 | 341.11 | 342.2[M + H]⁺ | A |
| 9004B | 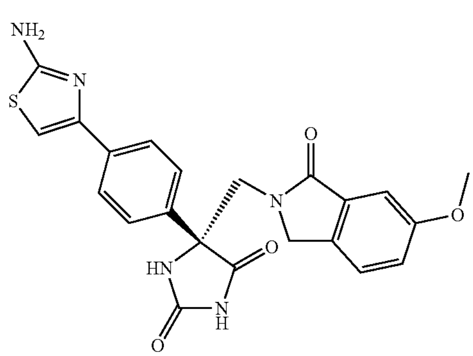 | 449.12 | 450.1[M + H]⁺ | A |

TABLE 6000-continued

| Compound ID | Structure | Exact Mass | Mass Obsvd | Ki (nM) |
|---|---|---|---|---|
| 9004C | 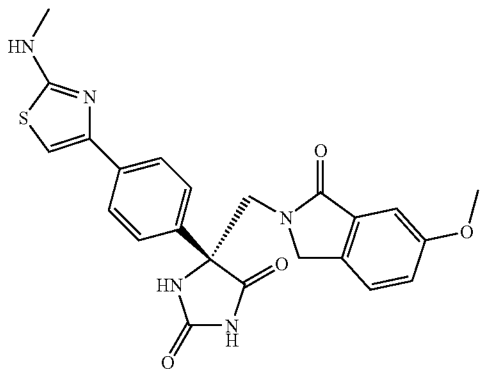 | 463.12 | 464.1 [M + H]+ | A |
| 9004D | 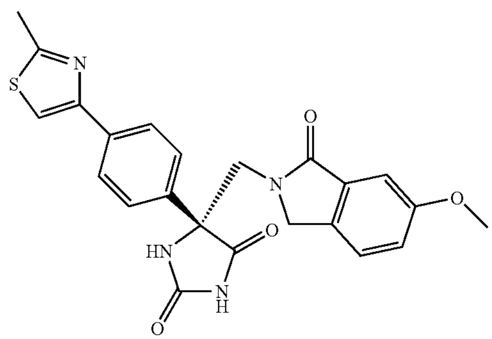 | 448.12 | 449.1 [M + H]+ | A |
| 9004E | 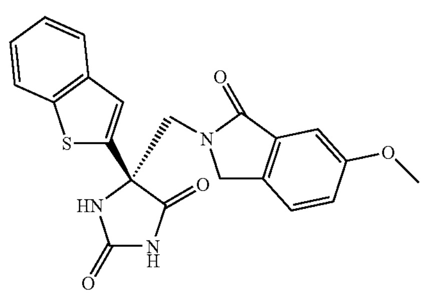 | 407.20 | 408.1 [M + H]+ | A |
| 9005 | 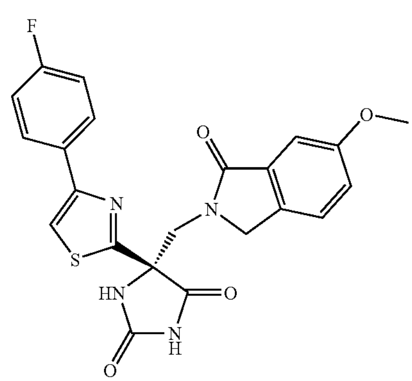 | 452.10 | 453.1 [M + H]+ | A |

TABLE 6000-continued

| Compound ID | Structure | Exact Mass | Mass Obsvd | Ki (nM) |
|---|---|---|---|---|
| 9930 | 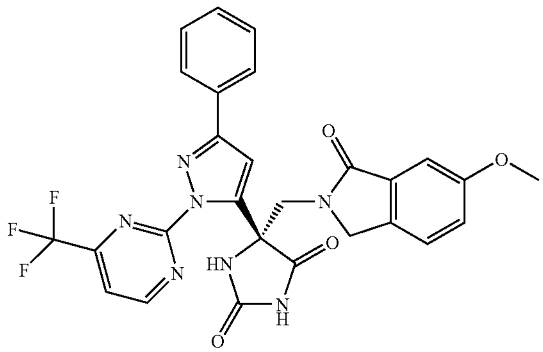 | 563.15 | 564.3[M + H]+ | A |
| 9931 | 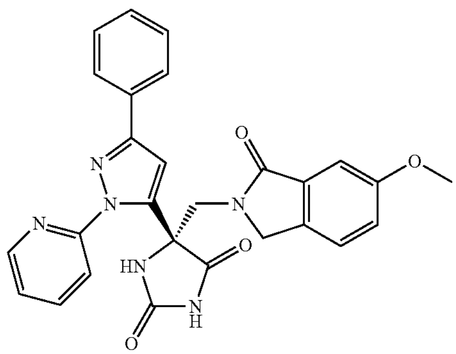 | 494.17 | 495.3[M + H]+ | A |
| 9932 | 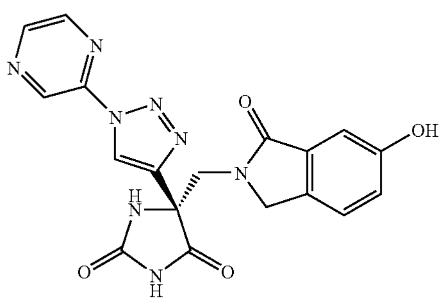 | 406.35 | 407.2[M + H]+ | A |
| 9933 | 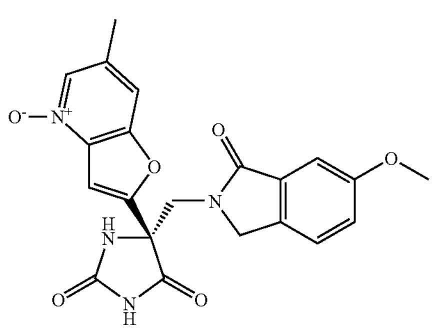 | 422.12 | 423.2[M + H]+ | A |

TABLE 6000-continued

| Compound ID | Structure | Exact Mass | Mass Obsvd | Ki (nM) |
|---|---|---|---|---|
| 9934 | 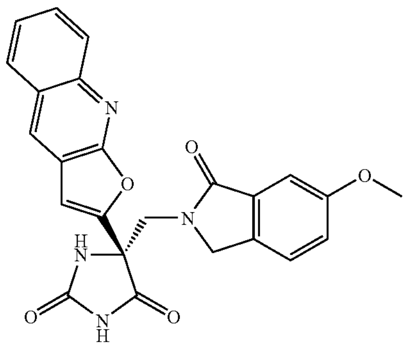 | 442.13 | 443.2[M + H]⁺ | A |
| 9935 | 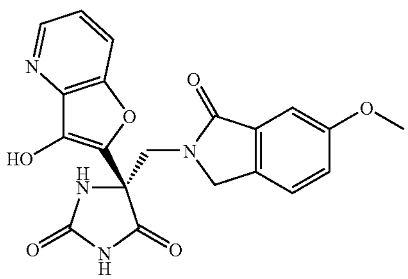 | 408.11 | 409.1[M + H]⁺ | A |
| 9937 | 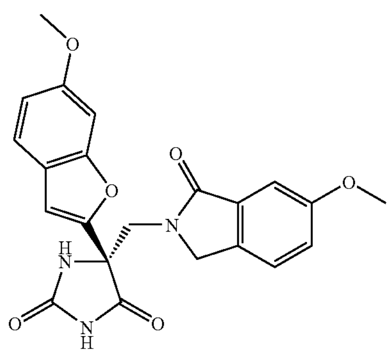 | 421.13 | 422.2[M + H]⁺ | A |
| 9938 | 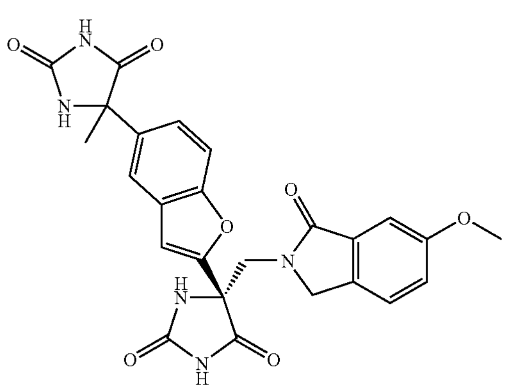 | 503.14 | 504.3[M + H]⁺ | A |

TABLE 6000-continued

| Compound ID | Structure | Exact Mass | Mass Obsvd | Ki (nM) |
|---|---|---|---|---|
| 9939 | 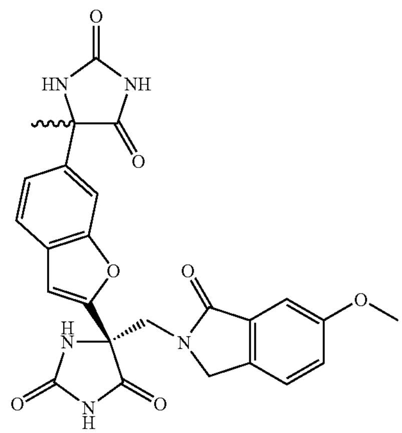 | 503.14 | 504.3[M + H]+ | A |
| 9940 | 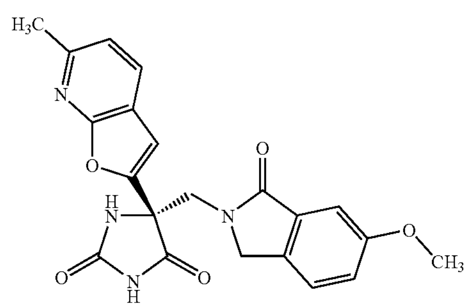 | 406.13 | 407.2[M + H]+ | A |
| 9941 | 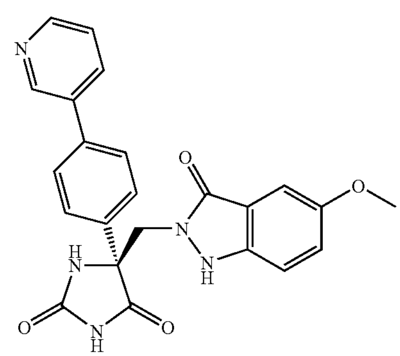 | 429.14 | 430.12[M + H]+ | >C |
| 9942 | 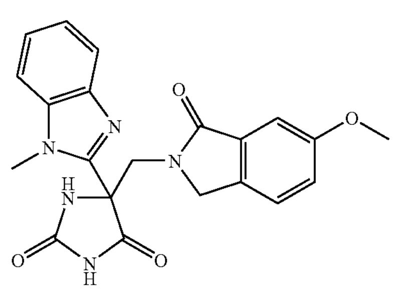 | 405.14 | 406.2[M + H]+ | A |

Example 9000

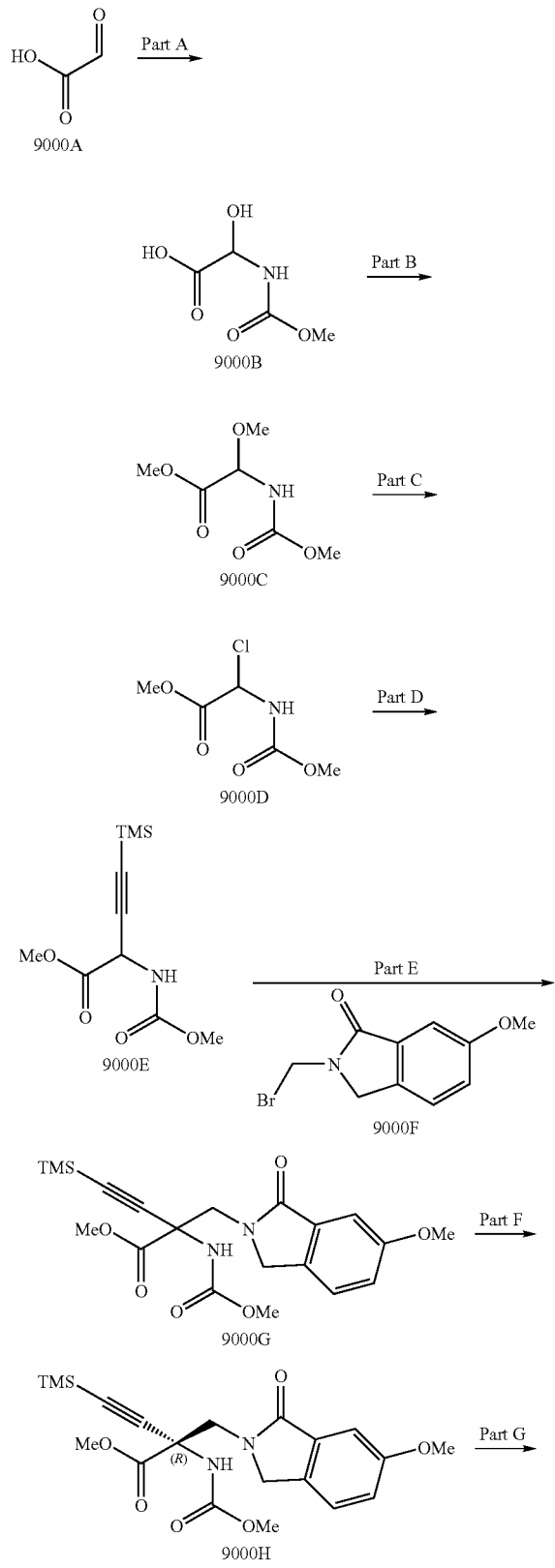

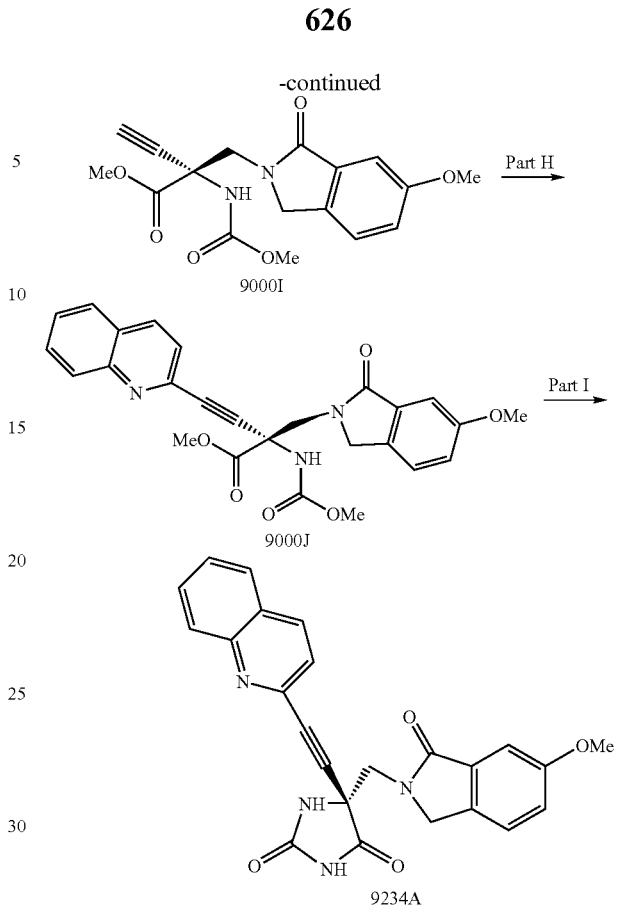

Part A:

Glyoxylic acid monohydrate (20.0 g, 218 mmol) and methyl carbamate (16.3 g, 218 mmol) were dissolved in diethyl ether (200 mL) and stirred overnight. The solids were filtered to provide the desired product 9000B (32.0 g, 98%).

Part B:

Compound 9000B (32.0 g, 214 mmol) was dissolved in MeOH (200 mL) and cooled in an ice bath. Concentrated sulfuric acid (8 mL) was added dropwise and the reaction was stirred overnight. The reaction mixture was diluted with ethyl acetate and water. The organic layer was washed with brine, dried over sodium sulfate, and concentrated to provide compound 9000C that was used without purification (27.0 g, 71%).

Part C:

Compound 9000C (27.0 g, 152 mmol) was dissolved in carbon tetrachloride (700 mL). Phosphorus pentachloride (50 g, 240 mmol) was added and the suspension was stirred for 18 hours (solution became clear over time). The solvent was removed under reduced pressure and the residue was stirred in petroleum ether (500 mL) overnight. The solids were filtered to provide compound 9000D with no need for purification (26.5 g, 96%). Trituration step was repeated if mass yield was too high.

Part D:

Compound 9000D (15.0 g, 82.7 mmol) was dissolved in methylene chloride (140 mL) and cooled in an ice bath. Bis(trimethylsilyl)acetylene (15.0 g, 88.2 mmol) was added in methylene chloride (20 mL). Freshly crushed aluminum chloride (11.0 g, 82.7 mmol) was added in portions over 20 minutes. The reaction mixture was allowed to slowly warm to room temperature and stirred overnight. The reaction was cooled in an ice bath and slowly quenched with water. The organic layer was washed several times with water, dried over sodium sulfate, and concentrated. The residue was triturated/recrystallized from hexanes to provide the desired product 9000E (14.8 g, 69%). HPLC-MS $t_R$=1.84 min (ELSD); mass calculated for formula $C_{10}H_{17}NO_4Si$ 243.09, observed LCMS m/z 244.1 (M+H).

Part E:

Compound 9000E (24.0 g, 98.7 mmol) and compound 9000F (25.1 g, 99.0 mmol) were dissolved in THF (300 mL) and cooled to −78° C. A 1M solution of LiHMDS (198 mL, 198 mmol) was added dropwise over 30 minutes and the reaction mixture was stirred for 2 hours. Saturated ammonium chloride solution was added slowly and the reaction was allowed to warm to room temperature. The aqueous layer was extracted with ethyl acetate. The combined organic layers were washed with water, brine, dried over sodium sulfate, and concentrated. Purification by column chromatography (SiO$_2$, 33% ethyl acetate/hexanes to 50% ethyl acetate/hexanes) afforded the desired product 9000G (26.0 g, 63%). HPLC-MS $t_R$=1.90 min (UV$_{254\ nm}$); mass calculated for formula $C_{20}H_{26}N_2O_6Si$ 418.15, observed LCMS m/z 419.2 (M+H).

Part F:

The two isomers were separated using a chiral OD column. One gram of material was injected into the column and the two peaks were separated by using a solvent mixture of 85% hexanes/ethanol. The second isomer was the desired compound 9000H (400 mg, 80%).

Part G:

Compound 9000H (8.0 g, 19.1 mmol) was dissolved in THF (250 mL) and cooled to 0° C. Tetrabutylammonium fluoride (1 M in THF, 22.9 mL, 22.9 mmol) was added dropwise and the reaction was stirred for 1 hour at room temperature. The reaction mixture was diluted with ethyl acetate and water. The organic layer was washed with water, saturated sodium bicarbonate, brine, dried over sodium sulfate and concentrated to provide compound 9000I (5.8 g, 88%). The product was used without purification.

Part H:

Compound 9000I (75 mg, 0.22 mmol) was combined with 3-bromoquinoline (0.032 mL, 0.24 mmol), Pd(PPh$_3$)$_2$Cl$_2$ (3 mg, 0.0044 mmol), CuI (2 mg, 0.009 mmol), diisopropylamine (0.062 mL, 0.44 mmol) in DMF (1 mL) and stirred overnight at 80° C. The reaction mixture was diluted with ethyl acetate and water. The organic layer was washed with water, brine, dried over sodium sulfate and concentrated. Purification by column chromatography (SiO$_2$, 50% ethyl acetate/hexane to 80% ethyl acetate/hexane) afforded the desired product 9000J (93 mg, 89%). HPLC-MS $t_R$=1.66 min (UV$_{254\ nm}$); mass calculated for formula $C_{26}H_{23}N_3O_6$ 473.16, observed LCMS m/z 474.1 (M+H).

Part I:

Compound 9000J (77 mg, 0.16 mmol) was dissolved in 7 M ammonia solution (3 mL) and stirred in a sealed pressure tube at 90° C. overnight. The reaction mixture was cooled to room temperature and concentrated to afford compound 9234A. HPLC-MS $t_R$=1.41 min (UV$_{254\ nm}$); mass calculated for formula $C_{24}H_{18}N_4O_4$ 426.13, observed LCMS m/z 427.0 (M+H).

Example 9001

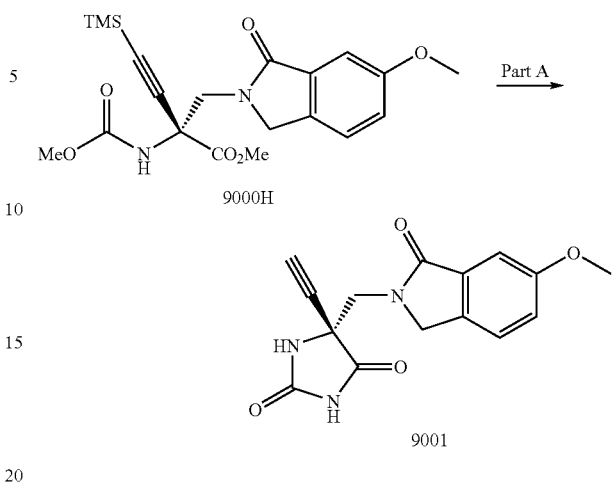

Part A:

Compound 9000H (1.26 g, 3.0 mmol) in 7 M ammonia in methanol (20 mL) was heated to 85° C. in a pressure bottle overnight. The reaction mixture was concentrated to afford 9001 (900 mg, 100%) which was used without further purification. HPLC-MS $t_R$=1.00 min (UV$_{254\ nm}$); mass calculated for formula $C_{15}H_{13}N_3O_4$ 299.09, observed LCMS m/z 300.1 (M+H).

Example 9243

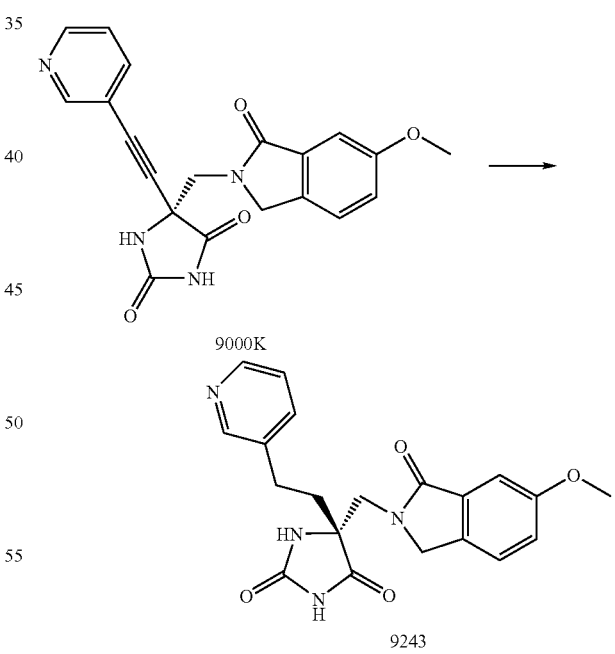

Compound 9000K (33.5 mg, 0.089 mmol) was dissolved in 5 mL MeOH. Lindlar's catalyst (25 mg) was added. A hydrogen balloon was attached and the solution was stirred under H$_2$ for 3 days. The catalyst was removed by filtration. The solvent was removed by rotary evaporator. The product was purified by sgc (CH$_2$Cl$_2$/MeOH/NH$_3$—H$_2$O: 15:1:0.1) to give compound 9243 (12.5 mg, 36.9%).

Example 9234

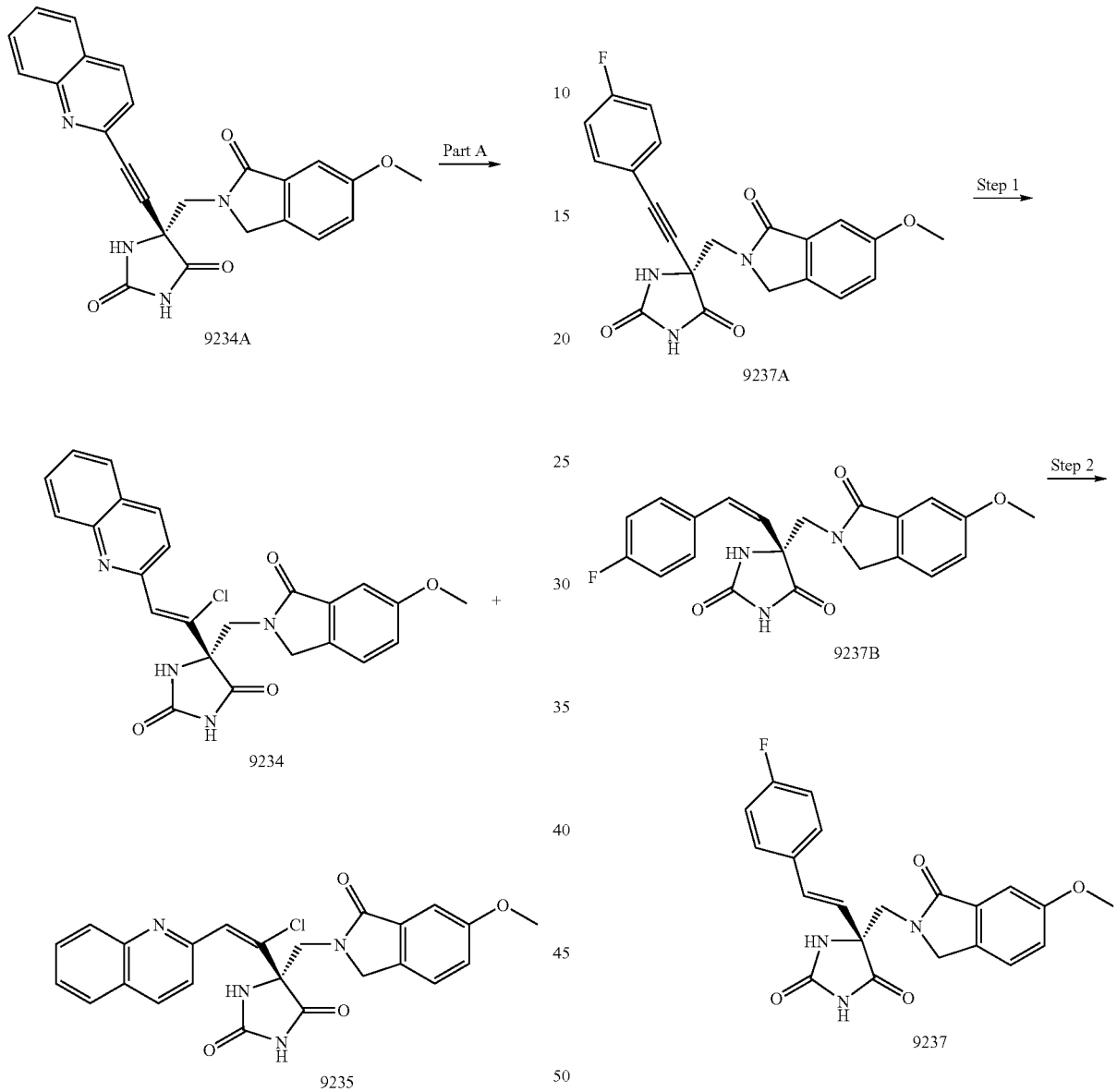

Compounds 9234 and 9235 was Synthesized Using Example 9234 and Procedures Described Previously

Example 9237

Part A:

Compound 9234A (prepared using previously described procedures) (68 mg, 0.16 mmol) was dissolved in methanol (2 mL) and treated with 4 M HCl in dioxane (1 mL). The reaction mixture was stirred a few minutes and concentrated. Purification by reverse phase prep HPLC afforded the 9234 (24 mg) and 9235 (7 mg). 9234: HPLC-MS $t_R$=1.43 min (UV$_{254\ nm}$); mass calculated for formula $C_{24}H_{19}ClN_4O_4$ 462.11, observed LCMS m/z 463.1 (M+H). 9235: HPLC-MS $t_R$=1.51 min (UV$_{254\ nm}$); mass calculated for formula $C_{24}H_{19}ClN_4O_4$ 462.11, observed LCMS m/z 463.1 (M+H).

Step 1

Compound 9237A was dissolved in 2 mL MeOH. Lindar's catalyst (10%) (5 mg) was added. The solution was stirred under H$_2$ balloon for 1.5 h. It was diluted with MeOH (3 mL) and the catalyst was removed by filtration. The solvent was removed by rotary evaporator to give compound 9237B, which was used without further purification.

Step 2

Compound 9237B was dissolved in CH$_2$Cl$_2$ (0.5 mL) and Pd(CH$_3$CN)$_2$Cl$_2$ was added. The solution was stirred overnight and the product was purified by silica gel prep TLC (CH$_2$Cl$_2$/MeOH/NH$_3$.H$_2$O: 20:1:0.1) to give compound 9237 (1.3 mg).

Example 9246

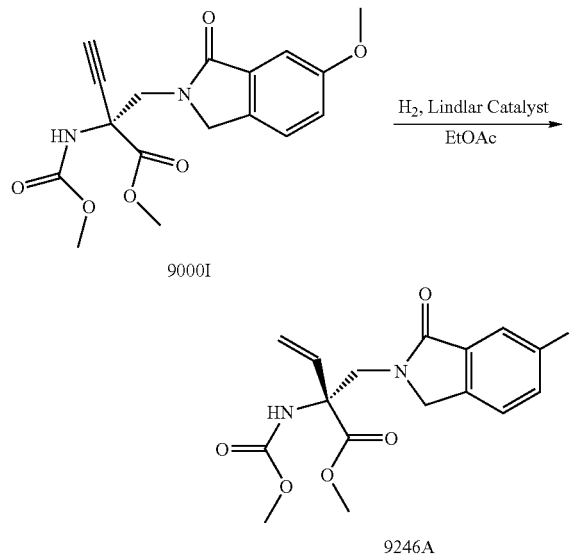

Compound 9000I (34 mg) was added to a 25 mL Schlenck tube equipped with a stir bar, and dissolved in EtOAc. Lindlar catalyst was added. The flask was placed under balloon pressure of H₂. The reaction mixture was stirred at rt overnight. The reaction mixture was filtered and concentrated to dryness. The crude product was purified via sgc using a 5% to 50% (5% MeOH in EtOAc)/Hexanes gradient as the mobile phase. Compound 9246A was collected as a clear oil (20 mg).

Compound 9246A was dissolved in 8 mL of methanolic ammonia (7N). The solution was added to a pressure tube equipped with a stir bar and capped tightly. The tube was placed in an oil bath, heated to 75 C, and stirred ON at that temperature. After 15 h, the reaction mixture was allowed to cool to rt. The reaction mixture was concentrated to dryness. The crude product was purified via sgc using a 5% to 60% (5% MeOH in EtOAc)/Hexanes gradient as the mobile phase. Compound 9246 was obtained as a clear oil.

Compound 9246 was Synthesized Using Example 9246 and Procedures Described Previously

Example 9202

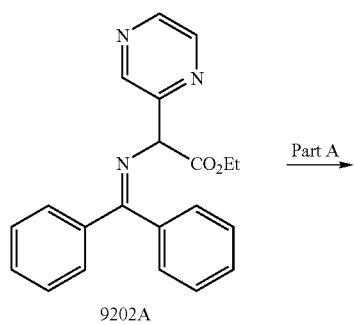

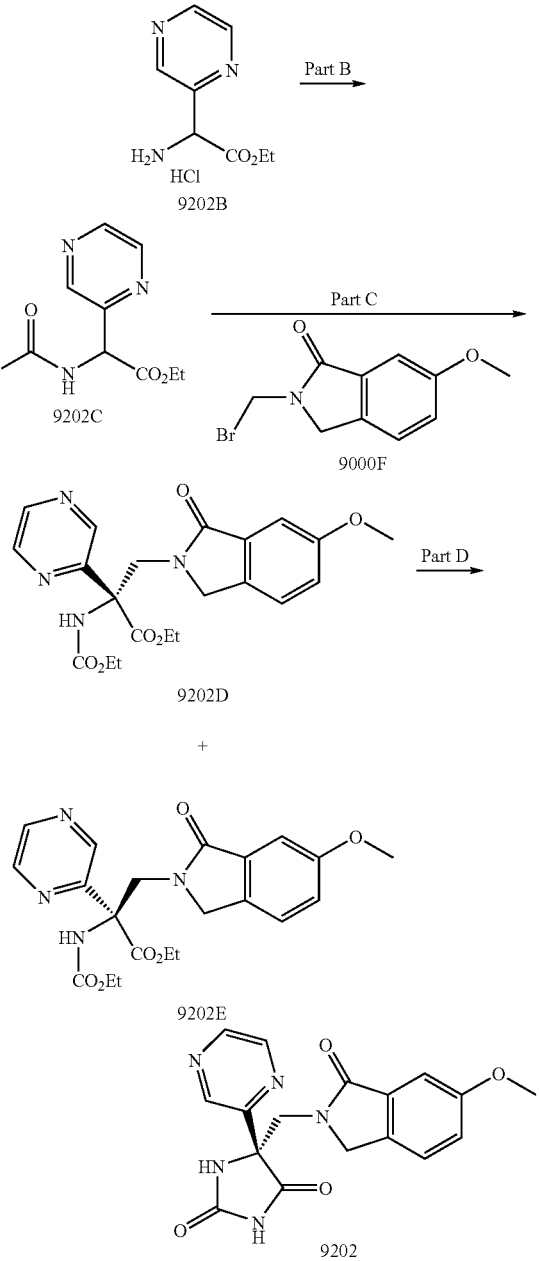

Part A:

Compound 9202A (prepared according to the procedures described in *J. Med Chem.* 1994, 37, 4567) (6.6 g, 19.1 mmol) was dissolved in diethyl ether (100 mL) and treated with 1 M HCl (aq. 23 mmol). The reaction mixture was stirred overnight at room temperature. The layers were separated and the aqueous layer was washed with diethyl ether (3×30 mL). The aqueous layer was concentrated and the residue was triturated with ethanol and acetone to afford 9202B (3.14 g, 75%) as an off white powder. HPLC-MS $t_R$=0.21 min (UV$_{254\ nm}$); mass calculated for formula $C_8H_{11}N_3O_2$ 181.09, observed LCMS m/z 182.1 (M+H).

Part B:

A mixture of 9202B (2.17 g, 10 mmol), ethyl chloroformate (1.05 mL, 11 mmol) and DIEA (2.14 mL, 12 mmol) in THF (20 mL) was stirred at room temperature overnight. The reaction mixture was diluted with ethyl acetate and water. The layers were separated and the aqueous layer was extracted with ethyl acetate. The combined organic layers were washed with 1.0 M HCl (aq.) and brine, dried over sodium sulfate and concentrated. Purification by silica gel chromatography (50% ethyl acetate/hexane) afforded 9202C (1.47 g, 58%) as an orange oil. HPLC-MS $t_R$=1.19 min ($UV_{254\ nm}$); mass calculated for formula $C_{11}H_{15}N_3O_4$ 253.11, observed LCMS m/z 254.2 (M+H).

Part C:

Compound 9202C (1.00 g, 3.95 mmol) in THF (10 mL) and HMPA (5 ml) was deprotonated with freshly prepared LDA solution (11.85 mmol) at −78° C. The anion solution was stirred for 1 hr before 9000F (1.13 g, 4.41 mmol) in THF (20 mL) was added at −78° C. The reaction mixture was stirred 2.5 hrs and quenched at −78° C. with HOAc (1 mL). The reaction mixture was purified silica gel chromatography (ethyl acetate/hexane to methanol/ethyl acetate) to afford the c-alkylated product (103 mg, 6%). The isomers were separated by chiral chromatography with an AD column to afford 9202E (36 mg) and 9202D (35 mg). HPLC-MS $t_R$=1.60 min ($UV_{254\ nm}$); mass calculated for formula $C_{21}H_{24}N_4O_6$ 428.17, observed LCMS m/z 429.1 (M+H).

Part D:

Compound 9202D (35 mg, 0.08 mmol) was heated in 7 M ammonia in methanol (5 mL) at 90° C. for 3 days. The reaction mixture was concentrated and lyophilized to afford 9202 (29 mg, 97%). HPLC-MS $t_R$=0.95 min ($UV_{254\ nm}$); mass calculated for formula $C_{17}H_{15}N_5O_4$ 353.11, observed LCMS m/z 354.1 (M+H).

Compound 9202 was Synthesized Using Example 9202 and Procedures Described Previously Example 9203

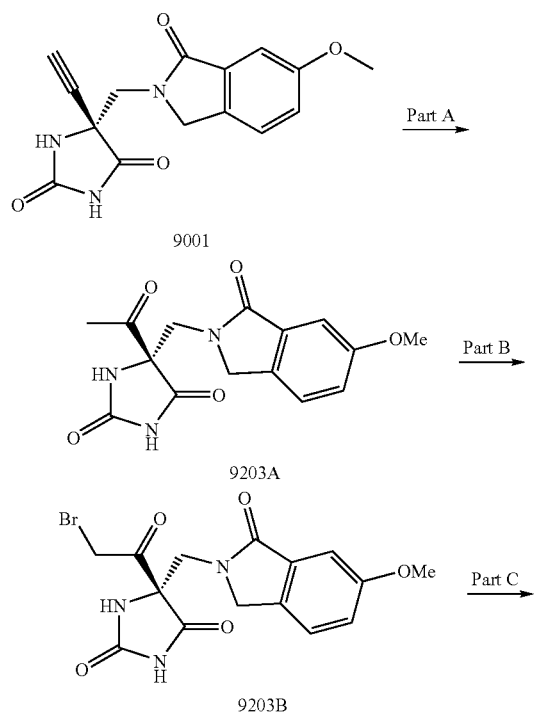

Part A:

Compound 9001 (600 mg, 2.01 mmol) in MeOH (5 mL) was added with 2N $H_2SO_4$ (5 mL) and HgO (100 mg) and stirred at 80° C. for 1 h. The reaction mixture was diluted with EtOAc. The solid was removed by filtration; and the filtrate was washed with $H_2O$, brine, dried over $Na_2SO_4$, and concentrated to dryness, affording crude compound 9203A as a white solid which was utilized for subsequent reaction (480 mg, 76%). HPLC-MS $t_R$=1.39 min ($UV_{254\ nm}$); mass calculated for formula $C_{15}H_{15}N_3O_5$ 317.10, observed LCMS m/z 318.1 (M+H).

Part B:

Crude compound 9203A (480 mg) in acetic acid (8 mL) was added dropwise with bromine (194 mg, 1.21 mmol) at room temperature. After stirring for 3 h at 50° C., the reaction mixture was concentrated to dryness, resulting in the crude product of compound 9203B (500 mg). HPLC-MS $t_R$=1.136 min ($UV_{254\ nm}$); mass calculated for formula $C_{15}H_{14}BrN_3O_5$ 395.01, observed LCMS m/z 396.0 (M+H).

Part C:

Crude compound 9203B (100 mg) and thiourea (100 mg) in DMF (1 mL) was stirred at room temperature for 12 h. After concentrating to dryness, the residue was dissolved in DMSO/ACN (3:1) and purified by reverse phase HPLC, resulting in compound 9203 as a white solid (25 mg). HPLC-MS (10 min) $t_R$=2.238 min ($UV_{254\ nm}$); mass calculated for formula $C_{16}H_{15}N_5O_4S$ 373.08, observed LCMS m/z 374.0 (M+H).

-continued

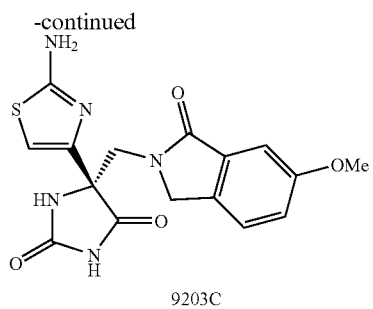

9203C

Compound 9203C was Synthesized Using Example 9203 and Procedures Described Previously Example 9200

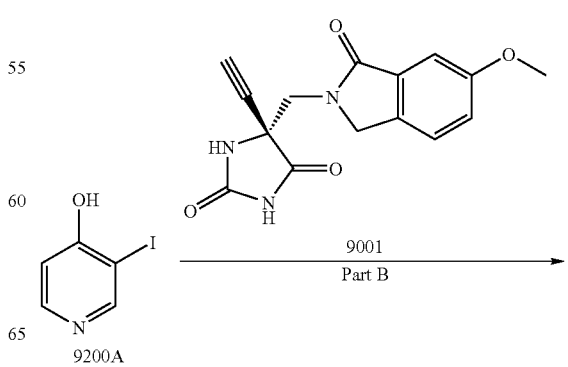

-continued

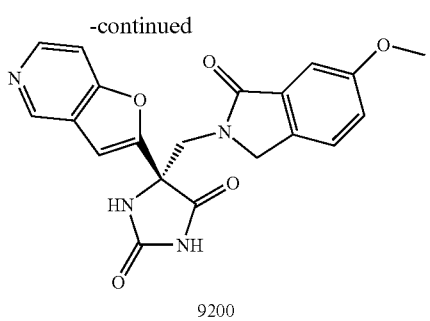

9200

Part B:

A mixture of 9200A (prepared according to the procedures in WO 9846609) (412 mg, 1.38 mmol), 9001 (305 mg, 1.38 mmol), copper iodide (16 mg, 0.083 mmol), Pd(PPh$_3$)$_2$Cl$_2$ (48 mg, 0.069 mmol) and triethylamine (0.232 mL, 1.66 mmol) in DMF (8 mL) was heated at 80° C. overnight. The reaction mixture was concentrated, purified by reverse-phase chromatography converted to an HCl salt and lyophilized to afford 9200 (252 mg, 42%) as a pale yellow powder.

HPLC-MS t$_R$=0.75 min (UV$_{254\ nm}$); mass calculated for formula C$_{20}$H$_{16}$N$_2$O$_5$ 392.11, observed LCMS m/z 393.1 (M+H).

Compound 9200 was Synthesized Using Example 9200 and Procedures Described Previously Example 9207

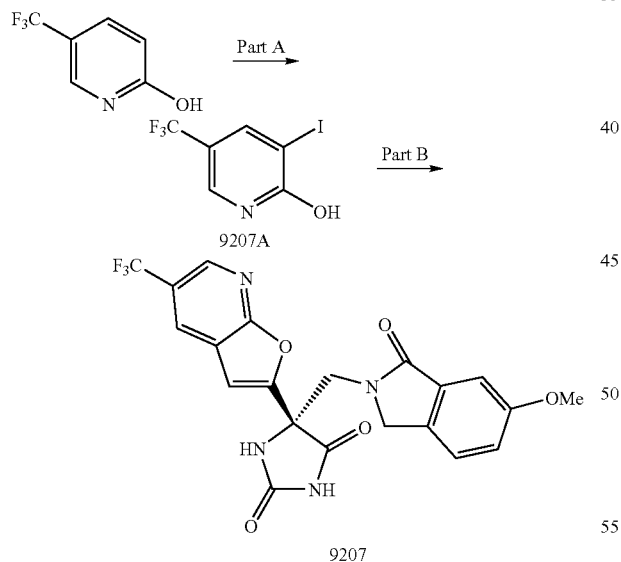

9207

Part A:

Compound 9207A was prepared from 5-trifluoromethyl-2-hydroxypyridine and NIS according to a procedure in the literature (A. Meana, J. F. Rodriguez, M. A. Sanz-Tejedor, J. L. Garcia-Ruano, *Synlett*, 2003, 1678-1682).

Part B:

Under argon, compound 9207A (87 mg, 0.3 mmol) and compound 9001 (60 mg, 0.2 mmol) in DMF (1 mL) were added with Pd$_2$(dba)$_3$ (4.6 mg, 0.005 mmol), dppf (5.5 mg, 0.01 mg), CuI (1.9 mg, 0.01 mmol) and DIEA (105 µL). After stirring at 100° C. for 12 h, the reaction mixture was diluted with acetonitrile (1 mL). Reverse phase HPLC purification afforded compound 9207 (38 mg, 41%) as a white solid. HPLC-MS (10 min) t$_R$=3.870 min (UV$_{254\ nm}$); mass calculated for formula C$_{22}$H$_{16}$F$_3$N$_3$O$_5$ 460.10, observed LCMS m/z 461.0 (M+H).

Compound 9207 was Synthesized Using Example 9207 and Procedures Described Previously Example 9216

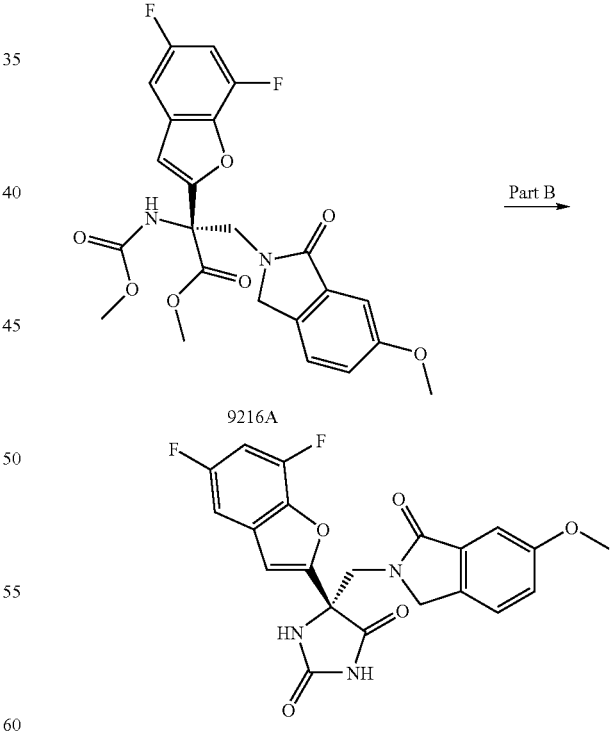

9216

Part A:

Compound 9216A was prepared from compound 90001 and 2-bromo-4,6-difluorophenol following the procedure described in Example 400 part H.

Part B:

Compound 9216A (80 mg, 0.19 mmol) was dissolved in 7 M ammonia solution (5 mL) in MeOH and stirred in a sealed pressure tube at 900C for 2 days. The reaction mixture was cooled to room temperature and concentrated. The residue was purified by RP-HPLC to provide compound 9216 (42 mg, 52%). HPLC-MS $t_R$=1.54 min (UV$_{254\ nm}$); mass calculated for formula $C_2, H_{15}F_2N_3O_5$ 427.10, observed LCMS m/z 428.0 (M+H).

Compound 9216 was Synthesized Using Example 9216 and Procedures Described Previously Example 9217

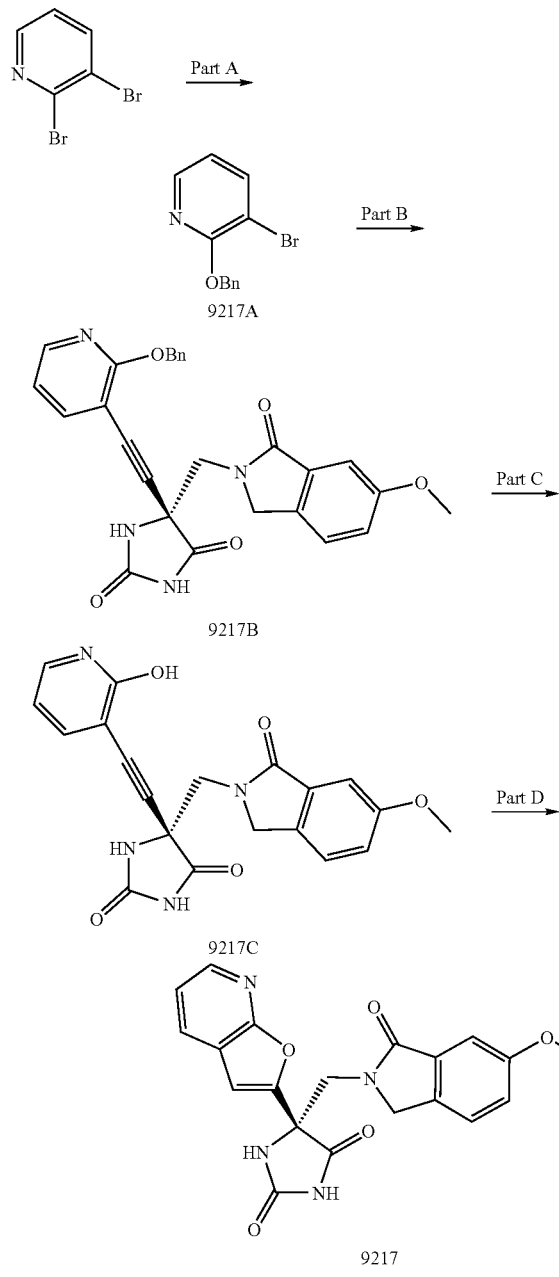

9217

Part A:

To a solution of benzyl alcohol (270 mg, 2.53 mmol) in THF (10 mL) at 0° C. was added sodium hydride (101 mg, 2.53 mmol). After 15 min, 2,3-dibromopyridine (500 mg, 2.11 mmol) was added and the resulting mixture was warmed to 50° C. overnight. The reaction mixture was diluted with EtOAc, washed with water and brine, dried over sodium sulfate and concentrated. The residue was purified by column chromatography (SiO$_2$, 2% EtOAc/hexane to 5% EtOAc/hexane) to afford 9217A as a colorless oil (235 mg, 42%). HPLC-MS $t_R$=2.21 min (UV$_{254\ nm}$); mass calculated for formula $C_{12}H_{10}BrNO$ 262.99, observed LCMS m/z 264.0 (M+H).

Part B:

Compound 9217B was prepared following the procedures described in Example 9000 part H and I.

Part C:

Compound 9217B (66 mg, 0.14 mmol) was treated with trifluoroacetic acid (3 mL) and CH$_2$Cl$_2$ (3 mL) overnight and the reaction mixture was concentrated. The residue was dissolved in acetonitrile (3 mL) and water (3 mL). The solvent was removed by lyophilization to provide compound 9217C (53 mg, 97%). HPLC-MS $t_R$=0.99 min (UV$_{254\ nm}$); mass calculated for formula $C_{20}H_{16}N_4O_5$ 392.11, observed LCMS m/z 393.1 (M+H).

Part D

To compound 9217C (25 mg, 0.064 mmol) in DMF (2 mL) was added CuI (26 mg, 0.14 mmol) and the resulting mixture was heated in a microwave at 100° C. for 30 min. The reaction mixture was concentrated and the residue was purified by RP-HPLC to provide compound 9217 (10 mg, 40%). HPLC-MS $t_R$=1.17 min (UV$_{254\ nm}$); mass calculated for formula $C_{20}H_{16}N_4O_5$ 392.11, observed LCMS m/z 393.1 (M+H).

Compounds 9217 was Synthesized Using Example 9217 and Procedures Described Previously Example 9220

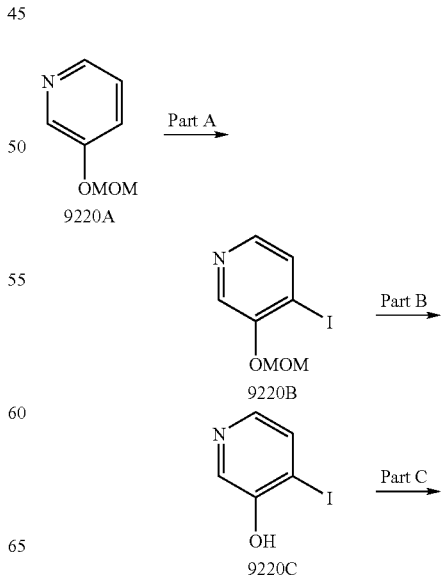

-continued

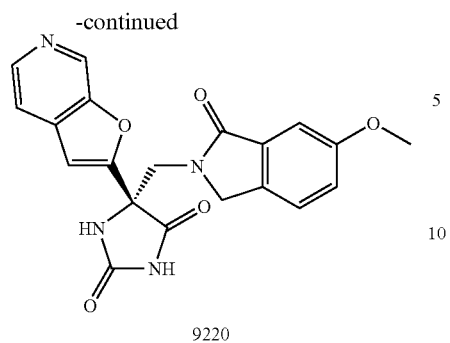

9220

Part A:

To 9220A (prepared from 3-hydroxypyridine following a procedure described in Shimano, M. et al. (*Tetrahedron*, 1998, 54, 12745-12774)) (300 mg, 2.16 mmol) in Et$_2$O (20 mL) at −78° C. was added $^t$BuLi (1.7 M in hexane, 2.5 mL, 4.32 mmol). After 30 min, a solution of 1-chloro-2-iodoethane (492 mg, 2.59 mmol) in THF (5 mL) was added dropwise. The resulting mixture was stirred for 30 min and treated with water and EtOAc. The organic layer was washed with water, brine, 9220 (478 mg), which was used without purification in the next step.

Part B:

Compound 9220B (87 mg, 0.33 mmol) was treated with trifluoroacetic acid (2 mL) and CH$_2$Cl$_2$ (2 mL) for 3 hours and the reaction mixture was concentrated to give 9220C (67 mg, 100%). HPLC-MS t$_R$=0.52 min (UV$_{254\ nm}$); mass calculated for formula C$_5$H$_{41}$NO 220.93, observed LCMS m/z 222.1 (M+H).

Part C:

Compound 9001 (60 mg, 0.20 mmol) was combined with 922° C. (57 mg, 0.26 mmol), Pd(PPh$_3$)$_2$Cl$_2$ (7.0 mg, 0.01 mmol), CuI (4.0 mg, 0.02 mmol), triethylamine (0.055 mL, 0.40 mmol) in THF (2 mL) and stirred overnight at 60° C. The reaction mixture was concentrated and the residue was purified by RP-HPLC to provide compound 9220 (43 mg, 54%). HPLC-MS t$_R$=0.75 min (UV$_{254\ nm}$); mass calculated for formula C$_{20}$H$_{16}$N$_4$O$_5$ 392.11, observed LCMS m/z 393.1 (M+H).

Compound 9220 was Synthesized Using Example 9220 and Procedures Described Previously Example 9225

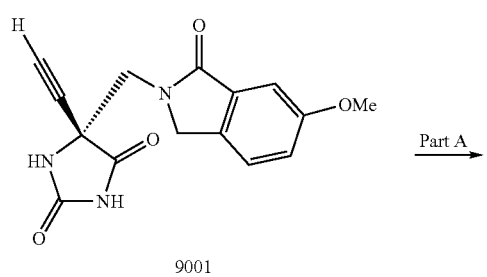

9001

-continued

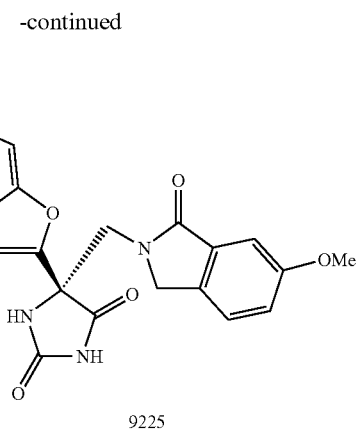

9225

Part A:

Under argon, compound 9001 (90 mg, 0.9 mmol) and 2-chloro-5-fluoro-3-hydroxypyridine (89 mg, 0.6 mmol), in DMF (1 mL) were added with Cs$_2$CO$_3$ (390 mg, 1.2 mmol) and bis(tri-tert-butylphosphine)palladium (7.7 mg, 0.015 mmol). After stirring at 100° C. for 12 h, the reaction mixture was diluted with acetonitrile (1 mL). Reverse phase HPLC purification afforded compound 9225 (41 mg, 34%) as a white solid. HPLC-MS (10 min) t$_R$=3.037 min (UV$_{254\ nm}$); mass calculated for formula C$_{20}$H$_{15}$FN$_4$O$_5$ 410.10, observed LCMS m/z 411.1 (M+H).

Compound 9225 was Synthesized Using Example 9225 and Procedures Described Previously Example 9228

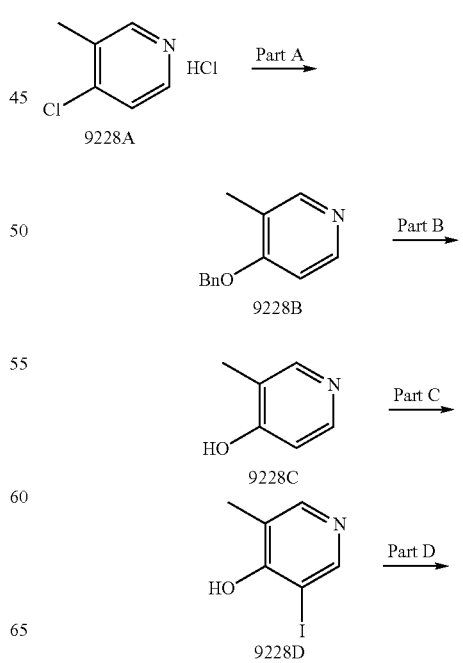

-continued

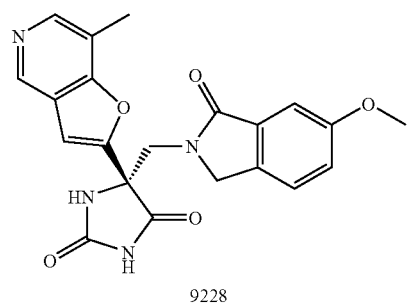

9228

Part A:

Benzyl alcohol (3.3 g, 30 mmol) was dissolved in THF (20 mL) and NaH (1.34 g, 33 mmol) was added slowly. After the bubbling ceased compound 9228A (2.0 g, 12.1 mmol) was added and the mixture was refluxed for 48 hours. The reaction mixture was quenched with water and extracted with ethyl acetate. The organic layer was dried over sodium sulfate and concentrated. Column chromatography (1:1 hexanes/ethyl acetate) provided compound 9228B (1.6 g, 67%). $^1$H NMR (400 MHz, CDCl$_3$) δ 8.35 (m, 1H), 8.3 (s, 1H), 7.4-7.3 (m, 5 H), 6.85 (d, 1H), 5.15 (s, 2H).

Part B:

Compound 9228B (120 mg, 0.61 mmol) was dissolved in methanol (10 mL) and Pd—C (20 mg) was added. The reaction mixture was stirred overnight under a hydrogen atmosphere at room temperature. The reaction mixture was filtered and the solvent was removed to provide the desired product (60 mg, 92%). $^1$H NMR (400 MHz, CDCl$_3$) δ 7.5 (m, 2H), 6.0 (s, 1H), 3.1 (s, 1H).

Part C:

Compound 9228C (60 mg, 0.56 mmol) was suspended in acetonitrile (5 mL) and N-iodosuccinimide (182 mg, 0.67 mmol) was added. The reaction mixture was refluxed for 2 hours. The solvent was evaporated and the remaining solid residue was triturated with methanol to provide the desired product (50 mg, 39%). $^1$H NMR (400 MHz, CDCl$_3$) δ 8.2 (d, 1H), 7.6 (s, 1H), 1.75 (s, 3H).

Part D:

Compound 9001 (410 mg, 1.37 mmol), compound 9228D (334 mg, 1.43 mmol), Pd(PPh$_3$)$_2$Cl$_2$ (30 mg), CuI (15 mg), and triethylamine (0.5 mL) were dissolved in DMF and stirred under an inert atmosphere at 80° C. overnight. The solvent was removed and the material was purified by reverse phase chromatography to provide the desired product (168.3 mg, 30%). HPLC-MS $t_R$=0.75 min (UV$_{254\,nm}$); mass calculated for formula C$_{21}$H$_{18}$N$_4$O$_5$ 406.39, observed LCMS m/z 407.1 (M+H). $^1$H NMR (400 MHz, DMSO-d6) δ 11.4 (s, 1H), 9.3 (s, 1H), 9.15 (s, 1H), 8.75 (s, 1H), 7.5 (m, 2H), 7.15 (m, 2H), 4.55 (m, 2H), 4.35 (m, 2H), 3.8 (s, 3H), 2.55 (s, 3H).

Compound 9228 was Synthesized Using Example 9228 and Procedures Described Previously Example 9600

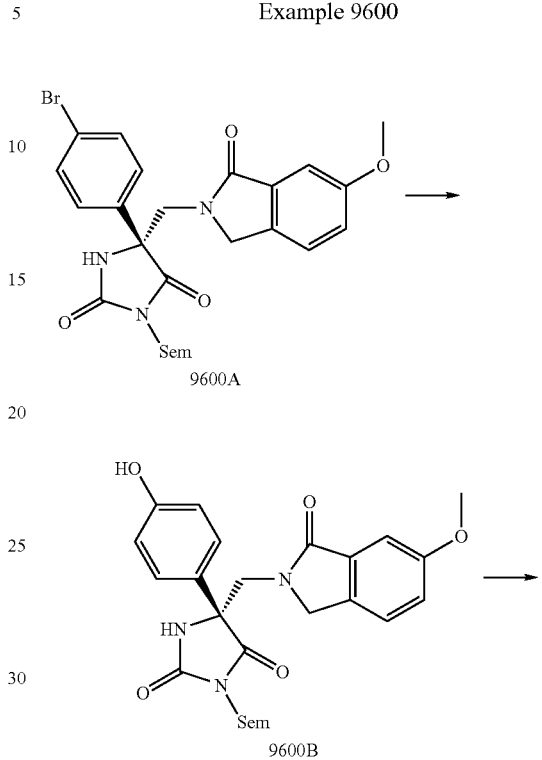

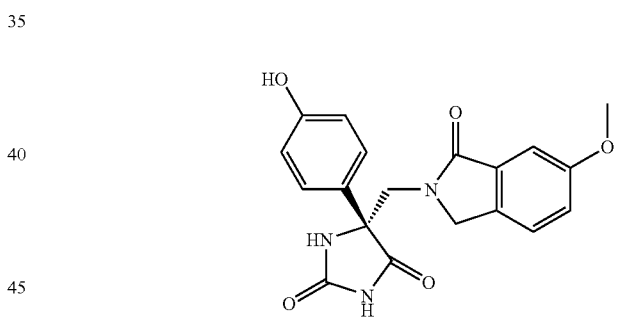

9600

Compound 9600A (1.50 g/2.68 mmol), pinocolatodiboron (816 mg, 3.21 mmol), potassium acetate (785 mg, 8.0 mmol), and palladium (II) dichloride (dppf) CH$_2$Cl$_2$ complex (250 mg, 0.306 mmol) were added to a 100 mL Schlenck flask equipped with a stir bar. The flask was capped with a septum, then cycled between vacuum and nitrogen four times. Dioxane (20 mL, Aldrich anhydrous) was added via syringe. The flask was cycled between vacuum and nitrogen three times, then placed in an 85° C. oil bath. The bath was heated to 100° C., then stirred for 1.5 h. the reaction mixture was allowed to cool to RT and diluted with EtOAc (80 mL). The resulting mixture was filtered through Celite. The Celite was rinsed with additional EtOAc. The combined filtrate was concentrated to near dryness then redissolved in EtOAc. The organic solution was washed with 1.0 M aq pH 7 sodium phosphate buffer, water, and brine. After drying with MgSO$_4$, the organic layer was concentrated to dryness. The crude product was purified via sgc using a 2%-4% MeOH/CH$_2$Cl$_2$ gradient as the mobile phase. A brown solid was obtained (1.9 g). The solid was dissolved in dioxane (16 mL) and water (11 mL) was added. Sodium perborate (3.0 g, 19.5 mmol) was added and the reaction mixture was stirred at rt overnight. The reaction mixture was diluted with EtOAc and aq 1M NH$_4$Cl. The layers were separated. The organic layer was washed with water and brine, dried with MgSO$_4$, filtered and concentrated to dryness, giving an off white solid (1.37 g). SGC using a gradient of 25% to 100% (5% Methanol in EtOAc)/Hexanes as the mobile phase gave 0.25 g of pure 9600B and 0.62 g of impure 9600B.

Compound 9600B (0.70 g, 1.40 mmol) was dissolved in 50 mL of Aldrich 4N HCl in dioxane and 50 mL of methanol. The solution was added to a pressure tube equipped with a stir bar. The tube was capped, placed in an oil bath, and heated to 95 C. The reaction was stirred at 95° C. for 4 h, then allowed to cool to rt. The reaction mixture was concentrated to dryness. Methanol was added and the reaction mixture was reconcentrated. Methanol (50 mL) was added, followed by triethylamine (5 mL). The reaction mixture was stirred at rt for 1 h, then concentrated to dryness. EtOAc and 1.0 M aq pH 5.5 sodium phosphate buffer were added. The layers were separated. The organic layer was washed with water and brine, dried with MgSO$_4$, filtered, and concentrated to dryness. The crude product was purified via SiO$_2$ chromatography. The mobile phase was a gradient of 10% to 100% of (100:10:1-CH$_2$Cl$_2$:MeOH:concentrated NH$_4$OH) in CH$_2$Cl$_2$. The main UV active peak was isolated as product giving 0.42 g of compound 9600 as white solid.

Compound 9600 was Synthesized Using Example 9600 and Procedures Described Previously Example 9601

Compound 9600B (218 mg, 0.44 mmol) was partially dissolved in THF (4 mL) and pyridine (3 mL). N-Chlorosuccinimide (62 mg) was added and the reaction mixture was left stirring ON at rt. After approximately 24 h, the reaction mixture was heated to 40° C. and stirred for 2 h. The reaction mixture was allowed to cool to rt and quenched with 1M aq sodium bisulfite. The resulting mixture was diluted with EtOAc. The layers were separated. The aq layer was extracted with additional EtOAc. The combined organic layer was washed with water and brine, dried with MgSO$_4$, filtered, and concentrated to an off white solid (0.22 g). The crude product was purified via prep TLC, giving starting material, Compound 9601A and Compound 9602A. The two products were converted to compounds 9601 and 9602 using SEM deprotection procedures similar to those described previously.

Compound 9600 to compound 9602 were synthesis using example 9600 and example 9601 and procedures described previously.

Example 9603

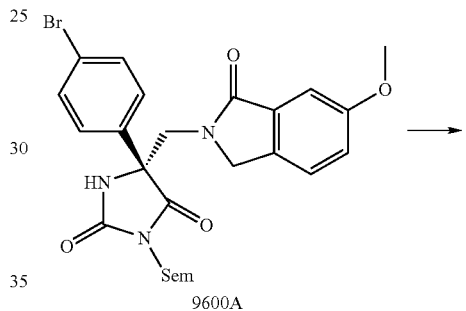

9600A

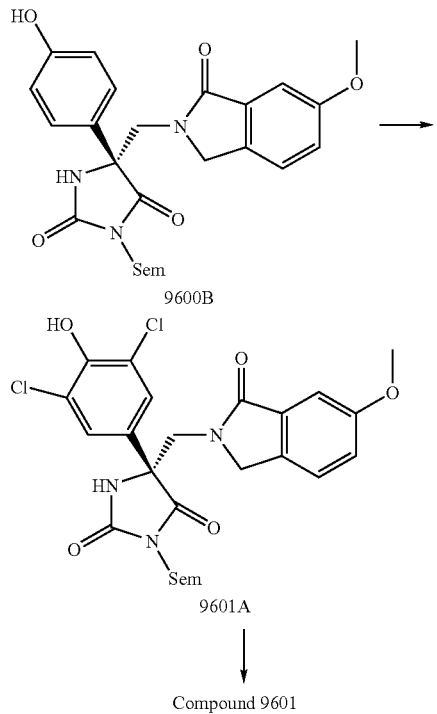

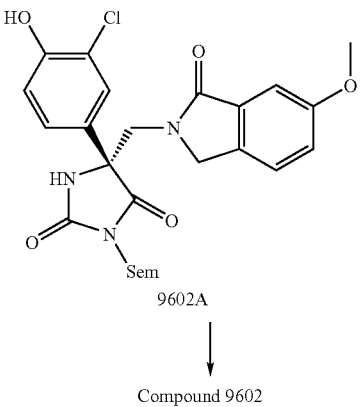

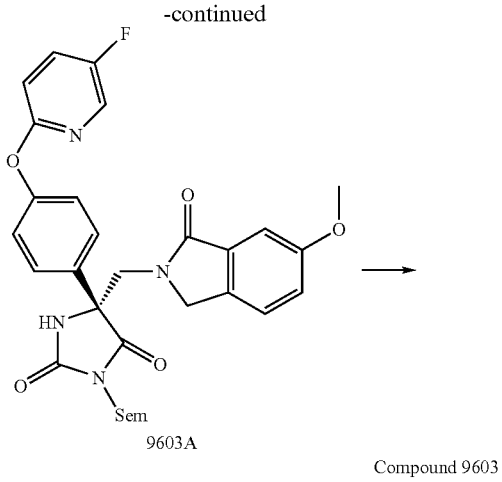

Compound 9603

The aryl ether compounds 9603 to 9621 were prepared from compound 9600A using a procedure based on that described by E. Buck and Z. J. Song in *Organic Synthesis* Vol 82, p. 69, followed by a standard SEM deprotection sequence. An example is provided below.

Compound 9600A (0.248 g, 0.442 mmol), 5-Fluoro-2-hydroxypyridine (128 mg, 1.13 mmol), cesium carbonate (374 mg, 1.14 mmol), and copper (I) chloride (48 mg, 0.48 mmol) were added to a 10 mL Schlenck tube equipped with a stir bar. The tube was capped with a septum and cycled between vacuum and $N_2$ three times. N-methyl-2-pyrrolidinone (2 mL) was added via syringe and the Schlenck tube was cycled between vacuum and $N_2$ three times. 2,2,6,6,6-Tetramethyl heptane-3,5-dione (33 μL) was added via syringe. The Schlenck tube was placed in a 100° C. oil bath and heated to 150° C. The reaction mixture was stirred for 23 h at 150° C. The reaction mixture was allowed to cool to rt, then diluted with EtOAc and water. Aqueous 1% EDTA was added and the layers were separated. The organic layer was washed with 1% aq EDTA, water, and brine. The resulting organic solution was dried with $MgSO_4$, filtered, and concentrated to dryness. A brown solid was obtained. The crude product was purified via sgc using a Biotage $SiO_2$ cartridge and a 1%-2.5% MeOH/$CH_2Cl_2$ gradient as the mobile phase. The major spot was collected as product, giving 0.04 g of compound 9603A.

Compound 9603A (0.04 g) was dissolved in (10 mL) anhydrous acetonitrile and concentrated to dryness on the rotovap. This step was repeated. The compound was redissolved in anhydrous acetonitrile (3 mL) and placed under $N_2$. The flask was cooled in an ice water bath. $BF_3$ etherate (90 μL) was added, the ice bath was removed, and the reaction mixture was stirred at rt for 7 h. The reaction mixture was capped and stored in a 4° C. freezer overnight. The reaction mixture was cooled in an ice-water bath. Diisopropylethylamine (1.5 mL) was added, followed by aq 3.0 M sodium hydroxide. The reaction was stirred for 15 min. The ice bath was removed, and the reaction mixture was stirred for 3 h at rt. Acetic acid was added until the reaction mixture was weakly acidic. The reaction mixture was partially concentrated on the rotovap. EtOAc and water were added. The layers were separated. The organic layer was washed with water and brine, dried with $MgSO_4$, filtered, and concentrated to dryness. The crude product was purified via reverse phase chromatography using an Isco C-18 cartridge (43 g). The mobile phase was a 15% to 80% $CH_3CN/H_2O$ gradient with 0.1% (volume) formic acid added to both components of the mobile phase. The main peak was isolated as product giving compound 9603.

Compound 9603 to compound 9619 were synthesis using example 9603 and procedures described previously.

Example 9624

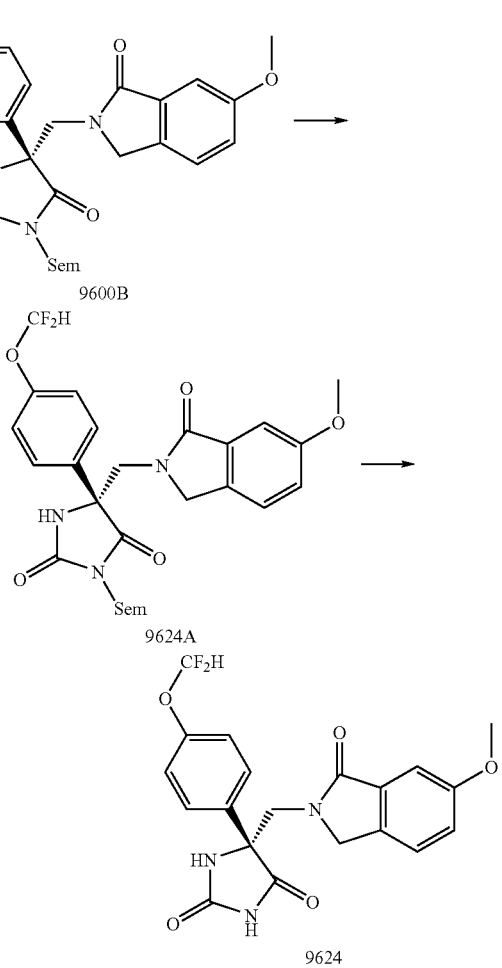

Compound 9600B (168 mg, 0.337) and cesium carbonate (342 mg, 1.0 mmol) were added to a 15 mL 2 necked flask. DMF (3.5 ml) was added. The flask was equipped with a septum in one outlet and cold finger condenser in the other. The condenser was filled with dry ice and 2-propanol and the flask was placed in a room temperature water bath. Chlorodifluoromethane gas was bubbled into the reaction mixture through a needle in the septum for ca 15 minutes. The reaction mixture was allowed to stir at rt. When the rate of condensation of the chlorodifluoromethane gas on the cold finger condenser decreased, additional chlorodifluoromethane was added. After approx 5 h stirring at rt, the gas was stopped and the reaction mixture was diluted with EtOAc. Aqueous pH 5.5 sodium phosphate buffer was added and the layers were separated. The organic layer was washed with water and brine, dried with $MgSO_4$, filtered, and concentrated to a yellow oil (0.28 g). The crude product was partially purified ve sgc using a 0% to 6% MeOH/$CH_2Cl_2$ gradient as the mobile phase. The resulting impure product was columned on $SiO_2$ using a gradient of 20% to 30% (5% MeOH in EtOAc)/Hexanes as the mobile phase to give 0.06 g of 9624A.

Compound 9624A was converted to compound 9624 via a procedure that is similar to the SEM deprotection procedure using the HCl in dioxane and methanol, followed by triethylamine in methanol described previously.

Example 9625

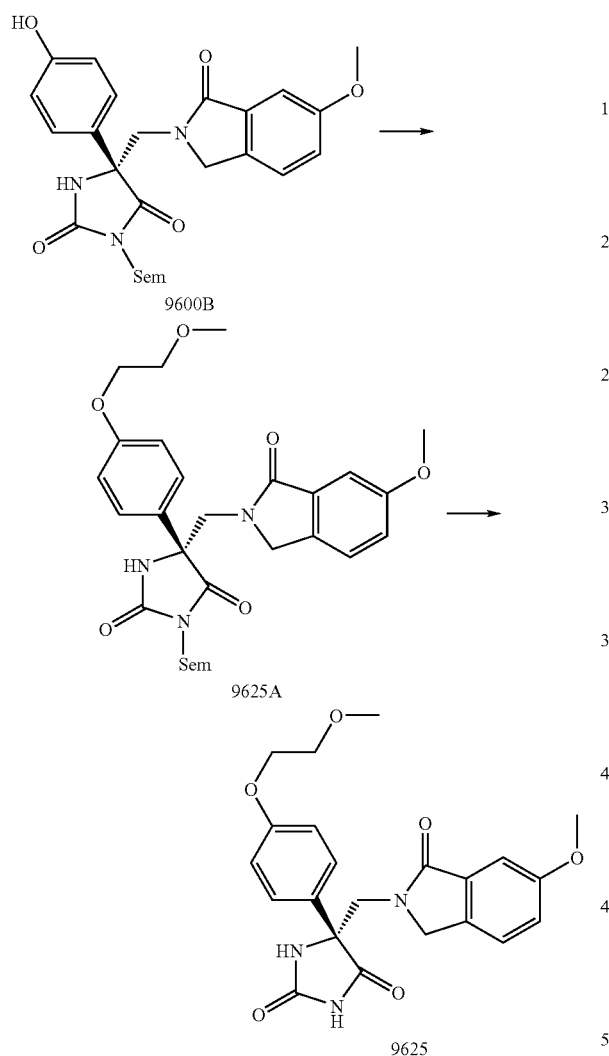

Compound 9600B (0.255 mg, 0.51 mmol) was dissolved in DMF (2.6 mL). Cesium carbonate was added (366 mg, 1.1 mmol). the reaction mixture was stirred at rt under N₂ for 20 min. 2-Bromoethyl methyl ether (112 mg, 0.81 mmol) was added and the reaction mixture was stirred at rt under N₂ over the weekend. The reaction mixture was diluted with EtOAc and 1.0 M aq pH 5.5 sodium phosphate buffer. the layers were separated. The organic layer was washed with water and brine, dried with MgSO₄, filtered, and concentrated to dryness. The crude product was purified via sgc using a 1% to 5% MeOH/CH₂Cl₂ gradient as the mobile phase to give compound 9625A.

Compound 9625A (0.1 g) was dissolved in 6 mL of Aldrich 4N HCl in dioxane and 3 mL of methanol. The solution was added to a pressure tube equipped with a stir bar. The tube was capped and placed in an 80° C. oil bath. The reaction was stirred at 80° C. for 21 h, then allowed to cool to rt. The reaction mixture was concentrated to dryness. Methanol was added and the reaction mixture was reconcentrated. Methanol (8 mL) was added, followed by triethylamine (3 mL). The reaction mixture was stirred at rt for 3 h, then concentrated to dryness. EtOAc and 1.0 M aq pH 5.5 sodium phosphate buffer were added. The layers were separated. The organic layer was washed with water and brine, dried with MgSO₄, filtered, and concentrated to dryness. The crude product was purified via reverse phase chromatography using an Isco C-18 cartridge (43 g). The mobile phase was a 15% to 80% CH₃CN/H₂O gradient with 0.1% (volume) formic acid added to both components of the mobile phase. The main peak was isolated as product giving 43 mg of 9625 as white solid.

Compound 9624 to compound 9634 were synthesis using example 9624 and example 9625 and procedures described previously.

Example 9638

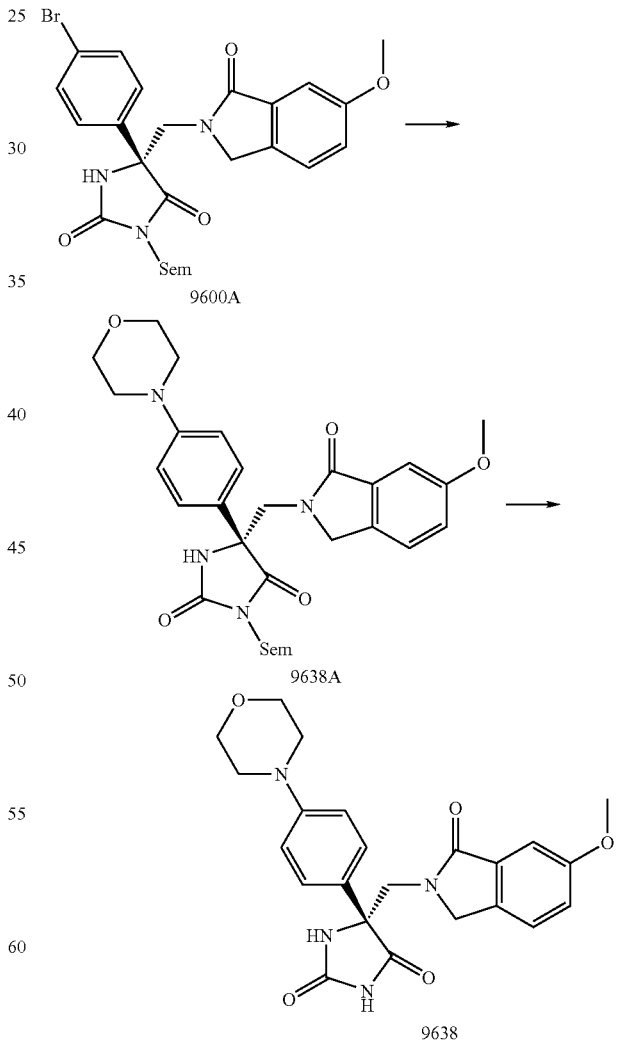

Compound 9638A (233 mg, 0.416 mmol), and palladium (II) acetate (15 mg, 0.067 mmol) were added to a Schlenck tube equipped with a stir bar. The flask was placed under $N_2$ flow and sodium tert butoxide was added (96 mg, 0.99 mmol), followed by ortho biphenyl-di-tert-butylphosphine (38 mg, 0.13 mmol). The flask was capped with a septum, then cycled between vacuum and $N_2$ four times. Toluene was added via syringe and the flask was cycled between vacuum and $N_2$ two times. The reaction mixture was stirred at rt for 20 min. Morpholine (45 mg, 0.52 mmol) was added via syringe. The tube was cycled between vacuum and $N_2$ once, then placed in a 90 C oil bath. The reaction mixture was stirred for 2.5 h, then allowed to cool to rt. The reaction mixture was stirred at rt ON. The reaction mixture was diluted with EtOAc and 1.0 M aqueous pH 5.5 sodium phosphate buffer. The layers were separated. The organic layer was washed with aq $NH_4Cl$, water and brine. The resulting organic solution was filtered, dried with $MgSO_4$, filtered, and concentrated to dryness. The crude product was purified via flash sgc using a 90 g $SiO_2$ cartridge. The mobile phase used was 30% (5% MeOH in EtOAc)/Hexanes, followed by 50% (5% MeOH in EtOAc)/Hexanes. The major UV active material was isolated as a white solid (0.16 g). This material was repurified via prep TLC using 95:5 $CH_2Cl_2$:MeOH as the mobile phase. Compound 9638A was isolated as clear oil that crystallized on standing.

Compound 9638A was converted to compound 9638 using SEM deprotection procedures similar to those described previously.

Compound 9638 was synthesis using example 9638 and procedures described previously.

Example 9650

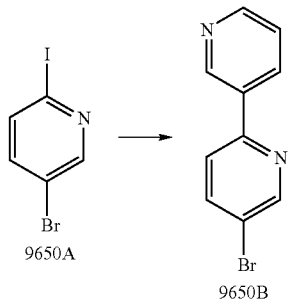

Compound 9650A (5.0 g, 17.61 mmol), 4-pyridine boronic acid (2.06 g, 16.73 mmol), and Pd(dppf)$C_{12}$—$CH_2Cl_2$ (644 mg, 0.88 mmol) were placed in a 500 mL flask. The flask was vacuumed for 1 minutes and then it was filled with $N_2$. This process was repeated for twice. $CH_3CN$ (200 mL) and $K_2CO_3$ (1M, 100 mL) were added. The solution was stirred in at 35° C. for two days. Additional Pd(dppf)$C_{12}$—$CH_2Cl_2$ (400 mg) was added in the second day. The aqueous layer was separated and it was extracted with EtOAc (50 mL) once. The organic layers were combined, washed with brine (100 mL) and dried over $Na_2SO_4$. The solution was concentrated and purified by sgc (Hexane/EtOAc 3:1 to 2:1) to give compound 9650B (3.1 g, 74.9%).

Compound 9650 to compound 9653 were synthesis using example 9650 and procedures described previously.

Example 9002

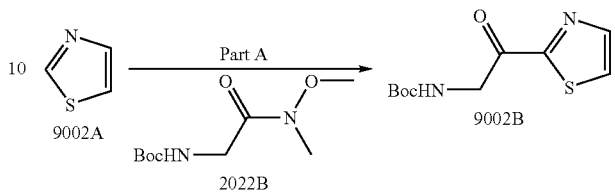

Part A:

To thiazole (9002A) (1.50 g, 17.6 mmol) in THF (20 mL) at −78° C. was added n-BuLi (2.5 M, 7.2 mL, 18 mmol). The reaction mixture was stirred for 1 hour then Weinreb amide 2022B (1.92 g, 8.8 mmol) in THF (10 ml) was added. The reaction mixture was warmed to room temperature and stirred overnight. The mixture was quenched with ammonium chloride solution and extracted with ethyl acetate. The combined organic layers were washed with brine, dried over sodium sulfate and concentrated. Purification by silica gel chromatography (30% ethyl acetate/hexane) afforded 9002B (980 mg, 46%) as an orange oil. HPLC-MS $t_R$=1.45 min £ ($UV_{254\ nm}$); mass calculated for formula $C_{10}H_{14}N_2O_3S$ 242.07, observed LCMS m/z 265.1 (M+Na).

Compound 9002C and compound 9002D were synthesis using example 9002 and procedures described previously.

Example 9003

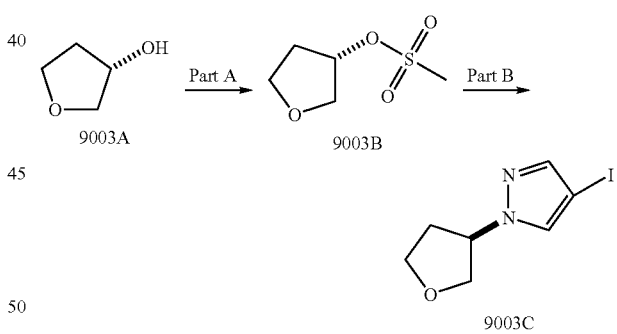

Part A:

According to a modification of a procedure by Ghosh, A. K. et. al. (*J. Med. Chem.* 1993, 36, 2300-2310) to an ice cold solution of (S)-(+)-3-hydroxytetrahydrofuran (9003A) (4.5 mL, 66.3 mmol) in DCM (50 mL) was added triethylamine (13.8 mL, 99.4 mmol) followed by methanesulfonyl chloride (5.64 mL, 73 mmol), and the resulting mixture was stirred at 0° C. for 1.5 h. The mixture was then quenched with water (15 mL), stirred at 0° C. for 10 min, and diluted with DCM (100 mL). After phase separation the organics were washed with 12% HCl solution, saturated sodium bicarbonate solution, brine, and then concentrated to give desired product 9003B as a dark yellow oil (5.3 g, 48%), which was used in the next step without further purification.

651

Part B:

To an ice cold mixture of sodium hydride (770 mg, 30.5 mmol) in DMF (20 mL) was added a solution of 4-iodopyrazole (5.38 g, 27.8 mmol) in DMF (10 mL) and the resulting slurry was stirred at 0° C. for 20 min. Then a solution of mesylate 9003B (5.3 g, 31.9 mmol) in DMF (10 mL) was added and the resulting mixture was allowed to warm up to rt, stirred at rt for 30 min, and then heated at 80° C. for 1.5 h. The reaction mixture was then concentrated and partitioned between ethyl acetate and water. The organics were washed with water, brine, dried and concentrated to give an oil, which was chromatographed (SiO$_2$, 20% to 30% ethyl acetate/hexanes) to afford a white solid. This solid was triturated with ether, and the resulting solid was filtered off to give desired 9003C. HPLC-MS $t_R$=1.32 min (UV); mass calculated for formula $C_7H_{91}N_2O$ 263.98, observed LCMS m/z 265.0 (M+H).

Compound 9003D and compound 9003M were synthesis using example 9003 and procedures described previously.

Example 9004

652

Part A:

The two isomers of 29004F were separated using a chiral AD column. One gram of material was injected into the column and the two peaks were separated by using a solvent mixture of 80% hexanes/2-propanol. The second isomer was the desired compound 9004A (400 mg, 80%).

Part B:

Compound 9004B was prepared from compound 9004A according to the procedures described in Example 2026 part E, F and G: HPLC-MS $t_R$=0.98 min (UV$_{254\,nm}$); mass calculated for formula $C_{22}H_{19}N_5O_4S$ 449.12, observed LCMS m/z 450.1 (M+H).

Compound 9004B and compound 9004E were synthesis using example 9004 and procedures described previously.

Example 9005

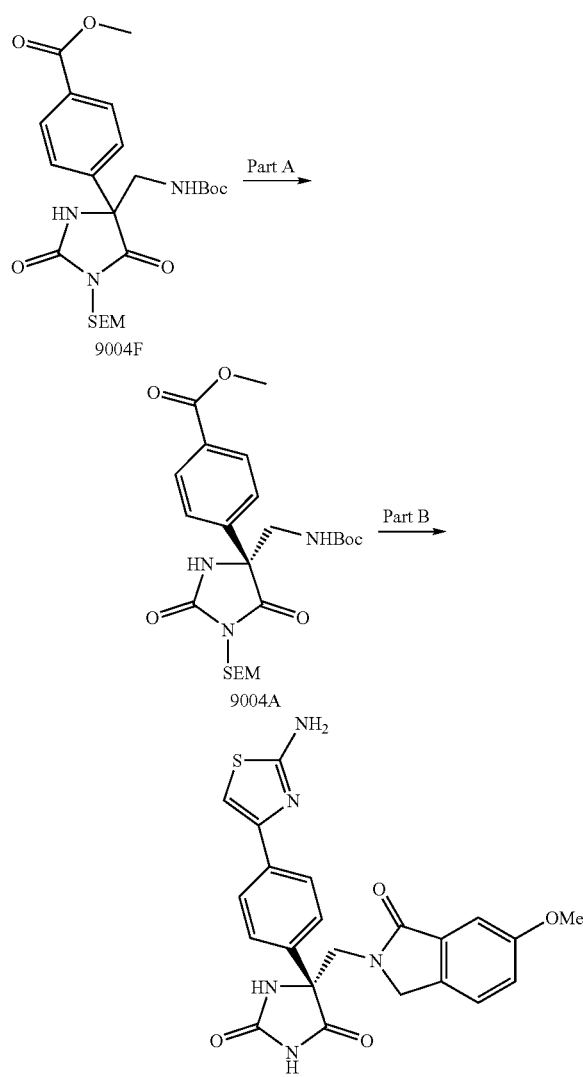

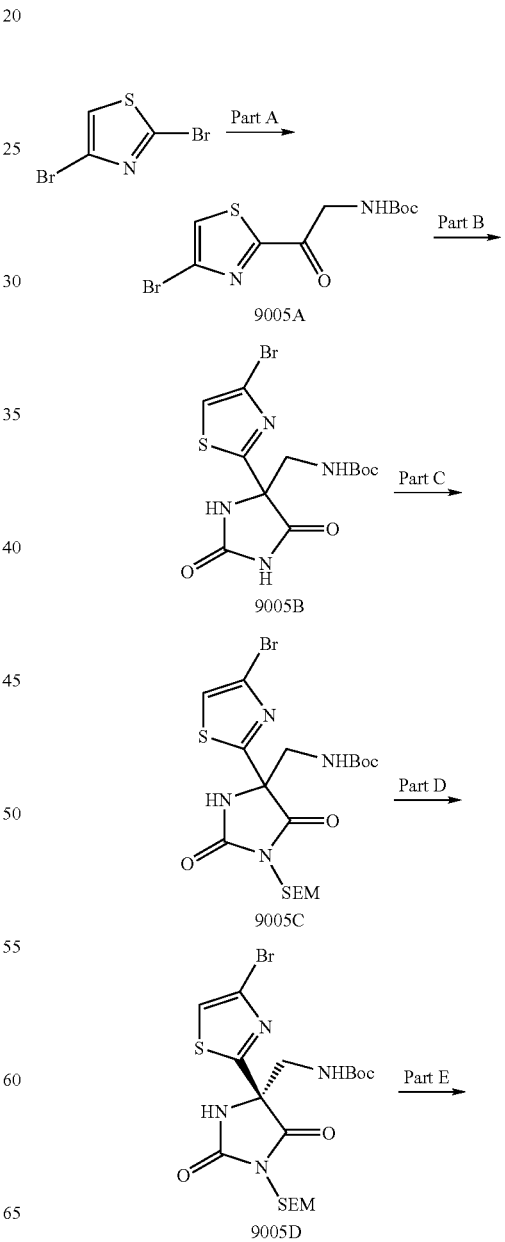

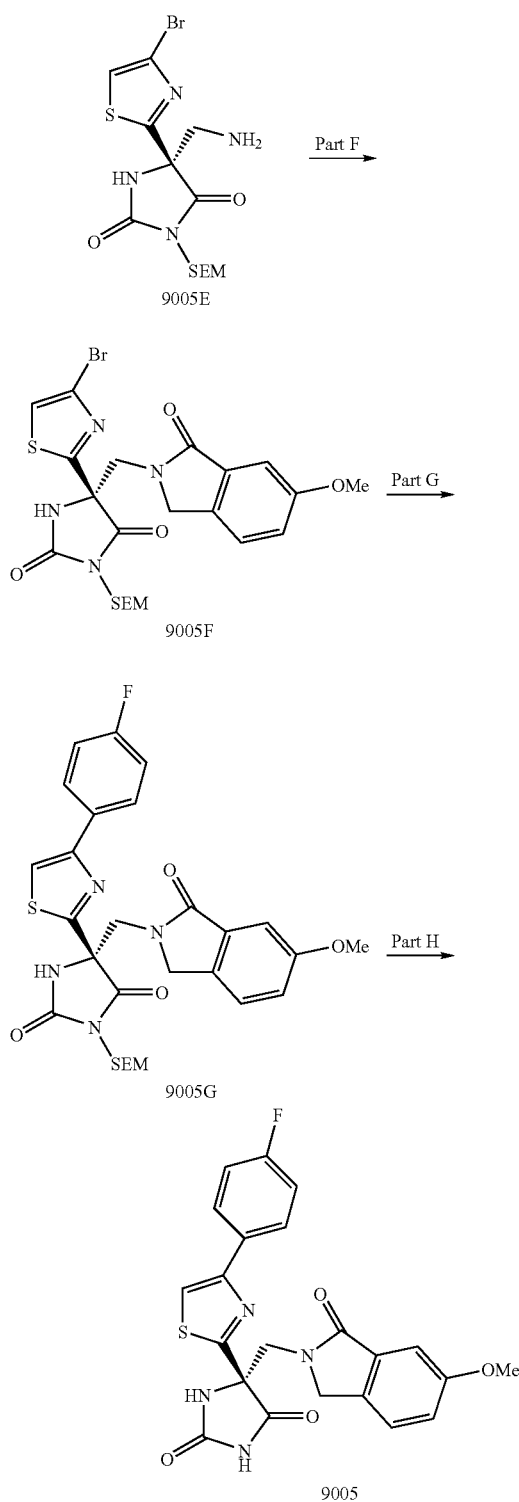

Part A:

i-PrMgCl (2M in Et$_2$O, 10.4 mL, 20.8 mmol) was added dropwise to a solution of 2,4-dibromothiazole (5.0 g, 20.75 mmol) in Et$_2$O (40 mL) at 0° C. After stirring for 15 min at this temperature, a solution of the Weinreb amide of N-Boc gly- cine (2.26 g, 10.4 mmol) in Et$_2$O (40 mL) and THF (20 mL) was added dropwise. The reaction mixture was then allowed to warm to room temperature and stirred for 1.5 h, then quenched with 1 N NH$_4$Cl aqueous solution. It was diluted with EtOAc; the organic layer was washed with H$_2$O, NaHCO$_3$, brine, dried over Na$_2$SO$_4$, and concentrated. Flash column chromatography afforded compound 9005A as a white solid (3.04 g, 89%) HPLC-MS t$_R$=1.75 min (UV$_{254\,nm}$); mass calculated for formula C$_{10}$H$_{13}$BrN$_2$O$_3$S 319.98, observed LCMS m/z 321.0 (M+H).

Part B:

Compound 9005A (3.20 g, 10 mmol) in 20 mL of 7 N NH$_3$ in MeOH was added into a mixture of KCN (0.98 g, 15 mmol) and (NH$_4$)$_2$CO$_3$ (3.36 g, 35 mmol) in H$_2$O (20 mL). The reaction mixture was stirred at 75° C. for 3 hours in a sealed pressure flask. After cooling to room temperature, the solution was transferred to a round bottom flask and concentrated to dryness. The residue was dissolved with EtOAc, washed with H$_2$O, brine, dried over Na$_2$SO$_4$, and concentrated to afford compound 9005B as a yellow solid (1.85 g, 47%). HPLC-MS t$_R$=1.32 min (UV$_{254\,nm}$); mass calculated for formula C$_{12}$H$_{15}$BrN$_4$O$_4$S 390.0, observed LCMS m/z 413.0 (M+Na).

Part C:

SEM-Cl (1 mL) was added dropwise to a solution of compound 9005B (1.85 g, 4.73 mmol) and DIEA (1.65 mL) in DMF (30 mL). After stirring for 2 h at room temperature, the reaction mixture was concentrated to dryness. It was then dissolved with EtOAc and H$_2$O. The organic layer was washed with H$_2$O, saturated Na$_2$HCO$_3$, brine, dried over Na$_2$SO$_4$, and concentrated. Flash column chromatography over silica gel (EtOAc/hexane 35:65) afforded Compound 9005C (2.22 g, 90%) as a white solid. HPLC-MS t$_R$=2.18 min (UV$_{254\,nm}$); mass calculated for formula C$_{18}$H$_{29}$BrN$_4$O$_5$SSi 520.1, observed LCMS m/z 543.1 (M+Na).

Part D:

The two isomers were separated using a chiral OD column. The racemate (400 mg) in 5 mL of IPA/hexane (1:1) was injected into the column and the two peaks were separated using a solvent mixture of 85% hexanes/isopropanol. The second isomer was the desired compound 9005D (112 mg, 56%).

Part E:

Compound 9005D (460 mg, 0.88 mmol) in dioxane (6 mL) was treated with 4 mL of 25% HCl in H$_2$O. After stirring at room temperature for 6 h, the reaction mixture was concentrated to dryness, giving rise to compound 9005E as a white solid (345 mg). HPLC-MS t$_R$=1.267 min (UV$_{254\,nm}$); mass calculated for formula C$_{13}$H$_{21}$BrN$_4$O$_3$SSi 420.0, observed LCMS m/z 421.0 (M+H).

Part F:

A mixture of compound 9005E (445 mg), compound 305 (342 mg, 1.32 mmol) and DIEA (384 μL, 2.2 mmol) in DMF (5 mL) was heated at 90° C. overnight. The solution was concentrated to dryness; the residue was then dissolved with EtOAc and H$_2$O. The organic layer was washed with 1N HCl, saturated NaHCO$_3$, brine, dried over Na$_2$SO$_4$, and concentrated. Flash column chromatography over SiO$_2$ (EtOAc/hexane 50:50) afforded compound 9005F (170 mg. 34%). HPLC-MS t$_R$=2.181 min (UV$_{254\,nm}$); mass calculated for formula C$_{22}$H$_{27}$BrN$_4$O$_5$SSi 566.1, observed LCMS m/z 567.1 (M+H).

Part G:

Under argon, a mixture of compound 9005F (70 mg, 0.123 mmol), 4-fluorophenylboronic acid (26 mg, 0.185 mmol), $K_3PO_4.H_2O$ (85 mg, 0.37 mmol), and $PdCl_2(dppf)$ (5 mg, 0.0062 mmol) in dioxane (5 mL) was stirred at 60° C. for 12 h. The reaction mixture was filtered through a plug of celite with the aid of EtOAc, and the solution was then concentrated to dryness. The residue was purified by flash column chromatography over $SiO_2$ (EtOAc/hexane 55:45), resulting in compound 9005G (50 mg, 70%). HPLC-MS $t_R$=2.15 min ($UV_{254\ nm}$); mass calculated for formula $C_{28}H_{31}FN_4O_5SSi$ 582.2, observed LCMS m/z 583.3 (M+H).

Part H:

Compound 9005G (50 mg, 0.086 mmol) in $CH_3CN$ (5 mL) was added dropwise with $BF_3.OEt_2$ (55 µL, 0.43 mmol) at 0° C. After stirring for 2 h at this temperature, DIEA (1 mL) and 1N NaOH (2 mL) were subsequently added. The reaction mixture was allowed to stir at room temperature for 12 h, then concentrated to dryness. The resulting solid was treated with $H_2O$ (10 mL), 1N HCl (6 mL). The precipitate was collected by filtration. HPLC purification afforded pure compound 9005 (27 mg) as a white solid. HPLC-MS (10 min) $t_R$=3.85 min ($UV_{254\ nm}$); mass calculated for formula $C_{22}H_{17}FN_4O_4S$ 452.10, observed LCMS m/z 453.1 (M+H).

Compound 9005 was synthesized using example 9005 and procedures described previously.

Example 9901

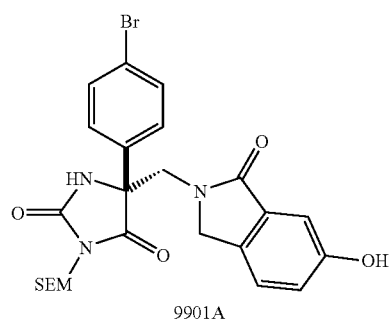

9901A

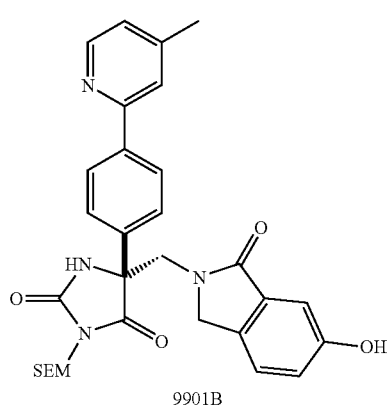

9901B

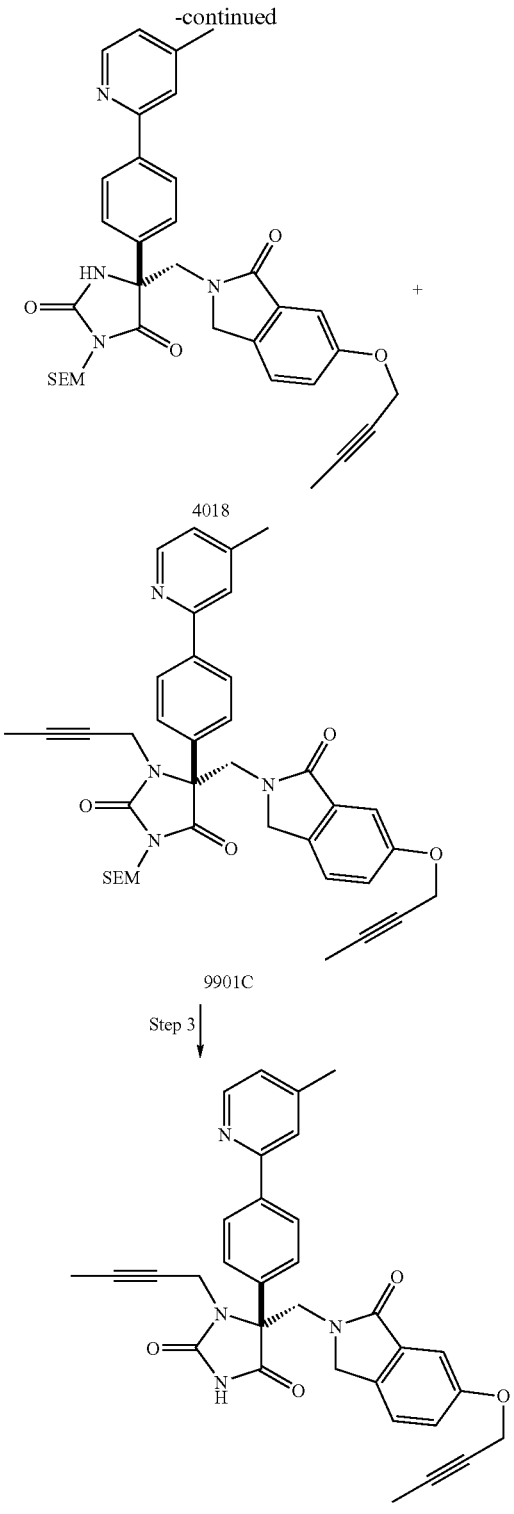

Step 1
Compound 9901A was converted to Compound 9901B as described in Example 1004.

Step 2
A mixture of Compound 9901B (200 mg, 0.358 mmol) and cesium carbonate (175 mg, 0.537 mmol) in DMF (3.0 mL)

was stirred for 30 min at 0° C. A solution of 1-bromo-2-butyne (57 mg, 0.430 mmol) in DMF (0.5 mL) was added at 0° C. and the reaction mixture was stirred for 1 h at 0° C., then overnight at rt. The reaction mixture was diluted with EtOAc and washed sequentially with saturated aq ammonium chloride, water, and brine. The organic phase was dried over MgSO₄, filtered, and concentrated. The residue was purified by sgc (0-100% EtOAc/hexanes gradient) to yield, in order of elution, Compound 9801 (110 mg, 51%) and then Compound 9901C (67 mg, 28%).

Step 3

Compound 9901C was converted to Compound 9901 as described in Example 1001, Step 4.

Compound 9901 was synthesized using example 9901 and procedures described previously.

Example 9916

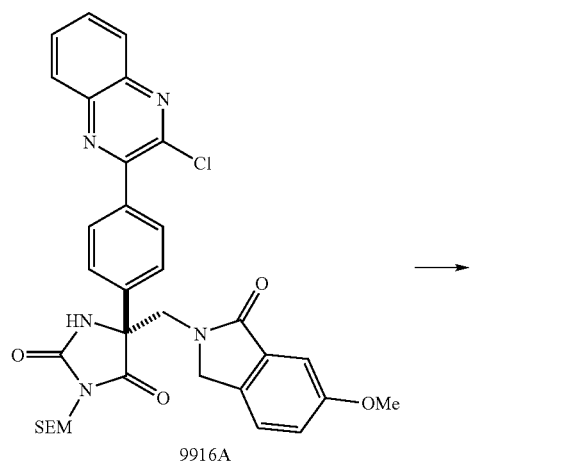

Compound 9916A was prepared according to procedures given in Examples 14, 1001, 1004 and 1008. Compound 9916A was converted to Compound 9916 using the procedure given in Example 1001, Step 4.

Compound 9916 was synthesized using example 9916 and procedures described previously.

Example 9229

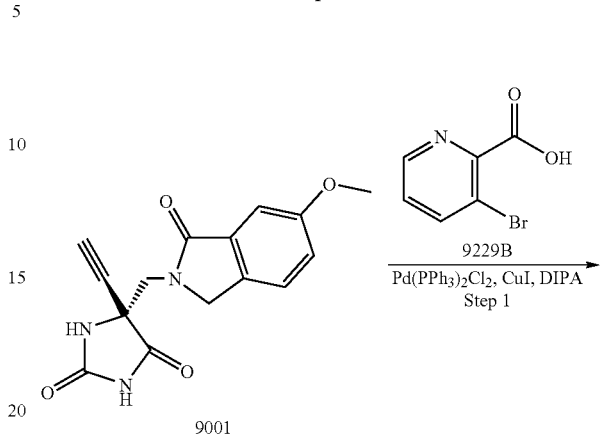

Step 1. Compound 9001 (100 mg, 0.33 mmol) was combined with compound 9229B (80 mg, 0.4 mmol), Pd(PPh₃)₂Cl₂ (8 mg, 0.012 mmol), CuI (17 mg, 0.1 mmol), diisopropylamine (0.08 mL, 0.58 mmol) in DMF (1 mL) and stirred at 85° C. for 2 h. The reaction mixture was purified on a Gilson reverse phase HPLC (0-40% acetonitrile in H₂O with formic acid 0.1%) afforded the desired product 9229 (18 mg, 13%).

Compound 9229 was Synthesized Using Example 9229 and Procedures Described Previously Example 9272

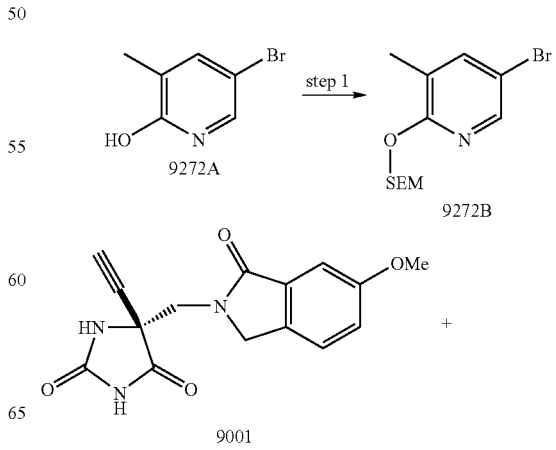

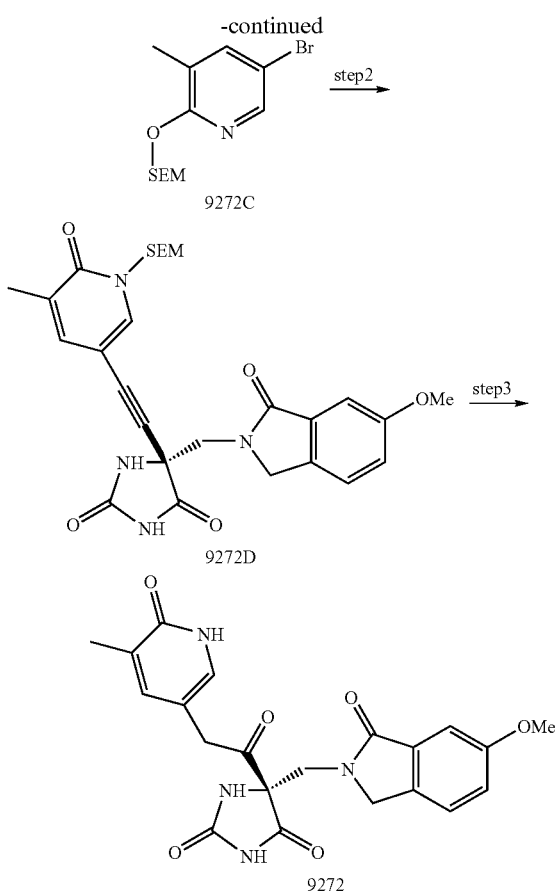

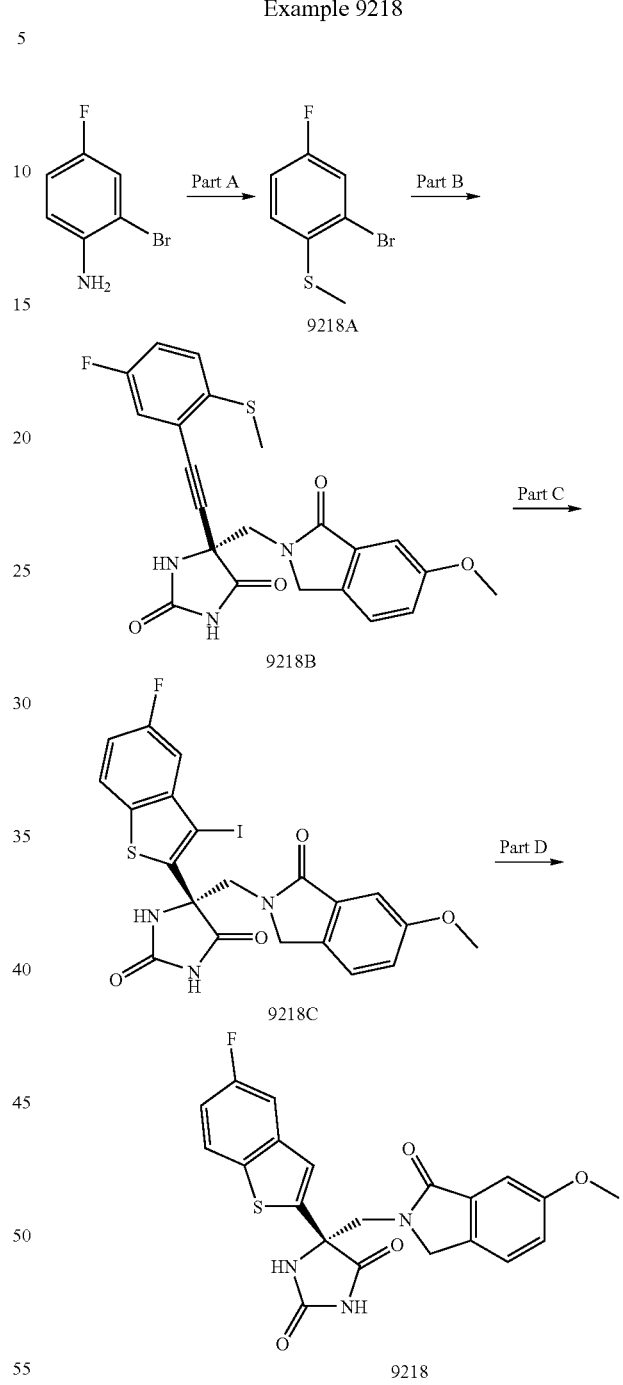

Compound 9272 was synthesized using example 9272 and procedures described previously.

Example 9218

Step 1

A mixture of 9272A (161 mg, 0.86 mmol), SEMCl (0.17 mL, 0.94 mmol), and diisopropylethylamine (0.22 mL, 1.28 mmol) in CH$_2$Cl$_2$ (3 mL) was stirred at 25° C. for 2 h. The mixture was added to an aqueous NaHCO$_3$ solution and the organic layers were extracted with CH$_2$Cl$_2$. The combined organic solution was washed with brine solution, dried (Na$_2$SO$_4$), and concentrated in vacuo. The residue was purified by SiO$_2$ column chromatography (CH$_2$Cl$_2$/hexane=2:1). to afford 9272B (200 mg, 74% yield).

Step 2

A mixture of 9001 (100 mg, 0.33 mmol), 9272C (165 mg, 0.52 mmol), Pd(PPh$_3$)$_2$Cl$_2$ (4.9 mg, 7 μmol), CuI (1.9 mg, 10 μmol), and diisopropylethylamine (0.17 mL, 0.99 mmol) in DMF (1.5 ml) was purged with N$_2$ and heated to 70° C. After heating for 17 h, the mixture was cooled to 25° C. and purified by column chromatography on a reverse phase C-18 column (0.01% HCO$_2$H in water/0.01% HCO$_2$H in CH$_3$CN) to afford 9272D (78 mg, 44% yield).

Step 3

9272D (78 mg, 0.14 mmol) was dissolved in MeOH (15 mL) and treated with 4 N HCl in dioxane (3 mL). The mixture was heated to 60° C. in a pressure vessel for 16 h and cooled to 25° C. The mixture was neutralized with NH$_3$-MeOH (7 N solution) and the resulting precipitate was filtered off. The filtrate was concentrated in vacuo and the residue was purified by preparative TLC (10% MeOH in CH$_2$Cl$_2$) to afford 9272 (25 mg, 40% yield).

Part A:

Compound 9218A was synthesized from 2-bromo-4-fluoroaniline according to a procedure described in Allaire, F. S. et al. (*Syn. Commun.*, 2001, 31, 1857-1861).

Part B:

Compound 9218B was prepared from 9218A following procedures described in Example 9000 part H and I. HPLC-MS t$_R$=1.60 min (UV$_{254\ nm}$); mass calculated for formula C$_{22}$H$_{18}$FN$_3$O$_4$S 439.10, observed LCMS m/z 440.0 (M+H).

Part C:

To compound 9218B (78 mg, 0.18 mmol) in $CH_2Cl_2$ (5 mL) was added iodine (90 mg, 0.36 mmol) in $CH_2Cl_2$ (5 mL) and the resulting mixture was stirred for 3 h. The mixture was diluted with $CH_2Cl_2$ and washed with 5% $NaHSO_3$, water and brine, dried over sodium sulfate and concentrated to give a white solid (92 mg) which was used directly in the next step without purification. HPLC-MS $t_R$=1.71 min ($UV_{254\ nm}$); mass calculated for formula $C_{21}H_{16}FIN_3O_4S$ 550.98, observed LCMS m/z 552.0 (M+H).

Part D:

Compound 9218C (92 mg, 0.17 mmol) and palladium on carbon (10%, 10 mg) in MeOH (3 mL) were stirred under $H_2$ for 4 days. The mixture was filtered through Celite and concentrated. The residue was purified through RP-HPLC to provide recovered starting 9218C (33 mg) and compound 9218 (7.4 mg, 16% based on conversion). HPLC-MS $t_R$=1.55 min ($UV_{254\ nm}$); mass calculated for formula $C_{21}H_{16}FN_3O_4S$ 425.08, observed LCMS m/z 426.1 (M+H).

Compound 92186 was Synthesized Using Example 99218 and Procedures Described Previously Example 9223

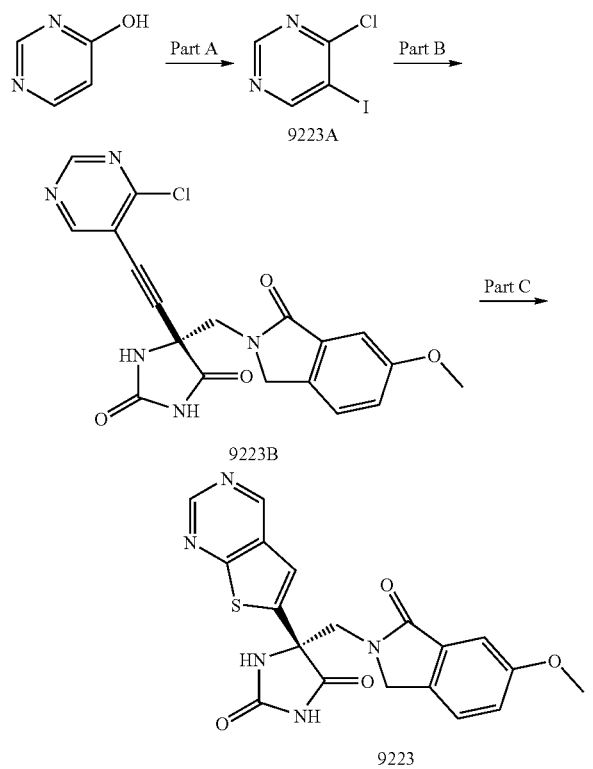

Part A:

Compound 9223A was synthesized from 4(3H)-pyrimidone according to a procedure described in Sakamoto, T. et al. (*Chem. Pharm. Bull.*, 1986, 34, 2719-2724).

Part B:

Compound 9223B was prepared from compound 9001 and compound 9223A according to the procedure described in Example 9000 part H: HPLC-MS $t_R$=1.21 min ($UV_{254\ nm}$); mass calculated for formula $C_{19}H_{14}ClN_5O_4S$ 411.07, observed LCMS m/z 412.1 (M+H).

Part C:

Compound 9223B (82 mg, 0.20 mmol) and NaSH (56 mg, 1.0 mmol) were heated in EtOH (3 mL) at 80° C. for 2 h. After the mixture was concentrated and ice water was added, the aqueous mixture was extracted with chloroform and the combined organic layers were washed with brine, dried over sodium sulfate and concentrated. The resulting residue was purified by RP-HPLC to provide 9223 (44 mg, 54%). HPLC-MS $t_R$=1.09 min ($UV_{254\ nm}$); mass calculated for formula $C_{19}H_{15}N_5O_4S$ 409.08, observed LCMS m/z 410.2 (M+H).

Compound 9223 was Synthesized Using Example 9223 and Procedures Described Previously Example 9231

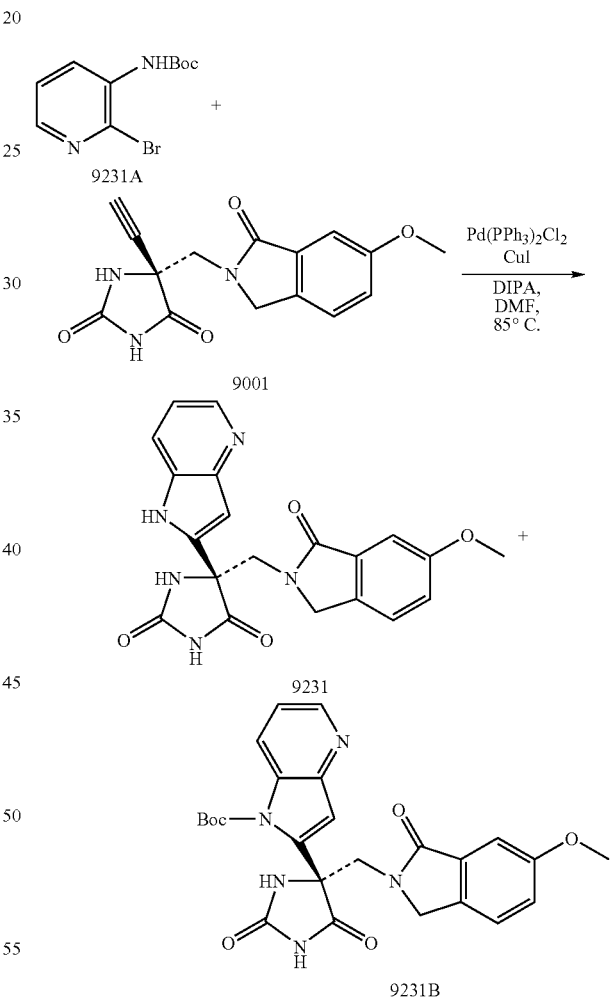

Step 1

Compound 9231A (80 mg, 0.29 mmol) was combined with compound 9001 (100 mg, 0.33 mmol), $Pd(PPh_3)_2Cl_2$ (5 mg, 0.007 mmol), CuI (12 mg, 0.06 mmol), diisopropylamine (0.16 mL, 1.13 mmol) in DMF (1 mL) and stirred at 85° C. The reaction mixture was neutralized with acetic acid and purified with Gilson reverse phase (0-40% acetonitrile in $H_2O$ with 0.1% formic acid) afforded the desired product 9231 (3 mg, 3%) mass calculated for formula $C_{20}H_{17}N_5O_4$ 391.13, observed LCMS m/z 392.2. (M+H) and compound 9231B (22 mg, 15%), mass calculated for formula $C_{25}H_{25}N_5O_6$ 491.18, observed LCMS m/z 492.2. (M+H)

Compound 9231 was synthesized using example 9231 and procedures described previously.

Example 9273

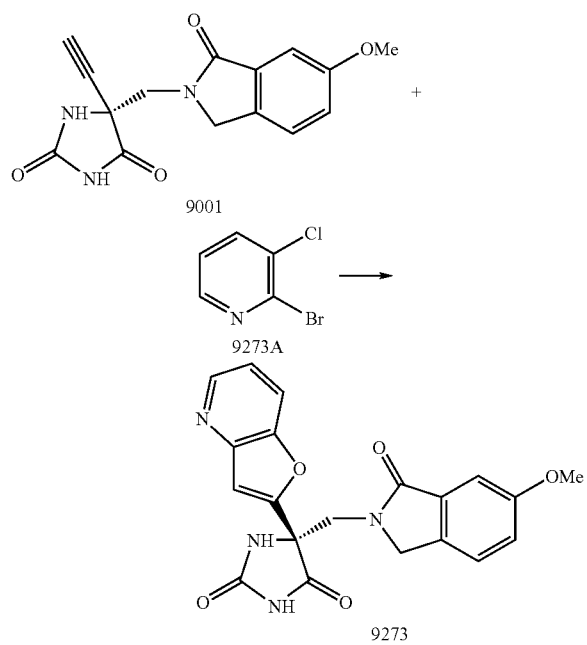

A mixture of 9001 (1.17 g, 3.91 mmol), 9273A (2.04 g, 11.7 mmol), $Pd(PPh_3)_2Cl_2$ (55 mg, 78 μmol), CuI (15 mg, 78 μmol), and diisopropylethylamine (3.0 mL, 17.6 mmol) in DMF (10 ml) was purged with $N_2$ and heated to 60° C. After heating for 17 h, the mixture was cooled to 25° C. and a half of the solvent was removed by evaporation. The reaction mixture in DMF was purified by column chromatography on a reverse phase C-18 column (0.01% $HCO_2H$ in water/0.01% $HCO_2H$ in $CH_3CN$) to afford 9273 (1.27 g, 84% yield).

Compound 9273 was synthesized using example 9273 and procedures described previously Example 9277

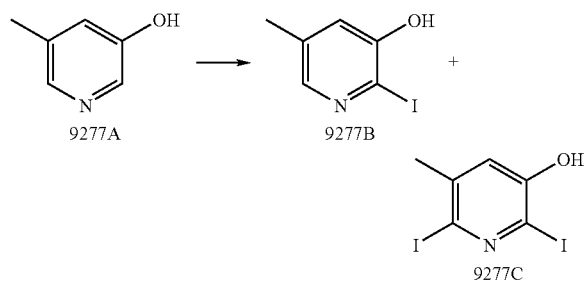

A suspension of 9277A (202 mg, 1.85 mmol) in water (5 mL) was treated with $Na_2CO_3$ (411 mg, 3.89 mmol) and iodine (470 mg, 1.85 mmol) at 25° C. The mixture was stirred for 3 h at the temperature and acidified to pH~4 by 1N HCl solution. The resulting precipitate was filtered, washed with water, and purified by $SiO_2$ column chromatography (0 to 5% MeOH in $CH_2Cl_2$) to afford 9277B (204 mg, 47% yield) and 9277C (58 mg, 9% yield).

Compound 9277 was Synthesized Using Example 9277 and Procedures Described Previously Example 9276

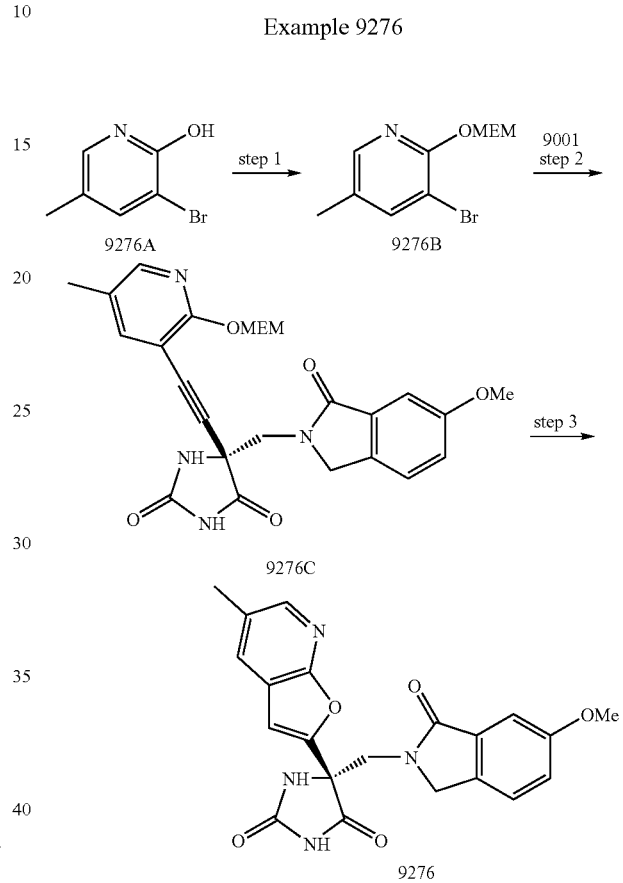

Step 1

A mixture of 9276A (200 mg, 2.12 mmol), MEMCl (0.31 mL, 2.76 mmol), and diisopropylethylamine (1.1 mL, 6.38 mmol) in $CH_2Cl_2$ (10 mL) was stirred at 25° C. for 26 h. The mixture was added to aqueous $NaHCO_3$ solution and the organic layers were extracted with EtOAc. The combined organic solution was washed with brine solution, dried ($Na_2SO_4$), and concentrated in vacuo. The residue was purified by $SiO_2$ column chromatography to afford 9276B (160 mg, 27% yield).

Step 2

A mixture of 9001 (80 mg, 0.26 mmol), 9276B (81 mg, 0.29 mmol), $Pd(PPh_3)_2Cl_2$ (5.6 mg, 8 μmol), CuI (5 mg, 26 μmol), and diisopropylethylamine (0.09 mL, 0.53 mmol) in DMF (3 ml) was purged with $N_2$ and heated to 70° C. After heating for 20 h, the mixture was cooled to 25° C. and the solvent was removed by evaporation. The residue was purified by preparative TLC (7% MeOH in $CH_2Cl_2$) to afford 9276C (20 mg, 16% yield).

Step 3

A solution of 9276C (20 mg, 0.04 mmol) in $CH_2Cl_2$ (2 mL) was treated with trifluoroacetic acid (0.5 mL) and the mixture was stirred at 25° C. for 16 h. The mixture was concentrated in vacuo and the residue was purified by preparative TLC to afford 9276 (3 mg, 18% yield).

Compound 9276 was Synthesized Using Example 9276 and Procedures Described Previously Example 9224

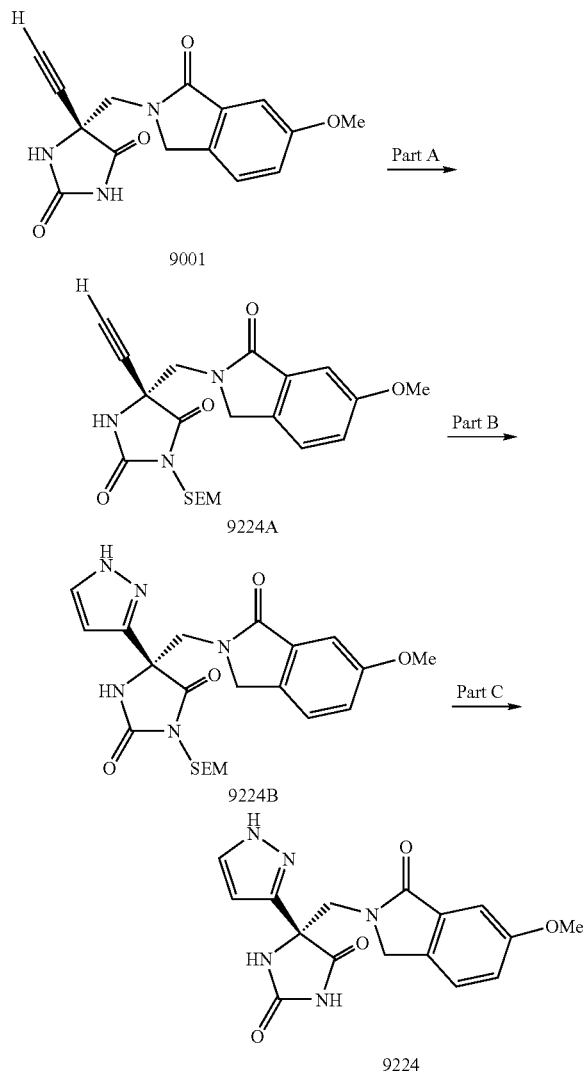

Part A:
SEM-Cl (627 mg, 3.76 mmol) was added dropwise to a solution of compound 9001 (940 mg, 3.14 mmol) and DIEA (487 mg, 3.77 mmol) in DMF (10 mL) at 0° C. After stirring at room temperature for 12 h, the reaction mixture was concentrated; the residue was dissolved with EtOAc and $H_2O$. The aqueous phase was extracted with EtOAc (20 mL×3); the organics were combined, washed with saturated $NaHCO_3$, brine, dried over $Na_2SO_4$, and concentrated. Flash column chromatography over $SiO_2$ (EtOAc/hexane: 60:40) afforded Compound 9224A as a white solid (1.22 g, 91%). HPLC-MS $t_R$=1.894 min ($UV_{254\ nm}$); mass calculated for formula $C_{21}H_{27}N_3O_5Si$ 429.27, observed LCMS m/z 452.2 (M+Na).

Part B:
A solution of trimethylsilyldiazomethane (1 mL, 2.0 M, 2.0 mmol) in $Et_2O$ was added into compound 9224A (430 mg, 1 mmol) in THF (5 mL). After stirring at 50° C. for 12 h, the reaction mixture was concentrated to dryness. Flash column chromatography over $SiO_2$ (EtOAc) afforded compound 9224B as a white solid (320 mg, 68%). HPLC-MS $t_R$=1.722 min ($UV_{254\ nm}$); mass calculated for formula $C_{22}H_{29}N_5O_5Si$ 471.19, observed LCMS m/z 943.3 (2M+H).

Part C:
Trifluoroboron etherate (0.1 mL) was added dropwise to a solution of Compound 9224B (85 mg, 0.18 mmol) in acetonitrile (5 mL) at 0° C. The reaction mixture was allowed to stir at room temperature for 30 min, then cooled to 0° C. DIEA (0.5 mL) and 2 mL of 1N NaOH solution was subsequently added. After stirring at room temperature for 12 h, the solution was concentrated, and extracted with EtOAc (20 mL×3). The organic phase was washed with brine, dried over $Na_2SO_4$, and concentrated. Reverse phase HPLC purification afforded compound 9224 (27 mg, 44%) as a white solid. HPLC-MS (10 min) $t_R$=2.189 min ($UV_{254\ nm}$); mass calculated for formula $C_{16}H_{15}N_5O_4$ 341.11, observed LCMS m/z 342.1 (M+H). $^1$H NMR (400 MHz, DMSO-d$^6$): δ 10.78 (s, 1H), 8.56 (d, J=1.20 Hz, 1H), 7.73 (d, J=2.43 Hz, 1H), 7.48 (d, J=8.27 Hz, 1H), 7.18-7.14 (m, 2H), 6.21 (d, J=2.20 Hz, 1H), 4.34-4.25 (m, 2H), 4.33-4.02 (m, 2H), 3.81 (s, 3H).

Compound 9224 was Synthesized Using Example 9224 and Procedures Described Previously Example 9247

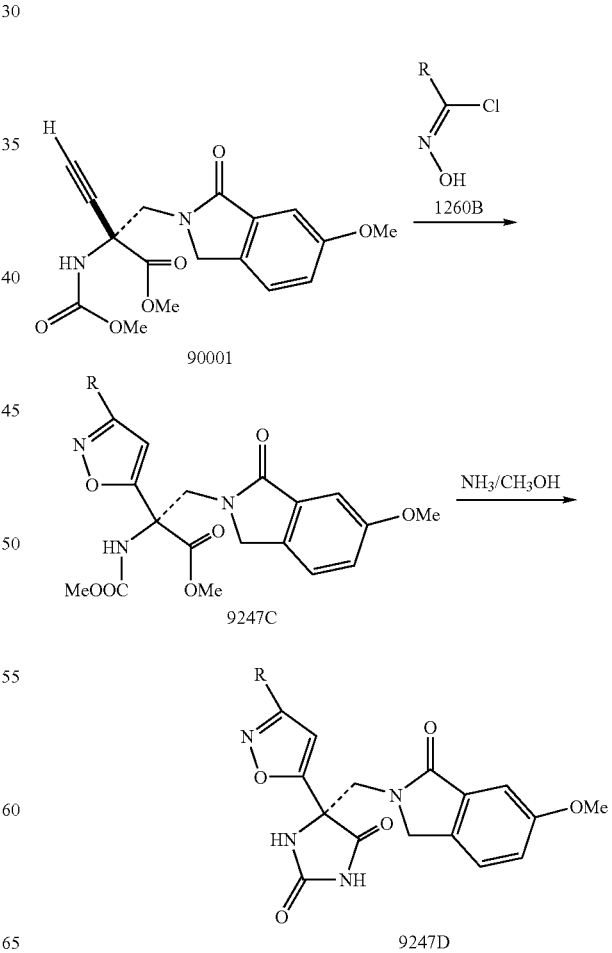

General Procedure for the Synthesis of Isoxazoles from Alkyne 9000I

As exemplified for phenylisoxazole derivative 9247: N-Hydroxybenzene-carboximidoyl chloride 9247B (70 mg, 0.17 mmol) and acetylene 9000I (30 mg, 0.2 mmol) were dissolved in 3 mL of a 1:1 tert-BuOH/H$_2$O mixture. While the mixture was being stirred, sodium ascorbate (1 M solution in water, 100 µL, 10 mol %) was added, followed by copper(II) sulfate pentahydrate (3 mg in 100 µL of H$_2$O, 2 mol %). The reaction mixture was then treated with KHCO$_3$ (100 mg, 1 mmol) and left stirring for 1 h at ambient temperature, after which time it was diluted with water and the product was extracted with 2×50 mL ethyl acetate. The crude product was subjected to silical gel chromatography using 30% ethyl acetate/n-hexane to provide pure product 9247C (62 mg).

Derivative 9247C was converted to 9247D using conditions described previously.

Example 9267

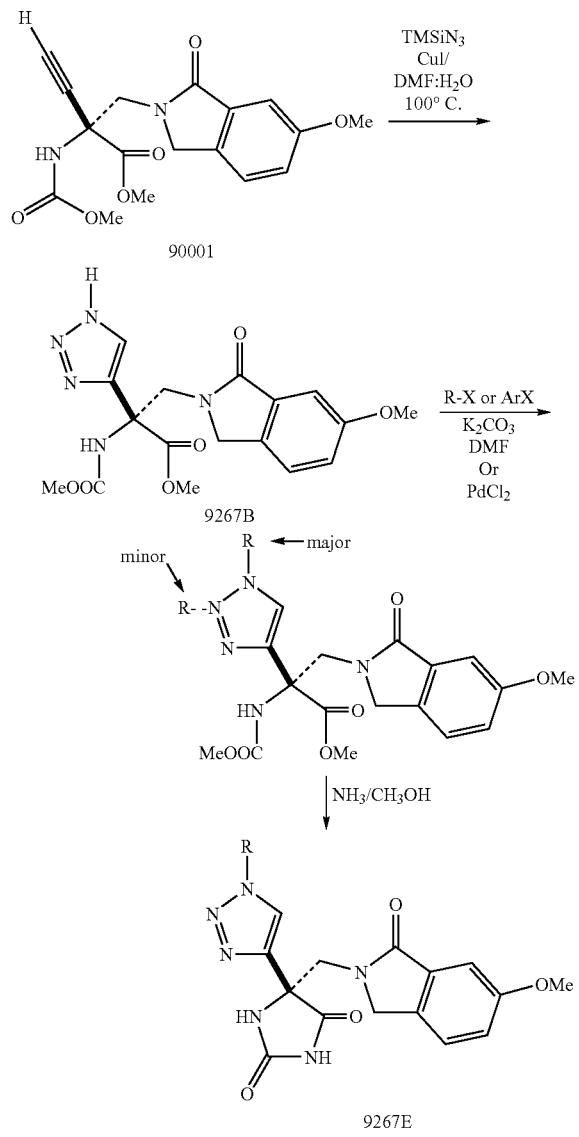

9267 1280B from 9000I: (Scheme 2). Trimethylsilyl azide (0.1 mL, 0.75 mmol) was added to a DMF and MeOH solution (1 mL, 9:1) of CuI (4.8 mg, 0.025 mmol) and acetylene 9000I (58 mg, 0.5 mmol) under N$_2$ in a pressure vial. The reaction mixture was stirred at 100° C. for 12 h. After consumption of 9000I, the mixture was cooled to room temperature. The residue was purified with silica gel column chromatography (n-hexane/EtOAc, 10:1 to 1:1) to afford 1,2,3-triazole 9267B.

Procedure for converting 9267B to 9267C: A mixture of Triazole (60 mg, 0.15 mmole) and K$_2$CO$_3$ (42 mg, 0.30 mmole) in DMF (3 ml) was stirred at r.t. for 10 minutes, followed by addition of Iodomethane (0.0115 mL, 0.18 mmole). Stirred at r.t. for 24 hours. By this time no more starting material left (checked by TLC). Reaction was diluted with water and extracted with EtOAc. Combined organic extract was washed with water (2×15 mL) and saline (1×15 mL), dried (Na$_2$SO$_4$), filtered and conc. The crude was separated by preparative TLC (using 5% MeOH/CH$_2$Cl$_2$) to give 1-substituted triazole, 0.03 g and 2-substituted triazole, 0.015 g.

Procedure for converting 9267B to 9267D: Following the reference procedure*, triazole (75 mg, 0.19 mmole) was coupled with 4-Fluoro-1-iodo benzene (51 mg, 0.23 mmole) using K$_3$PO$_4$ (81 mg, 0.38 mmole), CuI (1.8 mg, 0.0094 mmole) and Ligand (N,N-dimethyl cyclohexane diamine) (2.74 mg, 0.0192 mmole) in DMF ( ) 0.5 mL). Heated at 80° C. for 18 hours. Preparative chromatography using 5% MeOH/CH$_2$Cl$_2$ gave 1-substituted triazole, 0.03 g and 2-substituted substituted triazole (0.01 g).

*Reference: Jon C. Antilla, Jeremy M. Baskin, Timothy E. Barder, and Stephen L. Buchwald, J. Org. Chem 2004, 69, 5578-5587

Derivatives 9267C and 9267B were converted to 9267E using conditions described above.

Example 9259

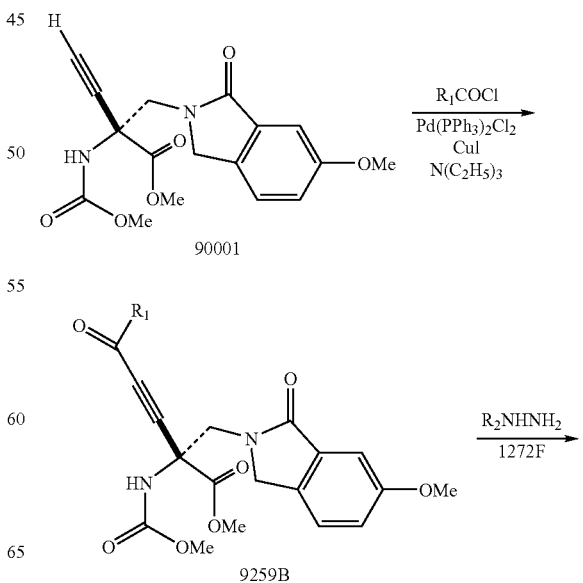

-continued

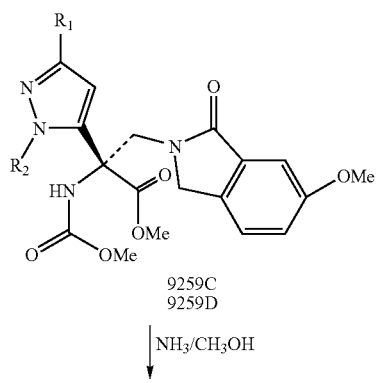

9259C
9259D

↓ NH₃/CH₃OH

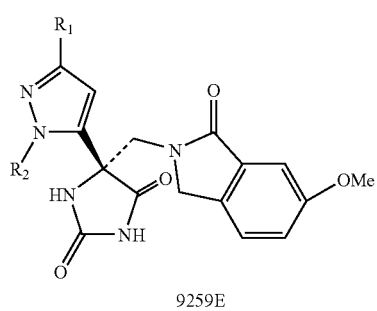

9259E

Procedure for synthesizing pyrazoles 10 (Scheme 3): A stirred mixture of Pd(PPh₃)₂Cl₂ (7 mg, 0.01 mmol) and CuI (4 mg, 0.025 mmol) in THF (2 mL) was degassed for 5 min. Then Et₃N (0.07 mL, 0.5 mmol), acid chloride (1 equiv) and acetylene 9000I (1 equiv) were added. The reaction mixture was stirred for 1 h under N₂ at r.t. until the alkyne was completely consumed. The solvent was removed and the product was isolated using 1:1 hexanes:ethyl acetate as the eluting solvent to provide 9259B (0.15 g).

To a solution of 9259B (75 mg, 0.16 mmol) in EtOH (3 mL) at r.t. was added methylhydrazine 9259F (0.008 mL, 0.17 mmol). The reaction was left for 1 h after which time EtOH was removed in vacuo to afford an orange oil which was purified by column chromatography (5% EtOAc in hexane) to afford 1-methyl-3-phenyl pyrazole (9259C, 31 mg).

To a solution of 9259B (75 mg, 0.16 mmol) in EtOH (3 mL) at r.t. under nitrogen was added phenylhydrazine (0.009 mL, 0.17 mmol). The solution was heated at reflux for 3-4 h and the EtOH was removed in vacuo. The residual crude was purified by column chromatography (40% EtOAc in hexane) to afford 1,5-diphenyl-pyrazole (9259D, 25 mg).

Derivatives 9259C and 9259D were converted to 9259E using conditions described above.

Compounds 9247-9271 were synthesized using examples 9247, 9267 and 9259 and procedures described previously.

Example 9933

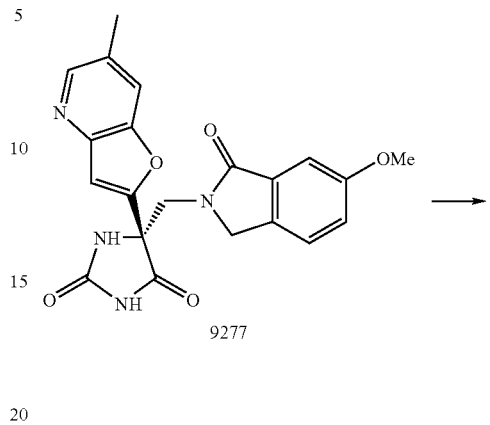

9277

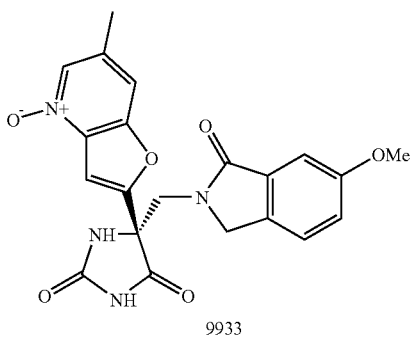

9933

To a solution of compound 9277 (70 mg, 0.13 mmol) in CH₂Cl₂ (3 mL) was added m-Chloroperbenzoic acid (70% purity, 45 mg, 0.16 mmol) at 25° C. The mixture was stirred for 20 h at the temperature and diluted in EtOAc. The organic solution was washed with aqueous NaHCO₃ solution and brine solution, dried (Na₂SO₄), and concentrated in vacuo. The residue was purified by reverse phase C-18 column chromatography (0.1% HCO₂H in H₂O-0.1% HCO₂H in CH₃CN) to afford compound 9933 (65 mg, 90% yield).

Example 9935

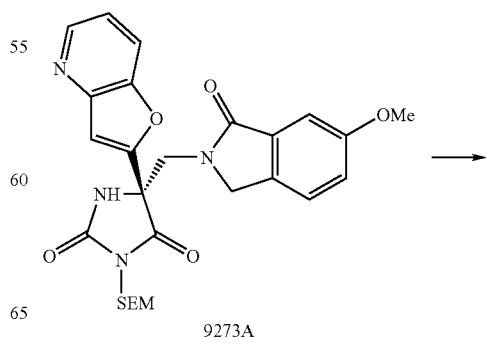

9273A

-continued

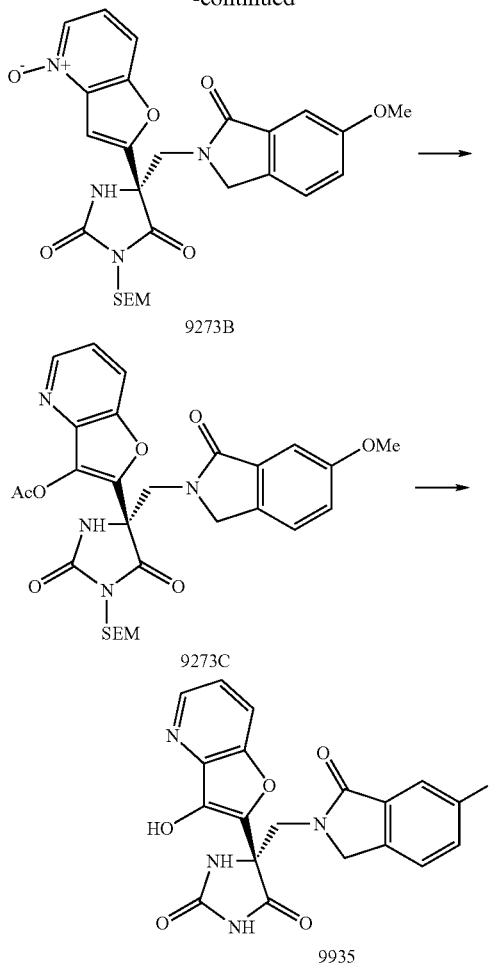

9273B

9273C

9935

Step 1

To a solution of compound 9273A (95 mg, 0.18 mmol) in CH$_2$Cl$_2$ (3 mL) was added m-Chloroperbenzoic acid (70% purity, 54 mg, 0.22 mmol) at 25° C. The mixture was stirred for 20 h at the temperature and diluted in EtOAc. The organic solution was washed with aqueous NaHCO$_3$ solution and brine solution, dried (Na$_2$SO$_4$), and concentrated in vacuo. The residue was purified by SiO$_2$ column chromatography (0% to 5% MeOH in CH$_2$Cl$_2$) to afford compound 9273B (75 mg, 77% yield).

Step 2

Compound 9273B (37 mg, 0.07 mmol) was dissolved in Ac$_2$O (1 mL) and the solution was heated to 80° C. After stirring for 24 h, the mixture was further stirred at 120° C. for 6 h. The mixture was cooled to 25° C. and concentrated in vacuo. The residue was purified by preparative TLC (5% MeOH in CH$_2$Cl$_2$) to afford 9273C (20.4 mg, 51% yield).

Step 3

A solution of 9273C (20 mg, 0.034 mmol) in MeOH (2.5 mL) was treated with 4N HCl in dioxane (0.6 mL). The mixture was stirred at 40° C. in a pressure vessel for 18 h and at 70° C. for 24 h. The mixture was cooled to 25° C. and concentrated in vacuo and the residue was purified by preparative TLC (5% MeOH in CH$_2$Cl$_2$) to afford compound 9935 (9.3 mg, 67% yield).

Compounds 9933 and 9935 were synthesized using examples 9933, 9935 and procedures described previously.

Example 9651

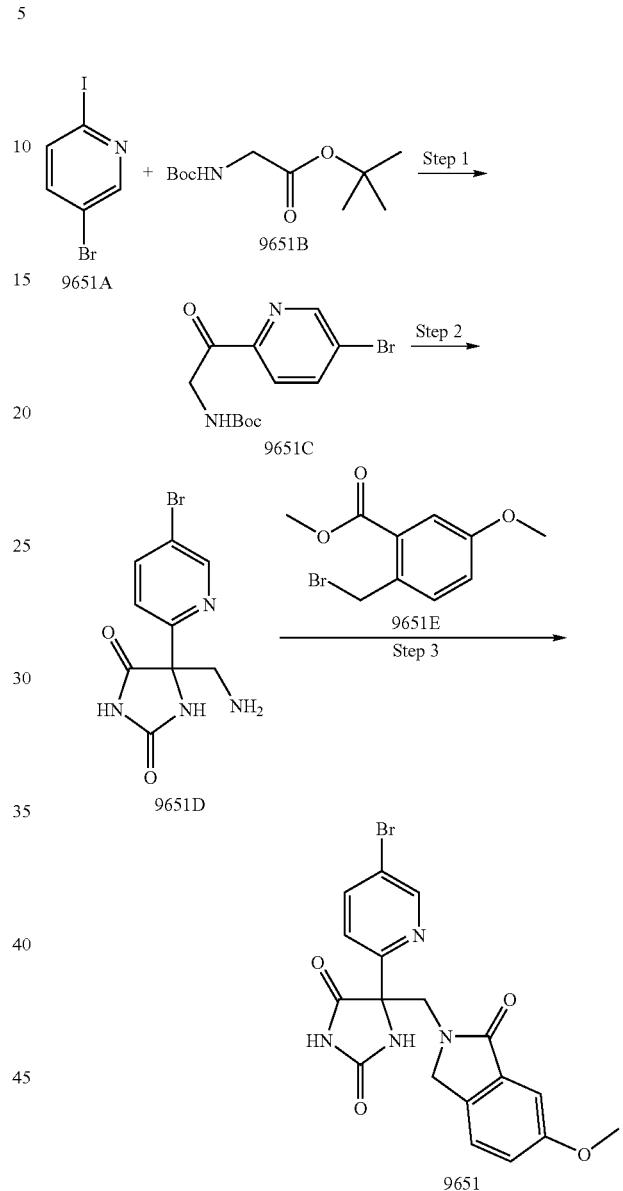

Step 1

Compounds 9651A (500 mg, 1.76 mmol) and 9651B (385 mg, 1.76 mmol) were added to a flame-dried 50 mL flask and dissolved in anhydrous THF (15 mL) under a nitrogen atmosphere. The solution was cooled to 0° C. and isopropyl magnesium chloride (2M in THF, 2.64 mL, 5.28 mmol) was added slowly, dropwise. The yellow solution was allowed to warm to 23° C. and stir for 20 h. Saturated aqueous NH$_4$Cl (35 mL) was added slowly to the solution and a white precipitate appeared which was dispersed by the addition of excess water. The solution was partitioned against EtOAc (50 mL) and saturated NaCl (50 mL) twice. The organic layers were combined and dried over Na$_2$SO$_4$. The solvent was removed in vacuum to give a viscous orange oil which was purified by SiO$_2$ column chromatography (Gradient: 0-30% EtOAc/Hexanes) to afford 9651C (2.16 g, 39%) as a white solid.

Step 2

Compound 9651C (2.21 g, 7.16 mmol), KCN (684 mg, 10.5 mmol), and (NH$_4$)$_2$CO$_3$ (2.75 g, 28.6 mmol) were added to a 150 mL pressure tube and dissolved in 7N NH$_3$/MeOH (16 mL) and water (16 mL). The flask was sealed and the solution was allowed to stir at 80° C. for 18 h. The yellow solution was immediately purified by C18 chromatography (Gradient: 5-95% H$_2$O/MeCN). The solvent was removed in vacuum and the solid was dissolved in MeOH (10 mL). 4M HCl in dioxanes (12 mL) was added and the solution was allowed to stir for 1 h at 23° C. The solvent was removed in vacuum to give 9651D (1.21 g, 60%) as a white solid.

Step 3

Compounds 9651D (797 mg, 2.02 mmol) and 9651E (562 mg, 2.02 mmol) were dissolved in anhydrous DMF (10 mL) in a 25 mL flame-dried flask. DIPEA (1.76 mL, 10.1 mmol) was added and the solution was allowed to stir at 60° C. for 18 h. The solvent was removed in vacuo and the crude product was applied to C18 chromatography (Gradient: 5-95% H$_2$O/MeCN). The solvent was removed in vacuo to afford compound 9651 (480 mg, 55%) as a white solid.

Example 9652

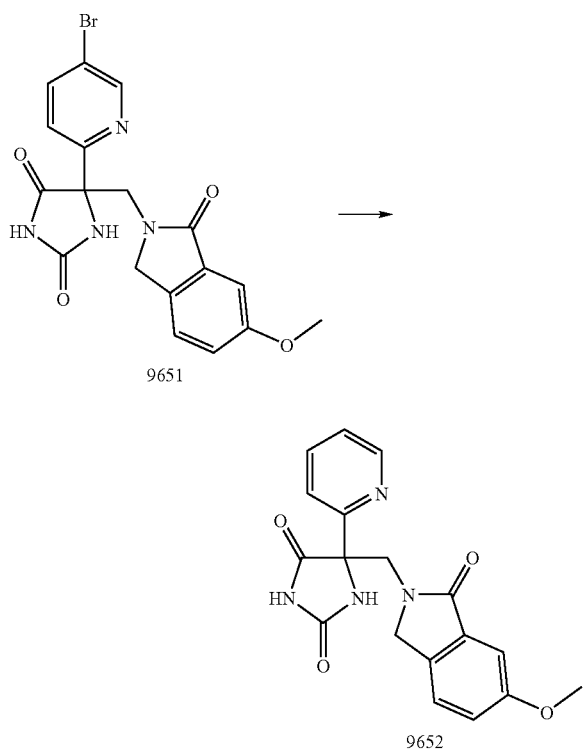

Compound 9651 was dissolved in MeOH (3 mL) and Pd/C (10%, 5 mg) was added. The suspension was allowed to stir for 5 h at 23° C. The solution was filtered and washed with DMF. C18 chromatography (Gradient: 5-90% MeCN/H$_2$O) afforded 9652 (7.9 mg, 33%) as a white solid.

Example 9938

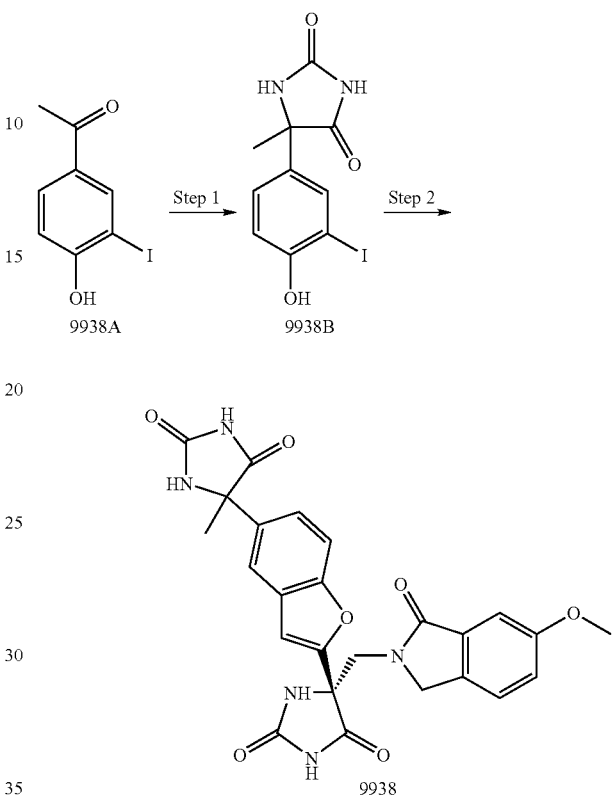

Step 1

Compound 9938A was prepared as described in *Journal of Chemical Society, Perkin Trans* 1, 90, 1977. Compound 9938A (4.06 g, 15.49 mmol), KCN (1.21 g, 18.59 mmol), (NH$_4$)$_2$CO$_3$ (6.0 g, 61.96 mmol), EtOH (20 mL), and water (20 mL) was suspended in a 125 mL flask and the solution was stirred at 80° C. for overnight. After cooling down, half the solution was applied to C18 reverse phase chromatography (130 g, CH$_3$CN/water 5% to 90%) to give Compound 9938B (850 mg, 33%).

Step 2

Compound 9001 (100 mg, 0.288 mmol), 9938B (96 mmol, 0.288 mmol), Pd(PPh$_3$)$_2$Cl$_2$ (5 mg), CuI (3 mg), and DIPA (0.2 mL) were dissolved in DMF (2 mL). The solution was degassed and filled with N$_2$. The solution was stirred at 60° C. for overnight. The solution was directed applied to C18 reverse phase chromatography (43 g, CH$_3$CN/water 5% to 90%) to give crude Compound 9938, which was combined with the crude 9938 obtained from a separated reaction in the scale of 50 mg of compound 9001, and further purified by sgc (CH$_2$Cl$_2$/MeOH/NH$_3$—H$_2$O: 15:1:0.1 to 10:1:0.1) to give Compound 9938 (24.5 mg, 11.3%).

Compound 9938 and 9939 was prepared as described in example 9000, 9001, and 9938.

The rest of compounds were synthesized using procedures described previously.

NMR spectral data of the some of the compounds above are given below:

Compound 9200. $^1$H NMR (400 Hz, DMSO-$d_6$) δ 11.36 (s, 1H), 9.31 (s, 1H, NH), 9.10 (d, 1H, J=1.4 Hz), 8.8 (bs, 1H), 8.23 (d, 1H, J=6.2 Hz), 7.50 (m, 2H), 7.18 (m, 2H), 4.39 (m, 4H), 3.80 (s, 3H).

Compound 9204. $^1$H NMR (400 Hz, DMSO-$d_6$) Compound 9200. $^1$H NMR (400 Hz, DMSO-$d_6$) δ11.36 (s, 1H), 9.31 (s, 1H, NH), 9.10 (d, 1H, J=1.4 Hz), 8.8 (bs, 1H), 8.23 (d, 1H, J=6.2 Hz), 7.50 (m, 2H), 7.18 (m, 2H), 4.39 (m, 4H), 3.80 (s, 3H).

Compound 9204. $^1$H NMR (400 Hz, DMSO-$d_6$) δ 10.74 (s, 1H), 8.39 (d, J=1.84 Hz, 1H), 7.02 (br s, 1H), 7.50 (d, J=8.28 Hz, 1H), 7.19-7.15 (m, 2H), 6.71 (s, 1H), 4.37 (s, 2H), 4.17 (dd, J=19.23, 13.97 Hz, 2H), 3.82 (s, 3H), 1.60 (d, J=6.79 Hz, 6H).

Compound 9217. $^1$H NMR (400 Hz, DMSO-$d_6$) (free form) δ11.20 (s, 1H), 8.94 (d, J=1.2 Hz, 1H), 8.32 (m, 1H), 8.15 (m, 1H), 7.48 (d, J=8.0 Hz, 1H), 7.37 (m, 1H), 7.17 (m, 3H), 4.39 (dd, J=32.8 Hz, 17.2 Hz, 2H), 4.29 (dd, J=25.6 Hz, 14.8 Hz, 2H), 3.80 (s, 3H).

Compound 9209. $^1$H NMR (400 Hz, DMSO-$d_6$) δ11.26 (s, 1H), 9.00 (s, 1H), 8.36 (s, 1H), 8.12 (dd, J=8.34, 2.57 Hz, 1H), 7.50 (d, J=8.38 Hz, 1H), 7.21-7.16 (m, 3H), 4.48-4.25 (m, 4H), 3.81 (s, 3H).

Compound 9221. $^1$H NMR (400 Hz, DMSO-$d_6$) δ11.24 (s, 1H), 9.20 (s, 1H), 9.02 (d, J=1.2 Hz, 1H), 8.99 (s, 1H), 7.49 (m, 1H), 7.30 (s, 1H), 7.16 (m, 3H), 4.42 (dd, J=34 Hz, 18 Hz, 2H), 4.29 (dd, J=30 Hz, 14 Hz, 2H), 3.80 (s, 3H).

Compound 9222. $^1$H NMR (400 Hz, DMSO-$d_6$) δ11.24 (s, 1H), 9.28 (m, 2H), 8.51 (d, J=5.6 Hz, 1H), 8.25 (m, 1H), 7.85 (s, 1H), 7.48 (m, 1H), 7.16 (m, 2H), 4.37 (m, 1H), 4.16 (m, 1H), 3.78 (s, 3H).

Compound 9224. $^1$H NMR (400 Hz, DMSO-$d_6$) δ10.78 (s, 1H), 8.56 (d, J=1.20 Hz, 1H), 7.73 (d, J=2.43 Hz, 1H), 7.48 (d, J=8.27 Hz, 1H), 7.18-7.14 (m, 2H), 6.21 (d, J=2.20 Hz, 1H), 4.34-4.25 (m, 2H), 4.33-4.02 (m, 2H), 3.81 (s, 3H).

Compound 9225. $^1$H NMR (400 Hz, DMSO-$d_6$) δ11.27 (s, 1H), 8.95 (d, J=1.08 Hz, 1H), 8.62 (dd, J=2.63, 1.58 Hz, 1H), 8.28-8.25 (m, 1H), 7.51 (d, J=8.30 Hz, 1H), 7.42 (s, 1H), 7.19-7.16 (m, 2H), 4.50-4.27 (m, 4H), 3.82 (s, 3H).

Compound 9226. $^1$H NMR (400 Hz, DMSO-$d_6$) δ11.32 (s, 1H), 9.02 (s, 1H), 8.96 (s, 1H), 8.47 (s, 1H), 7.51 (d, J=8.23 Hz, 1H), 7.46 (s, 1H), 7.21-7.16 (m, 2H), 4.49-4.30 (m, 4H), 3.81 (s, 3H).

Compound 9227. $^1$H NMR (400 Hz, DMSO-$d_6$) δ11.31 (s, 1H), 9.05 (d, J=1.28 Hz, 1H), 8.88 (d, J=1.18 Hz, 1H), 8.62 (d, J=2.87 Hz, 1H), 7.52-7.50 (m, 1H), 7.42 (d, J=2.82 Hz, 1H), 7.21-7.16 (m, 3H), 4.50-4.27 (m, 4H), 3.81 (s, 3H).

Compound 9228. $^1$H NMR (400 Hz, DMSO-$d_6$) δ11.4 (s, 1H), 9.3 (s, 1H), 9.15 (s, 1H), 8.75 (s, 1H), 7.5 (m, 2H), 7.15 (m, 2H), 4.55 (m, 2H), 4.35 (m, 2H), 3.8 (s, 3H), 2.55 (s, 3H).

Compound 9230. $^1$H NMR (500 Hz, MeOH-$d_4$) δ8.89 (bs, 1H), 8.19 (bs, 1H), 7.89 (bs, 1H), 7.43 (d, 1H, J=8.5 Hz), 7.29 (d, 1H, J=2.5 Hz), 7.195 (dd, 1H, J=8.5 Hz, 2 Hz), 6.93 (bs, 1H), 4.51 (dd, 2H, J=16.5 Hz, 9.5 Hz), 4.40 (dd, 2H, J=16 Hz, 28 Hz), 3.86 (s, 3H).

Compound 9220. $^1$H NMR (400 MHz, DMSO-$d_6$) δ11.36 (s, 1H), 9.43 (bs, 1H), 9.13 (d, J=1.2 Hz, 1H), 8.61 (m, 1H), 8.12 (m, 1H), 7.48 (m, 1H), 7.16 (m, 2H), 4.34 (m, 4H), 3.80 (s, 3H).

Compound 9273. $^1$H NMR (500 MHz, CDCl$_3$) δ8.53 (brs, 1H), 8.25 (s, 1H), 7.81 (d, 1H, J=8.4 Hz), 7.27 (s, 1H), 7.25 (brs, 1H), 7.15 (d, 1H, J=8.2 Hz), 7.04 (d, 1H, J=2.0 Hz), 6.98 (dd, 1H, J=8.1 Hz, 2.0 Hz), 4.53 (d, 1H, J=14.5 Hz), 4.43 (d, 1H, J=14.5 Hz), 4.38 (d, 1H, J=16.7 Hz), 4.15 (d, 1H, J=16.7 Hz), 3.71 (s, 3H).

Compound 9275. $^1$H NMR (500 MHz, DMSO-$d_6$) δ11.23 (s, 1H), 8.92 (s, 1H), 7.97 (dd, 1H, J=8.1 Hz, 1.0 Hz), 7.51 (d, 1H, J=8.1 Hz), 7.25 (d, 1H, J=1.0 Hz), 7.24 (d, 1H, J=8.6 Hz), 7.21 (d, 1H, J=2.6 Hz), 7.18 (dd, 1H, J=8.6 Hz, 2.6 Hz), 4.47 (d, 1H, J=17.0 Hz), 4.38 (d, 1H, J=17.0 Hz), 4.36 (d, 1H, J=14.5 Hz), 4.29 (d, 1H, J=14.5 Hz), 3.82 (s, 3H), 2.56 (s, 3H).

Compound 9248. $^1$H NMR (500 Hz, dmso-$d_6$) δ9.1 (bs, 1H), 8.76 (s, 2H), 7.9 (d, 2H, J=4 Hz), 7.54 (d, 2H, J=6 Hz), 7.48 (s, 1H), 7.19 (m, 3H), 4.2-4.5 (m, 4H), 3.8 (s, 3H).

Compound 9256. $^1$H NMR (500 Hz, dmso-$d_6$) δ8.98 (s, 1H), 7.52 (d, 1H, J=6 Hz), 7.16-7.2 (m, 2H), 6.58 (s, 1H), 4.35 (dd, 2H, J=16 Hz, 24 Hz), 4.21 (dd, 2H, J=16 Hz, 9 Hz), 3.82 (s, 3H), 2.22 (s, 3H).

Compound 9259. $^1$H NMR (500 Hz, dmso-$d_6$) δ8.8 (bs, 1H), 7.18-7.85 (m, 9H), 6.75 (s, 1H), 4.45 (dd, 2H, J=4 Hz, 8 Hz), 4.35 (dd, 2H, J=6 Hz, 8 Hz), 3.86 (s, 3H), 3.82 (s, 3H).

Compound 9264. $^1$H NMR (500 Hz, dmso-$d_6$), 10.93 (s, 1H), 8.66 (s, 1H), 8.34 (s, 1H), 7.52 (d, 1H, J=8.197 Hz), 7.18 (dd, 2H, J=8.197 Hz, J=2.52 Hz), 4.88-4.81 (quintet, 1H) 4.39 (s, 2H), 4.24 (dd, 2H, J=14.187 Hz, J=45.38 Hz), 3.8 (s, 3H), 1.50 (dd, 6H, J=1.57 Hz, J=6.62 Hz)

Compound 9271. $^1$H NMR (500 Hz, dmso-$d_6$), 8.59 (s, 1H), 7.926 (d, 1H, J=2.52 Hz), 7.82-7.8 (m, 1H), 7.48 (s, 1H), 6.654 (d, 1H, J=8.512 Hz), 6.487 (d, 1H, J=2.20 Hz), 6.4 (dd, 1H, J=2.52 Hz, J=8.197 Hz), 3.74 (d, 2H, J=4.41 Hz), 3.664 (s, 2H), 3.058 (s, 3H)

Compound 9003E. $^1$H NMR (400 Hz, DMSO-$d_6$) δ10.81 (d, 1H, J=1.2 Hz); 8.59 (d, 1H, J=1.5 Hz); 7.82 (d, 1H, J=0.8 Hz); 7.49 (d, 1H, J=0.8 Hz); 7.51-7.49 (m, 1H); 7.18-7.15 (m, 2H); 4.48 (quintet, 1H, J=6.6 Hz); 4.39-4.30 (d of d, 2H, J=0.5, 17.4); 4.05-3.96 (d of d, 2H, J=6.9, 13.8); 3.81 (s, 3H); 1.39 (d of d, 6H, J=0.8 Hz, 6.6 Hz).

Compound 9625. $^1$H NMR (500 MHz, MeOH-$d_6$) δ7.56-7.52 (m, 2H), 7.35-7.31 (m, 1H), 7.23-20 (m, 1H), 7.12-7.10 (m, 1H), 6.97-6.94 (m, 2H), 4.40-4.10 (m, 2H), 4.09-4.06 (m, 2H), 3.79 (s, 3H), 3.70-3.68 (m, 2H), 3.37 (s, 3H), 3.19-3.12 (m, 2H).

Compound 9243. $^1$H NMR (500 Hz, DMSO-$d_6$) δ 10.89 (s, 1H), 8.74 (br s, 1H), 8.29 (br. s, 1H), 8.15 (s, 1H), 7.88 (br. s, 1H), 7.53 (d, 1H, J=9 Hz), 7.19 (m, 2H), 4.47 (s, 2H), 3.90 (d, 1H, J=14.5 Hz), 3.82 (s, 3H), 3.73 (d, 1H, J=14.5 Hz), 2.80 (m, 1H), 2.67 (m, 1H), 2.11 (m, 1H), 1.96 (m, 1H).

Compound 9938: $^1$H NMR (500 Hz, DMSO-$d_6$) δ 7.63 (s, 1H), 7.45 (d, 1H, J=8.5 Hz), 7.44 (d, 1H, J=8.5 Hz), 7.34 (d, 1H, J=8.5 Hz), 7.18 (d, 1H, J=2.5 Hz), 7.12 (dd, 1H, J=8.5, 2.5 Hz), 6.81 (s, 1H), 4.55 (d, 1H, J=17.5 Hz), 4.37 (dd, 1H, J=5.14 Hz), 4.25 (d, 1H, J=17.5 Hz), 3.81 (s, 3H), 3.75 (dd, 1H, J=5.5, 14 Hz), 1.59 (s, 3H).

Compound 9759 $^1$H NMR (500 Hz, DMSO-$d_6$) δ 10.97 (S, 1H), 9.24 (d, 1H, J=1.89 Hz), 9.12 (d, 1H, J=2.20 Hz), 8.99 (d, 1H, J=1.26 Hz), 8.65 (t, 1H, J=2.20 Hz & J=2.20 Hz), 7.96 (d, 2H, J=8.82 Hz), 7.82 (d, 2H, J=8.51 Hz), 7.50 (d, 1H, J=8.51

Hz), 7.2 (d, 1H, J=2.20 Hz), 7.17 (dd, 1H, J=2.52 Hz, J=8.19 Hz), 3.82 (s, 3H), 3.74-3.66 (m, 2H), 3.52-3.44 (m, 2H), 3.58 (s, 3H)

Compound 9711. ¹H NMR (500 Hz, DMSO-d₆) δ10.92 (s, 1H), 8.92 (s, 1H), 8.36 (s, 1H), 7.88 (2, 1H), 7.83-7.79 (m, 3H), 7.73 (d, 2H, J=8.2 Hz), 7.50 (d, 1H, J=8.6 Hz), 7.39 (d, 1H, J=8.8 Hz), 7.20 (d, 1H, J=2.4 Hz), 7.17 (dd, 1H, J=8.6 Hz, 2.6 Hz), 4.36 (d, 1H, J=17.0 Hz), 4.30 (d, 1H, J=17.0 Hz), 4.27 (d, 1H, J=14.2 Hz), 4.20 (s, 3H), 4.14 (d, 1H, J=14.2 Hz), 3.82 (s, 3H). 10.74 (s, 1H), 8.39 (d, J=1.84 Hz, 1H), 7.02 (br s, 1H), 7.50 (d, J=8.28 Hz, 1H), 7.19-7.15 (m, 2H), 6.71 (s, 1H), 4.37 (s, 2H), 4.17 (dd, J=19.23, 13.97 Hz, 2H), 3.82 (s, 3H), 1.60 (d, J=6.79 Hz, 6H).

Compound 9217. ¹H NMR (400 Hz, DMSO-d₆) (freeform) δ11.20 (s, 1H), 8.94 (d, J=1.2 Hz, 1H), 8.32 (m, 1H), 8.15 (m, 1H), 7.48 (d, J=8.0 Hz, 1H), 7.37 (m, 1H), 7.17 (m, 3H), 4.39 (dd, J=32.8 Hz, 17.2 Hz, 2H), 4.29 (dd, J=25.6 Hz, 14.8 Hz, 2H), 3.80 (s, 3H).

Compound 9209. ¹H NMR (400 Hz, DMSO-d₆) δ11.26 (s, 1H), 9.00 (s, 1H), 8.36 (s, 1H), 8.12 (dd, J=8.34, 2.57 Hz, 1H), 7.50 (d, J=8.38 Hz, 1H), 7.21-7.16 (m, 3H), 4.48-4.25 (m, 4H), 3.81 (s, 3H).

Compound 9221. ¹H NMR (400 Hz, DMSO-d₆) δ11.24 (s, 1H), 9.20 (s, 1H), 9.02 (d, J=1.2 Hz, 1H), 8.99 (s, 1H), 7.49 (m, 1H), 7.30 (s, 1H), 7.16 (m, 3H), 4.42 (dd, J=34 Hz, 18 Hz, 2H), 4.29 (dd, J=30 Hz, 14 Hz, 2H), 3.80 (s, 3H).

Compound 9222. ¹H NMR (400 Hz, DMSO-d₆) δ11.24 (s, 1H), 9.28 (m, 2H), 8.51 (d, J=5.6 Hz, 1H), 8.25 (m, 1H), 7.85 (s, 1H), 7.48 (m, 1H), 7.16 (m, 2H), 4.37 (m, 1H), 4.16 (m, 1H), 3.78 (s, 3H).

Compound 9224. ¹H NMR (400 Hz, DMSO-d₆) δ10.78 (s, 1H), 8.56 (d, J=1.20 Hz, 1H), 7.73 (d, J=2.43 Hz, 1H), 7.48 (d, J=8.27 Hz, 1H), 7.18-7.14 (m, 2H), 6.21 (d, J=2.20 Hz, 1H), 4.34-4.25 (m, 2H), 4.33-4.02 (m, 2H), 3.81 (s, 3H).

Compound 9225. ¹H NMR (400 Hz, DMSO-d₆) δ 11.27 (s, 1H), 8.95 (d, J=1.08 Hz, 1H), 8.62 (dd, J=2.63, 1.58 Hz, 1H), 8.28-8.25 (m, 1H), 7.51 (d, J=8.30 Hz, 1H), 7.42 (s, 1H), 7.19-7.16 (m, 2H), 4.50-4.27 (m, 4H), 3.82 (s, 3H).

Compound 9226. ¹H NMR (400 Hz, DMSO-d₆) δ11.32 (s, 1H), 9.02 (s, 1H), 8.96 (s, 1H), 8.47 (s, 1H), 7.51 (d, J=8.23 Hz, 1H), 7.46 (s, 1H), 7.21-7.16 (m, 2H), 4.49-4.30 (m, 4H), 3.81 (s, 3H).

Compound 9227. ¹H NMR (400 Hz, DMSO-d₆) δ 11.31 (s, 1H), 9.05 (d, J=1.28 Hz, 1H), 8.88 (d, J=1.18 Hz, 1H), 8.62 (d, J=2.87 Hz, 1H), 7.52-7.50 (m, 1H), 7.42 (d, J=2.82 Hz, 1H), 7.21-7.16 (m, 3H), 4.50-4.27 (m, 4H), 3.81 (s, 3H).

Compound 9228. ¹H NMR (400 Hz, DMSO-d₆) δ11.4 (s, 1H), 9.3 (s, 1H), 9.15 (s, 1H), 8.75 (s, 1H), 7.5 (m, 2H), 7.15 (m, 2H), 4.55 (m, 2H), 4.35 (m, 2H), 3.8 (s, 3H), 2.55 (s, 3H).

Compound 9230. ¹H NMR (500 Hz, MeOH-d₄) δ8.89 (bs, 1H), 8.19 (bs, 1H), 7.89 (bs, 1H), 7.43 (d, 1H, J=8.5 Hz), 7.29 (d, 1H, J=2.5 Hz), 7.195 (dd, 1H, J=8.5 Hz, 2 Hz), 6.93 (bs, 1H), 4.51 (dd, 2H, J=16.5 Hz, 9.5 Hz), 4.40 (dd, 2H, J=16 Hz, 28 Hz), 3.86 (s, 3H).

Compound 9220. ¹H NMR (400 MHz, DMSO-d₆) δ11.36 (s, 1H), 9.43 (bs, 1H), 9.13 (d, J=1.2 Hz, 1H), 8.61 (m, 1H), 8.12 (m, 1H), 7.48 (m, 2H), 7.16 (m, 2H), 4.34 (m, 4H), 3.80 (s, 3H).

Compound 9273. ¹H NMR (500 MHz, CDCl₃) δ8.53 (brs, 1H), 8.25 (s, 1H), 7.81 (d, 1H, J=8.4 Hz), 7.27 (s, 1H), 7.25 (brs, 1H), 7.15 (d, 1H, J=8.2 Hz), 7.04 (d, 1H, J=2.0 Hz), 6.98 (dd, 1H, J=8.1 Hz, 2.0 Hz), 4.53 (d, 1H, J=14.5 Hz), 4.43 (d, 1H, J=14.5 Hz), 4.38 (d, 1H, J=16.7 Hz), 4.15 (d, 1H, J=16.7 Hz), 3.71 (s, 3H).

Compound 9275. ¹H NMR (500 MHz, DMSO-d₆) δ11.23 (s, 1H), 8.92 (s, 1H), 7.97 (dd, 1H, J=8.1 Hz, 1.0 Hz), 7.51 (d, 1H, J=8.1 Hz), 7.25 (d, 1H, J=1.0 Hz), 7.24 (d, 1H, J=8.6 Hz), 7.21 (d, 1H, J=2.6 Hz), 7.18 (dd, 1H, J=8.6 Hz, 2.6 Hz), 4.47 (d, 1H, J=17.0 Hz), 4.38 (d, 1H, J=17.0 Hz), 4.36 (d, 1H, J=14.5 Hz), 4.29 (d, 1H, J=14.5 Hz), 3.82 (s, 3H), 2.56 (s, 3H).

Compound 9248. ¹H NMR (500 Hz, dmso-d₆) δ9.1 (bs, 1H), 8.76 (s, 2H), 7.9 (d, 2H, J=4 Hz), 7.54 (d, 2H, J=6 Hz), 7.48 (s, 1H), 7.19 (m, 3H), 4.2-4.5 (m, 4H), 3.8 (s, 3H).

Compound 9256. ¹H NMR (500 Hz, dmso-d₆) δ8.98 (s, 1H), 7.52 (d, 1H, J=6 Hz), 7.16-7.2 (m, 2H), 6.58 (s, 1H), 4.35 (dd, 2H, J=16 Hz, 24 Hz), 4.21 (dd, 2H, J=16 Hz, 9 Hz), 3.82 (s, 3H), 2.22 (s, 3H).

Compound 9259. ¹H NMR (500 Hz, dmso-d₆) δ8.8 (bs, 1H), 7.18-7.85 (m, 9H), 6.75 (s, 1H), 4.45 (dd, 2H, J=4 Hz, 8 Hz), 4.35 (dd, 2H, J=6 Hz, 8 Hz), 3.86 (s, 3H), 3.82 (s, 3H).

Compound 9264. ¹H NMR (500 Hz, dmso-d₆), δ10.93 (s, 1H), 8.66 (s, 1H), 8.34 (s, 1H), 7.52 (d, 1H, J=8.197 Hz), 7.18 (dd, 2H, J=8.197 Hz, J=2.52 Hz), 4.88-4.81 (quintet, 1H) 4.39 (s, 2H), 4.24 (dd, 2H, J=14.187 Hz, J=45.38 Hz), 3.8 (s, 3H), 1.50 (dd, 6H, J=1.57 Hz, J=6.62 Hz)

Compound 9271. ¹H NMR (500 Hz, dmso-d₆), δ 8.59 (s, 1H), 7.926 (d, 1H, J=2.52 Hz), 7.82-7.8 (m, 1H), 7.48 (s, 1H), 6.654 (d, 1H, J=8.512 Hz), 6.487 (d, 1H, J=2.20 Hz), 6.4 (dd, 1H, J=2.52 Hz, J=8.197 Hz), 3.74 (d, 2H, J=4.41 Hz), 3.664 (s, 2H), 3.058 (s, 3H)

Compound 9003E. ¹H NMR (400 Hz, DMSO-d₆) δ10.81 (d, 1H, J=1.2 Hz); 8.59 (d, 1H, J=1.5 Hz); 7.82 (d, 1H, J=0.8 Hz); 7.49 (d, 1H, J=0.8 Hz); 7.51-7.49 (m, 1H); 7.18-7.15 (m, 2H); 4.48 (quintet, 1H, J=6.6 Hz); 4.39-4.30 (d of d, 2H, J=0.5, 17.4); 4.05-3.96 (d of d, 2H, J=6.9, 13.8); 3.81 (s, 3H); 1.39 (d of d, 6H, J=0.8 Hz, 6.6 Hz).

Compound 9625. ¹H NMR (500 MHz, MeOH-d₆) δ7.56-7.52 (m, 2H), 7.35-7.31 (m, 1H), 7.23-20 (m, 1H), 7.12-7.10 (m, 1H), 6.97-6.94 (m, 2H), 4.40-4.10 (m, 2H), 4.09-4.06 (m, 2H), 3.79 (s, 3H), 3.70-3.68 (m, 2H), 3.37 (s, 3H), 3.19-3.12 (m, 2H).

Compound 9243. ¹H NMR (500 Hz, DMSO-d₆) δ10.89 (s, 1H), 8.74 (br s, 1H), 8.29 (br. s, 1H), 8.15 (s, 1H), 7.88 (br. s, 1H), 7.53 (d, 1H, J=9 Hz), 7.19 (m, 2H), 4.47 (s, 2H), 3.90 (d, 1H, J=14.5 Hz), 3.82 (s, 3H), 3.73 (d, 1H, J=14.5 Hz), 2.80 (m, 1H), 2.67 (m, 1H), 2.11 (m, 1H), 1.96 (m, 1H).

Compound 9938: ¹H NMR (500 Hz, DMSO-d₆) δ7.63 (s, 1H), 7.45 (d, 1H, J=8.5 Hz), 7.44 (d, 1H, J=8.5 Hz), 7.34 (d, 1H, J=8.5 Hz), 7.18 (d, 1H, J=2.5 Hz), 7.12 (dd, 1H, J=8.5, 2.5 Hz), 6.81 (s, 1H), 4.55 (d, 1H, J=17.5 Hz), 4.37 (dd, 1H, J=5, 14 Hz), 4.25 (d, 1H, J=17.5 Hz), 3.81 (s, 3H), 3.75 (dd, 1H, J=5.5, 14 Hz), 1.59 (s, 3H).

Compound 9759 ¹H NMR (500 Hz, DMSO-d₆) δ10.97 (S, 1H), 9.24 (d, 1H, J=1.89 Hz), 9.12 (d, 1H, J=2.20 Hz), 8.99 (d, 1H, J=1.26 Hz), 8.65 (t, 1H, J=2.20 Hz & J=2.20 Hz), 7.96 (d, 2H, J=8.82 Hz), 7.82 (d, 2H, J=8.51 Hz), 7.50 (d, 1H, J=8.51 Hz), 7.2 (d, 1H, J=2.20 Hz), 7.17 (dd, 1H, J=2.52 Hz, J=8.19 Hz), 3.82 (s, 3H), 3.74-3.66 (m, 2H), 3.52-3.44 (m, 2H), 3.58 (s, 3H)

Compound 9711. ¹H NMR (500 Hz, DMSO-d₆) δ10.92 (s, 1H), 8.92 (s, 1H), 8.36 (s, 1H), 7.88 (2, 1H), 7.83-7.79 (m, 3H), 7.73 (d, 2H, J=8.2 Hz), 7.50 (d, 1H, J=8.6 Hz), 7.39 (d, 1H, J=8.8 Hz), 7.20 (d, 1H, J=2.4 Hz), 7.17 (dd, 1H, J=8.6 Hz, 2.6 Hz), 4.36 (d, 1H, J=17.0 Hz), 4.30 (d, 1H, J=17.0 Hz), 4.27 (d, 1H, J=14.2 Hz), 4.20 (s, 3H), 4.14 (d, 1H, J=14.2 Hz), 3.82 (s, 3H).

Specific TACE inhibitory activity (Ki values) of some representative compounds of the present invention described above is set forth below:

| Compounds | Structures | Exact Mass | Mass Obsvd | Ki (nM) |
|---|---|---|---|---|
| 8009 | 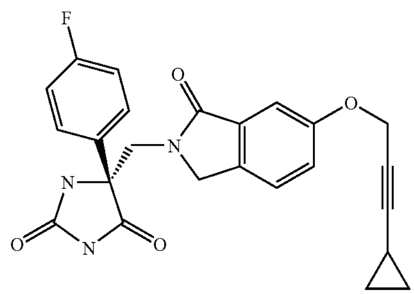 | 433.14 | 434.2 [M + H]+ | 0.79 |
| 3009 | 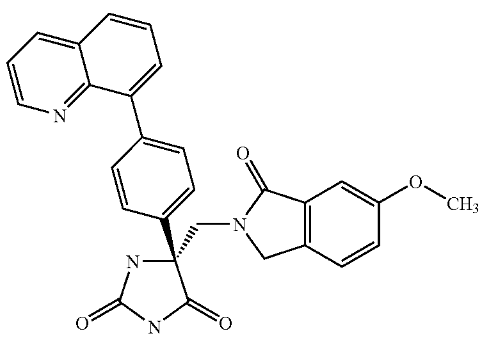 | 478.16 | 479.3 [M + H]+ | 1.47 |
| 3010 | 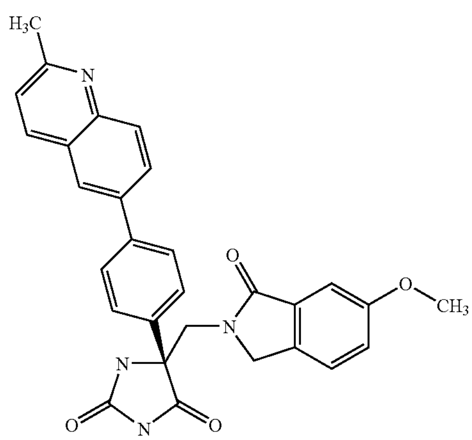 | 492.20 | 493.3 [M + H]+ | 5 |
| 8011 | 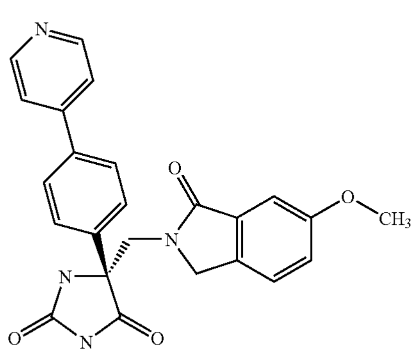 | 428.15 | 429.2 [M + H]+ | 0.64 |

-continued
| Compounds | Structures | Exact Mass | Mass Obsvd | Ki (nM) |
|---|---|---|---|---|
| 8012 | 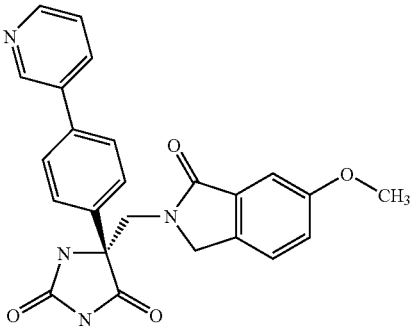 | 428.15 | 429.2 [M + H]+ | 0.8 |
| 7011 | 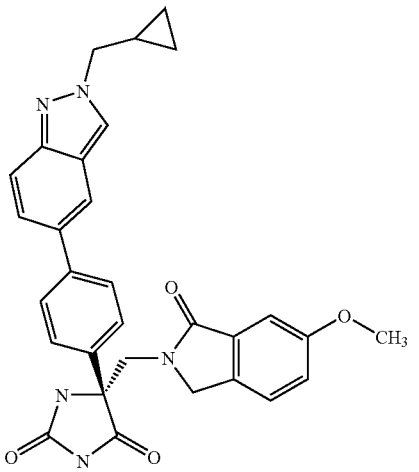 | 521.5665 | 522.3 [M + H]+ | 2.24 |
| 7012 | 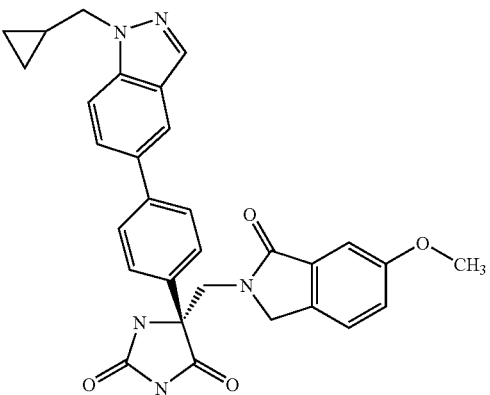 | 521.5665 | 522.3 [M + H]+ | 2.75 |
| 8015 | 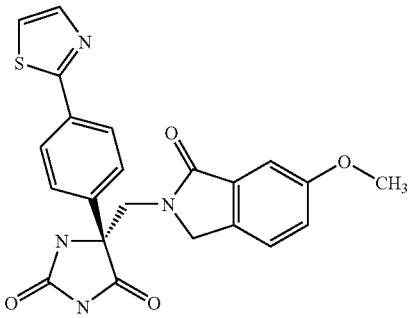 | 434.1 | 435.2 [M + H]+ | 0.63 |

-continued

| Compounds | Structures | Exact Mass | Mass Obsvd | Ki (nM) |
|---|---|---|---|---|
| 7016 | 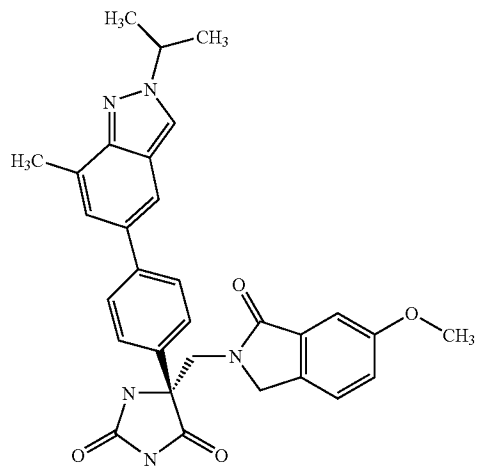 | 523.5824 | 524.3 [M + H]+ | 3.08 |
| 7017 | 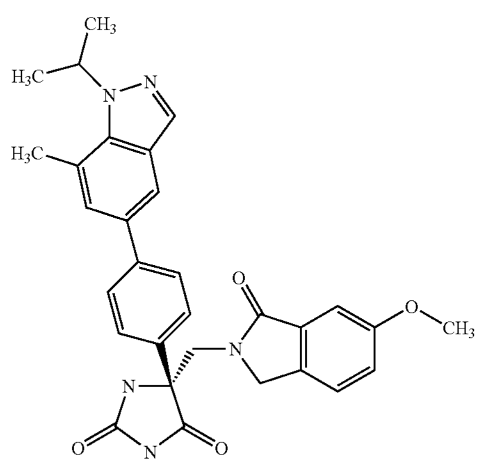 | 523.5824 | 524.3 [M + H]+ | 3.79 |
| 4013 | 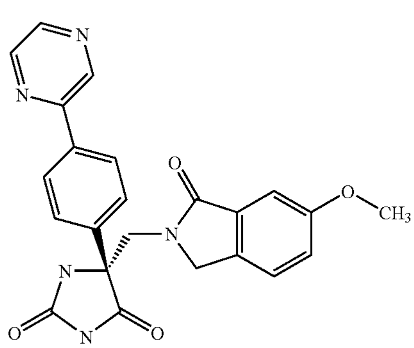 | 429.2 | 430.2 [M + H]+ | 1.2 |

| Compounds | Structures | Exact Mass | Mass Obsvd | Ki (nM) |
| --- | --- | --- | --- | --- |
| 7018 | 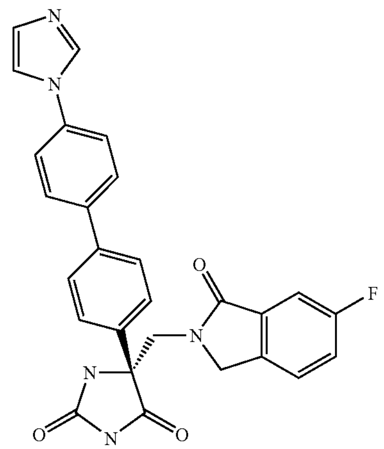 | 481.4778 | 482.3 [M + H]+ | 3.25 |
| 8016 | 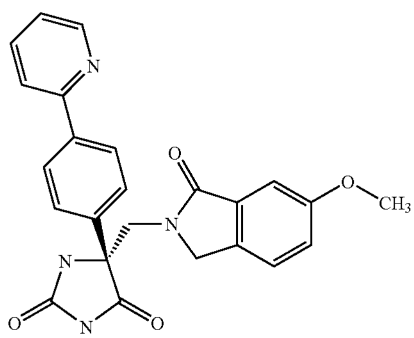 | 428.15 | 429.2 [M + H]+ | 0.48 |
| 8019 | 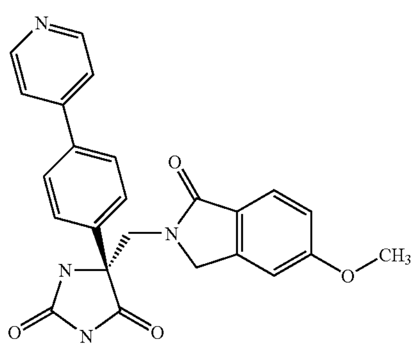 | 428.15 | 429.2 [M + H]+ | 1 |
| 5006 | 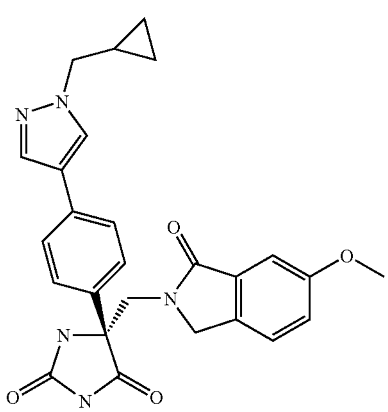 | 471.2 | 472.1 [M + H]+ | 0.5 |

-continued

| Compounds | Structures | Exact Mass | Mass Obsvd | Ki (nM) |
|---|---|---|---|---|
| 7020 | 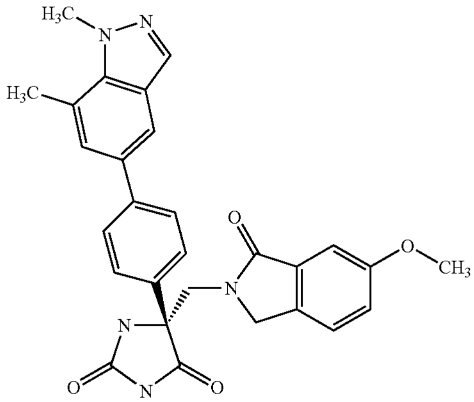 | 495.5292 | 496.3 [M + H]+ | 2.85 |
| 4025 | 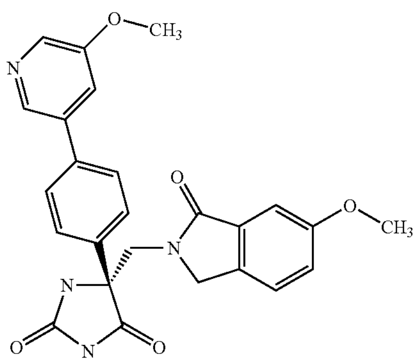 | 458.2 | 459.3 [M + H]+ | 0.84 |
| 5019 | 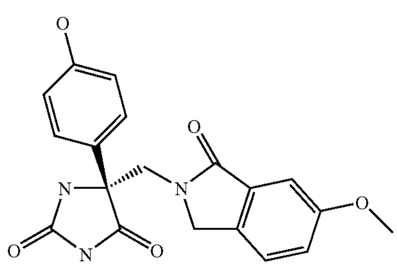 | 367.12 | 368.2 [M + H]+ | 2 |
| 5010 | 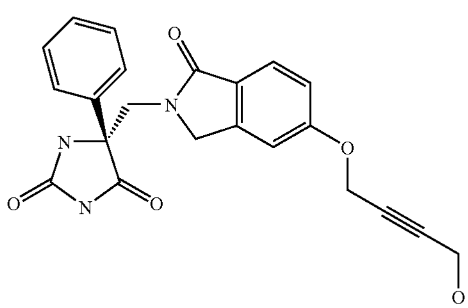 | 405.1 | 406.2 [M + H]+ | 0.2 |

-continued

| Compounds | Structures | Exact Mass | Mass Obsvd | Ki (nM) |
|---|---|---|---|---|
| 3041 | 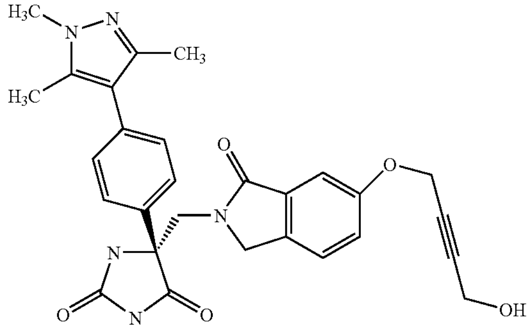 | 513.20 | 514.3 [M + H]+ | 1.44 |
| 4012 | 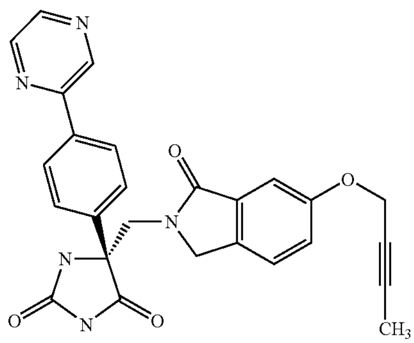 | 467.2 | 468.3 [M + H]+ | 0.5 |
| 9003E | 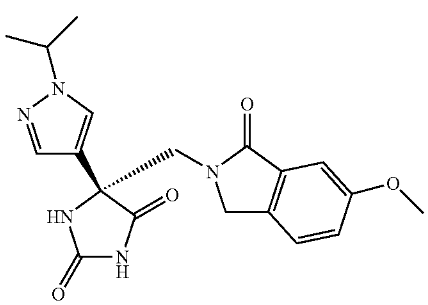 | 383.16 | 384.2 [M + H]+ | 2.8 |
| 9938 | 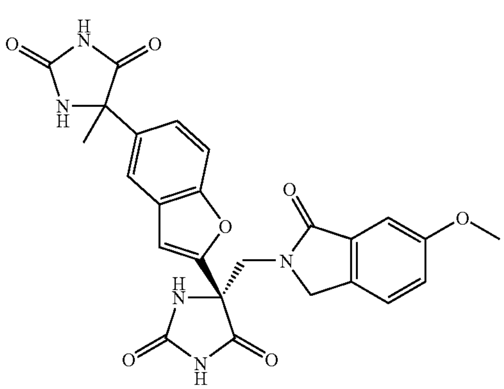 | 503.14 | 504.3 [M + H]+ | 0.37 |

-continued

| Compounds | Structures | Exact Mass | Mass Obsvd | Ki (nM) |
|---|---|---|---|---|
| 9217 | 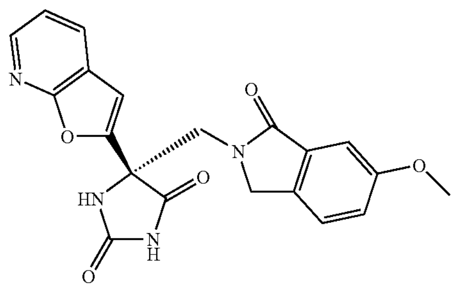 | 392.11 | 393.1 [M + H]+ | 0.70 |
| 9273 | 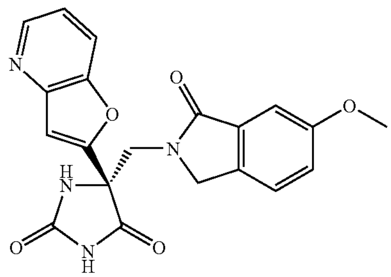 | 392.36 | 393.4 [M + H]+ | 1.84 |
| 9220 | 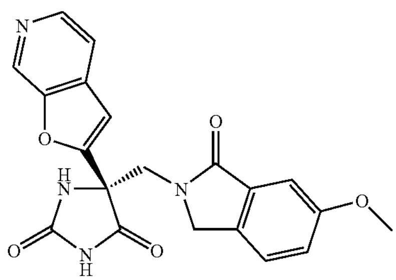 | 392.11 | 393.1 [M + H]+ | 0.75 |
| 9200 | 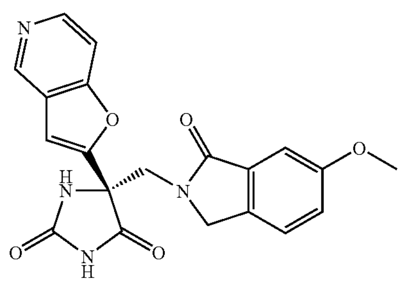 | 392.11 | 392.11 [M + H]+ | 0.78 |
| 9225 | 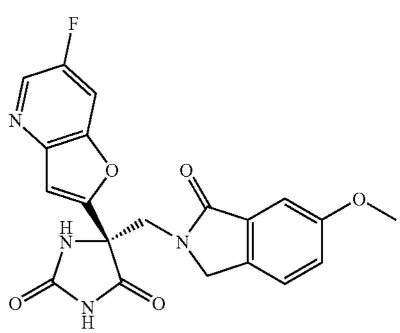 | 410.10 | 411.1 [M + H]+ | 1.18 |

-continued

| Compounds | Structures | Exact Mass | Mass Obsvd | Ki (nM) |
|---|---|---|---|---|
| 9227 | 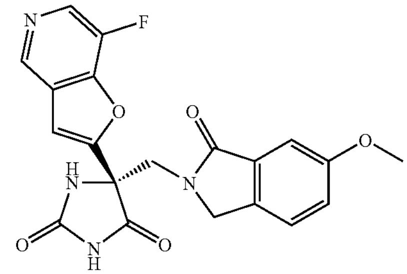 | 410.10 | 411.1 [M + H]+ | 2.14 |
| 9275 | 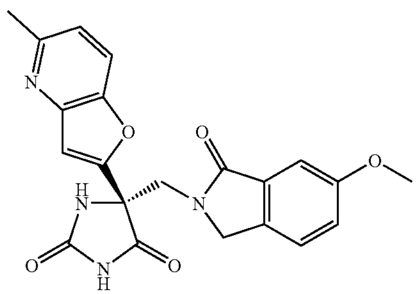 | 406.39 | 407.4 [M + H]+ | 0.98 |
| 9256 | 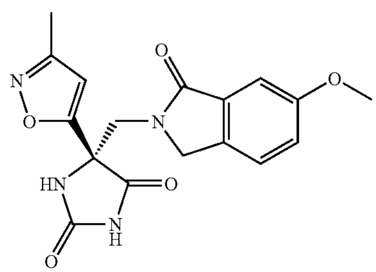 | 356.3 | 380.2 [M + H]+ | 2.02 |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Therefore, we claim:

1. A method of treating a condition or disease selected from the group consisting of septic shock, sepsis syndrome, post ischaemic reperfusion injury, meningitis, psoriasis, rheumatoid arthritis, ankylosing spondylitis, psoriatic arthritis, inflammatory bowel disease, adults Still's disease, non-insulin dependent diabetes mellitus, asthma, and chronic obstructive pulmonary disease, wherein the method comprises: administering to a patient in need of such treatment a therapeutically effective amount of at least one compound selected from one of the following compounds:

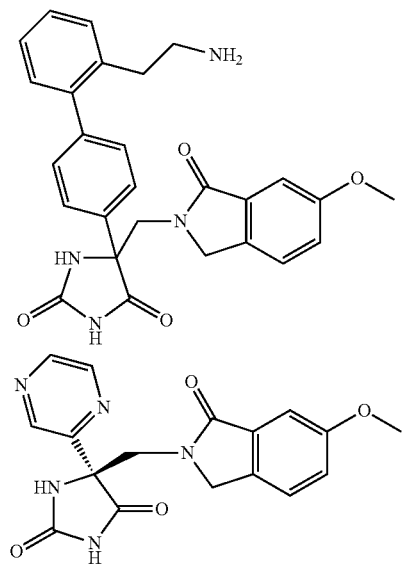

695
-continued
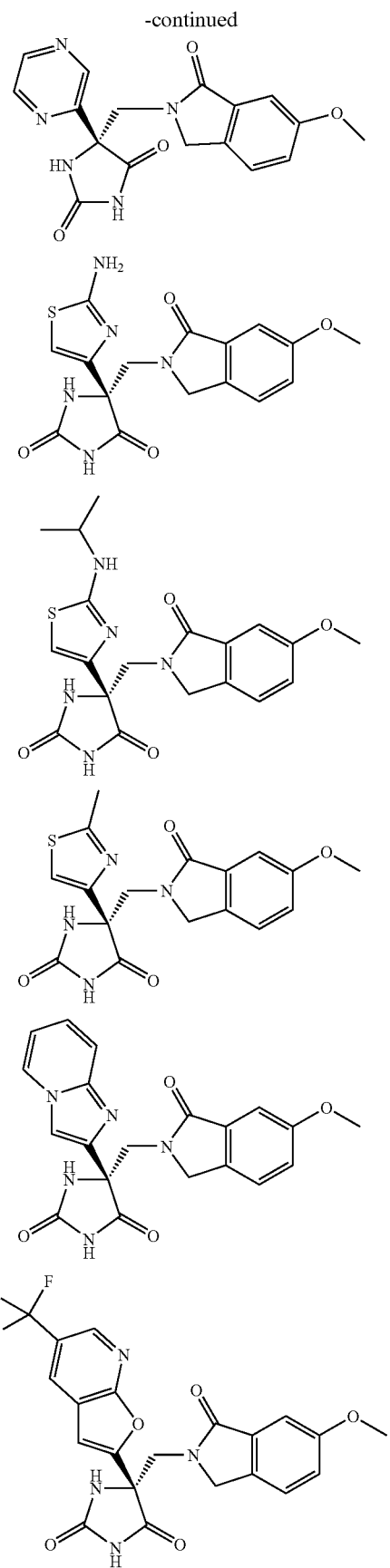
696
-continued
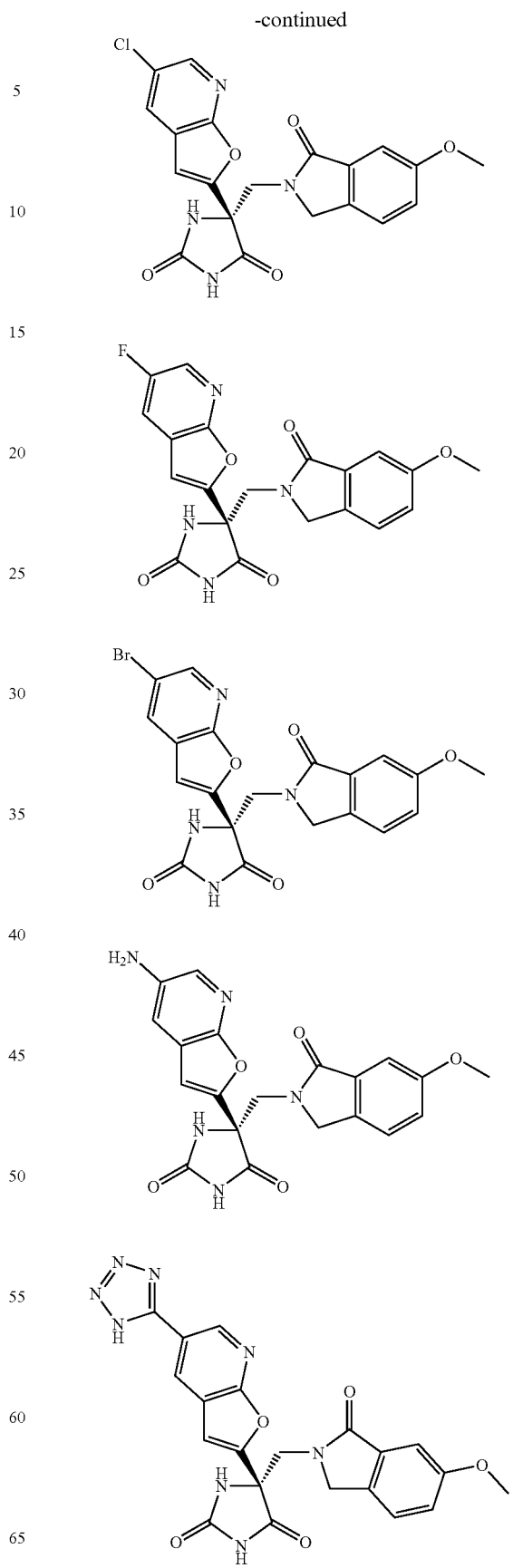

697 -continued
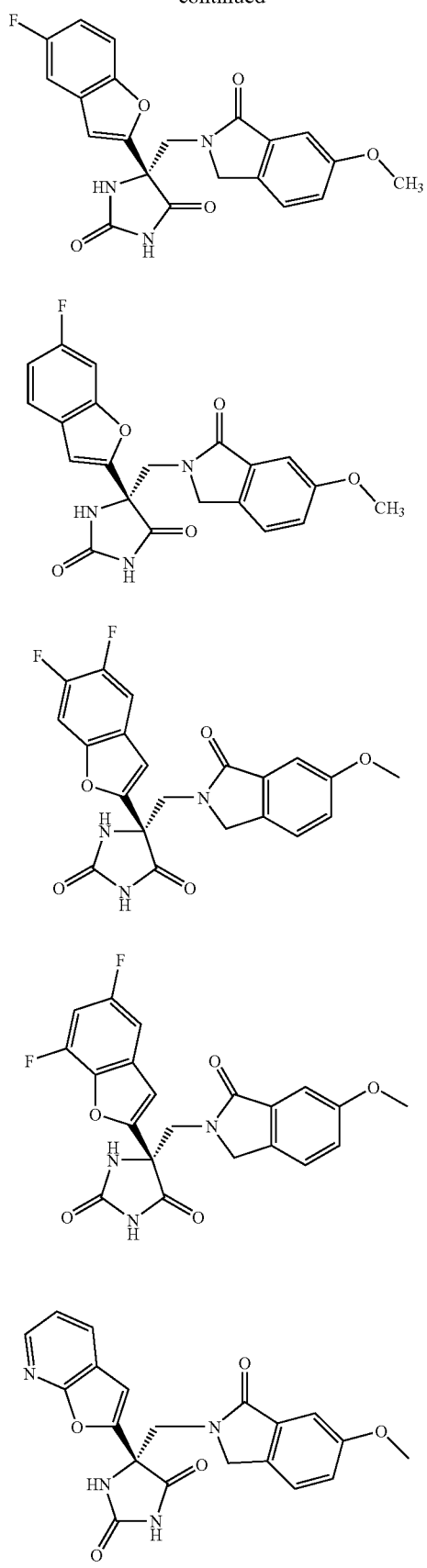
698 -continued
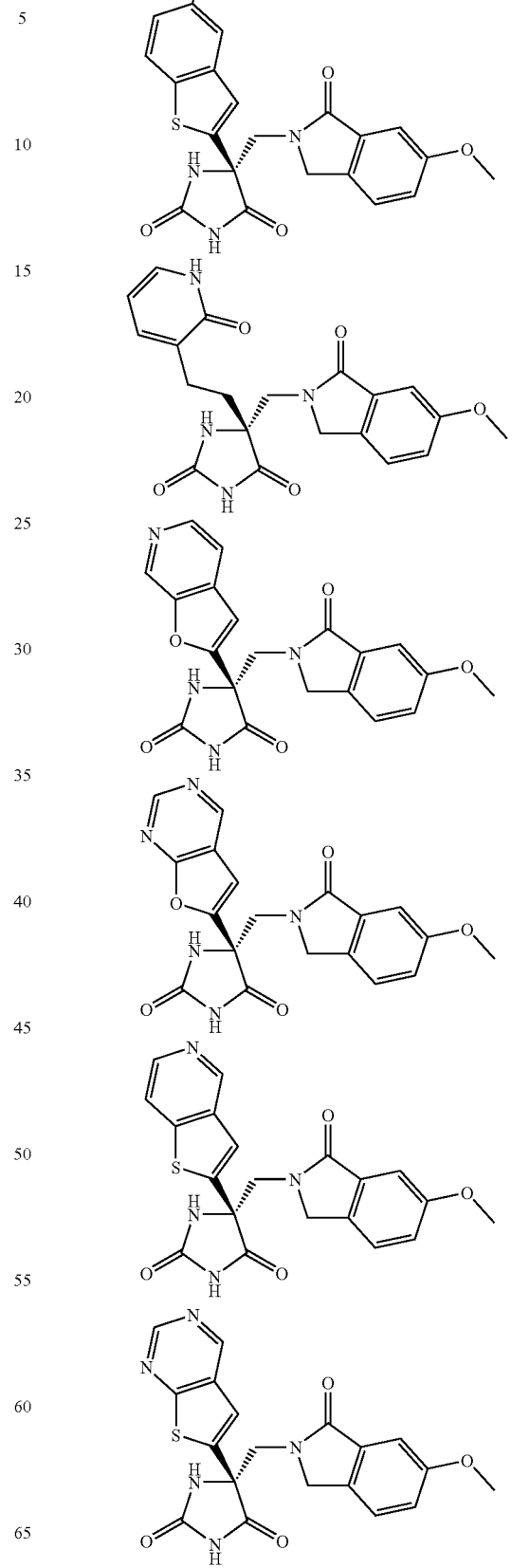

699 700
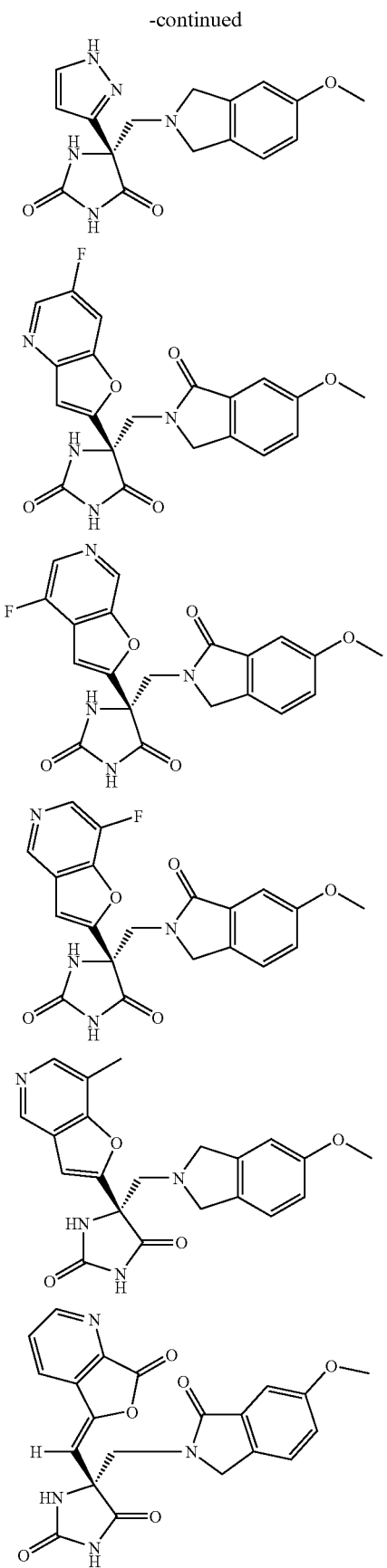
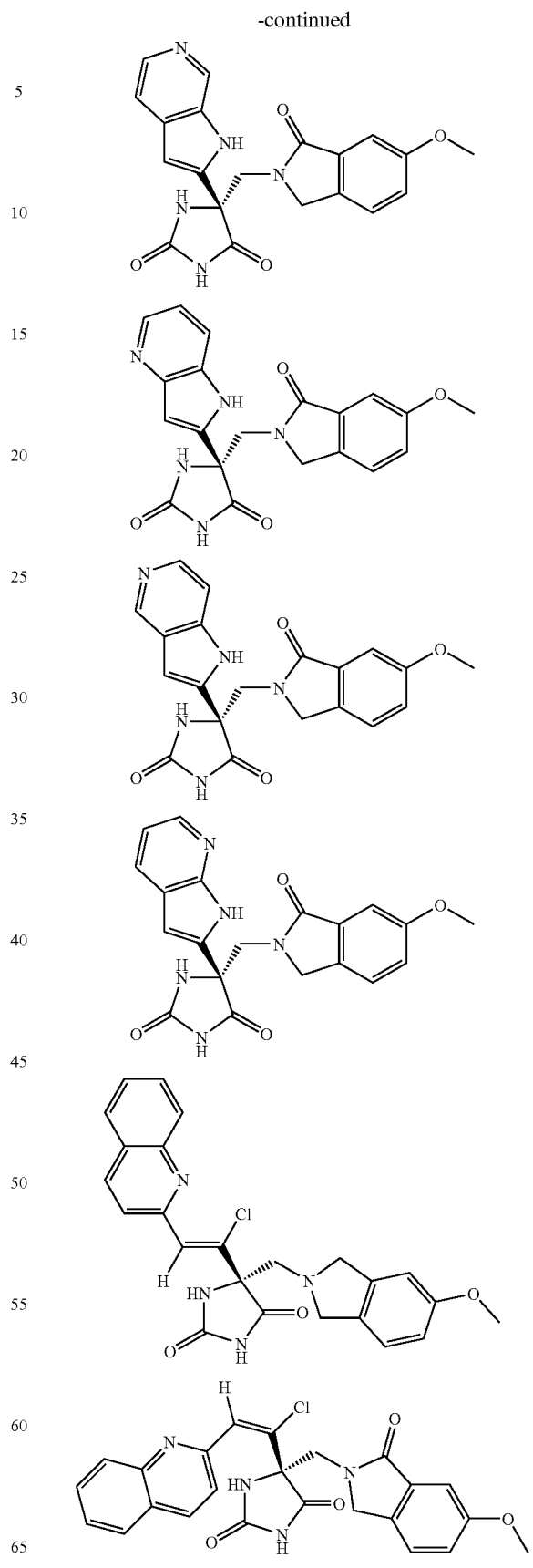

701
-continued
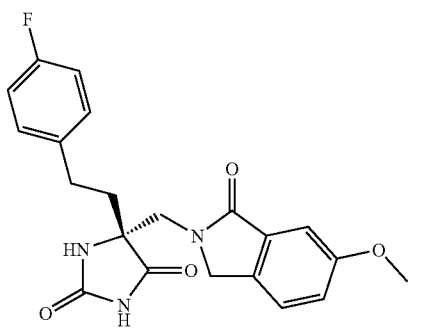
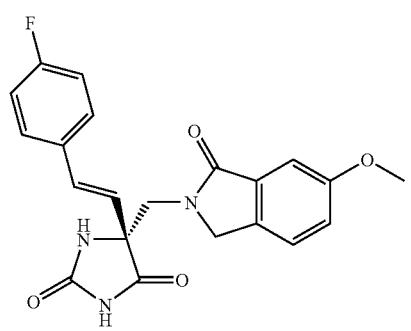
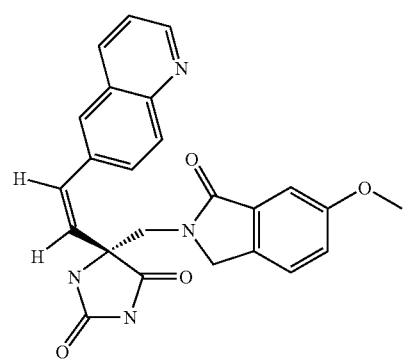
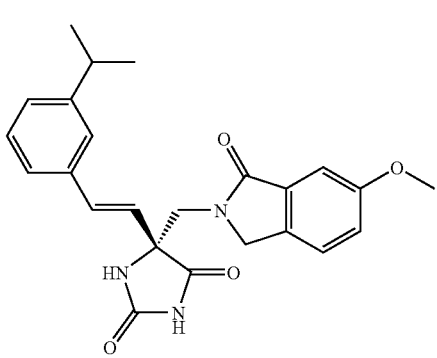
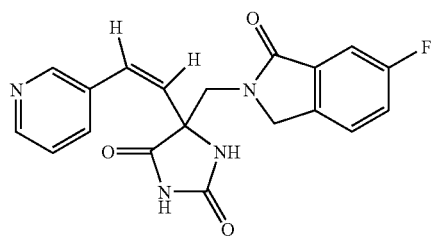
702
-continued
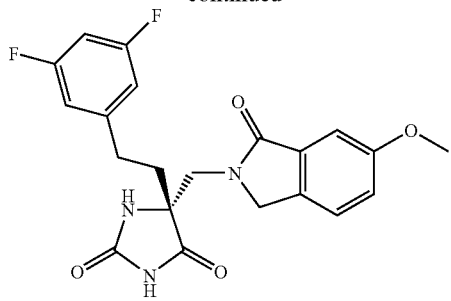
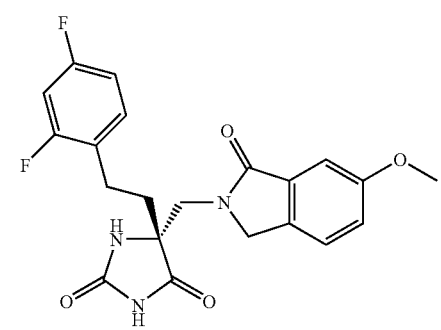
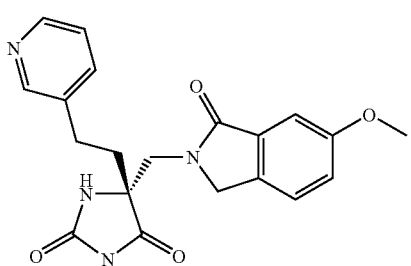
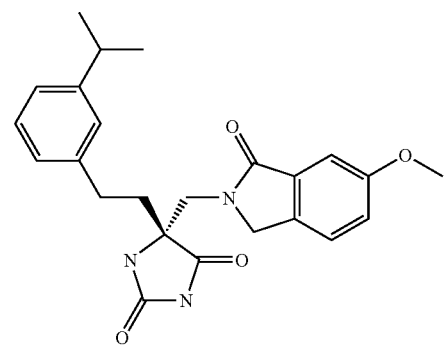
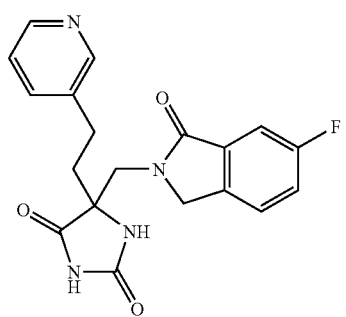

703
-continued
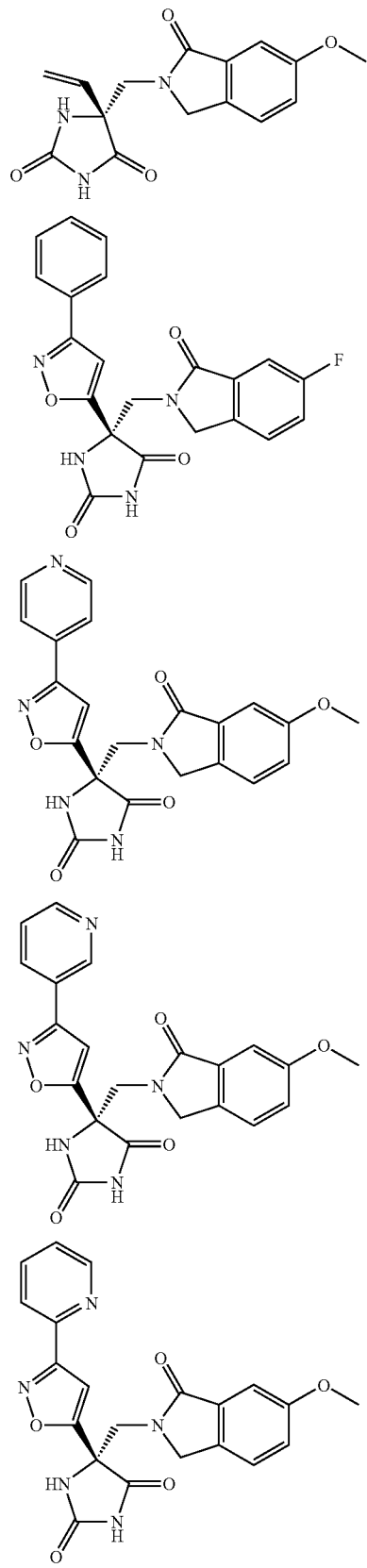
704
-continued
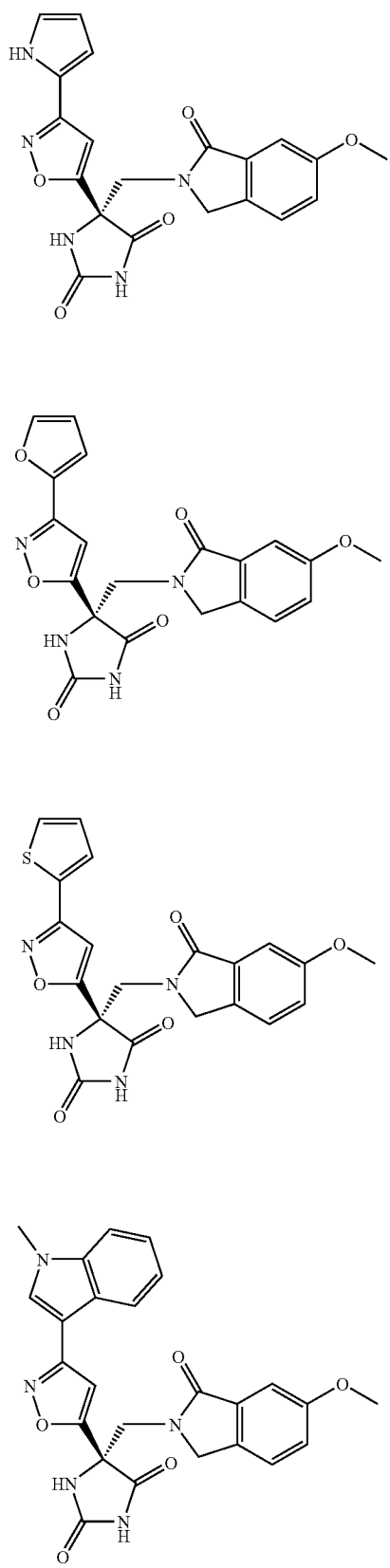

705
-continued
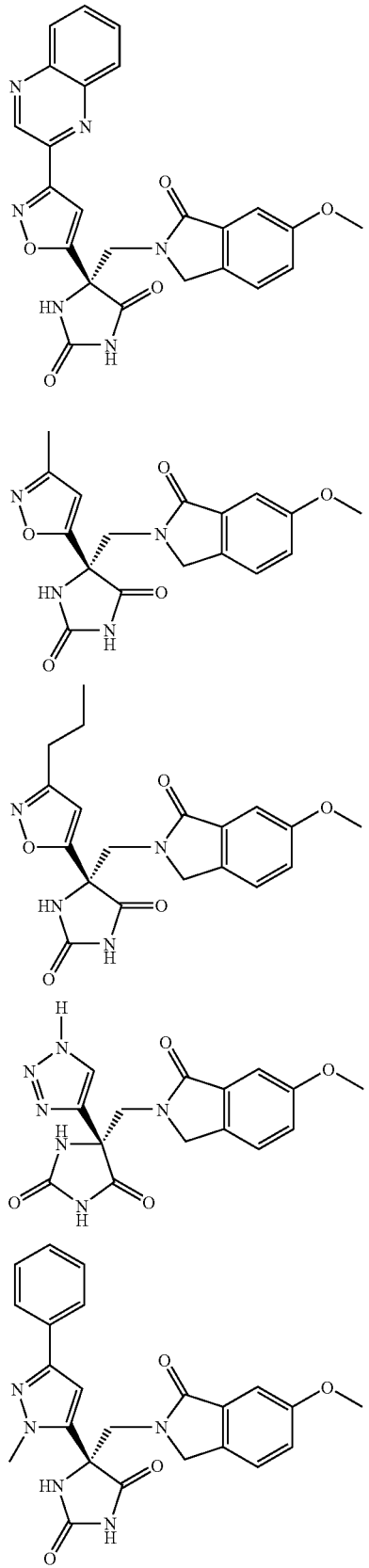
706
-continued
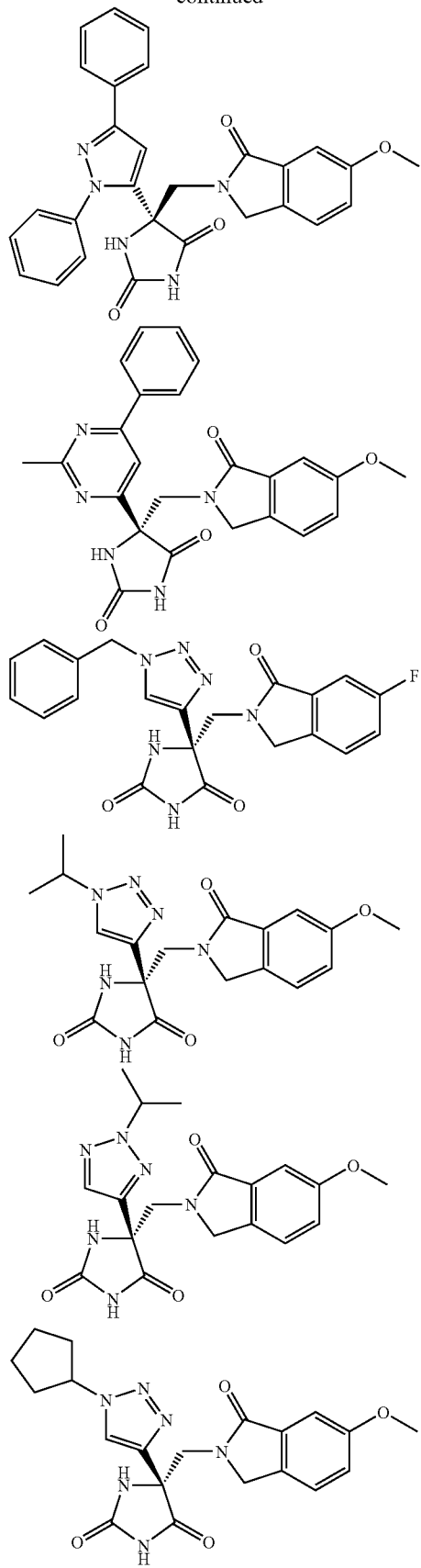

707                                              708
-continued                                    -continued
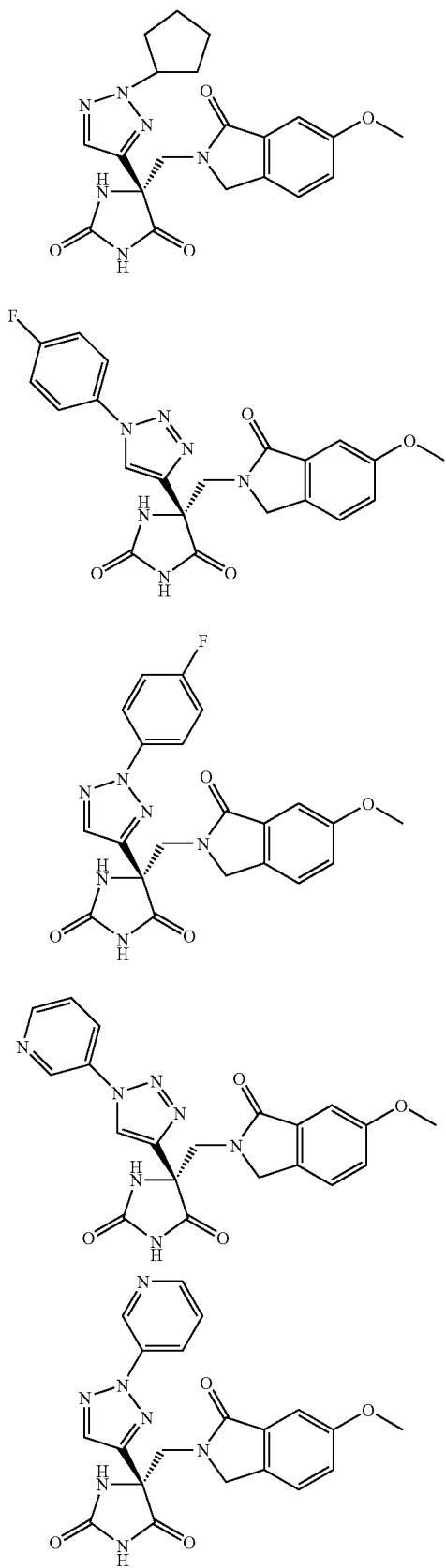
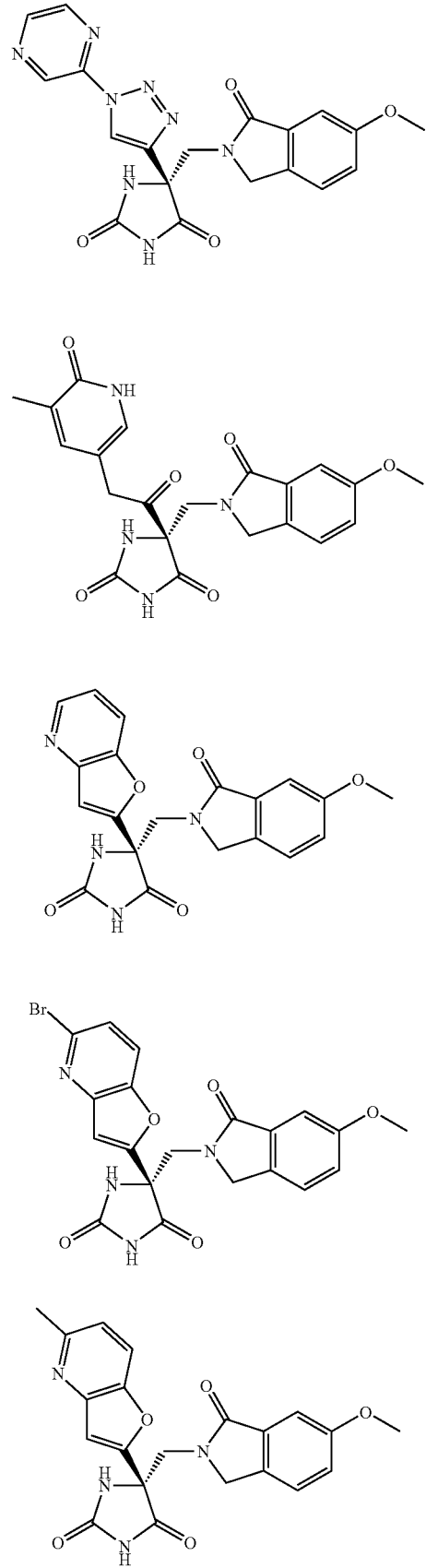

709
-continued
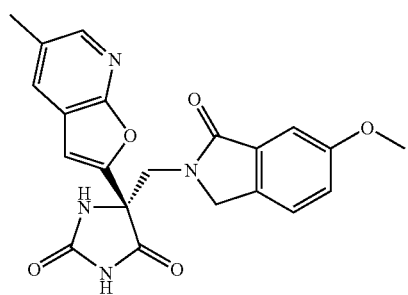
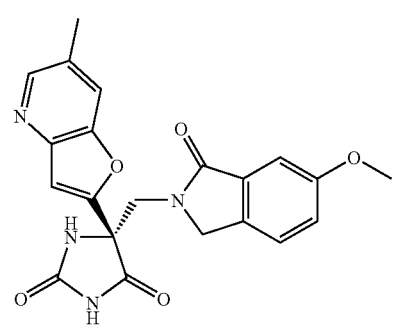
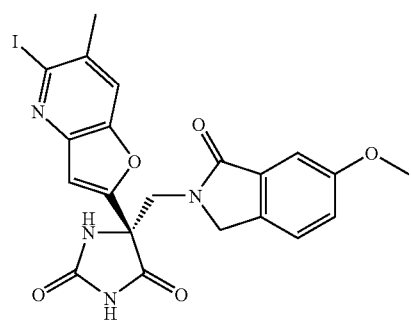
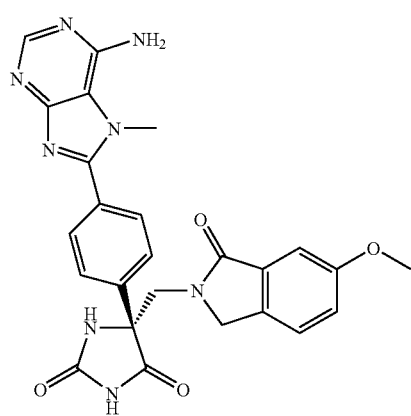
710
-continued
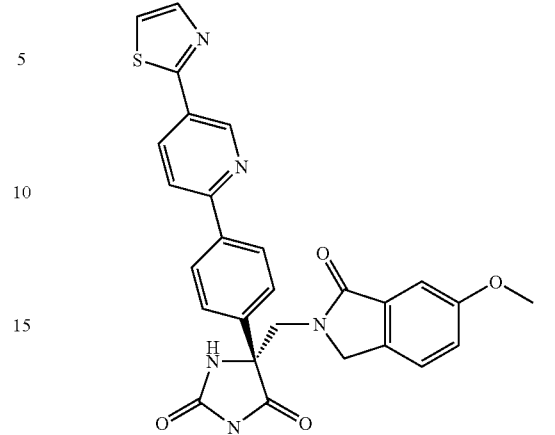
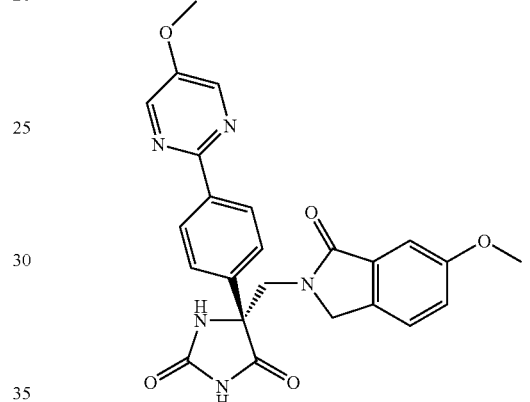
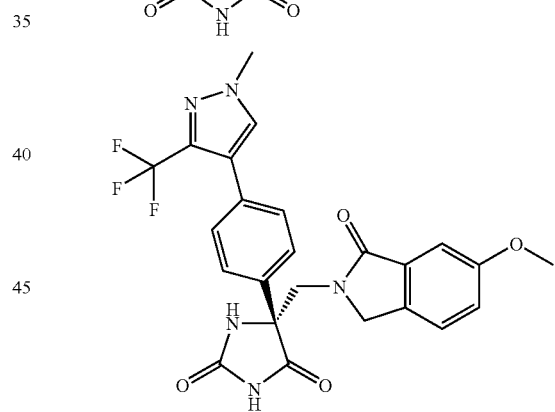
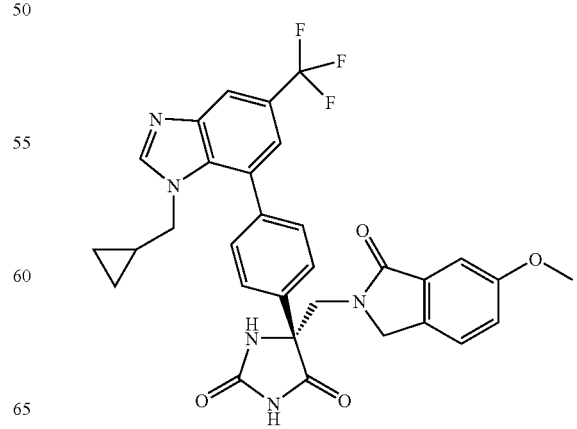

711 712
-continued -continued
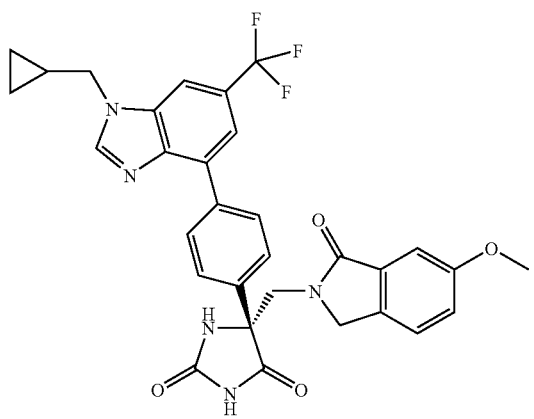
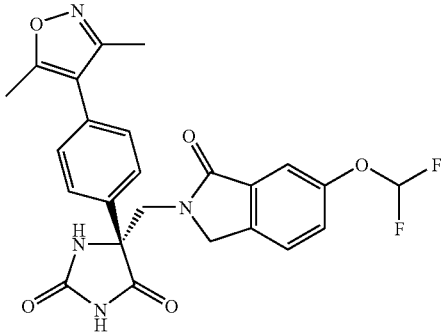
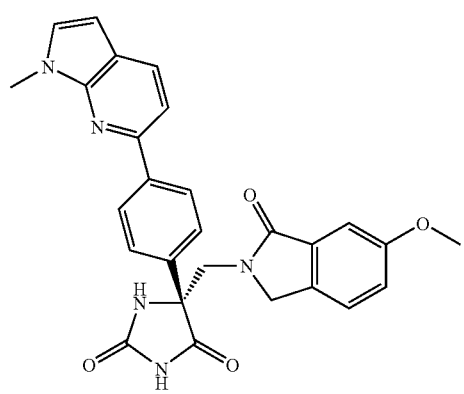
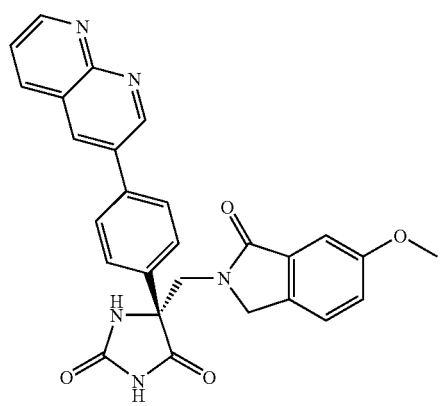
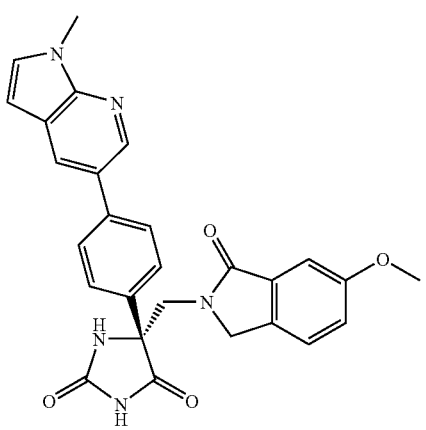
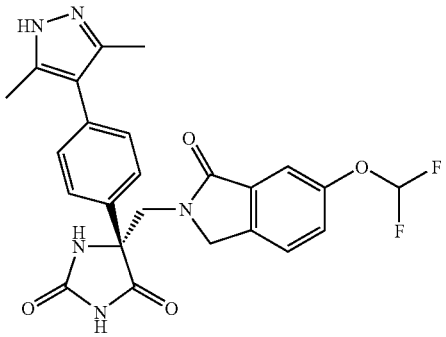
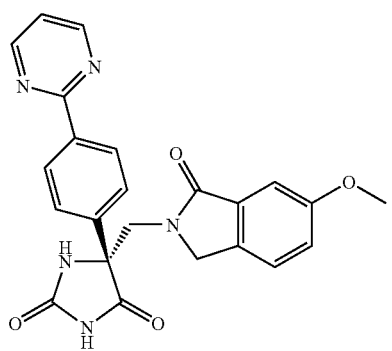
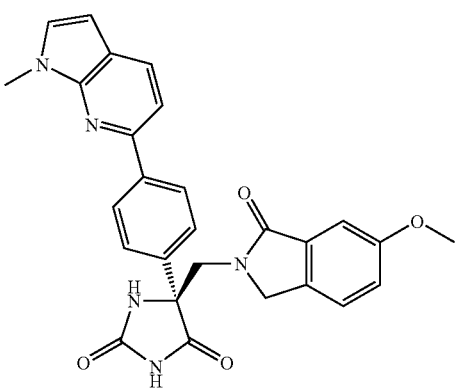

713
-continued
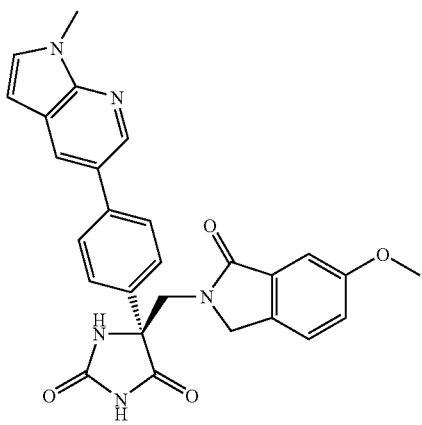
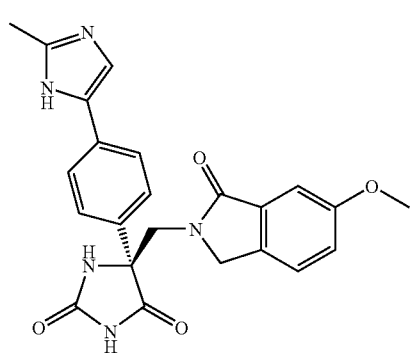
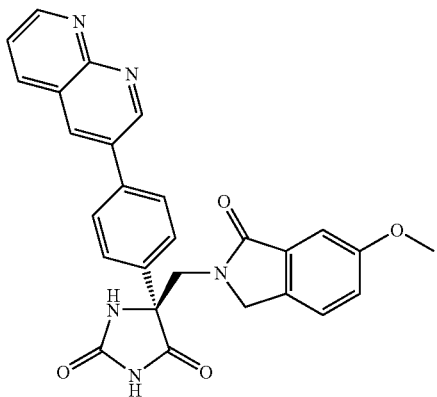
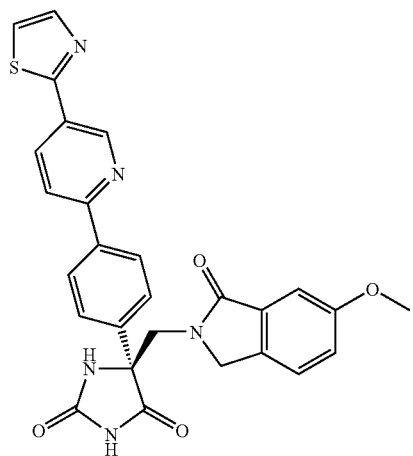
714
-continued
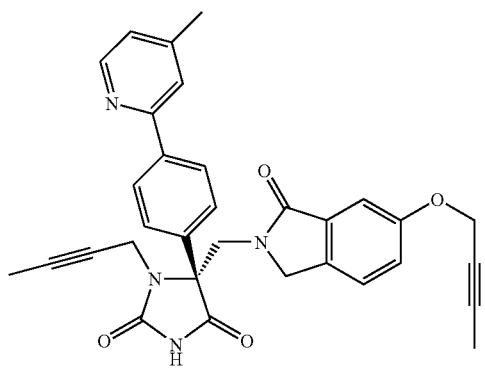
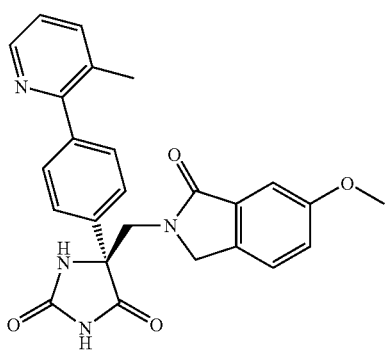
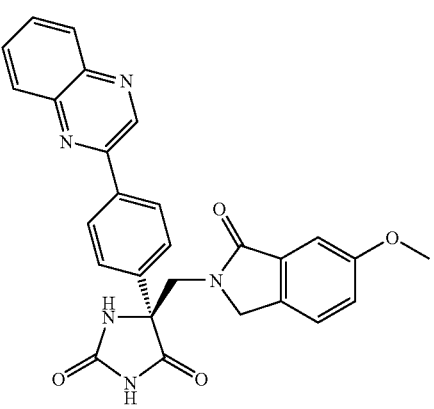
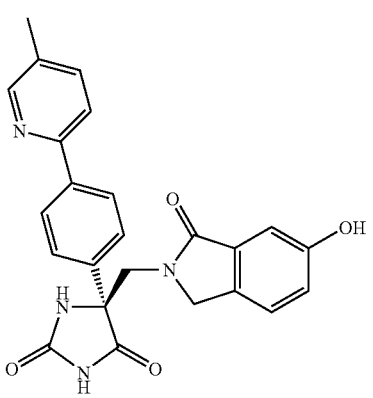

715
-continued
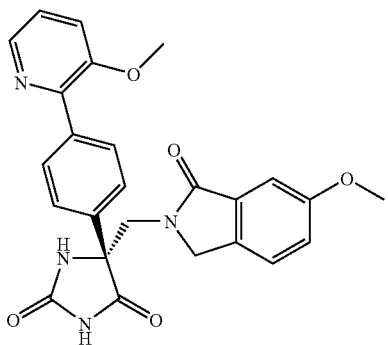
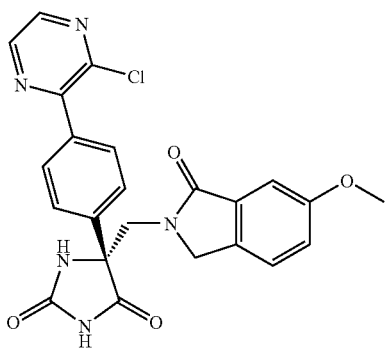
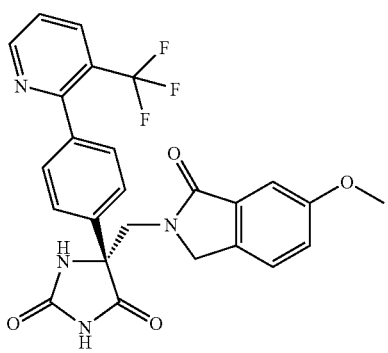
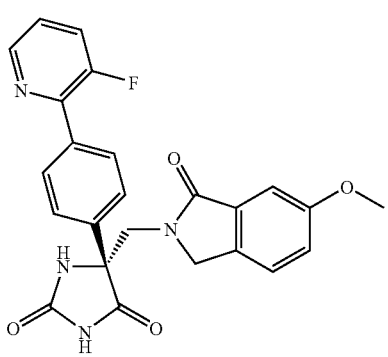
716
-continued
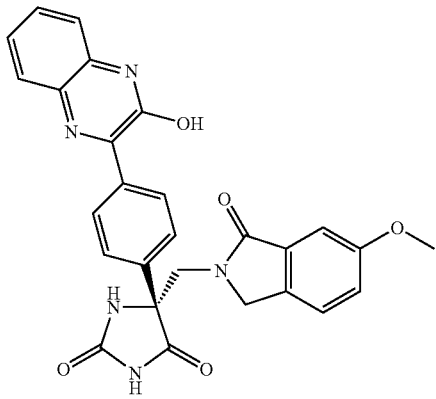
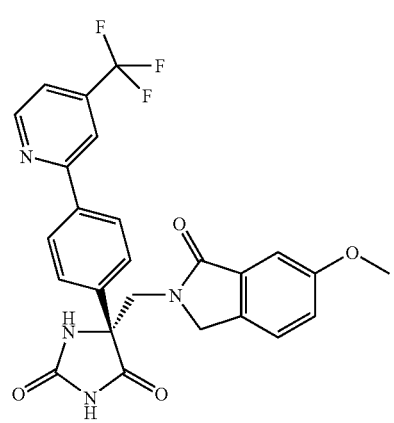
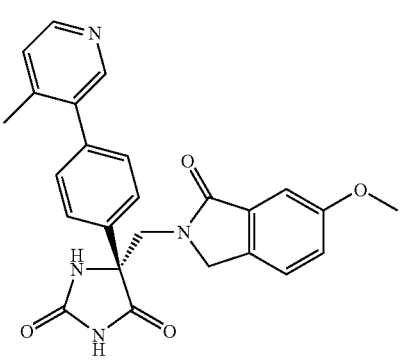
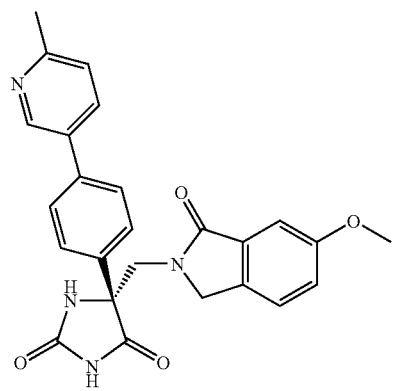

717
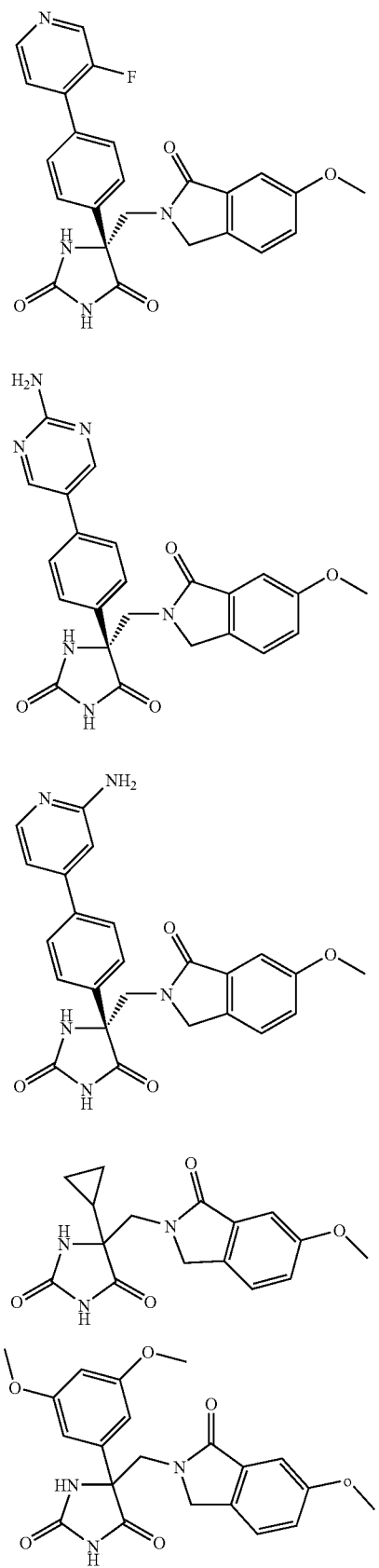
718
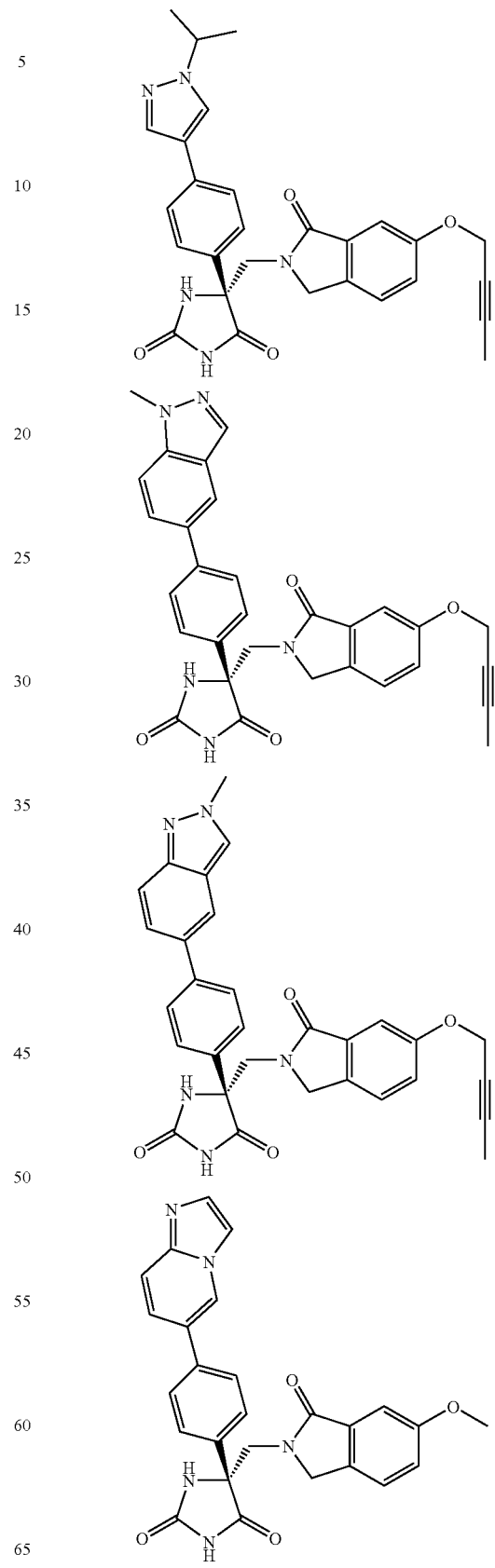

719 720
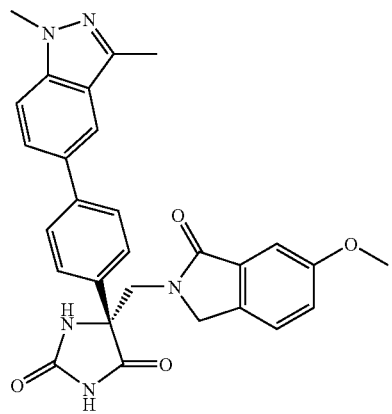
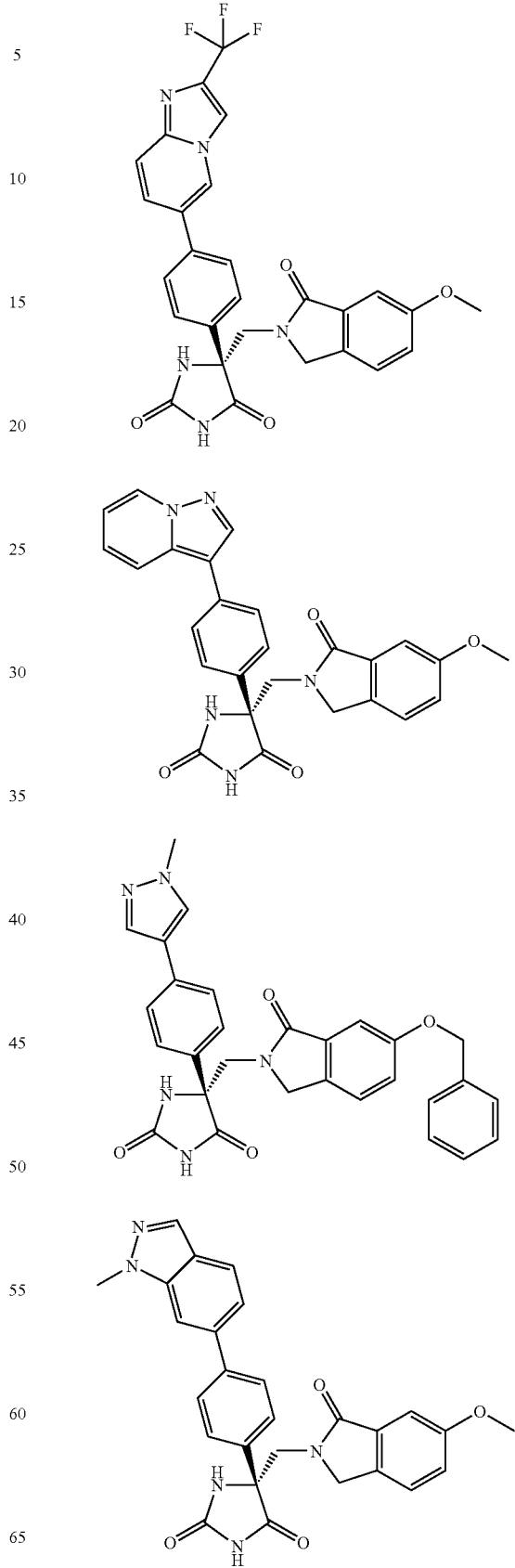

| 721 | 722 |
|---|---|
| -continued | -continued |
| 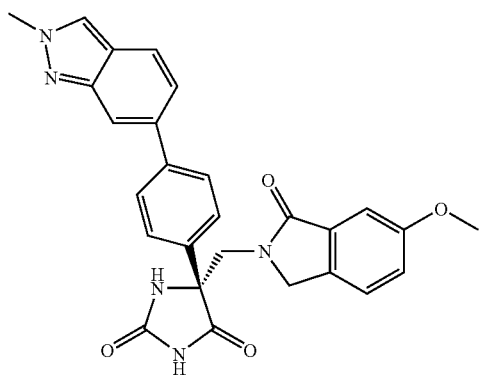 | 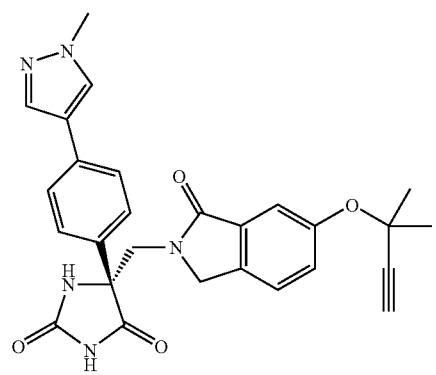 |
| 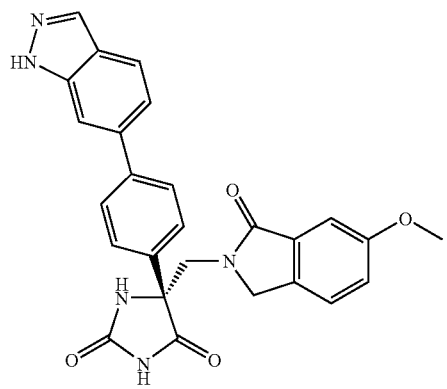 | 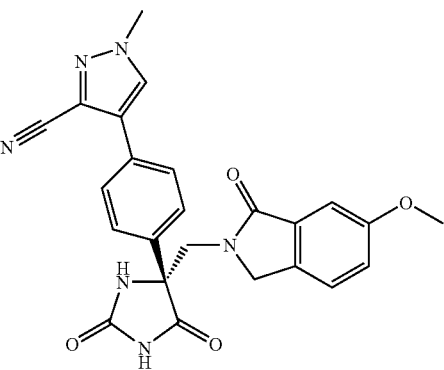 |
| 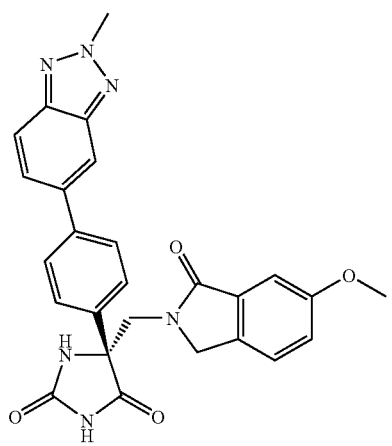 | 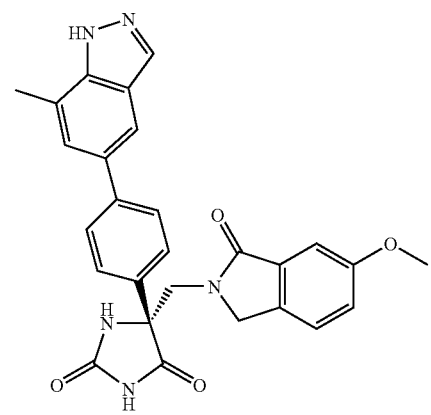 |
| 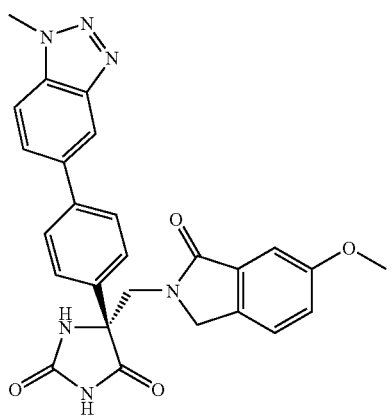 | 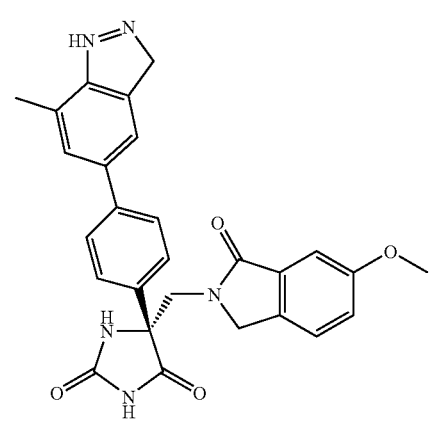 |

723
-continued
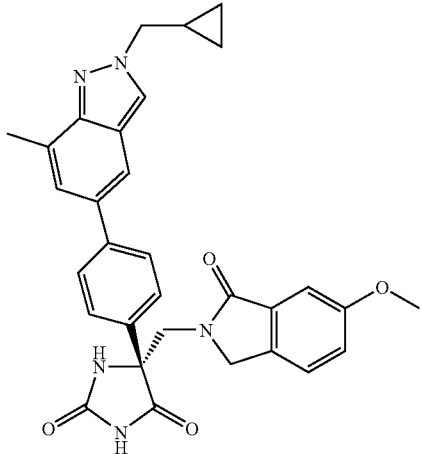
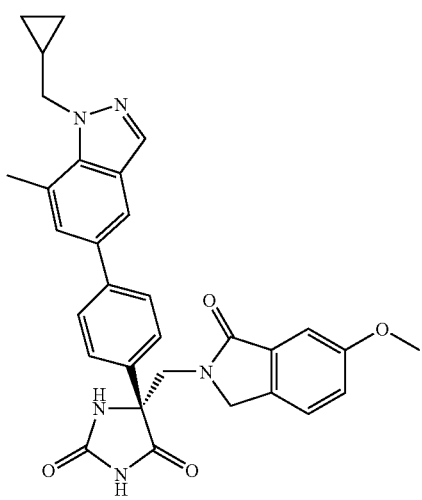
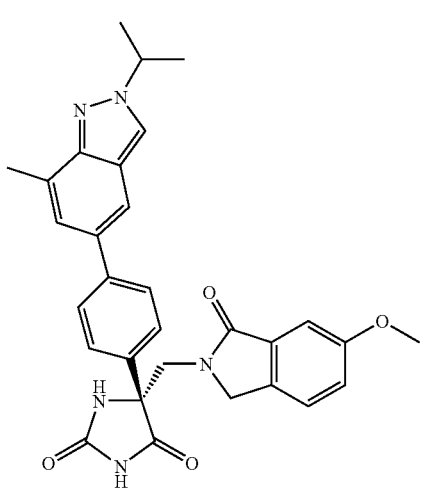
724
-continued
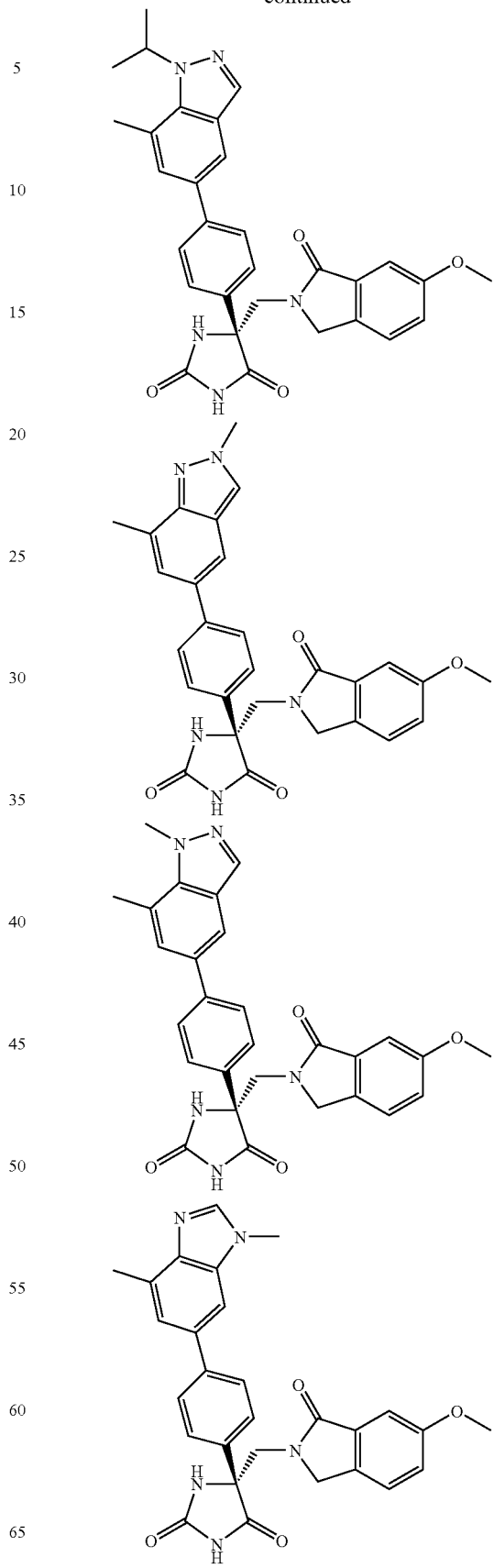

725
-continued
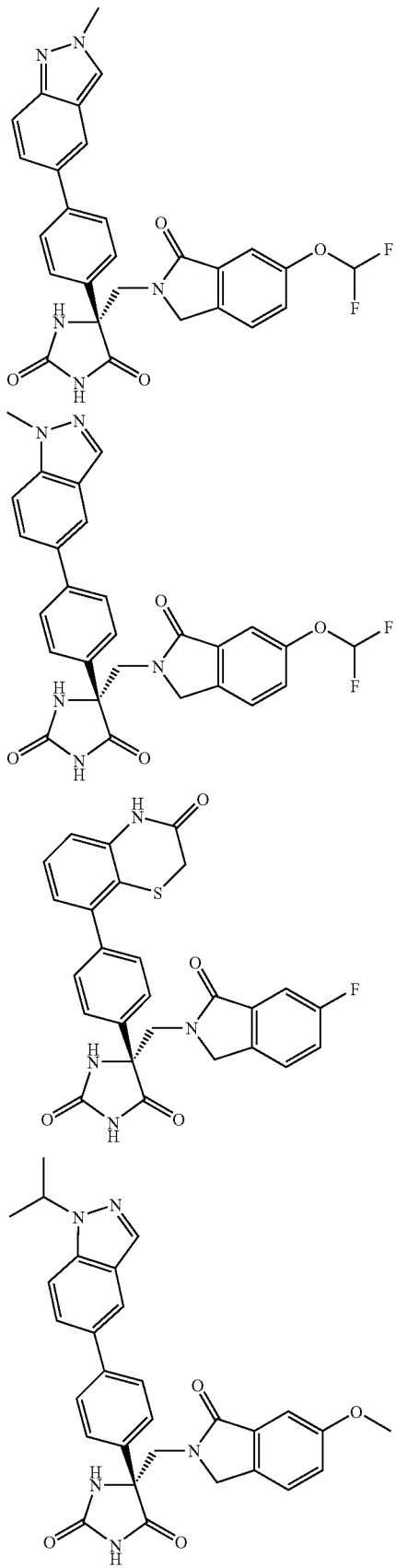
726
-continued
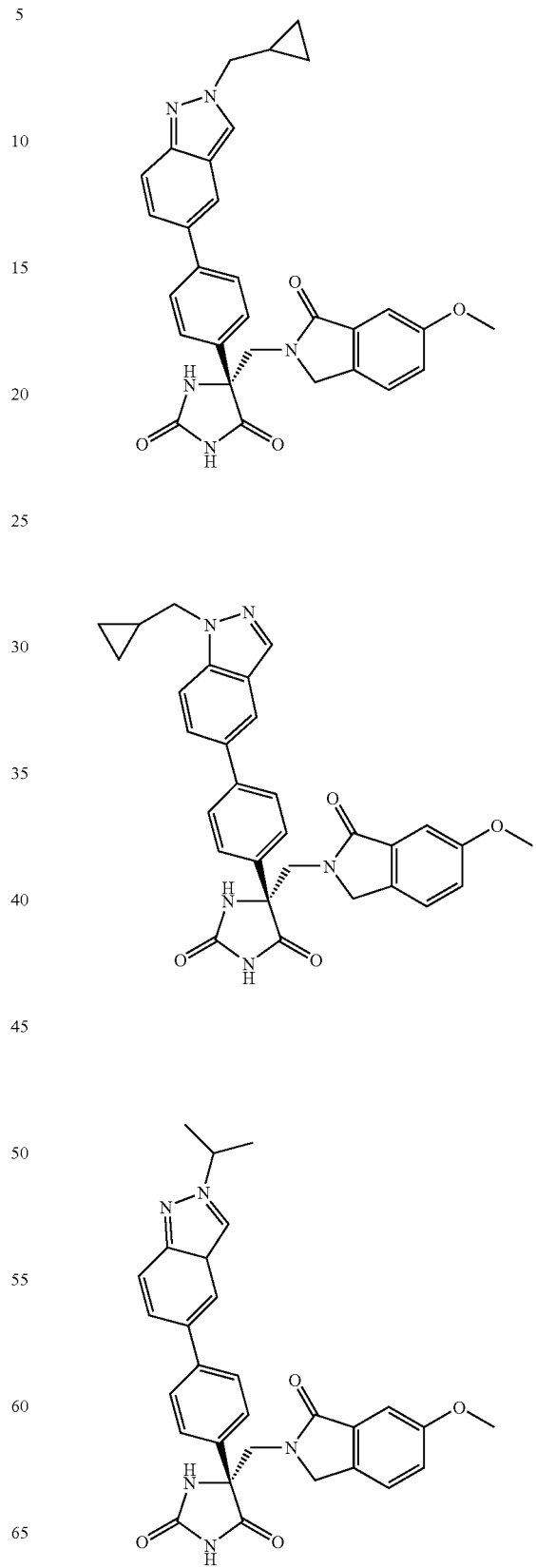

727
-continued
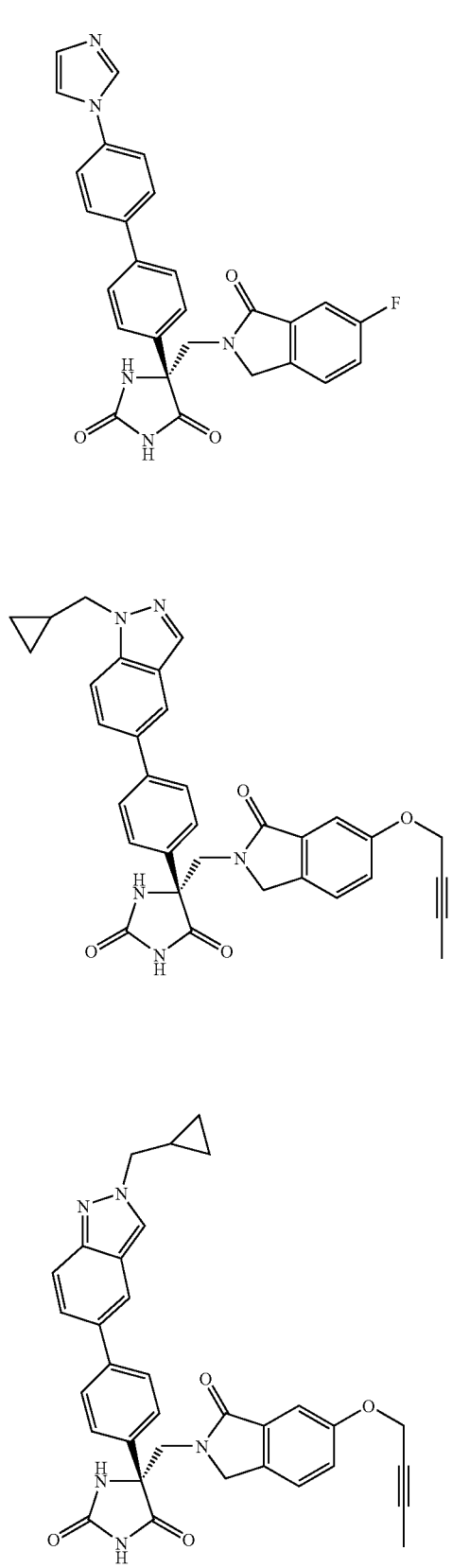
728
-continued
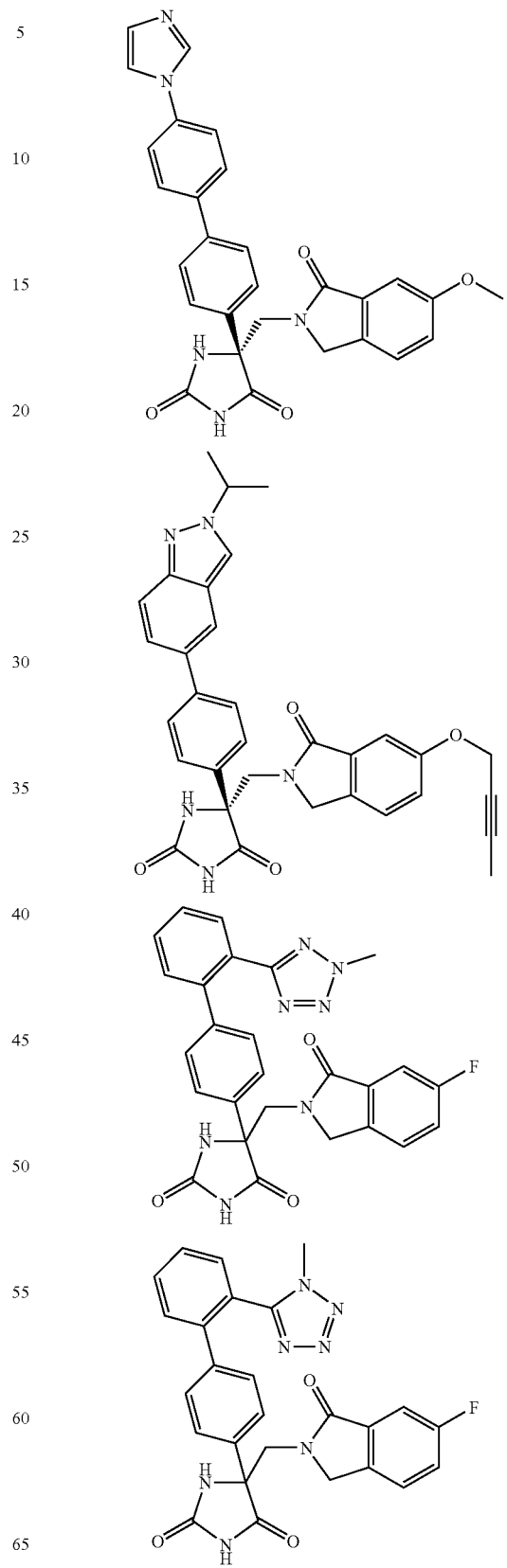

-continued
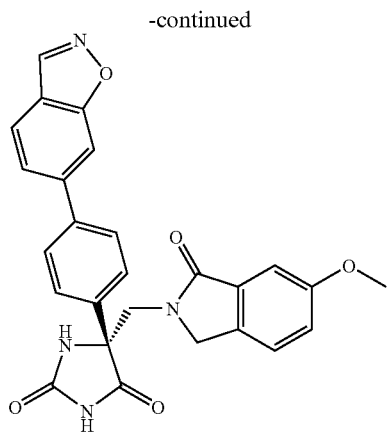
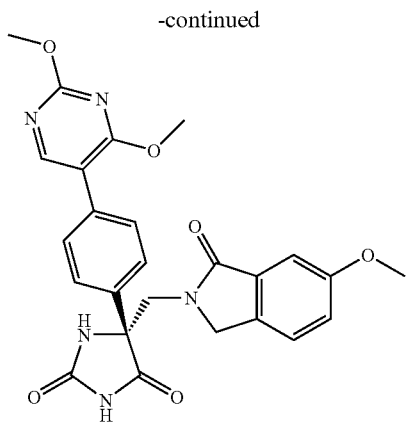
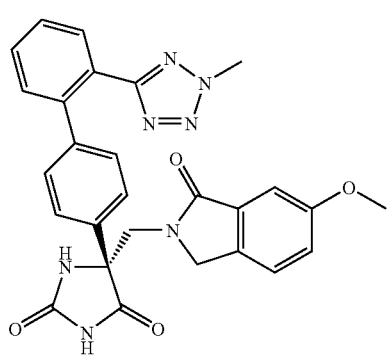
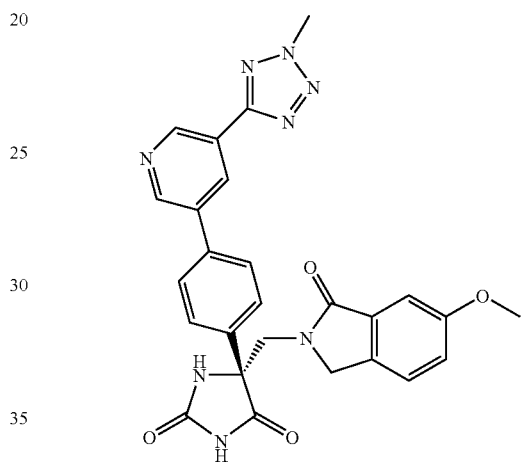
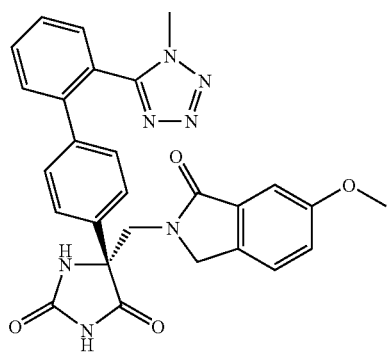
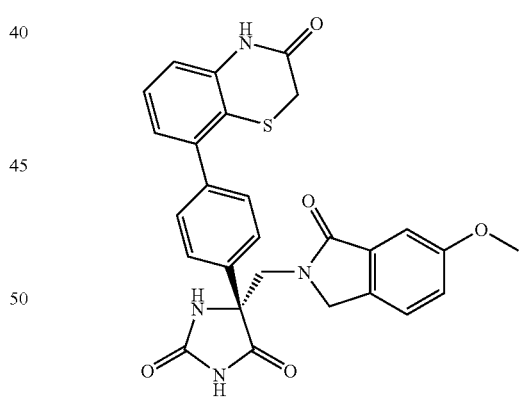
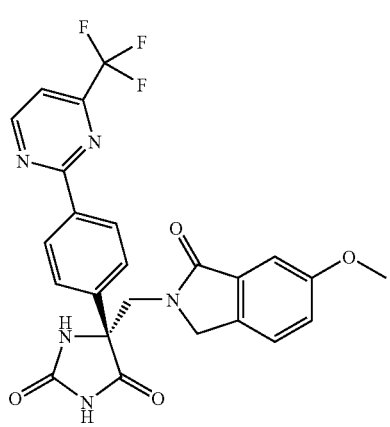
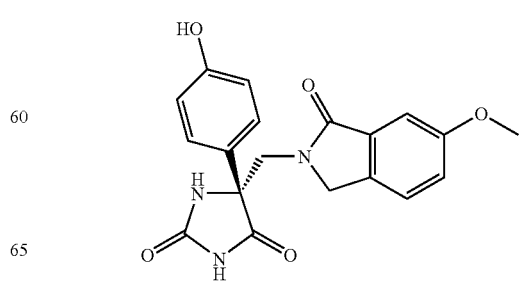

731 732
-continued
-continued
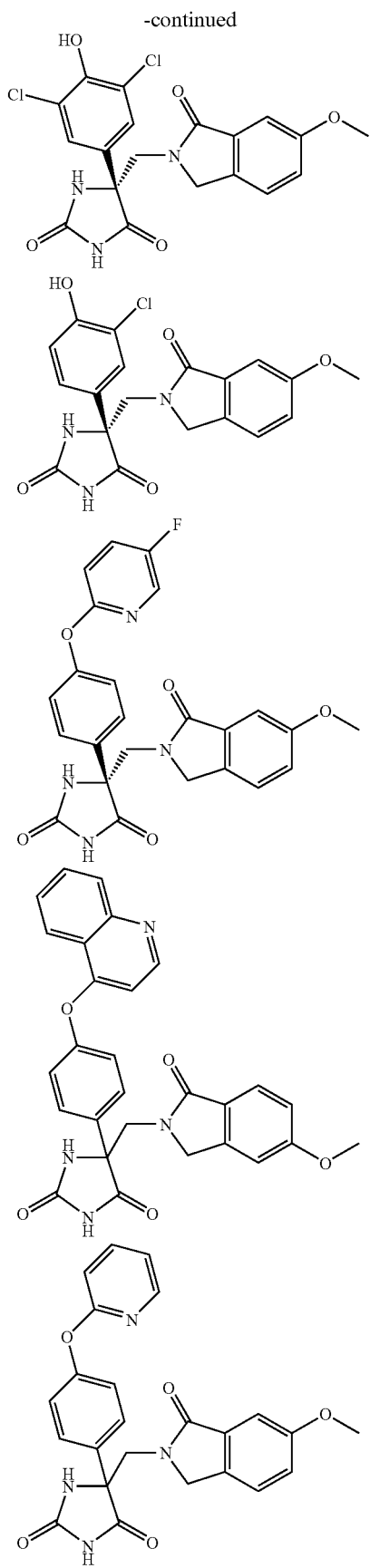
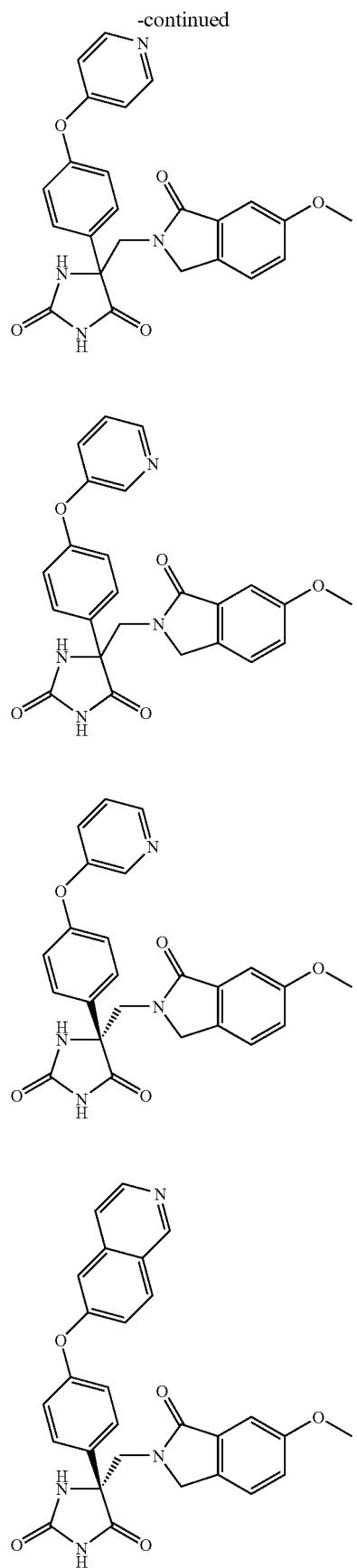

733
-continued
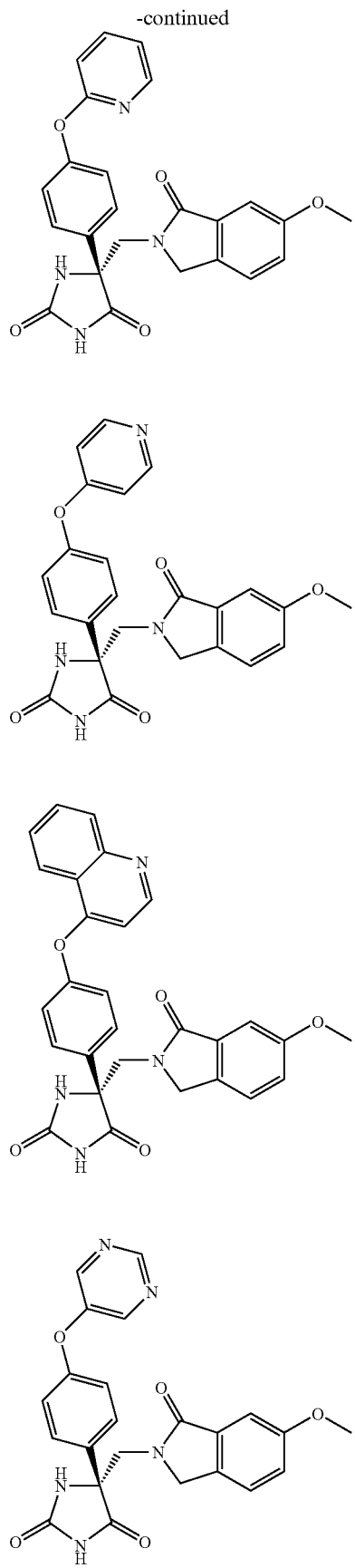
734
-continued
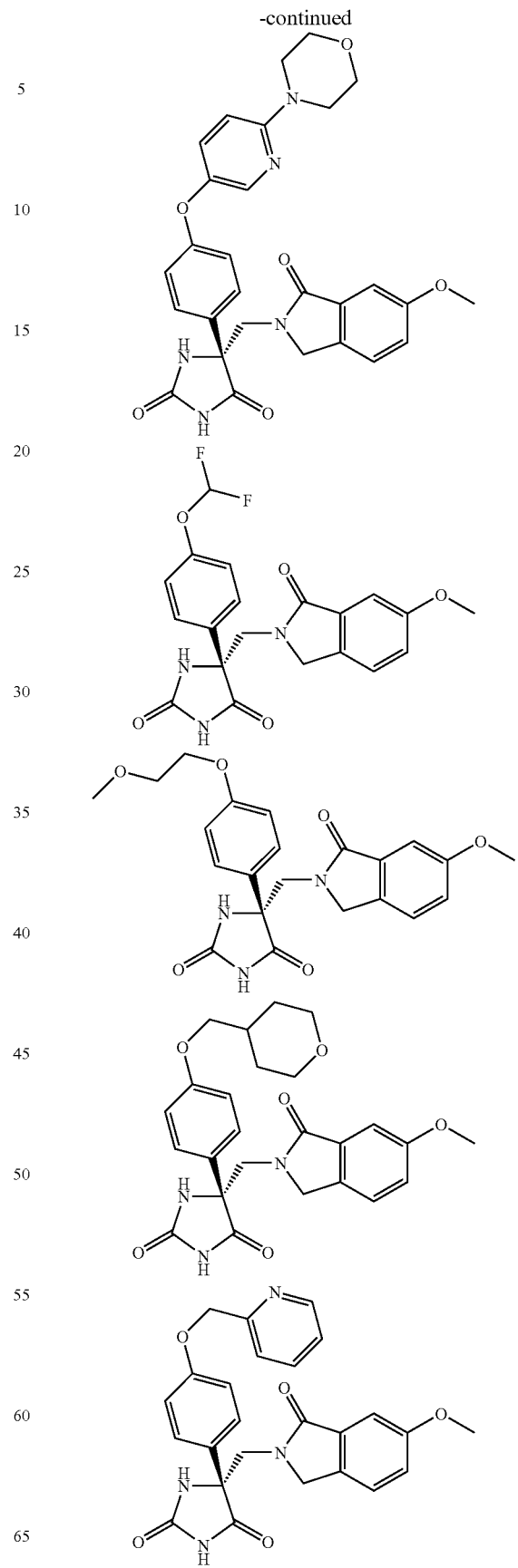

735
-continued
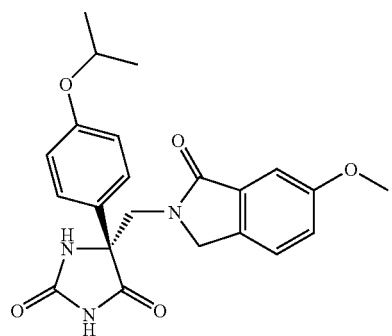
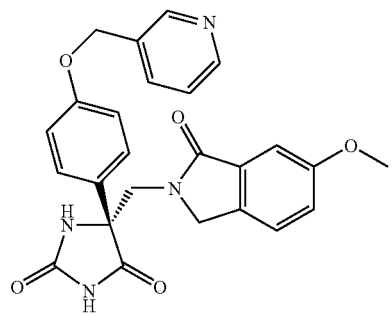
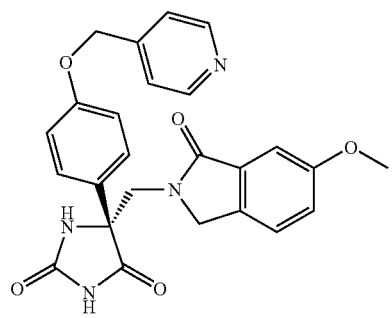
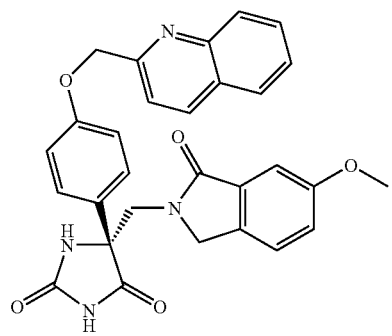
736
-continued
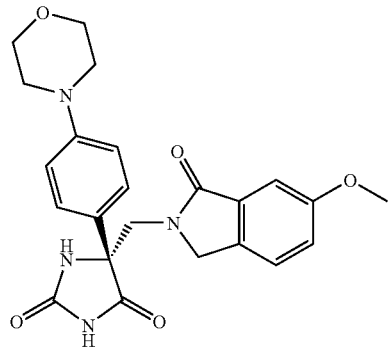
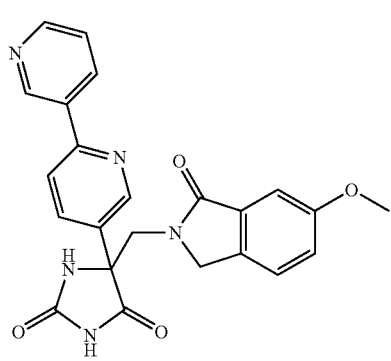
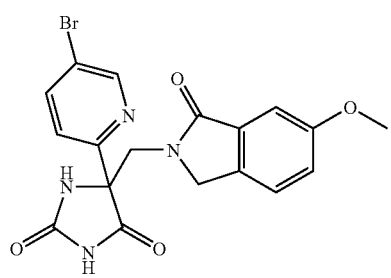
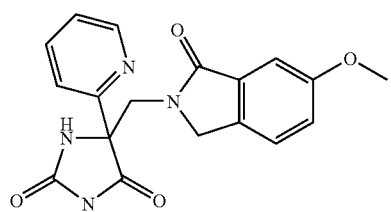
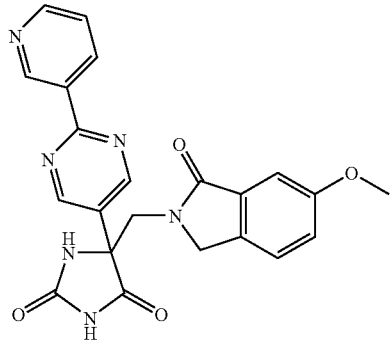

737                                    738
-continued                             -continued
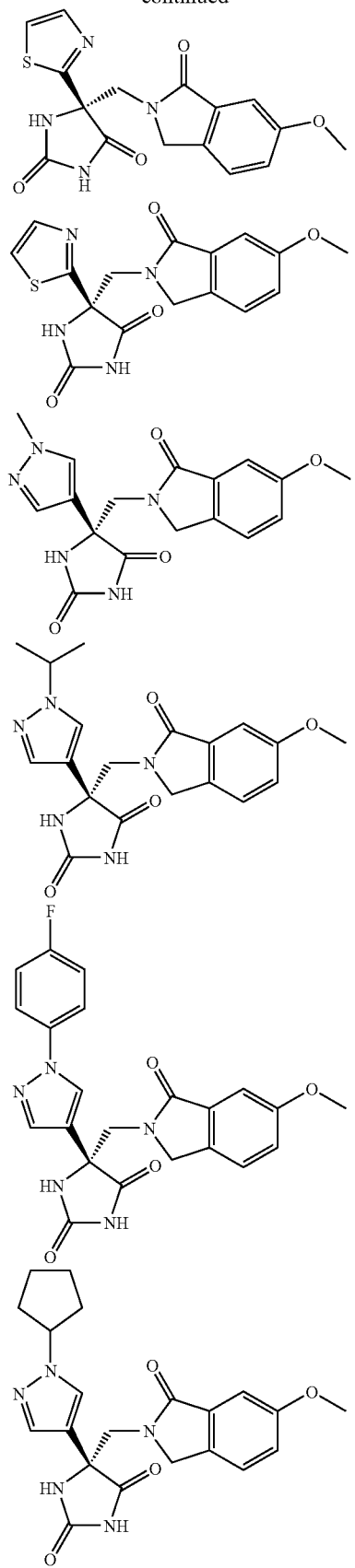
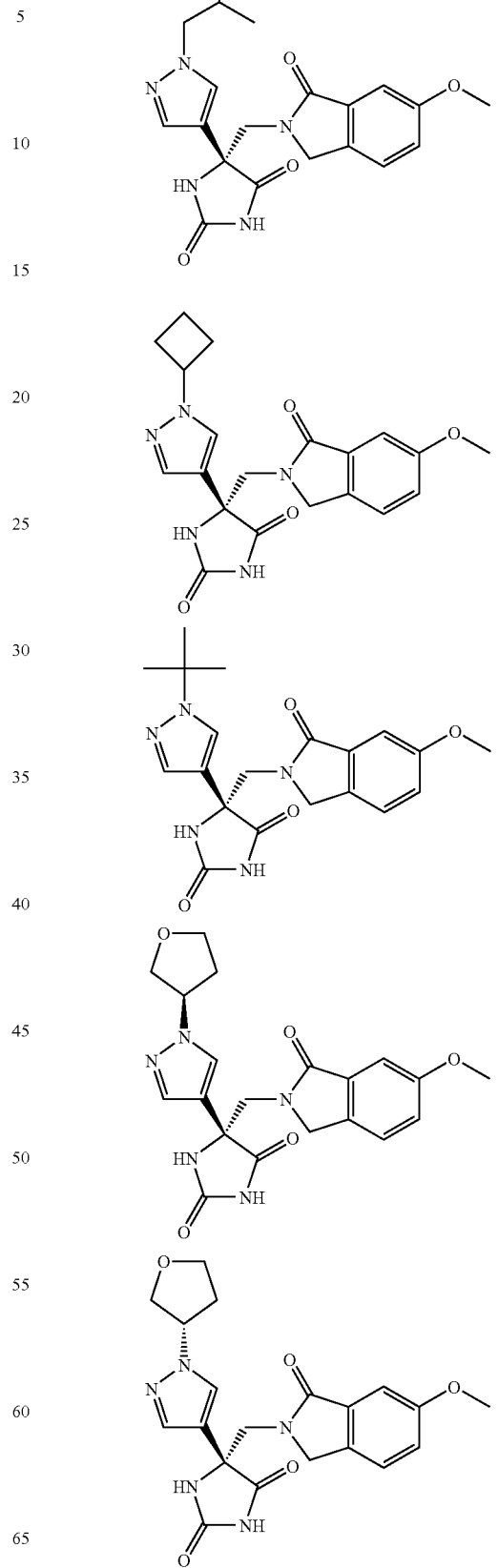

739
-continued
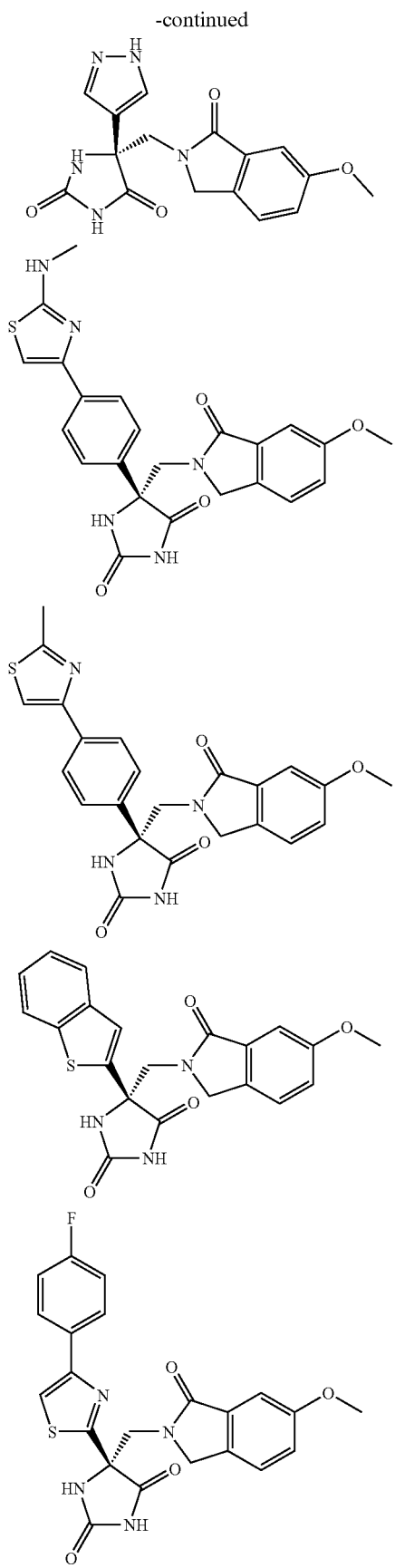
740
-continued
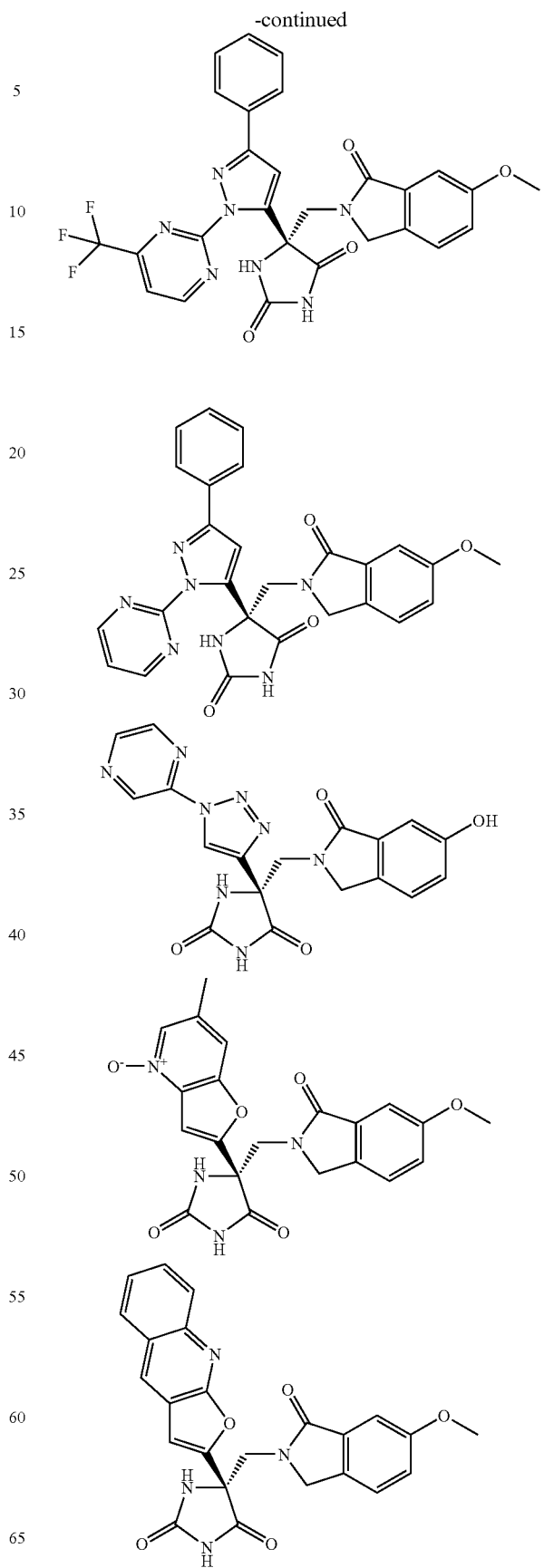

-continued
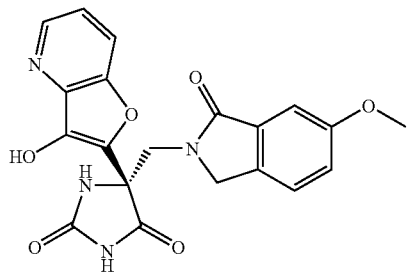
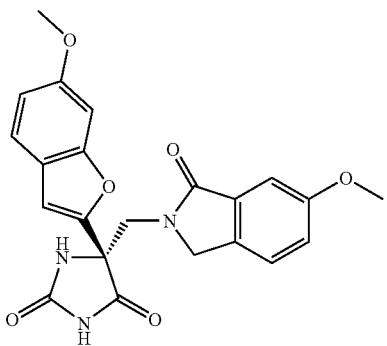
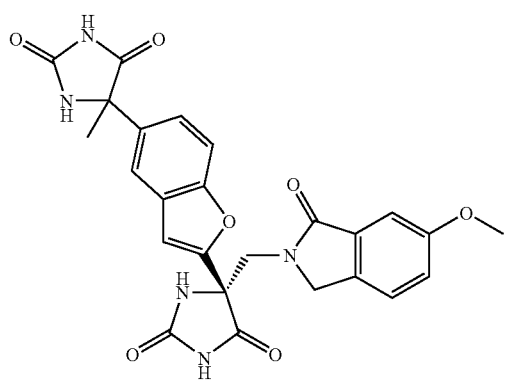
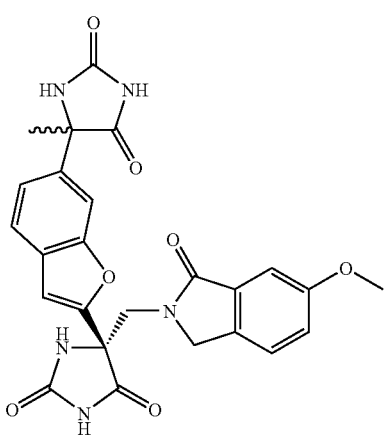
-continued
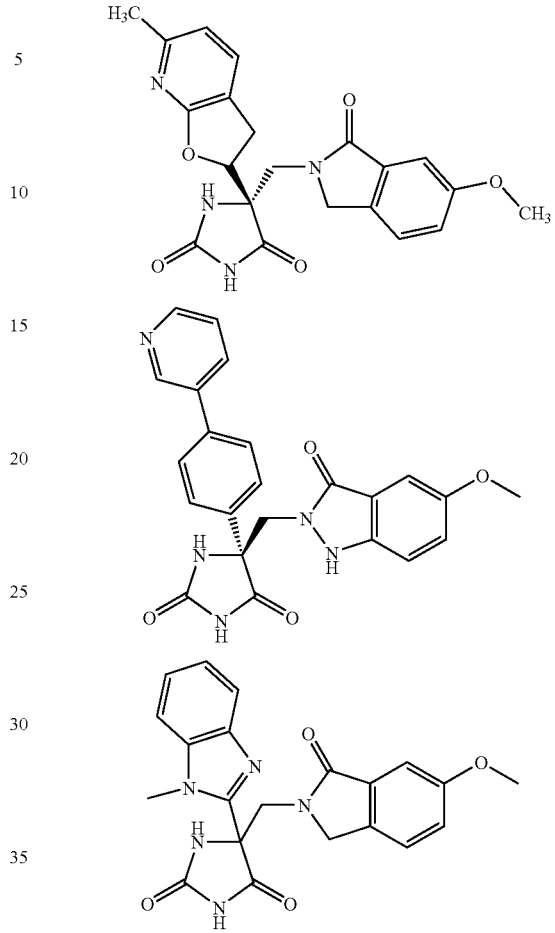
or a pharmaceutically acceptable salt thereof.
2. The method of claim 1, wherein the compound is selected from the group consisting of
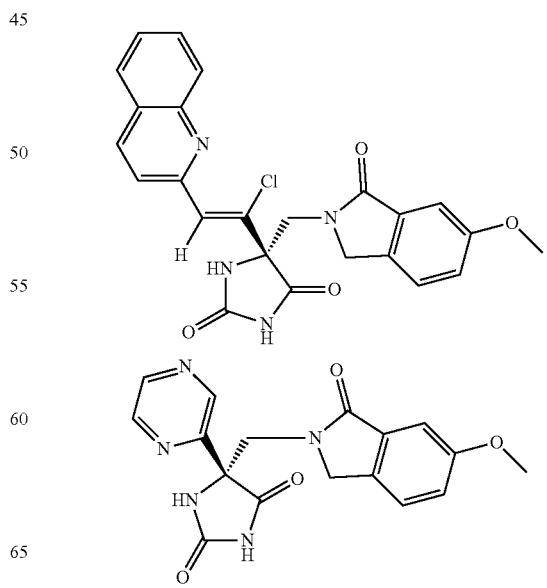

743
-continued
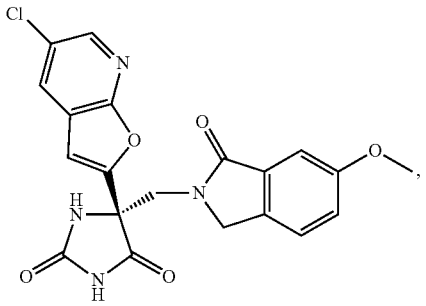
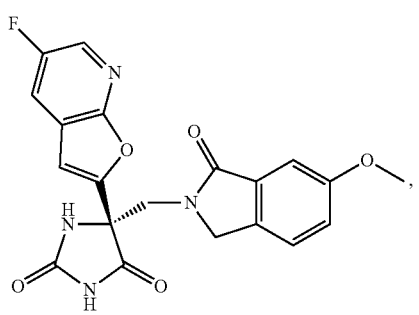
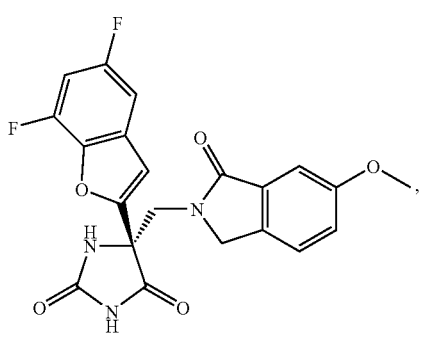
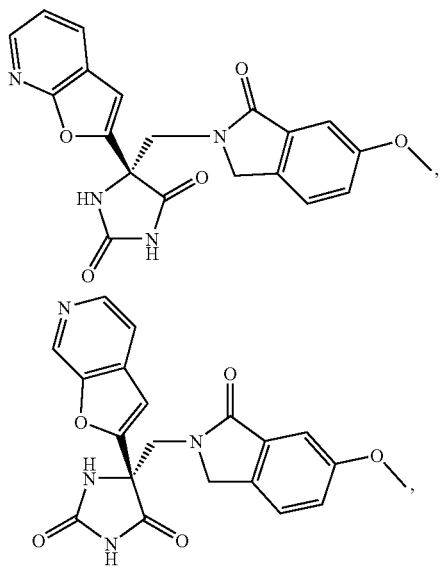
744
-continued
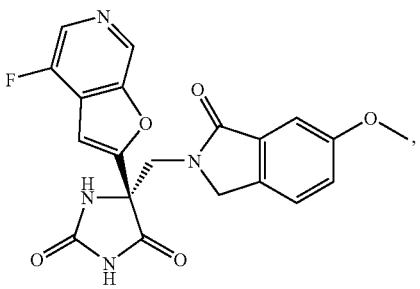
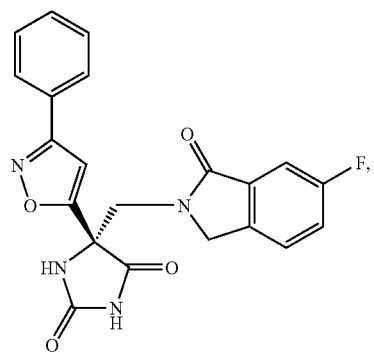
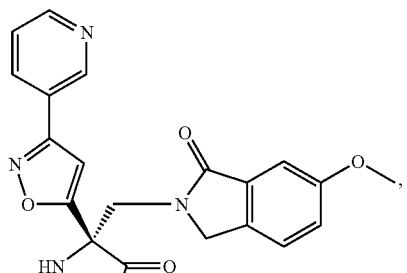
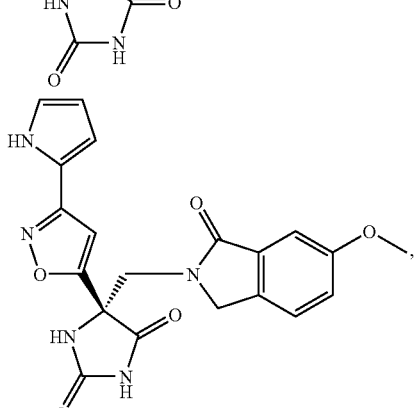
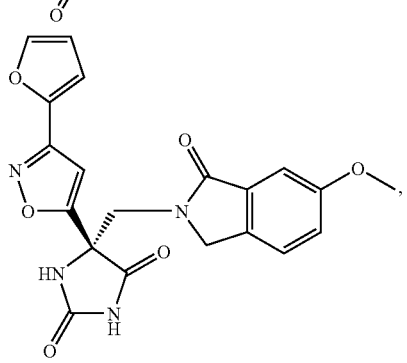

745
-continued
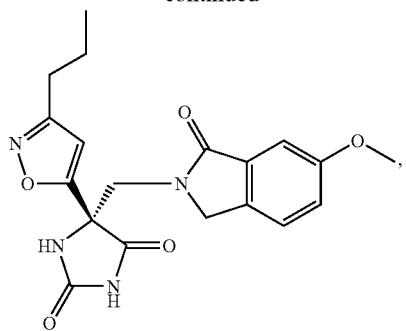
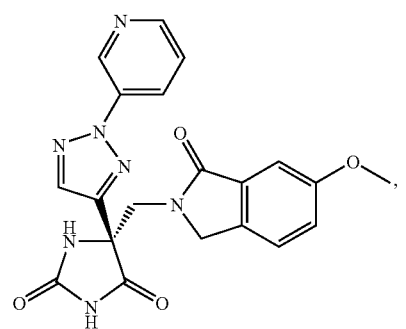
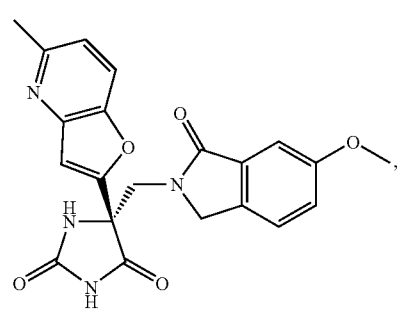
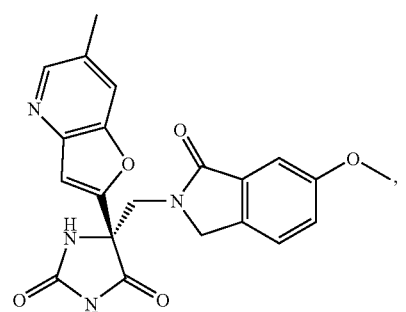
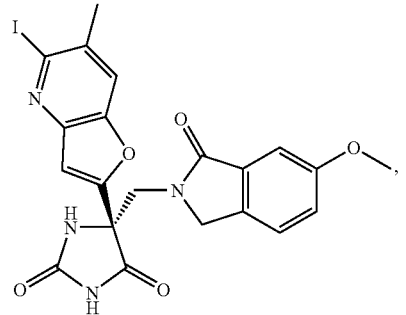
746
-continued
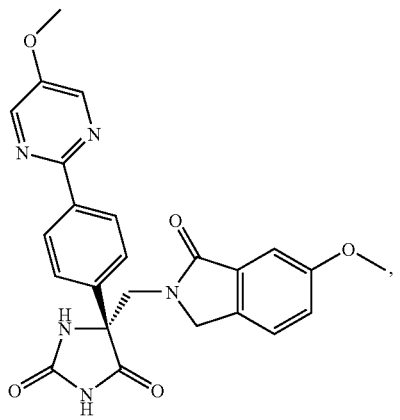
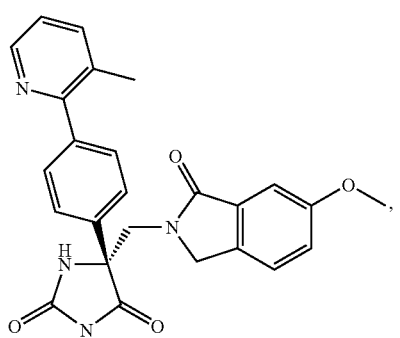
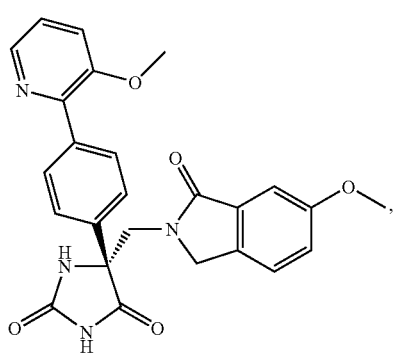
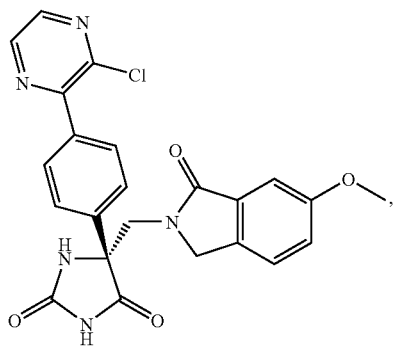

747
-continued
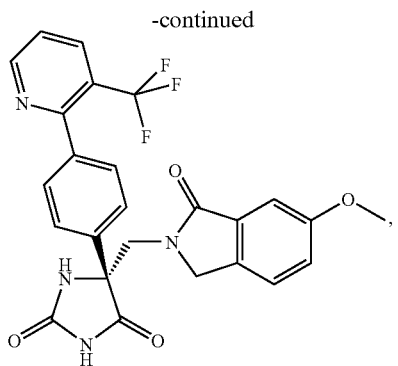
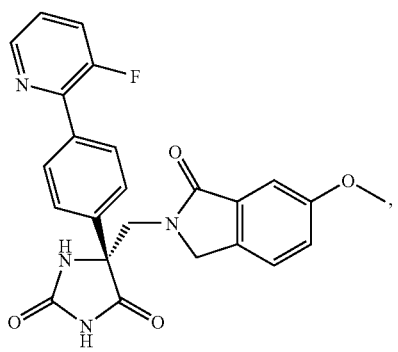
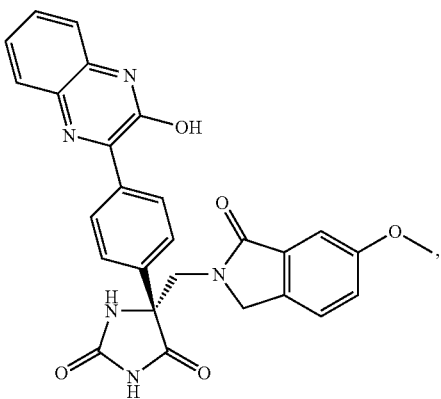
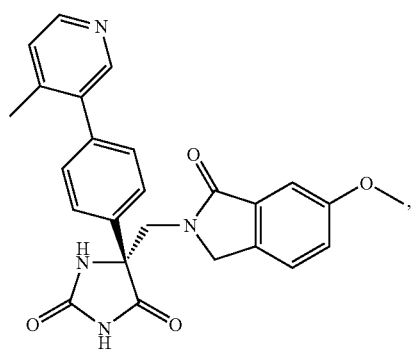
748
-continued
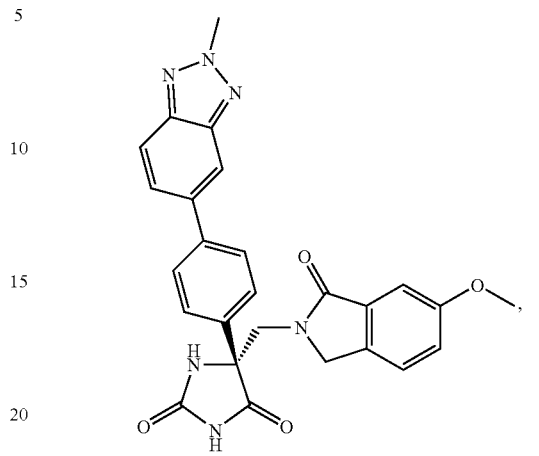
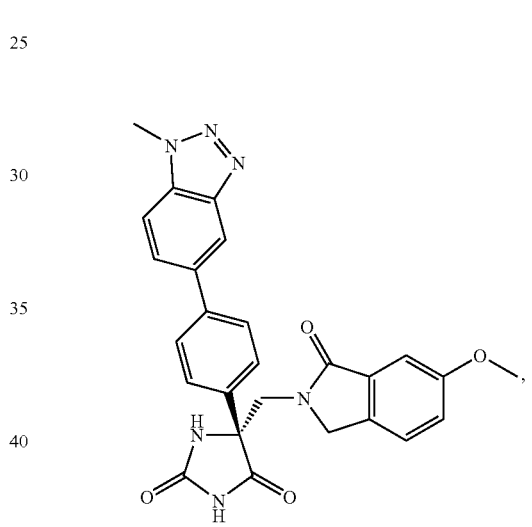
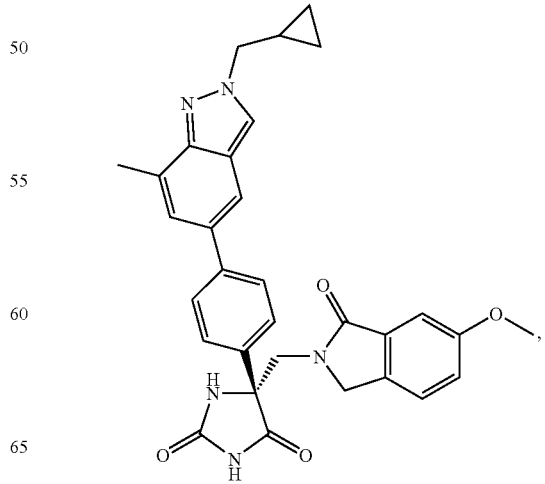

-continued
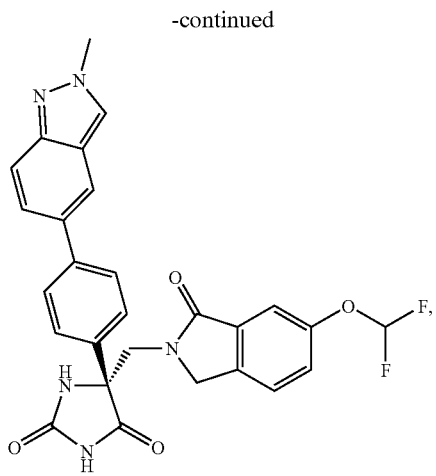
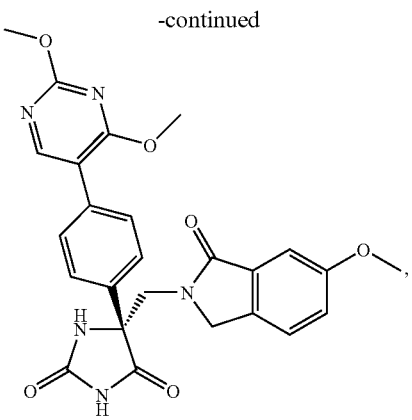
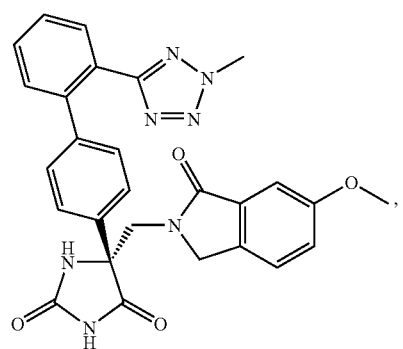
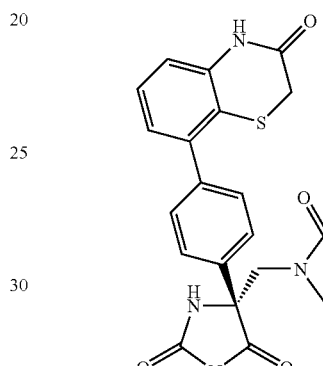
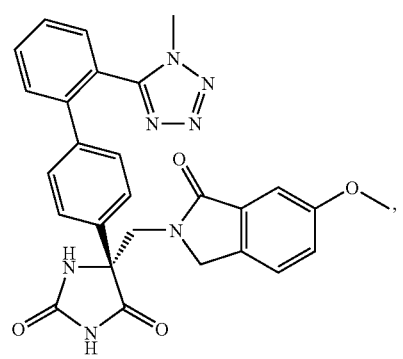
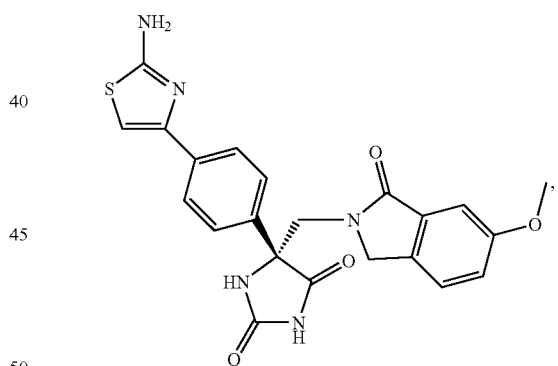
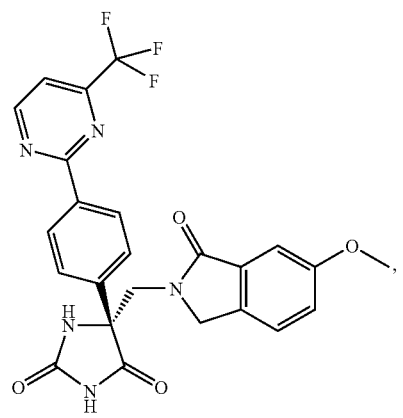
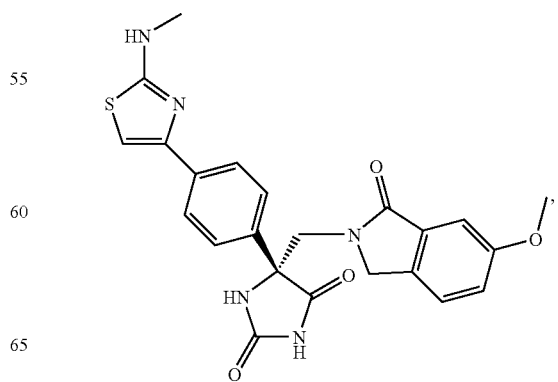

751
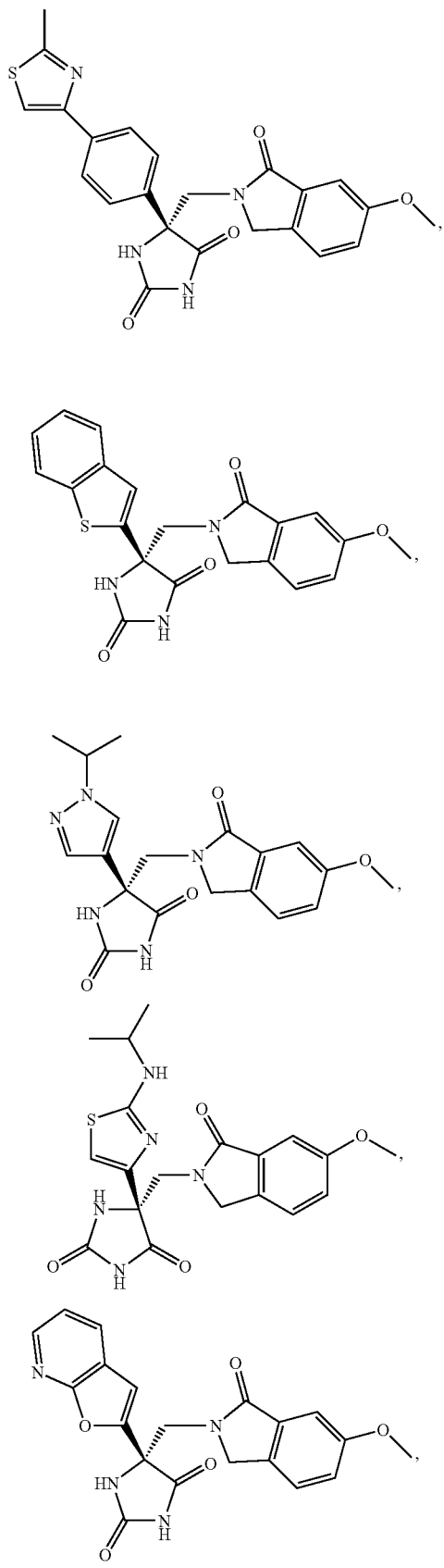
752
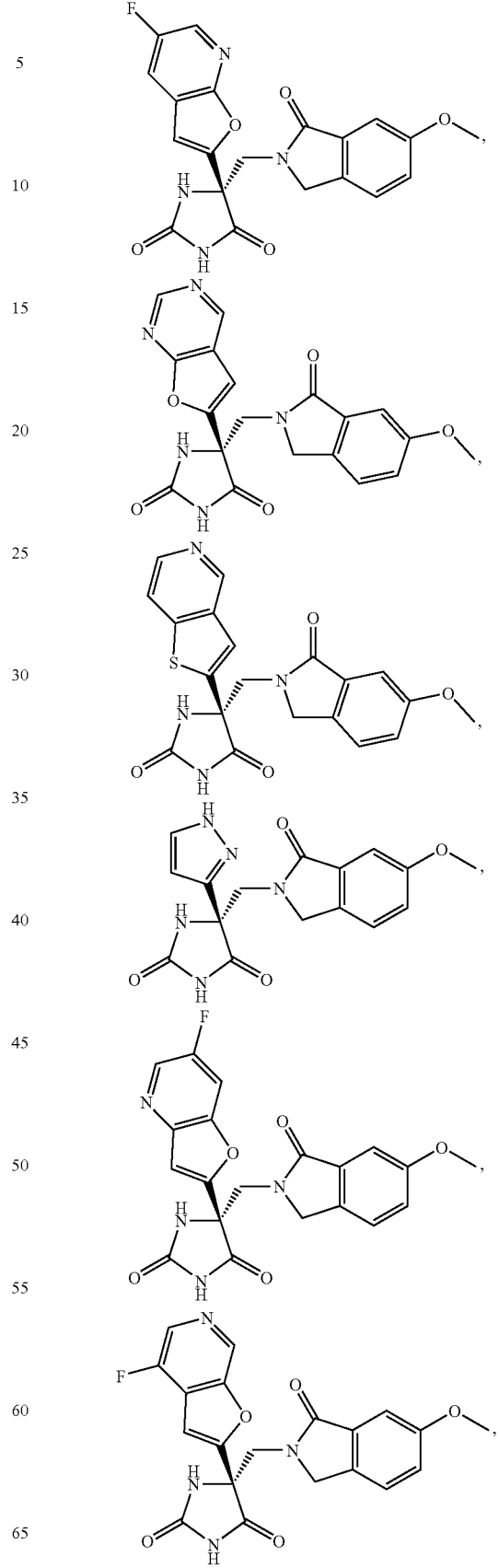

753
-continued
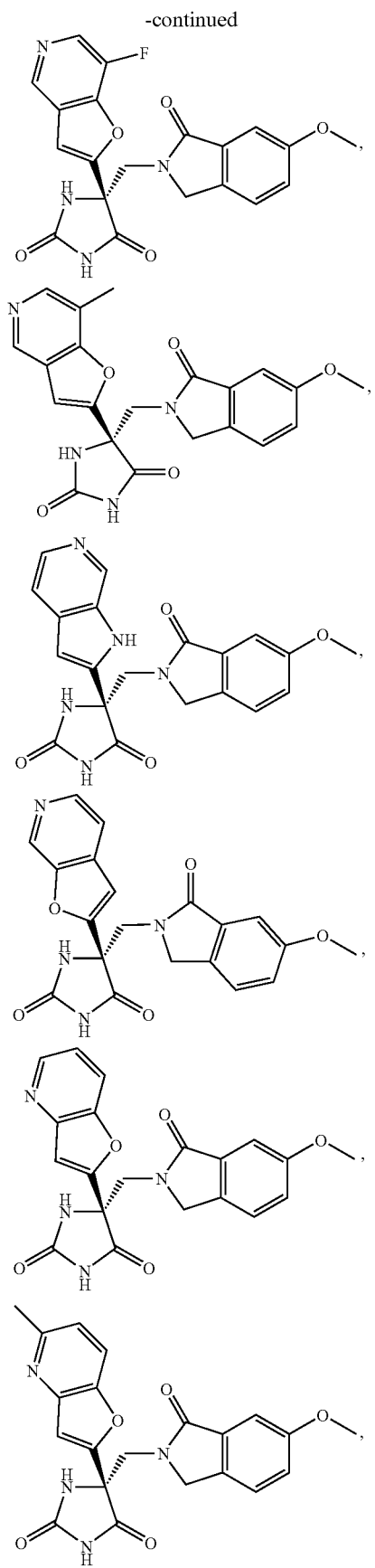
754
-continued
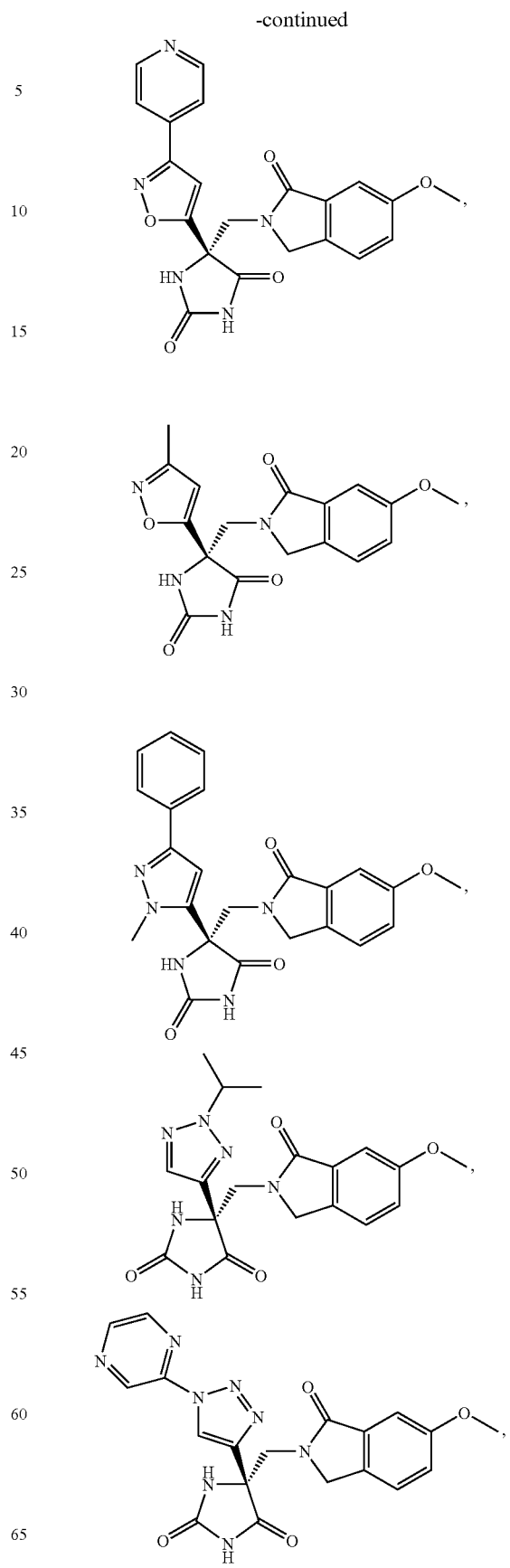

-continued
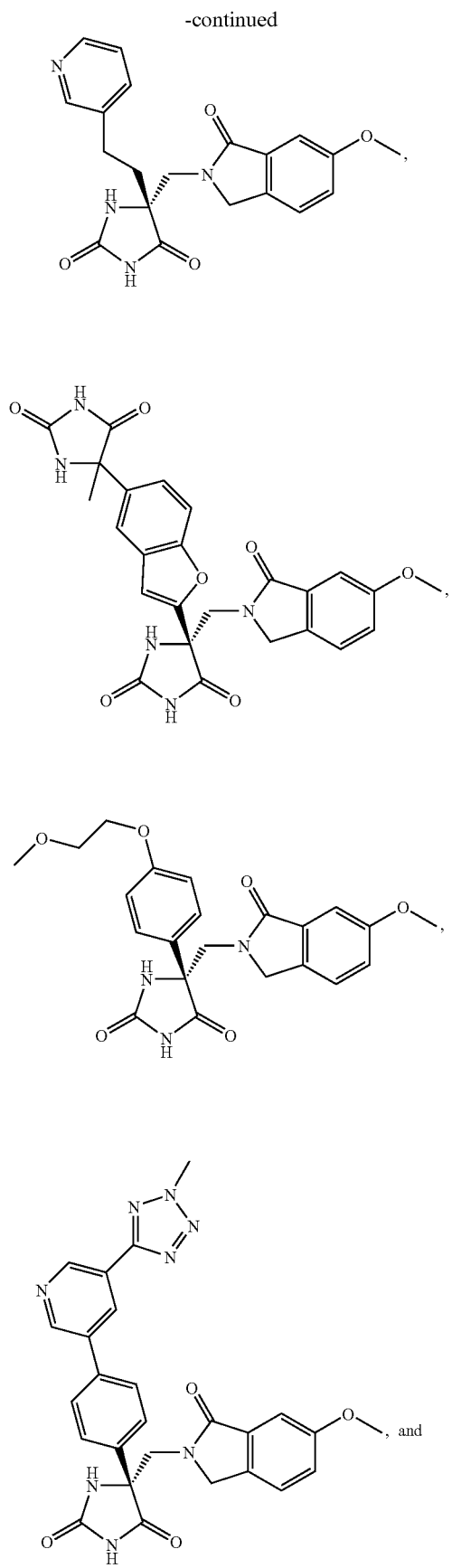
-continued
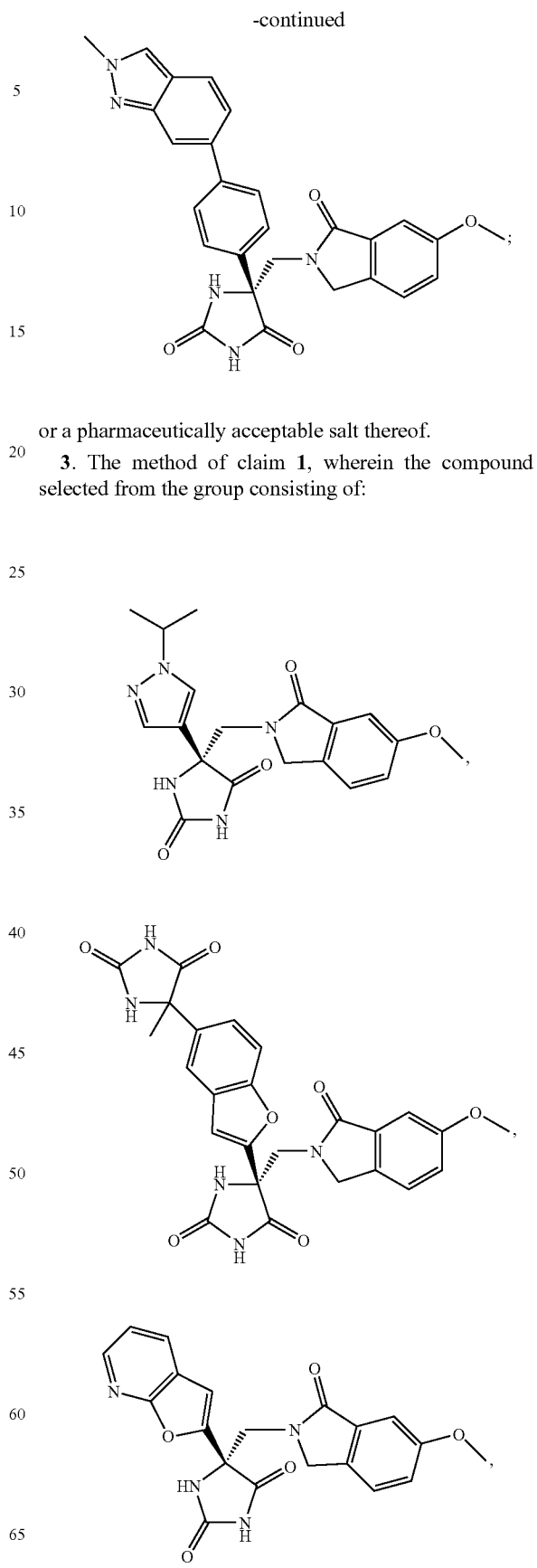
or a pharmaceutically acceptable salt thereof.
3. The method of claim 1, wherein the compound is selected from the group consisting of:

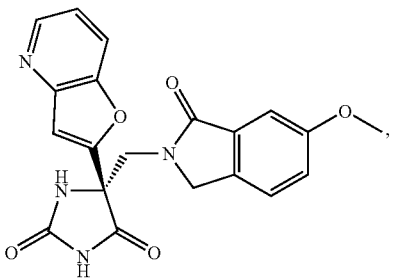

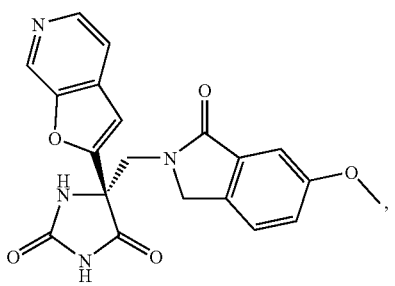

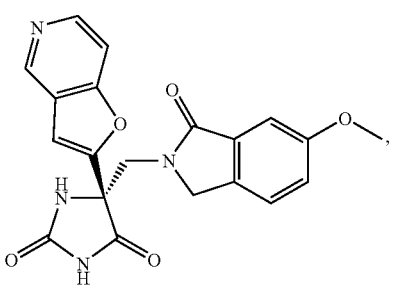

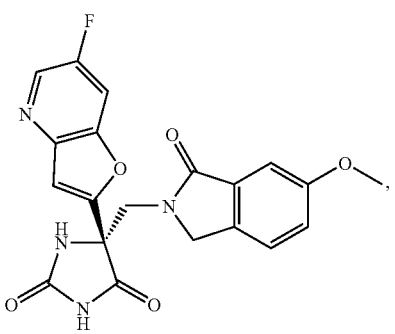

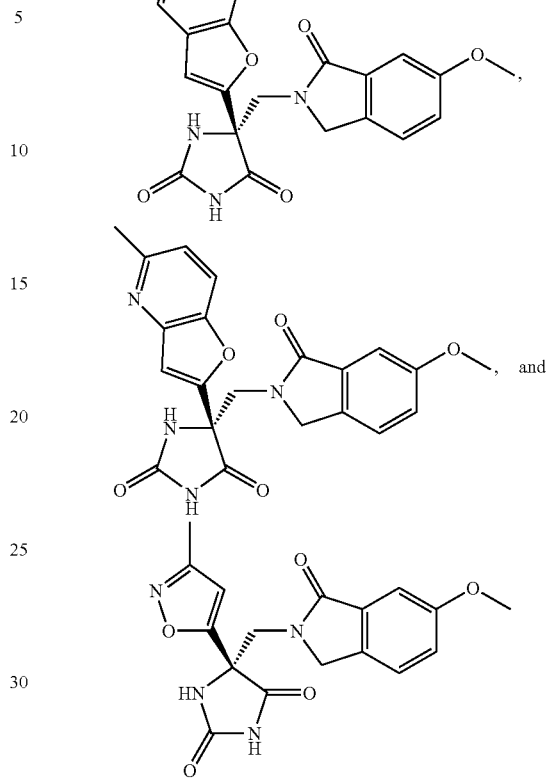

or a pharmaceutically acceptable salt thereof.

4. The method of claim 1, wherein the condition or disease is rheumatoid arthritis.

5. The method of claim 1, wherein the condition or disease is inflammatory bowel disease.

6. The method of claim 5, wherein the inflammatory bowel disease is Crohn's disease.

7. The method of claim 5, wherein the inflammatory bowel disease is colitis.

8. The method of claim 1, wherein the condition or disease is chronic obstructive pulmonary disorder.

9. The method of claim 1, wherein the condition or disease is psoriasis.

10. The method of claim 1, wherein the condition or disease is ankylosing spondylitis.

11. The method of claim 1, wherein the condition or disease is psoriatic arthritis.

* * * * *